(12) United States Patent
Kobayashi et al.

(10) Patent No.: US 8,546,380 B2
(45) Date of Patent: Oct. 1, 2013

(54) AMINODIHYDROTHIAZINE DERIVATIVES

(75) Inventors: Naotake Kobayashi, Osaka (JP); Kazuo Ueda, Osaka (JP); Naohiro Itoh, Shiga (JP); Shinji Suzuki, Osaka (JP); Gaku Sakaguchi, Shiga (JP); Akira Kato, Shiga (JP); Akira Yukimasa, Osaka (JP); Akihiro Hori, Osaka (JP); Yuji Koriyama, Osaka (JP); Hidekazu Haraguchi, Osaka (JP); Ken Yasui, Osaka (JP); Yasuhiko Kanda, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 13/243,971

(22) Filed: Sep. 23, 2011

(65) Prior Publication Data

US 2012/0022249 A1     Jan. 26, 2012

Related U.S. Application Data

(62) Division of application No. 12/089,409, filed as application No. PCT/JP2006/321015 on Oct. 23, 2006, now Pat. No. 8,173,642.

(30) Foreign Application Priority Data

Oct. 25, 2005 (JP) .................................. 2005-309642
Mar. 20, 2006 (JP) .................................. 2006-076636

(51) Int. Cl.
   *C07D 279/00* (2006.01)
   *C07D 265/00* (2006.01)
   *A61K 31/535* (2006.01)
   *A61K 31/541* (2006.01)

(52) U.S. Cl.
   USPC ........................................... 514/227.2; 544/53

(58) Field of Classification Search
   USPC ........................................ 544/53; 514/227.2
   See application file for complete search history.

(56) References Cited

U.S. PATENT DOCUMENTS

| | | | |
|---|---|---|---|
| 2,899,426 A | 8/1959 | Bloom et al. | |
| 3,115,494 A | 12/1963 | Joseph et al. | |
| 3,227,713 A | 1/1966 | Behner et al. | |
| 3,235,551 A | 2/1966 | Schubert et al. | |
| 3,636,116 A | 1/1972 | Trepanier | |
| 3,719,674 A | 3/1973 | Trepanier | |
| 3,775,409 A | 11/1973 | Harsanyi et al. | |
| 4,311,840 A | 1/1982 | Condon | |
| 4,895,841 A | 1/1990 | Sugimoto et al. | |
| 4,906,626 A | 3/1990 | Amrein et al. | |
| 5,100,901 A | 3/1992 | Sugimoto et al. | |
| 5,236,942 A | 8/1993 | Miller | |
| 5,328,915 A | 7/1994 | Long et al. | |
| 5,880,147 A | 3/1999 | Yoshida et al. | |
| 5,952,374 A | 9/1999 | Clarkson, Jr. et al. | |
| 6,096,753 A | 8/2000 | Spohr et al. | |
| 6,590,123 B2 | 7/2003 | Bekesi et al. | |
| 6,713,276 B2 | 3/2004 | Cordell et al. | |
| 7,183,070 B2 | 2/2007 | Cordell et al. | |
| 7,309,706 B2 | 12/2007 | Rupp et al. | |
| 7,326,792 B2 | 2/2008 | Shum et al. | |
| 7,414,050 B2 | 8/2008 | Illig et al. | |
| 7,763,609 B2 | 7/2010 | Zhu et al. | |
| 7,902,238 B2 | 3/2011 | Galley et al. | |
| 8,173,642 B2 | 5/2012 | Kobayashi et al. | |
| 2002/0019427 A1 | 2/2002 | Carry et al. | |
| 2005/0165080 A1 | 7/2005 | Rupp et al. | |
| 2006/0173006 A1 | 8/2006 | Sun et al. | |
| 2006/0183790 A1 | 8/2006 | Cole et al. | |
| 2006/0183792 A1 | 8/2006 | Fobare et al. | |
| 2006/0183943 A1 | 8/2006 | Hu | |
| 2007/0004730 A1 | 1/2007 | Zhou et al. | |
| 2007/0004786 A1 | 1/2007 | Malamas et al. | |
| 2007/0027199 A1 | 2/2007 | Malamas et al. | |
| 2007/0224656 A1 | 9/2007 | Cordell et al. | |

(Continued)

FOREIGN PATENT DOCUMENTS

| | | |
|---|---|---|
| DE | 140144 | 2/1980 |
| EP | 0798 292 | 10/1995 |

(Continued)

OTHER PUBLICATIONS

Vippagunta et al, "Crystalline Solids" Advanced Drug Delivery Reviews, vol. 48, pp. 3-26 (2001).*

(Continued)

*Primary Examiner* — Kahsay T Habte
(74) *Attorney, Agent, or Firm* — Hamre, Schumann, Mueller & Larson, P.C.

(57) ABSTRACT

A composition having BACE 1 inhibitory activity containing a compound represented by the formula (I):

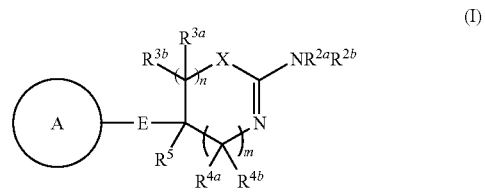

wherein ring A is an optionally substituted heterocyclic group;
E is lower alkylene;
X is S;
$R^1$ is a hydrogen atom or lower alkyl;
$R^{2a}$, $R^{2b}$, $R^{3a}$, $R^{3b}$, $R^{4a}$ and $R^{4b}$ is each independently a hydrogen atom, halogen, or hydroxy etc.;
n and m are each independently an integer of 0 to 3;
n+m is an integer of 0 to 3;
$R^5$ is a hydrogen atom or substituted lower alkyl;
or its pharmaceutically acceptable salt thereof.

11 Claims, No Drawings

(56) References Cited

U.S. PATENT DOCUMENTS

| | | |
|---|---|---|
| 2008/0200445 A1 | 8/2008 | Zhu et al. |
| 2009/0023729 A1 | 1/2009 | Nakamura et al. |
| 2009/0082560 A1 | 3/2009 | Kobayashi et al. |
| 2010/0075957 A1 | 3/2010 | Tamura et al. |
| 2010/0093999 A1 | 4/2010 | Motoki et al. |
| 2010/0160290 A1 | 6/2010 | Kobayashi et al. |
| 2010/0234365 A1 | 9/2010 | Liu et al. |
| 2010/0261727 A1 | 10/2010 | Chi et al. |
| 2011/0009395 A1 | 1/2011 | Audia et al. |
| 2011/0046122 A1 | 2/2011 | Andreini et al. |
| 2011/0065695 A1 | 3/2011 | Beauchamp et al. |
| 2011/0190279 A1 | 8/2011 | Hori et al. |
| 2011/0237576 A1 | 9/2011 | Yonezawa et al. |
| 2012/0015961 A1 | 1/2012 | Tamura et al. |
| 2012/0016116 A1 | 1/2012 | Kobayashi et al. |
| 2012/0172355 A1 | 7/2012 | Tamura et al. |
| 2012/0238548 A1 | 9/2012 | Gabellieri et al. |
| 2012/0238557 A1 | 9/2012 | Masui et al. |
| 2012/0245154 A1 | 9/2012 | Anan et al. |
| 2012/0245155 A1 | 9/2012 | Yoshida et al. |
| 2012/0245157 A1 | 9/2012 | Masui et al. |
| 2012/0253035 A1 | 10/2012 | Narquizian et al. |
| 2012/0258961 A1 | 10/2012 | Suzuki et al. |
| 2012/0258962 A1 | 10/2012 | Hilpert et al. |
| 2012/0295900 A1 | 11/2012 | Hilpert et al. |

FOREIGN PATENT DOCUMENTS

| | | |
|---|---|---|
| EP | 0713704 | 5/1996 |
| EP | 718 294 | 6/1996 |
| EP | 0717040 | 6/1996 |
| EP | 1043312 | 10/2000 |
| EP | 1 283 039 | 2/2003 |
| EP | 1 577 294 | 9/2005 |
| EP | 1 942 105 | 7/2008 |
| EP | 1942105 | 7/2008 |
| EP | 2147914 | 1/2010 |
| EP | 2151435 | 2/2010 |
| EP | 2 233 474 | 9/2010 |
| EP | 2305672 | 4/2011 |
| EP | 2332943 | 6/2011 |
| EP | 2 360 155 | 8/2011 |
| EP | 2415756 | 2/2012 |
| GB | 1001093 | 8/1965 |
| JP | 62-120374 | 6/1987 |
| JP | 8-231521 | 9/1996 |
| JP | 9-67355 | 3/1997 |
| JP | 10-505862 | 12/1999 |
| JP | 11-349572 | 12/1999 |
| JP | 2005-509651 | 4/2004 |
| JP | 2005-517634 | 6/2005 |
| JP | 2005-526005 | 9/2005 |
| JP | 2005-531520 | 10/2005 |
| JP | 2006-519758 | 8/2006 |
| JP | 2009-520685 | 5/2009 |
| WO | 94/12165 | 6/1994 |
| WO | 95/09619 | 4/1995 |
| WO | 96/09286 | 3/1996 |
| WO | 96/14842 | 5/1996 |
| WO | 96/18608 | 6/1996 |
| WO | 97/07098 | 2/1997 |
| WO | 97/014686 | 4/1997 |
| WO | 97/38977 | 10/1997 |
| WO | 99/18960 | 4/1999 |
| WO | 00/00200 | 1/2000 |
| WO | 01/19788 | 3/2001 |
| WO | 01/78709 | 10/2001 |
| WO | 01/87293 | 11/2001 |
| WO | 02/062766 | 8/2002 |
| WO | 02/088101 | 11/2002 |
| WO | 02/096897 | 12/2002 |
| WO | 03/039446 | 5/2003 |
| WO | 03/040096 | 5/2003 |
| WO | 03/040115 | 5/2003 |
| WO | 03/040142 | 5/2003 |
| WO | 03/082191 | 10/2003 |
| WO | 2004/009549 | 1/2004 |
| WO | 2004/014843 | 2/2004 |
| WO | 2004/031154 | 4/2004 |
| WO | 2004/039404 | 5/2004 |
| WO | 2004/043916 | 5/2004 |
| WO | 2004-149429 | 5/2004 |
| WO | 2004/096795 | 11/2004 |
| WO | 2005/014555 | 2/2005 |
| WO | 2005/032493 | 4/2005 |
| WO | 2005/058311 | 6/2005 |
| WO | 2005/097767 | 10/2005 |
| WO | 2005/111031 | 11/2005 |
| WO | 2005/121100 | 12/2005 |
| WO | 2006/009655 | 1/2006 |
| WO | 2006/023750 | 3/2006 |
| WO | 2006/029850 | 3/2006 |
| WO | 2006/014104 | 4/2006 |
| WO | 2006/041404 | 4/2006 |
| WO | 2006/041405 | 4/2006 |
| WO | 2006/065204 | 6/2006 |
| WO | 2006/065277 | 6/2006 |
| WO | 2006/076284 | 7/2006 |
| WO | 2006/099379 | 9/2006 |
| WO | 2006/138192 | 12/2006 |
| WO | 2006/138217 | 12/2006 |
| WO | 2006/138265 | 12/2006 |
| WO | 2006/138304 | 12/2006 |
| WO | 2007/002220 | 1/2007 |
| WO | 2007/005366 | 1/2007 |
| WO | 2007/005404 | 1/2007 |
| WO | 2007016012 | 2/2007 |
| WO | 2007/038271 | 4/2007 |
| WO | 2007/049532 | 5/2007 |
| WO | 2007/058580 | 5/2007 |
| WO | 2007/058582 | 5/2007 |
| WO | 2007/058583 | 5/2007 |
| WO | 2007/058601 | 5/2007 |
| WO | 2007/058602 | 5/2007 |
| WO | 2007/073284 | 6/2007 |
| WO | 2007/078813 | 7/2007 |
| WO | 2007/092846 | 8/2007 |
| WO | 2007/092854 | 8/2007 |
| WO | 2007/114771 | 10/2007 |
| WO | 2007/120096 | 10/2007 |
| WO | 2007/146225 | 12/2007 |
| WO | 2008/011560 | 1/2008 |
| WO | 2008/022024 | 2/2008 |
| WO | 2008/073365 | 6/2008 |
| WO | 2008/073370 | 6/2008 |
| WO | 2008/103351 | 8/2008 |
| WO | 2008/133273 | 11/2008 |
| WO | 2008/133274 | 11/2008 |
| WO | 2009/010454 | 1/2009 |
| WO | 2009-051828 | 3/2009 |
| WO | 2009/064418 | 5/2009 |
| WO | 2009/097278 | 8/2009 |
| WO | 2009/097401 | 8/2009 |
| WO | 2009/097578 | 8/2009 |
| WO | 2009/103626 | 8/2009 |
| WO | 2009/131974 | 10/2009 |
| WO | 2009/131975 | 10/2009 |
| WO | 2009/134617 | 11/2009 |
| WO | 2009/151098 | 12/2009 |
| WO | 2010/013302 | 2/2010 |
| WO | 2010/013794 | 2/2010 |
| WO | 2010/019392 | 2/2010 |
| WO | 2010/019393 | 2/2010 |
| WO | 2010/047372 | 4/2010 |
| WO | 2010/056194 | 5/2010 |
| WO | 2010/056195 | 5/2010 |
| WO | 2010/056196 | 5/2010 |
| WO | 2010/113848 | 10/2010 |
| WO | 2010/128058 | 11/2010 |
| WO | 2010/129864 | 11/2010 |
| WO | 2011/005738 | 1/2011 |
| WO | 2011/009897 | 1/2011 |
| WO | 2011/009898 | 1/2011 |
| WO | 2011/009943 | 1/2011 |
| WO | 2011/020806 | 2/2011 |

| WO | 2011/029803 | 3/2011 |
| WO | 2011/044181 | 4/2011 |
| WO | 2011/044184 | 4/2011 |
| WO | 2011/044185 | 4/2011 |
| WO | 2011/044187 | 4/2011 |
| WO | 2011/058763 | 5/2011 |
| WO | 2011/060207 | 5/2011 |
| WO | 2011/069934 | 6/2011 |
| WO | 2011/070029 | 6/2011 |
| WO | 2011/070781 | 6/2011 |
| WO | 2011/071057 | 6/2011 |
| WO | 2011/071109 | 6/2011 |
| WO | 2011/071135 | 6/2011 |
| WO | 2011/077726 | 6/2011 |
| WO | 2011/080176 | 7/2011 |
| WO | 2011/138293 | 11/2011 |
| WO | 2011/154374 | 12/2011 |
| WO | 2011/154431 | 12/2011 |
| WO | 2012/000933 | 1/2012 |
| WO | 2012/006953 | 1/2012 |
| WO | 2012/019966 | 2/2012 |
| WO | 2012/038438 | 3/2012 |
| WO | 2012/057247 | 5/2012 |
| WO | 2012/057248 | 5/2012 |
| WO | 2012/085038 | 6/2012 |
| WO | 2012/093148 | 7/2012 |
| WO | 2012/098064 | 7/2012 |
| WO | 2012/098213 | 7/2012 |
| WO | 2012/098461 | 7/2012 |
| WO | 2012/104263 | 8/2012 |
| WO | 2012/107371 | 8/2012 |
| WO | 2012/110440 | 8/2012 |
| WO | 2012/110441 | 8/2012 |
| WO | 2012/110459 | 8/2012 |
| WO | 2012/117027 | 9/2012 |
| WO | 2012/120023 | 9/2012 |
| WO | 2012/126791 | 9/2012 |
| WO | 2012/136603 | 10/2012 |
| WO | 2012/139993 | 10/2012 |
| WO | 2012/147762 | 11/2012 |
| WO | 2012/147763 | 11/2012 |
| WO | 2012/156284 | 11/2012 |
| WO | 2012/162330 | 11/2012 |
| WO | 2012/162334 | 11/2012 |
| WO | 2012/163790 | 12/2012 |
| WO | 2012/168164 | 12/2012 |
| WO | 2012/168175 | 12/2012 |

OTHER PUBLICATIONS

Gavezzotti, "Are Crystal Structures Predictable?" Accounts of Chemical Research, vol. 27, pp. 309-314 (1994).*
Cohen et al. "Synthesis of 2-Amino-5, +-dihydro-4H-1, 3-thiazines and Related Compounds by Acid Catalyzed Cyclization of Allylic Isothiuronium Salts." Journal of Heterocyclic Chemistry 14(5), 1977, p. 717-723.
Kuo et ai. "A Synthesis of Estrone via Novel intermediates. Mechanism of Coupling Reaction of a Vinyl Carbinol with a β Diketone." Journal of Organic Chemistry 33(8), Aug. 1968, p. 3126-3132.
Liebscher et al. "2-Arylimino-3-Thiazolines—Formation of Unusual Tautomers of 2-Arylamino-Thiazolines—A Revision." Tetrahedron Letters, 26(35), 1985, p. 4179-4180.
Fernández et al. "Syntheses and Spectral Properties of β-Iodoureas ans 2-Amino-4, 4-diphenyl-2-oxazolines." Journal of Heterocyclic Chemistry, 28(3), Apr.-May 1991, p. 777-780.
Schaumann et al. "Stickstoffhaltige Fünfring-Heterocyclen aus Carbodiimiden orderKeteniminen mit 3-Dimethylamino-2H-azirinen." Liebigs Annalen der Chemie, 1981, p. 290-305.
Cohen et al. "Synthesis of 2-Amino-5, +-dihydro-4H- 1, 3-thiazines and Related Compounds by Acid Catalyzed Cyclization of Allylic Isothiuronium Salts." Journal of Heterocyclic Chemistry 14(5), 1977, p. 717-723.
Fernández et al. "Syntheses of β-iodourea derivatives of carbohydrates and glycosylamino-ozazolines." Carbohydrate Research, 216, 1991, p. 21-32.
Cambie et al. "vic-Iodothiocyanates and Iodoisothiocyanates. Part 2. New Syntheses of Thiazolidin-2-ones and 2-Amino-thiazolines." Journal of the Chemical Society, Perkin Transactions I, 3, 1979, p. 765-770.
Kondrat'eva et al. "Noncyclic dimer of 4-methyl-2-(dimenthylamino)oxazole." Akademii Nauk SSSR, Seriya Khimicheskaya, 7, 1977, p. 1680-1682.
Hünig et al. "Azo dyes by oxidative coupling, XVIII. Synthesis of 3-substituted 2-thiazolone hydrazones and 2-thiazoione benzenesulfonylhydrazones," Ann. 647, 1961, p. 66-76.
Edwards et al., "Application of fragment-based lead generation to the discovery of novel, cyclic amidine β-secretase inhibitors with nanomolar potency, cellular activity, and high ligand efficiency", Journal of Medicinal Chemistry., vol. 50, No. 24, 2007, pp. 5912-5925.
Koriyama et al., "Reversal of diastereofacial selectivity in the nucleophilic addition reaction to chiral N-sulfinimine and application to the synthesis of indrizidine 223AB," Tetrahedron, vol. 58, 2002, pp. 9621-9628.
Fujisawa et al., "Switchover of diastereofacial selectivity in the condensation reaction of optically active N-sulfinimine with ester enolate," Tetrahedron Letters, vol. 37, No. 22, 1996, pp. 3881-3884.
Vilaivan et al,, "Recent Advances in Catalytic Asymmetric Addition to Imines and Related C=N Systems," Current Organic Chemistry, vol. 9, 2005, pp. 1315-1392.
Hua et al., "N-Alkylidenesulfinamides," Sulfur Reports, vol. 21, 1999, pp. 211-239.
Savoca et al., "1,5-Diazabicyclo[4.3.0]non-5-ene[1]," Encyclopedia of Reagents for Organic Synthesis, 2006, 10 pages total.
Creeke et al., "Synthesis and elaboration of heterocycles via iodocyclisation of unsaturated thioureas," Tetrahedron Letters, 1989, vol. 30, No. 33, pp. 4435-4438.
Mellor et al., A general route to spirocycles by radical additions to exocyclic unsaturated sulphides and related compounds, Tetrahedron Letters, 1991, vol. 32, No. 48, pp. 7111-7114.
Murai et al., "Iodo-cyclization of N-homoallyl thioamides leading to 2,4-diaryl-5,6-dihydro-4H-1,3-thiazines," Chemistry Letters, 2004, vol. 33, No. 5, pp. 508-509.
Singh et al., "Synthesis of heterocyclic compounds via enamines. Part 8.[†] Acid-catalysed transformations in a 4,4,6-trimethyl-1,4-dihydropyrimidine-2(3H)-thione derivatives and related compounds," J. Chem. Soc., Perkin Trans. 1, 1980, pp. 1013-1018.
Vippagunta et al. "Crystalline Solids", Advanced Drug Delivery: Reviews, vol. 48, 2001, pp. 3-26.
Gavezzotti. "Are Crystal Structures Predictable". Accounts of Chemical Research, vol. 27, 1994, pp. 309-314.
Kondrat'eva et al., "Noncyclic dimer of 4-methyl-2-dimethlaminooxazole," Izvestiya Akademii Nauk SSSR, Seriya Khimicheskaya, No. 7, Jul. 1977, pp. 1680-1682 (with English translation).
Database Registry [Online], Chemical Abstracts Service, Columbus, Ohio, US; May 29, 2007, "2H-Indol-2-ome,4-(-2-amino-5,6-dihydro-4-methyl-4H-1,3-thiazin-4-yl)-1,3-dihydro-", XP002646872, Database accession No. 935998-84-8.
Schubert et al., "Neue synthesen von 2-Amino-5,6-dihydro-4H-1,3-thiazinen," Archiv der Pharrnazie, 1968, vol. 301, No. 10, pp. 750-762.
Huang et al., "Pharmacophore model construction of β-secretase inhibitors," 2008, Acta Chimica Sinica, vol. 66, No. 16, pp. 1889-1897 (English language abstract provided).
Co-pending U.S. Appl. No. 13/260,103, entitled Isothiourea Derivatives or Isourea Derivatives Having BACE1 Inhibitory Activity, filed Sep. 23, 2011.
Clark, et al,, "Antitumor Imidazotetrazines, 32.[1] Synthesis of Novel Imidazotetrazinones and Related Bicyclic Heterocycles to Probe the Mode of Action of the Antitumor Drug Temozolomide", J. Med. Chem., vol. 38, 1995, pp. 1493-1504.
Congreve, et al., "Application of Fragment Screening by X-ray Crystallography to the Discovery of Aminopyridines as Inhibitors of β-Secretase[§]", J. Med. Chem., vol. 50, 2007, pp. 1124-1132.
Huang, et al., "Progress in the Development of Nonpeptidomimetic BACE 1 Inhibitors for Alzheimer's Disease", Current Medicinal Chemistry, vol. 16, 2009, pp. 1806-1820.
Goodyer et al., "Synthesis of N-benzyl- and N-phenyl-2-amino-4,5-dihydrothiazoles and thioureas and evaluation as modulators of the isoforms of nitric oxide synthase," Bioorganic & Medicinal Chemistry, 2003, vol. 11, pp. 4189-4206.

Siddiqui et al., "Some extensions of Von Bruan (BrCN) reaction on organic bases," Proc. Pakistan Acad Sci., 1988, vol. 25, No. 3, pp. 231-240.

Ozawa et al., Pharmacological actions of 2-Aminoethylisothiuronium (AET) derivatives. I[1)], Yakugaku Zasshi, 1968, vol. 88, No. 2, pp. 156-162 (with English language abstract).

Curtis et al., The byozynsethis of Phenols, Part VIII. The synthesis of (2-carboxy-3,5-dihydroxyphynyl)propan-2-one (C-acetyl-o-orsellinic acid). Journal of the Chemical Society, 1964, pp. 5382-5385.

Burton et al., "Addition reactions of quinones. Part I. The reaction of cysteine and thiourea and its derivatives with some quinones," Journal of the Chemical Society, 1952, pp, 2193-2196.

Matsui, "Yomo bochuzai no kenkyu (the 6th report) Kagaku kozo to yomo shokugai boshi koka tono kankei (III)," Journal of Synthetic Organic Chemistry, Japan, 1950, vol. 8, No. 10, pp. Ho61-Ho65 (and International Search Report issued in PCT/JP2010/055528, which corresponds to co-pending U.S. Appl. No. 13/260,103).

Desai et al., "The condensation of thiocarbamides with monochloroacetic acide and the conversion of arylformamidinethiolacetic acids into pseudothiohydantoin derivatives," Recuil des Travaux Chimiques des Pays-Bas et de la Belgique, 1935, pp. 118-121.

Cole et al., "Acylguanidines as small-molecule beta-secretase inhibitors," J. Med. Chem., 2006, pp. 6158-6161.

Co-pending U.S. Appl. No. 13/417,786, entitled Aminodihydrothiazine derivatives substituted with a cyclic group, filed Mar. 12, 2012.

Zhu et al., Two novel Diastereoselective Three-Component Reactions of Alkenes or 3,4-Dihydro-(2H)-pyran with Urea/Thiourea-Aldehyde Mixtures: [4+2] Cycloaddition vs Biginelli-Type Reaction, Organic Letters, 2006, vol. 8, No. 12, pp. 2599-2602.

Bol'but et al., Heterocyclizations of Functionalized Heterocumulenes with C,N- and C,O-Dinucleophiles: III. Cyclization of N-(1-Aryl-1-chloro-2,2,2-trifluoroethyl)-N'-arylcarbodiimides with 3-Substituted 1-Phenylpyrazol-5-ones, Russian Journal of Organic Chemistry, 2003, vol. 29, No. 2, pp. 1789-1791.

Trepanier et al., "Synthesis and screening for antidepressant activity of some aminoindanooxazolines, aminoindanooxazines, and aminoacenaphthoxazolines," Journal of Medicinal Chemistry, 1970, vol. 13, No. 4, pp. 729-733.

Sayed et al., "α-Enones in heterocyclic synthesis of indazole, thiazine, chromene and quinolone derivatives with their antimicrobial activities," Journal of Chemical Research, 2009, vol. 12, pp. 726-728.

Database Caplus [Online] Chemical Abstracts Service, Columbus, Ohio, US; Xu, Yungen et al: "Preparation of benzimidazolyl and benzothiazolyl isothiourea derivatives as nitric oxide synthase inhibitors", XP002679913, retrieved from STN Database accession No. 2005:46620 *abstract* Accessed Jul. 13, 2012.

Bol'but et al., "Synthesis of 4-imino-2-trifluoromethyl-3,4-dihydro-2h-Benzo-[1,3]Thiazines," Chemistry of Heterocyclic Compounds, 2001, vol. 37, No. 4, pp. 522-523.

Vovk et al., "Intramolecular thermal cyclization of N-(1-Aryl-1-aryloxy-2,2,2-trifluoroethyl)-N'-arylcarbodiimides," Russian Journal of Organic Chemistiy, 2000, vol. 36, No. 12, pp. 1739-1742.

Vovk et al., "Regioselective cyclization of 1-chloroalkylcarbodiimides with 1,1- and 1,2-bifunctional nucleophilic reagents," Russian Journal of Organic Chemistry, 1997, vol. 22, No. 1, pp. 96-102.

Potts et al., "N-Acyl-β-enamino Ketones: Versatile Heterocyclic Synthons," J. Org. Chem., 1983, 48, pp. 625-626.

Rivkin et al., "Piperazinyl pyrimidine derivatives as potent γ-secretase modulators," Bioorganic & Medicinal Chemistry Letters, 2010, 20, pp. 1269-1271.

Rivkin et al., "Purine derivatives as potent γ-secretase modulators," Bioorganic & Medicinal Chemistry Letters, 2010, 20, pp. 2279-2282. STN a the Web, RN 79005-45-1, 1964.

Calabrese et al. "NO Synthase and NO-Dependent Signal Pathways in Brain Aging and Neurodegenerative Disorders: The Role of Oxidant/Antioxidant Balance". Neurochemical Balance, vol. 25, No. 9/10, pp. 1315-1341 (2000).

Kavya et al. "Nitric oxide synthase regulation and diversity: Implications in Parkinson's Disease". Nitric Oxide: Biology and Chemistry, vol. 15, No. 4, pp. 280-294 (2006).

Chiou et al. "Review: Effects of Nitric Oxide on Eye Diseases and Their Treatment". Journal of Ocular Pharmacology and Therapeutics, vol. 17, No. 2, pp. 189-198 (2001).

Ishii et al. "Subacute NO generation induced by Alzheimer's β-amyloid in the living brain: reversal by inhibition of the inducible NO synthase". The Federation of American Societies for Experimental Biology Journal, vol. 14, pp. 1485-1489 (2000).

Pak et al. "Morphine via nitric oxide modulates β-amyloid metabolism: a novel protective mechanism for Alzheimer's disease". Medical Science Monitor, vol. 11, No. 10, pp. BR357-BR366 (2005).

Tian et al., "Radiosynthesis of 8-Fluoro-3-(4[$^{18}$F]Fluorophenyl)-3,4-Dihydro-l-Isoquinolinamine ([$^{18}$F]FFDI), a potential PET radiotracer for the inducible nitric oxide synthase," 2008, Current Radiopharmaceuticals, vol. 1, pp. 49-53.

Weinhardt et al. " Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No. 6, 1985, pp. 694-698.

Kiselyov et al., "Design and chemical synthesis of [1,2,4]triazol[1,5-c]pyrimidin-5-yl amines, a novel class of VEGFR-2 kinase inhibitors," 2009, Tetrahedron Letters, vol. 50, pp. 3809-3812.

Mulcahy et al., "A stereoselective synthesis of (+)-Gonyautoxin 3," Journal of the American Chemical Society, 2008, vol. 130, pp. 12630-12631.

"Diphenyl Cyanocarbonimidate," e-EROS Encyclopedia of Reagents for Organic Synthesis, 2001, 2 pages total.

Shafik et al., "Synthesis of novel 2-[2-(substituted amino)phenethyl]-1H-benzimidazoles; 3,4-dihydro and 1,2,3,4-tetrahydropyrimido[1,6-a]-benzimidazoles as potential antiulcer agents," 2004, Pharmazie, vol. 59, No. 12, pp. 899-905.

Pohl et al., "Synthesis of partially saturated condensed triazoles by reaction of ω-Aminoalkyl-1,2,4-triazoles with electrophiles," Journal fuer Praktische Chemie Chemiker-Zeitung, 1992, vol. 334, pp. 630-636.

Buschauer et al., "Isohistamine und Homologe als Bausteine von H$_2$-Antagonisten,"Arzneimittel-Forschung, 1985, vol. 35, pp. 1025-1029 (English language abstract provided).

Buschauer et al., "7,8-Dihydroimidazo[1,2-c]pyrimidin-5(6H)-one, -5(6H)-thione and -5(6H)-ylidencyanamide," Chemische Berichte, 1984, vol. 117, pp. 2597-2614.

Borchers et al., "H$_2$-Antihystaminika, 19. Mitt.[1)] Syntheses und H$_2$-antihistaminische Wirkung N$^α$-substituierter Histamine," Archiv der Pharmazie (Weinheim, Germany), 1984, vol. 317, pp. 455-459.

Cheong et al., "Pharmacophore elucidation for a new series of 2-aryl-pyrazolo-triazolo-pyrimidines as potent human A$_3$ adenosine receptor antagonists," Bioorganic & Medicinal Chemistry Letters, 2011, vol. 21, pp. 2898-2905.

Xu et al., "Copper-catalyzed cascade synthesis of benzimidazoquinazoline derivatives under mild condition," Chemical Communications, 2011, vol. 47, pp. 5596-5598.

Kishore et al., "QSAR of adenosine receptor antagonists: exploring physicochemical requirements for binding of pyrazolo[4,3-e]-1,2,4-triazolo[1,5-c]pyrimidine derivatives with human adenosine A$_3$ receptor subtype," Bioorganic & Medicinal Chemistry Letters, 2011, vol. 21, No. 2, pp. 818-823.

Dolzhenko et al., "8-methyl-2-[4-(trifluoromethyl)phenyl]-8H-pyrazolo[4,3-e][1,2,4]triazolo[1,5-c]-pyrimidin-5-amine methanol disolvate," Acta Crystallographica, Section E: Structure Reports Online, 2010, E66(7), 12 pages total.

Beaton et al., "3,4-dihydro-1-isoquinolinamines: a novel class of nitric oxide synthase inhibitors with a range of isoform selectivity and potency," Bioorganic & Medicinal Chemistry Letters, 2001, vol. 11, pp. 1023-1026.

Beaton et al., "The synthesis of 1-aminodihydroisoquinolines by an imine addition cyclisation reaction," 1998, Tetrahedron Letters, vol. 39, pp. 1227-1230.

Tian et al., "Radiosynthesis of 8-Fluoro-3-(4-[$^{18}$F]Fluorophenyl)-3,4-Dihydro-1-Isoquinolinamine ([$^{18}$F]FFDI), a potential PET radiotracer for the inducible nitric oxide synthase," 2008, Current Radiopharmaceuticals, vol. 1, pp. 49-53.

Weinhardt et al. "Synthesis and antidepressant profiles of phenyl-substituted 2-amino- and 2-((alkoxycarbonyl)amino)11,4,5,6-tetrahydropyrimidines," Journal of Medicinal Chemistry, vol. 28, No, 6, 1985, pp. 694-698.

Meschino et al., "2-Amino-5,6-dihydro-1,3-oxazines. The reduction of carboxylic esters with sodium borohydride," J. Org. Chem., vol. 28, 1963, pp. 3129-3134.

Poos et al., "2-amino-5-aryl-2-oxazolines. Potent new anorectic agent," J. Med. Chem., vol. 6, 1963, pp. 266-272.

Sandin et al., "A fast and parallel route to cyclic isothioureas and guanidines with use of microwave-assisted chemistry," J. Org. Chem., vol. 69, 2004, pp. 1571-1580.

Weinhardt et al., "Synthesis and central nervous system propreties of 2-[(Alkoxycarbonyl)amino]-4(5)-phenyl-2-imidazolines," Journal of Medicinal Chemistry, vol. 27, No. 5, 1984, pp. 616-627.

Woodgate et al., "A new synthesis of 2-amino-2-thiazolines," Heterocycles, vol. 7, No. 1, 1977, pp. 109-112.

U.S. Appl. No. 13/881,112, entitled Fused Aminodihydropyrimidine Derivative, filed Apr. 23, 2013.

U.S. Appl. No. 13/881,250, entitled Naphthyridine Derivative, filed Apr. 24, 2013.

* cited by examiner

AMINODIHYDROTHIAZINE DERIVATIVES

CROSS-REFERENCE TO RELATED APPLICATIONS

This application is a Division of application Ser. No. 12/089,409, filed Apr. 7, 2008, which is a U.S. National Stage of PCT/JP2006/321015, filed Oct. 23, 2006, which applications are incorporated herein by reference.

TECHNICAL FIELD

The present invention relates to a compound which has reducing effect to produce amyloid β protein and is useful as an agent for treating disease induced by production, secretion and/or deposition of amyloid β protein.

BACKGROUND ART

In the brain of Alzheimer's patient, the peptide composed of about 40 amino acids residue as is called amyloid β protein, that accumulates to form insoluble specks (senile specks) outside nerve cells is widely observed. It is concerned that this senile specks kill nerve cells to cause Alzheimer's disease. The therapeutic agents for Alzheimer's disease, such as decomposition agents of amyloid β protein and amyloid β vaccine, are under investigation.

Secretase is an enzyme which cleaves amyloid β precursor protein (APP) in cell and produce amyloid β protein. The enzyme which controls the production of N terminus of amyloid β protein is called as BACE 1 (beta-site APP-cleaving enzyme 1, β-secretase). It is thought that inhibition of this enzyme leads to reduction of producing amyloid β protein and that the therapeutic agent for Alzheimer's disease will be created by the inhibition.

Patent Literature 1 describes the compounds which are similar to those of the present invention, and the compounds have NO synthase enzyme inhibitory activity and are useful for dementia.

Patent Literatures 2 to 4 and Non-patent Literatures 1 and 2 describe the compounds which are similar to those of the present invention, and are useful for hypertensive agent, analgesic like morphine, or tranquilizers, intermediate for medicine, analgesic respectively.

Patent Literature 5 to 13 are known as BACE 1 inhibitor, however, all compounds in these literatures have different structures from the present invention.

[Patent Literature 1] International Patent Application Publication WO96/014842
[Patent Literature 2] U.S. Pat. No. 3,235,551
[Patent Literature 3] U.S. Pat. No. 3,227,713
[Patent Literature 4] JP Application Publication H09-067355
[Patent Literature 5] International Patent Application Publication WO01/187293
[Patent Literature 6] International Patent Application Publication WO04/014843
[Patent Literature 7] JP Application Publication 2004-149429
[Patent Literature 8] International Patent Application Publication WO02/96897
[Patent Literature 9] International Patent Application Publication WO04/043916
[Patent Literature 10] International Patent Application Publication WO2005/058311
[Patent Literature 11] International Patent Application Publication WO2005/097767
[Patent Literature 12] International Patent Application Publication WO2006/041404
[Patent Literature 13] International Patent Application Publication WO2006/041405
[Non-Patent Literature 1] Journal of Heterocyclic Chemistry, 14, 717-723 (1977)
[Non-Patent Literature 2] Journal of Organic Chemistry, 33, 8, 3126-3132 (1968)

DISCLOSURE OF INVENTION

Problems to be Solved by the Invention

The present invention provides compounds which have reducing effects to produce amyloid β protein, especially BACE 1 inhibitory activity, and are useful as an agent for treating disease induced by production, secretion and/or deposition of amyloid β protein.

Means to Solve the Problems

The present invention provides:
(a) a composition having BACE 1 inhibitory activity containing a compound represented by the general formula (I):

[Chemical formula 1]

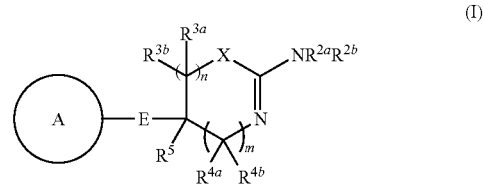

(I)

wherein ring A is an optionally substituted carbocyclic group or an optionally substituted heterocyclic group;

[Chemical formula 2]

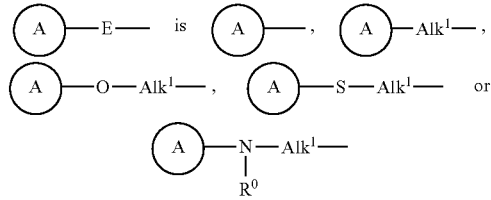

$Alk^1$ is lower alkylene or lower alkenylene;
$R^0$ is a hydrogen atom, lower alkyl or acyl;
X is S, O, or $NR^1$;
$R^1$ is a hydrogen atom or lower alkyl;
$R^{2a}$ and $R^{2b}$ are each independently a hydrogen atom, hydroxy, optionally substituted lower alkyl, optionally substituted lower alkenyl, optionally substituted amino, optionally substituted amidino, optionally substituted acyl, optionally substituted carbamoyl, optionally substituted carbamoylcarbonyl, optionally substituted lower alkylsulfonyl, optionally substituted arylsulfonyl, an optionally substituted carbocyclic group or an optionally substituted heterocyclic group;
$R^{3a}$, $R^{3b}$, $R^{4a}$ and $R^{4b}$ are each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group or an optionally substituted heterocyclic group;
n and m are each independently an integer of 0 to 3;
n+m is an integer of 1 to 3;
each $R^{3a}$, each $R^{3b}$, each $R^{4a}$, and each $R^{4b}$ may be independently different;
$R^5$ is a hydrogen atom, optionally substituted lower alkyl, optionally substituted lower alkenyl, optionally substituted lower alkynyl, an optionally substituted carbocyclic group or an optionally substituted heterocyclic group;

[Chemical formula 3]

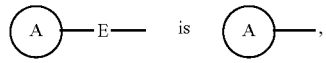

when
$R^5$ and ring A can be taken together to form

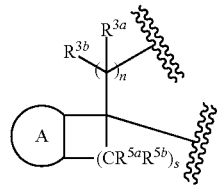

wherein $R^{5a}$ and $R^{5b}$ are each independently a hydrogen atom or lower alkyl;
s is an integer of 1 to 4;
each $R^{5a}$ and each $R^{5b}$ may be different;
with the proviso that the compound wherein n+m is 2; $R^5$ is a hydrogen atom; and ring A is non-substituted phenyl is excluded,
its pharmaceutically acceptable salt, or a solvate thereof,
(a1) a composition having BACE 1 inhibitory activity containing a compound represented by the general formula (I):

[Chemical formula 4]

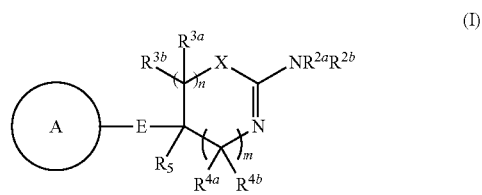

(I)

wherein ring A is an optionally substituted carbocyclic group or an optionally substituted heterocyclic group;

[Chemical formula 5]

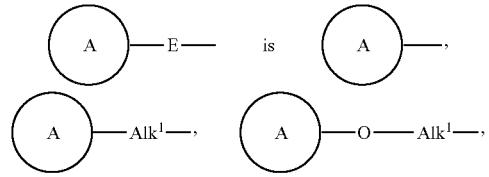

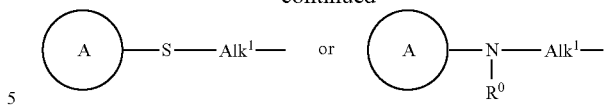

$Alk^1$ is lower alkylene;
$R^0$ is a hydrogen atom, lower alkyl or acyl;
X is S, O, or $NR^1$;
$R^1$ is a hydrogen atom or lower alkyl;
$R^{2a}$ and $R^{2b}$ are each independently a hydrogen atom, hydroxy, optionally substituted lower alkyl, optionally substituted lower alkenyl, optionally substituted amino, optionally substituted amidino, optionally substituted acyl, optionally substituted carbamoyl, optionally substituted lower alkylsulfonyl, optionally substituted arylsulfonyl, an optionally substituted carbocyclic group or an optionally substituted heterocyclic group;
$R^{3a}$, $R^{3b}$, $R^{4a}$, and $R^{4b}$ are each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group or an optionally substituted heterocyclic group;
n and m are each independently an integer of 0 to 3;
n+m is an integer of 1 to 3;
each $R^{3a}$, each $R^{3b}$, each $R^{4a}$, and each $R^{4b}$ may be independently different;
$R^5$ is a hydrogen atom, optionally substituted lower alkyl, optionally substituted lower alkenyl, optionally substituted lower alkynyl, an optionally substituted carbocyclic group or an optionally substituted heterocyclic group;

[Chemical formula 6]

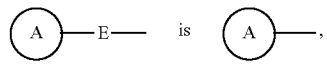

when
$R^5$ and ring A can be taken together to form

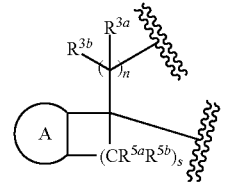

wherein $R^{5a}$ and $R^{5b}$ are each independently a hydrogen atom or lower alkyl;
s is an integer of 1 to 4;
each $R^{5a}$ and each $R^{5b}$ may be different;
with the proviso that the compound wherein n+m is 2; $R^5$ is a hydrogen atom; and
ring A is non-substituted phenyl is excluded, its pharmaceutically acceptable salt, or a solvate thereof,
(b) a composition having BACE 1 inhibitory activity according to (a), wherein X is S,
(c) a composition having BACE 1 inhibitory activity according to (a), wherein n is 2, and m is 0,
(d) a composition having BACE 1 inhibitory activity according to (a), wherein E is a bond, (e) a compound represented by the general formula (I):

[Chemical formula 7]

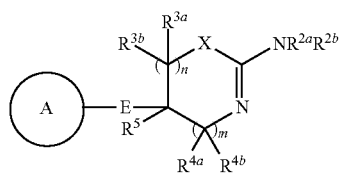

(I)

wherein each symbols are the same as described in (a), with the proviso that the compounds as shown below;
i) wherein n+m is 2, $R^5$ is a hydrogen atom, and ring A is non-substituted phenyl;
ii) wherein n is 2, m is 0, $R^{2a}$ is a hydrogen atom, $R^{2b}$ is a hydrogen atom or acetyl, $R^5$ is methyl, and ring A is phenyl or 4-methoxyphenyl;
iii) wherein n is 2, m is 0, $R^{2a}$ is a hydrogen atom, $R^{2b}$ is a hydrogen atom or acetyl, $R^5$ is ethyl, and ring A is 3,4-dimethoxyphenyl;
iv) wherein n is 2, m is 0, $R^{2a}$ is a hydrogen atom, $R^{2b}$ is a hydrogen atom or acetyl, and $R^5$ and ring A is phenyl;
v) wherein n is 2, m is 0, $R^{2a}$ and $R^{2b}$ is a hydrogen atom, $R^5$ and ring A are taken together to form

[Chemical formula 8]

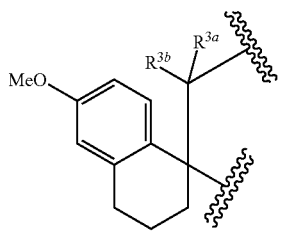

wherein Me is methyl, and each symbols are the same as described above; and
vi) wherein n+m is 2,
$R^5$ is a hydrogen atom,
ring A is phenyl substituted with one or two substituent(s) selected from the group of hydroxy, halogen, lower alkyl, lower alkoxy, nitro, amino, lower alkylcarbonylamino, mercapto, lower alkylthio, and carbamoyl, non-substituted phenyl,
or non-substituted naphthyl; are excluded,
its pharmaceutically acceptable salt, or a solvate thereof,
(f) the compound according to (e), wherein X is S, its pharmaceutically acceptable salt, or a solvate thereof,
(g) the compound according to (e) or (f), wherein n is 2, and m is 0,
its pharmaceutically acceptable salt, or a solvate thereof,
(h) the compound according to any one of (e) to (g), wherein $R^5$ is optionally substituted lower alkyl, optionally substituted lower alkenyl, optionally substituted lower alkynyl, an optionally substituted carbocyclic group or an optionally substituted heterocyclic group,
its pharmaceutically acceptable salt, or a solvate thereof,
(i) the compound according to any one of (e) to (h), wherein
$R^{2a}$ is a hydrogen atom;
$R^{2b}$ is a hydrogen atom, optionally substituted lower alkyl, optionally substituted acyl, optionally substituted lower alkylsulfonyl, or optionally substituted amidino, its pharmaceutically acceptable salt, or a solvate thereof,
(j) the compound according to any one of (e) to (h), wherein $NR^{2a}R^{2b}$ is represented by the formula:

[Chemical formula 9]

 (a)

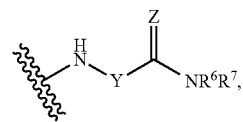 (b)

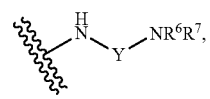 (c)

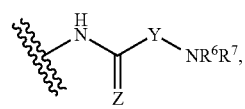 (d)

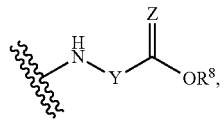 (e)

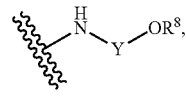 (f)

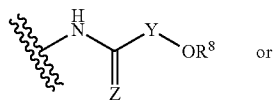 (g)

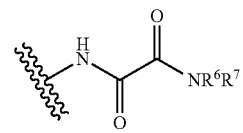 (h)

$R^6$, $R^7$, and $R^8$ are each independently a hydrogen atom, lower alkyl or acyl,
Y is optionally substituted lower alkylene, optionally substituted lower alkenylene or optionally substituted lower alkenylene;
Z is O or S;
its pharmaceutically acceptable salt, or a solvate thereof,
(k) the compound according to any one of (e) to (j), wherein ring A is substituted phenyl,
its pharmaceutically acceptable salt, or a solvate thereof, (l) the compound according to any one of (e) to (j), wherein ring A is represented by the formula:

[Chemical formula 10]

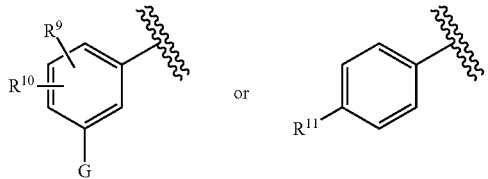

wherein $R^9$, $R^{10}$ and $R^{11}$ are hydrogen atom or G;

G is halogen, hydroxy, cyano, nitro, mercapto, optionally substituted lower alkyl, optionally substituted lower alkoxy, optionally substituted lower alkenyl, optionally substituted lower alkynyl, optionally substituted acyl, optionally substituted acyloxy, carboxy, optionally substituted lower alkoxycarbonyl, optionally substituted lower alkoxycarbonyloxy, optionally substituted aryloxycarbonyloxy, optionally substituted amino, optionally substituted carbamoyl, optionally substituted carbamoyloxy, optionally substituted lower alkylthio, optionally substituted arylthio, optionally substituted lower alkylsulfonyl, optionally substituted arylsulfonyl, optionally substituted lower alkylsulfinyl, optionally substituted arylsulfinyl, optionally substituted lower alkylsulfonyloxy, optionally substituted arylsulfonyloxy, an optionally substituted carbocyclic group, optionally substituted carbocyclicoxy, an optionally substituted heterocyclic group or optionally substituted heterocyclicoxy;

each G may be independently different;

its pharmaceutically acceptable salt, or a solvate thereof, (m) the compound according to (l), wherein G is represented by the formula:

[Chemical formula 11]

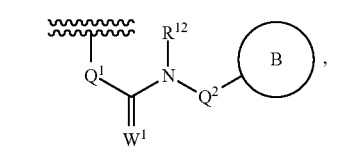 (i)

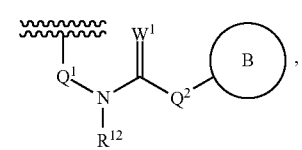 (ii)

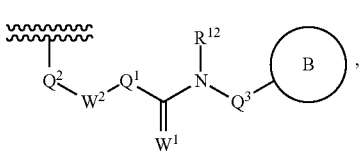 (iii)

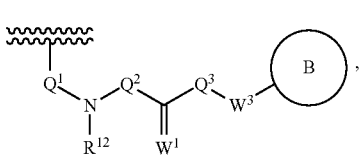 (iv)

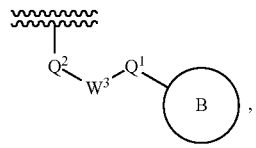 (v)

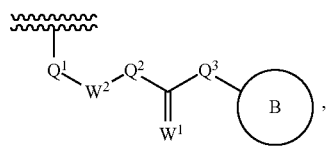 (vi)

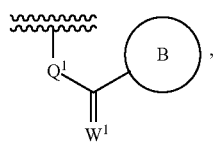 (vii)

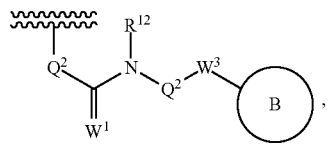 (viii)

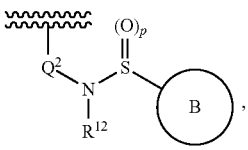 (ix)

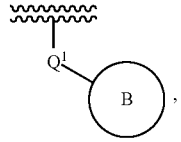 (x)

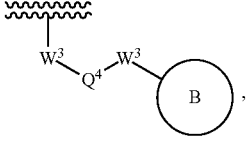 (xi)

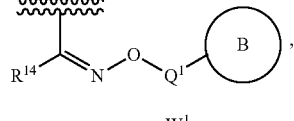 (xii)

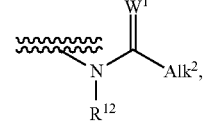 (xiii)

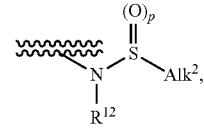 (xiv)

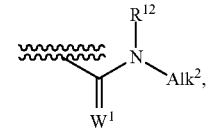 (xv)

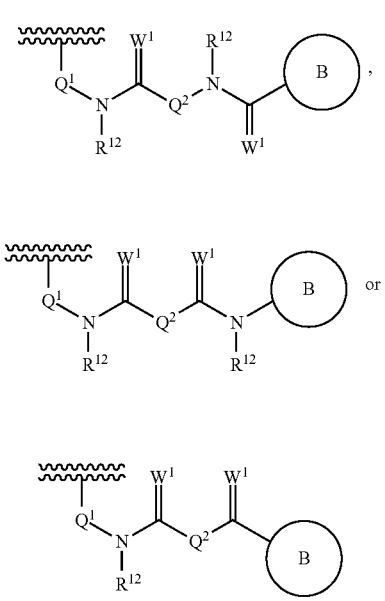

(xvi)

(xvii) or (xviii)

$Q^1$, $Q^2$, and $Q^3$ are each independently a bond, optionally substituted lower alkylene, or optionally substituted lower alkenylene;

$Q^4$ is optionally substituted lower alkylene or optionally substituted lower alkenylene;

$W^1$ and $W^2$ are each independently O or S;

$W^3$ is O, S or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl or acyl;

$R^{14}$ is a hydrogen atom or lower alkyl;

ring B is an optionally substituted carbocyclic group or an optionally substituted heterocyclic group;

$Alk^2$ is optionally substituted lower alkyl;

p is 1 or 2;

if there are multiple $W^1$, multiple $W^3$, and multiple $R^{12}$, each may be independently different;

in (xii), the position of an oxygen atom may be cis or trans to a substituent $R^{14}$, its pharmaceutically acceptable salt, or a solvate thereof, (n) the compound according to (m), wherein ring B is aryl optionally substituted with one or more substituents selected from the group of halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy or an optionally substituted heterocyclic group, or heteroaryl optionally substituted with one or more substituents selected from the group of halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy or an optionally substituted heterocyclic group, its pharmaceutically acceptable salt, or a solvate thereof, (o) the compound according to (m), wherein G is represented by the formula:

[Chemical formula 12]

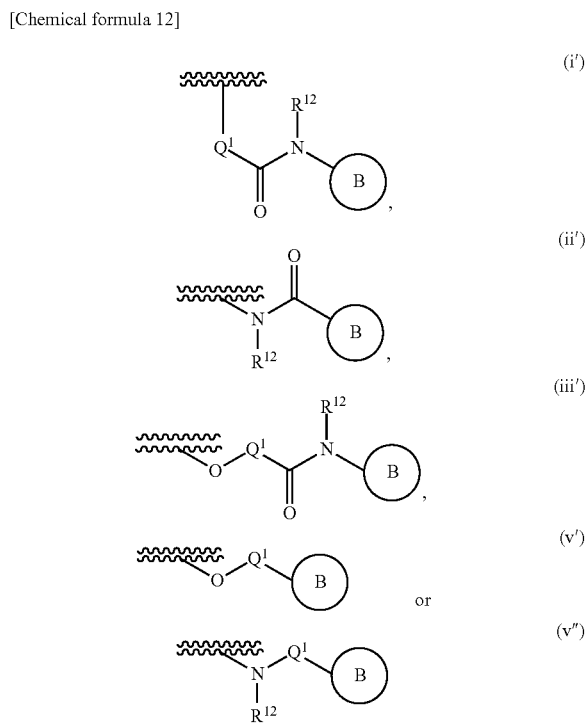

wherein, each symbols are the same as described above, its pharmaceutically acceptable salt, or a solvate thereof, (p) the compound according to any one of (e) to (o), wherein $R^5$ is C1 to C3 alkyl, its pharmaceutically acceptable salt, or a solvate thereof, (q) the compound according to any one of (e) to (o), wherein $R^5$ is methyl, its pharmaceutically acceptable salt, or a solvate thereof, (r) the compound according to any one of (e) to (q), wherein $R^{3a}$ and $R^{3b}$ are each independently a hydrogen atom, halogen, hydroxy, optionally substituted lower alkyl, optionally substituted lower alkoxy or optionally substituted aryl, its pharmaceutically acceptable salt, or a solvate thereof, (s) the compound according to any one of (e) to (q), wherein $R^{3a}$ and $R^{3b}$ are both hydrogen atoms, its pharmaceutically acceptable salt, or a solvate thereof, (t) a pharmaceutical composition containing the compound according to any one of (e) to (s), its pharmaceutically acceptable salt, or a solvate thereof as an active ingredient, (u) a composition having BACE 1 inhibitory activity containing the compound according to any one of (e) to (s), its pharmaceutically acceptable salt, or a solvate thereof, (v) a composition having BACE 1 inhibitory activity containing the compound according to any one of (a) to (d) or (u) as amyloid β reducing agent, (w) a composition having BACE 1 inhibitory activity according to any one of (a) to (d), (u) or (v) as therapeutic agent for disease induced by production, secretion and/or deposition of amyloid β protein, (x) a composition having BACE 1 inhibitory activity according to any one of (a) to (d), (u) or (v) as therapeutic agent for Alzheimer's disease.

in addition, the present invention provides:
(y) a method for treating disease induced by production, secretion and/or deposition of amyloid β protein comprising administering the compound as defined in any one of formula (I) in above (a),
its pharmaceutically acceptable salt, or a solvate thereof,
(z) use of compound as defined in any one of formula (I) in above (a),
its pharmaceutically acceptable salt, or a solvate thereof, in the manufacture of a medicament for the treatment of disease induced by production, secretion and/or deposition of amyloid β protein,
(aa) a method for treating Alzheimer's disease characterizing in administering the compound as defined in any one of formula (I) in above (a),
its pharmaceutically acceptable salt, or a solvate thereof,
(ab) use of compound as defined in any one of formula (I) in above (a),
its pharmaceutically acceptable salt, or a solvate thereof, in the manufacture of a medicament for the treatment of Alzheimer's disease.

Effect of the Invention

The compounds in this invention are useful as an agent for treating disease such as Alzheimer's disease induced by production, secretion and/or deposition of amyloid β protein.

BEST MODE FOR CARRYING OUT THE INVENTION

As used herein, the "halogen" includes fluorine, chlorine, bromine, and iodine. A halogen part of the "halogeno lower alkyl", the "halogen lower alkoxy", the "halogen acyl", the "halogen lower alkylthio" and the "halogeno lower alkoxycarbonyl" is the same.

The "lower alkyl" includes a straight or branched alkyl of a carbon number of 1 to 15, preferably a carbon number of 1 to 10, further preferably a carbon number of 1 to 6, and more further preferably a carbon number of 1 to 3, and examples include methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, isooctyl, n-nonyl, and n-decyl.

A lower alkyl part of the "carbocyclic lower alkyl", the "lower alkoxy", the "halogeno lower alkyl", the "halogeno lower alkoxy", the "halogen lower alkylthio", the "hydroxy lower alkyl", the "lower alkoxycarbonyl", the "halogeno lower alkoxycarbonyl", the "lower alkoxycarbonyl lower alkyl", the "lower alkoxycarbonyloxy", the "lower alkylamino", the "lower alkylcarbonylamino", the "lower alkoxycarbonylamino", the "lower alkoxy lower alkyl", the "lower alkylcarbamoyl", the "hydroxy lower alkylcarbamoyl", the "amino lower alkyl", the "hydroxy imino lower alkyl", the "lower alkoxy imino lower alkyl", the "lower alkylthio", the "lower alkylsulfonyl", the "lower alkyl sulfamoyl", the "lower alkylsulfinyl", the "lower alkylsulfonyloxy", the "lower alkoxycarbonyl lower alkynyl", the "lower alkylthio lower alkyl", the "aryl lower alkyl", the "aryl lower alkylamino", the "aryl lower alkoxycarbonyl", the "aryl lower alkylcarbamoyl", the "heterocyclic group lower alkylamino" and the "heterocyclic group lower alkylcarbamoyl" is the same as that of the aforementioned "lower alkyl".

The example of the "optionally substituted lower alkyl" as a substituent of ring A is lower alkyl optionally substituted with one or more substituents selected from the "substituent group α", "hydroxyimino" and "lower alkoxyimino"; the group defined as above (i), (ii), (iv), (vi), (viii), (x) (wherein each $Q^1$ is optionally substituted lower alkylene); the group defined as (iii), (v), (vii), (ix) (wherein $Q^2$ is optionally substituted lower alkylene); and the group (xii).

In other "optionally substituted lower alkyl" is optionally substituted with one or more substituents selected from the "substituent group α".

The "substituent group α" is selected from the group of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group.

Especially as a substituent of the "optionally substituted lower alkyl" in $Alk^2$, halogen, hydroxy, lower alkoxy, lower alkoxy lower alkoxy, lower alkoxycarbonyl, amino, acylamino, lower alkylamino and/or lower alkylthio are preferable.

The example of the "optionally substituted lower alkoxy" as a substituent of ring A is lower alkoxy optionally substituted with one or more substituents selected from the above "substituent group α"; above (iii) wherein $Q^1$ is optionally substituted lower alkylene, $Q^2$ is a bond, $W^2$ is O; above (v) wherein $Q^1$ is optionally substituted lower alkylene, $Q^2$ is a bond, $W^3$ is O; above (vi) wherein $Q^1$ is a bond, $Q^2$ is optionally substituted lower alkylene, $W^2$ is O; or above (xi) wherein $Q^4$ is optionally substituted lower alkylene, $W^2$ is O.

In other case, the substituents of the "optionally substituted lower alkoxy", the "optionally substituted lower alkoxycarbonyl", the "optionally substituted lower alkoxycarbonyloxy", the "optionally substituted lower alkylsulfonyl", the "optionally substituted lower alkylsulfinyl", the "optionally substituted lower alkylsulfonyloxy" and the "optionally substituted lower alkylthio" are one or more substituents selected from the "substituent group α".

The "lower alkenyl" includes a straight or branched alkenyl of a carbon number of 2 to 15, preferably a carbon number of 2 to 10, further preferably a carbon number of 2 to 6 and more further preferably a carbon number of 2 to 4 having one or more double bonds at an arbitrary position. Specifically examples include vinyl, allyl, propenyl, isopropenyl, butenyl, isobutenyl, prenyl, butadienyl, pentenyl, isopentenyl, hexenyl, isohexenyl, hexadienyl, heptenyl, octenyl, nonenyl, decenyl, undecenyl, dodenyl, tridecenyl, tetradecenyl, and pentadecenyl.

The "lower alkynyl" includes a straight or branched alkynyl of a carbon number of 2 to 10, preferably a carbon number of 2 to 8, further preferably a carbon number of 3 to 6, having one or more triple bonds at an arbitrary position. Specifically, examples include ethynyl, propenyl, butynyl, pentynyl, hexynyl, heptynyl, octynyl, nonynyl, and decynyl. These may further have a double bond at an arbitrary position.

A lower alkynyl part of the "lower alkoxycarbonyl lower alkynyl" is the same as that of above "lower alkynyl".

The example of the "optionally substituted lower alkenyl" as a substituent of ring A is lower alkenyl optionally substituted with one or more substituents selected from the above "substituent group α"; above (i), (ii), (iv), (vi), (viii) or (x), wherein $Q^1$ is optionally substituted lower alkenylene; (v), (vii) or (ix), wherein $Q^2$ is optionally substituted lower alkenylene.

In other case, the substituents of the "optionally substituted lower alkenyl" and the "optionally substituted lower alkynyl" are one or more substituents selected from the "substituent group α".

The example of the "optionally substituted lower amino" as a substituent of ring A is amino optionally substituted with one or more substituents selected from the group of lower alkyl, acyl, hydroxy, lower alkoxy, lower alkoxycarbonyl, a carbocyclic group and a heterocyclic group; (ii), wherein $Q^1$ is a bond; (iv), wherein $Q^1$ is a bond; (v), wherein $Q^2$ is a bond, $W^3$ is $NR^{12}$; (ix), wherein $Q^2$ is a bond; (xiii); or (xiv).

The example of the "optionally substituted carbamoyl" as a substituent of ring A is carbamoyl optionally substituted with one or more substituents selected from the group of lower alkyl, acyl, hydroxy, lower alkoxy, lower alkoxycarbonyl, a carbocyclic group and a heterocyclic group; (i), (viii), wherein each $Q^1$ is bond; or (xv).

In other case, the substituents of the "optionally substituted amino", the "optionally substituted amidino", the "optionally substituted carbamoyl", the "optionally substituted carbamoylcarbonyl", and the "optionally substituted carbamoyloxy" are one or two substituents selected from the group of lower alkyl, acyl, hydroxy, lower alkoxy, lower alkoxycarbonyl, a carbocyclic group and a heterocyclic group, and the like.

The "acyl" includes aliphatic acyl of a carbon number of 1 to 10, carbocyclic carbonyl and heterocyclic carbonyl. Specifically, formyl, acetyl, propyonyl, butylyl, isobutylyl, valeryl, pivaloyl, hexanoyl, acryloyl, propioloyl, methacryloyl, crotonoyl, benzoyl, cyclohexanecarbonyl, pyridinecarbonyl, furancarbonyl, thiophenecarbonyl, benzothiazolcarbonyl, pyradinecarbonyl, piperidinecarbonyl, thiomorpholinocarbonyl, and the like.

The part of the acyl of the "halogenoacyl", the "acylamino" and the "acyloxy" is the same as the aforementioned "acyl".

The substituent of the "optionally substituted acyl" and "optionally substituted acyloxy" is one or more substituents selected from the group of the "substituent group α". The ring part of the "carbocyclic carbonyl" and the "heterocyclic carbonyl" is optionally substituted with one or more substituents selected from the group of "lower alkyl"; the "substituent group α"; and "lower alkyl substituted with one or more substituents selected from the group of the substituent α".

The "carbocyclic group" includes cycloalkyl, cycloalkenyl, aryl and non-aromatic fused carbocyclic group.

The "cycloalkyl" includes a carbocyclic group of a carbon number of 3 to 10, preferably a carbon number of 3 to 8, further preferably a carbon number of 4 to 8, and examples include, cyclopropyl, cyclobutyl, cyclopentyl, cyclohexyl, cycloheptyl, cyclooctyl, cyclononyl, and cyclodecyl, and the like.

The "cycloalkenyl" includes cycloalkenyl having one or more double bonds at an arbitrary position in a ring of the aforementioned cycloalkyl, and examples include cyclopropenyl, cyclobutenyl, cyclopentenyl, cyclohexenyl, cycloheptenyl, cyclooctynyl, and cyclohexadienyl, and the like.

The "aryl" includes phenyl, naphthyl, anthryl, and phenanthryl, and the like, and phenyl is particularly preferable.

The "non-aromatic fused a carbocyclic group" includes group fused with two or more ring groups selected from the group of the above "cycloalkyl", the "cycloalkenyl" and the "aryl". Specifically, examples include indanyl, indenyl, tetrahydronaphthyl, and fluorenyl, and the like.

The carbocyclic part of the "carbocyclicoxy", and the "carbocyclic lower alkyl" is the same as the aforementioned "carbocyclic group".

The aryl part of the "aryl lower alkyl", the "aryloxy", the "aryloxycarbonyl", the "aryloxycarbonyloxy", the "aryl lower alkoxycarbonyl", the "arylthio", the "arylamino", the "aryl lower alkylamino", the "arylsulfonyl", the "arylsulfonyloxy", the "arylsulfinyl", the "arylsulfamoyl", the "arylcarbamoyl" and the "aryl lower alkylcarbamoyl" is the same as the aforementioned "aryl".

The "heterocyclic group" includes a heterocyclic group having one or more heteroatoms arbitrary selected from O, S, and N in a ring, specifically includes a 5- to 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, isothiazolyl, furyl and thienyl; a bicyclic fused heterocyclic group such as indolyl, isoindolyl, indazolyl, indolidinyl, indolinyl, isoindolinyl, quinolyl, isoquinolyl, cinnolinyl, phthalazinyl, quinazolinyl, naphthridinyl, quinoxalinyl, purinyl, pteridinyl, benzopyranyl, benzimidazolyl, benzioxazolyl, benzoxazolyl, benzoxadiazolyl, benzoisothiazolyl, benzothiazolyl, benzothiadiazolyl, benzofuryl, isobenzofuryl, benzothienyl, benzotriazolyl, imidazopyridyl, pyrazolopyridyl, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl; a tricyclic fused heterocyclic group such as carbazolyl, acridinyl, xanthenyl, phenothiazinyl, phenoxathiinyl, phenoxazinyl, dibenzofuryl, and imidazoquinolyl; a non-aromatic heterocyclic group such as dioxanyl, thiiranyl, oxyranyl, oxathioranyl, azethidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, dihydrobenzoimidazolyl, tetrahydropyridyl, tetrahydrofuryl, tetrahydropyranyl, tetrahydrothiazolyl, tetrahydroisothiazolyl, dihydroxadinyl, hexahydroazepinyl, tetrahydroazepyinyl. Preferable is a 5- to 6-membered heteroaryl, or a non-aromatic heterocyclic group.

The heterocyclic part of the "heterocyclicoxy", the "heterocyclic thio", the "heterocyclic carbonyl", the "heterocyclic amino", the "heterocyclic carbonylamino", the "heterocyclic sulfamoyl", the "heterocyclic sulfonyl", the "heterocyclic carbamoyl", the "heterocyclicoxycarbonyl", the "heterocyclic lower alkylamino" and the "heterocyclic lower alkyl carbamoyl" is the same as the aforementioned "heterocyclic group".

The example of the substituent of the "optionally substituted carbocyclic group" and the "optionally substituted heterocyclic group" in ring A is; the substituent α, wherein preferable is for example, halogen, hydroxy, acyl, acyloxy, carboxy, lower alkoxycarbonyl, carbamoyl, amino, lower alkylamino, lower alkylthio;

lower alkyl substituted with one or more substituents selected from the group of substituent α, wherein preferable is halogen, hydroxy, lower alkoxy, lower alkoxycarbonyl, and the like;

amino lower alkyl substituted with one or more substituents selected from the group of substituent α, wherein preferable is acyl, lower alkyl and for lower alkoxy, and the like;

hydroxyimino lower alkyl; lower alkoxyimino lower alkyl; lower alkenyl substituted with one or more substituents selected from the group of substituent α, wherein preferable is lower alkoxycarbonyl, halogen and/or halogeno lower alkoxycarbonyl, and the like;

lower alkynyl substituted with one or more substituents selected from the group of substituent α, wherein preferable is for example, lower alkoxycarbonyl, lower alkoxy substituted with one or more substituents selected from the group of substituent α, wherein preferable is for example, lower alkyl carbamoyl and/or hydroxy lower alkyl carbamoyl, lower alkylthio substituted with one or more substituents selected from the group of substituent α, lower alkylamino substituted with one or more substituents selected from the group of substituent α,
lower alkylsulfonyl substituted with one or more substituents selected from the group of substituent α,
aryl lower alkoxycarbonyl substituted with one or more substituents selected from the group of substituent α, azido, and lower alkyl,
acyl substituted with one or more substituents selected from the group of substituent α,
cycloalkyl substituted with one or more substituents selected from the group of substituent α, azido, and lower alkyl,
lower alkylsulfinyl substituted with one or more substituents selected from the group of substituent α,
sulfamoyl,
aryl substituted with one or more substituents selected from the group of substituent α, azido, and lower alkyl,
heterocyclic group substituted with one or more substituents selected from the group of substituent α, azido, and lower alkyl,
aryloxy substituted with one or more substituents selected from the group of substituent α, azido, and lower alkyl,
heterocyclicoxy substituted with one or more substituents selected from the group of substituent α, azido, and lower alkyl,
arylthio substituted with one or more substituents selected from the group of substituent α, azido, and lower alkyl,
heteroarylthio substituted with one or more substituents selected from the group of substituent α, azido, and lower alkyl,
arylamino substituted with one or more substituents selected from the group of substituent α, azido, and lower alkyl,
heterocyclicamino substituted with one or more substituents selected from the group of substituent α, azido, and lower alkyl,
aryl lower alkylamino substituted with one or more substituents selected from the group of substituent α, azido, and lower alkyl,
heterocyclic lower alkylamino substituted with one or more substituents selected from the group of substituent α, azido, and lower alkyl,
lower alkyl sulfamoyl substituted with one or more substituents selected from the group of substituent α,
aryl sulfamoyl substituted with one or more substituents selected from the group of substituent α, azido, and lower alkyl,
heterocyclic sulfamoyl substituted with one or more substituents selected from the group of substituent α, azido, and lower alkyl,
arylsulfonyl substituted with one or more substituents selected from the group of substituent α, azido, and lower alkyl,
heterocyclic sulfonyl substituted with one or more substituents selected from the group of substituent α, azido, and lower alkyl,
aryl carbamoyl substituted with one or more substituents selected from the group of substituent α, azido, and lower alkyl,
heterocyclic carbamoyl substituted with one or more substituents selected from the group of substituent α, azido, and lower alkyl,
aryl lower alkylcarbamoyl substituted with one or more substituents selected from the group of substituent α, azido, and lower alkyl,
heterocyclic lower alkylcarbamoyl substituted with one or more substituents selected from the group of substituent α, azido, and lower alkyl,
aryloxycarbonyl substituted with one or more substituents selected from the group of substituent α, azido, and lower alkyl,
heterocyclicoxycarbonyl substituted with one or more substituents selected from the group of substituent α, azido, and lower alkyl,
lower alkylenedioxy optionally substituted with halogen; oxo; azido;

[Chemical formula 13]

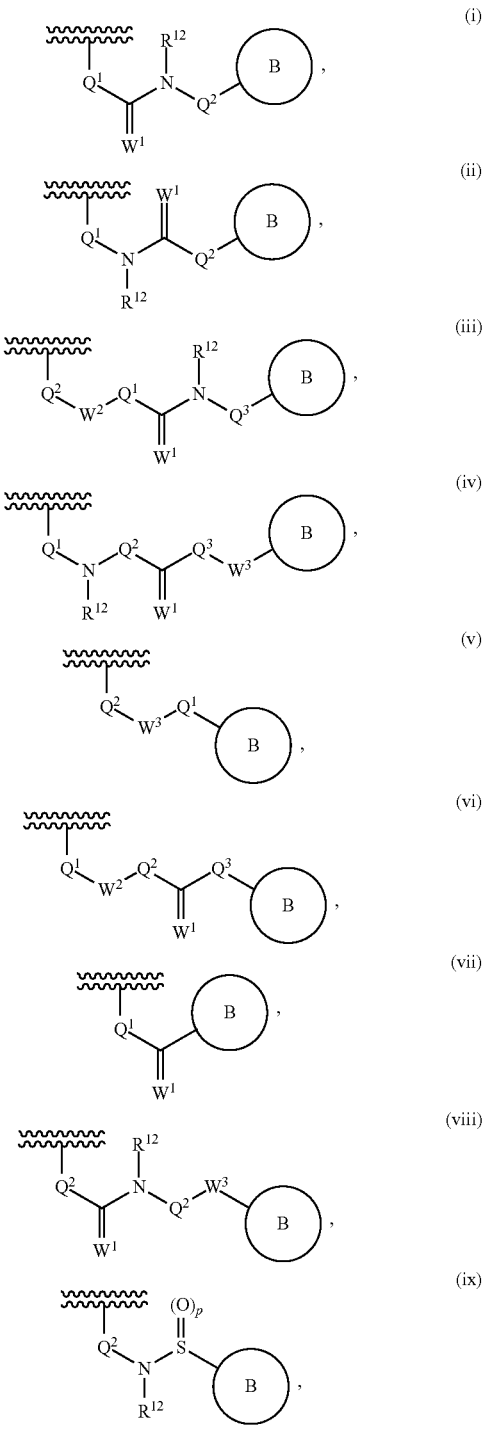

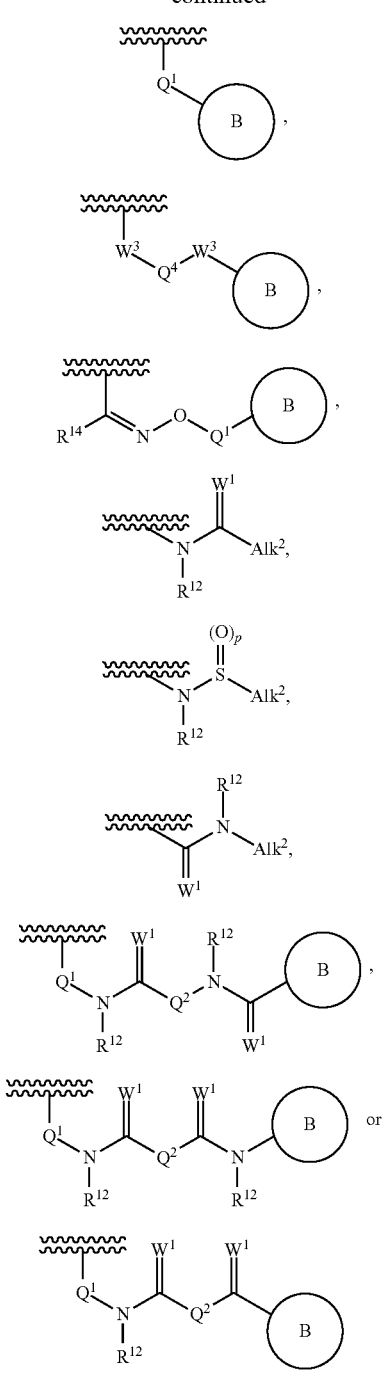

wherein Q$^1$, Q$^2$ and Q$^3$ are each independently a bond, optionally substituted lower alkylene or optionally substituted lower alkenylene;
Q$^4$ is optionally substituted lower alkylene or optionally substituted lower alkenylene;
W$^1$ and W$^2$ are each independently O or S;
W$^3$ is O, S or NR$^{12}$;
R$^{12}$ is a hydrogen atom, lower alkyl, hydroxy lower alkyl, lower alkoxy lower alkyl, lower alkoxycarbonyl lower alkyl, carbocyclic group lower alkyl or acyl;
R$^{14}$ is a hydrogen atom or lower alkyl;
ring B is an optionally substituted carbocyclic group or an optionally substituted heterocyclic group;
Alk$^2$ is optionally substituted lower alkyl;
and the ring A is optionally substituted with one or more substituents selected from these groups.

If there are multiple W$^1$, multiple W$^3$, and multiple R$^{12}$, each may be independently different.

In addition, an oxygen atom in (xii) may be cis or trans position to the substituent R$^{14}$.

The substituent of the "substituted phenyl" is, in the same way, phenyl substituted with one or two substituents selected preferably from the group of the substituent α or (i) to (xv).

The substituent of the "optionally substituted carbocyclic group" or the "optionally substituted heterocyclic group" in ring B is optionally substituted with one or more substituents selected from the following group of, for example; the substituent α, wherein preferable is halogen, hydroxy, lower alkoxy, carboxy, lower alkoxycarbonyl, acyl, amino, lower alkylamino, acylamino, carbamoyl, lower alkylcarbamoyl, cyano, and nitro, and the like;

lower alkyl substituted with one or more substituents selected from the group of the substituent α, wherein preferable is halogen, hydroxy, and lower alkoxy, and the like;

amino lower alkyl, hydroxyimino lower alkyl, or lower alkoxyimino lower alkyl, substituted with one or more substituents selected from the group of substituent α;

lower alkenyl substituted with one or more substituents selected from the group of substituent α;

lower alkynyl substituted with one or more substituents selected from the group of substituent α;

lower alkoxy substituted with one or more substituents selected from the group of substituent α, wherein preferable is halogen, hydroxy, and the like;

lower alkylthio substituted with one or more substituents selected from the group of substituent α, wherein preferable is halogen;

lower alkylamino substituted with one or more substituents selected from the group of substituent α, wherein preferable is amino;

lower alkylsulfonyl substituted with one or more substituents selected from the group of substituent α;

aryl lower alkoxycarbonyl substituted with one or more substituents selected from the group of substituent α and lower alkyl;

acyl substituted with one or more substituents selected from the group of substituent α, wherein preferable is halogen;

lower alkylsulfonyl substituted with one or more substituents selected from the group of substituent α; sulfamoyl;

lower alkyl sulfamoyl substituted with one or more substituents selected from the group of substituent α;

cycloalkyl substituted with one or more substituents selected from the group of substituent α, azido and lower alkyl;

aryl substituted with one or more substituents selected from the group of substituent α, azido and lower alkyl;

heterocyclic group substituted with one or more substituents selected from the group of substituent α, azido and lower alkyl, wherein preferable is halogen, lower alkyl, and the like;

aryloxy substituted with one or more substituents selected from the group of substituent α, azido and lower alkyl;

heterocyclicoxy substituted with one or more substituents selected from the group of substituent α, azido and lower alkyl;

arylthio substituted with one pr more substituents selected from the group of substituent α, azido and lower alkyl, wherein preferable is halogen, hydroxy, lower alkoxy, acyl, and the like;

heterocyclic thio substituted with one or more substituents selected from the group of substituent α, azido and lower alkyl;

arylamino substituted with one or more substituents selected from the group of substituent α, azido and lower alkyl, wherein preferable is halogen, hydroxy, lower alkoxy, acyl;
heterocyclic amino substituted with one or more substituents selected from the group of substituent α, azido and lower alkyl;
aryl lower alkylamino substituted with one or more substituents selected from the group of substituent α, azido and lower alkyl, wherein preferable is halogen, hydroxy, lower alkoxy, acyl;
heterocyclic lower alkylamino substituted with one or more substituents selected from the group of substituent α, azido and lower alkyl;
arylsulfamoyl substituted with one or more substituents selected from the group of substituent αazido and lower alkyl;
heterocyclic sulfamoyl substituted with one or more substituents selected from the group of substituent α, azido and lower alkyl;
arylsulfonyl substituted with one or more substituents selected from the group of substituent α, azido and lower alkyl;
heterocyclic sulfonyl substituted with one or more substituents selected from the group of substituent α, azido and lower alkyl;
arylcarbamoyl substituted with one or more substituents selected from the group of substituent α, azido and lower alkyl;
heterocyclic carbamoyl substituted with one or more substituents selected from the group of substituent α, azido and lower alkyl;
aryl lower alkylcarbamoyl substituted with one or more substituents selected from the group of substituent α, azido and lower alkyl;
heterocyclic lower alkylcarbamoyl substituted with one or more substituents selected from the group of substituent α, azido and lower alkyl;
aryloxy carbonyl substituted with one or more substituents selected from the group of substituent α, azido and lower alkyl;
heterocyclicoxycarbonyl substituted with one or more substituents selected from the group of substituent α, azido and lower alkyl;
lower alkylenedioxy optionally substituted with halogen; oxo; and the like.

In other case, the substituent of the "optionally substituted carbocyclic group", the "optionally substituted heterocyclic group", the "optionally substituted carbocyclicoxy", the "optionally substituted arylsulfonyl", the "optionally substituted aryloxycarbonyloxy", the "optionally substituted heterocyclicoxy", the "optionally substituted arylsulfinyl", the "optionally substituted arylsulfonyloxy", the "optionally substituted arylthio" is one or more substituents selected from the group of "lower alkyl" and the "substituent α".

"heteroaryl" include aromatic ring group in the aforementioned "heterocyclic group".

The substituent of the "optionally substituted 5- to 6-membered heteroaryl" is the same as the substituent of the "optionally substituted heterocyclic group" in the aforementioned "ring B". Preferable is one or more substituent selected from lower alkyl and a substituent α.

The "lower alkylene" includes a straight or branched bivalent carbon chain of a carbon number of 1 to 10, preferably a carbon number of 1 to 6, further preferably a carbon number of 1 to 3. Specifically, examples include methylene, dimethylene, trimethylene, teteramethylene, and methyltrimethylene, and the like.

The part of lower alkylene of the "lower alkylenedioxy" is the same as the aforementioned "lower alkylene".

The "lower alkenylene" includes a straight or branched bivalent carbon chain of a carbon number of 2 to 10, preferably a carbon number of 2 to 6, further preferably a carbon number of 2 to 4 having double bond at an arbitrary position. Specifically, examples include vinylene, propenylene, butenylene, butadienylene, methylpropenylene, pentenylene, and hexenylene, and the like.

The "lower alkynylene" includes a straight or branched bivalent carbon chain of a carbon number of 2 to 10, preferably a carbon number of 2 to 6, further preferably a carbon number of 2 to 4 having triple bond at an arbitrary position. Specifically, examples include ethynylene, propynylene, butynylene, pentynylene, and hexynylene, and the like.

The substituent of the "optionally substituted lower alkylene", the "optionally substituted lower alkenylene", the "optionally substituted lower alkynylene" is the substituent α, preferable is halogen, hydroxy and the like.

The "each $R^{3a}$, each $R^{3b}$, each $R^{4a}$, and each $R^{4b}$ may be independently different" means when n is 2 or 3, two or three $R^{3a}$ may be independently different, and two or three $R^{3b}$ may be independently different. In the same way, when m is 2 or 3, two or three $R^{4a}$ may be independently different, and two or three $R^{4b}$ may be independently different.

[Chemical formula 14]

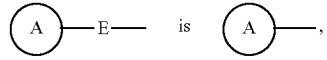

The case that
$R^5$ and ring A can be taken together to form

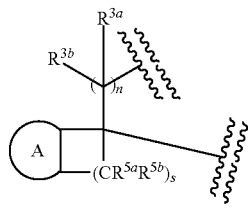

means for example, include the following structures.

[Chemical formula 15]

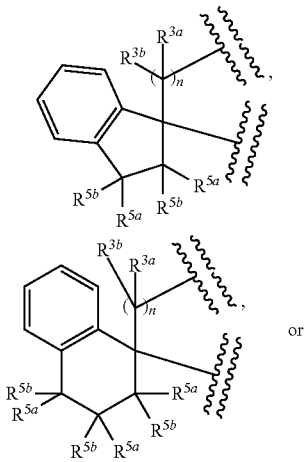

or

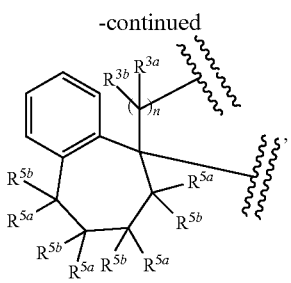

wherein each symbols are the same as described above;
preferably, $R^{5a}$ and $R^{5b}$ are all hydrogen atoms.

In this description, "solvate" includes, for example, a solvate with an organic solvent and a hydrate, and the like. When hydrate is formed, arbitrary number of water molecules may be coordinated.

The compound (I) includes a pharmaceutically acceptable salt. Examples include salts with alkali metals (lithium, sodium or potassium; and the like), alkaline earth metals (magnesium or calcium, and the like), ammonium, organic bases or amino acids, and salts with inorganic acids (hydrochloric acid, sulfuric acid, nitric acid, hydrobromic acid, phosphoric acid or hydroiodic acid, and the like), and organic acid (acetic acid, trifluoroacetic acid, citric acid, lactic acid, tartaric acid, oxalic acid, maleic acid, fumaric acid, manderic acid, glutaric acid, malic acid, benzoic acid, phthalic acid, benzenesulfonic acid, p-toluenesulfonic acid, methanesulfonic acid, or ethanesulfonic acid, and the like). Particularly, hydrochloric acid, phosphoric acid, tartaric acid, or methanesulfonic acid is preferable. These salts can be formed by a conventional method.

In addition, the compound (I) is not limited to a specific isomer, but includes all possible isomers (keto-enol isomer, imine-enamine isomer, diastereo isomer, optical isomer, and rotational isomer, and the like) and racemates. For example, the compound (I), wherein $R^{2a}$ is a hydrogen atom, includes following tautomer.

[Chemical formula 16]

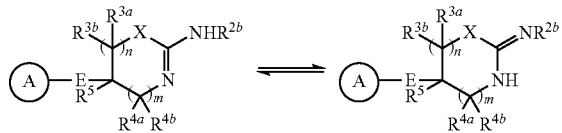

The compound (I) in this invention can be prepared by the process described in, for example Non-patent Document 1 or following process.

The synthesis of aminodihydrothiazine ring; Method A

[Chemical formula 17]

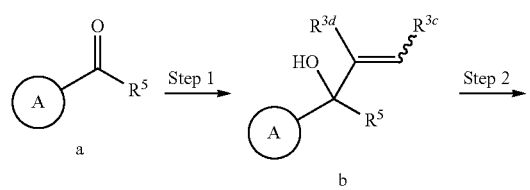

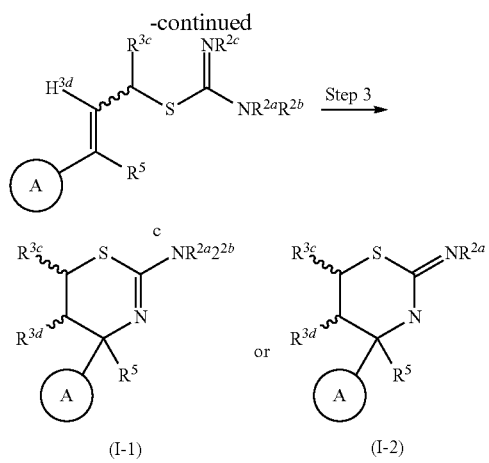

In formula, at least either $R^{2b}$ or $R^{2c}$ is a hydrogen atom, either $R^{3c}$ or $R^{3d}$ is each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group or an optionally substituted heterocyclic group. Other symbols are the same as described above.

(Step 1)

To a solution of compound (a), which is commercially available or prepared by known method, in appropriate solvent or mixture of solvents, such as ether, tetrahydrofuran, and the like is added the Grignard reagent having substituent corresponds to the target compound; for example vinylmagnesium chloride, vinylmagnesium bromide, or propenylmagnesium bromide, and the like; at −100° C. to 50° C., preferably −80° C. to 0° C. The mixture is reacted for 0.2 to 24 hours, preferably 0.5 to 5 hours, to obtain compound (b).

(Step 2)

The compound (b) in solvent, such as toluene or absence of solvent is treated with thiourea derivatives having substituent corresponds to the target compound, such as thiourea, N-methylthiourea, N,N'-dimethylthiourea, and the like in the presence of an acid or mixture of acids, such as acetic acid, trifluoroacetic acid, hydrochloric acid, or sulfuric acid, and the like. The mixture is reacted at −20° C. to 100° C., preferably 0° C. to 50° C. for 0.5 to 120 hours, preferably 1 to 72 hours, to obtain the compound (c).

(Step 3)

The compound (c) in solvent, such as toluene or absence of solvent is treated with an acid or mixture of acids, such as trifluoroacetic acid, methanesulfonic acid, trifluoromethanesulfonic acid, and the like. The mixture is reacted at −20° C. to 100° C., preferably 0° C. to 50° C. for 0.5 to 120 hours, preferably 1 to 72 hours, to obtain the compound (I-2), wherein $R^{2b}$ is a hydrogen atom, or the compound (I-1), wherein $R^{2c}$ is a hydrogen atom.

The synthesis of aminodihydrothiazine ring; Method B

[Chemical formula 18]

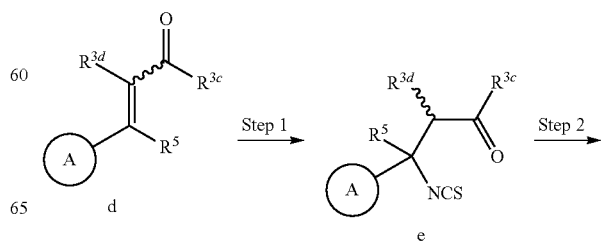

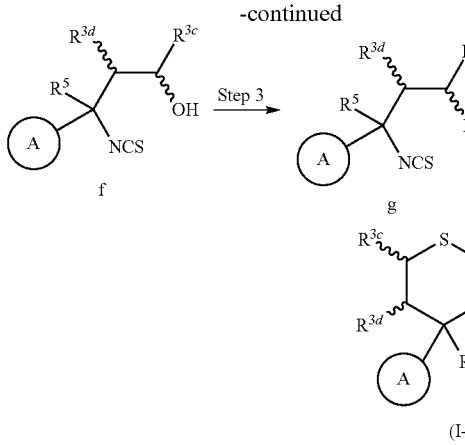

f g (I-3)

In formula, L is leaving group such as halogen or sulfonyloxy, and the like. Other symbols are the same as described above.

(Step 1)

The compound (d) which is commercially available or prepared by known method is reacted with thiocyanic acid; for example, sodium thiocyanic acid, ammonium thiocyanic acid, and the like; in solvent; for example, toluene, chloroform, tetrahydrofuran, and the like; in the presence of acid; for example, water, hydrochloric acid, sulfuric acid, and the like; at 0° C. to 150° C., preferably 20° C. to 100° C. for 0.5 to 24 hours, preferably 1 to 12 hours, to obtain the compound (e).

(Step 2)

To the compound (e) in solvent or mixture of solvents; for example, tetrahydrofuran, methanol, ethanol, water, and the like; in the presence or the absence of buffer like sodium dihydrorgen phosphate, and the like; reducing agent; for example sodium borohydride, and the like; is added and the mixture is reacted at −80° C. to 50° C., preferably −20° C. to 20° C. for 0.1 to 24 hours, preferably 0.5 to 12 hours, to obtain the compound (f).

(Step 3)

The compound (f) in the presence or the absence of solvent; for example, toluene, dichloromethane, and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hours, preferably 0.5 to 12 hours, to obtain the compound (g). Alternatively, the compound (f) in the presence or the absence of solvent; for example, toluene, dichloromethane, and the like; under base; for example triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours, to obtain the compound (g).

(Step 4)

To the compound (g) in solvent or mixture of solvents, for example methanol, ethanol, water, and the like; is reacted with primary amine; for example, ammonia or methylamine, and the like; at −20° C. to 80° C., preferably 0° C. to 40° C. for 0.5 to 48 hours, preferably 1 to 24 hours, to obtain the compound (I-3).

The synthesis of aminodihydrothiazine ring; Method C

[Chemical formula 19]

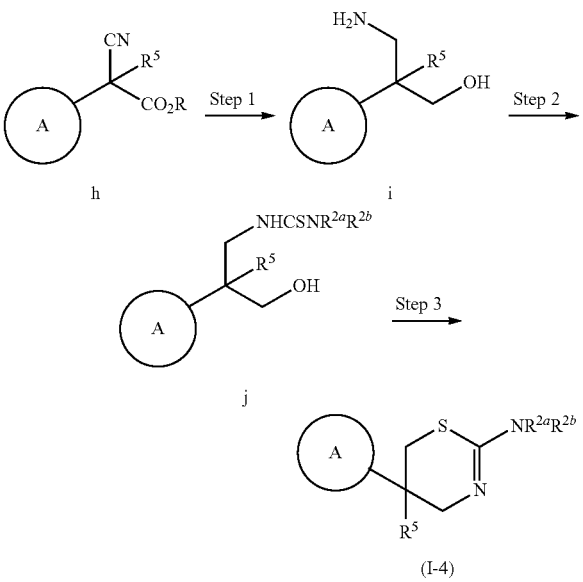

(I-4)

In formula, R is a hydrogen atom or protective groups of carboxyl group. Other symbols are the same as described above.

(Step 1)

The compound (h) which is commercially available or prepared by known method is reacted with reducing agent; for example, lithium aluminium hydride, diisobutyl aluminium hydride, and the like; in solvent; for example tetrahydrofuran, ether, and the like; at −80° C. to 150° C., preferably 25° C. to 100° C. for 0.1 to 24 hours, preferably 0.5 to 12 hours, to obtain the compound (i).

(Step 2)

The compound (i) in solvent; for example, toluene, chloroform, tetrahydrofuran, and the like; in the presence or the absence of base; for example, diisopropylethylamine, triethylamine, pyridine, sodium hydroxide, and the like; is reacted with corresponding isothiocyanate; for example, 4-methoxybenzylisothiocyanate, t-butylisothiocyanate, and the like; or corresponding thiocarbamoylhalide; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (j).

(Step 3)

The compound (j) in solvent; for example, acetonitrile, toluene, dichloromethane, and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hours, preferably 0.5 to 12 hours, or alternatively, the compound (j) in solvent; for example, toluene, dichloromethane, and the like; in the presence of base; for example triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-4).

The synthesis of aminodihydrothiazine ring; Method D
The synthesis of aminothiazoline ring; Method A
The synthesis of tetrahydrothiazepine ring; Method A

[Chemical formula 20]

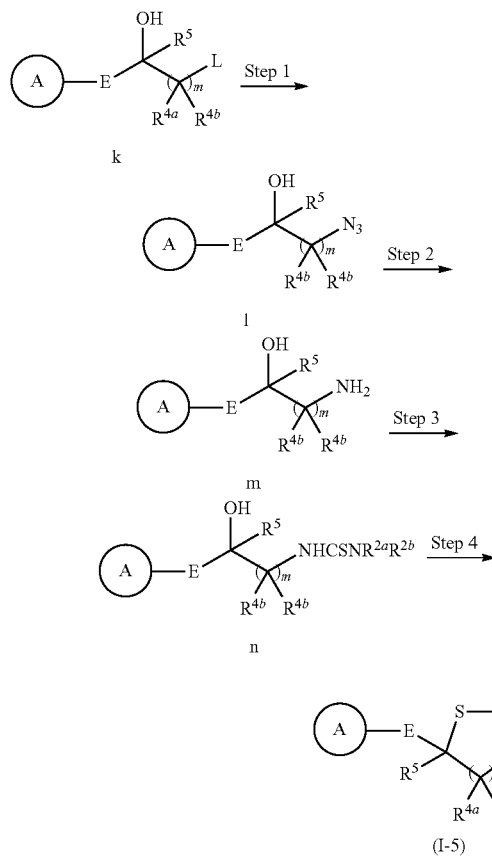

In formula, L is leaving group such as halogen or sulfonyloxy, and the like; m is an integer of 1 to 3; and the other symbols are the same as described above.

(Step 1)

The compound (k) which is commercially available or prepared by known method is reacted with azide reagent; for example, sodium azide, and the like; in solvent; for example N,N-dimethylformamide, tetrahydrofuran, and the like; at 0° C. to 200° C., preferably 40° C. to 150° C. for 0.5 to 24 hours, preferably 1 to 12 hours, to obtain the compound (l).

(Step 2)

The compound (l) is reacted with reducing agent; for example, lithium aluminium hydride, diisobutyl aluminium hydride, and the like; in solvent; for example tetrahydrofuran, ether, and the like; at −80° C. to 150° C., preferably 25° C. to 100° C. for 0.1 to 24 hours, preferably 0.5 to 12 hours, to obtain the compound (m).

(Step 3)

The compound (m) in solvent; for example, toluene, chloroform, tetrahydrofuran, and the like; is reacted with corresponding isothiocyanate; for example, methylisothiocyanate, ethylisothiocyanate, and the like; or corresponding thiocarbamoylhalide; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (n).

(Step 4)

The compound (n) in solvent; for example, acetonitrile, toluene, dichloromethane and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hours, preferably 0.5 to 12 hours, or alternatively, the compound (n) in solvent; for example, toluene, dichloromethane, and the like; in the presence of base; for example diisopropylethylamine, triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-5).

The synthesis of aminodihydrothiazine ring; Method E
The synthesis of aminothiazoline ring; Method B
The synthesis of tetrahydrothiazepine ring; Method B

[Chemical formula 21]

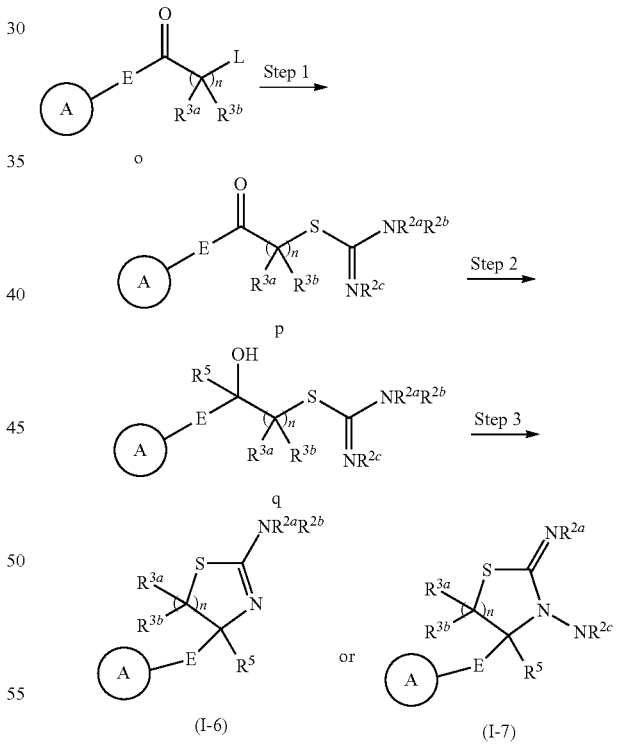

In formula, at lease one of $R^{2b}$ and $R^{2c}$ is a hydrogen atom, n is an integer of 1 to 3, and the other symbols are the same as described above.

(Step 1)

The compound (o) which is commercially available or prepared by known method is reacted with substituted thiourea; for example, thiourea, N-methylthiourea, N,N,-dimethylthiourea, N,N'-dimethylthiourea, and the like; in solvent; for example, ethanol, methanol, tetrahydrofuran, toluene, and the like; at −20° C. to 200° C., preferably 0° C. to 150° C. for 0.5 to 200 hours, preferably 1 to 120 hours, to obtain the compound (p).
(Step 2)
To the compound (p) in solvent or mixture of solvents; for example, ether, tetrahydrofuran, and the like; the Grignard reagent having substituent corresponding to target compound; for example methylmagnesium chloride, ethylmagnesium bromide, or benzylmagnesium bromide, and the like; is added at −100° C. to 50° C., preferably −80° C. to 30° C., and the mixture is reacted for 0.2 to 24 hours, preferably 0.5 to 5 hours, to obtain the compound (q).
(Step 3)
To the compound (q) in the presence or the absence of solvent; for example, toluene, and the like; acid or mixture of acids, such as trifluoroacetic acid, methanesulfonic acid, trifluoromethanesulfonic acid, and the like; is added and the mixture is reacted at −20° C. to 100° C., preferably 0° C. to 50° C. for 0.5 to 200 hours, preferably 1 to 150 hours, to obtain the compound (I-6)(wherein $R^{2c}$ is H), or the compound (I-7)(wherein $R^{2b}$ is H).

The synthesis of aminodihydrothiazine ring; Method F

[Chemical formula 22]

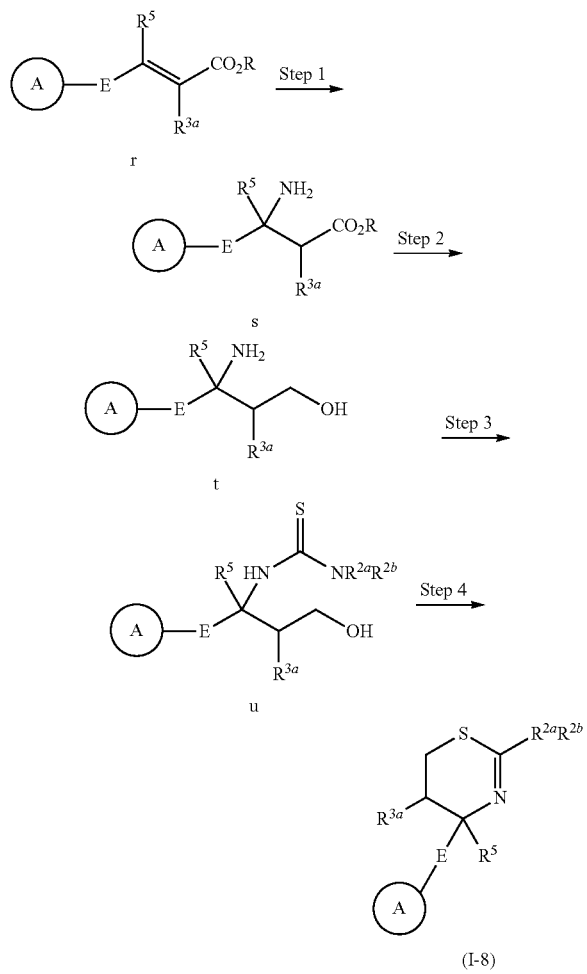

In formula, each symbols are the same as described above.
(Step 1)
The compound (r) which is commercially available or prepared by known method is reacted with ammonium chloride in solvent; for example, acetic acid, and the like; at 0° C. to 200° C., preferably 10° C. to 100° C. for 0.1 to 100 hours, preferably 0.5 to 24 hours, to obtain the compound (s).
(Step 2)
The compound (s) is reacted with reducing agent; for example, lithium aluminium hydride, diisobutyl aluminium hydride, and the like; in solvent; for example tetrahydrofuran, ether, and the like; at −80° C. to 150° C., preferably 0° C. to 100° C. for 0.1 to 24 hours, preferably 0.5 to 12 hours, to obtain the compound (t).
(Step 3)
The compound (t) in solvent; for example, toluene, chloroform, tetrahydrofuran, and the like; in the presence or the absence of base; for example, diisopropylethylamine, triethylamine, pyridine, sodium hydroxide, and the like; is reacted with corresponding isothiocyanate; for example, 4-methoxybenzylisothiocyanate, t-butylisothiocyanate, and the like; or corresponding carbamoylhalide; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (u).
(Step 4)
The compound (u) in solvent; for example, acetonitrile, toluene, dichloromethane, and the like; is reacted with halogenating agent; for example thionyl chloride, phosphorus oxychloride, carbon tetrabromide-triphenylphosphine, and the like; at −80° C. to 50° C., preferably −20° C. to 20° C. for 0.1 to 24 hours, preferably 0.5 to 12 hours, or alternatively, the compound (u) in solvent; for example, toluene, dichloromethane, and the like; in the presence of base; for example triethylamine, and the like; is reacted with sulfonating agent; for example, methanesulfonyl chloride, p-toluenesulfonylchloride, and the like; at −80° C. to 50° C., preferably −20° C. to 20° C. for 0.1 to 24 hours, preferably 0.5 to 12 hours. The obtained halogenated compound or sulfonylated compound is reacted with base; for example, diisopropylamine, potassium carbonate, sodium hydrogencarbonate, sodium hydride, sodium hydroxide, and the like; at 0° C. to 150° C., preferably 20° C. to 100° C. for 0.5 to 120 hours, preferably 1 to 72 hours, to obtain the compound (I-8).

The synthesis of aminodihydrooxazine ring; Method A
The synthesis of aminotetrahydrooxazepine ring; Method A

[Chemical formula 23]

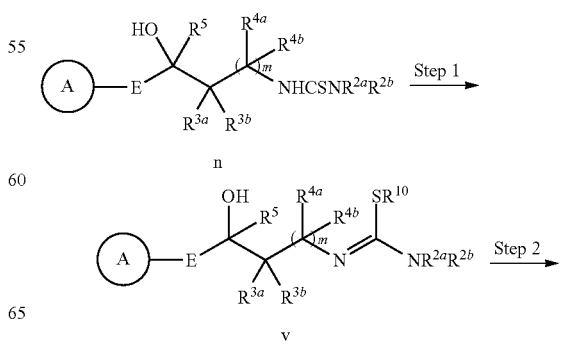

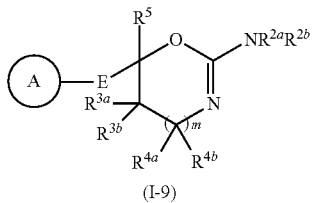

(I-9)

In formula, each symbols are the same as described above.

(Step 1)

The compound (n) which is obtained by Step 3(the compound (m) to the compound (n)) of "The synthesis of aminodihydrothiazine ring; Method D", in solvent; for example, methanol, ethanol, N,N-dimethylformamide, tetrahydrofuran, and the like; in the presence or the absence of base; for example, diisopropylethylamine, triethylamine, pyridine, sodium hydroxide, and the like; is reacted with alkylating agent; for example, methyl iodide, dimethyl sulfate, benzyl bromide, and the like; at 0° C. to 200° C., preferably 40° C. to 150° C. for 0.1 to 48 hours, preferably 0.5 to 24 hours, to obtain the compound (v).

(Step 2)

The compound (v) in solvent; for example, N,N-dimethylformamide, tetrahydrofuran, dichloromethane, and the like; in the presence or the absence of base; for example, diisopropylethylamine, triethylamine, pyridine, sodium hydroxide, and the like; is reacted with metallic oxide; for example, silver oxide, mercury oxide, manganese dioxide, and the like; at 0° C. to 200° C., preferably 10° C. to 150° C. for 1 to 120 hours, preferably 0.5 to 100 hours, to obtain the compound (I-9).

The Synthesis of aminodihydrooxazine Ring; Method B

The Synthesis of aminoxazoline Ring

The Synthesis of aminotetrahydrooxazepine Ring; Method B

[Chemical formula 24]

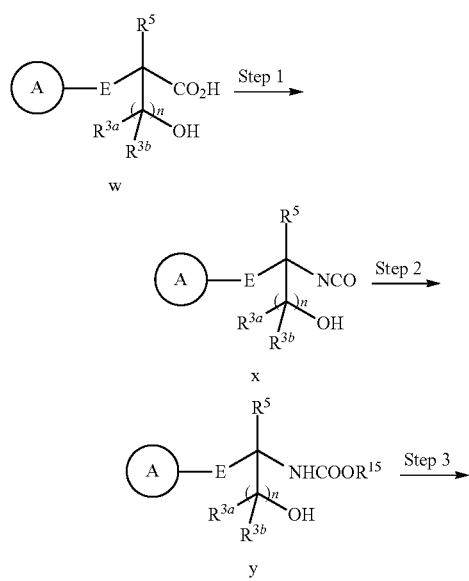

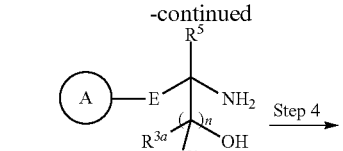

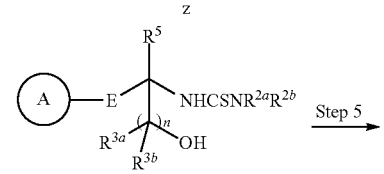

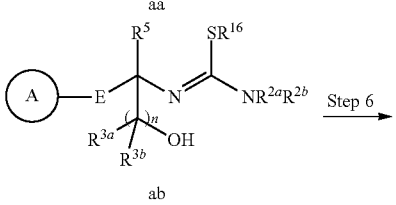

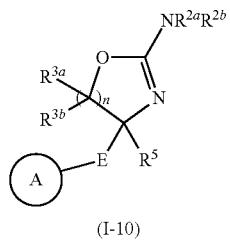

(I-10)

In formula, $R^{15}$ is optionally substituted lower alkyl; for example, t-butyl, benzyl, and the like; $R^{16}$ is hydrogen atom or lower alkyl; n is an integer of 1 to 3, and the other symbols are the same as described above.

(Step 1)

The compound (w) which is commercially available or prepared by known method in solvent; for example, toluene, t-butylalcohol, tetrahydrofuran, and the like; in the presence of base; for example, diisopropylethylamine, triethylamine, pyridine, and the like; is reacted with azide reagent; for example, diphenyl phosphoryl azide, and the like; at 0° C. to 200° C., preferably 40° C. to 150° C. for 1 to 48 hours, preferably 0.5 to 24 hours, to obtain the compound (x).

(Step 2)

The compound (x) in solvent; for example, toluene, xylene, N,N-dimethylformamide, tetrahydrofuran, and the like; is reacted with alcohol; for example, t-butylalcohol, 3,4-dimethoxybenzylalcohol, 4-methoxybenzylalcohol, and the like; at 0° C. to 300° C., preferably 50° C. to 200° C. for 1 to 800 hours, preferably 5 to 500 hours, to obtain the compound (y).

(Step 3)

The compound (y) in the presence or the absence of solvent; for example, water, toluene, dichloromethane, methanol, 1,4-dioxane, acetic acid, ethyl acetate, and the like; in the presence of acid; for example, hydrochloric acid, sulfuric acid, hydrobromic acid, trifluoroacetic acid, and the like; at 0° C. to 200° C., preferably 25° C. to 150° C. for 0.1 to 48 hours, preferably 0.5 to 24 hours, to obtain the compound (z).

(Step 4)

The compound (z) in solvent; for example, toluene, chloroform, tetrahydrofuran, and the like; in the presence of base; for example, diisopropylethylamine, triethylamine, pyridine, and the like; is reacted with corresponding isothiocyanate, or thiocarbamoylhalide corresponding to target compound; for example, N,N-dimethylthiocarbamoylchloride, N,N-diethylthiocarbamoylchloride, and the like; at 0° C. to 150° C., preferably 20° C. to 100° C. for 0.5 to 120 hours, preferably 1 to 72 hours, to obtain the compound (aa).

(Step 5)

The compound (aa) in solvent; for example, methanol, ethanol, N,N-dimethylformamide, tetrahydrofuran, and the like; in the presence or the absence of base; for example, diisopropylethylamine, triethylamine, pyridine, sodium hydroxide, and the like; is reacted with alkylating agent; for example, methyl iodide, dimethyl sulfate, benzyl bromide, and the like; at 0° C. to 200° C., preferably 40° C. to 150° C. for 1 to 48 hours, preferably 0.5 to 24 hours, to obtain the compound (ab).

(Step 6)

The compound (ab) in solvent; for example, N,N-dimethylformamide, tetrahydrofuran, dichloromethane, and the like; in the presence of base; for example, diisopropylethylamine, triethylamine, pyridine, sodium hydroxide, and the like; is reacted with metallic oxide; for example, silver oxide, mercury oxide, manganese dioxide, and the like; at 0° C. to 200° C., preferably 10° C. to 150° C. for 1 to 120 hours, preferably 0.5 to 100 hours, to obtain the compound (I-10).

The synthesis of aminotetrahydropyrimidine ring

[Chemical formula 25]

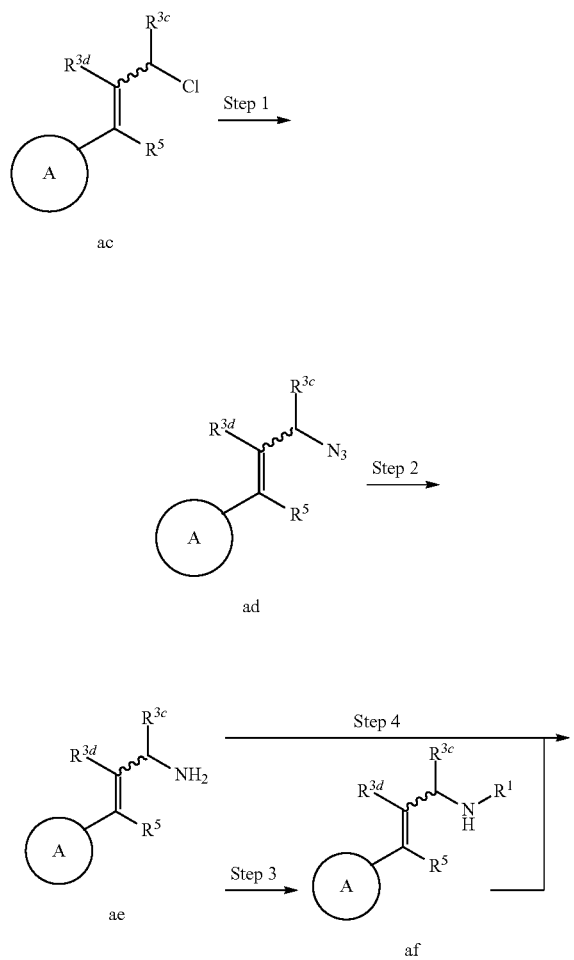

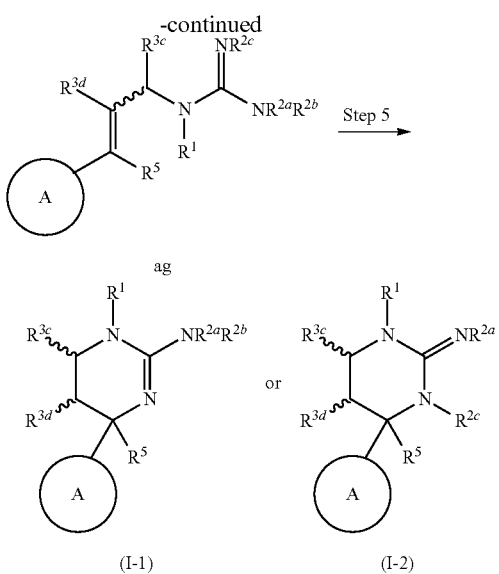

In formula, each symbols are the same as described above.

(Step 1)

To the compound (ac) prepared by known method in solvent; for example, N,N-dimethylformamide, methanol, and the like; is reacted with azide reagent; for example, sodium azide, lithium azide, and the like; at 20° C. to 150° C., preferably 50° C. to 100° C. for 0.5 to 120 hours, preferably 1 to 72 hours, to obtain the compound (ad).

(Step 2)

To the suspension of lithium aluminium hydride in solvent; for example, tetrahydrofuran, or ether, and the like; the compound (ad) dissolved in solvent; for example, tetrahydrofuran, or diethyl ether, and the like; is added under nitrogen atmosphere, at −80° C. to 20° C., preferably −30° C. to 0° C., and the mixture is reacted for 1 minute to 10 hours, preferably 10 minutes to 1 hour, or alternatively to the compound (ad) in solvent; for example, ethanol, isopropanol, or n-butanol, and the like; Raney-Nickel is added at 10° C. to 110° C., preferably 50° C. to 80° C., and reacted for 1 minute to 10 hours, preferably 10 minutes to 1 hour, to obtain the compound (ae).

(Step 3)

The compound (ae) in solvent; for example, tetrahydrofuran, dichloromethane, and the like; in the presence of acid; for example, acetic acid, or propionic acid, and the like; is reacted with reducing agent; for example, sodium cyanoborohydride, sodium triacetoxyborohydride, and the like; at −50° C. to 100° C., preferably 0° C. to 50° C., for 0.1 to 48 hours, preferably 0.5 to 24 hours, or the compound (ae) in solvent; for example, tetrahydrofuran, N,N-dimethylformamide, and the like; in the presence of dehydrating agent; for example, 1-ethyl-3-(3-dimethylaminopropyl)carbodiimide-N-hydroxybenzotriazole, carbonyldiimidazole, and the like; or in the presence of base; for example, triethylamine, potassium carbonate, and the like; is reacted with carboxylic acid; for example, formic acid, acetic acid, and the like; at −50° C. to 100° C., preferably 0° C. to 50° C. for 0.1 to 48 hours, preferably 0.5 to 16 hours, to obtain the compound (af). And next, to the suspension of lithium aluminium hydride in solvent; for example, tetrahydrofuran, or diethyl ether, and the like; the aforementioned amide compound dissolved in solvent; for example, tetrahydrofuran, or ether, and the like; is added at −50° C. to 60° C., preferably 0° C. to 50° C., and the mixture is reacted for 1 minute to 48 hours, preferably 10 minutes to 10 hours, to obtain the compound (af).

(Step 4)

The compound (ae) or the compound (af) in solvent; for example, acetonitrile, tetrahydrofuran, N,N-dimethylformamide, and the like; is reacted with 3,5-dimethylpyrazole-1-carboxyamidine or S-methylthiourea at 0° C. to 150° C., preferably 20° C. to 100° C., and the mixture is reacted for 0.5 to 120 hours, preferably 1 to 24 hours, to obtain the compound (ag).

(Step 5)

To the compound (ag) (wherein at least either $R^{2b}$ or $R^{2c}$ is a hydrogen atom) in the presence or the absence of solvent; for example, toluene, and the like; acid; for example, trifluoroacetic acid, methanesulfonic acid, trifluoromethanesulfonic acid, and the like, or the mixture thereof; is added and the mixture is reacted at −20° C. to 100° C., preferably 0° C. to 50° C., and the mixture is reacted for 0.5 to 120 hours, preferably 1 to 72 hours, to obtain the compound (I-2) (wherein $R^{2b}$ is a hydrogen atom) or the compound (I-1) (wherein $R^{2c}$ is a hydrogen atom) respectively. Proviso, if $R^{2a}$, $R^{2b}$, and $R^{2c}$ have fragile structure under acidic condition; for example, t-butyloxycarbonyl, and the like; $R^{2a}$, $R^{2b}$, and $R^{2c}$ in the compound (I-1) or the compound (I-2) may be transformed into a hydrogen atom.

The synthesis of aminothiazoline ring; Method C

[Chemical formula 26]

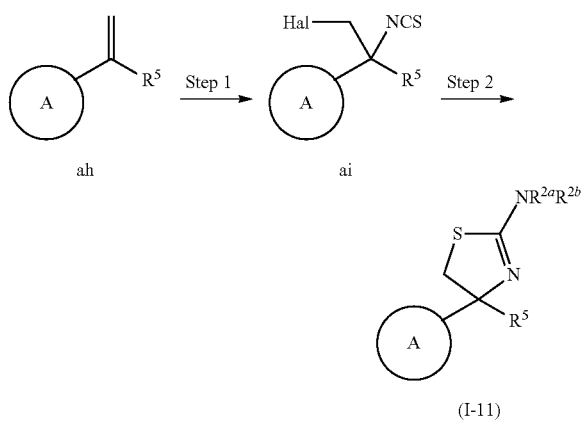

In formula, Hal is halogen, and other symbols are the same as described above.

(Step 1)

The compound (ah) which is commercially available or prepared by known method in solvent; for example, toluene, chloroform, tetrahydrofuran, and the like; or in mixed-solvent; for example, chloroform-water, and the like; is reacted with halogen; for example, including iodine, bromine, chorine; phase transfer catalyst; for example, sodium thiocyanic acid, ammonium thiocyanic acid, and the like; at 0° C. to 150° C., preferably 20° C. to 100° C., for 0.5 to 48 hours, preferably 1 to 24 hours, to obtain the compound (ai).

(Step 2)

The compound (ai) in solvent; for example, toluene, chloroform, tetrahydrofuran, and the like; is reacted with amine having substituent corresponding to target compound; for example ammonia, methylamine, diethylamine, and the like; at 0° C. to 150° C., preferably 20° C. to 100° C., for 0.5 to 48 hours, preferably 1 to 24 hours, to obtain the compound (I-11).

The aminoacyl derivative-1

[Chemical formula 27]

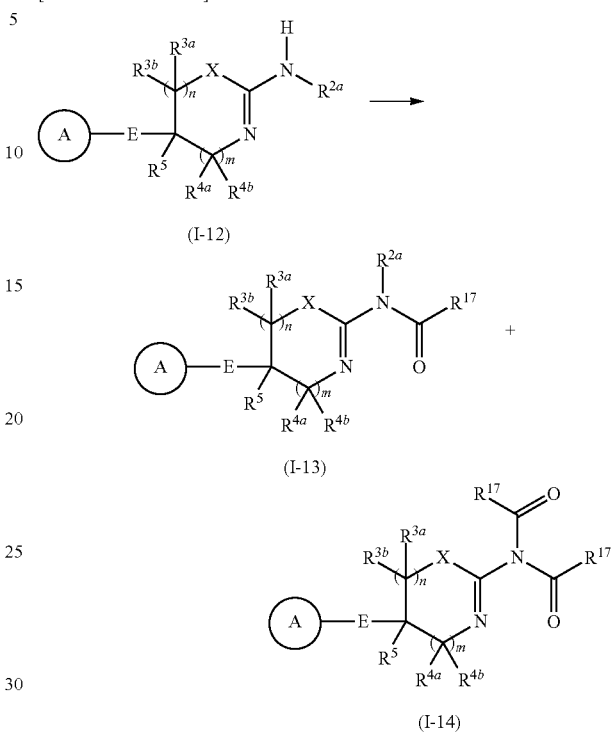

In formula, $R^{17}$ is optionally substituted lower alkyl, an optionally substituted carbocyclic group or an optionally substituted heterocyclic group, and the other symbols are the same as described above.

The compound (I-12) wherein $R^{2b}$ is a hydrogen atom in the presence or the absence of solvent; for example, tetrahydrofuran, dichloromethane, and the like; in the presence of base; for example, pyridine, triethylamine, and the like; is reacted with acylating agent having substituent corresponding to target compound; for example, benzoyl chloride, 2-furoyl chloride, acetic anhydride, and the like; at −80° C. to 100° C., preferably −20° C. to 40° C., for 0.1 to 24 hours, preferably 1 to 12 hours, or alternatively, the compound (I-12) in solvent; for example, N,N-dimethylformamide, tetrahydrofuran, dichloromethane, and the like; in the presence of dehydrating agent; for example, dicyclohexylcarbodiimide, carbonyldiimidazole, and the like; is reacted with carboxylic acid having substituent corresponding to target compound; for example, amino acid, glycolic acid, and the like; at −80° C. to 100° C., preferably −20° C. to 40° C., for 0.1 to 24 hours, preferably 1 to 12 hours, to obtain the compound (I-13) and/or the compound (I-14) (wherein $R^{2a}$ is a hydrogen atom).

The guanidino derivatives

[Chemical formula 28]

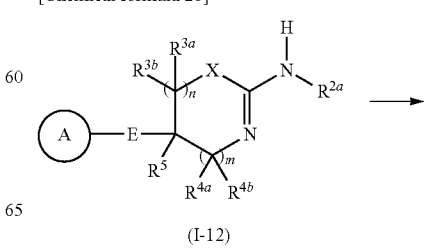

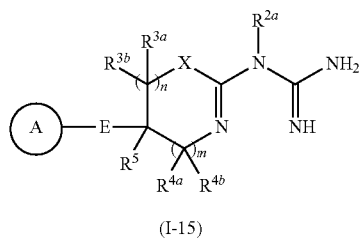

(I-15)

The acylamino derivative-2

[Chemical formula 30]

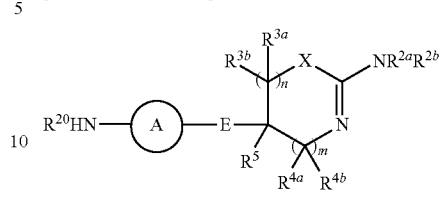

(I-18)

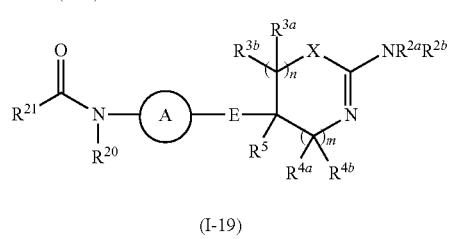

(I-19)

In formula, each symbols are the same as described above.

The compound (I-12) wherein $R^{2b}$ is a hydrogen atom in solvent; for example, acetonitrile, tetrahydrofuran, N,N-dimethylformamide, and the like; in the presence or the absence of base; for example, triethylamine, sodium hydrogencarbonate, and the like; is reacted with 3,5-dimethylpyrazole-1-carboxyamidine, or S-methylisothiourea etc. at 0° C. to 150° C., preferably 20° C. to 100° C., for 0.5 to 120 hours, preferably 1 to 24 hours, to obtain the compound (I-15).

The carbamoyl derivatives

[Chemical formula 29]

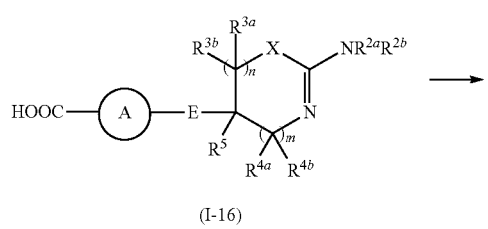

(I-16)

(I-17)

In formula, $CONR^{18}R^{19}$ is optionally substituted carbamoyl, and the other symbols are the same as described above.

The compound (I-16) having a carboxyl group as substituent of ring A in solvent; for example, N,N-dimethylformamide, tetrahydrofuran, dichloromethane, and the like; in the presence of dehydrating agent; for example, dicyclohexylcarbodiimide, carbonyldiimidazole, dicyclohexylcarbodiimide-N-hydroxybenzotriazole, and the like; is reacted with primary amine or secondary amine (aniline, 2-aminopyridine, dimethylamine etc.) at −80° C. to 100° C., preferably −20° C. to 40° C., for 0.1 to 24 hours, preferably 1 to 12 hours, to obtain the compound (I-17).

In formula, $NHR^{20}$ is optionally substituted amino; $NR^{20}COR^{21}$ is optionally substituted acyl amino, optionally substituted ureido, carboxy amino having substituent on oxygen atom, and the other symbols are the same as described above.

The compound (I-18) having an optionally substituted amino group on ring A in the presence or the absence of solvent; for example, tetrahydrofuran, dichloromethane, and the like; in the presence or the absence of base; for example, pyridine, triethylamine, and the like; is reacted with reagent including acid chloride, acid anhydride, chloroformate ester derivatives, isocyanate derivatives (benzoyl chloride, 2-furoyl chloride, acetic anhydride, benzyl chloroformate, di-t-butyl Bicarbonate, phenyl isocyanate etc.), at −80° C. to 100° C., preferably −20° C. to 40° C., for 0.1 to 24 hours, preferably 1 to 12 hours. Or alternatively, the compound (I-18) having an optionally substituted amino group on ring A in solvent; for example, N,N-dimethylformamide, tetrahydrofuran, dichloromethane, and the like; in the presence of dehydrating agent; for example, dicyclohexylcarbodiimide, carbonyldiimidazole, dicyclohexylcarbodiimide-N-hydroxybenzotriazole, and the like; is reacted with carboxylic acid having substituent corresponding to target compound; for example, benzoic acid, 2-pyridinecarboxylic acid, and the like; at −80° C. to 100° C., preferably −20° C. to 40° C., for 0.1 to 24 hours, preferably 1 to 12 hours, to obtain the compound (I-19).

The alkylamino derivatives

[Chemical formula 31]

(I-18)

-continued

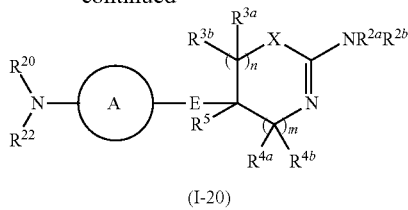

(I-20)

In formula, NHR$^{20}$ is optionally substituted amino, R$^{22}$ is lower alkyl.

The compound (I-18) having an amino group on ring A in solvent; for example, dichloromethane, tetrahydrofuran, and the like; in the presence or the absence of acid; for example, acetic acid, and the like; is reacted with aldehyde having substituent corresponding to target compound; for example, benzaldehyde, pyridine-2-carboaldehyde, and the like; and reducing agent; for example, sodium borohydride, sodium triacetoxyborohydride, and the like; at −80° C. to 100° C., preferably 0° C. to 40° C., for 0.5 to 150 hours, preferably 1 to 24 hours, to obtain the compound (I-20).

The substituted alkoxy derivatives

[Chemical formula 32]

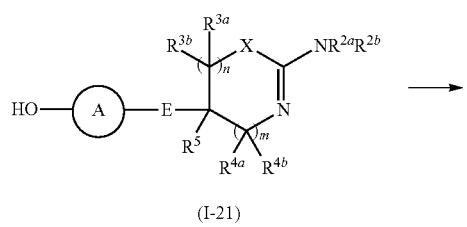

(I-21)

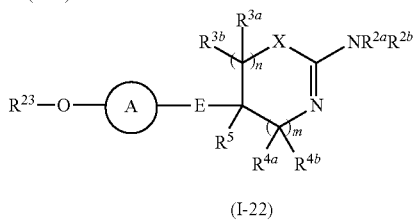

(I-22)

In formula, R$^{23}$ is optionally substituted lower alkyl, an optionally substituted carbocyclic group or an optionally substituted heterocyclic group, etc., and the other symbols are the same as described above.

The compound (I-21) having a hydroxy group as substituent of A ring in solvent; for example, N,N-dimethylformamide, tetrahydrofuran, and the like; in the presence of base; for example potassium carbonate, sodium hydroxide, sodium hydride, and the like; is reacted with alkylating agent having substituent corresponding to target compound; for example, benzylchloride, methyl iodide, and the like; at −80° C. to 100° C., preferably 0° C. to 40° C., for 0.5 to 150 hours, preferably 1 to 24 hours, or alternatively, the compound (I-18) in solvent; for example, N,N-dimethylformamide, tetrahydrofuran, and the like; under Mitsunobu reagent; for example triphenylphosphine-azodicarboxylic acid ethyl ester, and the like; is reacted with alcohol; for example, 2-aminoethanol, and the like; at −80° C. to 100° C., preferably 0° C. to 40° C., for 0.5 to 72 hours, preferably 1 to 24 hours, to obtain the compound (I-22).

The introduction of substituent with palladium coupling reaction

[Chemical formula 33]

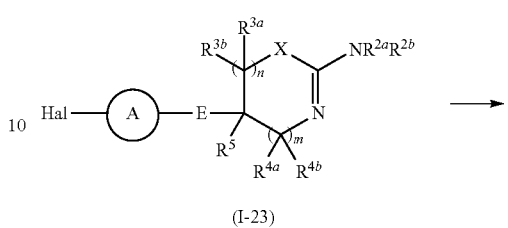

(I-23)

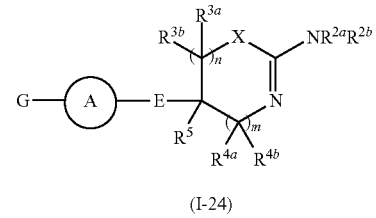

(I-24)

In formula, Hal is halogen, G is optionally substituted lower alkenyl, optionally substituted lower alkynyl, optionally substituted lower alkoxycarbonyl, an optionally substituted carbocyclic group or an optionally substituted heterocyclic group etc., and the other symbols are the same as described above.

The compound (I-23) having halogen as substituent of A ring in solvent; for example, tetrahydrofuran, N,N-dimethylformamide, 1,2-dimethoxyethane, methanol, and the like; in the presence of base; for example, triethylamine, sodium carbonate, and the like; palladium catalyst; for example, palladium acetate, palladium chloride, and the like; and ligand; for example triphenylphosphine, and the like; is reacted with compound having substituent corresponding to target compound (styrene, propargyl alcohol, aryl boronic acid, carbon monoxide), with or without microwave irradiation, at −80° C. to 150° C., preferably 0° C. to 100° C., for 0.5 to 72 hours, preferably 1 to 24 hours, to obtain the compound (I-24).

The oxime derivatives

[Chemical formula 34]

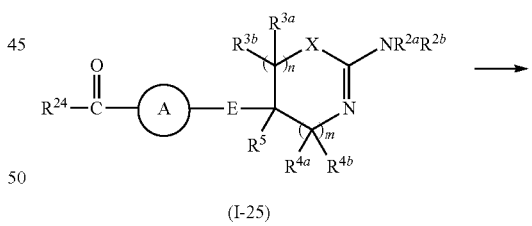

(I-25)

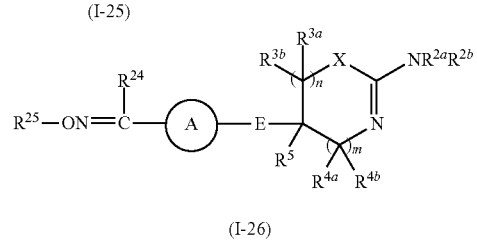

(I-26)

In formula, in R$^{24}$ is a hydrogen atom or optionally substituted lower alkyl etc., R$^{25}$ is a hydrogen atom, optionally substituted lower alkyl, optionally substituted lower alkenyl or an optionally substituted carbocyclic group or an optionally substituted heterocyclic group etc., and the other symbols are the same as described above.

The compound (I-25) having an acyl group as substituent of A ring in solvent; for example, methanol, ethanol, and the like; in the presence or the absence of additives; for example, potassium acetate, and the like; is reacted with hydroxylamine having substituent corresponding to target compound (hydroxylamine, methoxylamine, O-benzylhydroxylamine, etc.) or the salt thereof, at 0° C. to 100° C., preferably 0° C. to 40° C., for 0.5 to 150 hours, preferably 1 to 72 hours, to obtain the compound (I-26).

In all of above mentioned steps, if a compound having substituent which interrupts the reaction; (for example, hydroxy, mercapto, amino, formyl, carbonyl, carboxyl, etc.), the substituent of the compound is protected by methods described in Protective Groups in Organic Synthesis, Theodora W Green (John Wiley & Sons) beforehand, and is deprotected at preferable step.

The compound (I) in this invention presented below; in particular, X is S, and E is a bond or methylene; is preferable.
1) A compound represented by the general formula (I'),

[Chemical formula 35]

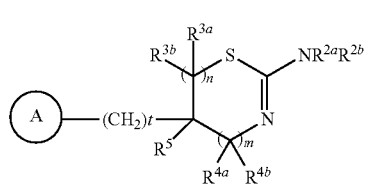

(I')

in formula, t is 0 or 1, the other symbols are the same as above (a), with the proviso that the compounds represented below;
i) wherein n+m is 2, $R^5$ is a hydrogen atom, and ring A is unsubstituted phenyl;
ii) wherein n is 2, m is 0, $R^{2a}$ is a hydrogen atom, $R^{2b}$ is a hydrogen atom or acetyl, $R^5$ is methyl, and ring A is phenyl or 4-methoxyphenyl;
iii) wherein n is 2, m is 0, $R^{2a}$ is a hydrogen atom, $R^{2b}$ is a hydrogen atom or acetyl, $R^5$ is ethyl, and ring A is 3,4-dimethoxyphenyl;
iv) wherein n is 2, m is 0, $R^{2a}$ is a hydrogen atom, $R^{2b}$ is a hydrogen atom or acetyl, $R^5$ and ring A are phenyl;
v) wherein n is 2, m is 0, $R^{2a}$ and $R^{2b}$ is a hydrogen atom, $R^5$ and ring A are taken together to form

[Chemical formula 36]

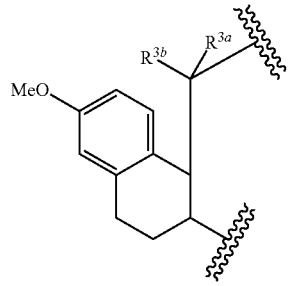

and
vi) the compound, wherein n+m is 1 or 2; $R^5$ is a hydrogen atom; ring A is phenyl substituted by one or two substituent selected from hydroxy, halogen, lower alkyl, lower alkoxy, nitro, amino, lower alkyl carbonylamino, mercapto, lower alkylthio, carbamoyl, lower alkylamino, lower alkyl carbamoyl and lower alkoxycarbonyl; non-substituted phenyl, or non-substituted naphthyl; are excluded.

In addition, in formula (I'), preferable is the compound represented below.
2) The compound, wherein n is 1 and m is 0 (this compound is represented by nm-1),
3) the compound, wherein n is 2 and m is 0 (this compound is represented by nm-2),
4) the compound, wherein n is 3 and m is 0 (this compound is represented by nm-3),
5) the compound, wherein $R^{2a}$ is a hydrogen atom; $R^{2b}$ is a hydrogen atom, optionally substituted lower alkyl, optionally substituted acyl, optionally substituted lower alkylsulfonyl, or optionally substituted amidino (this compound is represented by R2-1),
6) the compound, wherein $R^{2a}$ is a hydrogen atom; $R^{2b}$ is a hydrogen atom, optionally substituted lower alkyl or optionally substituted acyl (this compound is represented by R2-2),
7) the compound, wherein $NR^{2a}R^{2b}$ is represented by the following formula:

[Chemical formula 37]

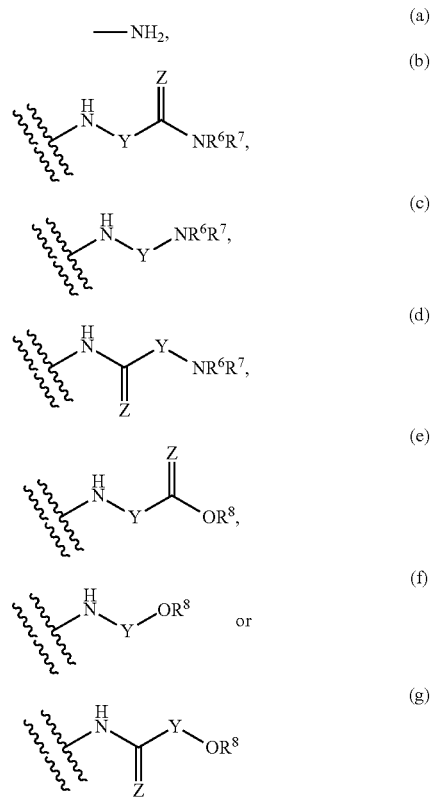

wherein each symbols are the same as described above.
$R^6$, $R^7$ and $R^8$ are each independently a hydrogen atom, lower alkyl or acyl,
Y is optionally substituted lower alkylene, optionally substituted lower alkenylene or optionally substituted lower alkynylene,
Z is O or S (this compound is represented by R2-3),
8) the compound, wherein $NR^{2a}R^{2b}$ is $NH_2$ (this compound is represented by R2-4),
9) the compound, wherein ring A is substituted phenyl or substituted pyridyl (this compound is represented by A-1), 10) the compound, wherein ring A is represented by the following formula:

[Chemical formula 38]

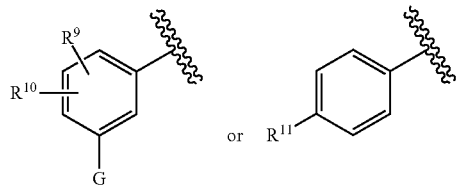

wherein $R^9$, $R^{10}$ and $R^{11}$ is a hydrogen atom or G,
G is halogen, hydroxy, cyano, nitro, mercapto, optionally substituted lower alkyl, optionally substituted lower alkoxy, optionally substituted lower alkenyl, optionally substituted lower alkynyl, optionally substituted acyl, optionally substituted acyloxy, carboxy, optionally substituted lower alkoxycarbonyl, optionally substituted lower alkoxycarbonyloxy, optionally substituted aryloxycarbonyloxy, optionally substituted amino, optionally substituted carbamoyl, optionally substituted carbamoyloxy, optionally substituted lower alkylthio, optionally substituted arylthio, optionally substituted lower alkylsulfonyl, optionally substituted arylsulfonyl, optionally substituted lower alkylsilfinyl, optionally substituted arylsulfinyl, optionally substituted lower alkylsulfonyloxy, optionally substituted arylsulfonyloxy, optionally substituted sulfamoyl, an optionally substituted carbocyclic group, optionally substituted carbocyclicoxy, an optionally substituted heterocyclic group or optionally substituted heterocyclicoxy, each G may be different (this compound is represented by A-2), 11) the compound, wherein ring A is represented by the following formula:

[Chemical formula 39]

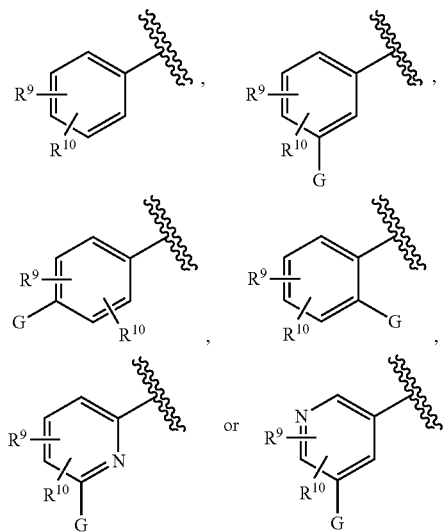

wherein $R^9$ and $R^{10}$ are each independently a hydrogen atom, halogen, hydroxy, optionally substituted lower alkyl, cyano, nitro, optionally substituted lower alkoxy, optionally substituted acyl, optionally substituted amino, optionally substituted carbamoyl, optionally substituted carbamoyloxy, optionally substituted lower alkylsulfonyl, optionally substituted arylsulfonyl, optionally substituted lower alkylsulfonyloxy, optionally substituted arylsulfonyloxy, an optionally substituted carboncyclic group, optionally substituted carbocyclicoxy, an optionally substituted heterocyclic group or optionally substituted heterocyclicoxy, G is the same as described above 10) (this compound is represented by A-3), 12) the compound, wherein ring A is represented by the following formula:

[Chemical formula 40]

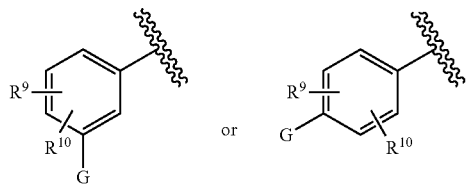

wherein $R^9$ and $R^{10}$ is the same as described in 11), G is the same as described in 10) (this compound is represented by A-4), 13) the compound, wherein ring A, $R^9$, and $R^{10}$ are defined in 11), G is optionally substituted amino (this compound is represented by A-5), 14) the compound, wherein ring A, $R^9$ and $R^{10}$ are defined in 11), G is optionally substituted arylcarbonylamino or optionally substituted heterocyclic carbonylamino, 15) the compound, wherein ring A, $R^9$ and $R^{10}$ are defined in 11), G is optionally substituted heterocyclic carbonylamino (this compound is represented by A-6), 16) the compound, wherein ring A is defined in 11), G is represented by the following formula:

[Chemical formula 41]

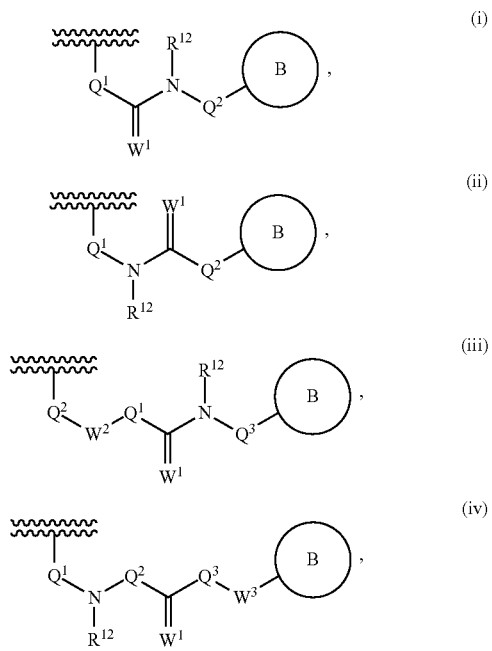

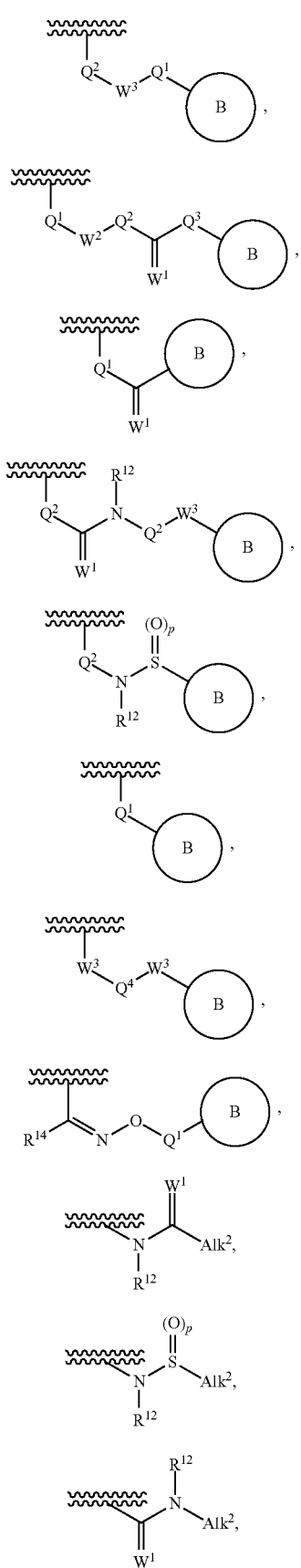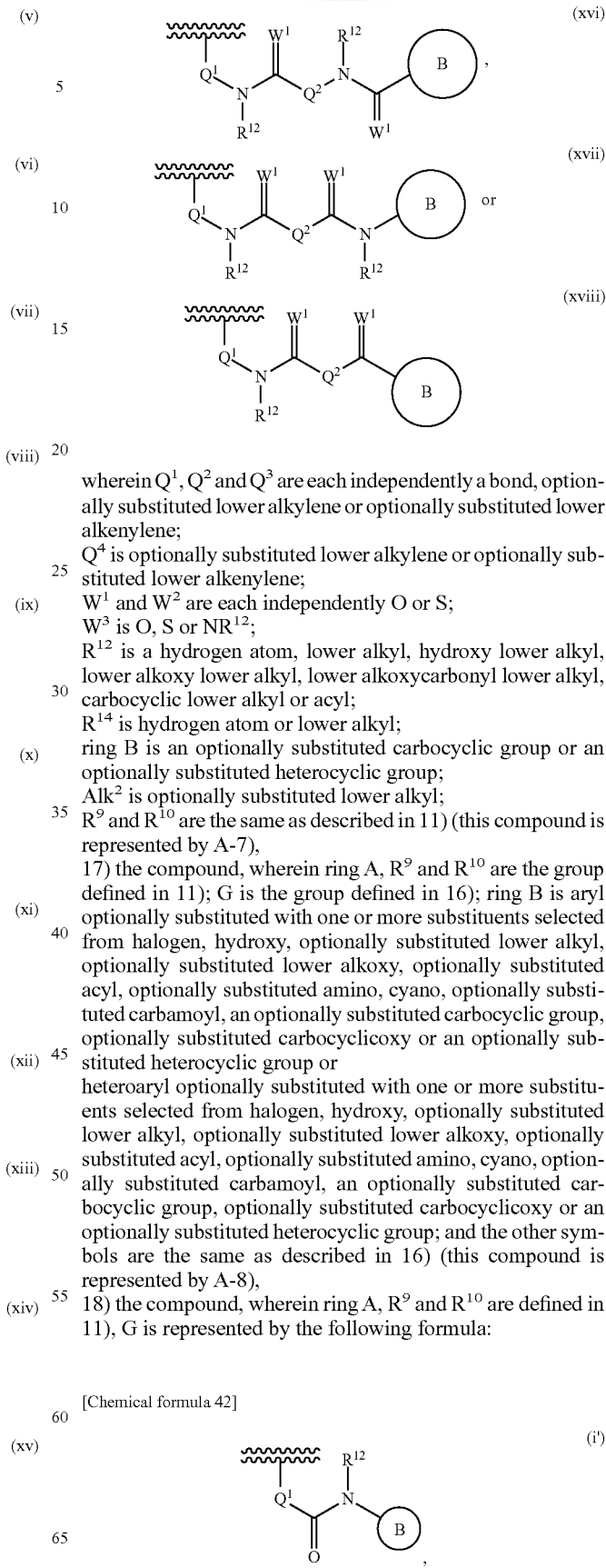

wherein $Q^1$, $Q^2$ and $Q^3$ are each independently a bond, optionally substituted lower alkylene or optionally substituted lower alkenylene;
$Q^4$ is optionally substituted lower alkylene or optionally substituted lower alkenylene;
$W^1$ and $W^2$ are each independently O or S;
$W^3$ is O, S or $NR^{12}$;
$R^{12}$ is a hydrogen atom, lower alkyl, hydroxy lower alkyl, lower alkoxy lower alkyl, lower alkoxycarbonyl lower alkyl, carbocyclic lower alkyl or acyl;
$R^{14}$ is hydrogen atom or lower alkyl;
ring B is an optionally substituted carbocyclic group or an optionally substituted heterocyclic group;
$Alk^2$ is optionally substituted lower alkyl;
$R^9$ and $R^{10}$ are the same as described in 11) (this compound is represented by A-7),
17) the compound, wherein ring A, $R^9$ and $R^{10}$ are the group defined in 11); G is the group defined in 16); ring B is aryl optionally substituted with one or more substituents selected from halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy or an optionally substituted heterocyclic group or
heteroaryl optionally substituted with one or more substituents selected from halogen, hydroxy, optionally substituted lower alkyl, optionally substituted lower alkoxy, optionally substituted acyl, optionally substituted amino, cyano, optionally substituted carbamoyl, an optionally substituted carbocyclic group, optionally substituted carbocyclicoxy or an optionally substituted heterocyclic group; and the other symbols are the same as described in 16) (this compound is represented by A-8),
18) the compound, wherein ring A, $R^9$ and $R^{10}$ are defined in 11), G is represented by the following formula:

[Chemical formula 42]

-continued

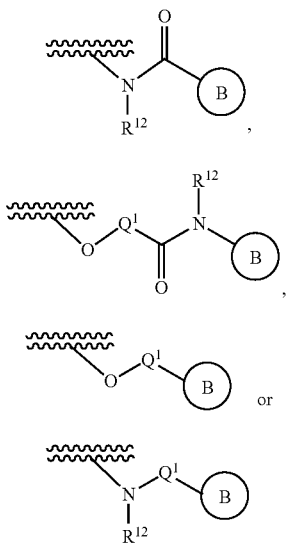

in formula, wherein each symbols are the same as described in 16) (this compound is represented by A-9), 19) the compound, wherein ring A is represented by the following formula:

[Chemical formula 43]

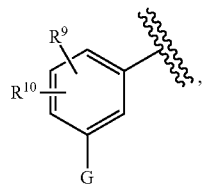

G is defined in 16), ring B is optionally substituted aryl or optionally substituted heteroaryl, either $R^9$ or $R^{10}$ is a hydrogen atom; and the other is a hydrogen atom, halogen, optionally substituted lower alkyl, cyano, nitro, optionally substituted lower alkoxy, optionally substituted amino, optionally substituted carbamoyl, optionally substituted lower alkylsulfonyl, an optionally substituted carbocyclic group or an optionally substituted heterocyclic group (this compound is represented by A-10), 20) the compound, wherein ring A is represented by the following formula:

[Chemical formula 44]

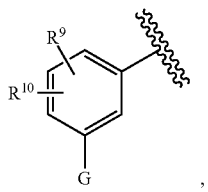

G is defined in 18), the other symbols are the same as described in 19) (this compound is represented by A-11), 21) the compound, wherein ring A is represented by the following formula:

[Chemical formula 45]

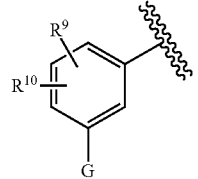

G is defined in 16), ring B is optionally substituted phenyl, 5- to 6-membered heteroaryl, benzothiazolyl or benzothienyl, $R^9$ and $R^{10}$ are the same as described in 19) (this compound is represented by A-12), 22) the compound, wherein ring A is represented by the following formula:

[Chemical formula 46]

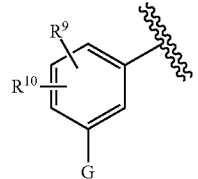

G is defined in 18), ring B is defined in 21), $R^9$ and $R^{10}$ are the same as described in 19) (this compound is represented by A-13), 23) the compound, wherein ring A is represented by the following formula:

[Chemical formula 47]

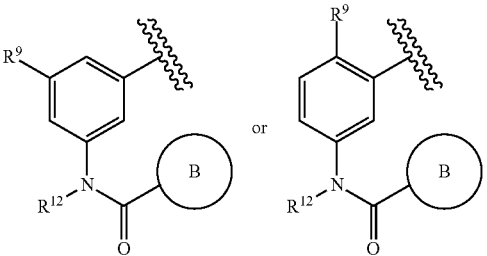

wherein $R^9$ is a hydrogen atom, halogen, optionally substituted lower alkyl, cyano, nitro, optionally substituted lower alkoxy, optionally substituted amino, optionally substituted carbamoyl, optionally substituted lower alkylsulfonyl, an optionally substituted carbocyclic group or an optionally substituted heterocyclic group, ring B is the same as described in 21); $R^{12}$ is a hydrogen atom or lower alkyl (this compound is represented by A-14), 24) the compound, wherein $R^5$ is a hydrogen atom or C1 to C3 alkyl (this compound is represented by R5-1), 25) the compound, wherein $R^9$ is C1 to C3 alkyl (this compound is represented by R5-2), 26) the compound, wherein $R^5$ is methyl (this compound is represented by R5-3), 27) the compound, wherein $R^{3a}$ and $R^{3b}$ are each independently a hydrogen atom, halogen, hydroxy, optionally substituted lower alkyl, optionally substituted lower alkoxy or optionally substituted aryl (this compound is represented by R3-1), 28) the compound wherein, $R^{3a}$ is a hydrogen atom, halogen, hydroxy, optionally substituted lower alkyl, optionally substituted lower alkoxy or optionally substituted aryl, $R^{3b}$ is a hydrogen atom, one $R^3$ is a hydrogen atom when n is 2, one or two $R^{2a}$ is(are) a hydrogen atom when n is 3 (this compound is represented by R3-2), 29) the compound, wherein $R^{3a}$ and $R^{3b}$ are all hydrogen atoms (this compound is represented by R3-3), and in a compound represented by the general formula (I'), a compound, wherein the combination of n, m, $R^{2a}$, $R^{2b}$, ring A, $R^5$, $R^{3a}$, and $R^{3b}$ (nm, $R^2$, A, $R^5$, $R^3$) is the following compound.

(m, $R^2$, A, $R^5$, $R^3$)=
(nm-1,R2-1,A-1,R5-1,R3-1),(nm-1,R2-1,A-1,R5-1,R3-2), (nm-1,R2-1,A-1,R5-2,R3-1),(nm-1,R2-1,A-1,R5-2,R3-2), (nm-1,R2-1,A-1,R5-3,R3-1),(nm-1,R2-1,A-1,R5-3,R3-2), (nm-1,R2-1,A-2,R5-1,R3-1),(nm-1,R2-1,A-2,R5-1,R3-2), (nm-1,R2-1,A-2,R5-2,R3-1),(nm-1,R2-1,A-2,R5-2,R3-2), (nm-1,R2-1,A-2,R5-3,R3-1),(nm-1,R2-1,A-2,R5-3,R3-2), (nm-1,R2-1,A-3,R5-1,R3-1),(nm-1,R2-1,A-3,R5-1,R3-2), (nm-1,R2-1,A-3,R5-2,R3-1),(nm-1,R 2-1,A-3,R5-2,R3-2), (nm-1,R2-1,A-3,R5-3,R3-1),(nm-1,R2-1,A-3,R5-3,R3-2), (nm-1,R2-1,A-4,R5-1,R3-1),(nm-1,R2-1,A-4,R5-1,R3-2), (nm-1,R2-1,A-4,R5-2,R3-1),(nm-1,R2-1,A-4,R5-2,R3-2), (nm-1,R2-1,A-4,R5-3,R3-1),(nm-1,R2-1,A-4,R5-3,R3-2), (nm-1,R2-1,A-5,R5-1,R3-1),(nm-1,R2-1,A-5,R5-1,R3-2), (nm-1,R2-1,A-5,R5-2,R3-1),(nm-1,R2-1,A-5,R5-2,R3-2), (nm-1,R2-1,A-5,R5-3,R3-1),(nm-1,R2-1,A-5,R5-3,R3-2), (nm-1,R2-1,A-6,R5-1,R3-1),(nm-1,R2-1,A-6,R5-1,R3-2), (nm-1,R2-1,A-6,R5-2,R3-1),(nm-1,R2-1,A-6,R5-2,R3-2), (nm-1,R2-1,A-6,R5-3,R3-1),(nm-1,R2-1,A-6,R5-3,R3-2), (nm-1,R2-1,A-7,R5-1,R3-1),(nm-1,R2-1,A-7,R5-1,R3-2), (nm-1,R2-1,A-7,R5-2,R3-1),(nm-1,R2-1,A-7,R5-2,R3-2), (nm-1,R2-1,A-7,R5-3,R3-1),(nm-1,R2-1,A-7,R5-3,R3-2), (nm-1,R2-1,A-8,R5-1,R3-1),(nm-1,R2-1,A-8,R5-1,R3-2), (nm-1,R2-1,A-8,R5-2,R3-1),(nm-1,R2-1,A-8,R5-2,R3-2), (nm-1,R2-1,A-8,R5-3,R3-1),(nm-1,R2-1,A-8,R5-3,R3-2), (nm-1,R2-1,A-9,R5-1,R3-1),(nm-1,R2-1,A-9,R5-1,R3-2), (nm-1,R2-1,A-9,R5-2,R3-1),(nm-1,R2-1,A-9,R5-2,R3-2), (nm-1,R2-1,A-9,R5-3,R3-1),(nm-1,R2-1,A-9,R5-3,R3-2), (nm-1,R2-1,A-10,R5-1,R3-1),(nm-1,R2-1,A-10,R5-1,R3-2),(nm-1,R2-1,A-10,R5-2,R3-1),(nm-1,R2-1,A-10,R5-2,R3-2),(nm-1,R2-1,A-10,R5-3,R3-1),(nm-1,R2-1,A-10,R5-3,R3-2),(nm-1,R2-1,A-11,R5-1,R3-1),(nm-1,R2-1,A-11,R5-1,R3-2),(nm-1,R2-1,A-11,R5-2,R3-1),(nm-1,R2-1,A-11,R5-2,R3-2),(nm-1,R2-1,A-11,R5-3,R3-1),(nm-1,R2-1,A-11,R5-3,R3-2),(nm-1,R2-1,A-12,R5-1,R3-1),(nm-1,R2-1,A-12,R5-1,R3-2),(nm-1,R2-1,A-12,R5-2,R3-1),(nm-1,R2-1,A-12,R5-2,R3-2),(nm-1,R2-1,A-12,R5-3,R3-1),(nm-1,R2-1,A-12,R5-3,R3-2),(nm-1,R2-1,A-13,R5-1,R3-1), (nm-1,R2-1,A-13,R5-1,R3-2),(nm-1,R2-1,A-13,R5-2,R3-1),(nm-1,R2-1,A-13,R5-2,R3-2),(nm-1,R2-1,A-13,R5-3,R3-1),(nm-1,R2-1,A-13,R5-3,R3-2),(nm-1,R2-1,A-14,R5-1,R3-1),(nm-1,R2-1,A-14,R5-1,R3-2),(nm-1,R2-1,A-14,R5-2,R3-1),(nm-1,R2-1,A-14,R5-2,R3-2),(nm-1,R2-1,A-14,R5-3,R3-1),(nm-1,R2-1,A-14,R5-3,R3-2),(nm-1,R2-2,A-1,R5-1,R3-1),(nm-1,R2-2,A-1,R5-1,R3-2),(nm-1,R2-2,A-1,R5-2,R3-1),(nm-1,R2-2,A-1,R5-2,R3-2),(nm-1,R2-2,A-1,R5-3,R3-1),(nm-1,R2-2,A-1,R5-3,R3-2),(nm-1,R2-2,A-2,R5-1,R3-1),(nm-1,R2-2,A-2,R5-1,R3-2),(nm-1,R2-2,A-2,R5-2,R3-1),(nm-1,R2-2,A-2,R5-2,R3-2),(nm-1,R2-2,A-2,R5-3,R3-1),(nm-1,R2-2,A-2,R5-3,R3-2),(nm-1,R2-2,A-3,R5-1,R3-1),(nm-1,R2-2,A-3,R5-1,R3-2),(nm-1,R2-2,A-3,R5-2,R3-1),(nm-1,R2-2,A-3,R5-2,R3-2),(nm-1,R2-2,A-3,R5-3,R3-1),(nm-1,R2-2,A-3,R5-3,R3-2),(nm-1,R2-2,A-4,R5-1,R3-1),(nm-1,R2-2,A-4,R5-1,R3-2),(nm-1,R2-2,A-4,R5-2,R3-1),(nm-1,R2-2,A-4,R5-2,R3-2),(nm-1,R2-2,A-4,R5-3,R3-1),(nm-1,R2-2,A-4,R5-3,R3-2),(nm-1,R2-2,A-5,R5-1,R3-1),(nm-1,R2-2,A-5,R5-1,R3-2),(nm-1,R2-2,A-5,R5-2,R3-1),(nm-1,R2-2,A-5,R5-2,R3-2),(nm-1,R2-2,A-5,R5-3,R3-1),(nm-1,R2-2,A-5,R5-3,R3-2),(nm-1,R2-2,A-6,R5-1,R3-1),(nm-1,R2-2,A-6,R5-1,R3-2),(nm-1,R2-2,A-6,R5-2,R3-1),(nm-1,R2-2,A-6,R5-2,R3-2),(nm-1,R2-2,A-6,R5-3,R3-1),(nm-1,R2-2,A-6,R5-3,R3-2),(nm-1,R2-2,A-7,R5-1,R3-1),(nm-1,R2-2,A-7,R5-1,R3-2),(nm-1,R2-2,A-7,R5-2,R3-1),(nm-1,R2-2,A-7,R5-2,R3-2),(nm-1,R2-2,A-7,R5-3,R3-1),(nm-1,R2-2,A-7,R5-3,R3-2),(nm-1,R2-2,A-8,R5-1,R3-1),(nm-1,R2-2,A-8,R5-1,R3-2),(nm-1,R2-2,A-8,R5-2,R3-1),(nm-1,R2-2,A-8,R5-2,R3-2),(nm-1,R2-2,A-8,R5-3,R3-1),(nm-1,R2-2,A-8,R5-3,R3-2),(nm-1,R2-2,A-9,R5-1,R3-1),(nm-1,R2-2,A-9,R5-1,R3-2),(nm-1,R2-2,A-9,R5-2,R3-1),(nm-1,R2-2,A-9,R5-2,R3-2),(nm-1,R2-2,A-9,R5-3,R3-1),(nm-1,R2-2,A-9,R5-3,R3-2),(nm-1,R2-2,A-10,R5-1,R3-1),(nm-1,R2-2,A-10,R5-1,R3-2),(nm-1,R2-2,A-10,R5-2,R3-1),(nm-1,R2-2,A-10,R5-2,R3-2),(nm-1,R2-2,A-10,R5-3,R3-1),(nm-1,R2-2,A-10,R5-3,R3-2),(nm-1,R2-2,A-11,R5-1,R3-1),(nm-1,R2-2,A-11,R5-1,R3-2), (nm-1,R2-2,A-11,R5-2,R3-1),(nm-1,R2-2,A-11,R5-2,R3-2),(nm-1,R2-2,A-11,R5-3,R3-1),(nm-1,R2-2,A-11,R5-3,R3-2),(nm-1,R2-2,A-12,R5-1,R3-1),(nm-1,R2-2,A-12,R5-1,R3-2),(nm-1,R2-2,A-12,R5-2,R3-1),(nm-1,R2-2,A-12,R5-2,R3-2),(nm-1,R2-2,A-12,R5-3,R3-1),(nm-1,R2-2,A-12,R5-3,R3-2),(nm-1,R2-2,A-13,R5-1,R3-1),(nm-1,R2-2,A-13,R5-1,R3-2),(nm-1,R2-2,A-13,R5-2,R3-1),(nm-1,R2-2,A-13,R5-2,R3-2),(nm-1,R2-2,A-13,R5-3,R3-1),(nm-1,R2-2,A-13,R5-3,R3-2),(nm-1,R2-2,A-14,R5-1,R3-1),(nm-1,R2-2,A-14,R5-1,R3-2),(nm-1,R2-2,A-14,R5-2,R3-1), (nm-1,R2-2,A-14,R5-2,R3-2),(nm-1,R2-2,A-14,R5-3,R3-1),(nm-1,R2-2,A-14,R5-3,R3-2),(nm-1,R2-3,A-1,R5-1,R3-1),(nm-1,R2-3,A-1,R5-1,R3-2),(nm-1,R2-3,A-1,R5-2,R3-1),(nm-1,R2-3,A-1,R5-2,R3-2),(nm-1,R2-3,A-1,R5-3,R3-1),(nm-1,R2-3,A-1,R5-3,R3-2),(nm-1,R2-3,A-2,R5-1,R3-1),(nm-1,R2-3,A-2,R5-3,R3-1),(nm-1,R2-3,A-2,R5-2,R3-1),(nm-1,R2-3,A-2,R5-2,R3-2),(nm-1,R2-3,A-2,R5-3,R3-1),(nm-1,R2-3,A-2,R5-3,R3-2),(nm-1,R2-3,A-3,R5-1,R3-1),(nm-1,R2-3,A-3,R5-1,R3-2),(nm-1,R2-3,A-3,R5-2,R3-1),(nm-1,R2-3,A-3,R5-2,R3-2),(nm-1,R2-3,A-3,R5-3,R3-1),(nm-1,R2-3,A-3,R5-3,R3-2),(nm-1,R2-3,A-4,R5-1,R3-1),(nm-1,R2-3,A-4,R5-1,R3-2),(nm-1,R2-3,A-4,R5-2,R3-1),(nm-1,R2-3,A-4,R5-2,R3-2),(nm-1,R2-3,A-4,R5-3,R3-1),(nm-1,R2-3,A-4,R5-3,R3-2),(nm-1,R2-3,A-5,R5-1,R3-1),(nm-1,R2-3,A-5,R5-1,R3-2),(nm-1,R2-3,A-5,R5-2,R3-1),(nm-1,R2-3,A-5,R5-2,R3-2),(nm-1,R2-3,A-5,R5-3,R3-1),(nm-1,R2-3,A-5,R5-3,R3-2),(nm-1,R2-3,A-6,R5-1,R3-1),(nm-1,R2-3,A-6,R5-1,R3-2),(nm-1,R2-3,A-6,R5-2,R3-1),(nm-1,R2-3,A-6,R5-2,R3-2),(nm-1,R2-3,A-6,R5-3,R3-1),(nm-1,R2-3,A-6,R5-3,R3-2),(nm-1,R2-3,A-7,R5-1,R3-1),(nm-1,R2-3,A-7,R5-1,R3-2),(nm-1,R2-3,A-7,R5-2,R3-1),(nm-1,R2-3,A-7,R5-2,R3-2),(nm-1,R2-3,A-7,R5-3,R3-1),(nm-1,R2-3,A-7,R5-3,R3-2),(nm-1,R2-3,A-8,R5-1,R3-1),(nm-1,R2-3,A-8,R5-1,R3-2),(nm-1,R2-3,A-8,R5-2,R3-1),(nm-1,R2-3,A-8,R5-2,R3-2),(nm-1,R2-3,A-8,R5-3,R3-1),(nm-1,R2-3,A-8,R5-3,R3-2),(nm-1,R2-3,A-9,R5-1,R3-1),(nm-1,R2-3,A-9,R5-1,R3-2),(nm-1,R2-3,A-9,R5-2,R3-1),(nm-1,R2-3,A-9,R5-2,R3-2),(nm-1,R2-3,A-9,R5-3,R3-1),(nm-1,R2-3,A-9,R5-2,R3-1),(nm-1,R2-3,A-10,R5-1,R3-1),(nm-1,R2-3,A-10,R5-1,R3-2),(nm-1,R2-3,A-10,R5-2,R3-1),(nm-1,R2-3,A-10,R5-2,R3-2),(nm-1,R2-3,A-10,R5-3,R3-1),(nm-1,R2-3,A-10,R5-3,R3-2),(nm-1,R2-3,A-11,R5-1,R3-1),(nm-1,R2-3,A-11,R5-1,R3-2),(nm-1,R2-3,A-11,R5-2,R3-1),(nm-1,R2-3,A-11,R5-2,R3-2),(nm-1,R2-3,A-11,R5-3,R3-1),(nm-1,R2-3,A-11,R5-3,R3-2),(nm-1,R2-3,A-12,R5-1,R3-1),(nm-1,R2-3,A-12,R5-1,R3-2),(nm-1,R2-3,A-12,R5-2,R3-1),(nm-1,R2-3,A-12,R5-2,R3-2),(nm-

1,R2-3,A-12,R5-3,R3-1),(nm-1,R2-3,A-12,R5-3,R3-2),
(nm-1,R2-3,A-13,R5-1,R3-1),(nm-1,R2-3,A-13,R5-1,R3-2),(nm-1,R2-3,A-13,R5-2,R3-1),(nm-1,R2-3,A-13,R5-2,R3-2),(nm-1,R2-3,A-13,R5-3,R3-1),(nm-1,R2-3,A-13,R5-3,R3-2),(nm-1,R2-3,A-14,R5-1,R3-1),(nm-1,R2-3,A-14,R5-1,R3-2),(nm-1,R2-3,A-14,R5-2,R3-1),(nm-1,R2-3,A-14,R5-2,R3-2),(nm-1,R2-3,A-14,R5-3,R3-1),(nm-1,R2-3,A-14,R5-3,R3-2),(nm-1,R2-4,A-1,R5-1,R3-1),(nm-1,R2-4,A-1,R5-1,R3-2),(nm-1,R2-4,A-1,R5-2,R3-1),(nm-1,R2-4,A-1,R5-2,R3-2),(nm-1,R2-4,A-1,R5-3,R3-1),(nm-1,R2-4,A-1,R5-3,R3-2),(nm-1,R2-4,A-2,R5-1,R3-1),(nm-1,R2-4,A-2,R5-1,R3-2),(nm-1,R2-4,A-2,R5-2,R3-1),(nm-1,R2-4,A-2,R5-2,R3-2),(nm-1,R2-4,A-2,R5-3,R3-1),(nm-1,R2-4,A-2,R5-3,R3-2),(nm-1,R2-4,A-3,R5-1,R3-1),(nm-1,R2-4,A-3,R5-1,R3-2),(nm-1,R2-4,A-3,R5-2,R3-1),(nm-1,R2-4,A-3,R5-2,R3-2),(nm-1,R2-4,A-3,R5-3,R3-1),(nm-1,R2-4,A-3,R5-3,R3-2),(nm-1,R2-4,A-4,R5-1,R3-1),(nm-1,R2-4,A-4,R5-1,R3-2),(nm-1,R2-4,A-4,R5-2,R3-1),(nm-1,R2-4,A-4,R5-2,R3-2),(nm-1,R2-4,A-4,R5-3,R3-1),(nm-1,R2-4,A-4,R5-3,R3-2),(nm-1,R2-4,A-5,R5-1,R3-1),(nm-1,R2-4,A-5,R5-1,R3-2),(nm-1,R2-4,A-5,R5-2,R3-1),(nm-1,R2-4,A-5,R5-2,R3-2),(nm-1,R2-4,A-5,R5-3,R3-1),(nm-1,R2-4,A-5,R5-3,R3-2),(nm-1,R2-4,A-6,R5-1,R3-1),(nm-1,R2-4,A-6,R5-1,R3-2),(nm-1,R2-4,A-6,R5-2,R3-1),(nm-1,R2-4,A-6,R5-2,R3-2),(nm-1,R2-4,A-6,R5-3,R3-1),(nm-1,R2-4,A-6,R5-3,R3-2),(nm-1,R2-4,A-7,R5-1,R3-1),(nm-1,R2-4,A-7,R5-1,R3-2),(nm-1,R2-4,A-7,R5-2,R3-1),(nm-1,R2-4,A-7,R5-2,R3-2),(nm-1,R2-4,A-7,R5-3,R3-1),(nm-1,R2-4,A-7,R5-3,R3-2),(nm-1,R2-4,A-8,R5-1,R3-1),(nm-1,R2-4,A-8,R5-1,R3-2),(nm-1,R2-4,A-8,R5-2,R3-1),(nm-1,R5-4,A-8,R5-2,R6-2),(nm-1,R2-4,A-8,R5-3,R3-1),(nm-1,R2-4,A-8,R5-3,R3-2),(nm-1,R2-4,A-9,R5-1,R3-1),(nm-1,R2-4,A-9,R5-1,R3-2),(nm-1,R2-4,A-9,R5-2,R3-1),(nm-1,R2-4,A-9,R5-2,R3-2),(nm-1,R2-4,A-9,R5-3,R3-1),(nm-1,R2-4,A-9,R5-3,R3-2),(nm-1,R2-4,A-10,R5-1,R3-1),(nm-1,R2-4,A-10,R5-1,R3-2),(nm-1,R2-4,A-10,R5-2,R3-1),(nm-1,R2-4,A-10,R5-2,R3-2),(nm-1,R2-4,A-10,R5-3,R3-1),(nm-1,R2-4,A-10,R5-3,R3-2),(nm-1,R2-4,A-11,R5-1,R3-1),(nm-1,R2-4,A-11,R5-1,R3-2),(nm-1,R2-4,A-11,R5-2,R3-1),(nm-1,R2-4,A-11,R5-2,R3-2),(nm-1,R2-4,A-11,R5-3,R3-1),(nm-1,R2-4,A-11,R5-3,R3-2),(nm-1,R2-4,A-12,R5-1,R3-1),(nm-1,R2-4,A-12,R5-1,R3-2),(nm-1,R2-4,A-12,R5-2,R3-1),(nm-1,R2-4,A-12,R5-2,R3-2),(nm-1,R2-4,A-12,R5-3,R3-1),(nm-1,R2-4,A-12,R5-3,R3-2),(nm-1,R2-4,A-13,R5-1,R3-1),(nm-1,R2-4,A-13,R5-1,R3-2),(nm-1,R2-4,A-13,R5-2,R3-1),(nm-1,R2-4,A-13,R5-2,R3-2),(nm-1,R2-4,A-13,R5-3,R3-1),(nm-1,R2-4,A-13,R5-3,R3-2),(nm-1,R2-4,A-14,R5-1,R3-1),(nm-1,R2-4,A-14,R5-1,R3-2),(nm-1,R2-4,A-14,R5-2,R3-1),(nm-1,R2-4,A-14,R5-2,R3-2),(nm-1,R2-4,A-14,R5-3,R3-1),(nm-1,R2-4,A-14,R5-3,R3-2), (nm-2,R2-1,A-1,R5-1,R3-1),(nm-2,R2-1,A-1,R5-1,R3-2),(nm-2,R2-1,A-1,R5-2,R3-1),(nm-2,R2-1,A-1,R5-2,R3-2),(nm-2,R2-1,A-1,R5-3,R3-1),(nm-2,R2-1,A-1,R5-3,R3-2),(nm-2,R2-1,A-2,R5-1,R3-1),(nm-2,R2-1,A-2,R5-1,R3-2),(nm-2,R2-1,A-2,R5-2,R3-1),(nm-2,R2-1,A-2,R5-2,R3-2),(nm-2,R2-1,A-2,R5-3,R3-1),(nm-2,R2-1,A-2,R5-3,R3-2),(nm-2,R2-1,A-3,R5-1,R3-1),(nm-2,R2-1,A-3,R5-1,R3-2),(nm-2,R2-1,A-3,R5-2,R3-1),(nm-2,R2-1,A-3,R5-2,R3-2),(nm-2,R2-1,A-3,R5-3,R3-1),(nm-2,R2-1,A-3,R5-3,R3-2),(nm-2,R2-1,A-4,R5-1,R3-1),(nm-2,R2-1,A-4,R5-1,R3-2),(nm-2,R2-1,A-4,R5-2,R3-1),(nm-2,R2-1,A-4,R5-2,R3-2),(nm-2,R2-1,A-4,R5-3,R3-1),(nm-2,R2-1,A-4,R5-3,R3-2),(nm-2,R2-1,A-5,R5-1,R3-1),(nm-2,R2-1,A-5,R5-1,R3-2),(nm-2,R2-1,A-5,R5-2,R3-1),(nm-2,R2-1,A-5,R5-2,R3-2),(nm-2,R2-1,A-5,R5-3,R3-1),(nm-2,R2-1,A-5,R5-3,R3-2),(nm-2,R2-1,A-6,R5-1,R3-1),(nm-2,R2-1,A-6,R5-1,R3-2),(nm-2,R2-1,A-6,R5-2,R3-1),(nm-2,R2-1,A-6,R5-2,R3-2),(nm-2,R2-1,A-6,R5-3,R3-1),(nm-2,R2-1,A-6,R5-3,R3-2),(nm-2,R2-1,A-7,R5-1,R3-1),(nm-2,R2-1,A-7,R5-1,R3-2),(nm-2,R2-1,A-7,R5-2,R3-1),(nm-2,R2-1,A-7,R5-2,R3-2),(nm-2,R2-1,A-7,R5-3,R3-1),(nm-2,R2-1,A-7,R5-3,R3-2),(nm-2,R2-1,A-8,R5-1,R3-1),(nm-2,R2-1,A-8,R5-1,R3-2),(nm-2,R2-1,A-8,R5-2,R3-1),(nm-2,R2-1,A-8,R5-2,R3-2),(nm-2,R2-1,A-8,R5-3,R3-1),(nm-2,R2-1,A-8,R5-3,R3-2),(nm-2,R2-1,A-9,R5-1,R3-1),(nm-2,R2-1,A-9,R5-1,R3-2),(nm-2,R2-1,A-9,R5-2,R3-1),(nm-2,R2-1,A-9,R5-2,R3-2),(nm-2,R2-1,A-9,R5-3,R3-1),(nm-2,R2-1,A-9,R5-3,R3-2),(nm-2,R2-1,A-10,R5-1,R3-1),(nm-2,R2-1,A-10,R5-1,R3-2),(nm-2,R2-1,A-10,R5-2,R3-1),(nm-2,R2-1,A-10,R5-2,R3-2),(nm-2,R2-1,A-10,R5-3,R3-1),(nm-2,R2-1,A-10,R5-3,R3-2),(nm-2,R2-1,A-11,R5-1,R3-1),(nm-2,R2-1,A-11,R5-1,R3-2),(nm-2,R2-1,A-11,R5-2,R3-1),(nm-2,R2-1,A-11,R5-2,R3-2),(nm-2,R2-1,A-11,R5-3,R3-1),(nm-2,R2-1,A-11,R5-3,R3-2),(nm-2,R2-1,A-12,R5-1,R3-1),(nm-2,R2-1,A-12,R5-1,R3-2),(nm-2,R2-1,A-12,R5-2,R3-1),(nm-2,R2-1,A-12,R5-2,R3-2),(nm-2,R2-1,A-12,R5-3,R3-1),(nm-2,R2-1,A-12,R5-3,R3-2),(nm-2,R2-1,A-13,R5-1,R3-1),(nm-2,R2-1,A-13,R5-1,R3-2),(nm-2,R2-1,A-13,R5-2,R3-1),(nm-2,R2-1,A-13,R5-2,R3-2),(nm-2,R2-1,A-13,R5-3,R3-1),(nm-2,R2-1,A-13,R5-3,R3-2),(nm-2,R2-1,A-14,R5-1,R3-1),(nm-2,R2-1,A-14,R5-1,R3-2),(nm-2,R2-1,A-14,R5-2,R3-1),(nm-2,R2-1,A-14,R5-2,R3-2),(nm-2,R2-1,A-14,R5-3,R3-1),(nm-2,R2-1,A-14,R5-3,R3-2),(nm-2,R2-2,A-1,R5-1,R3-1),(nm-2,R2-2,A-1,R5-1,R3-2),(nm-2,R2-2,A-1,R5-2,R3-1),(nm-2,R2-2,A-1,R5-2,R3-2),(nm-2,R2-2,A-1,R5-3,R3-1),(nm-2,R2-2,A-1,R5-3,R3-2),(nm-2,R2-2,A-2,R5-1,R3-1),(nm-2,R2-2,A-2,R5-1,R3-2),(nm-2,R2-2,A-2,R5-2,R3-1),(nm-2,R2-2,A-2,R5-2,R3-2),(nm-2,R2-2,A-2,R5-3,R3-1),(nm-2,R2-2,A-2,R5-3,R3-2),(nm-2,R2-2,A-3,R5-1,R3-1),(nm-2,R2-2,A-3,R5-1,R3-2),(nm-2,R2-2,A-3,R5-2,R3-1),(nm-2,R2-2,A-3,R5-2,R3-2),(nm-2,R2-2,A-3,R5-3,R3-1),(nm-2,R2-2,A-3,R5-3,R3-2),(nm-2,R2-2,A-4,R5-1,R3-1),(nm-2,R2-2,A-4,R5-1,R3-2),(nm-2,R2-2,A-4,R5-2,R3-1),(nm-2,R2-2,A-4,R5-2,R3-2),(nm-2,R2-2,A-4,R5-3,R3-1),(nm-2,R2-2,A-4,R5-3,R3-2),(nm-2,R2-2,A-5,R5-1,R3-1),(nm-2,R2-2,A-5,R5-2,R3-1),(nm-2,R2-2,A-5,R5-2,R3-2),(nm-2,R2-2,A-5,R5-3,R3-1),(nm-2,R2-2,A-5,R5-3,R3-2),(nm-2,R2-2,A-6,R5-1,R3-1),(nm-2,R2-2,A-6,R5-1,R3-2),(nm-2,R2-2,A-6,R5-2,R3-1),(nm-2,R2-2,A-6,R5-2,R3-2),(nm-2,R2-2,A-6,R5-3,R3-1),(nm-2,R2-2,A-6,R5-3,R3-2),(nm-2,R2-2,A-7,R5-1,R3-1),(nm-2,R2-2,A-7,R5-1,R3-2),(nm-2,R2-2,A-7,R5-2,R3-1),(nm-2,R2-2,A-7,R5-2,R3-2),(nm-2,R2-2,A-7,R5-3,R3-1),(nm-2,R2-2,A-7,R5-3,R3-2),(nm-2,R2-2,A-8,R5-1,R3-1),(nm-2,R2-2,A-8,R5-1,R3-2),(nm-2,R2-2,A-8,R5-2,R3-1),(nm-2,R2-2,A-8,R5-2,R3-2),(nm-2,R2-2,A-8,R5-3,R3-1),(nm-2,R2-2,A-8,R5-3,R3-2),(nm-2,R2-2,A-9,R5-1,R3-1),(nm-2,R2-2,A-9,R5-1,R3-2),(nm-2,R2-2,A-9,R5-2,R3-1),(nm-2,R2-2,A-9,R5-2,R3-2),(nm-2,R2-2,A-9,R5-3,R3-1),(nm-2,R2-2,A-9,R5-3,R3-2),(nm-2,R2-2,A-10,R5-1,R3-1),(nm-2,R2-2,A-10,R5-1,R3-2),(nm-2,R2-2,A-10,R5-2,R3-1),(nm-2,R2-2,A-10,R5-2,R3-2),(nm-2,R2-2,A-10,R5-3,R3-1),(nm-2,R2-2,A-10,R5-3,R3-2),(nm-2,R2-2,A-11,R5-1,R3-1),(nm-2,R2-2,A-11,R5-1,R3-2),(nm-2,R2-2,A-11,R5-2,R3-1),(nm-2,R2-2,A-11,R5-2,R3-2),(nm-2,R2-2,A-11,R5-3,R3-1),(nm-2,R2-2,A-11,R5-3,R3-2),(nm-2,R2-2,A-12,R5-1,R3-1),(nm-2,R2-2,A-12,R5-1,R3-2),(nm-2,R2-2,A-12,R5-2,R3-1),(nm-2,R2-2,A-12,R5-2,R3-2),(nm-2,R2-2,A-12,R5-3,R3-1),(nm-2,R2-2,A-12,R5-3,R3-2),(nm-2,R2-2,A-13,R5-1,R3-1),(nm-2,R2-2,A-13,R5-1,R3-2),(nm-2,R2-2,A-13,R5-2,R3-1),(nm-2,R2-2,A-13,R5-2,R3-2),(nm-2,R2-2,A-13,R5-3,R3-1),(nm-2,R2-2,A-13,R5-3,R3-2),(nm-2,R2-2,A-14,R5-1,R3-1),(nm-2,R2-2,A-14,R5-1,R3-2),(nm-

2,R2-2,A-14,R5-2,R3-1),(nm-2,R2-2,A-14,R5-2,R3-2),
(nm-2,R2-2,A-14,R5-3,R3-1),(nm-2,R2-2,A-14,R5-3,R3-2),(nm-2,R2-3,A-1,R5-1,R3-1),(nm-2,R2-3,A-1,R5-1,R3-2),(nm-2,R2-3,A-1,R5-2,R3-1),(nm-2,R2-3,A-1,R5-2,R3-2),(nm-2,R2-3,A-1,R5-3,R3-1),(nm-2,R2-3,A-1,R5-3,R3-2),(nm-2,R2-3,A-2,R5-1,R3-1),(nm-2,R2-3,A-2,R5-1,R3-2),(nm-2,R2-3,A-2,R5-2,R3-1),(nm-2,R2-3,A-2,R5-2,R3-2),(nm-2,R2-3,A-2,R5-3,R3-1),(nm-2,R2-3,A-2,R5-3,R3-2),(nm-2,R2-3,A-3,R5-1,R3-1),(nm-2,R2-3,A-3,R5-1,R3-2),(nm-2,R2-3,A-3,R5-2,R3-1),(nm-2,R2-3,A-3,R5-2,R3-2),(nm-2,R2-3,A-3,R5-3,R3-1),(nm-2,R2-3,A-3,R5-3,R3-2),(nm-2,R2-3,A-4,R5-1,R3-1),(nm-2,R2-3,A-4,R5-1,R3-2),(nm-2,R2-3,A-4,R5-2,R3-1),(nm-2,R2-3,A-4,R5-2,R3-2),(nm-2,R2-3,A-4,R5-3,R3-1),(nm-2,R2-3,A-4,R5-3,R3-2),(nm-2,R2-3,A-5,R5-1,R3-1),(nm-2,R2-3,A-5,R5-1,R3-2),(nm-2,R2-3,A-5,R5-2,R3-1),(nm-2,R2-3,A-5,R5-2,R3-2),(nm-2,R2-3,A-5,R5-3,R3-1),(nm-2,R2-3,A-5,R5-3,R3-2),(nm-2,R2-3,A-6,R5-1,R3-1),(nm-2,R2-3,A-6,R5-1,R3-2),(nm-2,R2-3,A-6,R5-2,R3-1),(nm-2,R2-3,A-6,R5-2,R3-2),(nm-2,R2-3,A-6,R5-3,R3-1),(nm-2,R2-3,A-6,R5-3,R3-2),(nm-2,R2-3,A-7,R5-1,R3-1),(nm-2,R2-3,A-7,R5-1,R3-2),(nm-2,R2-3,A-7,R5-2,R3-1),(nm-2,R2-3,A-7,R5-2,R3-2),(nm-2,R2-3,A-7,R5-3,R3-1),(nm-2,R2-3,A-7,R5-3,R3-2),(nm-2,R2-3,A-8,R5-1,R3-1),(nm-2,R2-3,A-8,R5-1,R3-2),(nm-2,R2-3,A-8,R5-2,R3-1),(nm-2,R2-3,A-8,R5-2,R3-2),(nm-2,R2-3,A-8,R5-3,R3-1),(nm-2,R2-3,A-8,R5-3,R3-2),(nm-2,R2-3,A-9,R5-1,R3-1),(nm-2,R2-3,A-9,R5-1,R3-2),(nm-2,R2-3,A-9,R5-2,R3-1),(nm-2,R2-3,A-9,R5-2,R3-2),(nm-2,R2-3,A-9,R5-3,R3-1),(nm-2,R2-3,A-9,R5-3,R3-2),(nm-2,R2-3,A-10,R5-1,R3-1),(nm-2,R2-3,A-10,R5-1,R3-2),(nm-2,R2-3,A-10,R5-2,R3-1),(nm-2,R2-3,A-10,R5-2,R3-2),(nm-2,R2-3,A-10,R5-3,R3-1),(nm-2,R2-3,A-10,R5-3,R3-2),(nm-2,R2-3,A-11,R5-1,R3-1),(nm-2,R2-3,A-11,R5-1,R3-2),(nm-2,R2-3,A-11,R5-2,R3-1),(nm-2,R2-3,A-11,R5-2,R3-2),(nm-2,R2-3,A-11,R5-3,R3-1),(nm-2,R2-3,A-11,R5-3,R3-2),(nm-2,R2-3,A-12,R5-1,R3-1),(nm-2,R2-3,A-12,R5-1,R3-2),(nm-2,R2-3,A-12,R5-2,R3-1),(nm-2,R2-3,A-12,R5-2,R3-2),(nm-2,R2-3,A-12,R5-3,R3-1),(nm-2,R2-3,A-12,R5-3,R3-2),(nm-2,R2-3,A-13,R5-1,R3-1),(nm-2,R2-3,A-13,R5-1,R3-2),(nm-2,R2-3,A-13,R5-2,R3-1),(nm-2,R2-3,A-13,R5-2,R3-2),(nm-2,R2-3,A-13,R5-3,R3-1),(nm-2,R2-3,A-13,R5-3,R3-2),(nm-2,R2-3,A-14,R5-1,R3-1),(nm-2,R2-3,A-14,R5-1,R3-2),(nm-2,R2-3,A-14,R5-2,R3-1),(nm-2,R2-3,A-14,R5-2,R3-2),(nm-2,R2-3,A-14,R5-3,R3-1),(nm-2,R2-3,A-14,R5-3,R3-2),(nm-2,R2-4,A-1,R5-1,R3-1),(nm-2,R2-4,A-1,R5-1,R3-2),(nm-2,R2-4,A-1,R5-2,R3-1),(nm-2,R2-4,A-1,R5-2,R3-2),(nm-2,R2-4,A-1,R5-3,R3-1),(nm-2,R2-4,A-1,R5-3,R3-2),(nm-2,R2-4,A-2,R5-1,R3-1),(nm-2,R2-4,A-2,R5-1,R3-2),(nm-2,R2-4,A-2,R5-2,R3-1),(nm-2,R2-4,A-2,R5-2,R3-2),(nm-2,R2-44-2,R5-3,R3-1),(nm-2,R2-4,A-2,R5-3,R3-2),(nm-2,R2-4,A-3,R5-1,R3-1),(nm-2,R2-4,A-3,R5-1,R3-2),(nm-2,R2-4,A-3,R5-2,R3-1),(nm-2,R2-4,A-3,R5-2,R3-2),(nm-2,R2-4,A-3,R5-3,R3-1),(nm-2,R2-4,A-3,R5-3,R3-2),(nm-2,R2-4,A-4,R5-1,R3-1),(nm-2,R2-4,A-4,R5-1,R3-2),(nm-2,R2-4,A-4,R5-2,R3-1),(nm-2,R2-4,A-4,R5-2,R3-2),(nm-2,R2-4,A-4,R5-3,R3-1),(nm-2,R2-4,A-4,R5-3,R3-2),(nm-2,R2-4,A-5,R5-1,R3-1),(nm-2,R2-4,A-5,R5-1,R3-2),(nm-2,R2-4,A-5,R5-2,R3-1),(nm-2,R2-4,A-5,R5-2,R3-2),(nm-2,R2-4,A-5,R5-3,R3-1),(nm-2,R2-4,A-5,R5-3,R3-2),(nm-2,R2-4,A-6,R5-1,R3-1),(nm-2,R2-4,A-6,R5-1,R3-2),(nm-2,R2-4,A-6,R5-2,R3-1),(nm-2,R2-4,A-6,R5-2,R3-2),(nm-2,R2-4,A-6,R5-3,R3-1),(nm-2,R2-4,A-6,R5-3,R3-2),(nm-2,R2-4,A-7,R5-1,R3-1),(nm-2,R2-4,A-7,R5-1,R3-2),(nm-2,R2-4,A-7,R5-2,R3-1),(nm-2,R2-4,A-7,R5-2,R3-2),(nm-2,R2-4,A-7,R5-3,R3-1),(nm-2,R2-4,A-7,R5-3,R3-2),(nm-2,R2-4,A-8,R5-1,R3-1),(nm-2,R2-4,A-8,R5-1,R3-2),(nm-2,R2-4,A-8,R5-2,R3-1),(nm-2,R2-4,A-8,R5-2,R3-2),(nm-2,R2-4,A-8,R5-3,R3-1),(nm-2,R2-4,A-8,R5-3,R3-2),(nm-2,R2-4,A-9,R5-1,R3-1),(nm-2,R2-4,A-9,R5-1,R3-2),(nm-2,R2-4,A-9,R5-2,R3-1),(nm-2,R2-4,A-9,R5-2,R3-2),(nm-2,R2-4,A-9,R5-3,R3-1),(nm-2,R2-4,A-9,R5-3,R3-2),(nm-2,R2-4,A-10,R5-1,R3-1),(nm-2,R2-4,A-10,R5-1,R3-2),(nm-2,R2-4,A-10,R5-2,R3-1),(nm-2,R2-4,A-10,R5-2,R3-2),(nm-2,R2-4,A-10,R5-3,R3-1),(nm-2,R2-4,A-10,R5-3,R3-2),(nm-2,R2-4,A-11,R5-1,R3-1),(nm-2,R2-4,A-11,R5-1,R3-2),(nm-2,R2-4,A-11,R5-2,R3-1),(nm-2,R2-4,A-11,R5-2,R3-2),(nm-2,R2-4,A-11,R5-3,R3-1),(nm-2,R2-4,A-11,R5-3,R3-2),
(nm-2,R2-4,A-12,R5-1,R3-1),(nm-2,R2-4,A-12,R5-1,R3-2),(nm-2,R2-4,A-12,R5-2,R3-1),(nm-2,R2-4,A-12,R5-2,R3-2),(nm-2,R2-4,A-12,R5-3,R3-1),(nm-2,R2-4,A-12,R5-3,R3-2),(nm-2,R2-4,A-13,R5-1,R3-1),(nm-2,R2-4,A-13,R5-1,R3-2),(nm-2,R2-4,A-13,R5-2,R3-1),(nm-2,R2-4,A-13,R5-2,R3-2),(nm-2,R2-4,A-13,R5-3,R3-1),(nm-2,R2-4,A-13,R5-3,R3-2),(nm-2,R2-4,A-14,R5-1,R3-1),(nm-2,R2-4,A-14,R5-1,R3-2),(nm-2,R2-4,A-14,R5-2,R3-1),(nm-2,R2-4,A-14,R5-2,R3-2),(nm-2,R2-4,A-14,R5-3,R3-1),(nm-2,R2-4,A-14,R5-3,R3-2),
(nm-3,R2-1,A-1,R5-1,R3-1),(nm-3,R2-1,A-1,R5-1,R3-2),(nm-3,R2-1,A-1,R5-2,R3-1),(nm-3,R2-1,A-1,R5-2,R3-2),(nm-3,R2-1,A-1,R5-3,R3-1),(nm-3,R2-1,A-1,R5-3,R3-2),(nm-3,R2-1,A-2,R5-1,R3-1),(nm-3,R2-1,A-2,R5-1,R3-2),(nm-3,R2-1,A-2,R5-2,R3-1),(nm-3,R2-1,A-2,R5-2,R3-2),(nm-3,R2-1,A-2,R5-3,R3-1),(nm-3,R2-1,A-2,R5-3,R3-2),(nm-3,R2-1,A-3,R5-1,R3-1),(nm-3,R2-1,A-3,R5-1,R3-2),(nm-3,R2-1,A-3,R5-2,R3-1),(nm-3,R2-1,A-3,R5-2,R3-2),(nm-3,R2-1,A-3,R5-3,R3-1),(nm-3,R2-1,A-3,R5-3,R3-2),(nm-3,R2-1,A-4,R5-1,R3-1),(nm-3,R2-1,A-4,R5-1,R3-2),(nm-3,R2-1,A-4,R5-2,R3-1),(nm-3,R2-1,A-4,R5-2,R3-2),(nm-3,R2-1,A-4,R5-3,R3-1),(nm-3,R2-1,A-4,R5-3,R3-2),(nm-3,R2-1,A-5,R5-1,R3-1),(nm-3,R2-1,A-5,R5-1,R3-2),(nm-3,R2-1,A-5,R5-2,R3-1),(nm-3,R2-1,A-5,R5-2,R3-2),(nm-3,R2-1,A-5,R5-3,R3-1),(nm-3,R2-1,A-5,R5-3,R3-2),(nm-3,R2-1,A-6,R5-1,R3-1),(nm-3,R2-1,A-6,R5-1,R3-2),(nm-3,R2-1,A-6,R5-2,R3-1),(nm-3,R2-1,A-6,R5-2,R3-2),(nm-3,R2-1,A-6,R5-3,R3-1),(nm-3,R2-1,A-6,R5-3,R3-2),(nm-3,R2-1,A-7,R5-1,R3-1),(nm-3,R2-1,A-7,R5-1,R3-2),(nm-3,R2-1,A-7,R5-2,R3-1),(nm-3,R2-1,A-7,R5-2,R3-2),(nm-3,R2-1,A-7,R5-3,R3-1),(nm-3,R2-1,A-7,R5-3,R3-2),(nm-3,R2-1,A-8,R5-1,R3-1),(nm-3,R2-1,A-8,R5-1,R3-2),(nm-3,R2-1,A-8,R5-2,R3-1),(nm-3,R2-1,A-8,R5-2,R3-2),(nm-3,R2-1,A-8,R5-3,R3-1),(nm-3,R2-1,A-8,R5-3,R3-2),(nm-3,R2-1,A-9,R5-1,R3-1),(nm-3,R2-1,A-9,R5-1,R3-2),(nm-3,R2-1,A-9,R5-2,R3-1),(nm-3,R2-1,A-9,R5-2,R3-2),(nm-3,R2-1,A-9,R5-3,R3-1),(nm-3,R2-1,A-9,R5-3,R3-2),(nm-3,R2-1,A-10,R5-1,R3-1),(nm-3,R2-1,A-10,R5-1,R3-2),(nm-3,R2-1,A-10,R5-2,R3-1),(nm-3,R2-1,A-10,R5-2,R3-2),(nm-3,R2-1,A-10,R5-3,R3-1),(nm-3,R2-1,A-10,R5-3,R3-2),(nm-3,R2-1,A-11,R5-1,R3-1),(nm-3,R2-1,A-11,R5-1,R3-2),(nm-3,R2-1,A-11,R5-2,R3-1),(nm-3,R2-1,A-11,R5-2,R3-2),(nm-3,R2-1,A-11,R5-3,R3-1),(nm-3,R2-1,A-11,R5-3,R3-2),(nm-3,R2-1,A-12,R5-1,R3-1),(nm-3,R2-1,A-12,R5-1,R3-2),(nm-3,R2-1,A-12,R5-2,R3-1),(nm-3,R2-1,A-12,R5-2,R3-2),(nm-3,R2-1,A-12,R5-3,R3-1),(nm-3,R2-1,A-12,R5-3,R3-2),(nm-3,R2-1,A-13,R5-1,R3-1),(nm-3,R2-1,A-13,R5-1,R3-2),(nm-3,R2-1,A-13,R5-2,R3-1),(nm-3,R2-1,A-13,R5-2,R3-2),(nm-3,R2-1,A-13,R5-3,R3-1),(nm-3,R2-1,A-13,R5-3,R3-2),(nm-3,R2-1,A-14,R5-1,R3-1),(nm-3,R2-1,A-14,R5-1,R3-2),(nm-3,R2-1,A-14,R5-2,R3-1),(nm-3,R2-1,A-14,R5-2,R3-2),(nm-3,R2-1,A-14,R5-3,R3-1),(nm-3,R2-1,A-14,R5-3,R3-2),(nm-3,R2-2,A-1,R5-1,R3-1),(nm-3,R2-2,A-1,R5-1,R3-2),(nm-3,R2-2,A-1,R5-2,R3-1),(nm-3,R2-2,A-1,R5-2,R3-2),(nm-3,R2-2,A-1,R5-3,R3-1),(nm-3,R2-2,A-1,R5-3,R3-2),(nm-3,R2-2,

A-2,R5-1,R3-1),(nm-3,R2-2,A-2,R5-1,R3-2),(nm-3,R2-2, A-2,R5-2,R3-1),(nm-3,R2-2,A-2,R5-2,R3-2),(nm-3,R2-2, A-2,R5-3,R3-1),(nm-3,R2-2,A-2,R5-3,R3-2),(nm-3,R2-2, A-3,R5-1,R3-1),(nm-3,R2-2,A-3,R5-1,R3-2),(nm-3,R2-2, A-3,R5-2,R3-1),(nm-3,R2-2,A-3,R5-2,R3-2),(nm-3,R2-2, A-3,R5-3,R3-1),(nm-3,R2-2,A-3,R5-3,R3-2),(nm-3,R2-2, A-4,R5-1,R3-1),(nm-3,R2-2,A-4,R5-1,R3-2),(nm-3,R2-2, A-4,R5-2,R3-1),(nm-3,R2-2,A-4,R5-2,R3-2),(nm-3,R2-2, A-4,R5-3,R3-1),(nm-3,R2-2,A-4,R5-3,R3-2),(nm-3,R2-2, A-5,R5-1,R3-1),(nm-3,R2-2,A-5,R5-1,R3-2),(nm-3,R2-2, A-5,R5-2,R3-1),(nm-3,R2-2,A-5,R5-2,R3-2),(nm-3,R2-2, A-5,R5-3,R3-1),(nm-3,R2-2,A-5,R5-3,R3-2),(nm-3,R2-2, A-6,R5-1,R3-1),(nm-3,R2-2,A-6,R5-1,R3-2),(nm-3,R2-2, A-6,R5-2,R3-1),(nm-3,R2-2,A-6,R5-2,R3-2),(nm-3,R2-2, A-6,R5-3,R3-1),(nm-3,R2-2,A-6,R5-3,R3-2),(nm-3,R2-2, A-7,R5-1,R3-1),(nm-3,R2-2,A-7,R5-1,R3-2),(nm-3,R2-2, A-7,R5-2,R3-1),(nm-3,R2-2,A-7,R5-2,R3-2),(nm-3,R2-2, A-7,R5-3,R3-1),(nm-3,R2-2,A-7,R5-3,R3-2),(nm-3,R2-2, A-8,R5-1,R3-1),(nm-3,R2-2,A-8,R5-1,R3-2),(nm-3,R2-2, A-8,R5-2,R3-1),(nm-3,R2-2,A-8,R5-2,R3-2),(nm-3,R2-2, A-8,R5-3,R3-1),(nm-3,R2-2,A-8,R5-3,R3-2),(nm-3,R2-2, A-9,R5-1,R3-1),(nm-3,R2-2,A-9,R5-1,R3-2),(nm-3,R2-2, A-9,R5-2,R3-1),(nm-3,R2-2,A-9,R5-2,R3-2),(nm-3,R2-2, A-9,R5-3,R3-1),(nm-3,R2-2,A-9,R5-3,R3-2),(nm-3,R2-2, A-10,R5-1,R3-1),(nm-3,R2-2,A-10,R5-1,R3-2),(nm-3,R2-2,A-10,R5-2,R3-1),(nm-3,R2-2,A-10,R5-2,R3-2),(nm-3,R2-2,A-10,R5-3,R3-1),(nm-3,R2-2,A-10,R5-3,R3-2),(nm-3,R2-2,A-11,R5-1,R3-1),(nm-3,R2-2,A-11,R5-1,R3-2),(nm-3,R2-2,A-11,R5-2,R3-1),(nm-3,R2-2,A-11,R5-2,R3-2),(nm-3,R2-2,A-11,R5-3,R3-1),(nm-3,R2-2,A-11,R5-3,R3-2),(nm-3,R2-2,A-12,R5-1,R3-1),(nm-3,R2-2,A-12,R5-1,R3-2),(nm-3,R2-2,A-12,R5-2,R3-1),(nm-3,R2-2,A-12,R5-2,R3-2),(nm-3,R2-2,A-12,R5-3,R3-1),(nm-3,R2-2,A-12,R5-3,R3-2),(nm-3,R2-2,A-13,R5-1,R3-1),(nm-3,R2-2,A-13,R5-1,R3-2),(nm-3,R2-2,A-13,R5-2,R3-1),(nm-3,R2-2,A-13,R5-2,R3-2),(nm-3,R2-2,A-13,R5-3,R3-1),(nm-3,R2-2,A-13,R5-3,R3-2),(nm-3,R2-2,A-14,R5-1,R3-1),(nm-3,R2-2,A-14,R5-1,R3-2),(nm-3,R2-2,A-14,R5-2,R3-1),(nm-3,R2-2,A-14,R5-2,R3-2),(nm-3,R2-2,A-14,R5-3,R3-1),(nm-3,R2-2,A-14,R5-3,R3-2),(nm-3,R2-3,A-1,R5-1,R3-1),(nm-3,R2-3,A-1,R5-1,R3-2),(nm-3,R2-3,A-1,R5-2,R3-1),(nm-3,R2-3,A-1,R5-2,R3-2),(nm-3,R2-3,A-1,R5-3,R3-1),(nm-3,R2-3,A-1,R5-3,R3-2),(nm-3,R2-3,A-2,R5-1,R3-1),(nm-3,R2-3,A-2,R5-1,R3-2),(nm-3,R2-3,A-2,R5-2,R3-1),(nm-3,R2-3,A-2,R5-2,R3-2),(nm-3,R2-3,A-2,R5-3,R3-1),(nm-3,R2-3,A-2,R5-3,R3-2),(nm-3,R2-3,A-3,R5-1,R3-1),(nm-3,R2-3,A-3,R5-1,R3-2),(nm-3,R2-3,A-3,R5-2,R3-1),(nm-3,R2-3,A-3,R5-2,R3-2),(nm-3,R2-3,A-3,R5-3,R3-1),(nm-3,R2-3,A-3,R5-3,R3-2),(nm-3,R2-3,A-4,R5-1,R3-1),(nm-3,R2-3,A-4,R5-1,R3-2),(nm-3,R2-3,A-4,R5-2,R3-1),(nm-3,R2-3,A-4,R5-2,R3-2),(nm-3,R2-3,A-4,R5-3,R3-1),(nm-3,R2-3,A-4,R5-3,R3-2),(nm-3,R2-3,A-5,R5-1,R3-1),(nm-3,R2-3,A-5,R5-1,R3-2),(nm-3,R2-3,A-5,R5-2,R3-1),(nm-3,R2-3,A-5,R5-2,R3-2),(nm-3,R2-3,A-5,R5-3,R3-1),(nm-3,R2-3,A-5,R5-3,R3-2),(nm-3,R2-3,A-6,R5-1,R3-1),(nm-3,R2-3,A-6,R5-1,R3-2),(nm-3,R2-3,A-6,R5-2,R3-1),(nm-3,R2-3,A-6,R5-2,R3-2),(nm-3,R2-3,A-6,R5-3,R3-1),(nm-3,R2-3,A-6,R5-3,R3-2),(nm-3,R2-3,A-7,R5-1,R3-1),(nm-3,R2-3,A-7,R5-1,R3-2),(nm-3,R2-3,A-7,R5-2,R3-1),(nm-3,R2-3,A-7,R5-2,R3-2),(nm-3,R2-3,A-7,R5-3,R3-1),(nm-3,R2-3,A-7,R5-3,R3-2),(nm-3,R2-3,A-8,R5-1,R3-1),(nm-3,R2-3,A-8,R5-1,R3-2),(nm-3,R2-3,A-8,R5-2,R3-1),(nm-3,R2-3,A-8,R5-2,R3-2),(nm-3,R2-3,A-8,R5-3,R3-1),(nm-3,R2-3,A-8,R5-3,R3-2),(nm-3,R2-3,A-9,R5-1,R3-1),(nm-3,R2-3,A-9,R5-1,R3-2),(nm-3,R2-3,A-9,R5-2,R3-1),(nm-3,R2-3,A-9,R5-2,R3-2),(nm-3,R2-3,A-9,R5-3,R3-1),(nm-3,R2-3,A-9,R5-3,R3-2),(nm-3,R2-3,A-10,R5-1,R3-1),(nm-3,R2-3,A-10,R5-1,R3-2),(nm-3,R2-3,A-10,R5-2,R3-1),(nm-3,R2-3,A-10,R5-2,R3-2),(nm-3,R2-3,A-10,R5-3,R3-1),(nm-3,R2-3,A-10,R5-3,R3-2),(nm-3,R2-3,A-11,R5-1,R3-1),(nm-3,R2-3,A-11,R5-1,R3-2),(nm-3,R2-3,A-11,R5-2,R3-1),(nm-3,R2-3,A-11,R5-2,R3-2),(nm-3,R2-3,A-11,R5-3,R3-1),(nm-3,R2-3,A-11,R5-3,R3-2),(nm-3,R2-3,A-12,R5-1,R3-1),(nm-3,R2-3,A-12,R5-1,R3-2),(nm-3,R2-3,A-12,R5-2,R3-1),(nm-3,R2-3,A-12,R5-2,R3-2),(nm-3,R2-3,A-12,R5-3,R3-1),(nm-3,R2-3,A-12,R5-3,R3-2), (nm-3,R2-3,A-13,R5-1,R3-1),(nm-3,R2-3,A-13,R5-1,R3-2),(nm-3,R2-3,A-13,R5-2,R3-1),(nm-3,R2-3,A-13,R5-2,R3-2),(nm-3,R2-3,A-13,R5-3,R3-1),(nm-3,R2-3,A-13,R5-3,R3-2),(nm-3,R2-3,A-14,R5-1,R3-1),(nm-3,R2-3,A-14,R5-1,R3-2),(nm-3,R2-3,A-14,R5-2,R3-1),(nm-3,R2-3,A-14,R5-2,R3-2),(nm-3,R2-3,A-14,R5-3,R3-1),(nm-3,R2-3,A-14,R5-3,R3-2),(nm-3,R2-4,A-1,R5-1,R3-1),(nm-3,R2-4,A-1,R5-1,R3-2),(nm-3,R2-4,A-1,R5-2,R3-1),(nm-3,R2-4,A-1,R5-2,R3-2),(nm-3,R2-4,A-1,R5-3,R3-1),(nm-3,R2-4,A-1,R5-3,R3-2),(nm-3,R2-4,A-2,R5-1,R3-1),(nm-3,R2-4,A-2,R5-1,R3-2),(nm-3,R2-4,A-2,R5-2,R3-1),(nm-3,R2-4,A-2,R5-2,R3-2),(nm-3,R2-4,A-2,R5-3,R3-1),(nm-3,R2-4,A-2,R5-3,R3-2),(nm-3,R2-4,A-3,R5-1,R3-1),(nm-3,R2-4,A-3,R5-1,R3-2),(nm-3,R2-4,A-3,R5-2,R3-1),(nm-3,R2-4,A-3,R5-2,R3-2),(nm-3,R2-4,A-3,R5-3,R3-1),(nm-3,R2-4,A-3,R5-3,R3-2),(nm-3,R2-4,A-4,R5-1,R3-1),(nm-3,R2-4,A-4,R5-1,R3-2),(nm-3,R2-4,A-4,R5-2,R3-1),(nm-3,R2-4,A-4,R5-2,R3-2),(nm-3,R2-4,A-4,R5-3,R3-1),(nm-3,R2-4,A-4,R5-3,R3-2),(nm-3,R2-4,A-5,R5-1,R3-1),(nm-3,R2-4,A-5,R5-1,R3-2),(nm-3,R2-4,A-5,R5-2,R3-1),(nm-3,R2-4,A-5,R5-2,R3-2),(nm-3,R2-4,A-5,R5-3,R3-1),(nm-3,R2-4,A-5,R5-3,R3-2),(nm-3,R2-4,A-6,R5-1,R3-1),(nm-3,R2-4,A-6,R5-1,R3-2),(nm-3,R2-4,A-6,R5-2,R3-1),(nm-3,R2-4,A-6,R5-2,R3-2),(nm-3,R2-4,A-6,R5-3,R3-1),(nm-3,R2-4,A-6,R5-3,R3-2),(nm-3,R2-4,A-7,R5-1,R3-1),(nm-3,R2-4,A-7,R5-1,R3-2),(nm-3,R2-4,A-7,R5-2,R3-1),(nm-3,R2-4,A-7,R5-2,R3-2),(nm-3,R2-4,A-7,R5-3,R3-1),(nm-3,R2-4,A-7,R5-3,R3-2),(nm-3,R2-4,A-8,R5-1,R3-1),(nm-3,R2-4,A-8,R5-1,R3-2),(nm-3,R2-4,A-8,R5-2,R3-1),(nm-3,R2-4,A-8,R5-2,R3-2),(nm-3,R2-4,A-8,R5-3,R3-1),(nm-3,R2-4,A-8,R5-3,R3-2),(nm-3,R2-4,A-9,R5-1,R3-1),(nm-3,R2-4,A-9,R5-1,R3-2),(nm-3,R2-4,A-9,R5-2,R3-1),(nm-3,R2-4,A-9,R5-2,R3-2),(nm-3,R2-4,A-9,R5-3,R3-1),(nm-3,R2-4,A-9,R5-3,R3-2),(nm-3,R2-4,A-10,R5-1,R3-1),(nm-3,R2-4,A-10,R5-1,R3-2),(nm-3,R2-4,A-10,R5-2,R3-1),(nm-3,R2-4,A-10,R5-2,R3-2),(nm-3,R2-4,A-10,R5-3,R3-1),(nm-3,R2-4,A-10,R5-3,R3-2),(nm-3,R2-4,A-11,R5-1,R3-1),(nm-3,R2-4,A-11,R5-1,R3-2),(nm-3,R2-4,A-11,R5-2,R3-1),(nm-3,R2-4,A-11,R5-2,R3-2),(nm-3,R2-4,A-11,R5-3,R3-1),(nm-3,R2-4,A-11,R5-3,R3-2),(nm-3,R2-4,A-12,R5-1,R3-1),(nm-3,R2-4,A-12,R5-1,R3-2),(nm-3,R2-4,A-12,R5-2,R3-1),(nm-3,R2-4,A-12,R5-2,R3-2),(nm-3,R2-4,A-12,R5-3,R3-1),(nm-3,R2-4,A-12,R5-3,R3-2),(nm-3,R2-4,A-13,R5-1,R3-1),(nm-3,R2-4,A-13,R5-1,R3-2),(nm-3,R2-4,A-13,R5-2,R3-1),(nm-3,R2-4,A-13,R5-2,R3-2),(nm-3,R2-4,A-13,R5-3,R3-1),(nm-3,R2-4,A-13,R5-3,R3-2),(nm-3,R2-4,A-14,R5-1,R3-1),(nm-3,R2-4,A-14,R5-1,R3-2),(nm-3,R2-4,A-14,R5-2,R3-1),(nm-3,R2-4,A-14,R5-2,R3-2),(nm-3,R2-4,A-14,R5-3,R3-1),(nm-3,R2-4,A-14,R5-3,R3-2),(nm-3,R2-4,A-14,R5-3,R3-3).

In a compound represented by the general formula (I'), a compound, wherein the combination of n, m, $R^{2a}$, $R^{2b}$, ring A, $R^5$, $R^{3a}$, and $R^{5b}$ (m, $R^2$, A, $R^5$, $R^3$) is one of the above compound, and E is a bond.

The compounds of the invention can be employed in the treatment and/or prevention of disease associated with the generation, secretion or deposition of β-amyloid protein, such as dementia of the Alzheimer's type (Alzheimer's disease, senile dementia of Alzheimer type), Down's syndrome, memory impairment, prion disease (Creutzfeldt-Jakob disease), mild cognitive impairment (MCI), Dutch type of hereditary cerebral hemorrhage with amyloidosis, cerebral amyloid angiopathy, other type of degenerative dementia, mixed dementia with Alzheimer's and vascular type, dementia with Parkinson's Disease, dementia with progressive supranuclear palsy, dementia with Cortico-basal degeneration, Alzheimer's disease with diffuse Lewy body disease, age-related macular degeneration, Parkinson's Disease, amyloid angiopathy and so on.

The compounds of the invention can be administrated in combination with other pharmaceutical agents such as other therapeutic drugs for Alzheimer's disease, acetylcholinesterase inhibitors and so on. The compounds of the invention can be treated with concomitantly with the anti-dementia agents such as Donepezil Hydrochloride, Tacrine, Galantamine, Rivastigmine, Zanapezil, Memantine, Vinpocetine.

When the present compound is administered to a human, it can be administered orally as powders, granules, tablets, capsules, pills, solutions, or the like, or parenterally as injectables, suppositories, transdermal absorbable agents, absorbable agents, or the like. In addition, the present compound can be formulated into pharmaceutical preparations by adding pharmaceutical additives such as excipients, binders, wetting agents, disintegrating agents, lubricants and the like, which are suitable for formulations and an effective amount of the present compound.

A dose is different depending on state of disease, an administration route, and an age and a weight of a patient, and is usually 0.1 μg to 1 g/day, preferably 0.01 to 200 mg/day when orally administered to an adult, and is usually 0.1 μg to 10 g/day, preferably 0.1 to 2 g/day when parenterally administered.

Following examples and test examples illustrate the present invention in more detail, but the present invention is not limited by these examples.

In example, the meaning of each abbreviation is following.
Me methyl
Et ethyl
iPr or Pr$^i$ isopropyl
Ph phenyl
Bn benzyl
Boc t-butoxycarbonyl
TBDPS t-butyldiphenylsilyl Example 1

The Synthesis of Compound 588

[Chemical formula 48]

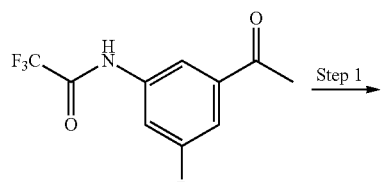

1-1

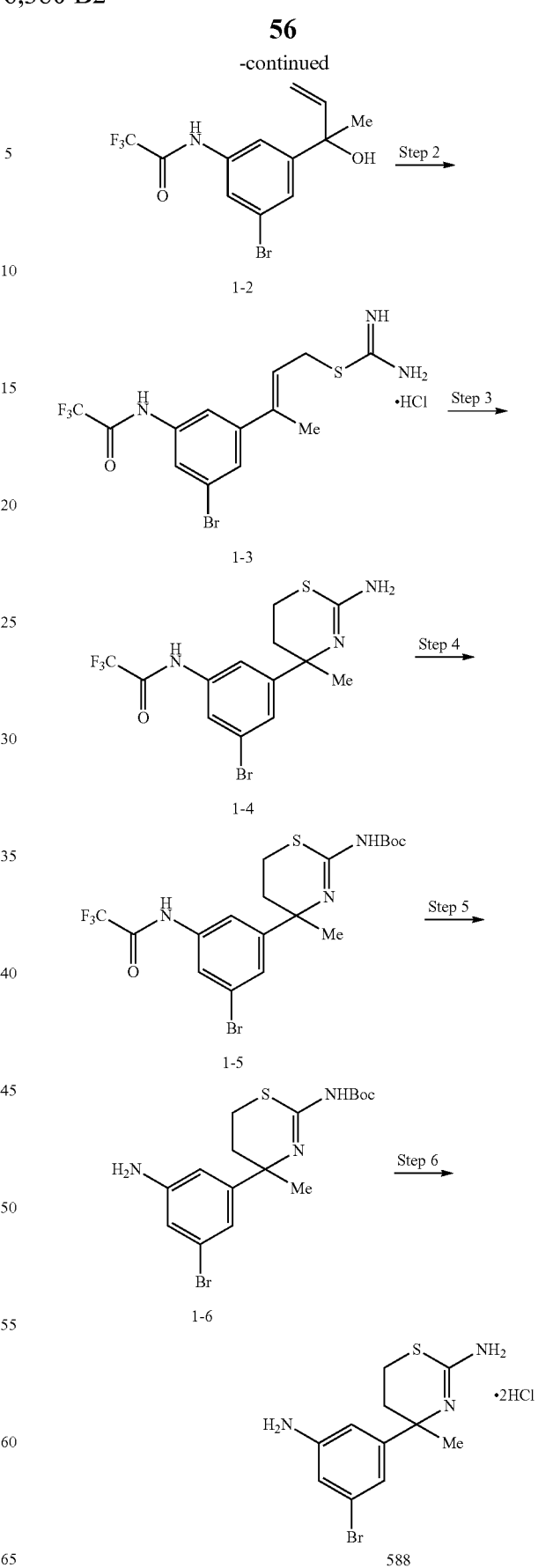

Step 1

Under nitrogen atmosphere, the compound (I-1)(7.98 g) was dissolved into diethyl ether (330 ml)-tetrahydrofuran (36 ml), vinylmagnesium chloride in tetrahydrofuran solution (1.32 mol/L, 44.8 ml) was added under cooling with dryice-acetone bath, and stirred for 20 min. Then, the reaction solution was stirred for 30 min under cooling with ice-water bath and stirred for 35 min at room temperature. And then, saturated ammonium chloride solution was added to the mixture, the mixture was extracted with ethyl acetate, and organic layer was washed with saturated ammonium chloride solution, saturated sodium hydrogencarbonate solution, and brine, and dried over anhydrous magnesium sulfate, and the solvent was evaporated. Then, the residue was purified by silica gel column chromatography to afford the compound (I-2)(6.00 g).

$^1$H-NMR (CDCl$_3$): 1.63 (3H, s), 2.08 (1H, br), 5.20 (1H, dd, J=10.6, 1.6 Hz), 5.31 (1H, dd, J=17.1, 1.6 Hz), 6.09 (1H, m), 7.46 (1H, m), 7.52 (1H, dd, J=3.4, 2.6 Hz), 7.80 (1H, dd, J=3.9, 2.6 Hz), 8.06 (1H, br)

Step 2

The compound (1-2)(6.36 g) was dissolved into acetic acid (30 ml), and added thiourea (1.50 g), 1 mol/L hydrochloride-acetic acid solution (20.7 ml). The reaction mixture was stirred at room temperature for 3 hours, then stirred at 40° C. for 3 hours, then stirred at room temperature for 66 hours, and at 40° C. for 19 hours. Thiourea (0.450 g), and 1 mol/L hydrochloric acid-acetic acid solution (7.53 ml) was added, and stirred at 40° C. for 23 hours. After the consumption of the compound (1-2), the solvent was evaporated under reduced pressure, then the obtained residue was crystallized from methanol-diethyl ether to afford the compound (1-3)(5.23 g) as crystal. On the other hand, mother liquid was evaporated under reduced pressure, and the compound (1-3)(3.00 g) was obtained as crude solid product.

$^1$H-NMR (DMSO-d$_6$): 2.09 (3H, s), 4.10 (2H, d, J=7.3 Hz), 5.94 (1H, t, J=7.7 Hz), 7.50 (1H, s), 7.75 (1H, s), 7.87 (1H, s), 9.17 (3H, br), 11.46 (1H, s)

Step 3

The compound (1-3)(5.23 g) dissolved in trifluoroacetic acid (25 ml) was added methanesulfonic acid (2.14 ml) dropwise under cooling with ice-water bath. After addition, the reaction mixture was stirred at room temperature for 3.5 hours. After the consumption of the compound (1-3), the solvent was evaporated under reduced pressure. To the residue obtained was added water and sodium carbonate, and then extracted with ethyl acetate. The organic layer was washed with saturated sodium hydrogencarbonate solution, and was dried over anhydrous magnesium sulfate, and the solvent was evaporated under reduced pressure to afford the compound (1-4)(4.90 g) as crude product.

$^1$H-NMR (CDCl$_3$): 1.53 (3H, s), 1.90 (1H, m), 2.09 (1H, m), 2.74 (1H, m), 2.97 (1H, m), 4.32 (2H, br), 7.34 (1H, t, J=1.6 Hz), 7.37 (1H, t, J=1.8 Hz), 7.86 (1H, t, J=1.8 Hz)

Step 4

Under nitrogen atmosphere, the compound (I-4)(4.90 g) dissolved in tetrahydrofuran was added di-t-butyl-dicarbonate (2.97 g) and triethylamine (1.89 ml) under cooling with ice-water bath and then stirred for 2 hours. The reaction mixture was stirred at room temperature for 3 hours. The reaction mixture was added water, and then extracted with ethyl acetate. The organic layer was washed with water, and dried over anhydrous magnesium sulfate, then the solvent was evaporated under reduced pressure. Then the obtained residue was crystallized from ethyl acetate-diethyl ether to afford the compound (1-5)(4.62 g) as crystal.

$^1$H-NMR (CDCl$_3$): 1.36 (9H, s), 1.72 (3H, s), 2.10 (1H, m), 2.41 (1H, m), 2.62 (1H, m), 2.75 (1H, m), 7.22 (1H, s), 7.48 (1H, s), 8.29 (1H, s)

Step 5

The compound (1-5)(1.00 g) was dissolved into tetrahydrofuran (8.7 ml), and 1 mol/L lithium hydroxide (4.43 ml) was added and stirred at 50° C. for 4 hours. Water was added to the reaction mixture, and the mixture was extracted with ethyl acetate, and the organic layer was washed with water, brine successively, and dried over anhydrous magnesium sulfate, and the solution was evaporated under reduced pressure. The obtained residue was purified by medium-pressured silica gel column chromatography to afford the compound (1-6)(0.668 g).

$^1$H-NMR (CDCl$_3$): 1.51 (9H, s), 1.63 (3H, s), 2.06 (1H, m), 2.40 (1H, m), 2.68-2.74 (2H, m), 3.83 (2H, br), 6.51 (1H, t, J=1.8 Hz), 6.72-6.74 (2H, m)

Step 6

The compound (1-6)(20.0 mg) was dissolved into 4 mol/L hydrochloric acid in 1,4-dioxane, and the mixture was stirred for 16 hours. The reaction solvent was evaporated under reduced pressure and the obtained residue was crystallized from methanol-diethyl ether to afford the compound (588) (14.7 mg).

$^1$H-NMR (DMSO-d$_6$): 1.59 (3H, s), 2.09-2.76 (4H, m), 6.44 (1H, t, J=1.6 Hz), 6.60 (1H, t J=1.9 Hz), 6.71 (1H, t, J=2.0 Hz), 10.4 (1H, s)

Example 2

The Synthesis of Compound 835

[Chemical formula 49]

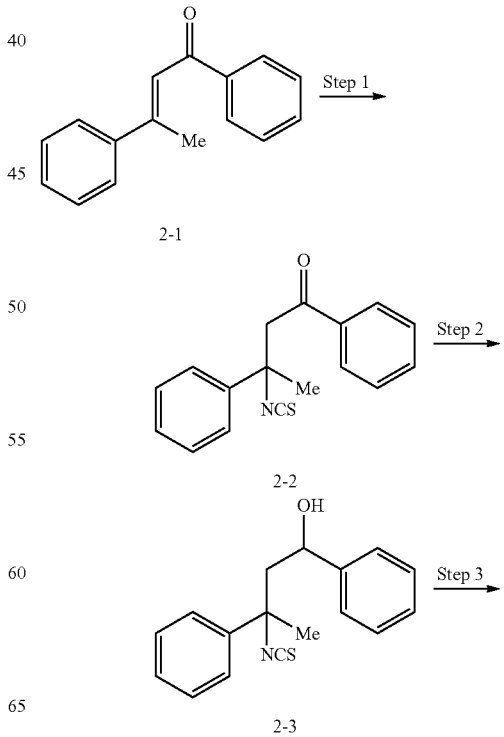

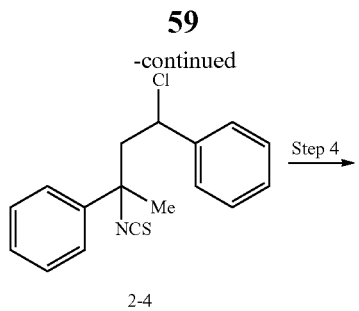

2-4

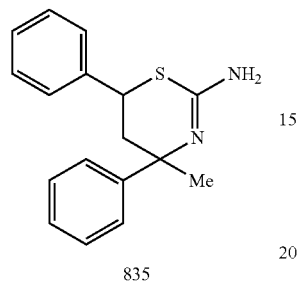

835

Step 1

The compound (2-1)(2020 mg) was dissolved into chloroform (20 ml), then water (4 ml) and sodium thiocyanic acid (1470 mg) were added at room temperature with stirring, and then sulfuric acid (1.94 ml) was added dropwise under cooling with ice-water bath. After an addition was complete, the reaction mixture was warmed to room temperature and then stirred for 345 minutes, then stirred at 60° C. overnight. Because the compound (2-1) was remained (checked by TLC), the reaction mixture was cooled to room temperature, then sodium thiocyanic acid (1470 mg), water (5 ml) and sulfuric acid (1.94 ml) were added successively. After the reaction mixture was warmed to 60° C., the mixture was stirred for 1 day. Saturated sodium carbohydrate solution was added to the reaction mixture to be basic condition under cooling with ice-water bath, and then the reaction mixture was extracted with ethyl acetate. The organic layer was washed with brine, then dried over anhydrous magnesium sulfate. The solvent was evaporated and the obtained residue was purified by silica gel column chromatography to afford the compound (2-2)(968 mg).

$^1$H-NMR (CDCl$_3$, 270 MHz): 1.99 (3H, s), 3.55 (1H, d, J=16.1 Hz), 3.69 (1H, d, J=16.1 Hz), 7.12-7.64 (8H, m), 7.82-7.95 (2H, m)

Step 2

The compound (2-2)(842 mg) was dissolved into ethanol (8.4 ml), sodium dihydrorgen phosphate, sodium borohydride (113.2 mg), and water (2.8 ml), were added successively under cooling with ice-water bath with stirring, and the mixture was stirred for 30 minutes. After the consumption of the compound (2-2)(checked by TLC), ethyl acetate and water were added to the reaction mixture under cooling with ice-water bath, and then stirred for a few minutes. The reaction mixture was extracted with ethyl acetate. The organic layer was washed with water, brine successively, and dried over anhydrous magnesium sulfate. The solvent was evaporated to afford the compound (2-3)(904.8 mg) as crude product.

Step 3

To a solution of compound (2-3)(900 mg) in toluene (10 ml) was added a solution of thionyl chloride (0.7 ml) in toluene (5 ml) under cooling with ice-water bath, and then stirred for 1 hour. After the consumption of the compound (2-3)(checked by TLC), the reaction solvent was evaporated under reduced pressure to afford the compound (2-4)(1076.8 mg) as crude product.

Step 4

The compound (2-4)(1070 mg) was dissolved into about 7 mol/L ammonia in methanol (20 ml) at room temperature, then the mixture was stirred for 1 day. After the consumption of the compound (2-4)(checked by TLC), the reaction solvent was evaporated under reduced pressure to afford the compound (835)(2633 mg) as crude product.

Example 3

The Synthesis of Compound 561

[Chemical formula 50]

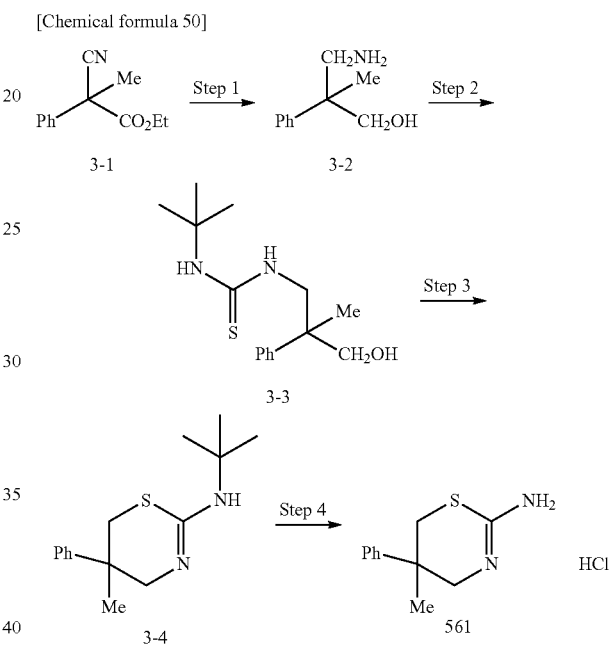

Step 1

To tetrahydrofuran (30 ml) under cooling with ice-water bath with stirring, lithium aluminium hydride (0.63 g) was added portionwise, then a solution of compound (3-1)(1.94 g) in tetrahydrofuran (40 ml) was added dropwise. The reaction mixture was reacted for 20 minutes at room temperature, then reacted for 3 hours under reflux. Then ice was added in small portions under cooling, and then stirred for 1 day at room temperature. The reaction mixture was filtered and the filtrate was evaporated under reduced pressure, and the residue was purified by silica gel column chromatography to afford the compound (3-2)(0.90 g).

$^1$H-NMR (CDCl$_3$): 1.22 (3H, s), 3.08 (1H, d, J=12.5 Hz), 3.34 (1H, d, J=12.5 Hz), 3.85 (1H, d, J=11.0 Hz), 4.11 (1H, d, J=11.0 Hz), 7.21-7.25 (1H, m), 7.34-7.40 (2H, m), 7.46-7.50 (2H, m).

Step 2

The compound (3-2)(0.90 g) was dissolved into tetrahydrofuran (15 ml), t-butylisothiocyanate (0.69 g) in tetrahydrofuran (5 ml) was added under cooling with ice-water bath with stirring. The reaction mixture was stirred for 3 days at room temperature, water was added and extracted with dichloromethane. The organic layer was dried over anhydrous magnesium sulfate, then the solvent was evaporated under reduced pressure. The residue was purified by silica gel column chromatography to afford the compound (3-3)(1.33 g).

¹H-NMR (CDCl₃): 1.12 (9H, s), 1.34 (3H, s), 3.15 (1H, br), 3.76 (1H, d, J=11.2 Hz), 3.87 (1H, dd, J=14.2, 4.6 Hz), 4.13 (1H, d, J=11.2 Hz), 4.23 (1H, dd, J=14.2, 6.6 Hz), 5.18 (1H, br), 6.01 (1H, br), 7.23-7.28 (1H, m), 7.34-7.41 (4H, m).

Step 3

The compound (3-3)(315 mg) was dissolved into acetonitrile (3 ml), triphenylphosphine (440 mg), and carbon tetrachloride (520 mg) in acetonitrile (3 ml) were added under cooling with ice-water bath with stirring. The reaction mixture was stirred for 1 hour at room temperature, and then potassium carbonate (460 mg) was added and stirred for 2 days at room temperature. Then water was added to the reaction mixture and the mixture was extracted with dichloromethane. The organic layer was dried over anhydrous magnesium sulfate, and then the solvent was evaporated under reduced pressure. The residue was purified by silica gel column chromatography to afford the compound (3-4)(0.23 g).

¹H-NMR (CDCl₃): 1.30 (9H, s), 1.36 (3H, s), 3.13 (1H, d, J=12.2 Hz), 3.24 (1H, dd, J=12.2, 2.3 Hz), 3.51 (1H, br), 3.53 (1H, d, J=15.2 Hz), 3.99 (1H, dd, J=15.2, 2.3 Hz), 7.20-7.25 (1H, m), 7.30-7.36 (2H, m), 7.39-7.43 (2H, m).

Step 4

To the compound (3-4)(0.22 g), conc. hydrochloric acid (4.5 ml) was added, then stirred for 2 hours under reflux, and then the reaction solvent was evaporated under reduced pressure. The obtained residue was crystallized from methanol-diethyl ether to afford the compound (561)(0.16 g).

¹H-NMR (DMSO-d₆): 1.33 (3H, s), 3.33-3.49 (2H, m), 3.65-3.96 (2H, m), 7.29 (1H, t. J=7.6 Hz), 7.40 (2H, t. J=7.6 Hz), 7.48 (2H, t. J=7.6 Hz).

Example 4

The Synthesis of Compound 534

[Chemical formula 51]

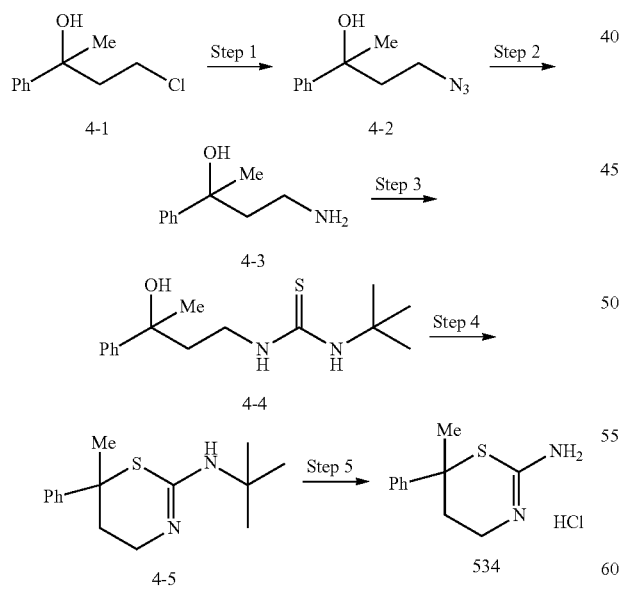

Step 1

The compound (4-1)(0.72 g) was dissolved into N,N-dimethylformamide (15 ml), then sodium azide (0.31 g) was added. The reaction mixture was stirred at 100° C. for 13 hours, then water was added and the mixture was extracted with diethyl ether, the organic layer was dried over anhydrous magnesium sulfate to afford the compound (4-2)(0.71 g) as crude product.

Step 2

To a solution of the compound (4-2)(0.71 g) in tetrahydrofuran (10 ml), lithium aluminium hydride (0.14 g) was added portionwise under cooling with ice-water bath with stirring, then stirred for 2 hours at room temperature. After the consumption of the starting material, ice was added in small portions, then stirred for 18 hours at room temperature. The reaction mixture was filtered then filtrate was evaporated under reduced pressure to afford the compound (4-3)(0.89 g) as crude product.

Step 3

The compound (4-3)(0.89 g) was dissolved into tetrahydrofuran (10 ml), then t-butylisothiocyanate (0.56 g) in tetrahydrofuran (5 ml) was added under cooling with ice-water bath with stirring. The reaction mixture was stirred for 4 hours at room temperature, and water was added, and then extracted with dichloromethane, and the organic layer was dried over anhydrous magnesium sulfate. Then the residue was purified by silica gel column chromatography to afford the compound (4-4)(0.72 g).

¹H-NMR (CDCl₃): 1.39 (9H, s), 2.08 (3H, s), 2.09-2.15 (2H, m), 3.37-3.44 (1H, m), 3.80-3.87 (1H, m), 5.97 (1H, br.), 6.86 (1H, br.), 7.28-7.43 (5H, m).

Step 4

The compound (4-4)(120 mg) was dissolved into acetonitrile (2 ml), triphenylphosphine (170 mg), and carbon tetrachloride (200 mg) in acetonitrile (1 ml) were added under cooling with ice-water bath with stirring. The reaction mixture was stirred for 5 hours at room temperature, and then potassium carbonate (177 mg) was added and stirred for 5 days at room temperature. Then water was added to the reaction mixture and the mixture was extracted with dichloromethane, the organic layer was dried over anhydrous magnesium sulfate, then the solvent was evaporated under reduced pressure. The residue was purified by silica gel column chromatography to afford the compound (4-5)(0.06 g).

¹H-NMR (CDCl₃): 1.35 (9H, s), 1.59 (3H, s), 1.91 (1H, ddd, J=13.5, 8.8, 5.0 Hz), 2.06 (1H, dt, J=13.5, 5.0 Hz), 3.00 (1H, ddd, J=15.1, 8.8, 5.0 Hz), 3.30 (1H, dt, J=15.1, 5.0 Hz), 7.24-7.38 (5H, m).

Step 5

To the compound (4-5)(0.06 g), conc. hydrochloric acid (3 ml) was added, then the mixture was stirred for 1 hour under reflux, and the solvent was evaporated under reduced pressure. The obtained residue was crystallized from methanol-water to afford the compound (534)(0.02 g).

¹H-NMR (DMSO-d₆): 1.43 (3H, s), 1.77 (1H, dt. J=8.4, 3.4 Hz), 2.11 (1H, d. J=9.2 Hz), 2.48-2.50 (1H, m), 2.83-2.99 (1H, m), 6.12 (1H, br), 6.65 (1H, br), 7.21-7.24 (1H, m), 7.31-7.37 (4H, m).

Example 5

The Synthesis of Compound 1008

[Chemical formula 52]

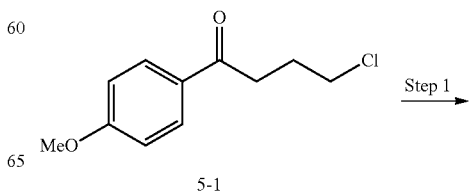

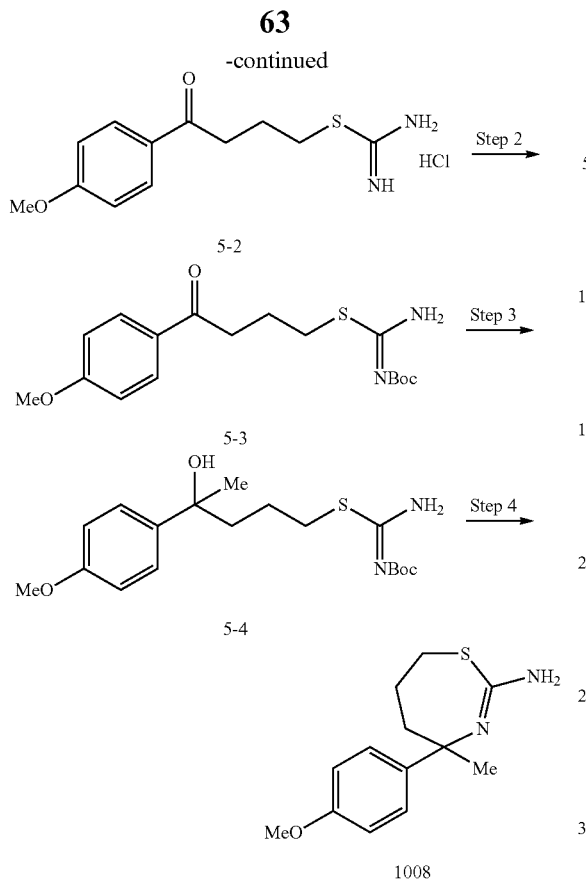

Step 1

The compound (5-1)(3.00 g) was dissolved into ethanol (30 ml), and thiourea (1.13 g) was added, and then the mixture was refluxed for 26 hours, and the solvent was evaporated under reduced pressure. The obtained residue was crystallized from ethyl acetate/hexane to afford the compound (5-2) (4.03 g).

$^1$H-NMR (DMSO-$d_6$): 1.95 (2H, quint, J=6.8 Hz), 3.13 (2H, t, J=6.8 Hz), 3.21 (2H, t, J=6.8 Hz), 3.85 (3H, s), 7.06 (2H, d, J=8.8 Hz), 7.95 (2H, d, J=8.8 Hz), 9.18 (4H, br).

Step 2

The compound (5-2)(1.00 g) was dissolved into tetrahydrofuran (25 ml), then di-t-butyl-dicarbonate (1.74 g), and triethylamine (0.88 g) were added, and then the mixture was stirred for 3 hours at room temperature. Water was added to the reaction mixture, and the mixture was extracted with dichloromethane. The organic layer was dried over anhydrous magnesium sulfate, and then the solvent was evaporated under reduced pressure. The residue was purified by silica gel column chromatography to afford the compound (5-3)(1.24 g).

$^1$H-NMR (CDCl$_3$): 1.50 (9H, s), 2.07-2.17 (2H, m), 2.98 (2H, t, J=7.8 Hz), 3.09 (2H, t, J=6.3 Hz), 6.95 (2H, d, J=8.9 Hz), 7.95 (2H, d, J=8.9 Hz).

Step 3

The compound (5-3)(1.18 g) was dissolved into tetrahydrofuran (12 ml), then 0.9 mol/L methylmagnesium bromide in tetrahydrofuran solution (10.1 ml) was added under cooling with acetonitrile-dryice bath with stirring, and then reaction mixture was stirred for 1 hour, then stirred for 30 minutes at room temperature. After the reaction, saturated ammonium chloride solution was added under cooling with ice-water bath with stirring, then the mixture was extracted with diethyl ether, and the organic layer was dried over anhydrous magnesium sulfate, and then the solvent was evaporated under reduced pressure. The obtained residue was purified by silica gel column chromatography to afford the compound (5-4) (0.39 g).

$^1$H-NMR (CDCl$_3$): 1.51 (9H, s), 1.63 (3H, s), 1.55-1.65 (2H, m), 1.87-1.91 (2H, m), 2.96-3.12 (2H, m), 6.86 (2H, d, J=8.9 Hz), 7.36 (2H, d, J=8.9 Hz).

Step 4

The compound (5-4)(0.24 g) was dissolved into trifluoroacetic acid (6 ml), and stirred for 20 hours at room temperature, then the reaction solvent was evaporated under reduced pressure. To the residue, water and saturated sodium hydrogencarbonate was added, and then extracted with dichloromethane. The organic layer was dried over anhydrous sodium sulfate, and then the solvent was evaporated under reduced pressure. The residue was purified by silica gel column chromatography to afford the compound (1008)(0.06 g).

$^1$H-NMR (CDCl$_3$): 1.54 (3H, s), 1.77-1.87 (1H, m), 1.90-1.97 (1H, m), 2.20-2.36 (2H, m), 2.67-2.79 (2H, m), 3.81 (3H, s), 5.30 (2H, br), 6.87 (2H, d, J=9.0 Hz), 7.33 (2H, d, J=9.0 Hz).

Example 6

The Synthesis of Compound 783

[Chemical formula 53]

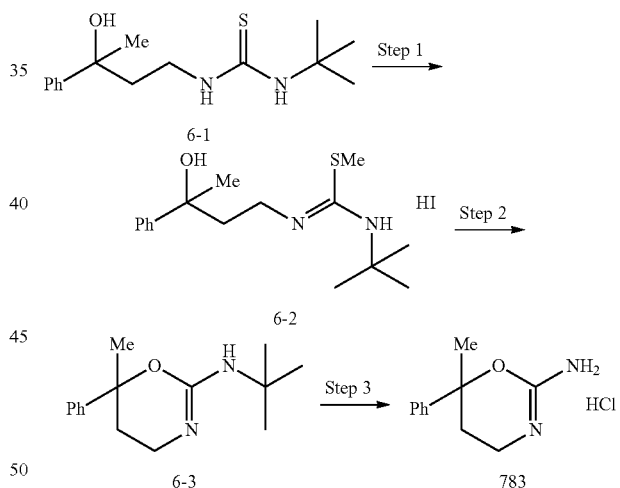

Step 1

The compound (6-1)(0.55 g) was dissolved into methanol (7 ml), and methyl iodide (0.36 g) was added at room temperature with stirring. The mixture was stirred at room temperature for 18 hours, then the reaction solvent was evaporated under reduced pressure to afford the compound (6-2) (0.92 g) as crude product.

Step 2

The compound (6-2)(0.92 g) was dissolved into tetrahydrofuran (7 ml), then triethylamine (0.24 g) and silver oxide (1.1 g) was added. The mixture was stirred at room temperature for 3 days, then the insolubles was removed by filtration, then the filtrate was evaporated under reduced pressure, and then the obtained residue was purified by silica gel column chromatography to afford the compound (6-3)(0.31 g).

$^1$H-NMR (CDCl$_3$): 1.35 (9H, s), 1.60 (3H, s), 1.92 (1H, ddd, J=9.2, 5.8, 3.4 Hz), 2.07 (1H, dt, J=9.2, 3.4 Hz), 3.00 (1H, ddd, J=9.2, 5.8, 3.4 Hz), 3.30 (1H, dt, J=9.2, 3.4 Hz), 7.24-7.38 (5H, m).

Step 3

To the compound (6-3)(0.22 g), conc. hydrochloric acid (3 ml) was added, then the mixture was stirred for 1 hour under reflux, and then the reaction solvent was evaporated under reduced pressure. The obtained residue was crystallized from water to afford the compound (783)(0.13 g).

$^1$H-NMR (DMSO-d$_6$): 1.44 (3H, s), 1.78 (1H, dt. J=12.4, 4.2 Hz), 2.12 (1H, d. J=8.9 Hz), 2.51-2.52 (1H, m), 2.96 (1H, d. J=4.2 Hz), 6.12 (1H, br), 6.66 (1H, br), 7.21-7.24 (1H, m), 7.32-7.37 (4H, m).

Example 7

The Synthesis of Compound 69

[Chemical formula 54]

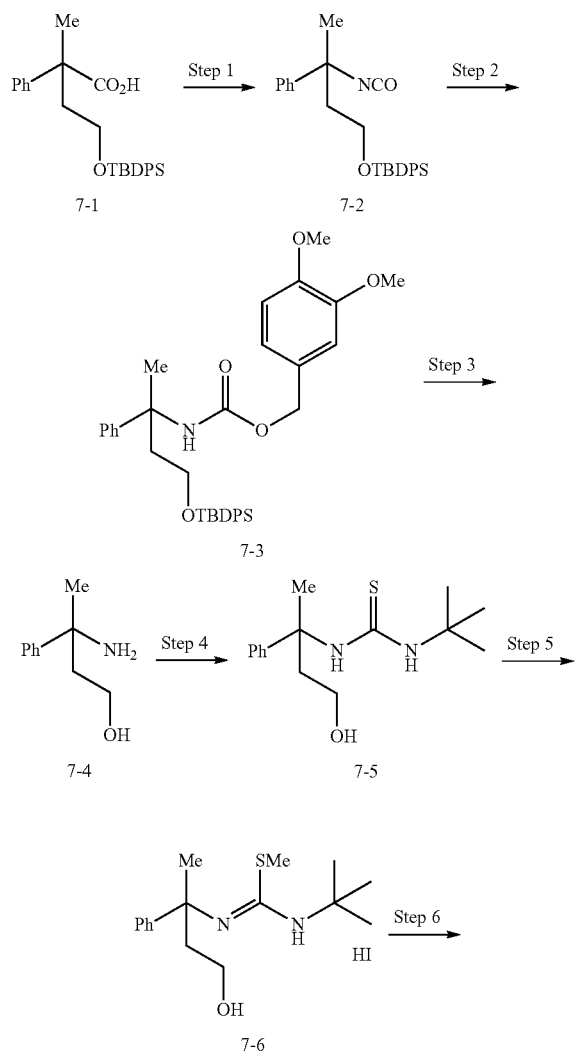
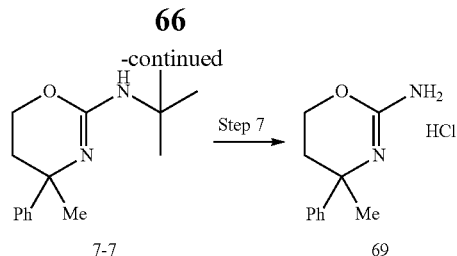

Step 1

A solution of the compound (7-1)(1.93 g), diphenylphosphoryl azide (1.60 g), and triethylamine (0.59 g) in toluene (20 ml) was stirred at 80° C. for 3 hours, and water was added, and then the mixture was extracted with diethyl ether. The organic layer was dried over anhydrous sodium sulfate, and then the solvent was evaporated under reduced pressure. The obtained residue was purified by silica gel column chromatography to afford the compound (7-2)(1.69 g).

$^1$H-NMR(CDCl$_3$): 1.00 (9H, s), 1.72 (3H, s), 2.17-2.22 (2H, m), 3.49-3.58 (1H, m), 3.70-3.80 (1H, m), 7.20-7.42 (10H, m), 7.58-7.63 (5H, m).

Step 2

The compound (7-2)(1.68 g) was dissolved into toluene (9 ml), and 3,4-dimethoxybenzylalcohol (0.79 g) was added, the mixture was refluxed for 8 hours. To the reaction mixture, water was added, then the mixture was extracted with dichloromethane, and the organic layer was dried over anhydrous sodium sulfate, and the solvent was evaporated under reduced pressure. The obtained residue was purified by silica gel column chromatography to afford the compound (7-3)(2.09 g).

$^1$H-NMR (CDCl$_3$): 1.03 (9H, s), 1.87 (3H, s), 2.04 (2H, m) 3.48 (1H, m), 3.51 (1H, m), 3.62 (3H, s), 3.65 (3H, s), 4.95 (1H, d, J=12.2 Hz), 5.03 (1H, d, J=12.2 Hz), 6.80-7.09 (3H, m), 7.22-7.42 (10H, m), 7.56-7.64 (5H, m).

Step 3

The compound (7-3)(2.09 g) was dissolved into 1,4-dioxane (15 ml), and 4 mol/L hydrochloric acid-1,4-dioxane (15 ml) solution was added, then stirred at room temperature for 24 hours. To the reaction mixture, water and 1 mol/L—sodium hydroxide solution were added and extracted with dichloromethane, then the organic layer was dried over anhydrous sodium sulfate, and then the solvent was evaporated under reduced pressure. The obtained residue was purified by silica gel column chromatography to afford the compound (7-4)(0.45 g).

$^1$H-NMR (CDCl$_3$): 1.57 (3H, s), 1.07-1.98 (2H, m), 3.48-3.56 (1H, m), 3.72-3.86 (1H, m), 7.23-7.45 (15H, m).

Step 4

The compound (7-4)(0.44 g) was dissolved into tetrahydrofuran (16 ml), t-butylisothiocyanate (0.41 g) and diisopropylethylamine (0.46 g) were added. After the mixture was stirred at room temperature for 3 days, water was added, and extracted with dichloromethane, then the organic layer was dried over anhydrous sodium sulfate, and then the solvent was evaporated under reduced pressure. The obtained residue was purified by silica gel column chromatography to afford the compound (7-5)(0.17 g).

$^1$H-NMR (CDCl$_3$): 1.79 (3H, s), 1.82-2.20 (2H, m), 3.71-3.81 (2H, m), 5.09 (1H, br), 7.30-7.52 (5H, m).

Step 5

The compound (7-5)(0.17 g) was dissolved into tetrahydrofuran (3.4 ml), then methyl iodide (0.11 g) was added at room temperature with stirring. The mixture was stirred for 23 hours, the reaction solvent was evaporated under reduced pressure to afford the compound (7-6)(0.28 g) as crude product.

Step 6

The compound (7-6)(0.28 g) was dissolved into tetrahydrofuran (5 ml), then triethylamine (74 mg) and silver oxide (0.34 g) were added. The mixture was stirred at room temperature for 20 hours, then insolubles were removed by filtration, and then the filtrate was evaporated under reduced pressure. The obtained residue was purified by silica gel column chromatography to afford the compound (7-7)(0.14 g).

$^1$H-NMR (CDCl$_3$): 1.36 (9H, s), 1.49 (3H, s), 1.96-2.09 (2H, m), 2.77-3.83 (1H, m), 4.05-4.10 (1H, m), 7.19 (1H, t, J=7.3 Hz), 7.31 (2H, t, J=7.3 Hz), 7.44 (2H, d, J=7.3 Hz).

Step 7

To the compound (7-7)(0.12 g) conc. hydrochloric acid (9 ml) was added, then stirred for 1 hour under reflux, and then the reaction solvent was evaporated under reduced pressure. The obtained residue was crystallized from methanol-water to afford the compound (69)(0.10 g).

$^1$H-NMR (DMSO-d$_6$): 1.65 (3H, s), 2.28-2.35 (1H, m), 2.39-2.44 (1H, m), 3.97 (1H, dt, J=7.8, 3.0 Hz), 4.53 (1H, dt, J=7.8, 3.0 Hz), 7.32-7.44 (5H, m), 8.44 (2H, br), 10.33 (1H, s).

Example 8

The Synthesis of Compound 256

[Chemical formula 55]

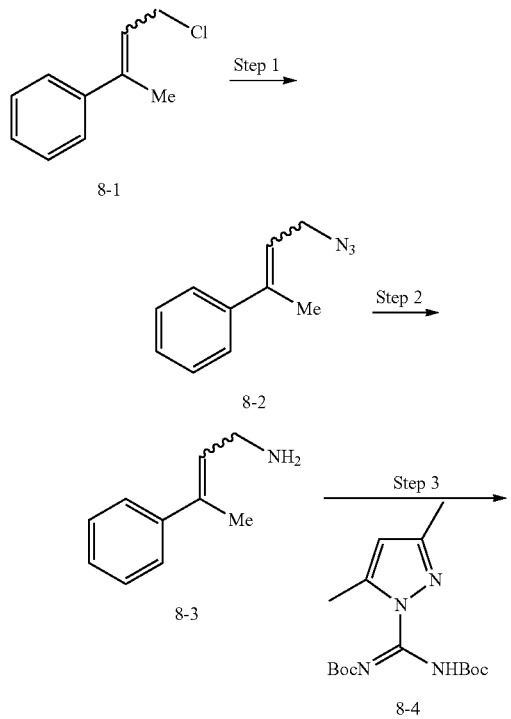
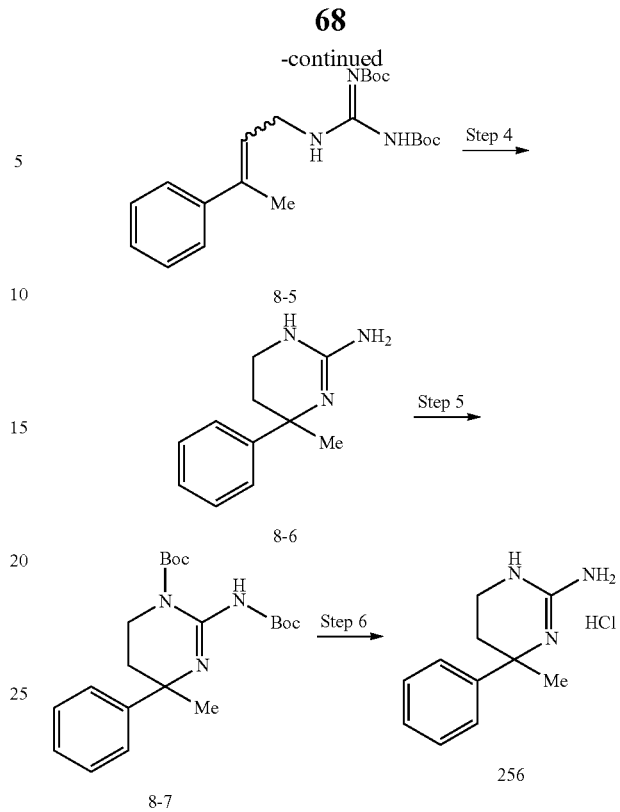

Step 1

The compound (8-1)(4890 mg) was dissolved into N,N-dimethylformamide (100 ml), then sodium azide (5720 mg) was added at room temperature with stirring, and the solution was warmed to 80° C., and stirred for 12 hours. After the consumption of the compound (8-1)(checked by TLC), the reaction mixture was cooled to room temperature, then diethyl ether and water were added, and then the mixture was extracted with diethyl ether. The organic layer was washed with brine, and dried over magnesium sulfate. The solvent was evaporated under reduced pressure to afford the compound (8-2)(4940 mg) as crude product.

Step 2

To the suspension of lithium aluminium hydride (1080 mg) in tetrahydrofuran (90 ml) under nitrogen atmosphere under cooling with ice-water bath, the compound (8-2)(4940 mg) in tetrahydrofuran (15 ml) solution was added, the reaction mixture was stirred for 30 minutes. After the consumption of the compound (8-2)(checked by TLC), 1 mol/L sodium hydroxide solution was added under cooling with ice-water bath, then stirred for a while. The generated gel was removed with filtration, and the mother liquid was extracted with diethyl ether. The organic layer was washed with brine, and dried over magnesium sulfate. The solvent was evaporated under reduced pressure to afford the compound (8-3)(4219.1 mg) as crude product.

Step 3

The compound (8-3)(800 mg) was dissolved into acetonitrile (16 ml), the compound (8-4)(1840 mg) was added with stirring at room temperature, and stirred for 13 hours. After the consumption of the compound (8-3)(checked by TLC), the reaction solvent was evaporated under reduced pressure, the obtained residue was purified by silica gel column chromatography to afford the compound (8-5)(1550.7 mg).

8-5-(Z) $^1$H-NMR (CDCl$_3$, 270 MHz): 1.49 (18H, s), 2.06 (3H, d, J=1.4 Hz), 3.91-4.00 (2H, m), 5.54 (1H, td, J=7.1, 1.4 Hz), 7.12-7.41 (5H, m), 8.17-8.25 (1H, m), 11.47 (1H, s)

8-5-(E) $^1$H-NMR (CDCl$_3$, 270 MHz): 1.49 (9H, s), 1.52 (9H, s), 2.09 (3H, d, J=1.5 Hz), 4.24 (2H, dd, J=6.6, 5.3 Hz), 5.80 (1H, td, J=6.6, 1.5 Hz), 7.21-7.48 (5H, m), 8.28-8.38 (1H, m), 11.51 (1H, s)

Step 4

The compound (8-5)(474.1 mg) was dissolved into trifluoroacetic acid (4.5 ml) under cooling with ice-water bath, then warmed to room temperature, and stirred for 4 hours. After the consumption of the compound (8-5)(checked by NMR), the reaction mixture was poured into floating ice—1 mol/L sodium hydroxide solution to be neutralized, then the mixture was extracted with ethyl acetate. The organic layer was washed with brine, and dried over magnesium sulfate. The solvent was evaporated under reduced pressure to afford the compound (8-6)(326.4 mg) as crude product.

Step 5

The compound (8-6)(326.4 mg) was dissolved into 1,4-dioxane (2.4 ml), sodium hydroxide (195 mg) and water (1.2 ml) were added successively, then di-t-butyl dicarbonate (0.84 ml) was added under cooling with ice-water bath. The reaction mixture was warmed to room temperature, and stirred for 15 hours, then the consumption of the compound (8-6) was checked by LC-MS. After added water to the reaction mixture, the mixture was extracted with ethyl acetate. The organic layer was washed with brine, and dried over magnesium sulfate. The solvent was evaporated under reduced pressure, and the obtained residue was purified by silica gel column chromatography to afford the compound (8-7)(113.6 mg).

$^1$H-NMR (CDCl$_3$, 400 MHz): 1.46 (9H, s), 1.51 (9H, s), 1.64 (3H, s), 2.06 (1H, ddd, J=13.4, 11.4, 5.0 Hz), 2.27 (1H, dt, J=13.4, 4.6 Hz), 3.15 (1H, ddd, J=12.9, 11.3, 4.6 Hz), 3.70 (1H, dt, J=12.9, 4.7 Hz), 7.23-7.29 (1H, m), 7.33-7.38 (4H, m)

Step 6

The compound (8-7)(110 mg) was dissolved into 4 mol/L hydrochloric acid-1,4-dioxane solution (1 ml) under cooling ice-water bath, the mixture was warmed to room temperature, and stirred for 2 days, then the consumption of the compound (8-7) was checked by LC-MS, and diethyl ether and water were added at room temperature. After separation of diethyl ether layer, water layer was evaporated under reduced pressure. To the obtained residue, methanol was added, then the generated crystal was filtered. The methanol in mother liquid was evaporated under reduced pressure to afford the compound (256)(69 mg).

$^1$H-NMR (DMSO-d$_6$, 400 MHz): 1.57 (3H, s), 1.87-1.96 (1H, m), 2.30 (1H, dt, J=13.6, 3.8 Hz), 2.60 (1H, td, J=12.0, 3.7 Hz), 3.25 (1H, ddd, J=12.8, 8.2, 4.4 Hz), 6.93 (2H, s), 7.27-7.44 (5H, m), 7.94 (1H, s), 8.63 (1H, s)

Example 9

The Synthesis of Compound 24

[Chemical formula 56]

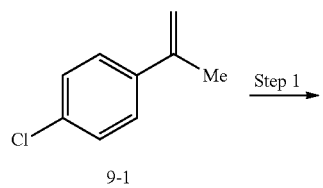

Step 1

The compound (9-1)(0.39 g) was dissolved into chloroform (20 ml), iodine (1.53 g), potassium thiocyanate (1.25 g), catalytic amount of tetrabutylammonium chloride, and water (1 ml) were added at room temperature, then stirred for 15 hours. To the reaction mixture, 10% thiosodium sulfate solution and water were added, and the mixture was extracted with dichloromethane. The organic layer was dried over anhydrous sodium sulfate, the solvent was evaporated under reduced pressure. The obtained residue was purified by silica gel column chromatography to afford the compound (9-2) (0.56 g).

$^1$H-NMR (CDCl$_3$): 1.95 (3H, s), 3.62 (2H, s), 7.30-7.40 (4H, m).

Step 2

To a solution of the compound (9-2)(0.56 g) in tetrahydrofuran (10 ml), t-butylamine (0.24 g) was added and stirred at room temperature for 18 hours. The reaction solvent was evaporated under reduced pressure, then the obtained residue was purified by silica gel column chromatography to afford the compound (9-3)(190 mg).

$^1$H-NMR (CDCl$_3$): 1.43 (9H, s), 1.56 (3H, s), 3.27 (1H, d, J=10.6 Hz), 3.36 (1H, d, J=10.6 Hz), 7.28 (2H, d, J=8.2 Hz), 7.43 (2H, d, J=8.2 Hz).

Step 3

To the compound (9-3)(190 mg), conc. hydrochloric acid (3 ml) was added, then stirred at 100° C. for 3 hours. To the reaction mixture, 6 mol/L sodium hydroxide was added to neutralize, the mixture was extracted with dichloromethane. The organic layer was dried with anhydrous sodium sulfate, and the solvent was evaporated under reduced pressure. The obtained residue was purified by silica gel column chromatography, then crystallized from dichloromethane/n-hexane to afford the compound (24)(110 mg).

¹H-NMR (CDCl₃): 1.62 (3H, s), 3.47 (1H, d, J=10.6 Hz), 3.52 (1H, d, J=10.6 Hz), 4.59 (2H, br), 7.29 (2H, d, J=8.6 Hz), 7.39 (2H, d, J=8.6 Hz).

Example 10

The Synthesis of Compound 48

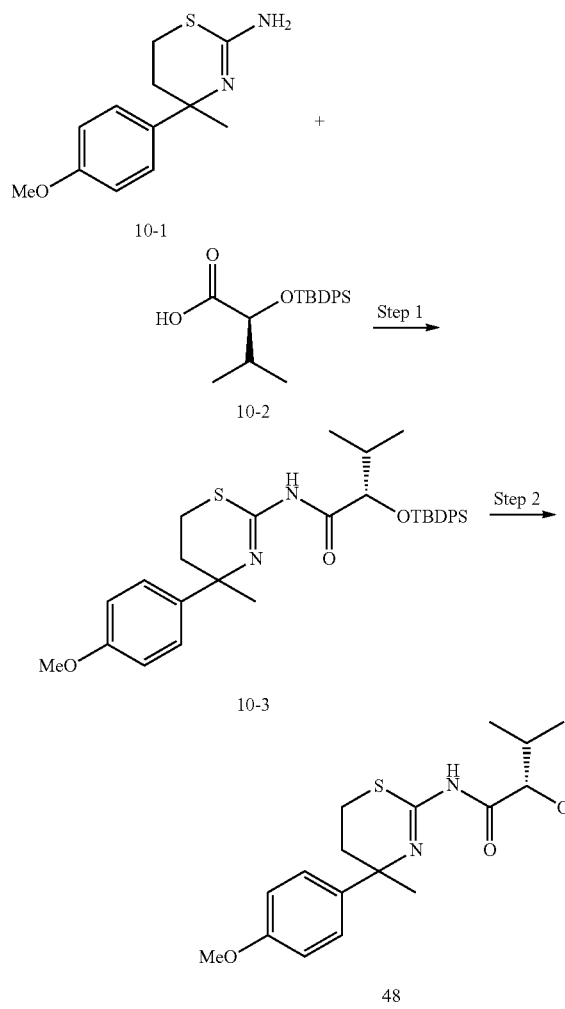

Step 1

The compound (10-1)(79.6 mg) and (10-2)(120 mg) were dissolved into N,N-dimethylformamide (3 ml), then 1-hydroxybenzotriazole (54.6 mg) and N,N'-diisopropylcarbodiimide (0.063 ml) were added, then the reaction mixture was stirred overnight at room temperature. Then after the consumption of the compound (10-1), water was added, and the mixture was extracted with ethyl acetate. The organic layer was washed with brine, and dried over magnesium sulfate, and the solvent was evaporated under reduced pressure. The obtained residue was purified by silica gel column chromatography to afford the compound (10-3)(110.2 mg) as crude product of diastereomer.

¹H-NMR (CDCl₃): 0.78-1.00 (6H, m,), 1.14 (9/2H, s), 1.16 (9/2H, s) 1.52 (3/2H, s), 1.54 (3/2H, s) 1.86-2.28 (3H, m), 2.56-2.89 (2H, m), 3.80 (3/2H, s), 3.81 (3/2H, s) 4.04-4.14 (1H, m), 6.80-6.91 (2H, m), 7.08-7.22 (2H, m), 7.30-7.51 (6H, m), 7.61-7.76 (4H, m)

Step 2

The compound (10-3)(100 mg) was dissolved into tetrahydrofuran (3 ml) under nitrogen atmosphere, then 1 mol/L tetrabutylammonium fluoride in tetrahydrofuran (0.18 ml) was added at 0° C. with stirring, then the reaction mixture was stirred at 0° C. for 5 minutes. After the consumption of the compound (10-3), water was added, and the mixture was extracted with ethyl acetate. The organic layer was washed with brine, and dried over magnesium sulfate, then the solvent was evaporated under reduced pressure. The obtained residue was purified by silica gel column chromatography to afford the compound (48)(40.7 mg) as a mixture of diastereomers.

¹H-NMR (CDCl₃): 0.80-0.90 (3H, m) 1.01-1.12 (3H, m) 1.70 (3H, m), 2.02-2.31 (2H, m) 2.39-2.55 (1H, m), 2.61-2.90 (2H, m) 3.53-3.70 (1H, m) 3.81 (3H, m), 3.96-4.08 (1H, m) 6.87-6.96 (2H, m), 7.13-7.22 (2H, m)

Example 11

The Synthesis of Compound 707

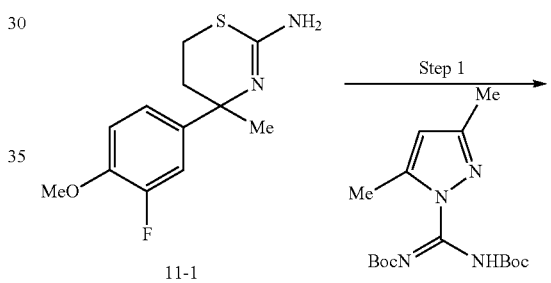

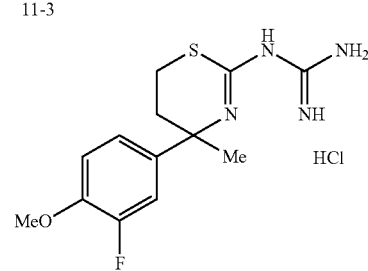

Step 1

The compound (11-1)(150 mg) was dissolved into acetonitrile (5 ml), then the compound (11-2)(219.6 mg) was added at room temperature with stirring, and then the reaction mixture was warmed to 60° C., and stirred for 25 hours. The compound (11-1) was remained (checked by TLC). The reaction solvent was evaporated under reduced pressure, then the obtained residue was purified by silica gel column chromatography to afford the compound (11-1)(211.4 mg).

¹H-NMR (CDCl₃, 400 MHz) 1.46 (9H, s), 1.50 (9H, s), 1.57 (3H, s), 1.90 (1H, ddd, J=13.7, 10.0, 3.8 Hz) 2.11 (1H, ddd, J=13.7, 6.5, 3.7 Hz) 2.68-2.76 (1H, m), 2.86-2.93 (1H, m), 3.88 (3H, s), 6.91 (1H, t, J=8.6 Hz) 6.99-7.03 (1H, m), 7.06 (1H, dd, J=13.0, 2.2 Hz), 10.14 (1H, s), 13.93 (1H, s)

Step 2

The compound (11-3)(210 mg) was dissolved into 4 mol/L hydrochloric acid in 1,4-dioxane (4 ml) under cooling with ice-water bath, then the mixture was warmed to room temperature and stirred for 67 hours. After the consumption of the compound (11-3)(checked by LC/MS), the reaction solvent was evaporated under reduced pressure. The obtained residue was crystallized from methanol-diethyl ether, and crystal was collected by filtration and washed with diethyl ether to afford compound (707)(140.2 mg).

¹H-NMR (DMSO-d₆, 400 MHz): 1.56 (3H, s), 1.90-2.01 (1H, m), 2.43-2.62 (2H, m), 2.95-3.03 (1H, m), 3.84 (3H, s), 7.10-7.27 (3H, m) 7.76 (3H, br s), 8.26 (1H, br s), 9.42 (1H, s)

Example 12

The Synthesis of Compound 845

[Chemical formula 59]

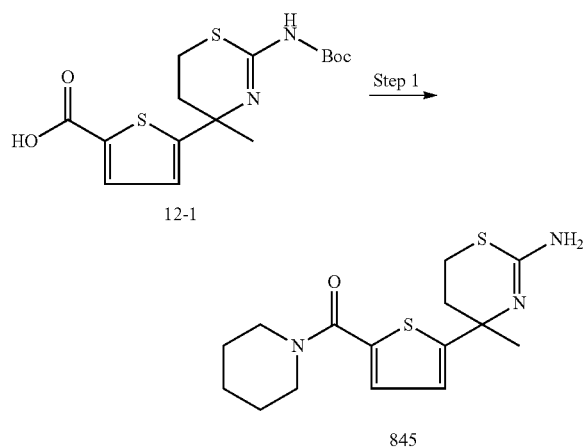

Step 1

The compound (12-1)(50 mg) and piperidine (17.9 mg) were dissolved into N,N-dimethylformamide (2 ml), then O-(7-azabenzotriazo-1-yl)-1,1,3,3-tetramethyluronium-hexafluorophosphate (79.8 mg) was added, and then the mixture was stirred at room temperature for 40 hours. After the consumption of the compound (12-1), the solvent was evaporated under reduced pressure with heating. To the obtained residue, saturated sodium hydrogencarbonate solution was added, and extracted with ethyl acetate. The organic layer was washed with brine, and dried over magnesium sulfate, then the solvent was evaporated under reduced pressure. The obtained residue was purified by silica gel column chromatography to afford the compound (845)(30.7 mg).

¹H-NMR (CDCl₃): 1.60 (3H, s), 1.51-1.82 (6H, m), 1.87-1.98 (1H, m), 2.09-2.19 (1H, m), 2.91-2.97 (2H, m), 3.64-3.68 (4H, m), 6.73 (1H, d, J=4.05 Hz), 7.14 (1H, d, J=4.05 Hz)

Example 13

The Synthesis of Compound 1262

[Chemical formula 60]

Step 1

The compound (13-1)(50.0 mg) was dissolved into tetrahydrofuran (1 ml) under nitrogen atmosphere, then triethylamine (19 μl), and 4-bromobenzoyl chloride (30.1 mg) were added under cooling with ice-water bath, and stirred for 40 minutes. The reaction solvent was evaporated under reduced pressure, and then the obtained residue was dissolved into ethyl acetate. The solution was washed with saturated sodium hydrogencarbonate solution, and dried over magnesium sulfate, and then the solvent was evaporated under reduced pressure. The generated crystal was collected by filtration to afford the compound (13-2)(57.2 mg).

¹H-NMR (CDCl₃): 1.48 (9H, s), 1.68 (3H, s), 2.08 (1H, m), 2.44 (1H, m), 2.65 (1H, m), 2.76 (1H, m), 7.18 (1H, s), 7.32 (1H, s), 7.64 (2H, d, J=8.2 Hz), 7.78 (2H, d, J=8.2 Hz), 8.15 (1H, s), 8.25 (1H, br)

Step 2

The compound (13-2)(62.3 mg) was dissolved into 4 mol/L hydrochloric acid-1,4-dioxane and stirred for 24 hours. The reaction solvent was evaporated under reduced pressure. The obtained residue was crystallized from methanol/diethyl ether to afford the compound (1262)(44.7 mg).

¹H-NMR (DMSO-d₆): 1.67 (3H, s), 2.10 (1H, m), 2.50-2.61 (3H, m), 7.33 (1H, s), 7.74 (1H, s), 7.77 (2H, d, J=8.6 Hz), 7.91 (2H, d, J=8.6 Hz), 8.08 (1H, s), 10.6 (1H, s)

Example 14

The Synthesis of Compound 753

[Chemical formula 61]

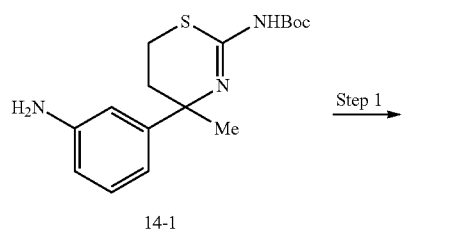

14-1

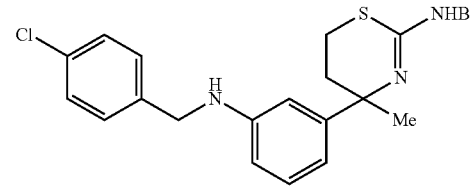

14-2

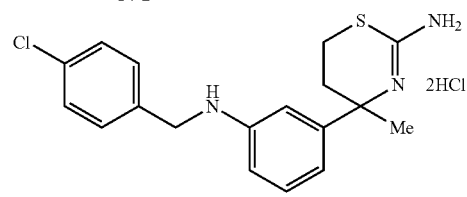

753

Step 1

The compound (14-1)(46 mg) was dissolved into dichloromethane (2 ml), then 4-chlorobenzaldehyde (20 mg) and acetic acid (17 mg) was added at room temperature, and then stirred for 20 minutes, and then sodium triacetoxyborohydride (45 mg) was added under cooling with ice-water bath. The mixture was stirred at room temperature for 14 hours, and then water was added and extracted with dichloromethane. The organic layer was dried over sodium sulfate, and then the solvent was evaporated under reduced pressure. The obtained residue was purified by silica gel column chromatography to afford the compound (14-2)(52 mg).

¹H-NMR (CDCl₃): 1.50 (9H, s), 1.64 (3H, s), 2.02-2.10 (1H, m), 2.40 (1H, dt, J=14.0, 4.1 Hz), 2.62-2.74 (2H, m), 4.30 (2H, s), 6.49 (1H, ddd, J=, 7.8, 2.0, 0.8 Hz), 6.52 (1H, t, J=2.0 Hz), 6.60 (1H, ddd, J=, 7.8, 2.0, 0.8 Hz), 7.16 (1H, t, J=7.8 Hz), 7.18-7.33 (4H, m).

Step 2

To the compound (14-2)(52 mg), 4 mol/L hydrochloric acid in 1,4-dioxane solution (4 ml) was added, then the mixture was stirred at room temperature for 4 days, and then the reaction solvent was evaporated under reduced pressure. The obtained residue was crystallized from methanol/diethyl ether to afford the compound (753)(42 mg).

¹H-NMR (DMSO-d₆): 1.58 (3H, s), 2.00 (1H, ddd, J=, 14.3, 11.3, 3.3 Hz), 2.49-2.57 (2H, m), 3.07 (1H, dt, J=12.7, 3.3 Hz), 4.27 (2H, s), 6.47 (1H, d, J=8.2 Hz), 6.51-6.53 (2H, m), 7.08 (1H, t, J=8.2 Hz), 7.37 (4H, s), 8.80 (2H, br).

Example 15

The Synthesis of Compound 1135

[Chemical formula 62]

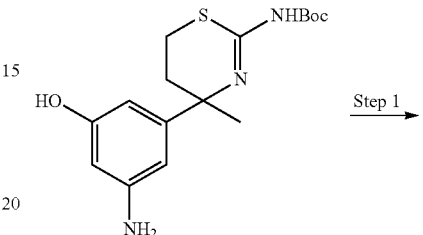

15-1

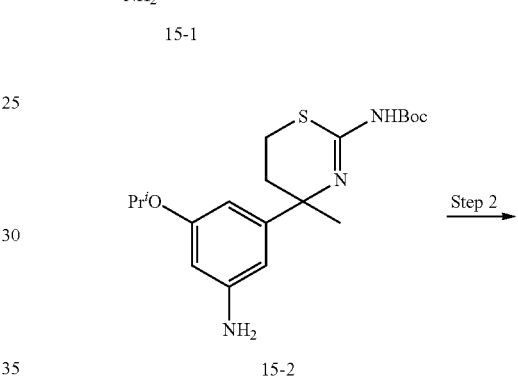

15-2

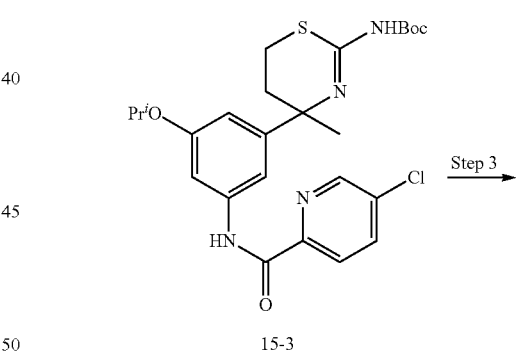

15-3

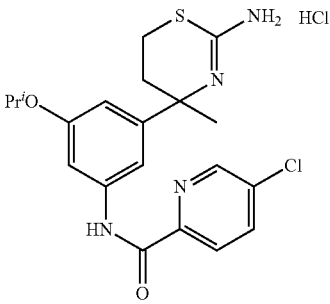

1135

Step 1

To a solution of the compound (15-1)(101 mg), 2-propanol (56 μl), and triphenylphosphine (189 mg) in tetrahydrofuran (2 ml), diethyl azodicarboxylate (2.2 mol/L) in toluene (3280 was added dropwise, then stirred for 1 hour at room temperature. After the consumption of the compound (15-1), the solvent was evaporated under reduced pressure. The obtained residue was purified by silica gel column chromatography to afford the compound (15-2)(280 mg) as a mixture of triphenylphosphine oxide and diethyl hydrazodicarboxylate.

Step 2

To the suspension of 5-chloropyridine-2-carboxylic acid (47 mg) in toluene (1 ml), N,N-dimethylformamide (1 drop) and thionylchloride (91 μl) were added and stirred at 100° C. for 1 hour. The solvent was evaporated under reduced pressure, then the obtained residue was dissolved into tetrahydrofuran (1 ml), and then the mixture of the compound (15-2) (280 mg), and pyridine (194 μl) in tetrahydrofuran (0.5 ml) were added dropwise at 0° C. and stirred for 10 minutes. After the consumption of the compound (15-2), water was added and the mixture was extracted with ethyl acetate. The organic layer was washed with water, and then the solvent was evaporated under reduced pressure. The obtained residue was purified by silica gel column chromatography to afford the compound (15-3)(68 mg) as a mixture of diethyl hydrazodicarboxylate.

Step 3

To the compound (15-3)(68 mg) as a mixture of diethyl hydrazodicarboxylate, 4 mol/L in hydrochloric acid in 1,4-dioxane solution (1 ml) was added, then the mixture was stirred at room temperature for 16 hours. After the consumption of the compound (44), the reaction solvent was evaporated under reduced pressure. The obtained residue was crystallized from 2-propanol/diethyl ether to afford the compound (1135)(36 mg).

$^1$H-NMR (DMSO-$d_6$): 1.30 (3H, d, J=6.4 Hz), 1.31 (3H, d, J=6.4 Hz), 1.65 (3H, s), 2.04-2.11 (1H, m), 2.50-2.64 (2H, m), 3.12-3.16 (1H, m), 4.61 (1H, sep, J=6.4 Hz), 6.66 (1H, t, J=2.0 Hz), 7.48 (1H, t, J=2.0 Hz), 7.60 (1H, t, J=2.0 Hz), 8.16 (1H, dd, J=8.4, 0.8 Hz), 8.22 (1H, dd, J=8.4, 2.4 Hz), 8.79 (1H, dd, J=2.4, 0.8 Hz), 10.33 (1H, s), 10.72 (1H, s).

Example 16

The Synthesis of Compound 161

[Chemical formula 63]

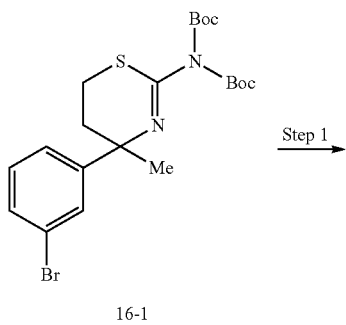

16-1

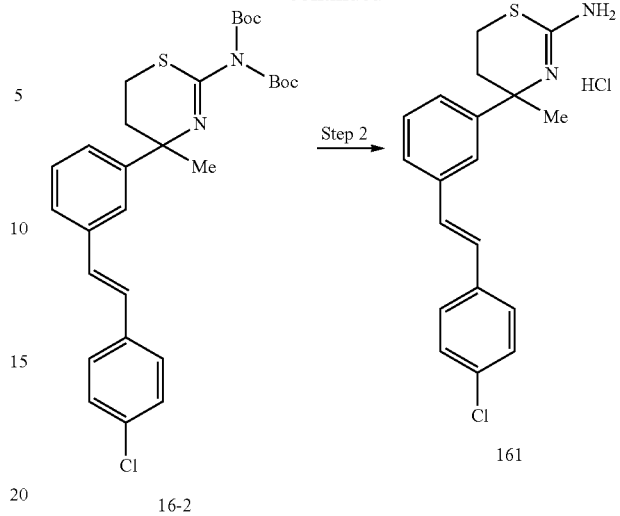

16-2

Step 1

The compound (16-1)(200 mg), palladium acetate (4.7 mg), and tri-(o-tolyl)phosphine (12.5 mg), were dissolved into N,N-dimethylformamide (2 ml) under nitrogen atmosphere, then n-butylamine (0.196 ml), and p-chlorostyrene (0.074 ml) were added at room temperature with stirring, then the solution was warmed to 80° C., and stirred for 3 hours. After the consumption of the compound (16-1)(checked by TLC), the reaction mixture was cooled to room temperature, and saturated ammonium chloride solution was added to the mixture. The mixture was extracted with ethyl acetate, the organic layer was washed with water and brine, and dried over magnesium sulfate, and then the solvent was evaporated under reduced pressure. The obtained residue was purified by silica gel column chromatography to afford the compound (16-2)(213.1 mg).

$^1$H-NMR (CDCl$_3$, 400 MHz): 1.54 (18H, s), 1.64 (3H, s), 1.96 (1H, ddd, J=13.7, 9.1, 4.0 Hz) 2.10 (1H, ddd, J=13.7, 8.1, 3.4 Hz) 2.86 (1H, ddd, J=12.3, 9.1, 3.4 Hz), 3.03 (1H, ddd, J=12.3, 8.1, 4.0 Hz), 7.08 (1H, d, J=16.4 Hz) 7.15 (1H, d, J=16.4 Hz), 7.27-7.40 (5H, m) 7.44 (2H, d, J=8.8 Hz), 7.58 (1H, s)

Step 2

The compound (16-2)(213 mg) was dissolved into 4 mol/L hydrochloric acid in 1,4-dioxane (5 ml) under cooling with ice-water bath, then the mixture was warmed to room temperature and stirred for 63 hours. After the consumption of the compound (16-2)(checked by LC/MS), the reaction mixture was diluted with diethyl ether. The generated crystal was collected by filtration, and washed with diethyl ether to afford the compound (161)(108.6 mg).

$^1$H-NMR (DMSO-$d_6$, 400 MHz): 1.69 (3H, s), 2.08-2.18 (1H, m), 2.56-2.70 (2H, m), 3.13-3.20 (1H, m), 7.23 (1H, d, J=8.0 Hz), 7.31 (1H, d, J=17.0 Hz), 7.35 (1H, d, J=17.0 Hz), 7.45 (2H, d, J=8.6 Hz), 7.46 (1H, t, 7.6 Hz), 7.59 (1H, d, J=2.0 Hz), 7.61-7.64 (1H, m), 7.64 (2H, d, J=8.6 Hz), 8.53-9.50 (2H, br), 10.67 (1H, br s)

Example 17

The Synthesis of Compound 597

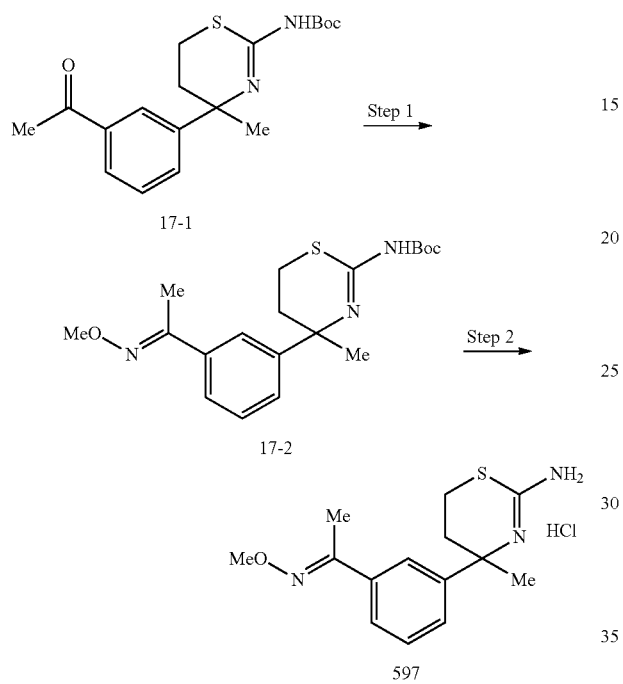

Step 1

The solution of compound (17-1)(135 mg), O-methxylhydroxylamine hydrochloride (39 mg), and potassium acetate (27 mg) in methanol (3 ml) was stirred at room temperature for 16 hours, then water was added. The mixture was extracted with dichloromethane, the organic layer was dried over anhydrous sodium sulfate, then the solvent was evaporated under reduced pressure. The obtained residue was purified by silica gel column chromatography to afford the compound (17-2)(110 mg).

$^1$H-NMR (CDCl$_3$): 1.51 (9H, a), 1.70 (3H, s), 2.14 (1H, ddd, J=14.4, 11.4, 3.4 Hz), 2.22 (3H, s), 2.48 (1H, m), 2.65 (1H, dt, J=12.6, 11.4 Hz), 2.78 (1H, ddd, J=12.6, 5.6, 3.4 Hz), 4.00 (3H, s), 7.30 (1H, d, J=7.8 Hz), 7.38 (1H, d, J=7.8 Hz), 7.54-7.57 (2H, m).

Step 2

To the compound (17-2)(110 mg), 4 mol/L hydrochloric acid in 1,4-dioxane (4.5 ml) solution was added and stirred for 4 days at room temperature, then the reaction solvent was evaporated under reduced pressure. The obtained residue was crystallized from methanol/diethyl ether to afford compound (597)(65 mg).

$^1$H-NMR (DMSO-d$_6$): 1.67 (3H, s), 2.08-2.15 (1H, m), 2.20 (3H, s), 2.56-2.64 (2H, m), 3.14-3.17 (1H, m), 3.92 (3H, s), 7.37 (1H, d, J=8.0 Hz), 7.48 (1H, d, J=8.0 Hz), 7.56 (1H, s), 7.62 (1H, d, J=8.0 Hz).

The other compounds were synthesized in the same way. The structural formulas and physical constants are shown below.

TABLE 1

| Compound No. | Chemical structure |
|---|---|
| 1 | 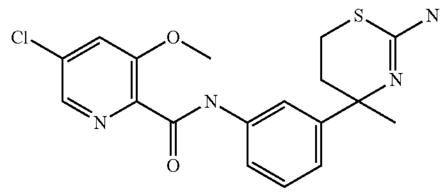 [SMILES: COc1cc(Cl)cnc1C(=O)Nc1cccc(C2(C)CCSC(N)=N2)c1] |
| 2 | 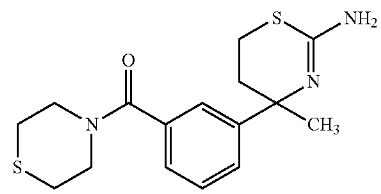 [SMILES: CC1(c2cccc(C(=O)N3CCSCC3)c2)CCSC(N)=N1] |
| 3 | 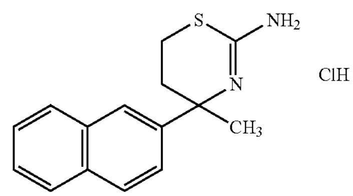 [SMILES: CC1(c2ccc3ccccc3c2)CCSC(N)=N1 ; Cl] |
| 4 | 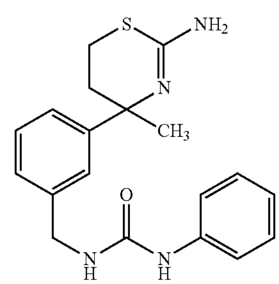 [SMILES: CC1(c2cccc(CNC(=O)Nc3ccccc3)c2)CCSC(N)=N1] |
| 5 | 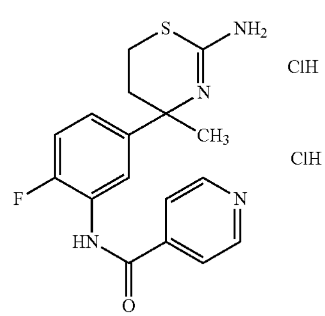 [SMILES: CC1(c2ccc(F)c(NC(=O)c3ccncc3)c2)CCSC(N)=N1 ; Cl ; Cl] |
| 6 | 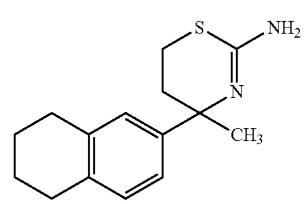 [SMILES: CC1(c2ccc3c(c2)CCCC3)CCSC(N)=N1] |

TABLE 1-continued

| Compound No. | Chemical structure |
|---|---|
| 7 | (2-amino-4-methyl-5,6-dihydro-4H-1,3-thiazin-4-yl)phenyl 3-(trifluoromethyl)benzamide |
| 8 | 2-amino-4-(4-methoxyphenyl)-4,5-dimethyl-5,6-dihydro-4H-1,3-thiazine HCl |
| 9 | N-[3-(2-amino-4-methyl-5,6-dihydro-4H-1,3-thiazin-4-yl)-5-(methoxymethyl)phenyl]-N-methylmethanesulfonamide |

TABLE 2

| Compound No. | Chemical structure |
|---|---|
| 10 | 4-chloro-N-[3-(2-amino-4-methyl-5,6-dihydro-4H-1,3-thiazin-4-yl)phenyl]-1,3-dimethyl-1H-pyrazolo[3,4-b]pyridine-5-carboxamide |
| 11 | N-[3-(2-amino-4-methyl-5,6-dihydro-4H-1,3-thiazin-4-yl)phenyl]-3-methoxybenzamide |
| 12 | N-[3-(2-amino-4-methyl-5,6-dihydro-4H-1,3-thiazin-4-yl)phenyl]-2,4-dimethylbenzamide |
| 13 | N-[3-(2-amino-4-methyl-5,6-dihydro-4H-1,3-thiazin-4-yl)phenyl]-6-chloropyridine-3-carboxamide |
| 14 | N-[4-(2-amino-4-methyl-5,6-dihydro-4H-1,3-thiazin-4-yl)benzoyl]-5,6-dimethyl-1H-benzimidazol-2-amine |
| 15 | N-[3-(2-amino-4-methyl-5,6-dihydro-4H-1,3-thiazin-4-yl)phenyl]-2-phenyl-1,3-thiazole-4-carboxamide |
| 16 | [4-(2-amino-4-methyl-5,6-dihydro-4H-1,3-thiazin-4-yl)phenyl][4-(3-methoxyphenyl)piperazin-1-yl]methanone |

TABLE 2-continued
17 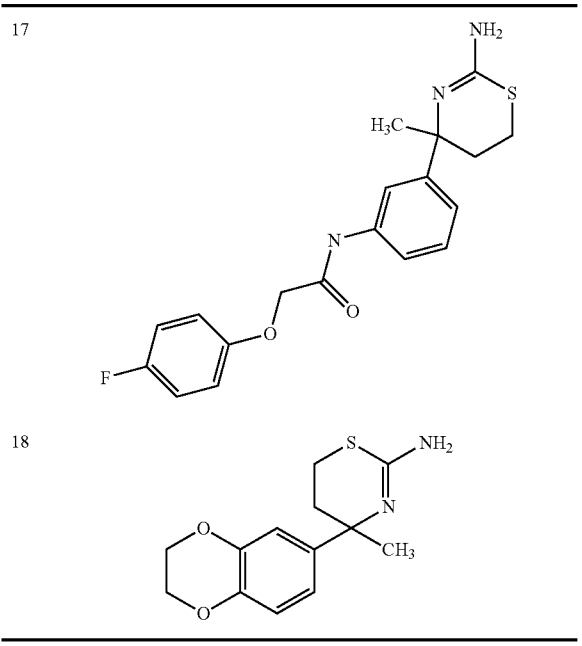
18
TABLE 3
19 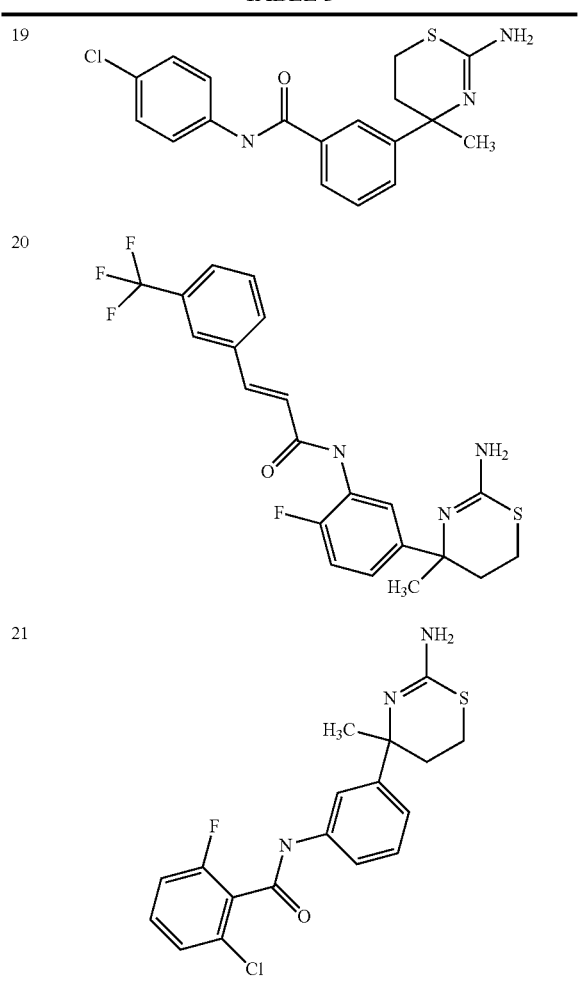
20
21
TABLE 3-continued
22 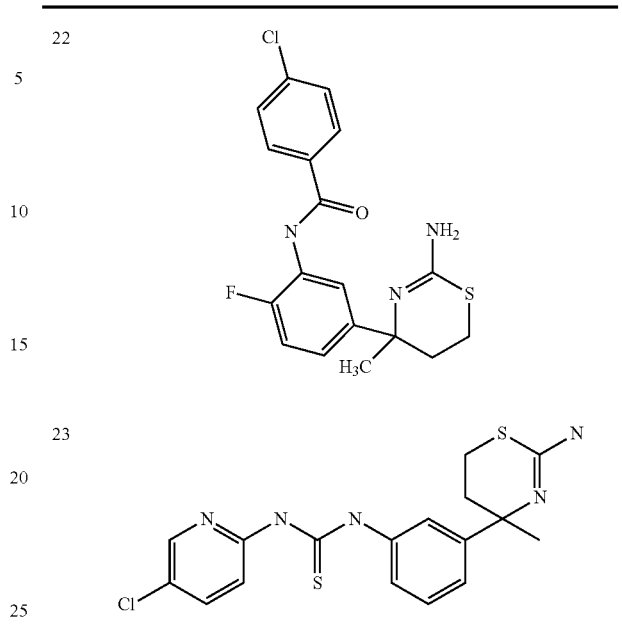
23
24
25 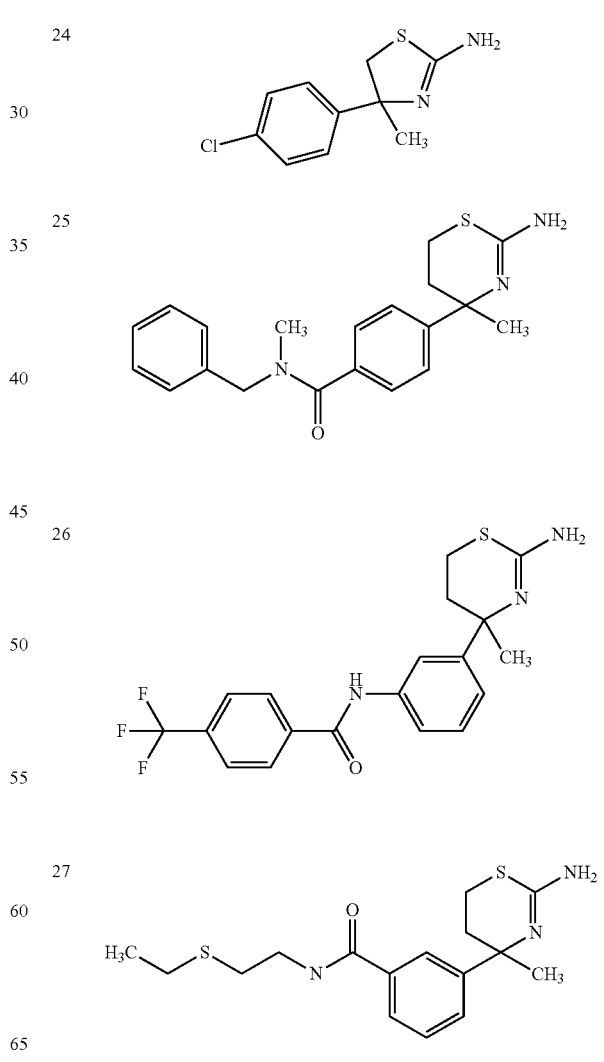
26
27

TABLE 3-continued
| 28 | 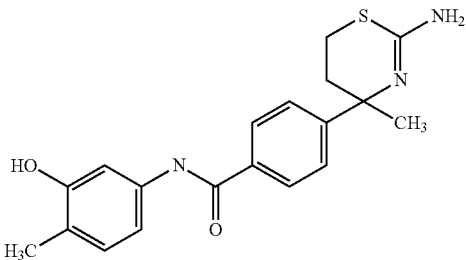 [SMILES: Cc1ccc(NC(=O)c2ccc(C3(C)CCSC(N)=N3)cc2)cc1O] |
TABLE 4
| 29 | 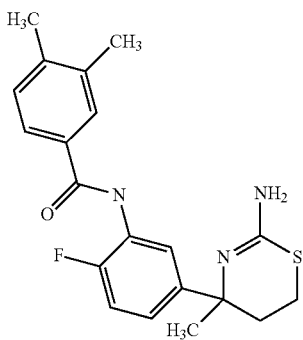 [SMILES: Cc1ccc(C(=O)Nc2cc(C3(C)CCSC(N)=N3)ccc2F)cc1C] |
| 30 | 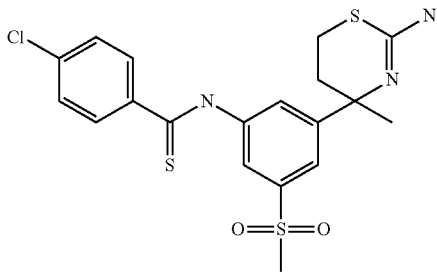 |
| 31 | 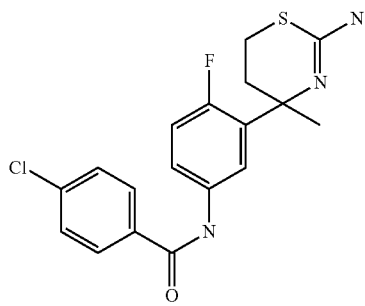 [SMILES: CC1(c2cc(NC(=O)c3ccc(Cl)cc3)ccc2F)CCSC(N)=N1] |
| 32 | 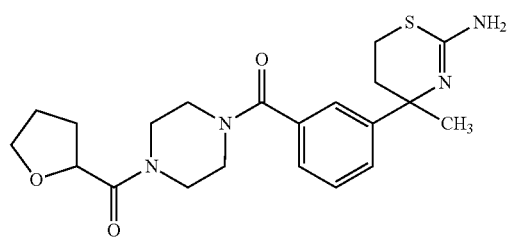 [SMILES: CC1(c2cccc(C(=O)N3CCN(C(=O)C4CCCO4)CC3)c2)CCSC(N)=N1] |
TABLE 4-continued
| 33 | 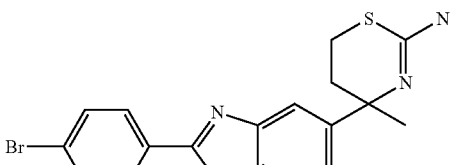 |
| 34 | 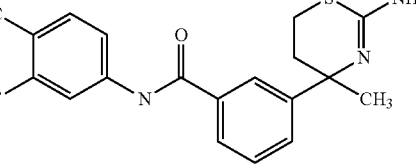 |
| 35 | 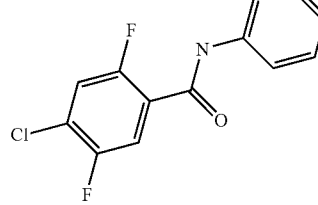 |
| 36 | 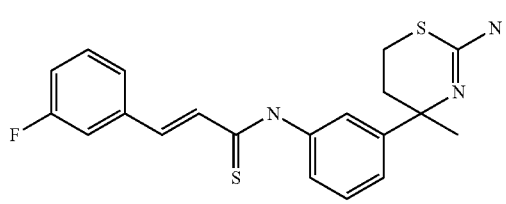 [SMILES: CC1(c2cccc(NC(=S)/C=C/c3cccc(F)c3)c2)CCSC(N)=N1] |
| 37 | 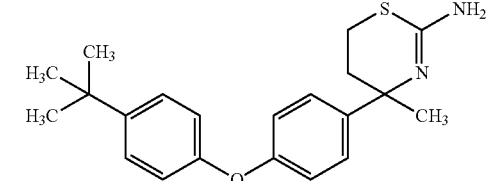 |
| 38 | 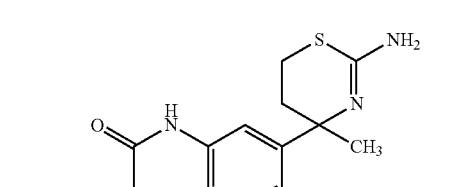 |
| 39 | 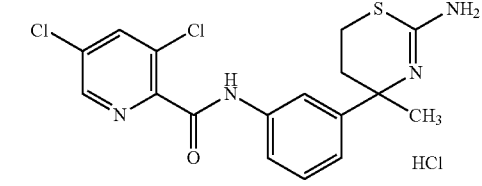 [SMILES: CC1(c2cccc(NC(=O)c3ncc(Cl)cc3Cl)c2)CCSC(N)=N1 ; Cl] HCl |

TABLE 5
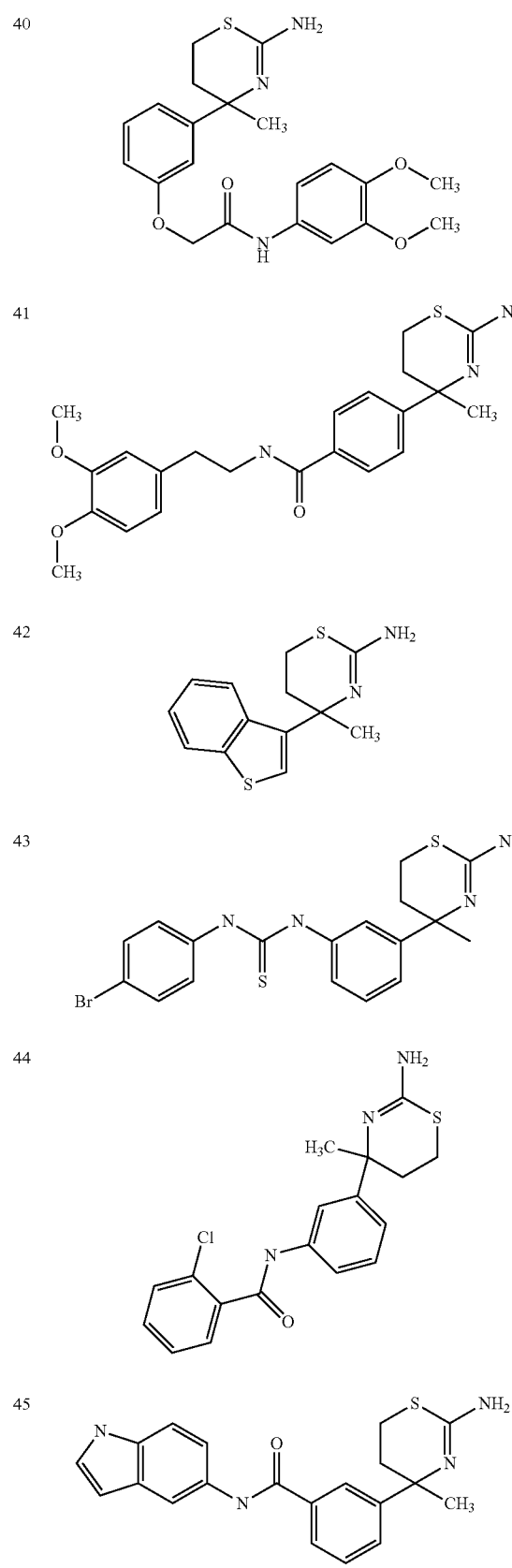
TABLE 5-continued
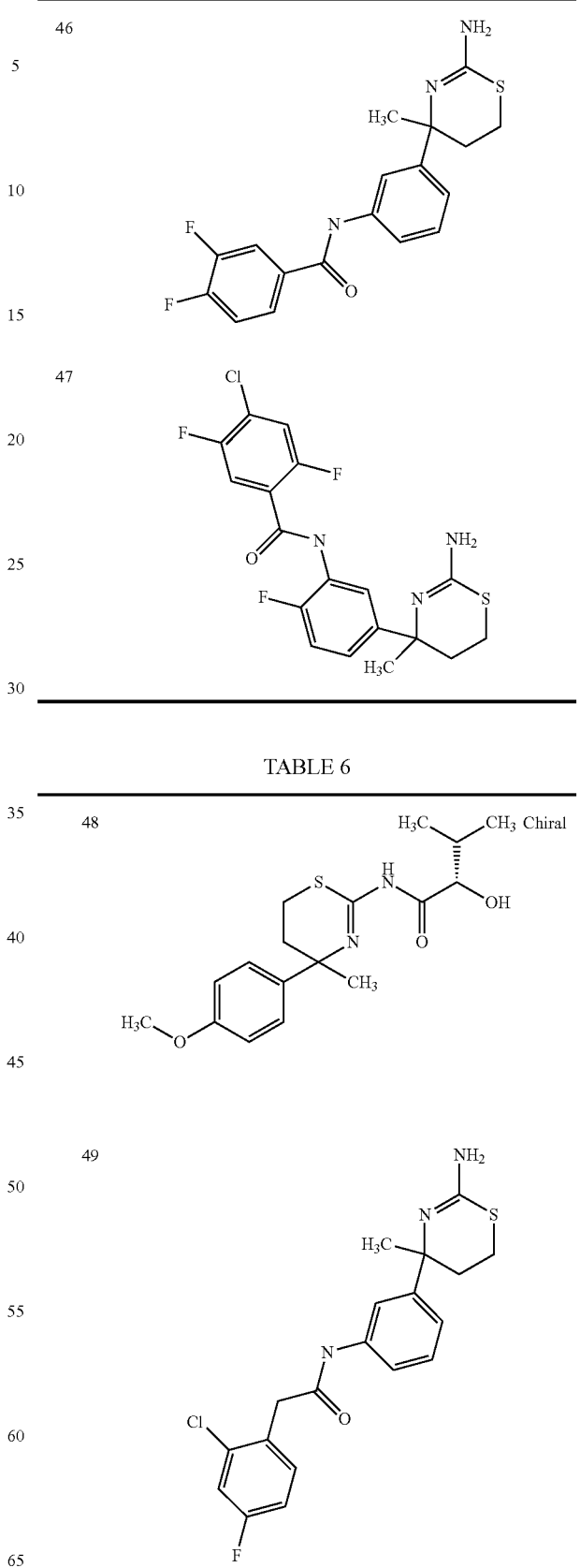
TABLE 6

TABLE 6-continued
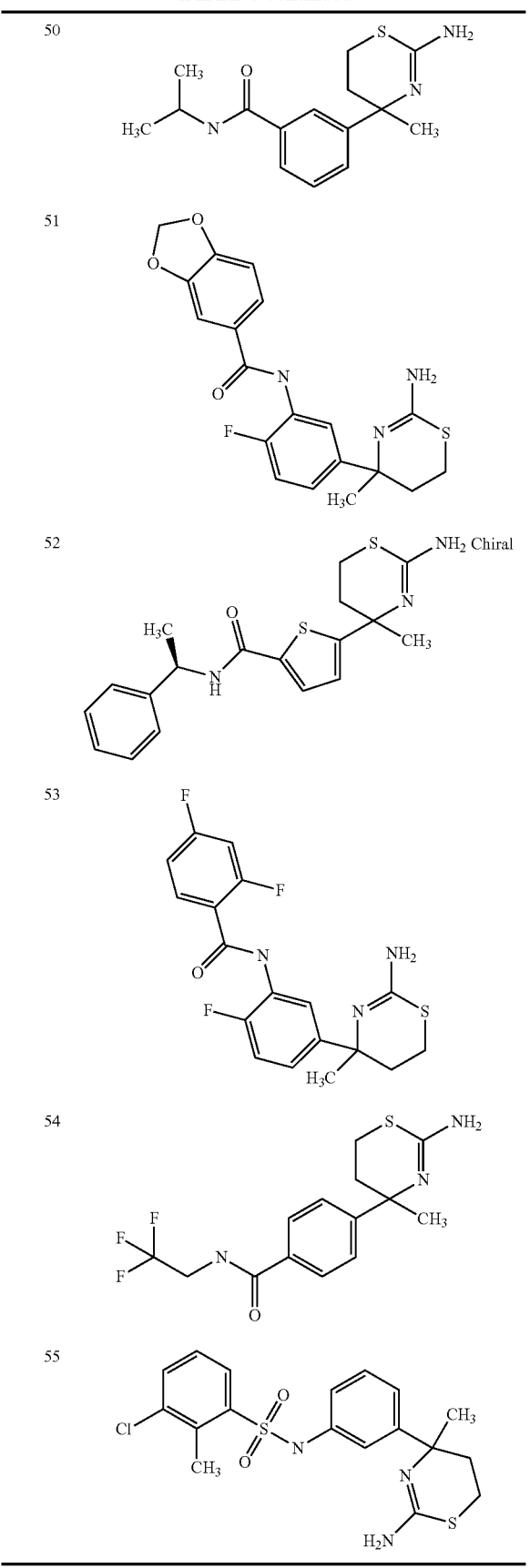
TABLE 7
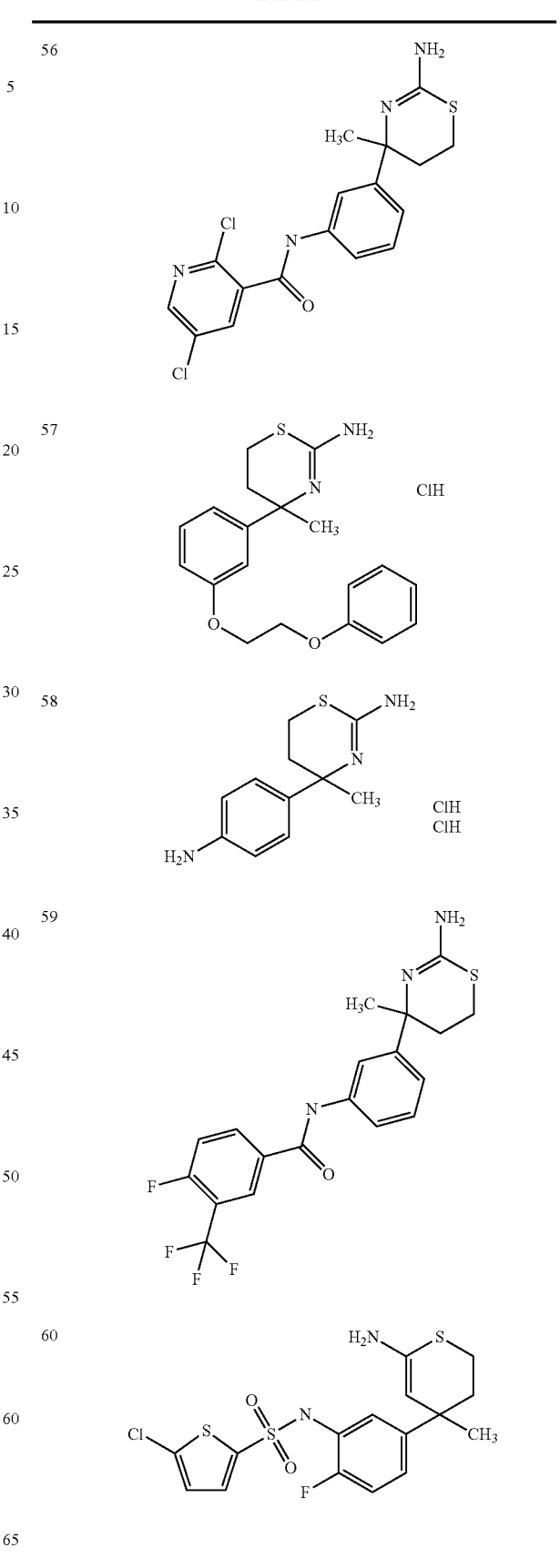

TABLE 7-continued
| 61 | 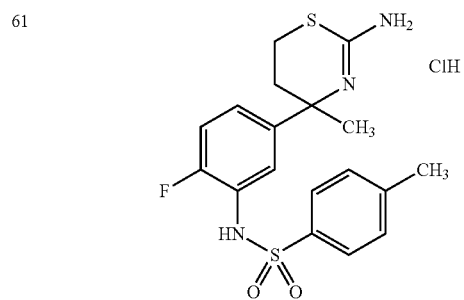 |
| 62 | 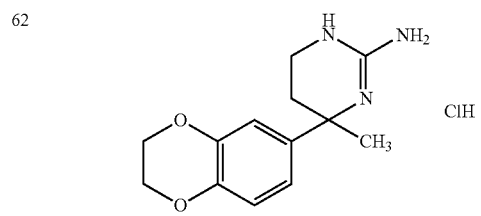 |
| 63 | 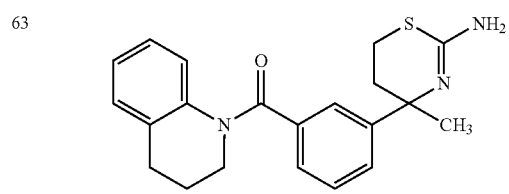 |
| 64 | 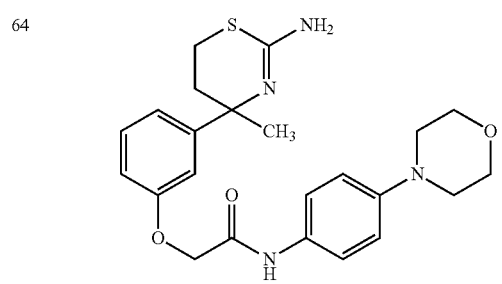 |
| 65 | 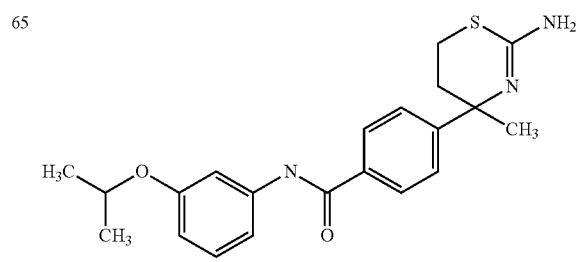 |
TABLE 8
| 66 | 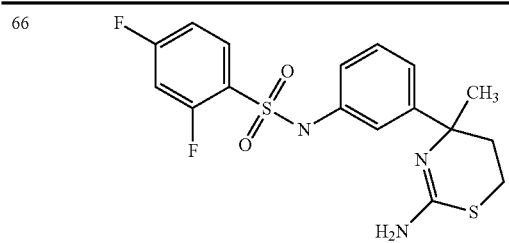 |
TABLE 8-continued
| 67 | 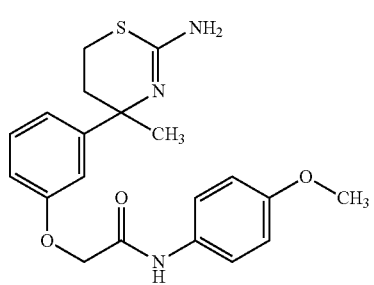 [SMILES: COc1ccc(NC(=O)COc2cccc(C3(C)CCSC(N)=N3)c2)cc1] |
| 68 | 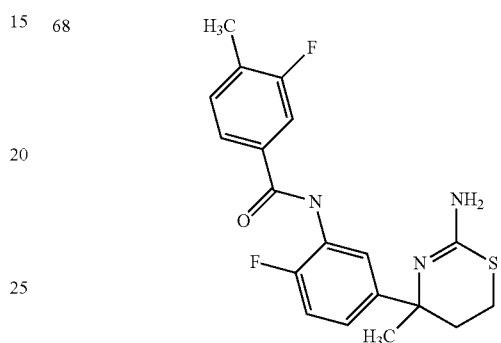 |
| 69 | 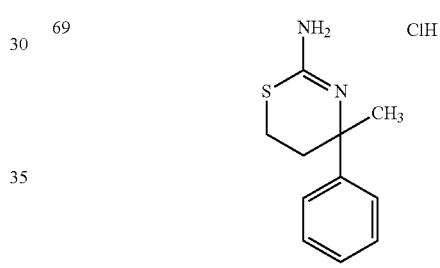 |
| 70 | 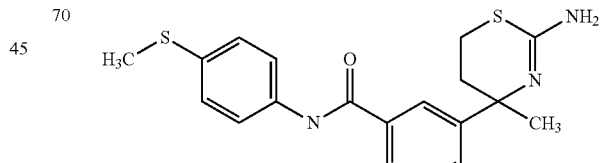 |
| 71 | |

TABLE 8-continued
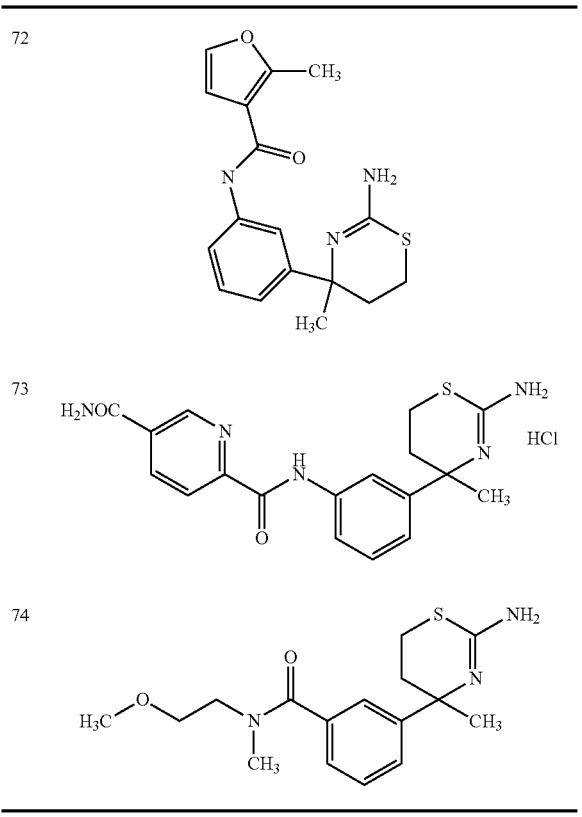
TABLE 9
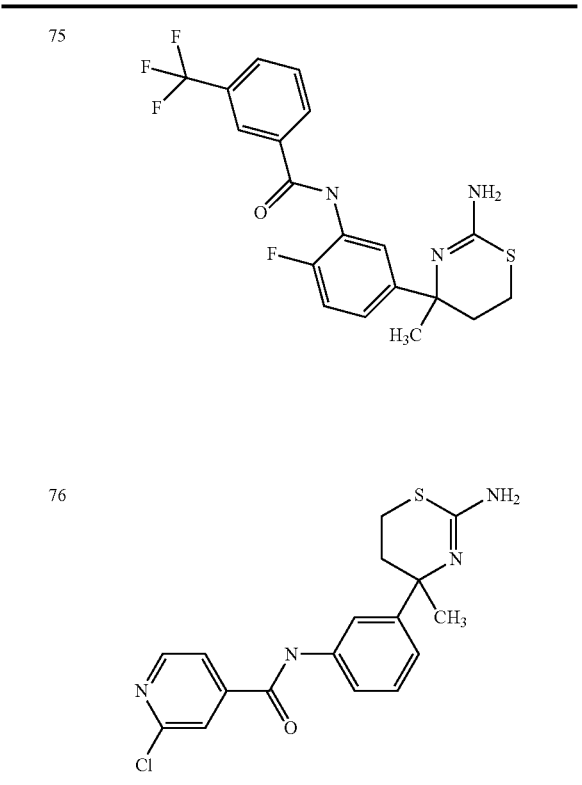
TABLE 9-continued
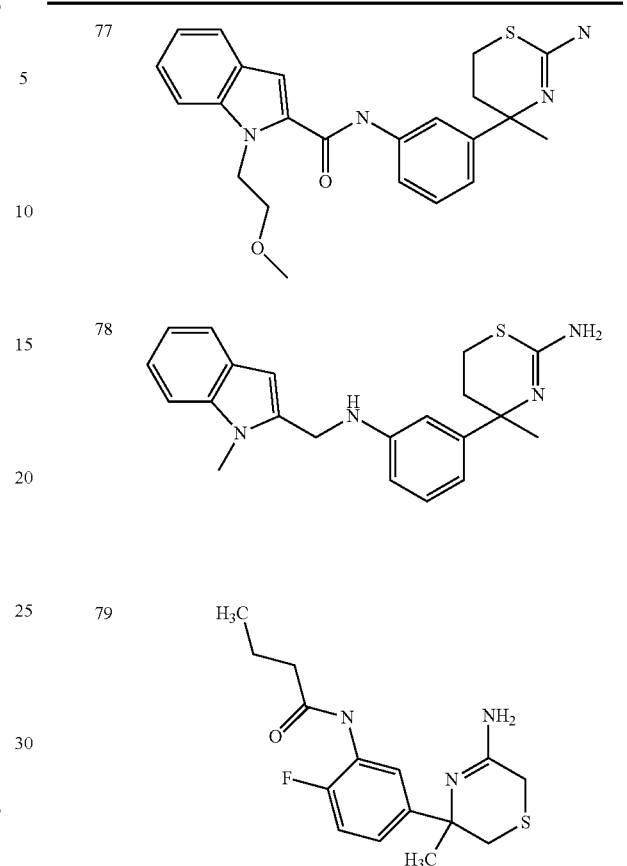
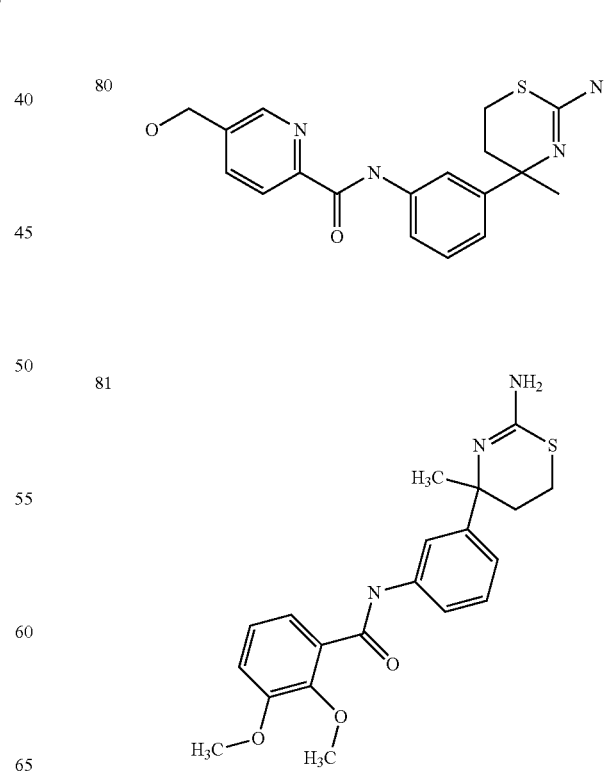

TABLE 9-continued
82 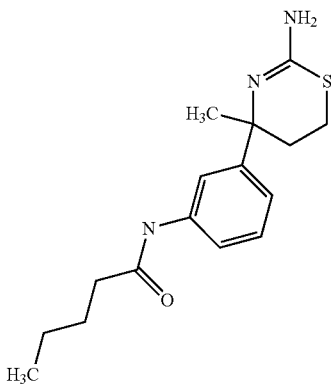 [SMILES: CCCCC(=O)Nc1cccc(C2(C)CCSC(N)=N2)c1]
TABLE 10
83 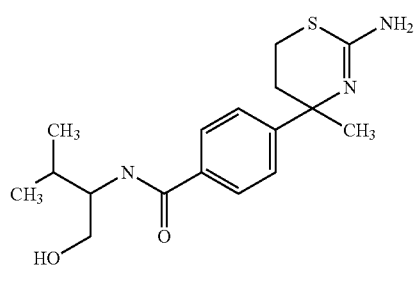 [SMILES: CC(C)C(CO)NC(=O)c1ccc(C2(C)CCSC(N)=N2)cc1]
84 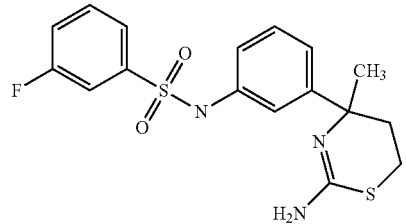 [SMILES: CC1(c2cccc(NS(=O)(=O)c3cccc(F)c3)c2)CCSC(N)=N1]
85 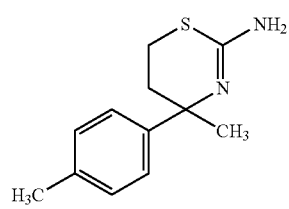
86 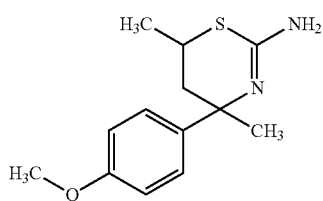 [SMILES: COc1ccc(C2(C)CC(C)SC(N)=N2)cc1]
TABLE 10-continued
87 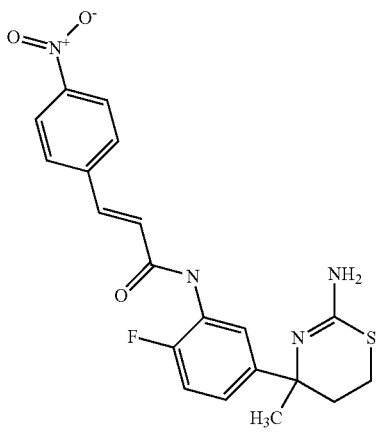 [SMILES: CC1(c2ccc(F)c(NC(=O)/C=C/c3ccc([N+](=O)[O-])cc3)c2)CCSC(N)=N1]
88 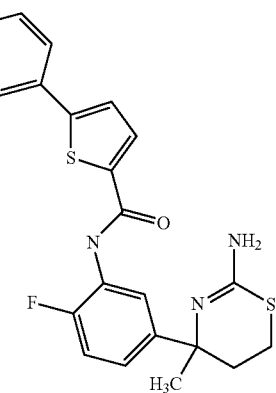
89 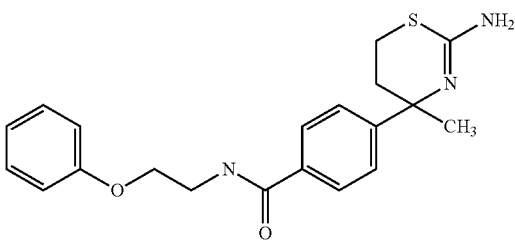 [SMILES: CC1(c2ccc(C(=O)NCCOc3ccccc3)cc2)CCSC(N)=N1]
90 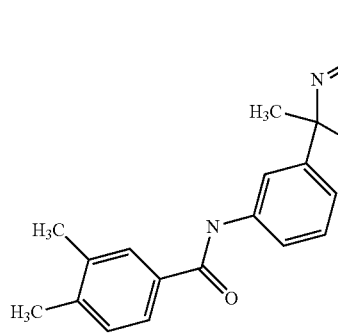

TABLE 10-continued
| 91 | 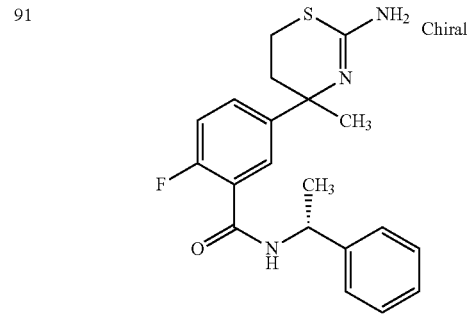 Chiral |
TABLE 11
| 92 | 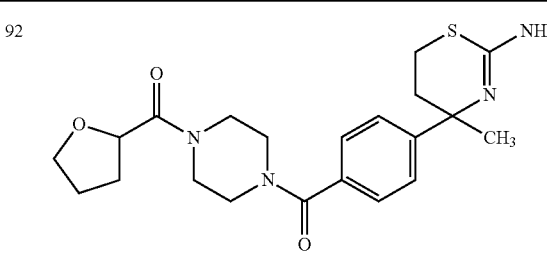 |
| 93 | 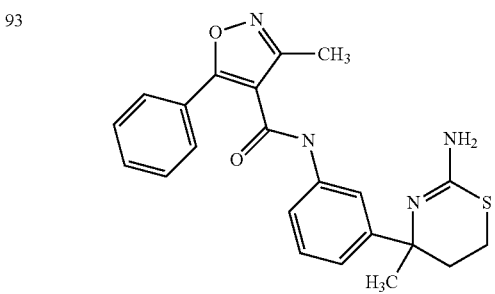 |
| 94 | 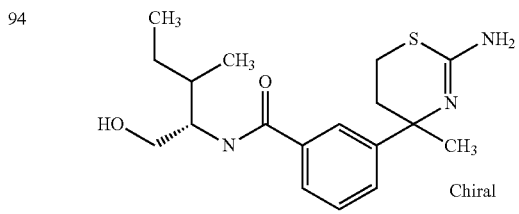 Chiral |
| 95 | 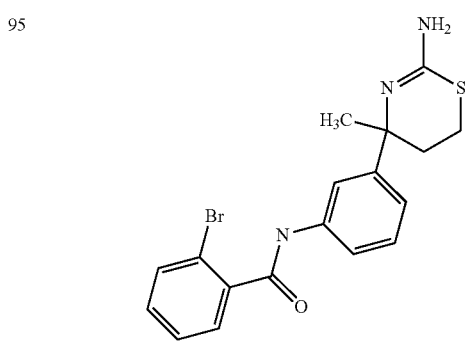 |
TABLE 11-continued
| 96 | 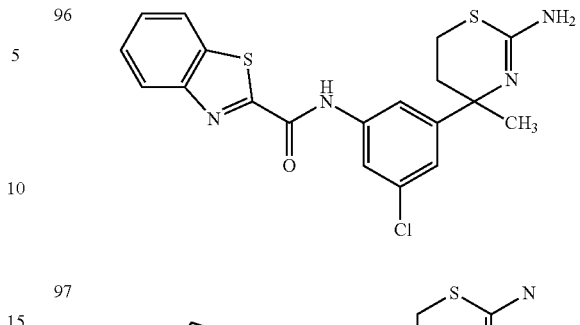 |
| 97 | 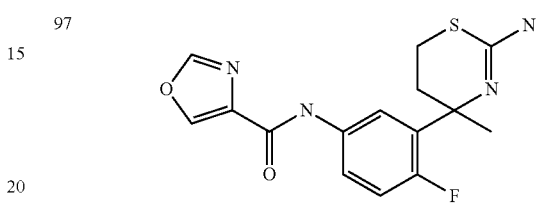 |
| 98 | 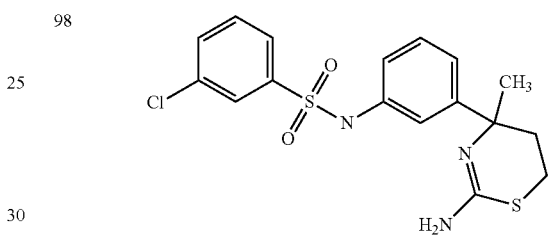 |
| 99 | 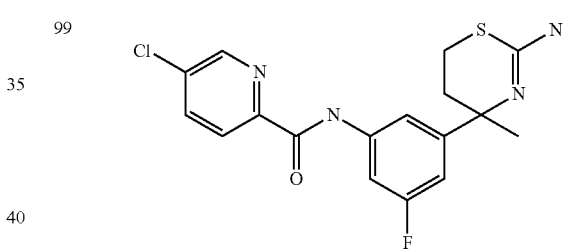 |
| 100 | 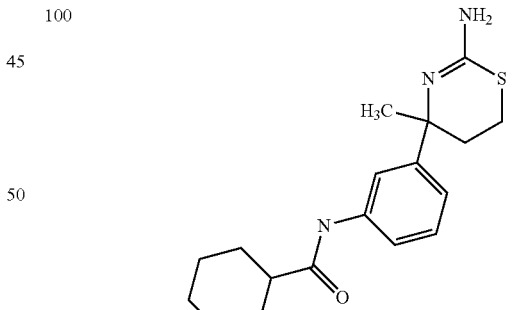 |
| 101 | 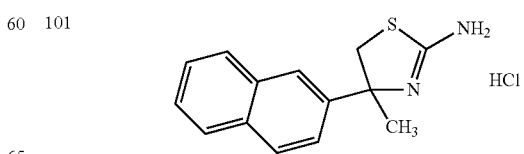 HCl |

TABLE 12
102 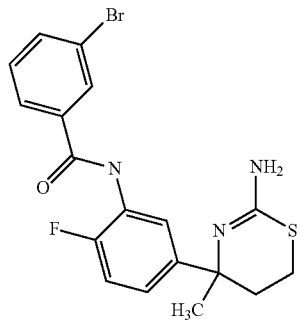
103 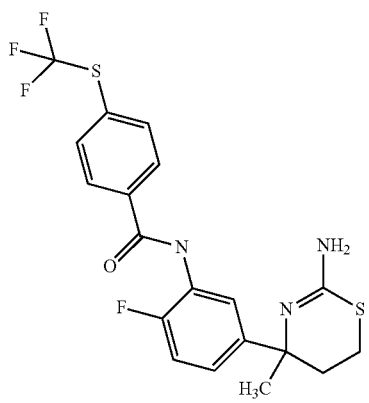
104 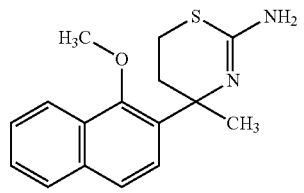 [SMILES: COc1c(C2(C)CCSC(N)=N2)ccc2ccccc12]
105 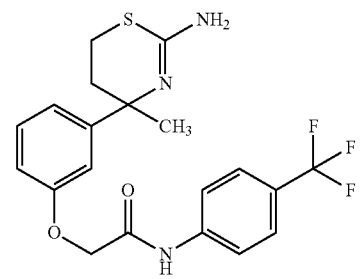 [SMILES: CC1(c2cccc(OCC(=O)Nc3ccc(C(F)(F)F)cc3)c2)CCSC(N)=N1]
106 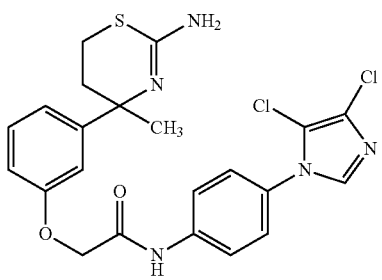 [SMILES: CC1(c2cccc(OCC(=O)Nc3ccc(-n4cnc(Cl)c4Cl)cc3)c2)CCSC(N)=N1]
TABLE 12-continued
107 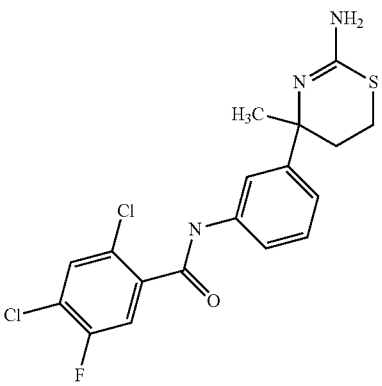 [SMILES: CC1(c2cccc(NC(=O)c3cc(F)c(Cl)cc3Cl)c2)CCSC(N)=N1]
108 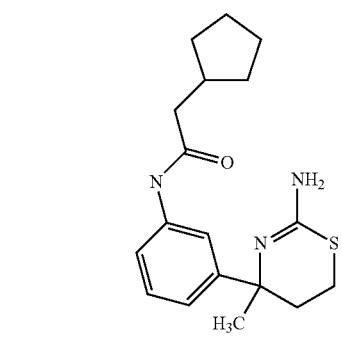 [SMILES: CC1(c2cccc(NC(=O)CC3CCCC3)c2)CCSC(N)=N1]
109 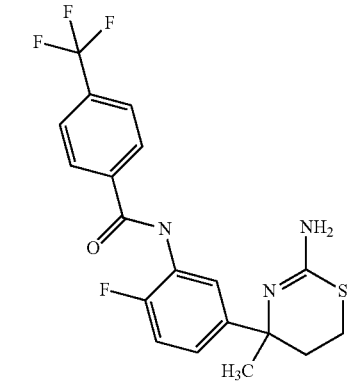 [SMILES: CC1(c2ccc(F)c(NC(=O)c3ccc(C(F)(F)F)cc3)c2)CCSC(N)=N1]
TABLE 13
110 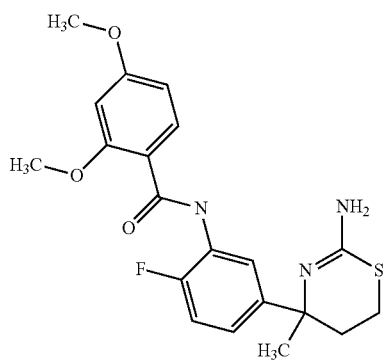 [SMILES: COc1ccc(C(=O)Nc2cc(C3(C)CCSC(N)=N3)ccc2F)c(OC)c1]

TABLE 13-continued
111 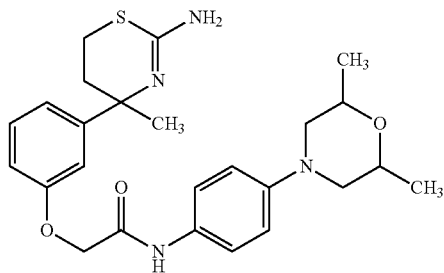 [SMILES: CC1CN(c2ccc(NC(=O)COc3cccc(C4(C)CCSC(N)=N4)c3)cc2)CC(C)O1]
112 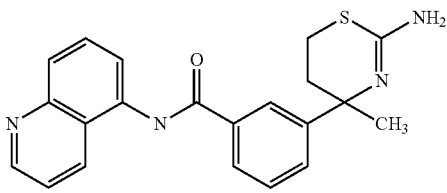 [SMILES: CC1(c2cccc(C(=O)Nc3cccc4ncccc34)c2)CCSC(N)=N1]
113 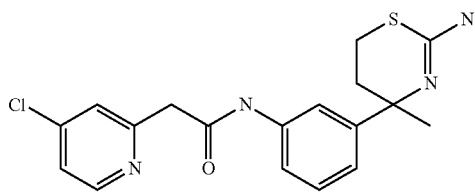 [SMILES: CC1(c2cccc(NC(=O)Cc3cc(Cl)ccn3)c2)CCSC(N)=N1]
114 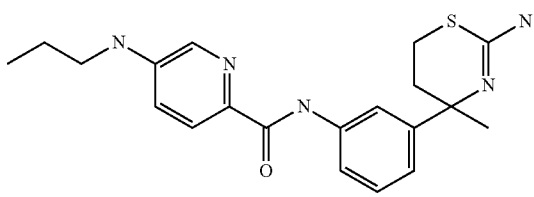 [SMILES: CCCNc1ccc(C(=O)Nc2cccc(C3(C)CCSC(N)=N3)c2)nc1]
115 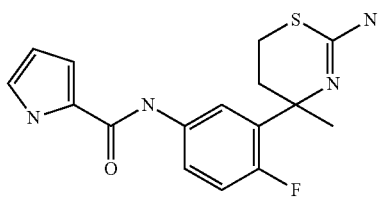 [SMILES: CC1(c2cc(NC(=O)c3ccc[nH]3)ccc2F)CCSC(N)=N1]
116 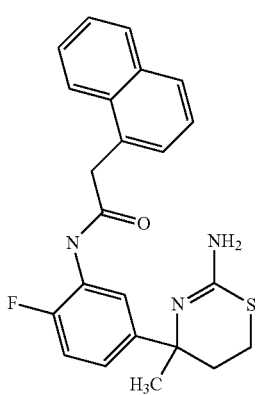 [SMILES: CC1(c2ccc(F)c(NC(=O)Cc3cccc4ccccc34)c2)CCSC(N)=N1]
TABLE 13-continued
117 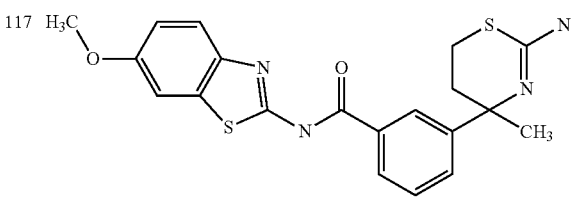
118 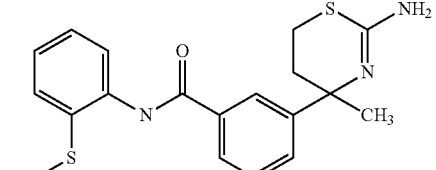
119 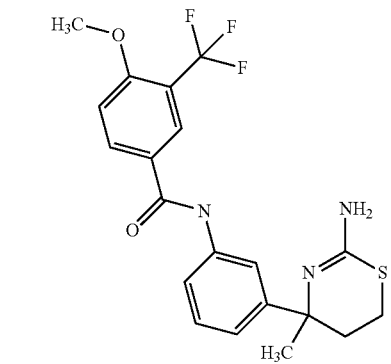 [SMILES: COc1ccc(C(=O)Nc2cccc(C3(C)CCSC(N)=N3)c2)cc1C(F)(F)F]
TABLE 14
120 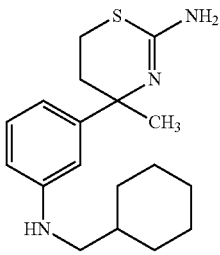 [SMILES: CC1(c2cccc(NCC3CCCCC3)c2)CCSC(N)=N1]
121 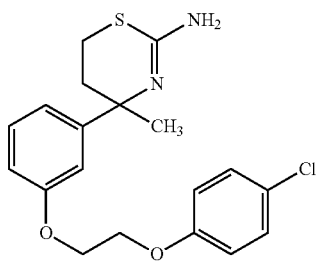

TABLE 14-continued
122 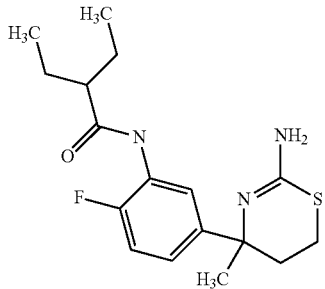 [SMILES: CCC(CC)C(=O)Nc1cc(C2(C)CCSC(N)=N2)ccc1F]
124 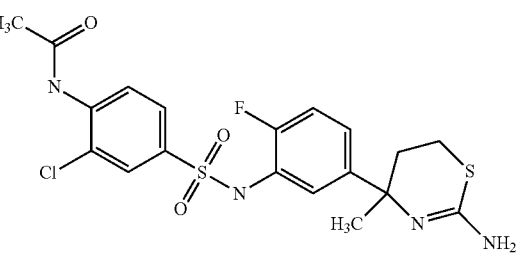
125 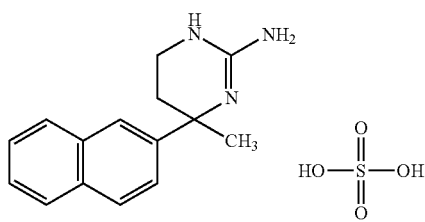 [SMILES: CC1(c2ccc3ccccc3c2)CCNC(N)=N1 ; O=S(=O)(O)O]
126 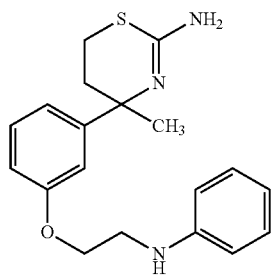 [SMILES: CC1(c2cccc(OCCNc3ccccc3)c2)CCSC(N)=N1]
127 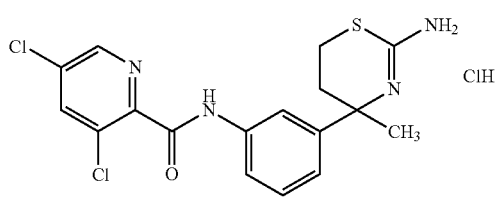 [SMILES: CC1(c2cccc(NC(=O)c3ncc(Cl)cc3Cl)c2)CCSC(N)=N1 ; Cl]
128 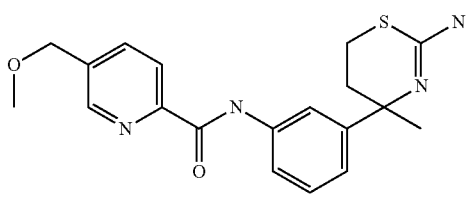 [SMILES: COCc1ccc(C(=O)Nc2cccc(C3(C)CCSC(N)=N3)c2)nc1]
TABLE 14-continued
129 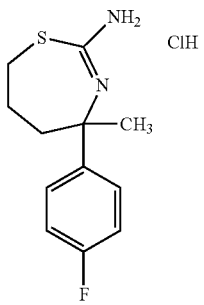 [SMILES: CC1(c2ccc(F)cc2)CCCSC(N)=N1 ; Cl]
130 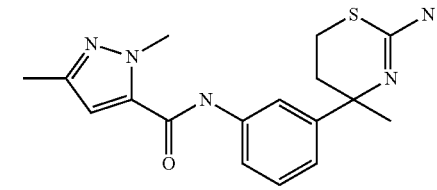 [SMILES: Cc1cc(C(=O)Nc2cccc(C3(C)CCSC(N)=N3)c2)n(C)n1]
TABLE 15
131 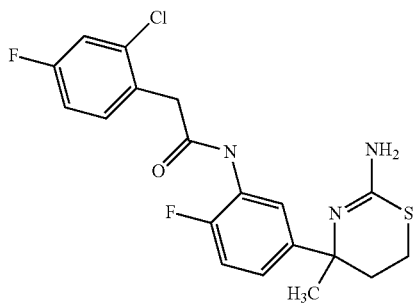 [SMILES: CC1(c2ccc(F)c(NC(=O)Cc3ccc(F)cc3Cl)c2)CCSC(N)=N1]
132 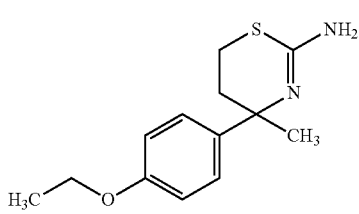 [SMILES: CCOc1ccc(C2(C)CCSC(N)=N2)cc1]
133 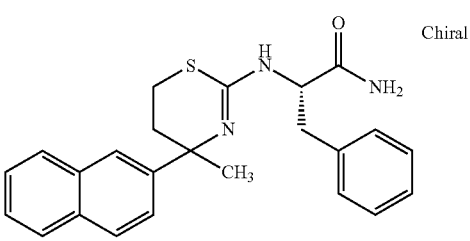 [SMILES: CC1(c2ccc3ccccc3c2)CCSC(N[C@@H](Cc2ccccc2)C(N)=O)=N1]
134 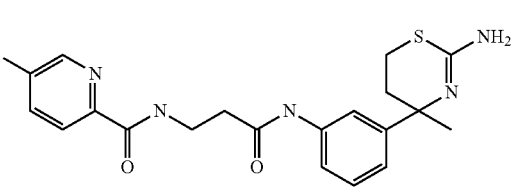

TABLE 15-continued
| | |
|---|---|
| 135 | 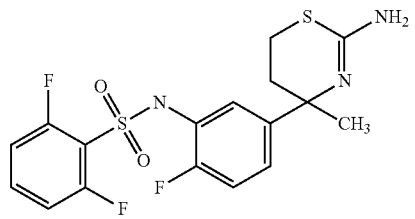 [SMILES: CC1(c2ccc(F)c(NS(=O)(=O)c3c(F)cccc3F)c2)CCSC(N)=N1] |
| 136 | 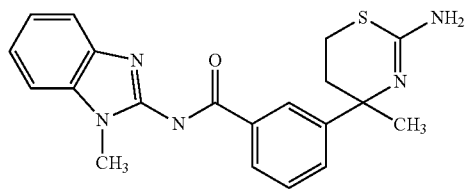 |
| 137 | 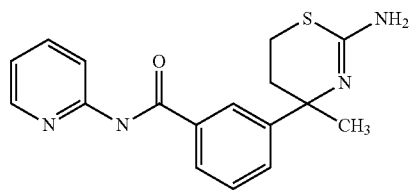 [SMILES: CC1(c2cccc(C(=O)Nc3ccccn3)c2)CCSC(N)=N1] |
| 138 | 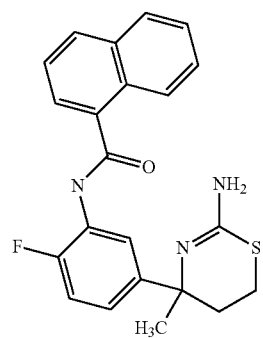 [SMILES: CC1(c2ccc(F)c(NC(=O)c3cccc4ccccc34)c2)CCSC(N)=N1] |
| 139 | 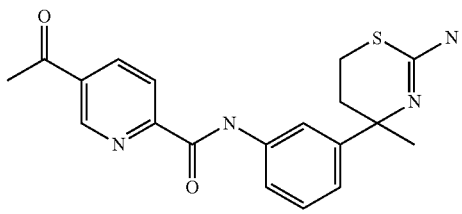 [SMILES: CC(=O)c1ccc(C(=O)Nc2cccc(C3(C)CCSC(N)=N3)c2)nc1] |
| 140 | 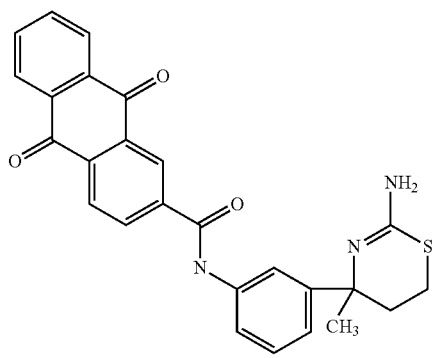 [SMILES: CC1(c2cccc(NC(=O)c3ccc4c(c3)C(=O)c3ccccc3C4=O)c2)CCSC(N)=N1] |
TABLE 15-continued
| | |
|---|---|
| 141 | 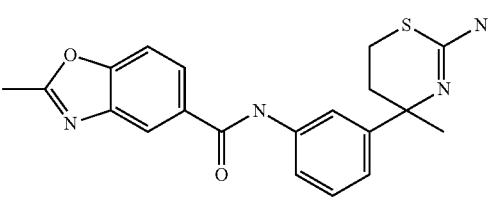 [SMILES: Cc1nc2cc(C(=O)Nc3cccc(C4(C)CCSC(N)=N4)c3)ccc2o1] |
TABLE 16
| | |
|---|---|
| 142 | 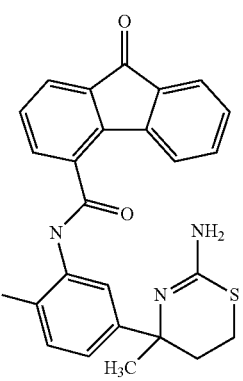 |
| 143 | 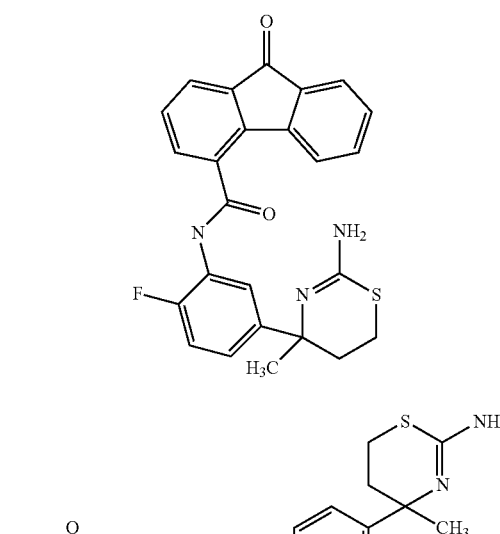 |
| 144 | 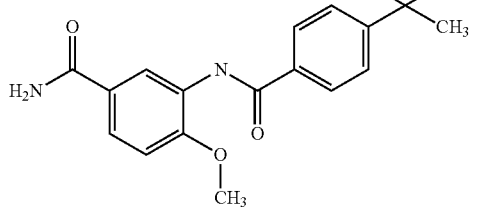 |
| 145 | 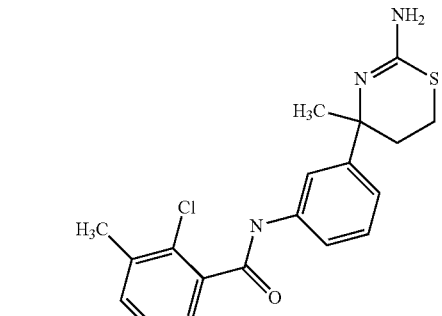 |

TABLE 16-continued
| 146 | 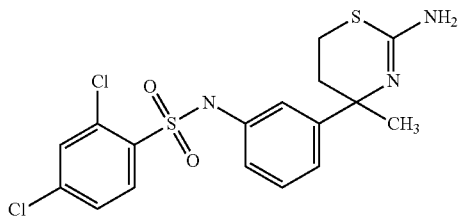 [SMILES: CC1(c2cccc(NS(=O)(=O)c3ccc(Cl)cc3Cl)c2)CCSC(N)=N1] |
| --- | --- |
| 147 | 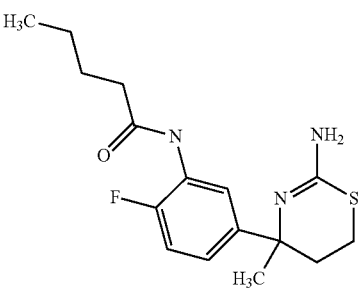 [SMILES: CCCCC(=O)Nc1cc(C2(C)CCSC(N)=N2)ccc1F] |
| 148 | 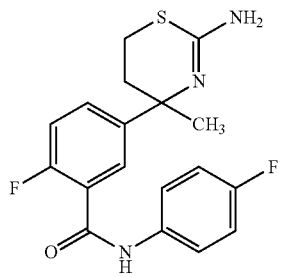 [SMILES: CC1(c2ccc(F)c(C(=O)Nc3ccc(F)cc3)c2)CCSC(N)=N1] |
| 149 | 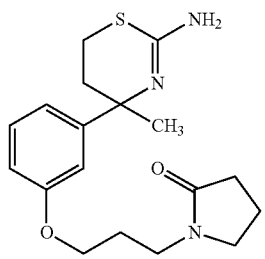 [SMILES: CC1(c2cccc(OCCCN3CCCC3=O)c2)CCSC(N)=N1] |
| 150 | 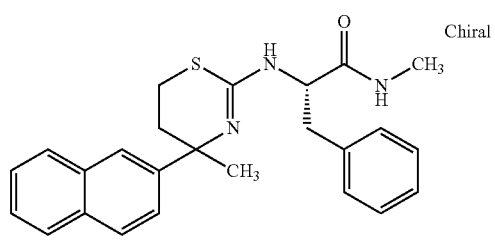 [SMILES: CNC(=O)[C@H](Cc1ccccc1)NC1=NC(C)(c2ccc3ccccc3c2)CCS1] |
TABLE 17
| 151 | 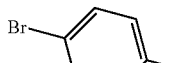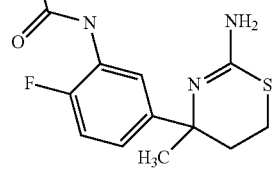 |
| --- | --- |
| 152 | 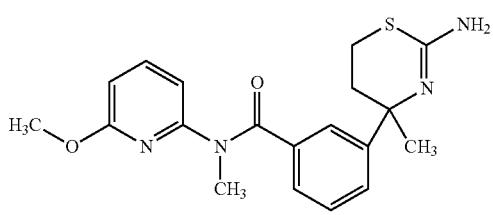 [SMILES: COc1cccc(N(C)C(=O)c2cccc(C3(C)CCSC(N)=N3)c2)n1] |
| 153 | 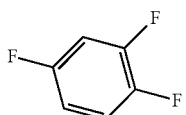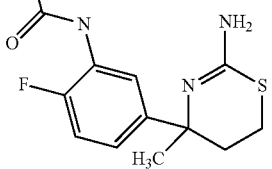 |
| 154 | 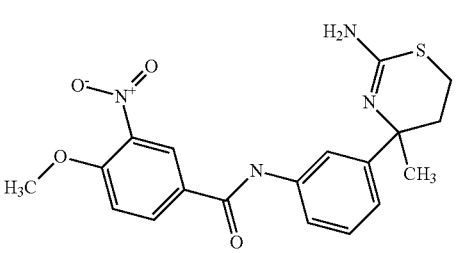 [SMILES: COc1ccc(C(=O)Nc2cccc(C3(C)CCSC(N)=N3)c2)cc1[N+](=O)[O-]] |
| 155 | 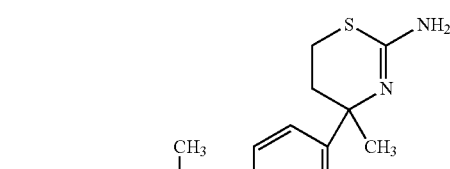 |
| 156 | 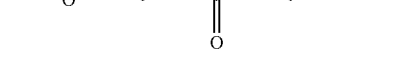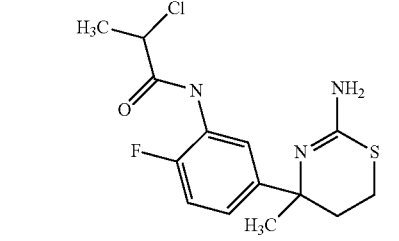 [SMILES: CC(Cl)C(=O)Nc1cc(C2(C)CCSC(N)=N2)ccc1F] |

TABLE 17-continued
157 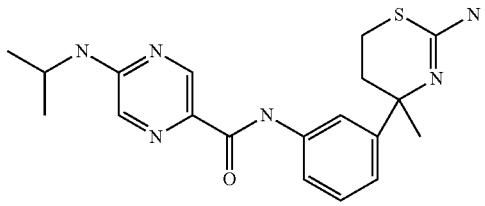 [SMILES: CC(C)Nc1cnc(C(=O)Nc2cccc(C3(C)CCSC(N)=N3)c2)cn1]
158 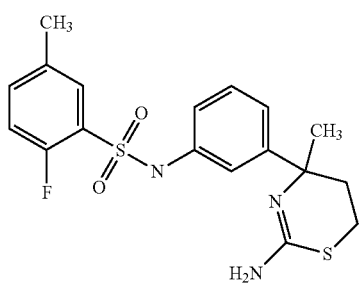 [SMILES: Cc1ccc(F)c(S(=O)(=O)Nc2cccc(C3(C)CCSC(N)=N3)c2)c1]
159 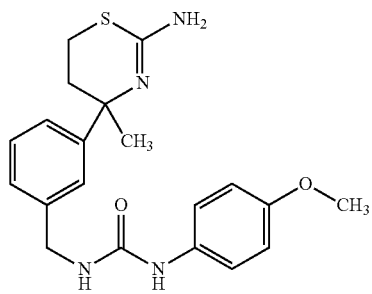 [SMILES: COc1ccc(NC(=O)NCc2cccc(C3(C)CCSC(N)=N3)c2)cc1]
TABLE 18
160 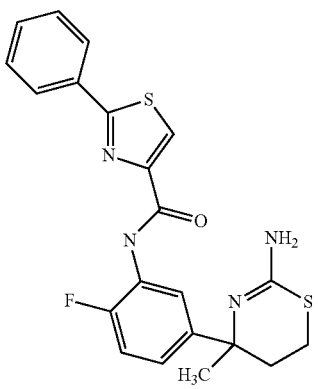 [SMILES: CC1(c2ccc(F)c(NC(=O)c3csc(-c4ccccc4)n3)c2)CCSC(N)=N1]
TABLE 18-continued
161 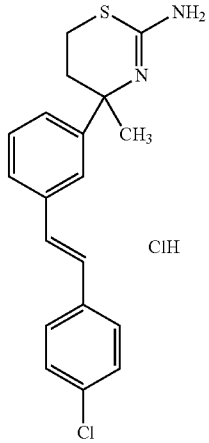 [SMILES: CC1(c2cccc(/C=C/c3ccc(Cl)cc3)c2)CCSC(N)=N1 ; Cl]
162 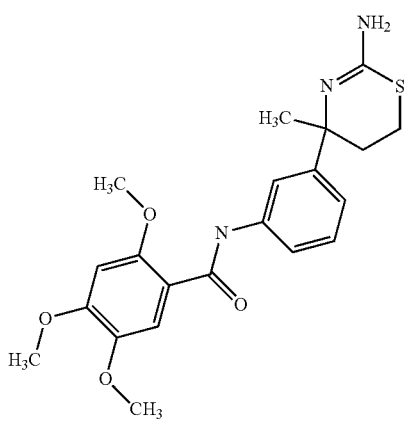 [SMILES: COc1cc(OC)c(C(=O)Nc2cccc(C3(C)CCSC(N)=N3)c2)cc1OC]
163 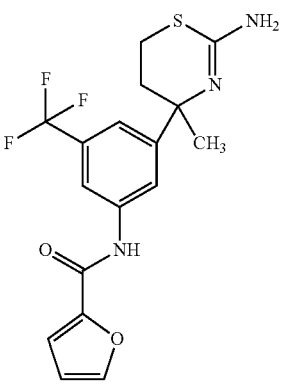 [SMILES: CC1(c2cc(NC(=O)c3ccco3)cc(C(F)(F)F)c2)CCSC(N)=N1]
164 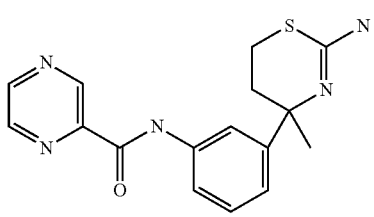 [SMILES: CC1(c2cccc(NC(=O)c3cnccn3)c2)CCSC(N)=N1]

TABLE 18-continued
165 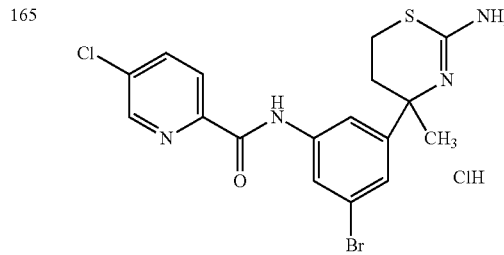
166 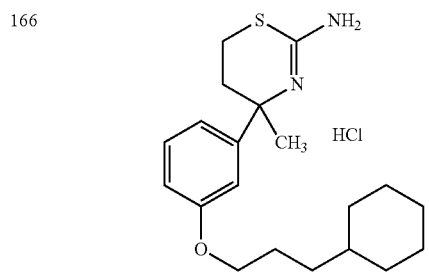
TABLE 19
167 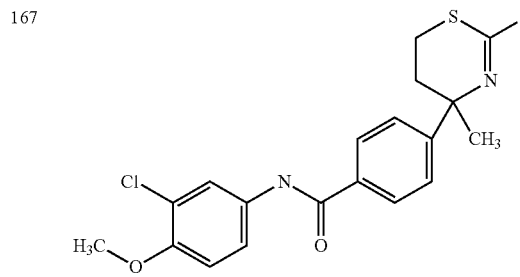
168 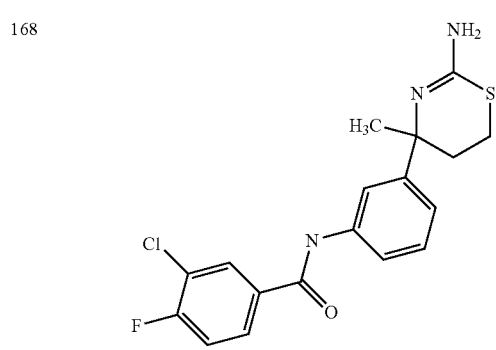
169 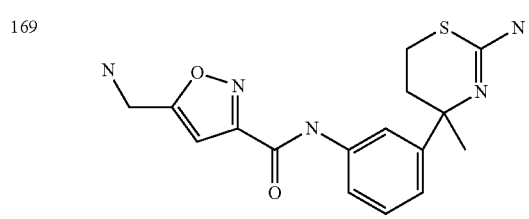
TABLE 19-continued
170 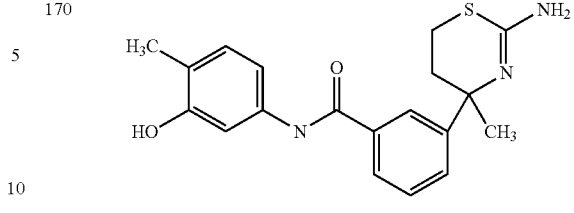
171 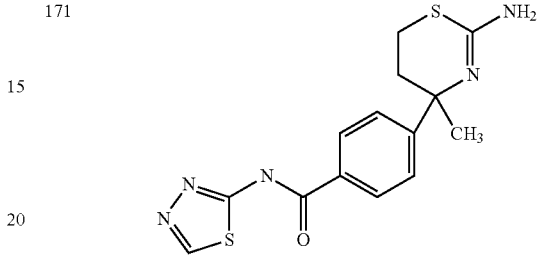
172 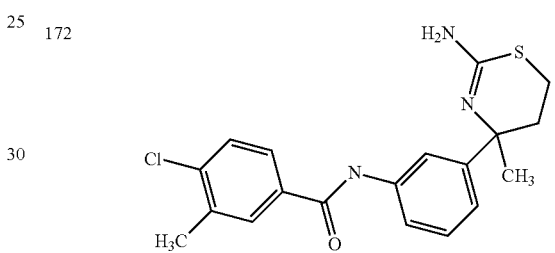
173 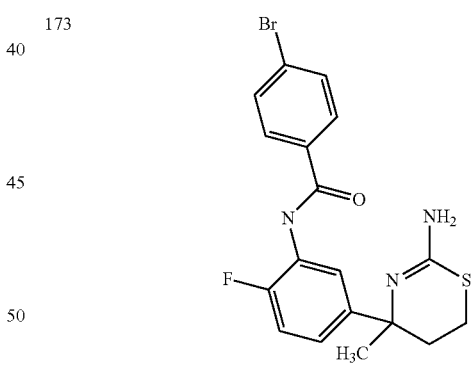
174 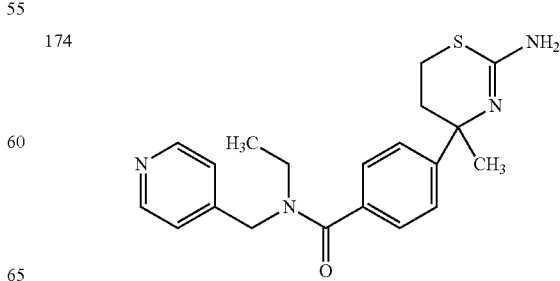

TABLE 19-continued
175 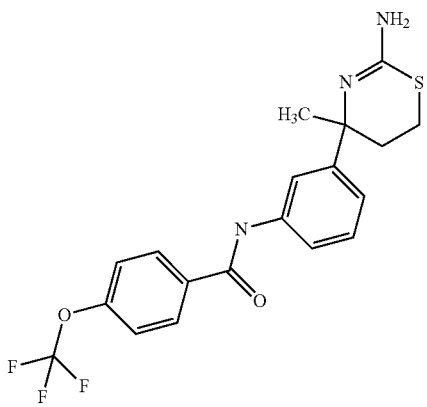 [SMILES: CC1(c2cccc(NC(=O)c3ccc(OC(F)(F)F)cc3)c2)CCSC(N)=N1]
176 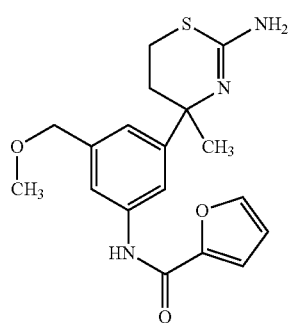 [SMILES: COCc1cc(NC(=O)c2ccco2)cc(C2(C)CCSC(N)=N2)c1]
TABLE 20
177 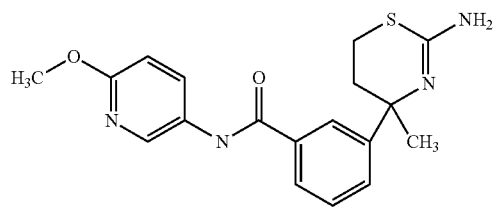 [SMILES: COc1ccc(NC(=O)c2cccc(C3(C)CCSC(N)=N3)c2)cn1]
178 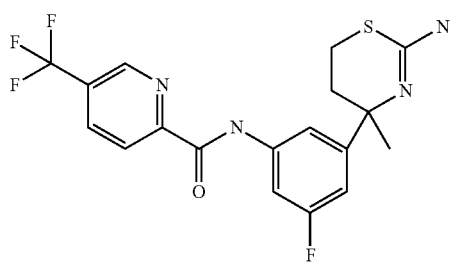 [SMILES: CC1(c2cc(F)cc(NC(=O)c3ccc(C(F)(F)F)cn3)c2)CCSC(N)=N1]
179 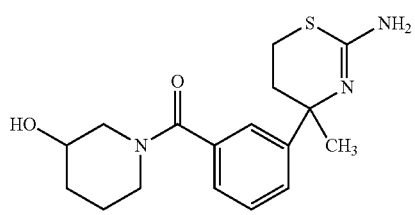 [SMILES: CC1(c2cccc(C(=O)N3CCCC(O)C3)c2)CCSC(N)=N1]
TABLE 20-continued
180 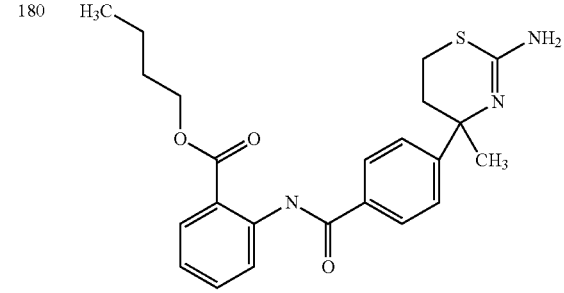
181 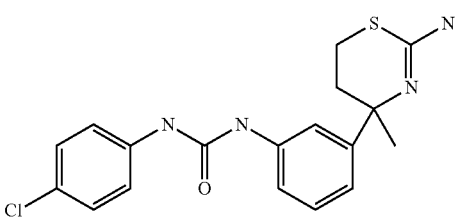 [SMILES: CC1(c2cccc(NC(=O)Nc3ccc(Cl)cc3)c2)CCSC(N)=N1]
182 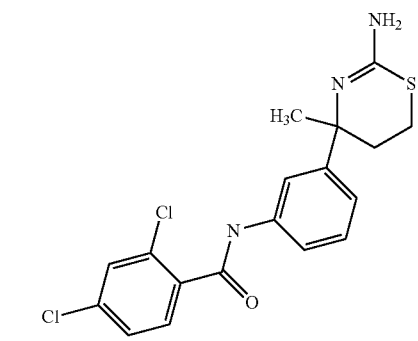
183 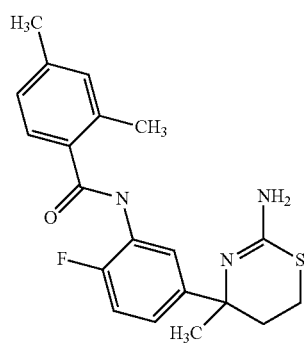 [SMILES: Cc1ccc(C(=O)Nc2cc(C3(C)CCSC(N)=N3)ccc2F)c(C)c1]
184 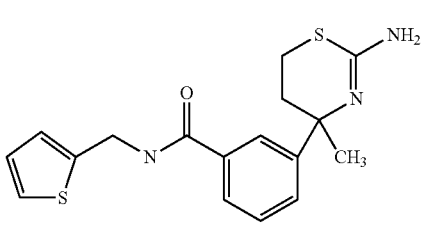 [SMILES: CC1(c2cccc(C(=O)NCc3cccs3)c2)CCSC(N)=N1]

TABLE 20-continued
185 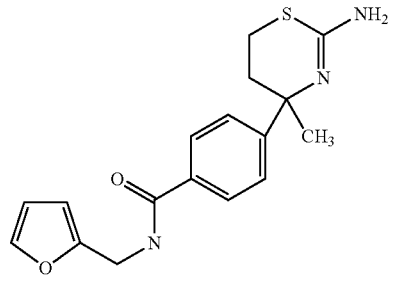 [SMILES: CC1(c2ccc(C(=O)NCc3ccco3)cc2)CCSC(N)=N1]
186 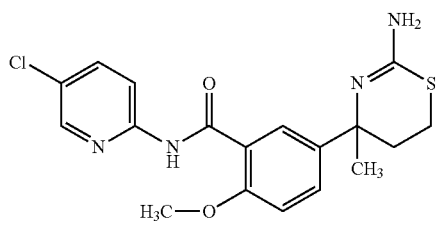 [SMILES: COc1ccc(C2(C)CCSC(N)=N2)cc1C(=O)Nc1ccc(Cl)cn1]
187 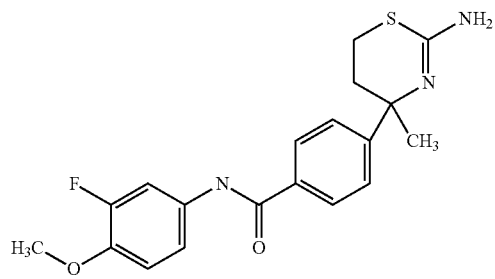 [SMILES: COc1ccc(NC(=O)c2ccc(C3(C)CCSC(N)=N3)cc2)cc1F]
188 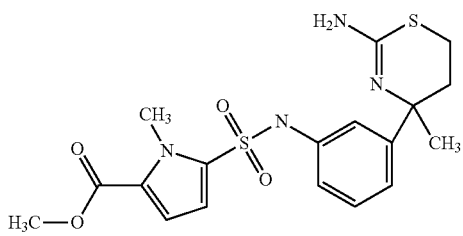 [SMILES: COC(=O)c1ccc(S(=O)(=O)Nc2cccc(C3(C)CCSC(N)=N3)c2)n1C]
TABLE 21
189 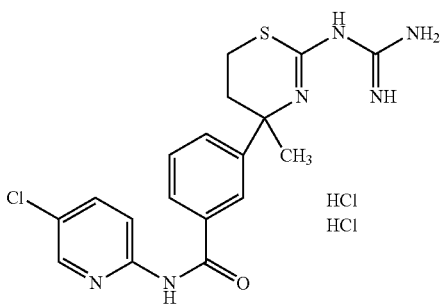 [SMILES: CC1(c2cccc(C(=O)Nc3ccc(Cl)cn3)c2)CCSC(NC(=N)N)=N1 ; Cl ; Cl]
TABLE 21-continued
190 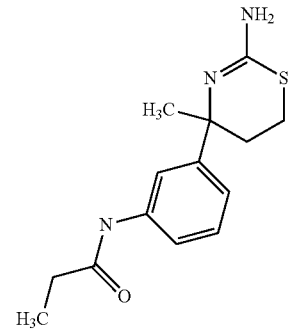 [SMILES: CCC(=O)Nc1cccc(C2(C)CCSC(N)=N2)c1]
191 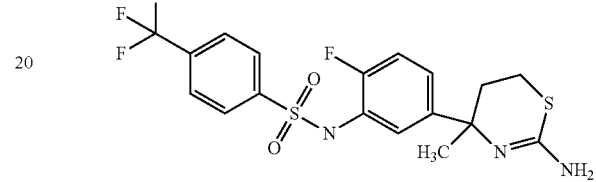
192 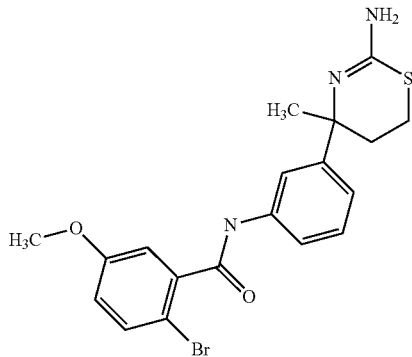 [SMILES: COc1ccc(Br)c(C(=O)Nc2cccc(C3(C)CCSC(N)=N3)c2)c1]
193 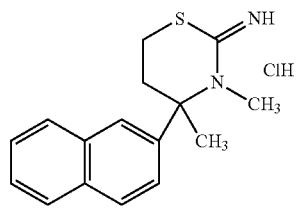 [SMILES: CN1C(=N)SCCC1(C)c1ccc2ccccc2c1 ; Cl]
194 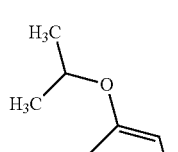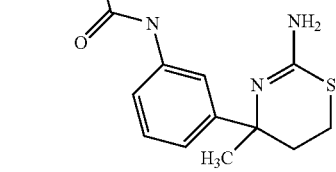

TABLE 21-continued
195 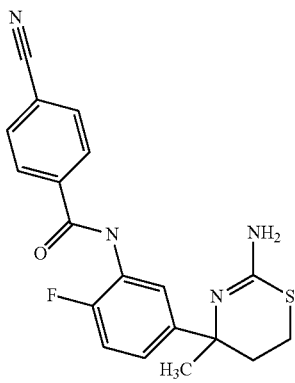 [SMILES: CC1(c2ccc(F)c(NC(=O)c3ccc(C#N)cc3)c2)CCSC(N)=N1]
196 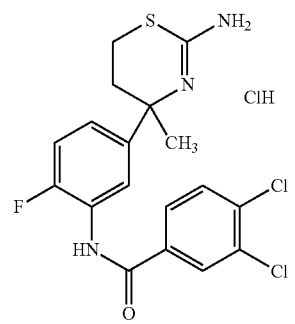 [SMILES: CC1(c2ccc(F)c(NC(=O)c3ccc(Cl)c(Cl)c3)c2)CCSC(N)=N1 ; Cl]
TABLE 22
197 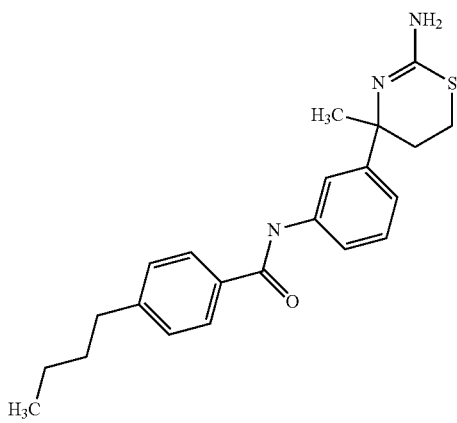 [SMILES: CCCCc1ccc(C(=O)Nc2cccc(C3(C)CCSC(N)=N3)c2)cc1]
198 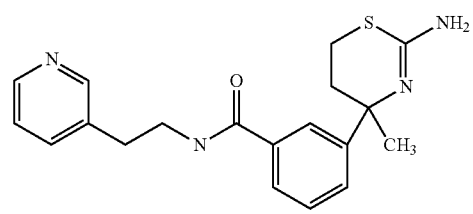 [SMILES: CC1(c2cccc(C(=O)NCCc3cccnc3)c2)CCSC(N)=N1]
TABLE 22-continued
199 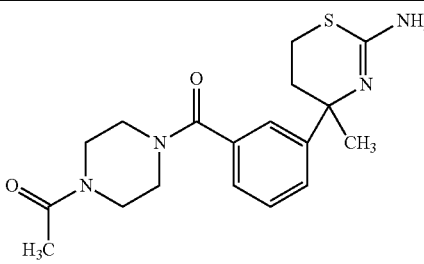
200 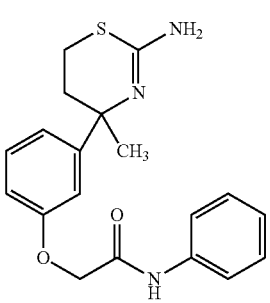 [SMILES: CC1(c2cccc(OCC(=O)Nc3ccccc3)c2)CCSC(N)=N1]
201 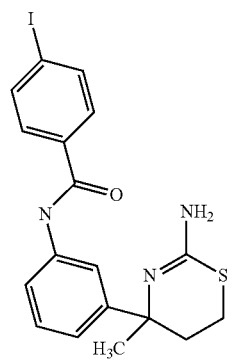 [SMILES: CC1(c2cccc(NC(=O)c3ccc(I)cc3)c2)CCSC(N)=N1]
202 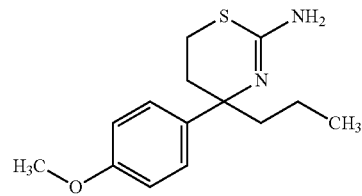 [SMILES: CCCC1(c2ccc(OC)cc2)CCSC(N)=N1]
203 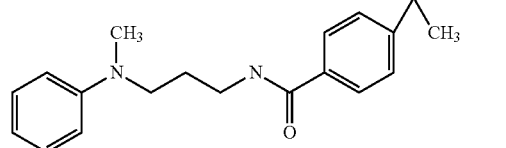
204 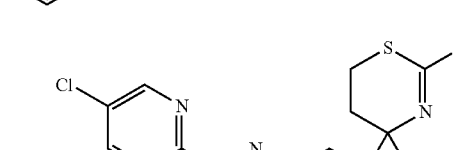

TABLE 22-continued
205 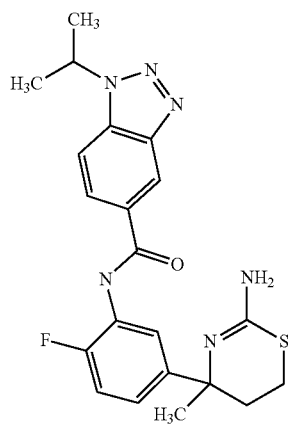 [SMILES: CC(C)n1nnc2cc(C(=O)Nc3cc(C4(C)CCSC(N)=N4)ccc3F)ccc21]
206 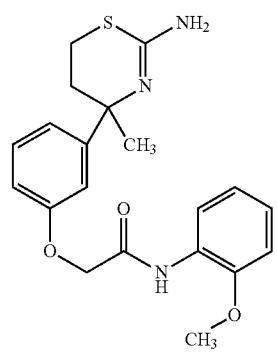 [SMILES: COc1ccccc1NC(=O)COc1cccc(C2(C)CCSC(N)=N2)c1]
TABLE 23
207 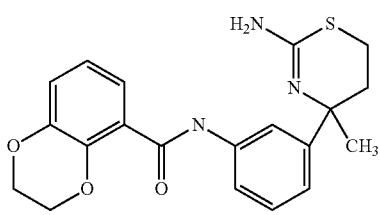 [SMILES: CC1(c2cccc(NC(=O)c3cccc4c3OCCO4)c2)CCSC(N)=N1]
208 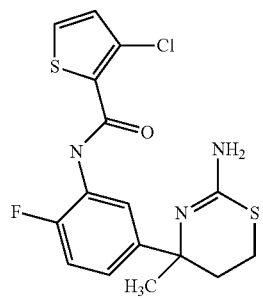 [SMILES: CC1(c2ccc(F)c(NC(=O)c3sccc3Cl)c2)CCSC(N)=N1]
TABLE 23-continued
209 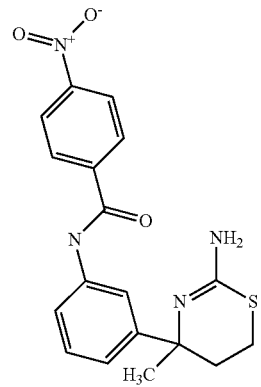 [SMILES: CC1(c2cccc(NC(=O)c3ccc([N+](=O)[O-])cc3)c2)CCSC(N)=N1]
210 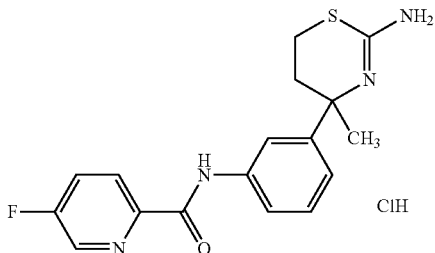
211 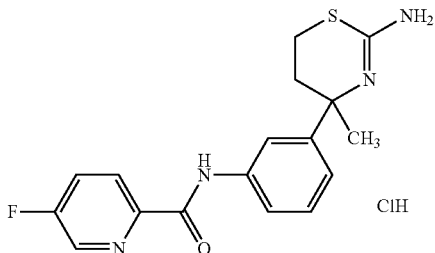
212 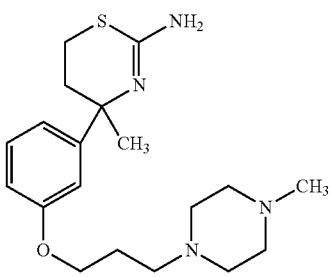 [SMILES: CN1CCN(CCCOc2cccc(C3(C)CCSC(N)=N3)c2)CC1]
213 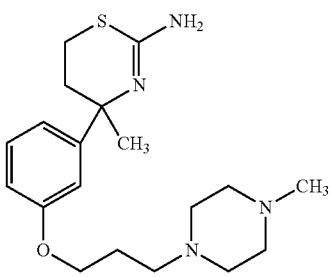 [SMILES: CN1CCN(CCCOc2cccc(C3(C)CCSC(N)=N3)c2)CC1]

TABLE 23-continued
214 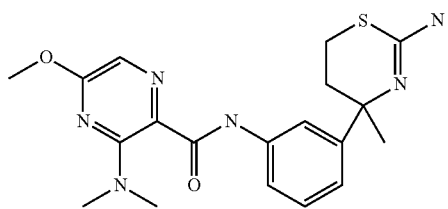 [SMILES: COc1cnc(C(=O)Nc2cccc(C3(C)CCSC(N)=N3)c2)c(N(C)C)n1]
215 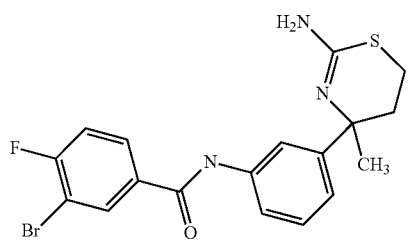 [SMILES: CC1(c2cccc(NC(=O)c3ccc(F)c(Br)c3)c2)CCSC(N)=N1]
TABLE 24
216 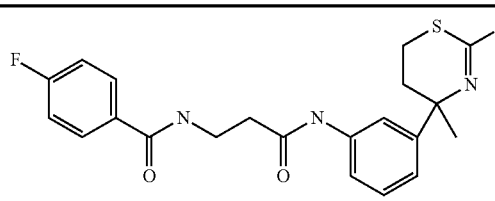
217 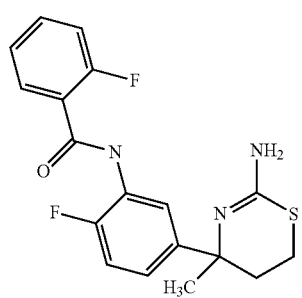 [SMILES: CC1(c2ccc(F)c(NC(=O)c3ccccc3F)c2)CCSC(N)=N1]
218 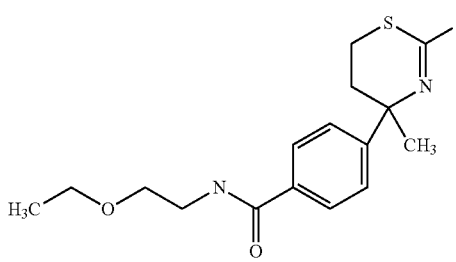
219 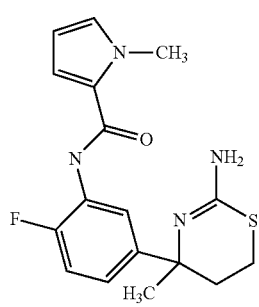 [SMILES: Cn1cccc1C(=O)Nc1cc(C2(C)CCSC(N)=N2)ccc1F]
TABLE 24-continued
220 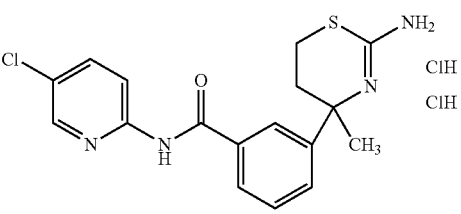 [SMILES: CC1(c2cccc(C(=O)Nc3ccc(Cl)cn3)c2)CCSC(N)=N1 ; Cl ; Cl]
221 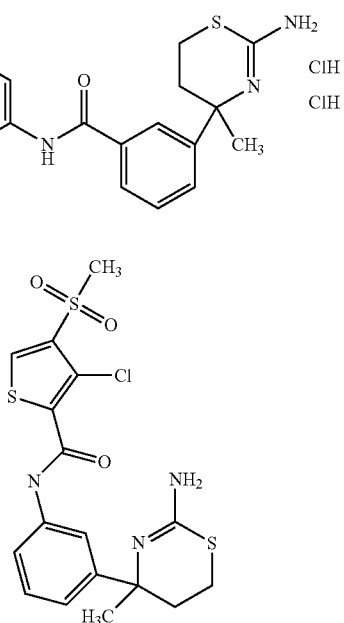
222 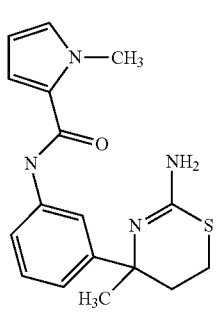 [SMILES: Cn1cccc1C(=O)Nc1cccc(C2(C)CCSC(N)=N2)c1]
223 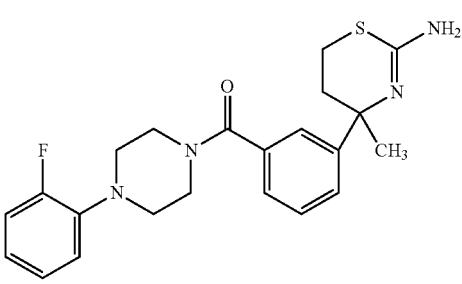 [SMILES: CC1(c2cccc(C(=O)N3CCN(c4ccccc4F)CC3)c2)CCSC(N)=N1]
224 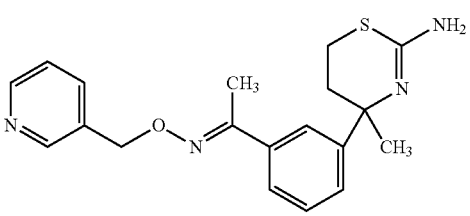 [SMILES: C/C(=N\OCc1cccnc1)c1cccc(C2(C)CCSC(N)=N2)c1]

TABLE 25
225 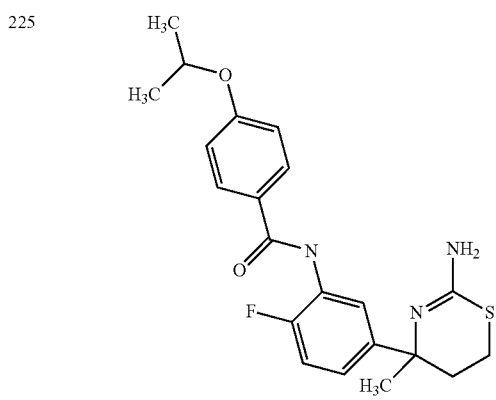
226 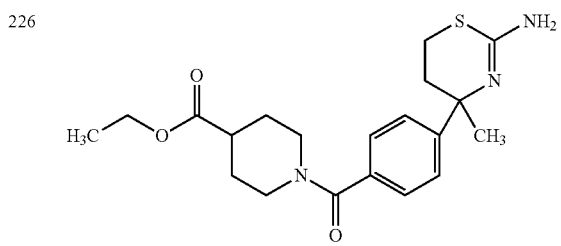
227 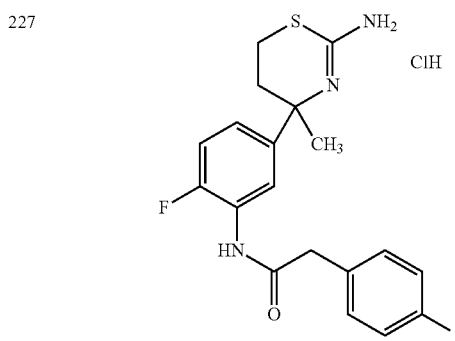
228 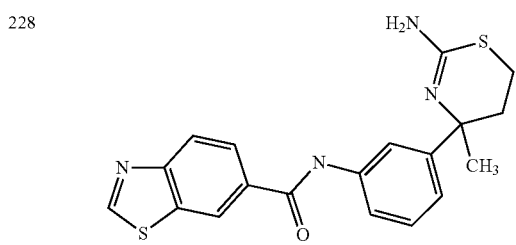
229 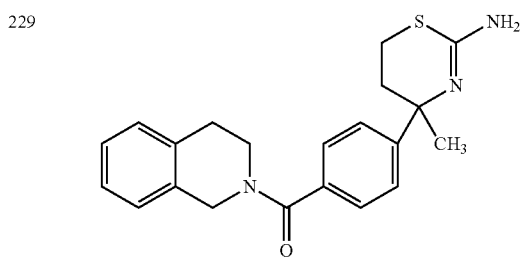
TABLE 25-continued
230 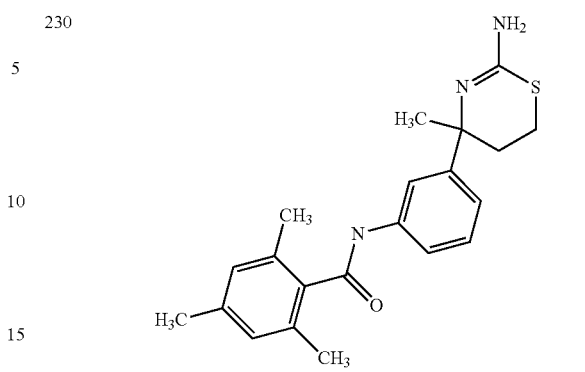
231 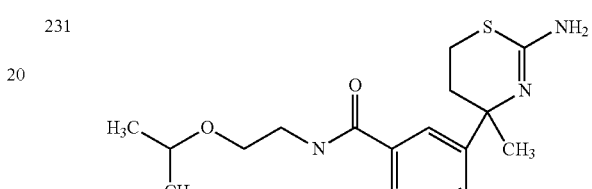
232 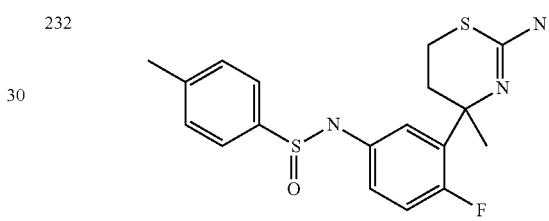
233 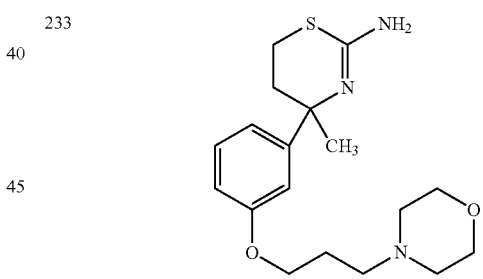
234 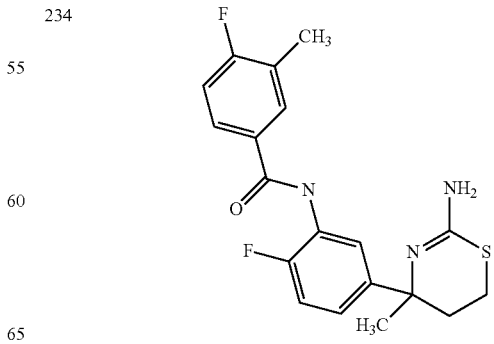

TABLE 26
235 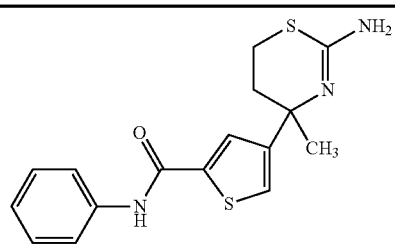
236 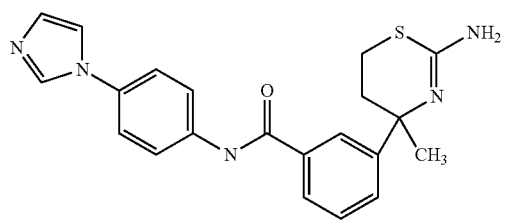 [SMILES: CC1(c2cccc(C(=O)Nc3ccc(-n4ccnc4)cc3)c2)CCSC(N)=N1]
237 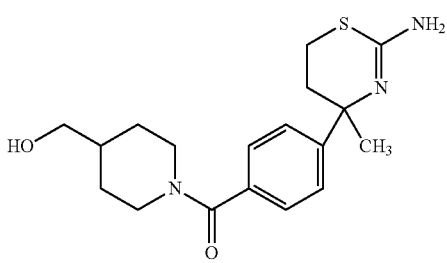 [SMILES: CC1(c2ccc(C(=O)N3CCC(CO)CC3)cc2)CCSC(N)=N1]
238 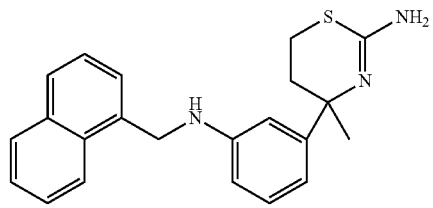 [SMILES: CC1(c2cccc(NCc3cccc4ccccc34)c2)CCSC(N)=N1]
239 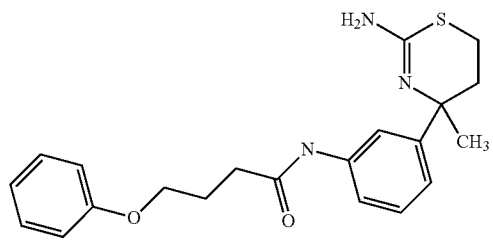 [SMILES: CC1(c2cccc(NC(=O)CCCOc3ccccc3)c2)CCSC(N)=N1]
240 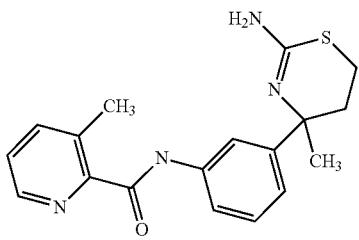 [SMILES: Cc1cccnc1C(=O)Nc1cccc(C2(C)CCSC(N)=N2)c1]
241 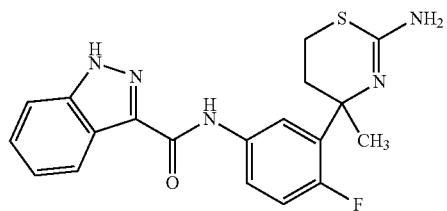 [SMILES: CC1(c2cc(NC(=O)c3n[nH]c4ccccc34)ccc2F)CCSC(N)=N1]
TABLE 26-continued
242 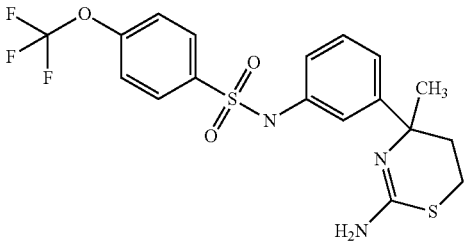 [SMILES: CC1(c2cccc(NS(=O)(=O)c3ccc(OC(F)(F)F)cc3)c2)CCSC(N)=N1]
243 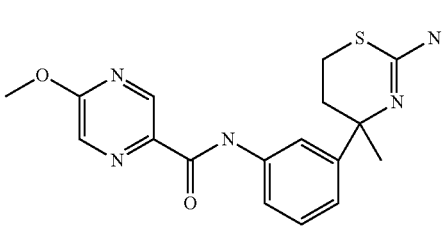 [SMILES: COc1cnc(C(=O)Nc2cccc(C3(C)CCSC(N)=N3)c2)cn1]
244 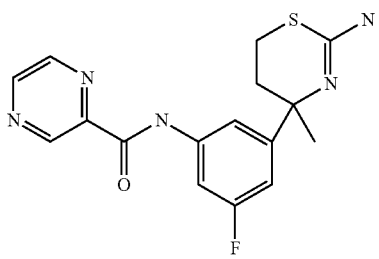 [SMILES: CC1(c2cc(F)cc(NC(=O)c3cnccn3)c2)CCSC(N)=N1]
245 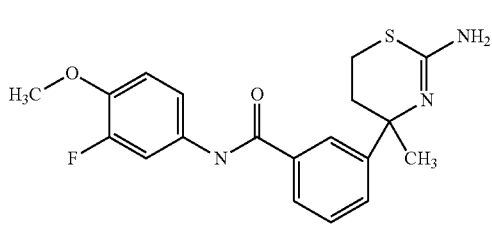 [SMILES: COc1ccc(NC(=O)c2cccc(C3(C)CCSC(N)=N3)c2)cc1F]
246 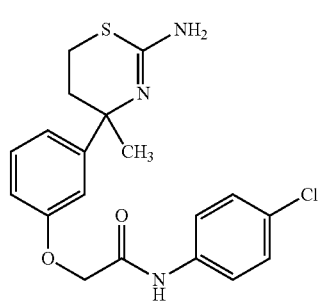 [SMILES: CC1(c2cccc(OCC(=O)Nc3ccc(Cl)cc3)c2)CCSC(N)=N1]

TABLE 27
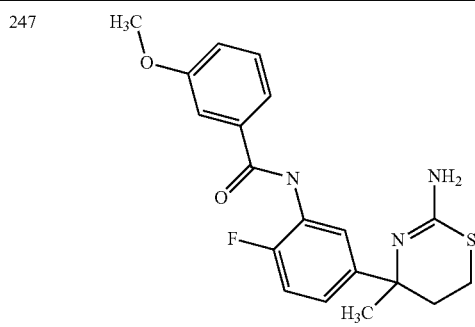
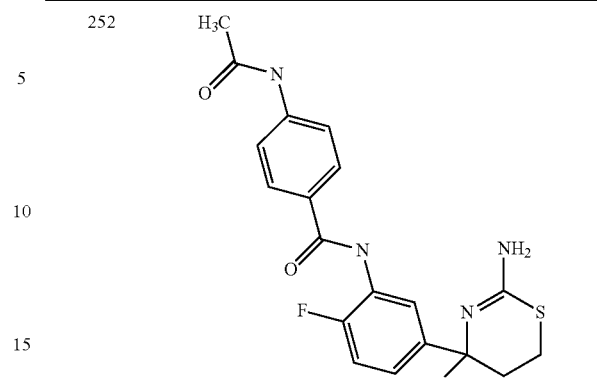
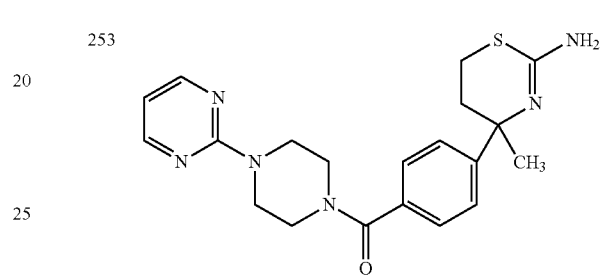
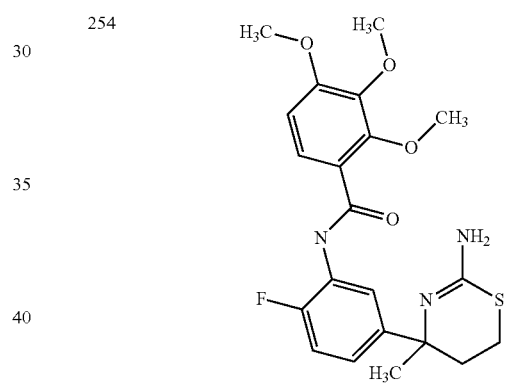
TABLE 28
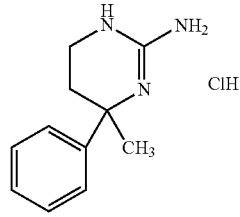

TABLE 28-continued
257 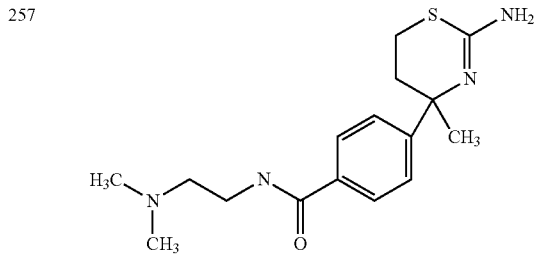
258 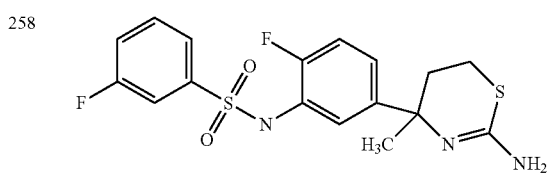
259 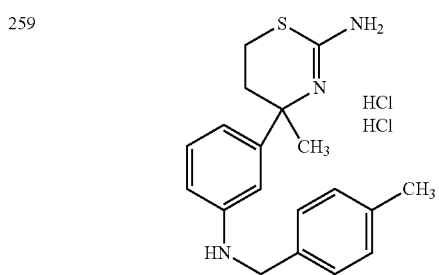
260 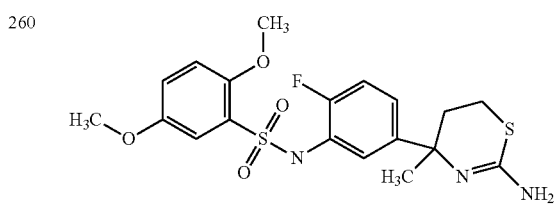
261 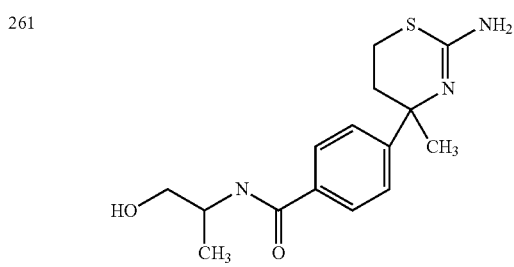
262 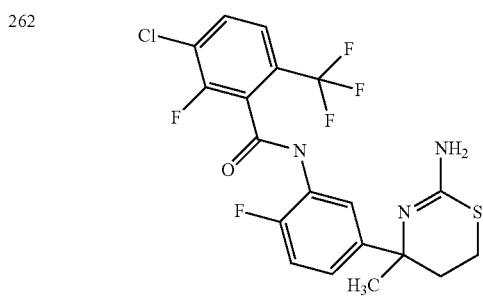
TABLE 28-continued
263 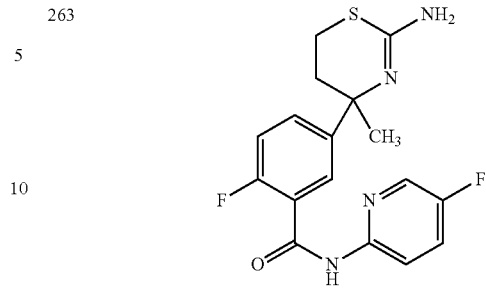
264 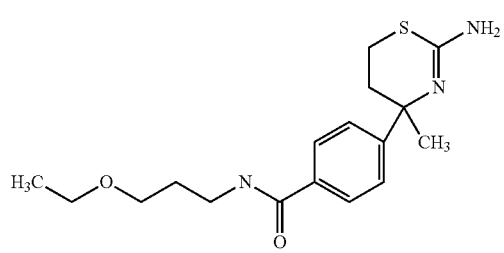 [SMILES: CCOCCCNC(=O)c1ccc(C2(C)CCSC(N)=N2)cc1]
265 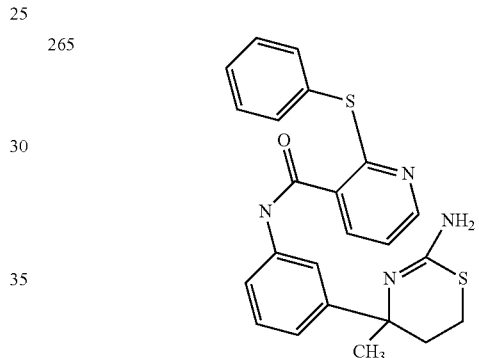
266 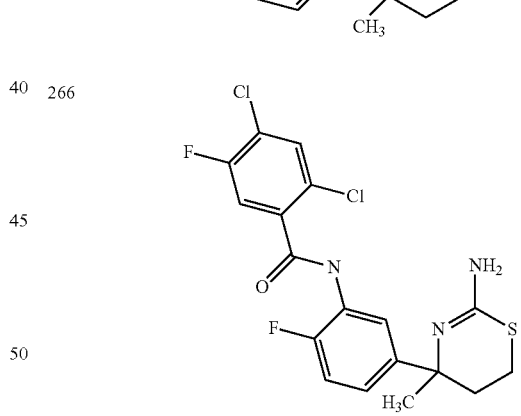
TABLE 29
267 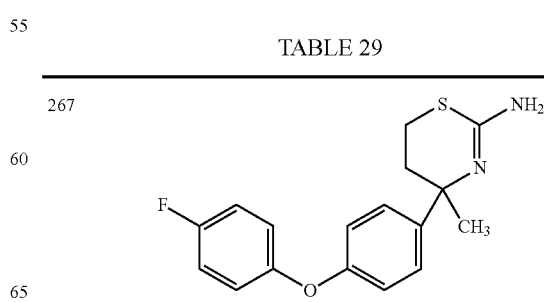

TABLE 29-continued
268 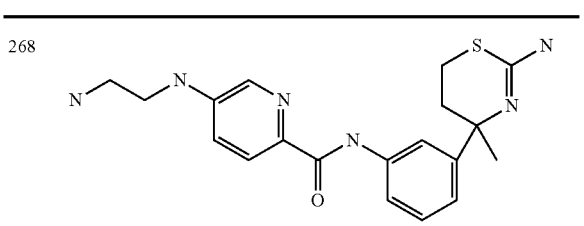
269 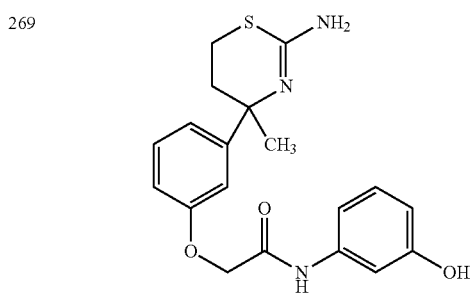
270 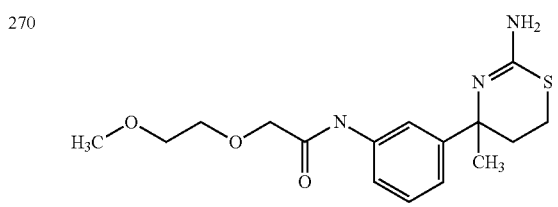
271 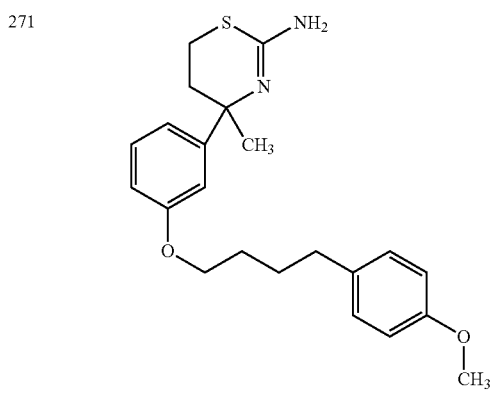
272 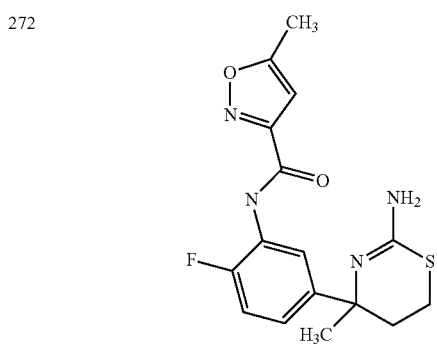
TABLE 29-continued
273 
274 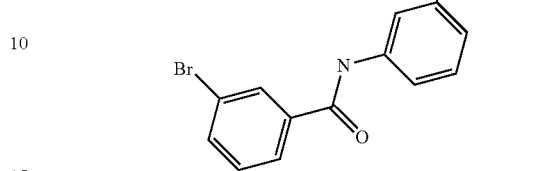
275 
TABLE 30
276 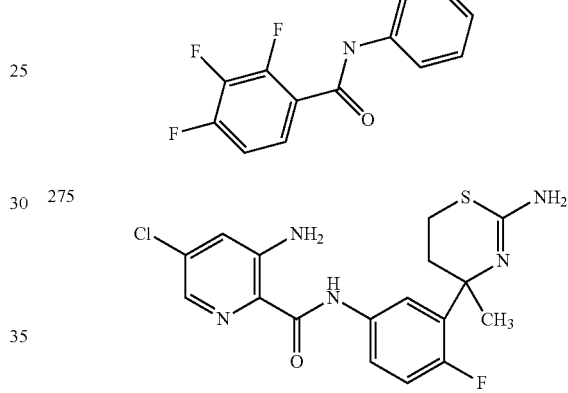
277 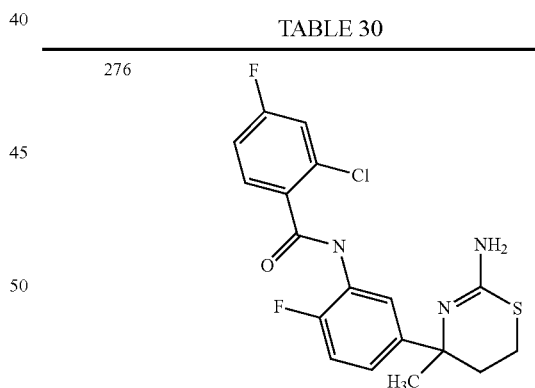
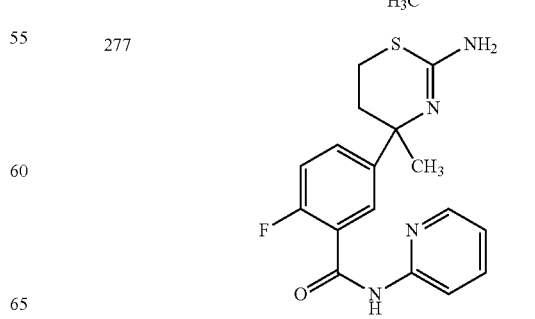

TABLE 30-continued
| 278 | 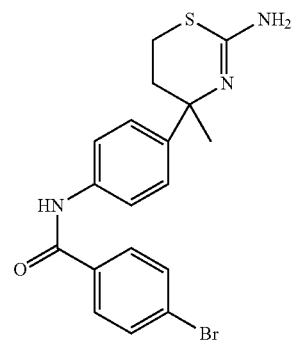 [SMILES: CC1(c2ccc(NC(=O)c3ccc(Br)cc3)cc2)CCSC(N)=N1] |
| --- | --- |
| 279 | 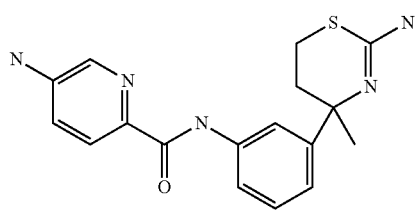 [SMILES: CC1(c2cccc(NC(=O)c3ccc(N)cn3)c2)CCSC(N)=N1] |
| 280 | 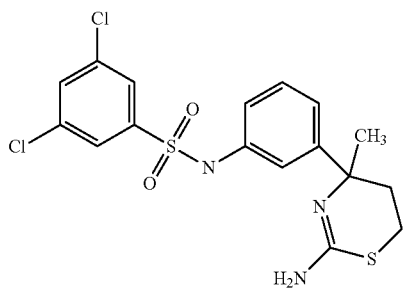 [SMILES: CC1(c2cccc(NS(=O)(=O)c3cc(Cl)cc(Cl)c3)c2)CCSC(N)=N1] |
| 281 | 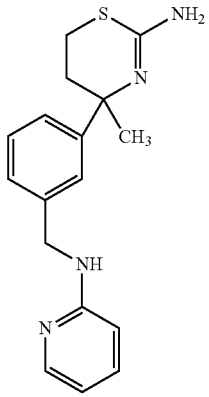 |
| 282 | 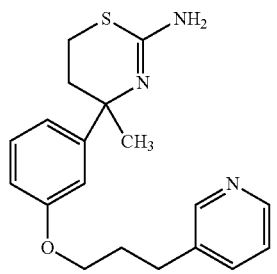 [SMILES: CC1(c2cccc(OCCCc3cccnc3)c2)CCSC(N)=N1] |
TABLE 30-continued
| 283 | 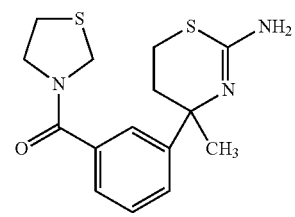 [SMILES: CC1(c2cccc(C(=O)N3CCSC3)c2)CCSC(N)=N1] |
| --- | --- |
| 284 | 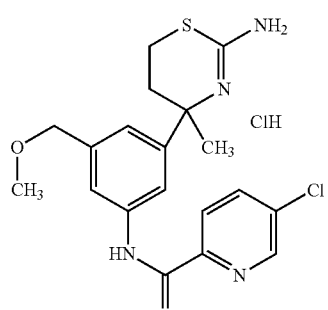 |
TABLE 31
| 285 | 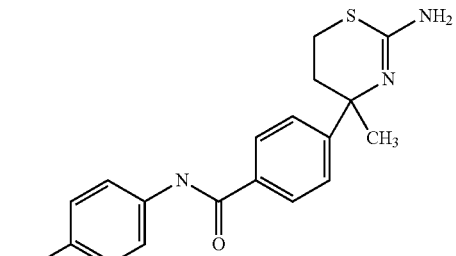 |
| --- | --- |
| 286 | 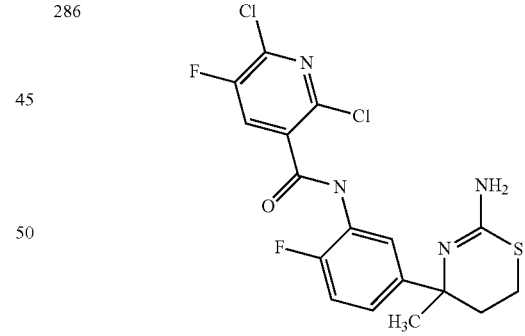 |
| 287 | 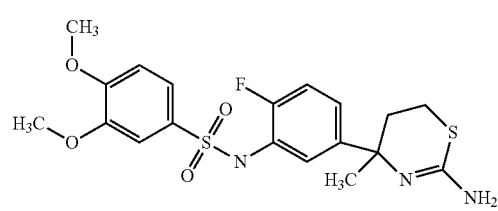 [SMILES: COc1ccc(S(=O)(=O)Nc2cc(C3(C)CCSC(N)=N3)ccc2F)cc1OC] |

TABLE 31-continued
288 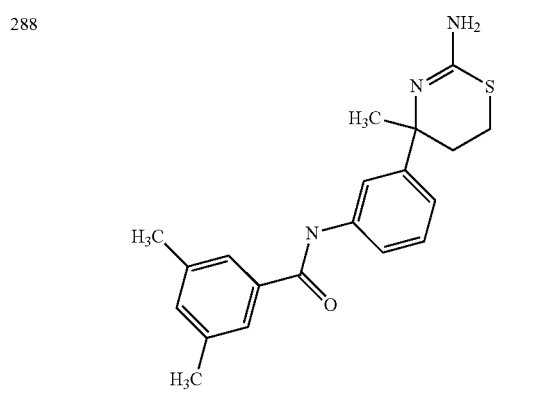
289 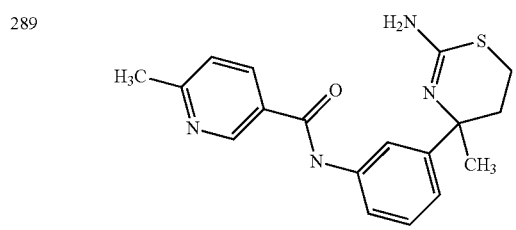
290 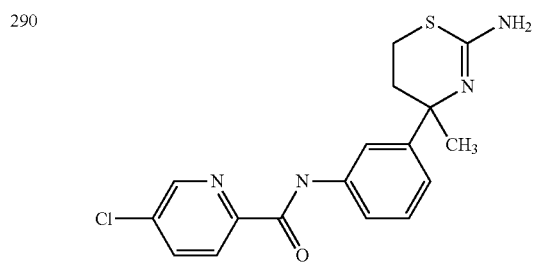
291 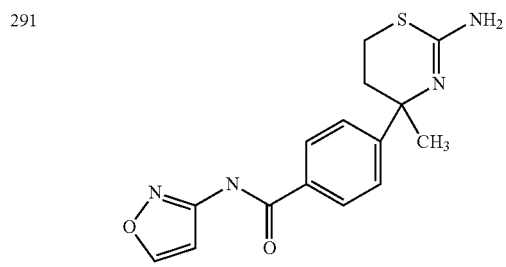
292 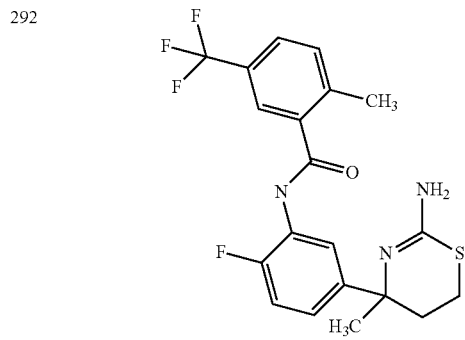
TABLE 31-continued
293 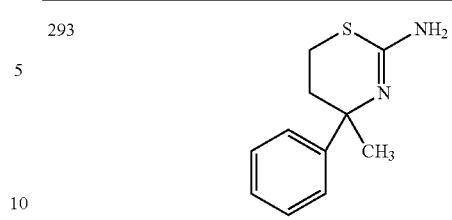
TABLE 32
294 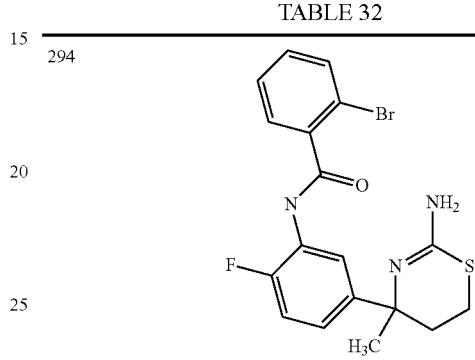
295 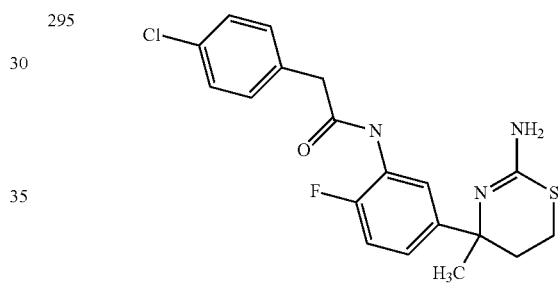
296 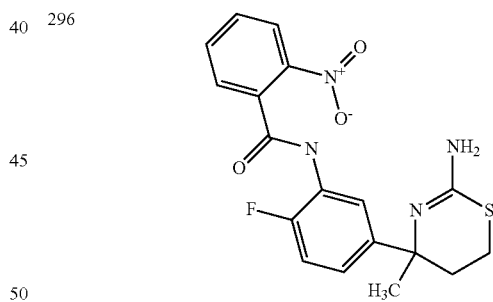
297 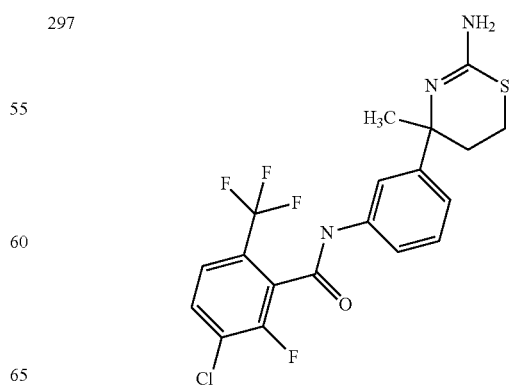

TABLE 32-continued
298 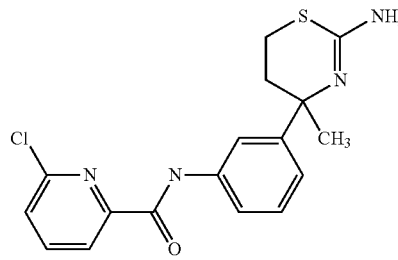
299 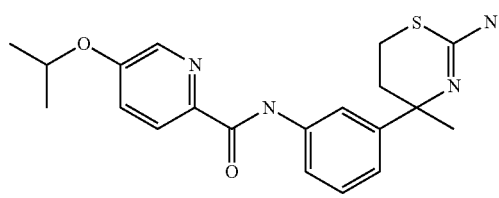
300 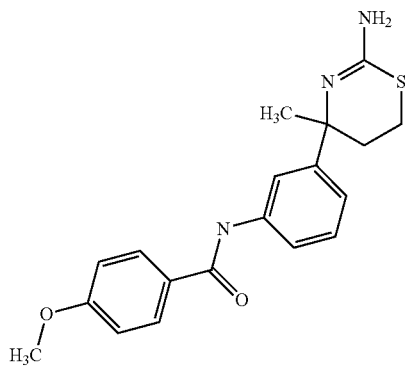
301 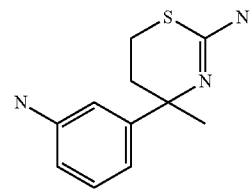
302 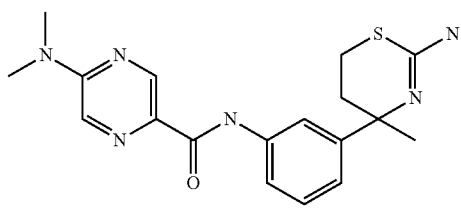 [SMILES: CN(C)c1cnc(C(=O)Nc2cccc(C3(C)CCSC(N)=N3)c2)cn1]
TABLE 33
303 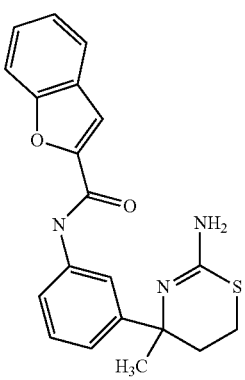 [SMILES: CC1(c2cccc(NC(=O)c3cc4ccccc4o3)c2)CCSC(N)=N1]
304 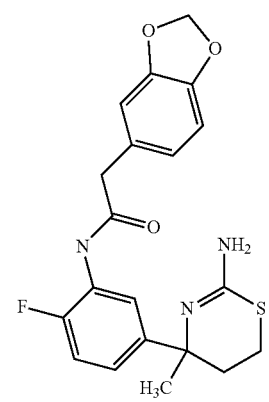 [SMILES: CC1(c2ccc(F)c(NC(=O)Cc3ccc4c(c3)OCO4)c2)CCSC(N)=N1]
305 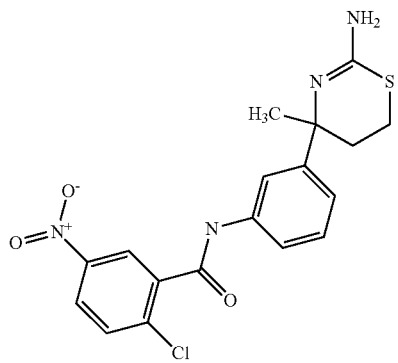 [SMILES: CC1(c2cccc(NC(=O)c3cc([N+](=O)[O-])ccc3Cl)c2)CCSC(N)=N1]
306 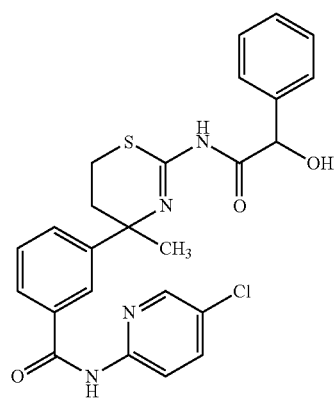 [SMILES: CC1(c2cccc(C(=O)Nc3ccc(Cl)cn3)c2)CCSC(NC(=O)C(O)c2ccccc2)=N1]

TABLE 33-continued
307 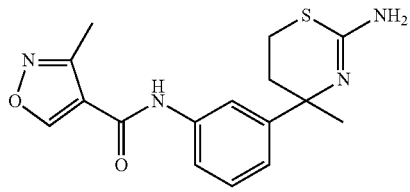 [SMILES: Cc1nocc1C(=O)Nc1cccc(C2(C)CCSC(N)=N2)c1]
308 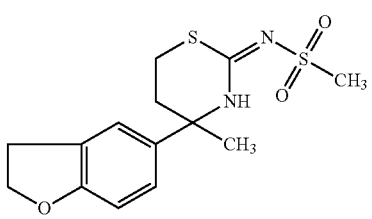 [SMILES: CC1(c2ccc3c(c2)CCO3)CCS/C(=N/S(C)(=O)=O)N1]
309 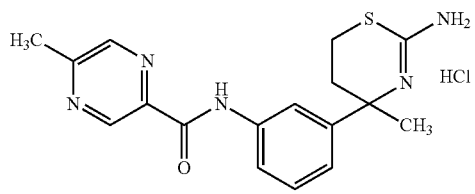 [SMILES: Cc1cnc(C(=O)Nc2cccc(C3(C)CCSC(N)=N3)c2)cn1 ; Cl]
TABLE 34
310 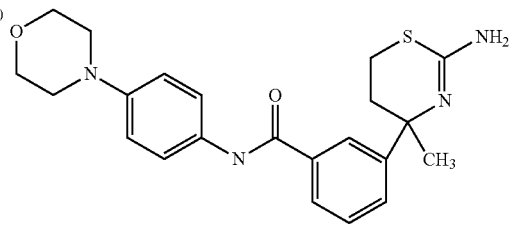
311 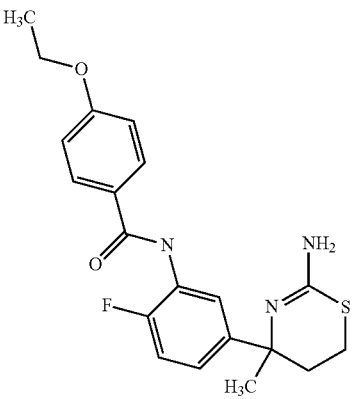
TABLE 34-continued
312 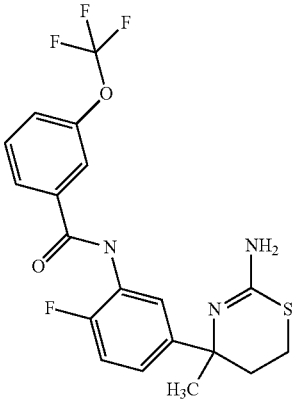 [SMILES: CC1(c2ccc(F)c(NC(=O)c3cccc(OC(F)(F)F)c3)c2)CCSC(N)=N1]
313 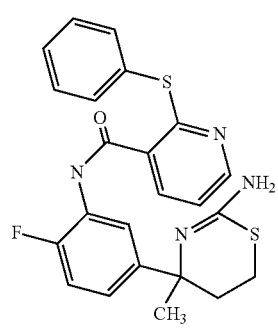 [SMILES: CC1(c2ccc(F)c(NC(=O)c3cccnc3Sc3ccccc3)c2)CCSC(N)=N1]
314 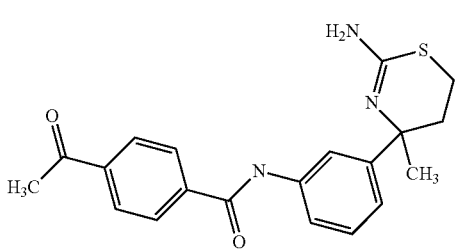 [SMILES: CC(=O)c1ccc(C(=O)Nc2cccc(C3(C)CCSC(N)=N3)c2)cc1]
315 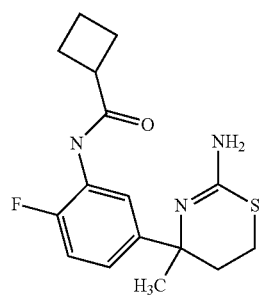 [SMILES: CC1(c2ccc(F)c(NC(=O)C3CCC3)c2)CCSC(N)=N1]

TABLE 34-continued
316
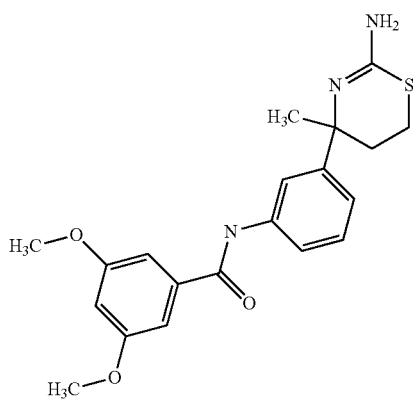 [SMILES: COc1cc(OC)cc(C(=O)Nc2cccc(C3(C)CCSC(N)=N3)c2)c1]
317
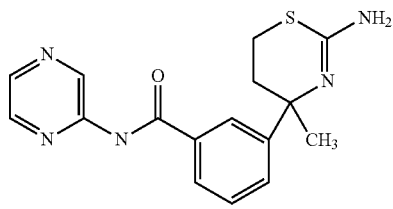 [SMILES: CC1(c2cccc(C(=O)Nc3cnccn3)c2)CCSC(N)=N1]
TABLE 35
318
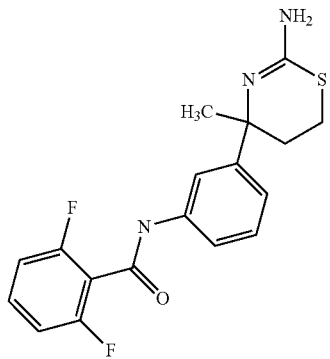
319
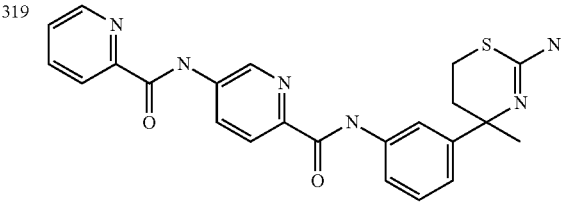
320
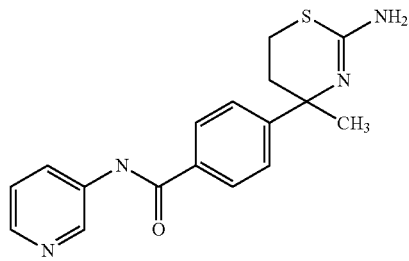 [SMILES: CC1(c2ccc(C(=O)Nc3cccnc3)cc2)CCSC(N)=N1]
TABLE 35-continued
321
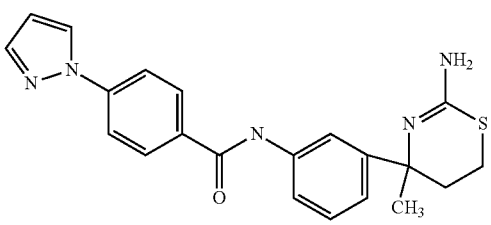 [SMILES: CC1(c2cccc(NC(=O)c3ccc(-n4cccn4)cc3)c2)CCSC(N)=N1]
322
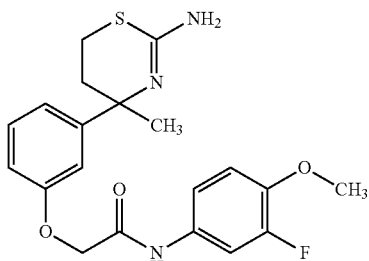
323
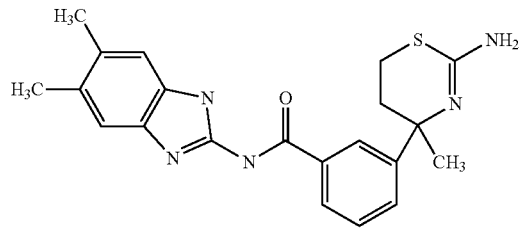 [SMILES: Cc1cc2nc(NC(=O)c3cccc(C4(C)CCSC(N)=N4)c3)[nH]c2cc1C]
324
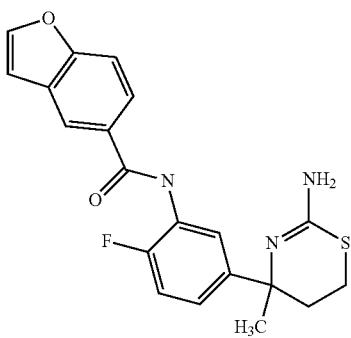 [SMILES: CC1(c2ccc(F)c(NC(=O)c3ccc4occc4c3)c2)CCSC(N)=N1]
325
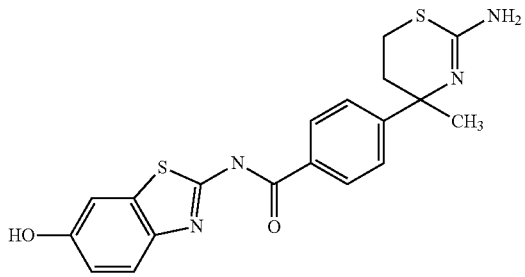 [SMILES: CC1(c2ccc(C(=O)Nc3nc4ccc(O)cc4s3)cc2)CCSC(N)=N1]
326
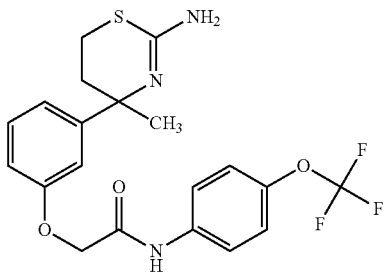 [SMILES: CC1(c2cccc(OCC(=O)Nc3ccc(OC(F)(F)F)cc3)c2)CCSC(N)=N1]

TABLE 35-continued
327 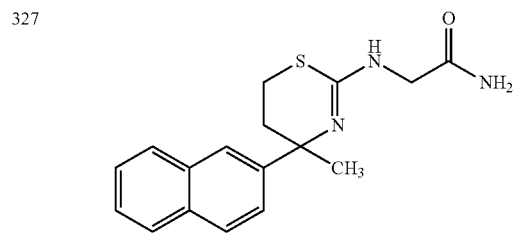
328 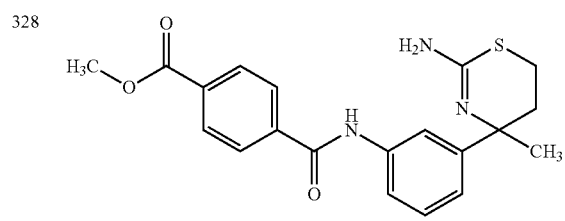
TABLE 36
329 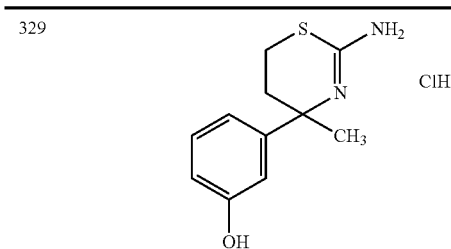  ClH
330 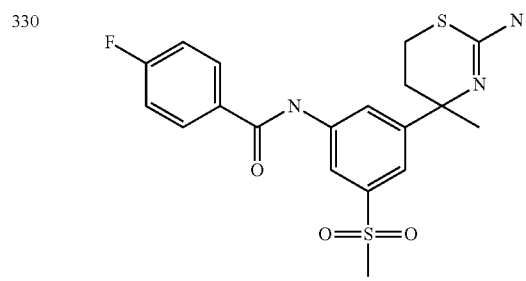
331 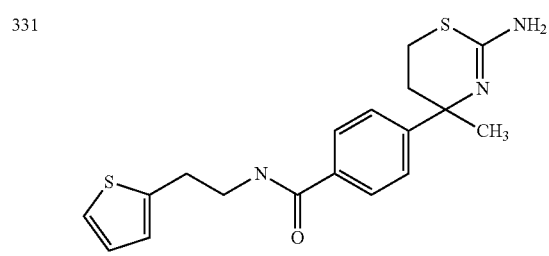
332 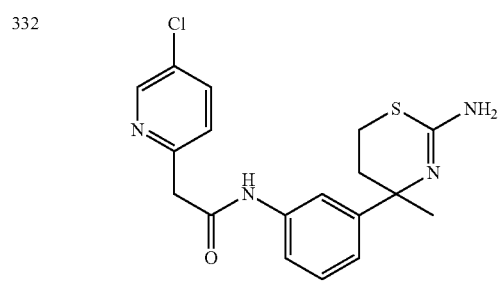
TABLE 36-continued
333 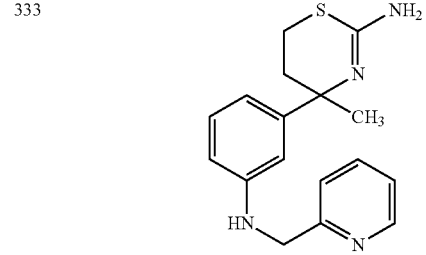
334 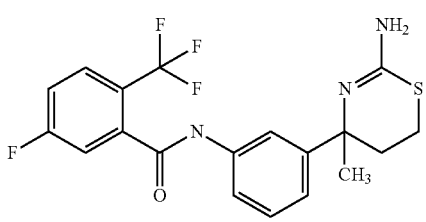 [SMILES: CC1(c2cccc(NC(=O)c3cc(F)ccc3C(F)(F)F)c2)CCSC(N)=N1]
335 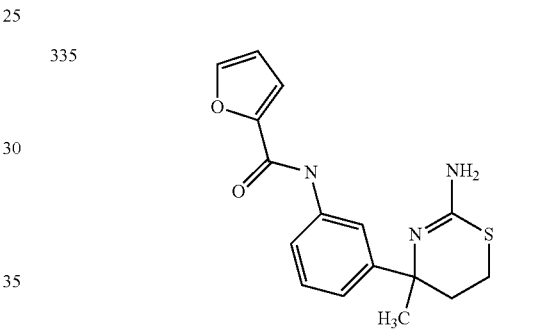
336 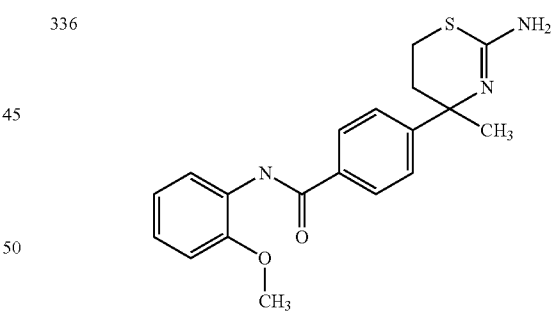
337 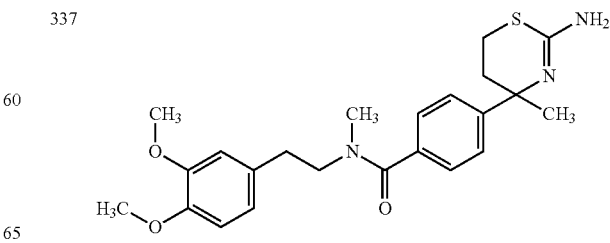

TABLE 36-continued
338
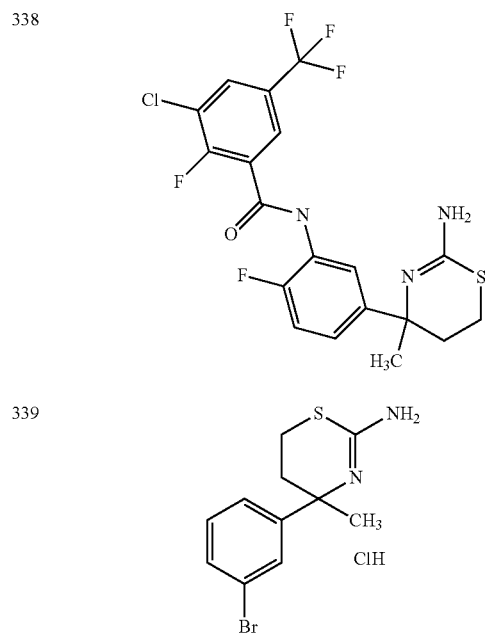
339
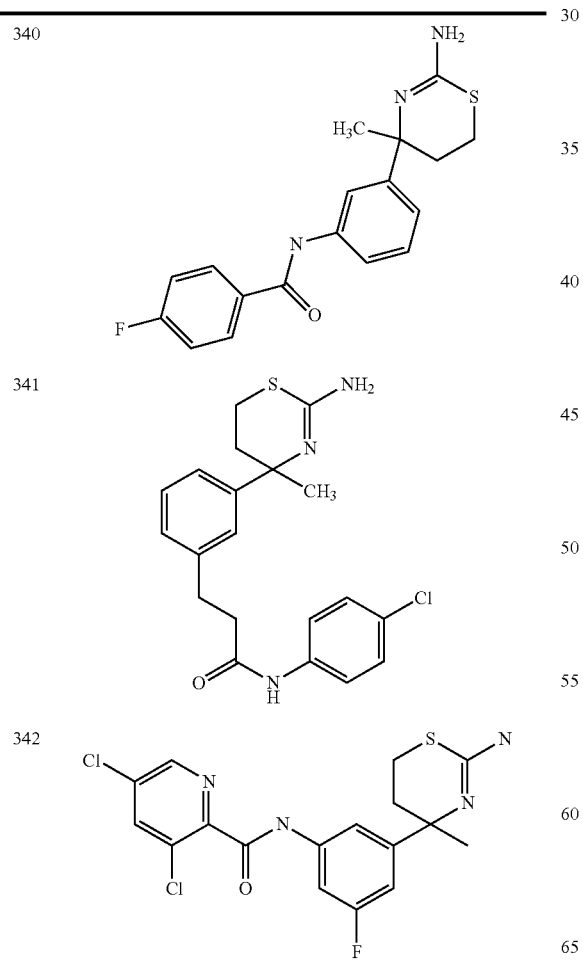
TABLE 37
340
341
342
343
344
345
346
347
348
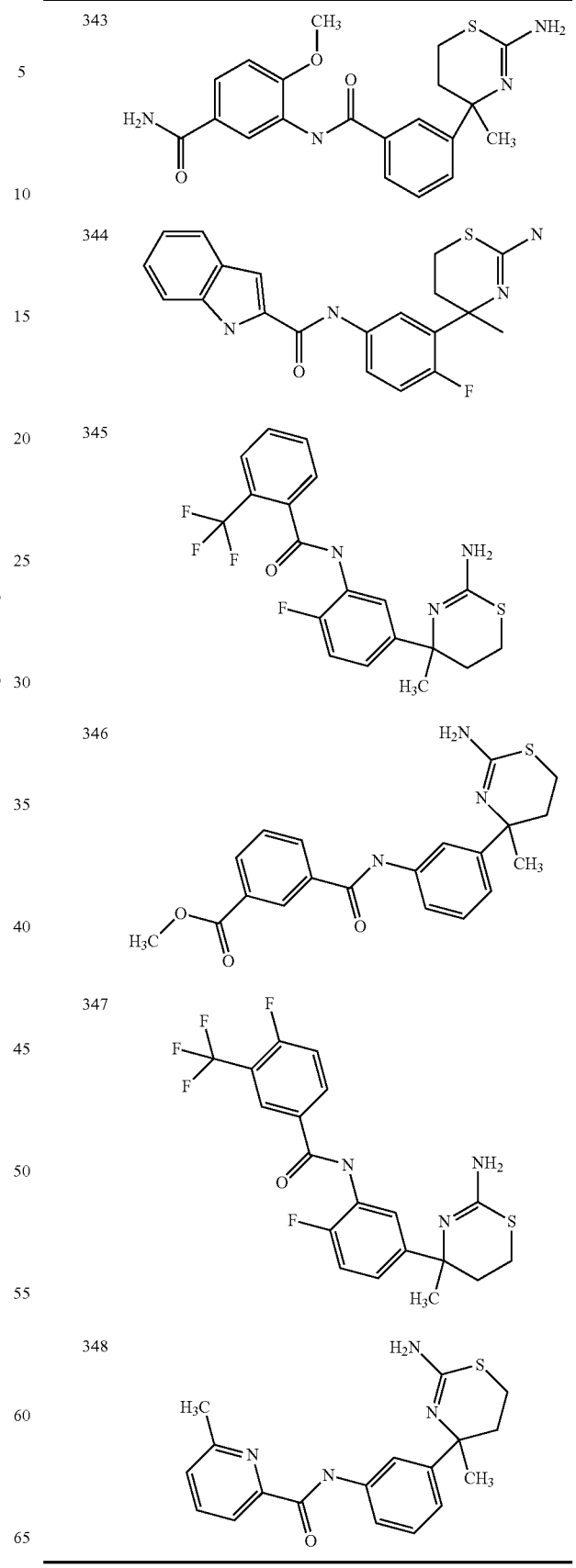

TABLE 38
349 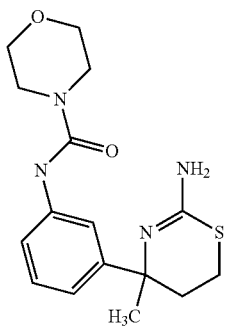 [SMILES: CC1(c2cccc(NC(=O)N3CCOCC3)c2)CCSC(N)=N1]
350 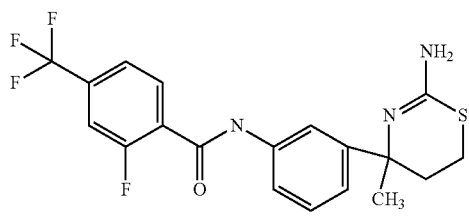 [SMILES: CC1(c2cccc(NC(=O)c3ccc(C(F)(F)F)cc3F)c2)CCSC(N)=N1]
351 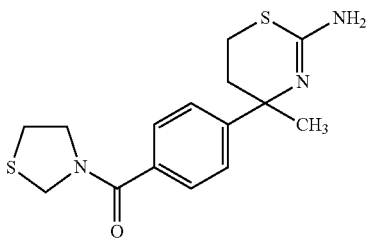 [SMILES: CC1(c2ccc(C(=O)N3CCSC3)cc2)CCSC(N)=N1]
352 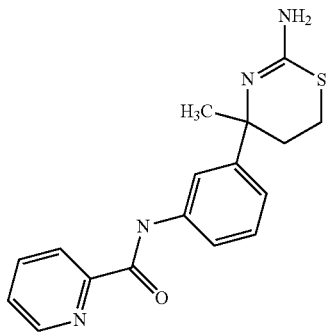 [SMILES: CC1(c2cccc(NC(=O)c3ccccn3)c2)CCSC(N)=N1]
353 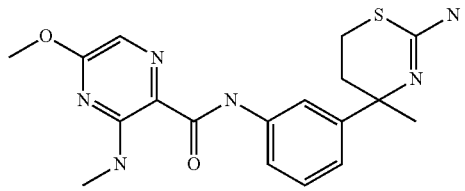 [SMILES: CNc1nc(OC)cnc1C(=O)Nc1cccc(C2(C)CCSC(N)=N2)c1]
TABLE 38-continued
354 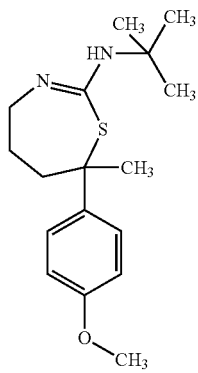 [SMILES: COc1ccc(C2(C)CCCN=C(NC(C)(C)C)S2)cc1]
355 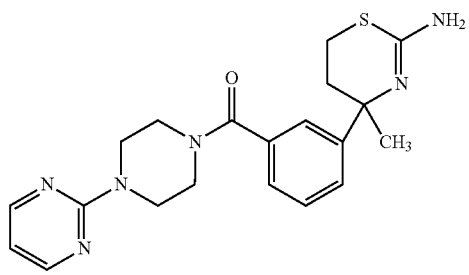 [SMILES: CC1(c2cccc(C(=O)N3CCN(c4ncccn4)CC3)c2)CCSC(N)=N1]
356 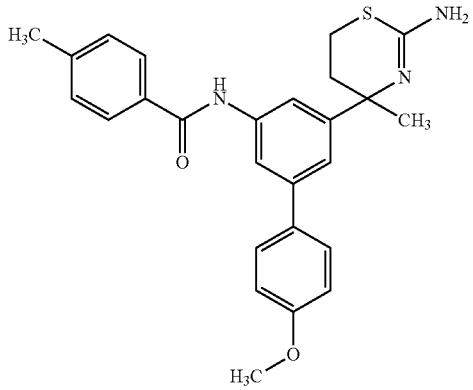 [SMILES: COc1ccc(-c2cc(NC(=O)c3ccc(C)cc3)cc(C3(C)CCSC(N)=N3)c2)cc1]
357 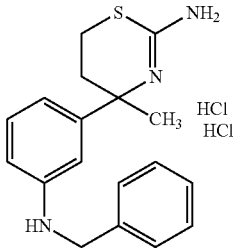 [SMILES: CC1(c2cccc(NCc3ccccc3)c2)CCSC(N)=N1 ; Cl ; Cl]
TABLE 39
358 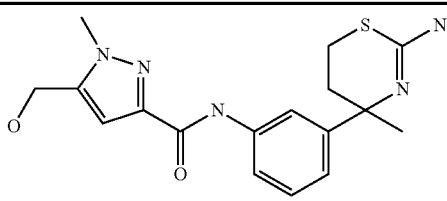

TABLE 39-continued
| 359 | 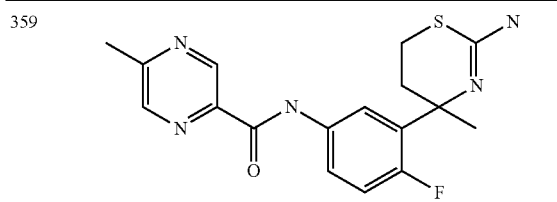 |
| --- | --- |
| 360 | 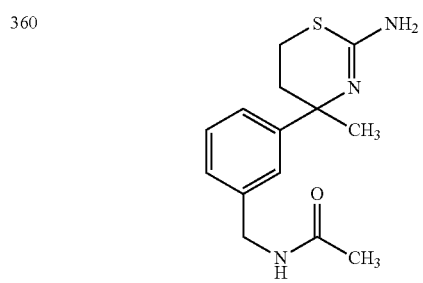 |
| 361 | 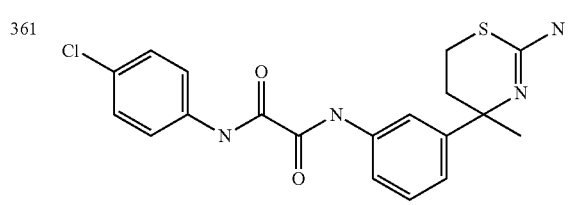 |
| 362 | 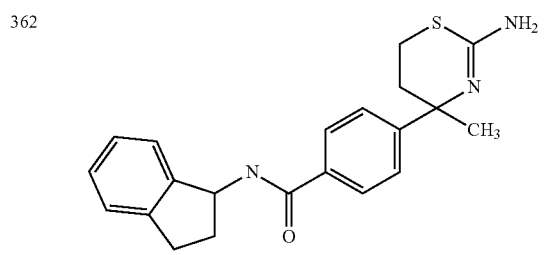 |
| 363 | 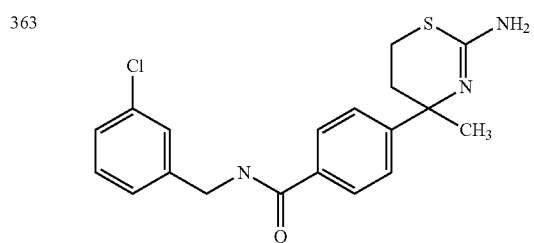 |
| 364 | 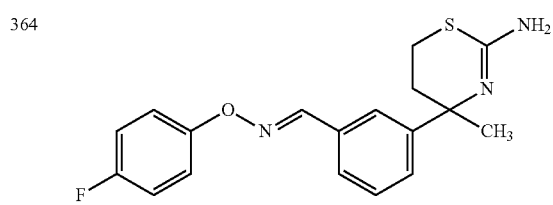 |
| 365 | 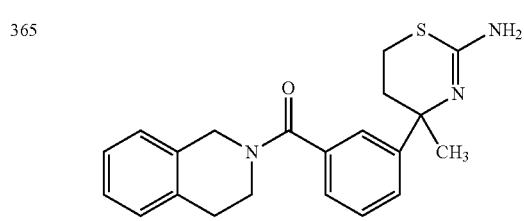 |
TABLE 39-continued
| 366 | 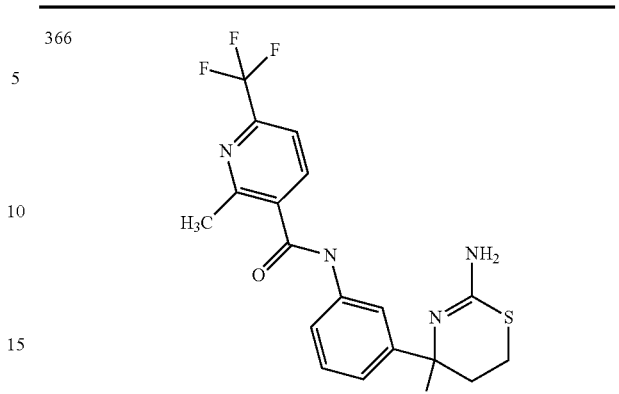 |
| --- | --- |
| 367 | 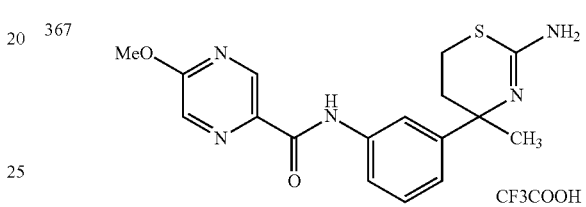 CF3COOH |
| 368 | 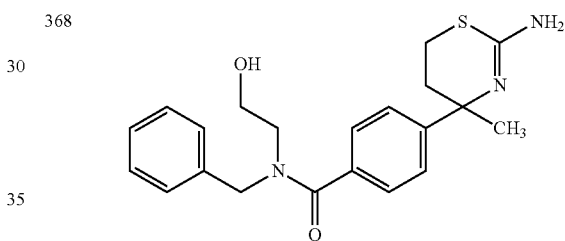 |
| 369 | 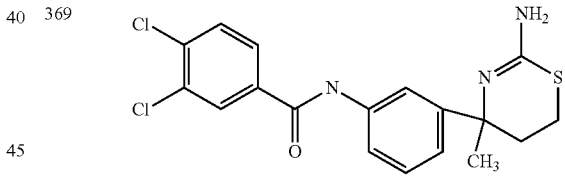 |
TABLE 40
| 370 | 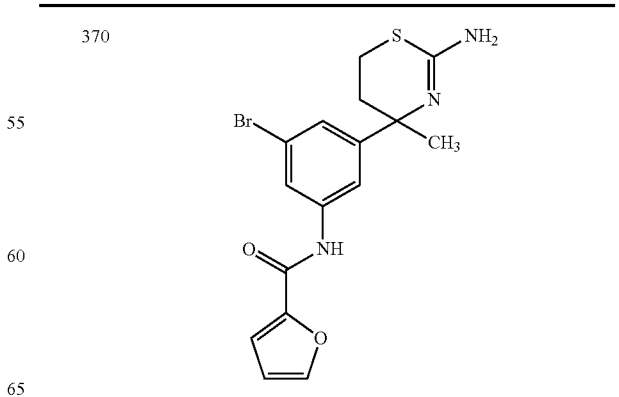 |
| --- | --- |

TABLE 40-continued
371 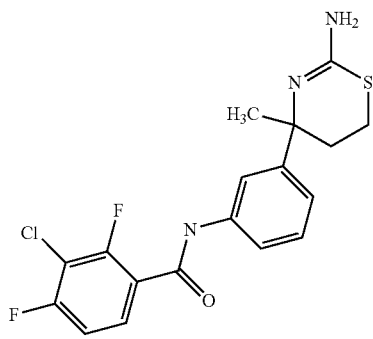 [SMILES: CC1(c2cccc(NC(=O)c3ccc(F)c(Cl)c3F)c2)CCSC(N)=N1]
372 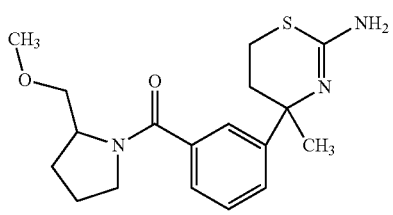 [SMILES: COCC1CCCN1C(=O)c1cccc(C2(C)CCSC(N)=N2)c1]
373 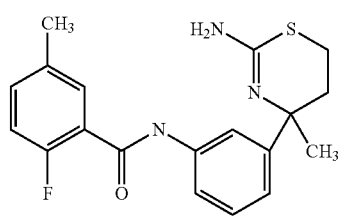 [SMILES: Cc1ccc(F)c(C(=O)Nc2cccc(C3(C)CCSC(N)=N3)c2)c1]
374 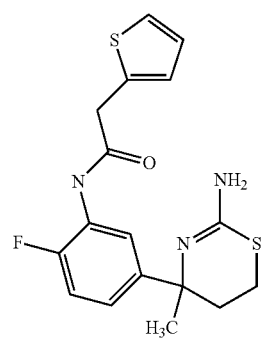 [SMILES: CC1(c2ccc(F)c(NC(=O)Cc3cccs3)c2)CCSC(N)=N1]
375 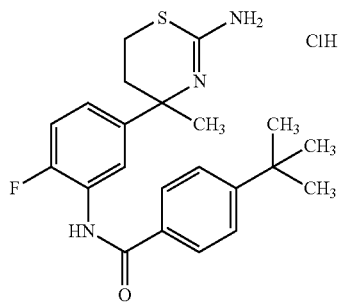 [SMILES: CC(C)(C)c1ccc(C(=O)Nc2cc(C3(C)CCSC(N)=N3)ccc2F)cc1 ; Cl]
TABLE 40-continued
376 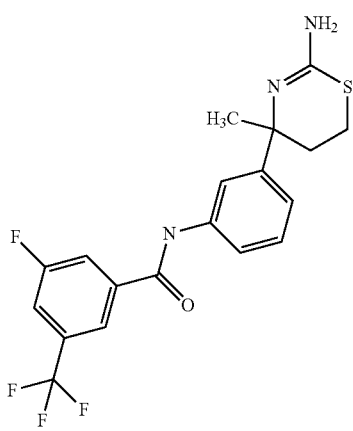 [SMILES: CC1(c2cccc(NC(=O)c3cc(F)cc(C(F)(F)F)c3)c2)CCSC(N)=N1]
377 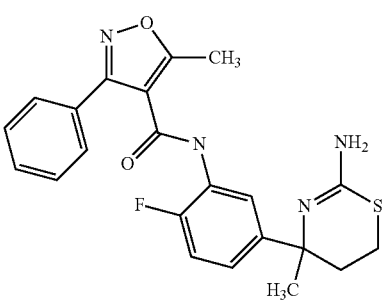 [SMILES: Cc1onc(-c2ccccc2)c1C(=O)Nc1cc(C2(C)CCSC(N)=N2)ccc1F]
378 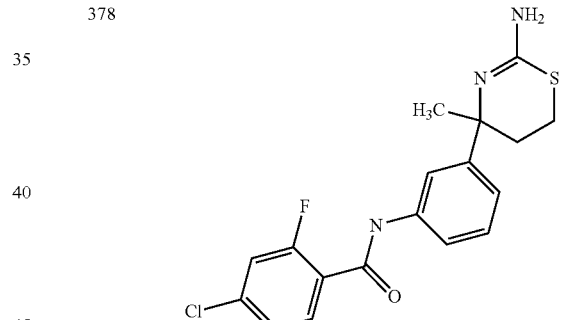
TABLE 41
379 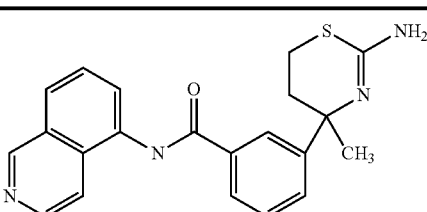
380 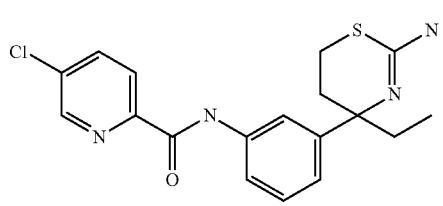 [SMILES: CCC1(c2cccc(NC(=O)c3ccc(Cl)cn3)c2)CCSC(N)=N1]

TABLE 41-continued
381 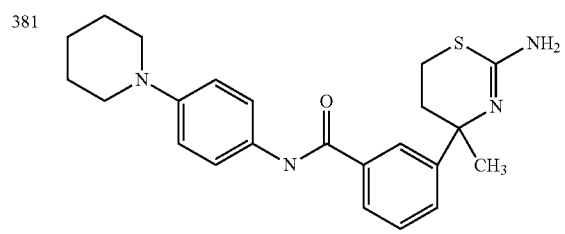
382 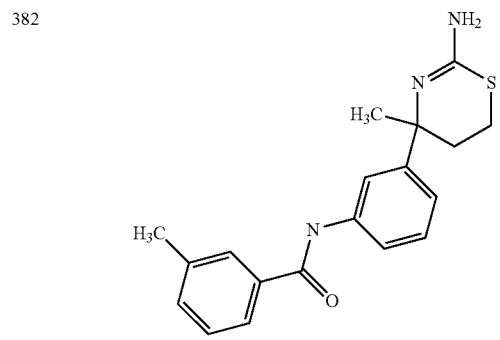
383 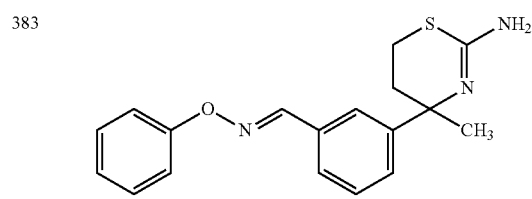
384 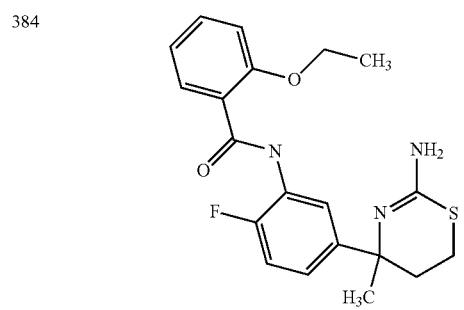
385 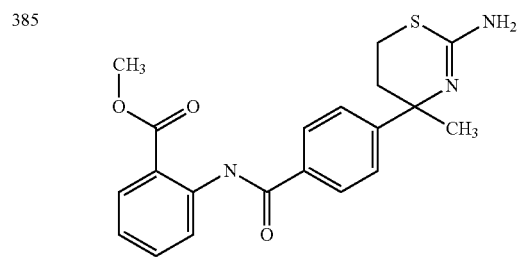
386 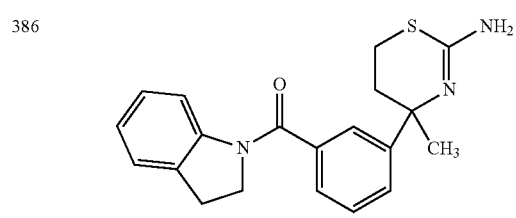
TABLE 41-continued
387 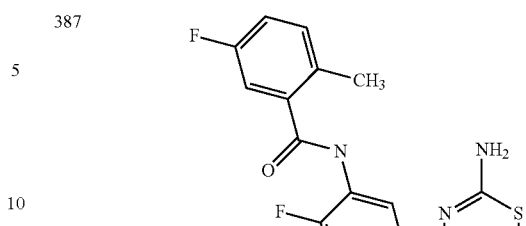
388 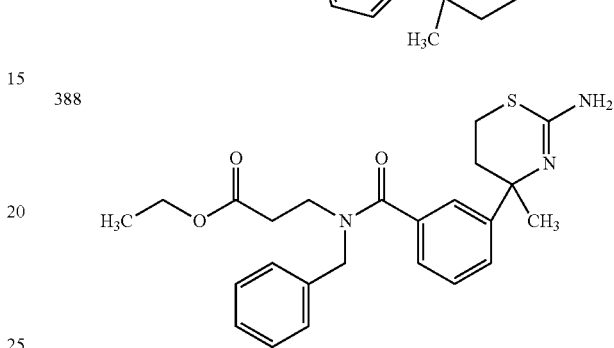
389 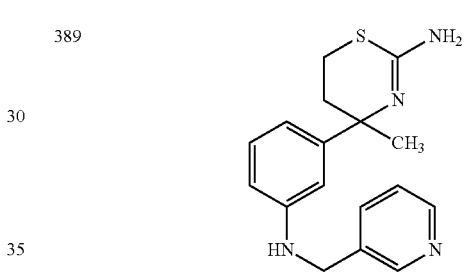
TABLE 42
390 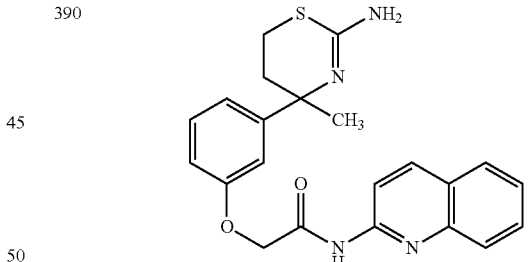
391 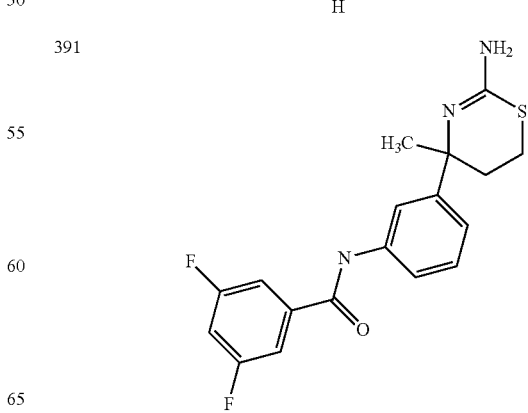

TABLE 42-continued
392 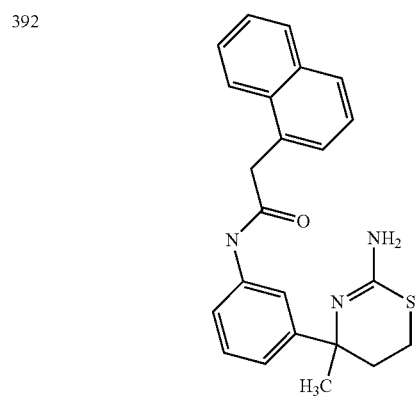
393 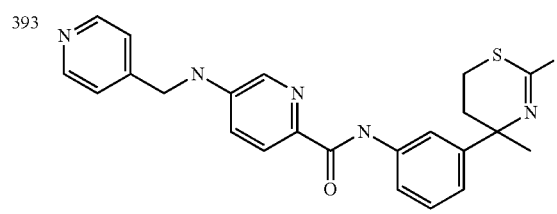
394 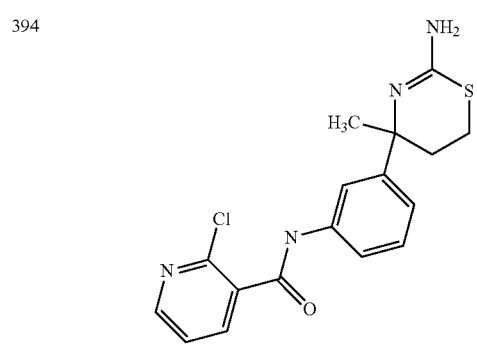
395 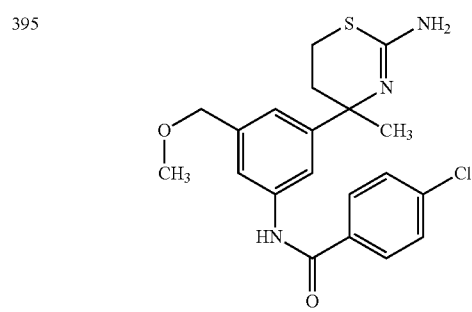
396 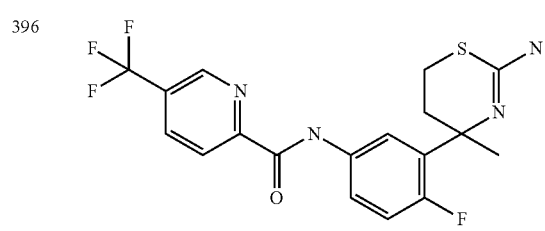
TABLE 42-continued
397 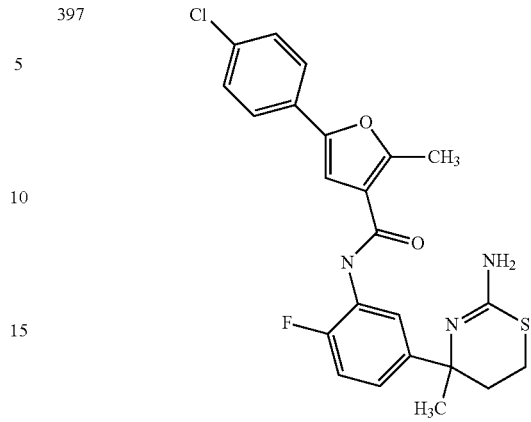
TABLE 43
398 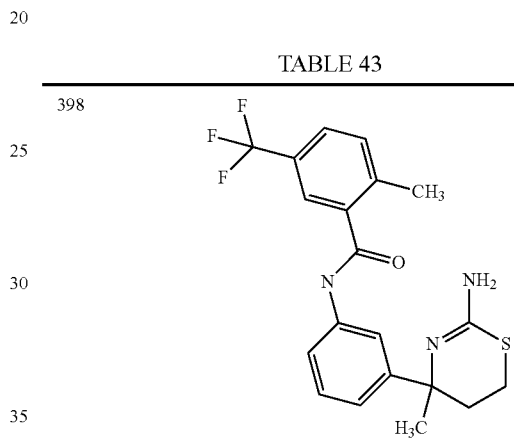
399 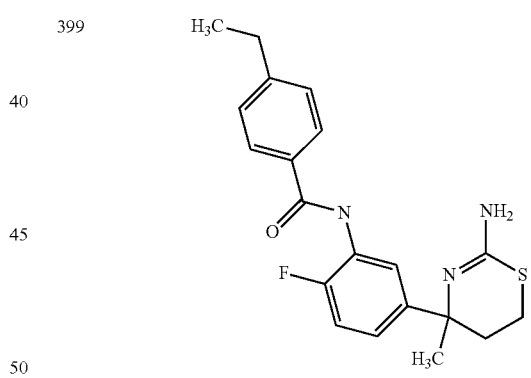
400 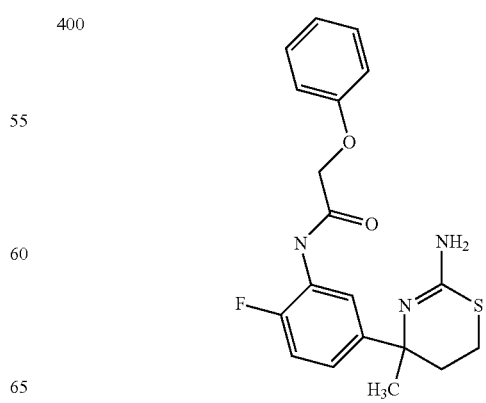

TABLE 43-continued
401 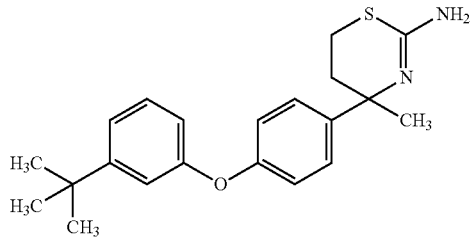 [SMILES: CC(C)(C)c1cccc(Oc2ccc(C3(C)CCSC(N)=N3)cc2)c1]
402 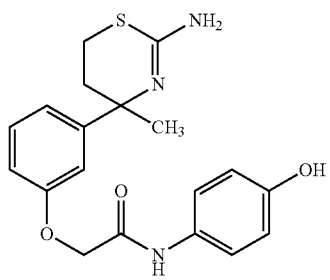 [SMILES: CC1(c2cccc(OCC(=O)Nc3ccc(O)cc3)c2)CCSC(N)=N1]
403 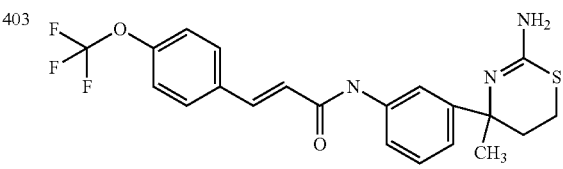
404 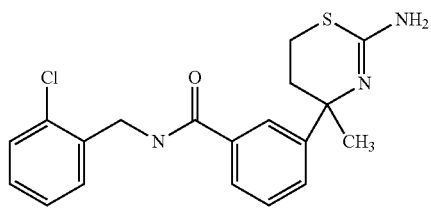 [SMILES: CC1(c2cccc(C(=O)NCc3ccccc3Cl)c2)CCSC(N)=N1]
405 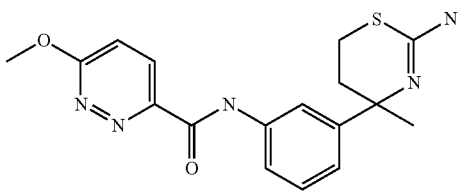 [SMILES: COc1ccc(C(=O)Nc2cccc(C3(C)CCSC(N)=N3)c2)nn1]
406 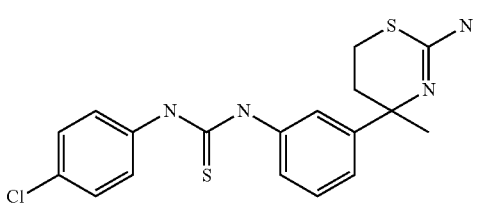 [SMILES: CC1(c2cccc(NC(=S)Nc3ccc(Cl)cc3)c2)CCSC(N)=N1]
TABLE 43-continued
407 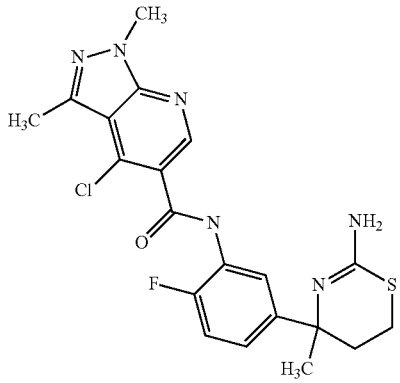 [SMILES: Cc1nn(C)c2ncc(C(=O)Nc3cc(C4(C)CCSC(N)=N4)ccc3F)c(Cl)c12]
TABLE 44
408 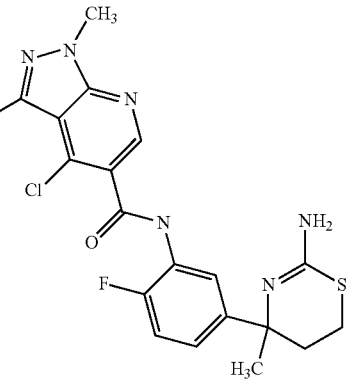
409 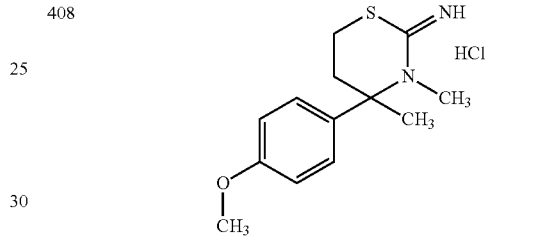
410 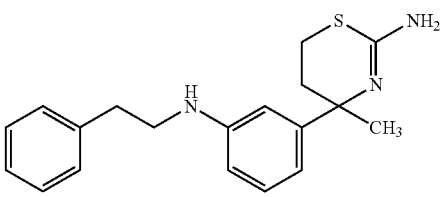
411 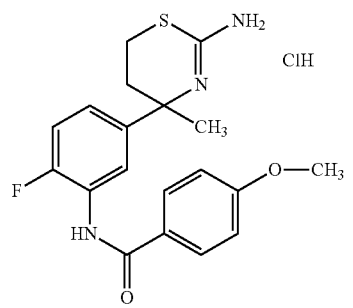 [SMILES: COc1ccc(C(=O)Nc2cc(C3(C)CCSC(N)=N3)ccc2F)cc1 ; Cl]

TABLE 44-continued
412 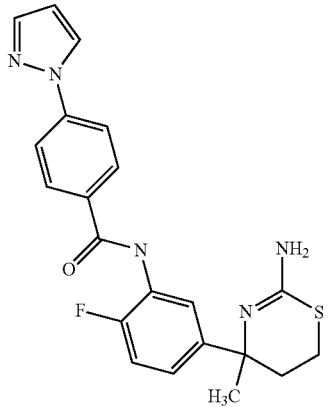 [SMILES: CC1(c2ccc(F)c(NC(=O)c3ccc(-n4cccn4)cc3)c2)CCSC(N)=N1]
413 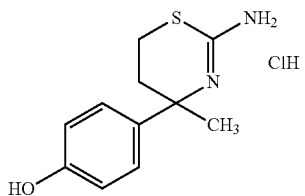
414 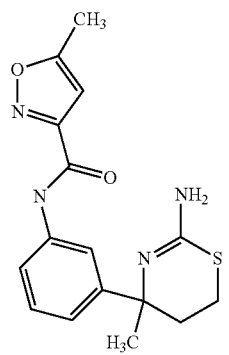 [SMILES: Cc1cc(C(=O)Nc2cccc(C3(C)CCSC(N)=N3)c2)no1]
415 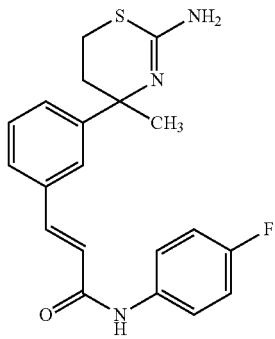 [SMILES: CC1(c2cccc(/C=C/C(=O)Nc3ccc(F)cc3)c2)CCSC(N)=N1]
416 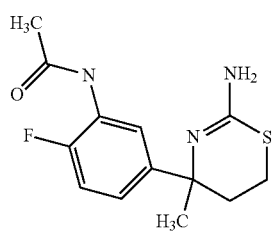 [SMILES: CC(=O)Nc1cc(C2(C)CCSC(N)=N2)ccc1F]
TABLE 45
417 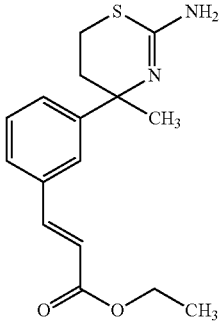 [SMILES: CCOC(=O)/C=C/c1cccc(C2(C)CCSC(N)=N2)c1]
418 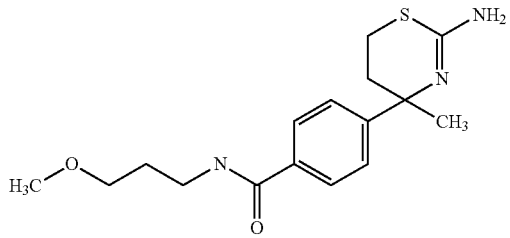 [SMILES: COCCCNC(=O)c1ccc(C2(C)CCSC(N)=N2)cc1]
419
420
421 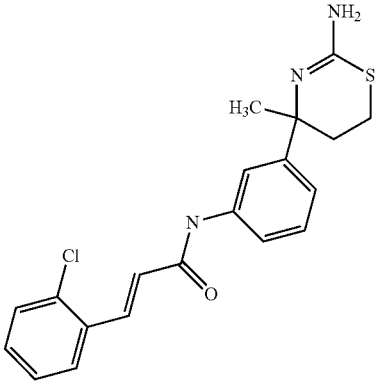 [SMILES: CC1(c2cccc(NC(=O)/C=C/c3ccccc3Cl)c2)CCSC(N)=N1]

TABLE 45-continued
422 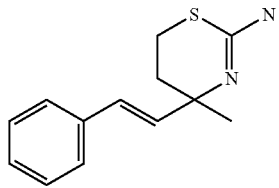 [SMILES: CC1(/C=C/c2ccccc2)CCSC(N)=N1]
423 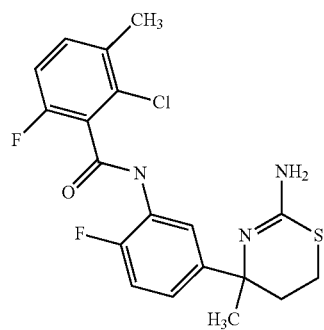 [SMILES: Cc1ccc(F)c(C(=O)Nc2cc(C3(C)CCSC(N)=N3)ccc2F)c1Cl]
424 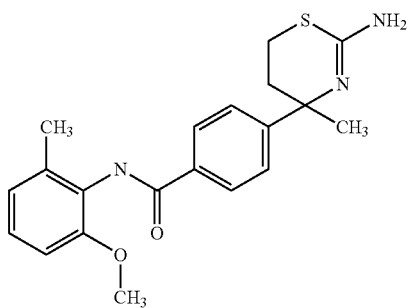 [SMILES: COc1cccc(C)c1NC(=O)c1ccc(C2(C)CCSC(N)=N2)cc1]
TABLE 46
425 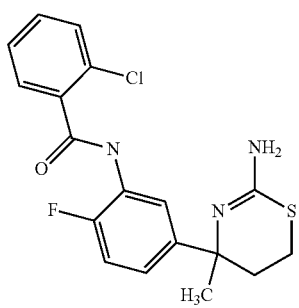 [SMILES: CC1(c2ccc(F)c(NC(=O)c3ccccc3Cl)c2)CCSC(N)=N1]
426 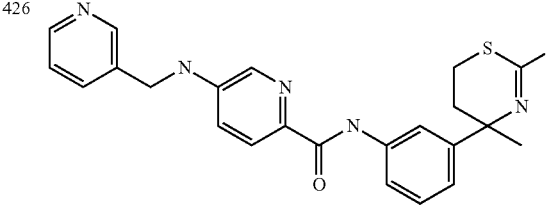
TABLE 46-continued
427 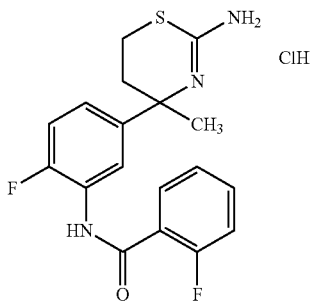 [SMILES: CC1(c2ccc(F)c(NC(=O)c3ccccc3F)c2)CCSC(N)=N1 ; Cl]
ClH
428 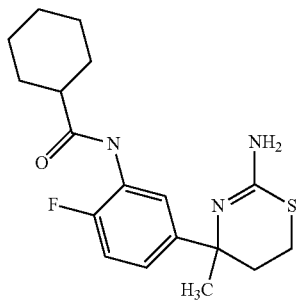 [SMILES: CC1(c2ccc(F)c(NC(=O)C3CCCCC3)c2)CCSC(N)=N1]
429 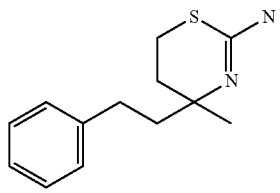 [SMILES: CC1(CCc2ccccc2)CCSC(N)=N1]
ClH
430 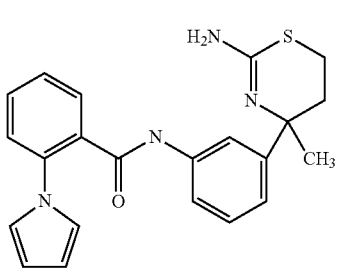 [SMILES: CC1(c2cccc(NC(=O)c3ccccc3-n3cccc3)c2)CCSC(N)=N1]
431 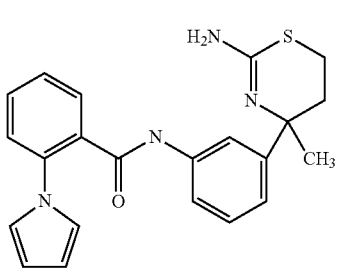 [SMILES: CC1(c2cccc(NC(=O)c3ccccc3-n3cccc3)c2)CCSC(N)=N1]
432 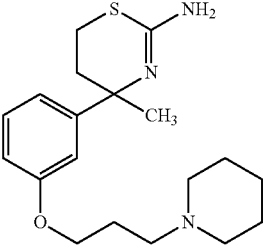 [SMILES: CC1(c2cccc(OCCCN3CCCCC3)c2)CCSC(N)=N1]

TABLE 46-continued
433 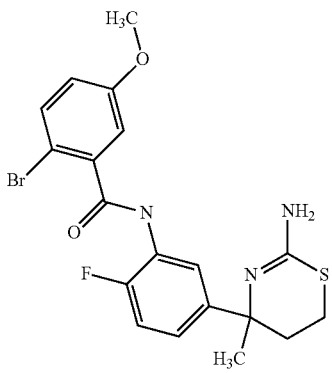 [SMILES: COc1ccc(Br)c(C(=O)Nc2cc(C3(C)CCSC(N)=N3)ccc2F)c1]
TABLE 47
434 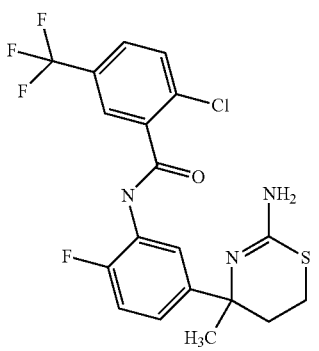 [SMILES: CC1(c2ccc(F)c(NC(=O)c3cc(C(F)(F)F)ccc3Cl)c2)CCSC(N)=N1]
435 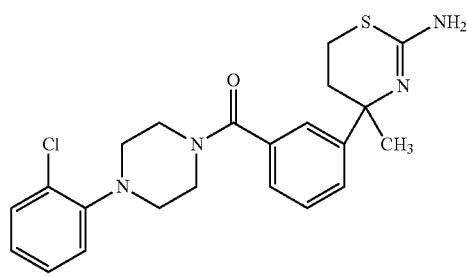
436 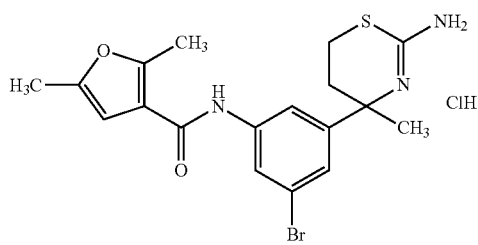 [SMILES: Cc1cc(C(=O)Nc2cc(Br)cc(C3(C)CCSC(N)=N3)c2)c(C)o1 ; Cl]
ClH
TABLE 47-continued
437 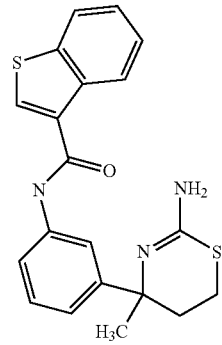 [SMILES: CC1(c2cccc(NC(=O)c3csc4ccccc34)c2)CCSC(N)=N1]
438 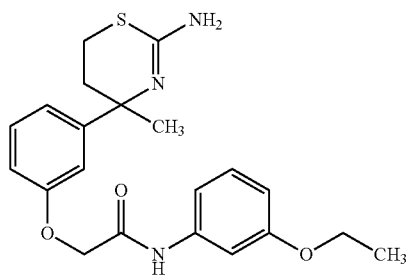 [SMILES: CCOc1cccc(NC(=O)COc2cccc(C3(C)CCSC(N)=N3)c2)c1]
439 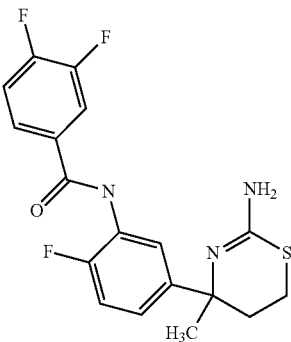 [SMILES: CC1(c2ccc(F)c(NC(=O)c3ccc(F)c(F)c3)c2)CCSC(N)=N1]
440 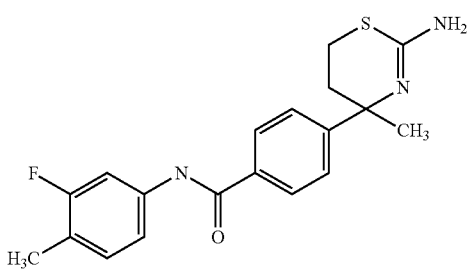
441 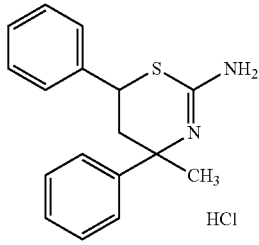 [SMILES: CC1(c2ccccc2)CC(c2ccccc2)SC(N)=N1 ; Cl]
HCl TABLE 47-continued
442 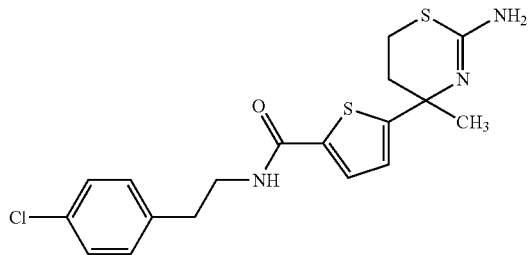 [SMILES: CC1(c2ccc(C(=O)NCCc3ccc(Cl)cc3)s2)CCSC(N)=N1]
TABLE 48
443 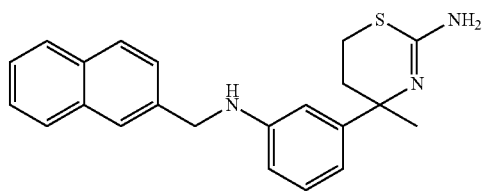 [SMILES: CC1(c2cccc(NCc3ccc4ccccc4c3)c2)CCSC(N)=N1]
444 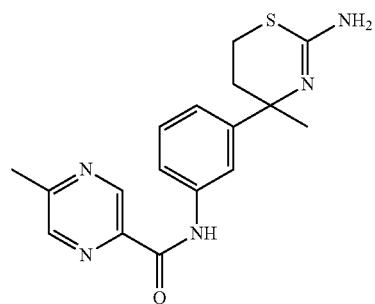 [SMILES: Cc1cnc(C(=O)Nc2cccc(C3(C)CCSC(N)=N3)c2)cn1]
445 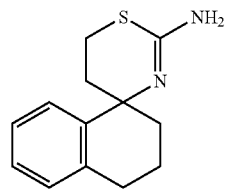 [SMILES: NC1=NC2(CCCc3ccccc32)CCS1]
446 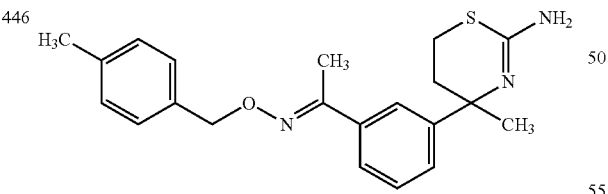
447 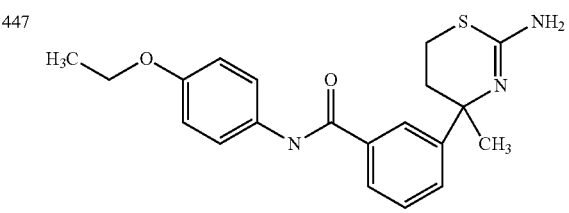
TABLE 48-continued
448 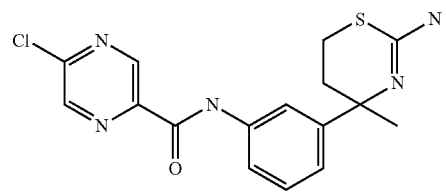 [SMILES: CC1(c2cccc(NC(=O)c3cnc(Cl)cn3)c2)CCSC(N)=N1]
449 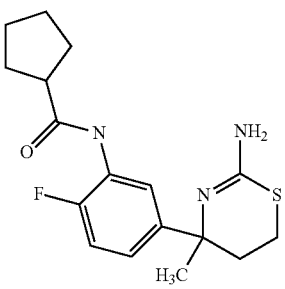 [SMILES: CC1(c2ccc(F)c(NC(=O)C3CCCC3)c2)CCSC(N)=N1]
450
451
452
453 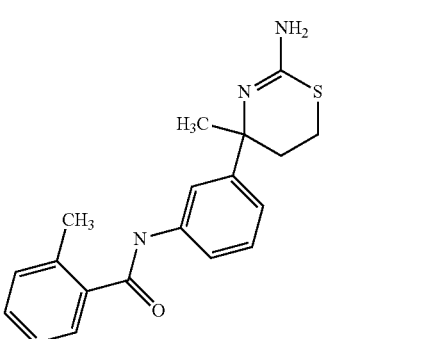

TABLE 49
454 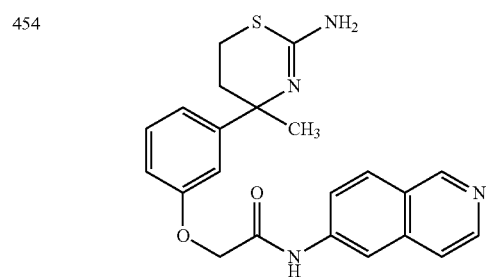
455 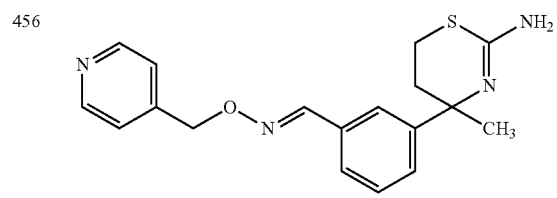
456 
457 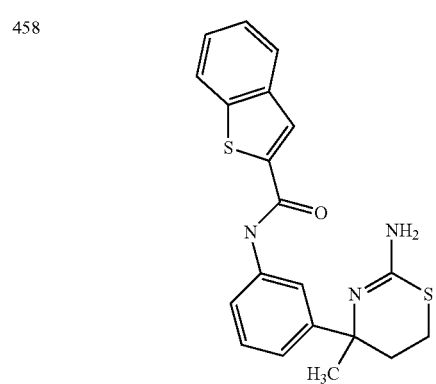
458 
459 
TABLE 49-continued
460 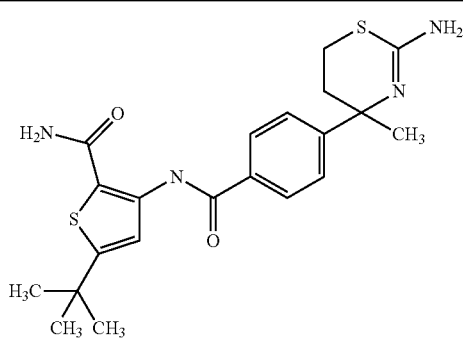
461 
462 
463 
464 

TABLE 50
465 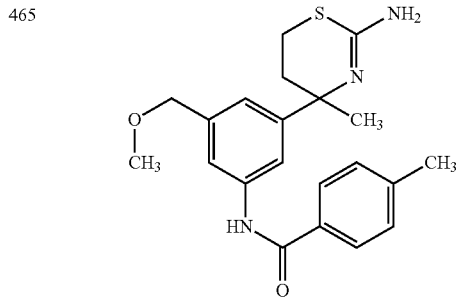
466 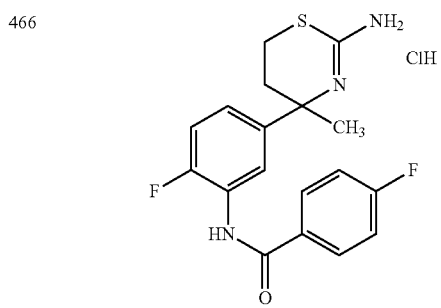
467 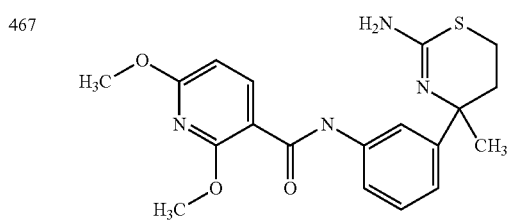
468 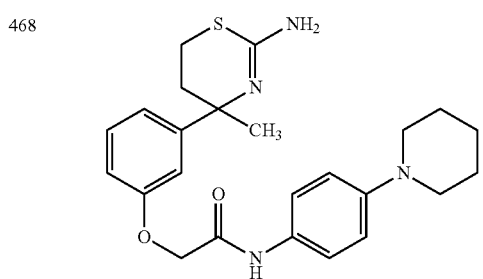
469 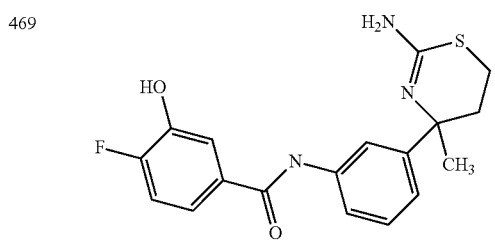
TABLE 50-continued
470 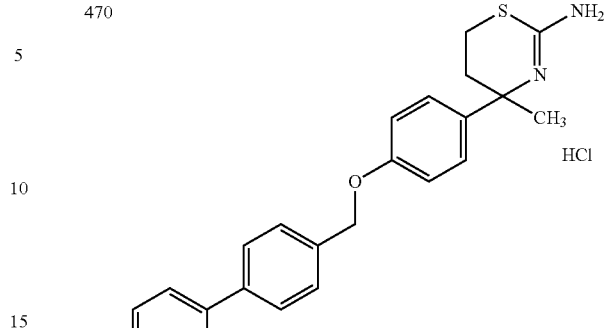
471 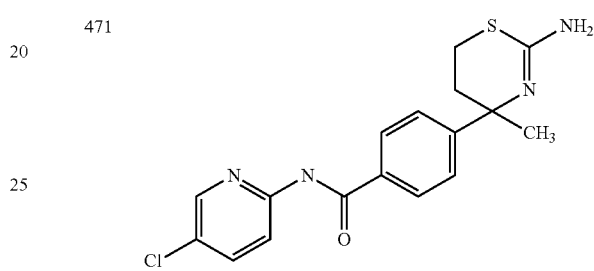
472 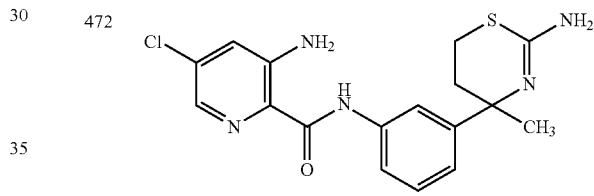
473 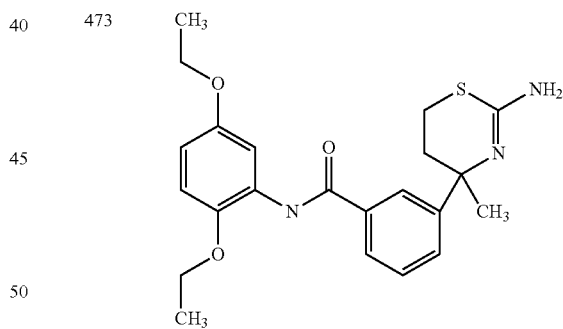
474 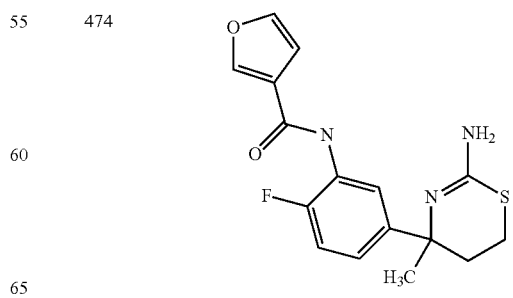

TABLE 51
475 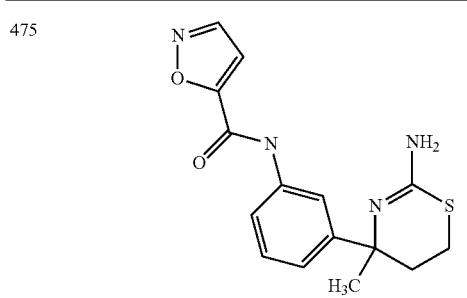
476
477
478
479
TABLE 51-continued
480 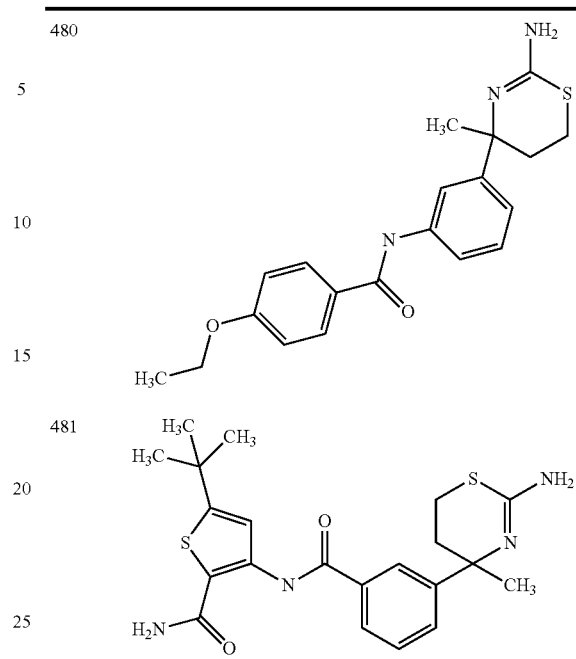
481
482
483
TABLE 52
484 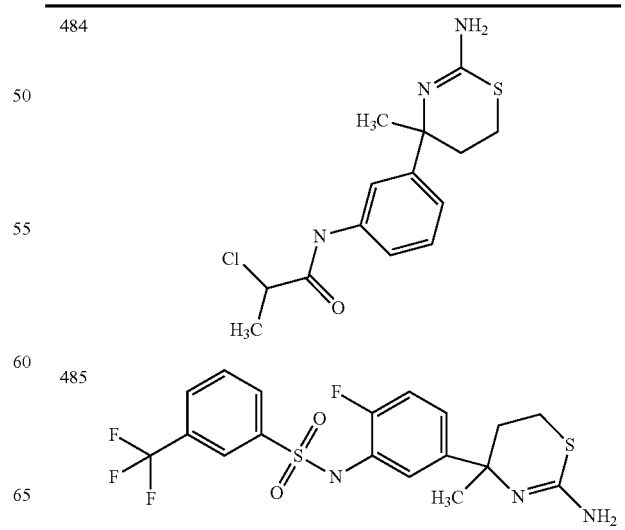
485

TABLE 52-continued
486 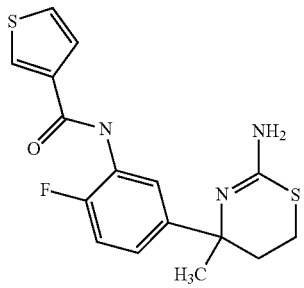 [SMILES: CC1(c2ccc(F)c(NC(=O)c3ccsc3)c2)CCSC(N)=N1]
487 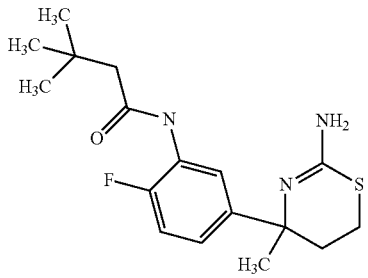 [SMILES: CC(C)(C)CC(=O)Nc1cc(C2(C)CCSC(N)=N2)ccc1F]
488 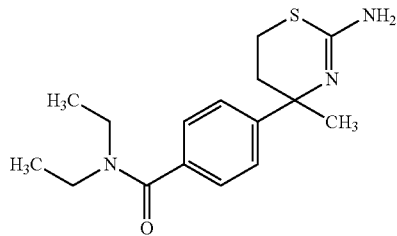 [SMILES: CCN(CC)C(=O)c1ccc(C2(C)CCSC(N)=N2)cc1]
489 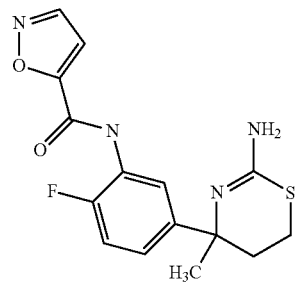
490 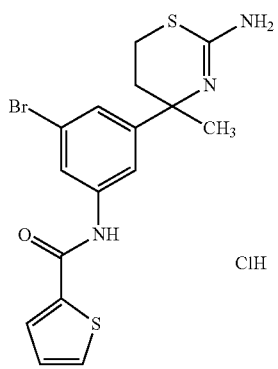 [SMILES: CC1(c2cc(Br)cc(NC(=O)c3cccs3)c2)CCSC(N)=N1 ; Cl]
TABLE 52-continued
491 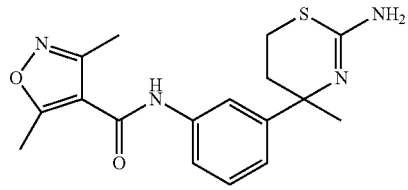 [SMILES: Cc1noc(C)c1C(=O)Nc1cccc(C2(C)CCSC(N)=N2)c1]
492 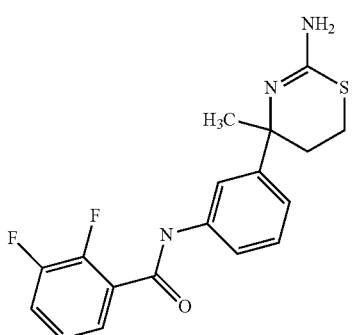
TABLE 53
493 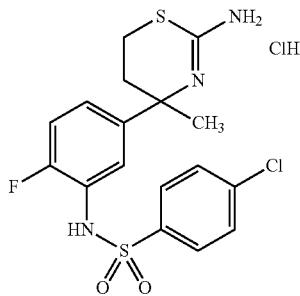 [SMILES: CC1(c2ccc(F)c(NS(=O)(=O)c3ccc(Cl)cc3)c2)CCSC(N)=N1 ; Cl]
494 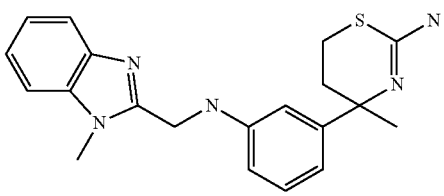 [SMILES: Cn1c(CNc2cccc(C3(C)CCSC(N)=N3)c2)nc2ccccc21]
495 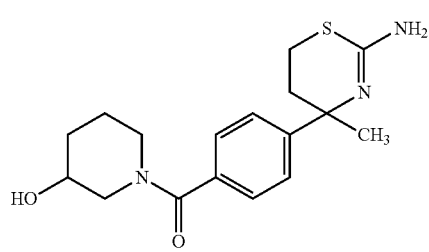 [SMILES: CC1(c2ccc(C(=O)N3CCCC(O)C3)cc2)CCSC(N)=N1]
496 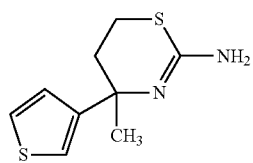

TABLE 53-continued
497 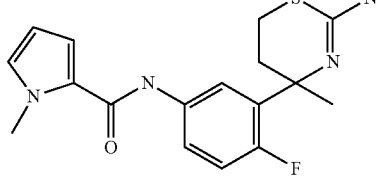
498 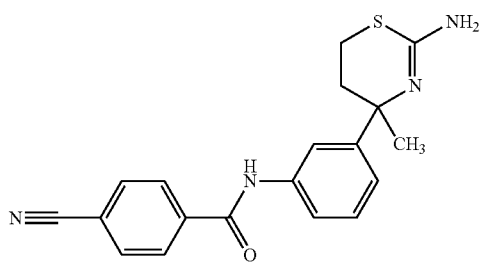 [SMILES: CC1(c2cccc(NC(=O)c3ccc(C#N)cc3)c2)CCSC(N)=N1]
499 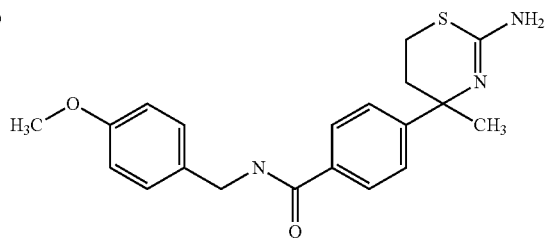
500 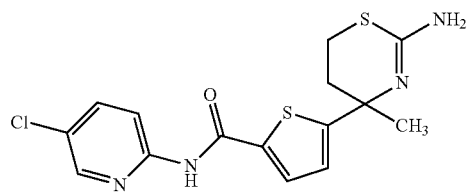 [SMILES: CC1(c2ccc(C(=O)Nc3ccc(Cl)cn3)s2)CCSC(N)=N1]
501 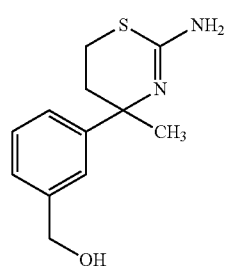 [SMILES: CC1(c2cccc(CO)c2)CCSC(N)=N1]
502 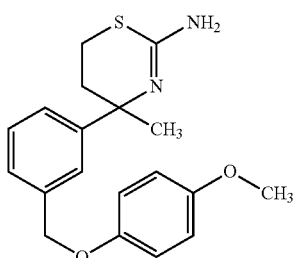
TABLE 53-continued
503 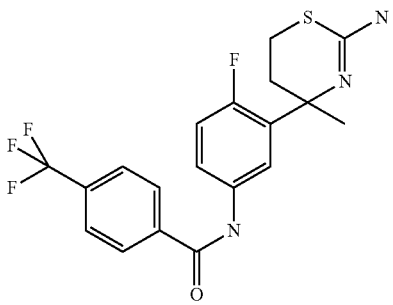 [SMILES: CC1(c2cc(NC(=O)c3ccc(C(F)(F)F)cc3)ccc2F)CCSC(N)=N1]
TABLE 54
504 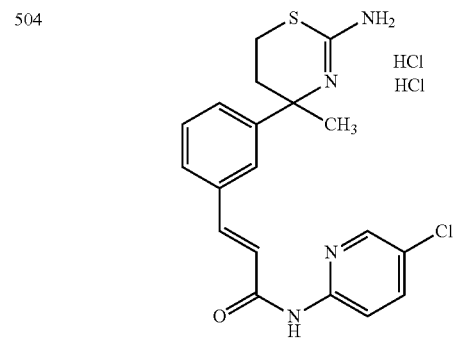
505 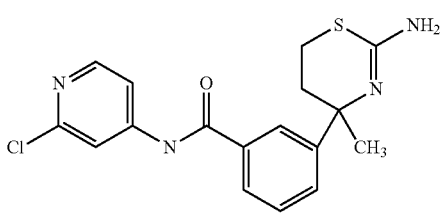 [SMILES: CC1(c2cccc(C(=O)Nc3ccnc(Cl)c3)c2)CCSC(N)=N1]
506 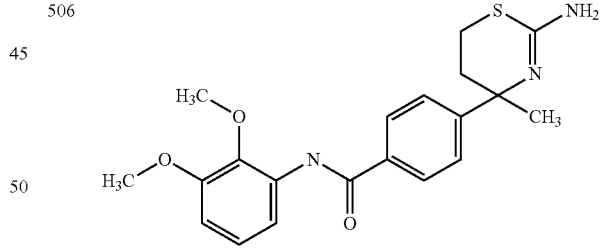
507 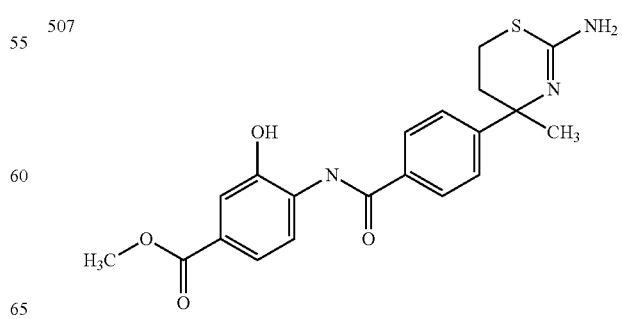

TABLE 54-continued
| 508 | 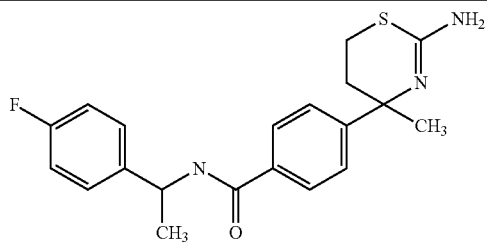 |
| --- | --- |
| 509 | 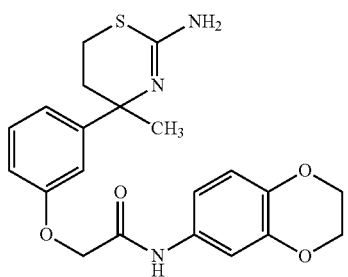 [SMILES: CC1(c2cccc(OCC(=O)Nc3ccc4c(c3)OCCO4)c2)CCSC(N)=N1] |
| 510 | 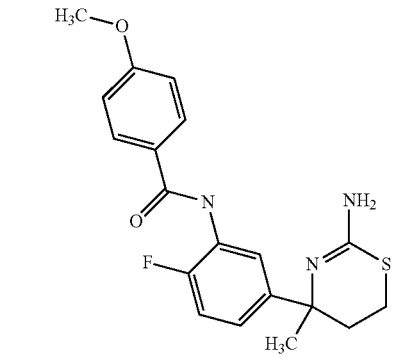 [SMILES: COc1ccc(C(=O)Nc2cc(C3(C)CCSC(N)=N3)ccc2F)cc1] |
| 511 | 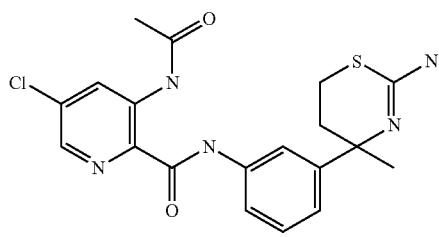 [SMILES: CC(=O)Nc1cc(Cl)cnc1C(=O)Nc1cccc(C2(C)CCSC(N)=N2)c1] |
| 512 | 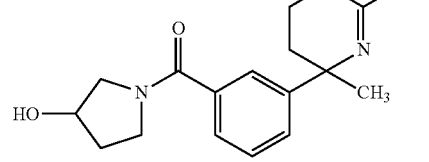 |
| 513 | 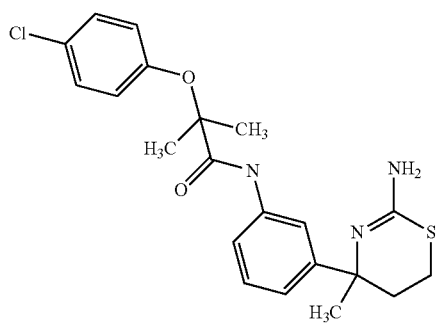 [SMILES: CC(C)(Oc1ccc(Cl)cc1)C(=O)Nc1cccc(C2(C)CCSC(N)=N2)c1] |
TABLE 54-continued
| 514 | 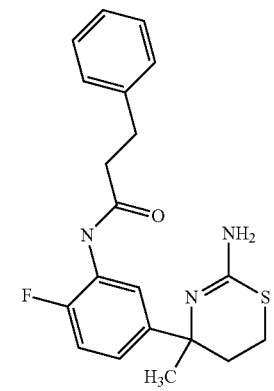 [SMILES: CC1(c2ccc(F)c(NC(=O)CCc3ccccc3)c2)CCSC(N)=N1] |
| --- | --- |
TABLE 55
| 515 | 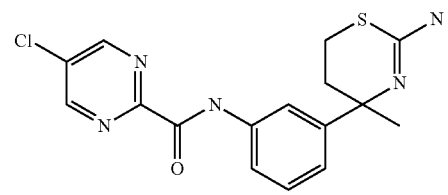 [SMILES: CC1(c2cccc(NC(=O)c3ncc(Cl)cn3)c2)CCSC(N)=N1] |
| --- | --- |
| 516 | 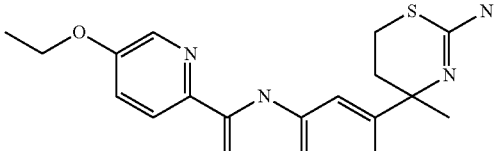 |
| 517 | 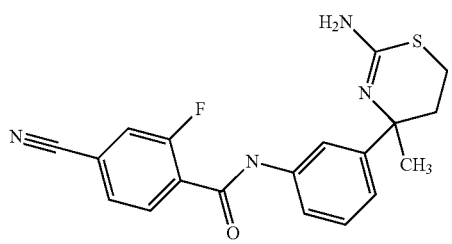 [SMILES: CC1(c2cccc(NC(=O)c3ccc(C#N)cc3F)c2)CCSC(N)=N1] |
| 518 | 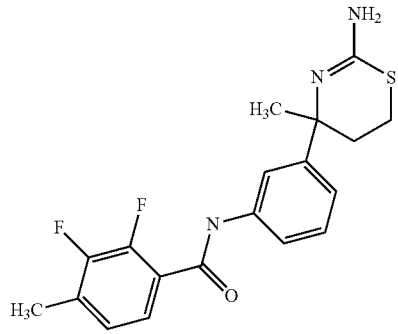 [SMILES: Cc1ccc(C(=O)Nc2cccc(C3(C)CCSC(N)=N3)c2)c(F)c1F] |

TABLE 55-continued
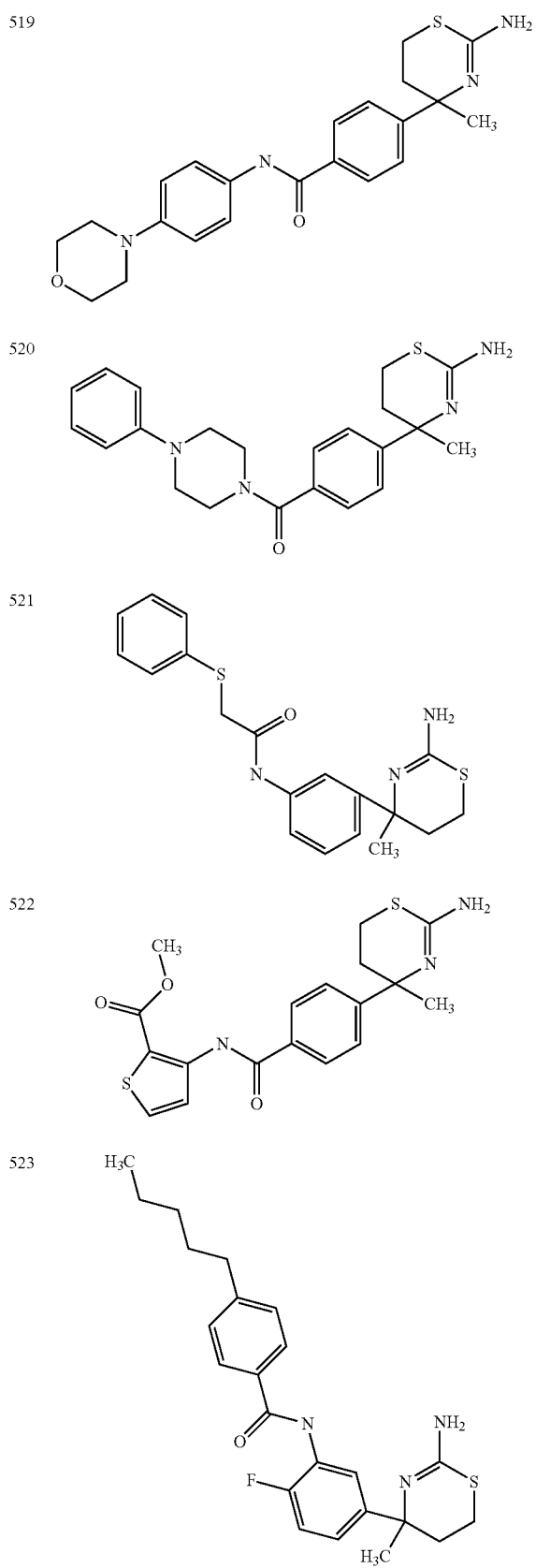
TABLE 55-continued
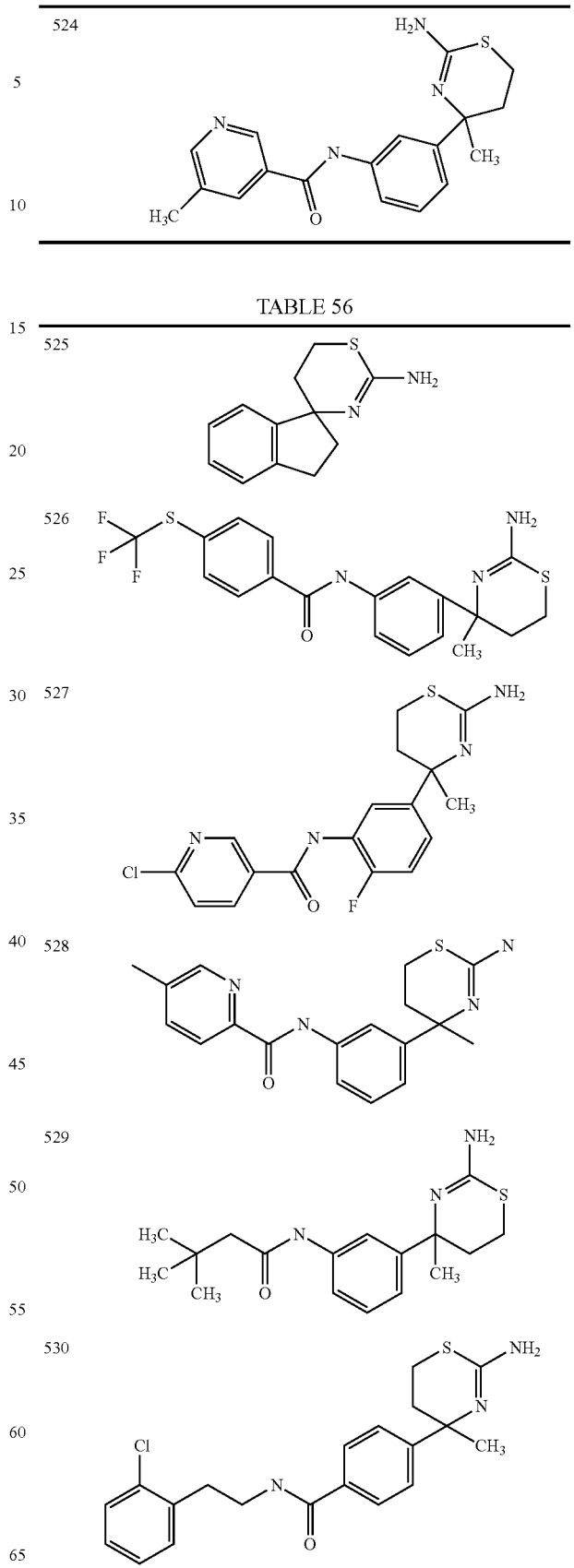
TABLE 56

TABLE 56-continued
531 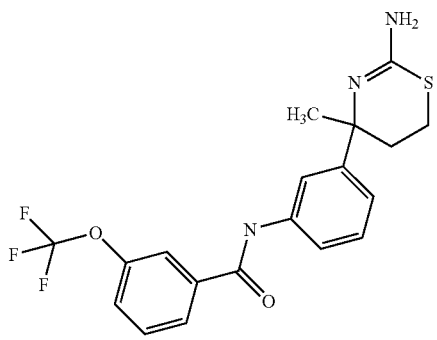 [SMILES: CC1(c2cccc(NC(=O)c3cccc(OC(F)(F)F)c3)c2)CCSC(N)=N1]
532 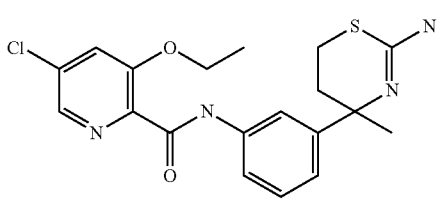 [SMILES: CCOc1cc(Cl)cnc1C(=O)Nc1cccc(C2(C)CCSC(N)=N2)c1]
533 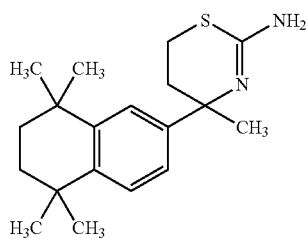 [SMILES: CC1(C)CCC(C)(C)c2cc(C3(C)CCSC(N)=N3)ccc21]
534 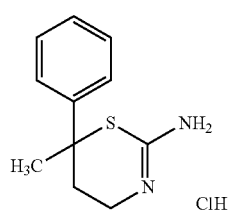
535 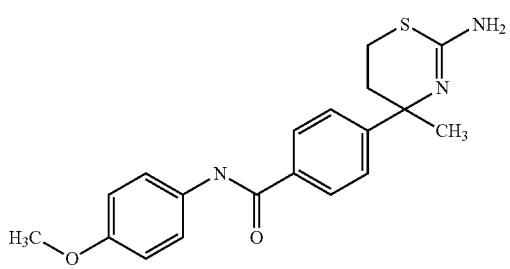 [SMILES: COc1ccc(NC(=O)c2ccc(C3(C)CCSC(N)=N3)cc2)cc1]
TABLE 57
536 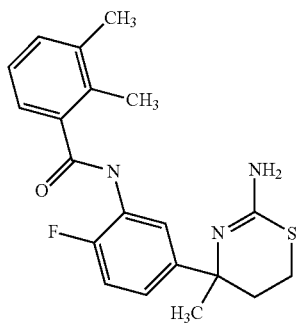 [SMILES: Cc1cccc(C(=O)Nc2cc(C3(C)CCSC(N)=N3)ccc2F)c1C]
537 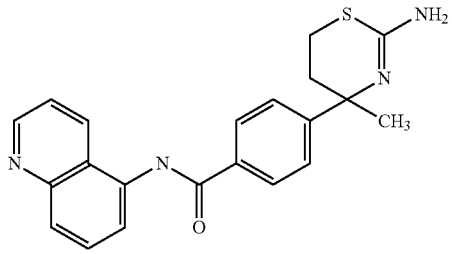 [SMILES: CC1(c2ccc(C(=O)Nc3cccc4ncccc34)cc2)CCSC(N)=N1]
538 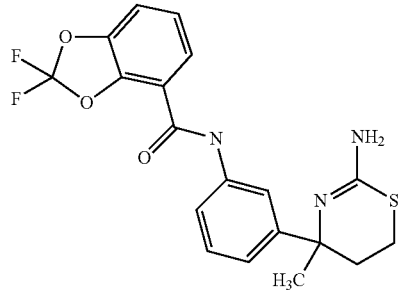 [SMILES: CC1(c2cccc(NC(=O)c3cccc4c3OC(F)(F)O4)c2)CCSC(N)=N1]
539 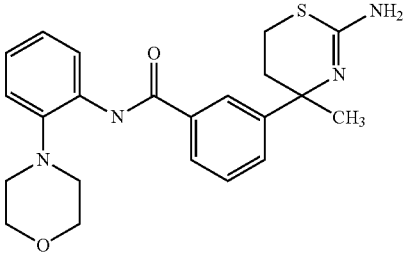 [SMILES: CC1(c2cccc(C(=O)Nc3ccccc3N3CCOCC3)c2)CCSC(N)=N1]
540 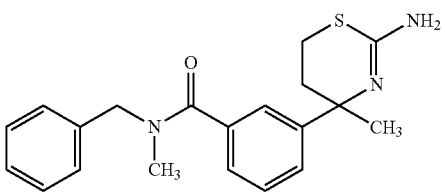 [SMILES: CN(Cc1ccccc1)C(=O)c1cccc(C2(C)CCSC(N)=N2)c1]
541 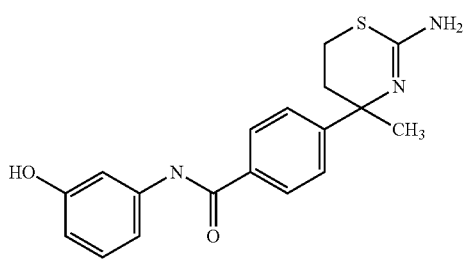 [SMILES: CC1(c2ccc(C(=O)Nc3cccc(O)c3)cc2)CCSC(N)=N1]

TABLE 57-continued
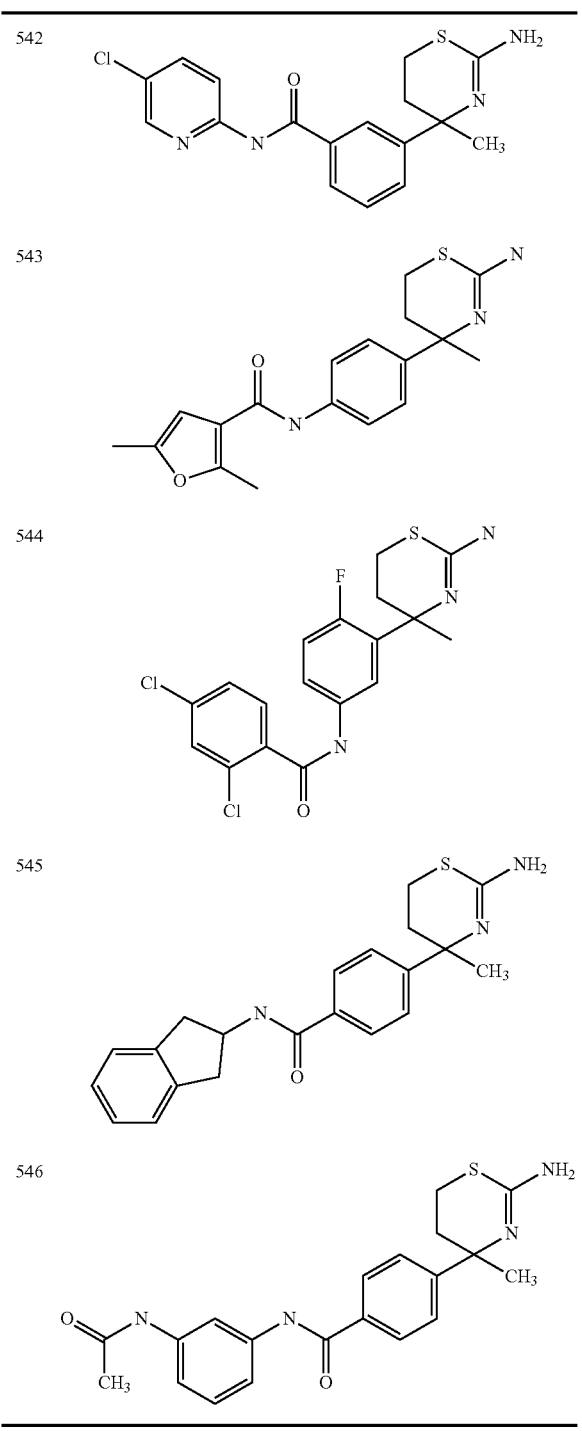
TABLE 58
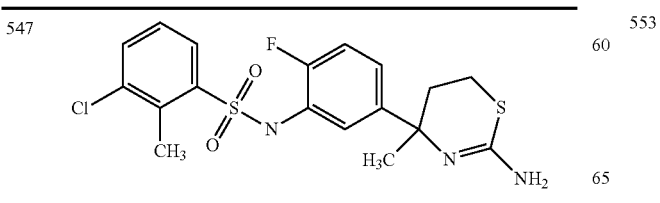
TABLE 58-continued
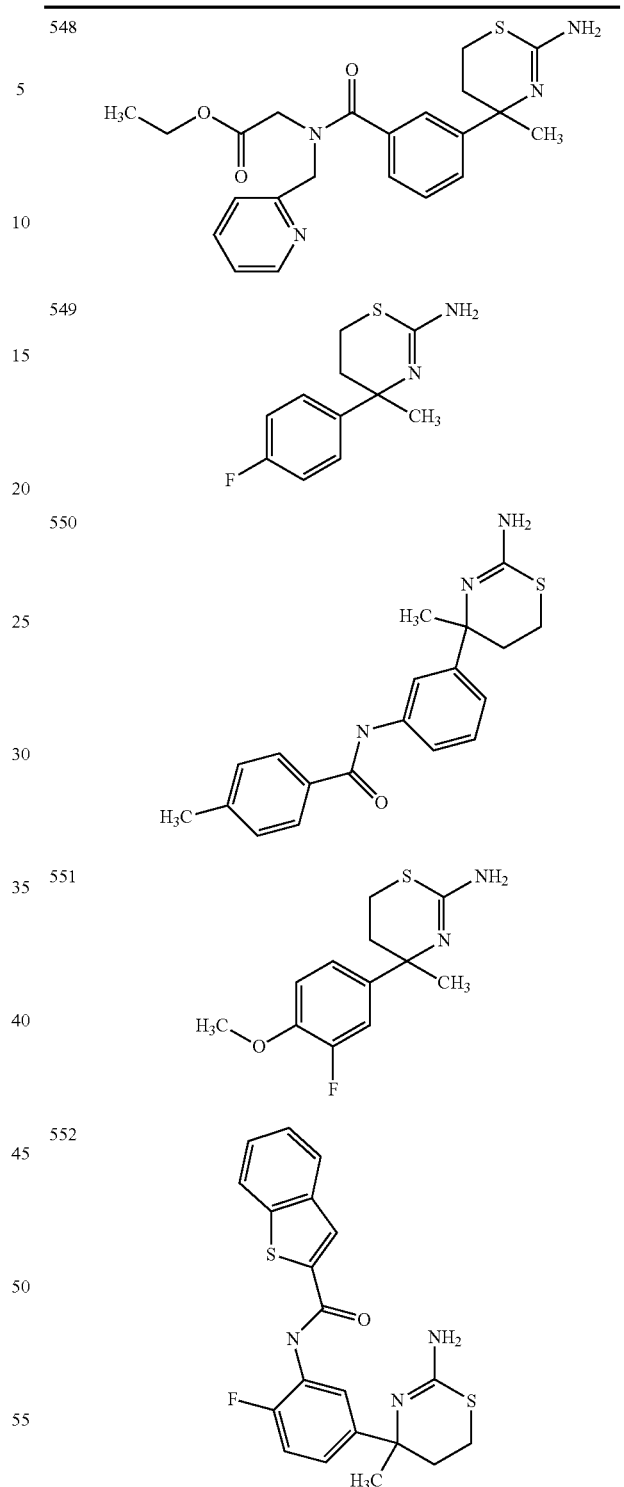
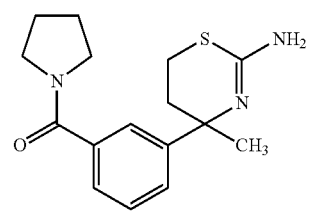 [SMILES: CC1(c2cccc(C(=O)N3CCCC3)c2)CCSC(N)=N1]

TABLE 58-continued
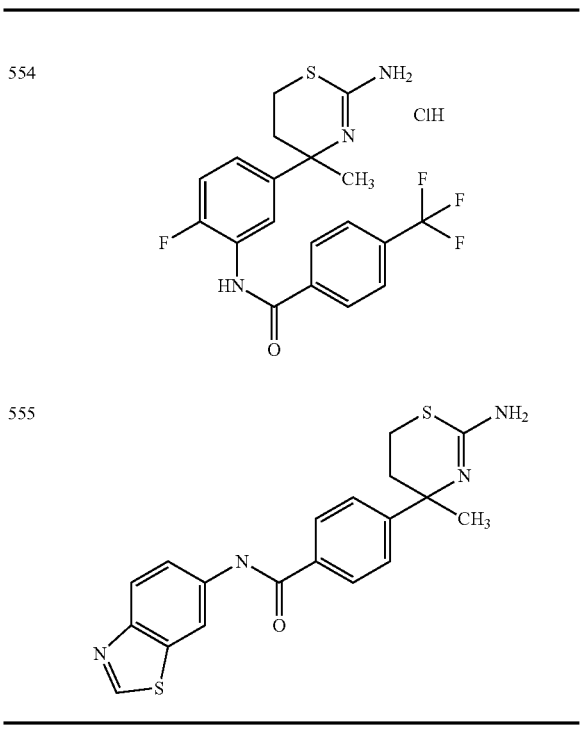
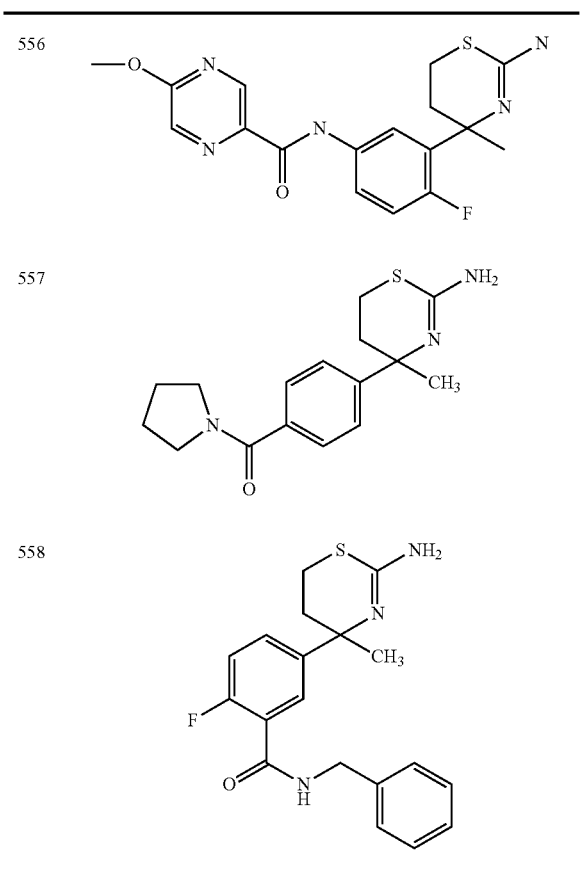
TABLE 59
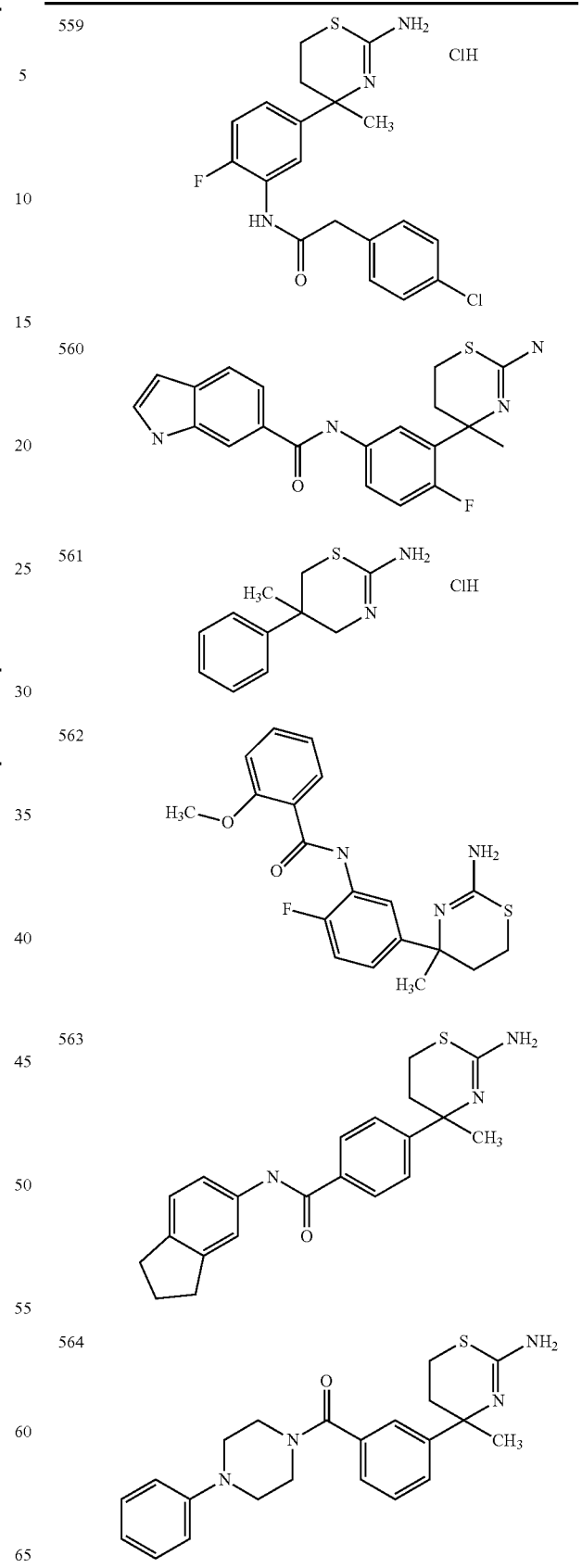

TABLE 59-continued
565 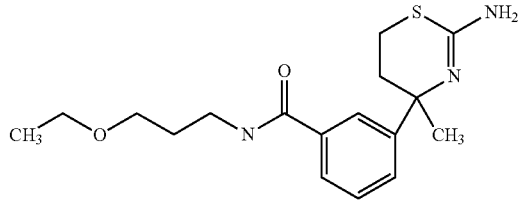 [SMILES: CCOCCCNC(=O)c1cccc(C2(C)CCSC(N)=N2)c1]
566 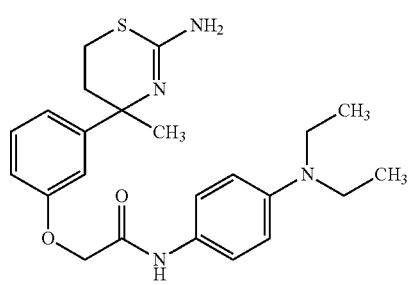 [SMILES: CCN(CC)c1ccc(NC(=O)COc2cccc(C3(C)CCSC(N)=N3)c2)cc1]
TABLE 60
567 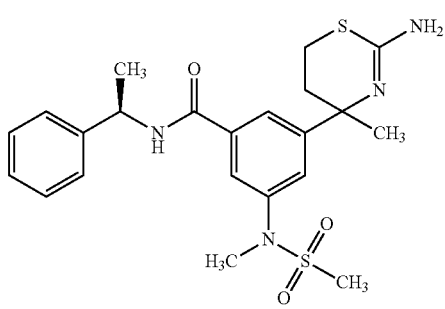 [SMILES: C[C@@H](NC(=O)c1cc(N(C)S(C)(=O)=O)cc(C2(C)CCSC(N)=N2)c1)c1ccccc1]
568 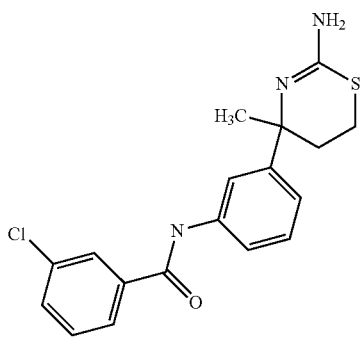 [SMILES: CC1(c2cccc(NC(=O)c3cccc(Cl)c3)c2)CCSC(N)=N1]
569 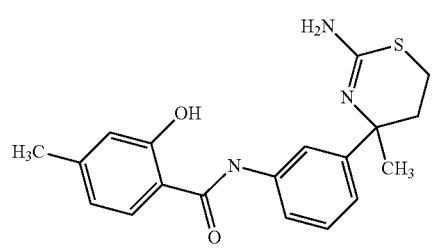 [SMILES: Cc1ccc(C(=O)Nc2cccc(C3(C)CCSC(N)=N3)c2)c(O)c1]
TABLE 60-continued
570 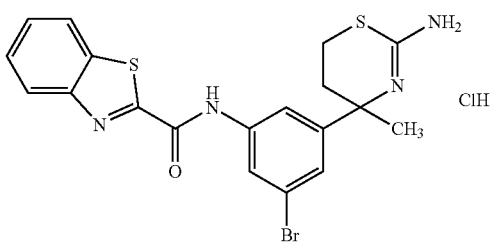 [SMILES: CC1(c2cc(Br)cc(NC(=O)c3nc4ccccc4s3)c2)CCSC(N)=N1 ; Cl]
571 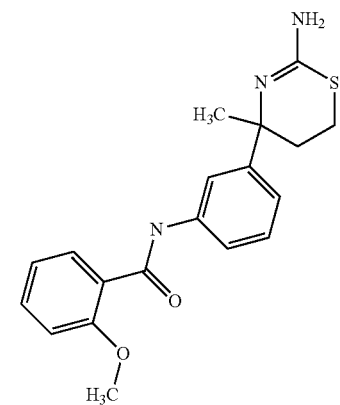 [SMILES: COc1ccccc1C(=O)Nc1cccc(C2(C)CCSC(N)=N2)c1]
572 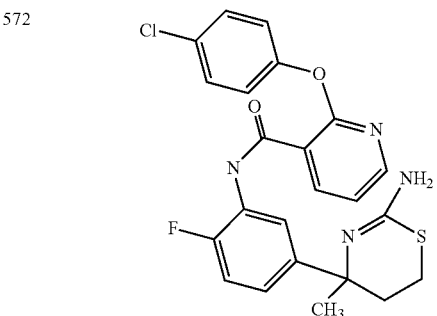
573 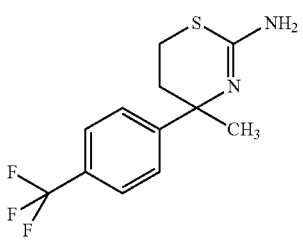 [SMILES: CC1(c2ccc(C(F)(F)F)cc2)CCSC(N)=N1]
574 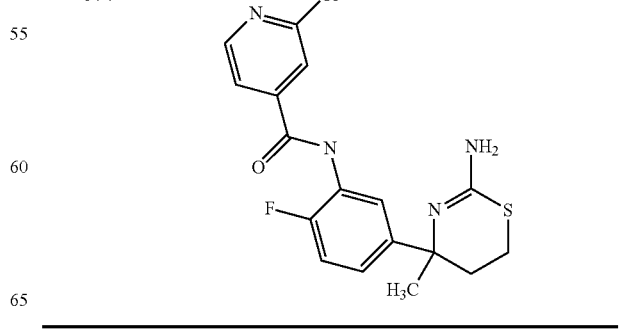

TABLE 61
575 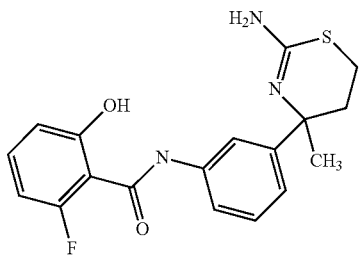 [SMILES: CC1(c2cccc(NC(=O)c3c(O)cccc3F)c2)CCSC(N)=N1]
576 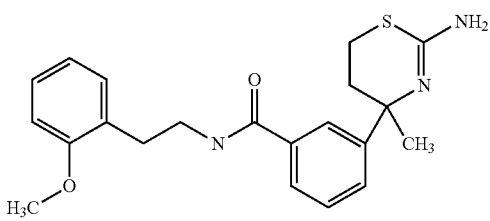 [SMILES: COc1ccccc1CCNC(=O)c1cccc(C2(C)CCSC(N)=N2)c1]
577 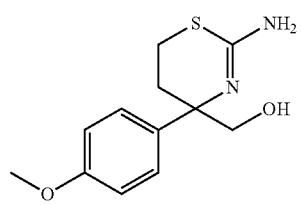 [SMILES: COc1ccc(C2(CO)CCSC(N)=N2)cc1]
578 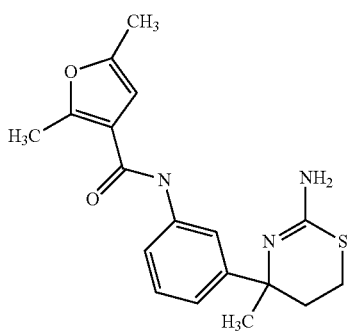 [SMILES: Cc1cc(C(=O)Nc2cccc(C3(C)CCSC(N)=N3)c2)c(C)o1]
579 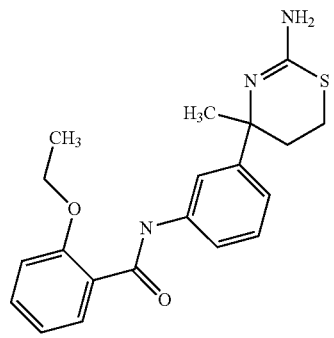 [SMILES: CCOc1ccccc1C(=O)Nc1cccc(C2(C)CCSC(N)=N2)c1]
580 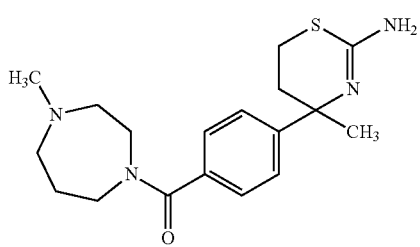 [SMILES: CN1CCCN(C(=O)c2ccc(C3(C)CCSC(N)=N3)cc2)CC1]
TABLE 61-continued
581 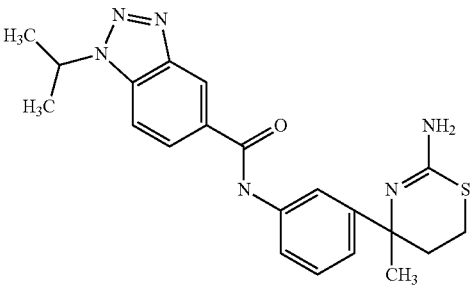 [SMILES: CC(C)n1nnc2cc(C(=O)Nc3cccc(C4(C)CCSC(N)=N4)c3)ccc21]
582 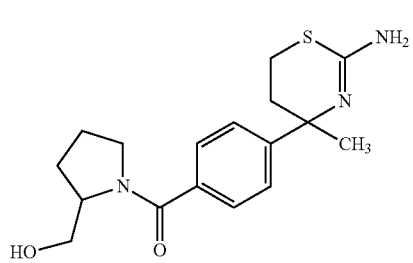 [SMILES: CC1(c2ccc(C(=O)N3CCCC3CO)cc2)CCSC(N)=N1]
583 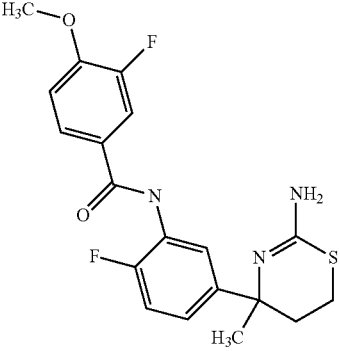 [SMILES: COc1ccc(C(=O)Nc2cc(C3(C)CCSC(N)=N3)ccc2F)cc1F]
584 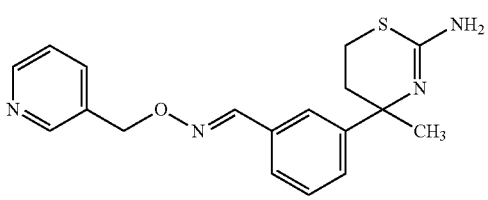 [SMILES: CC1(c2cccc(/C=N/OCc3cccnc3)c2)CCSC(N)=N1]
TABLE 62
585 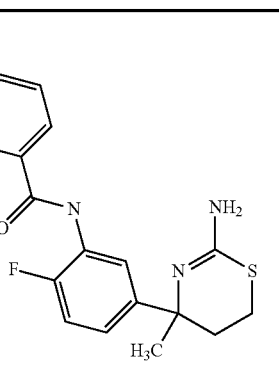

TABLE 62-continued
| 586 | 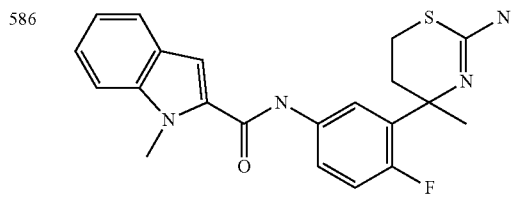 |
| --- | --- |
| 587 | 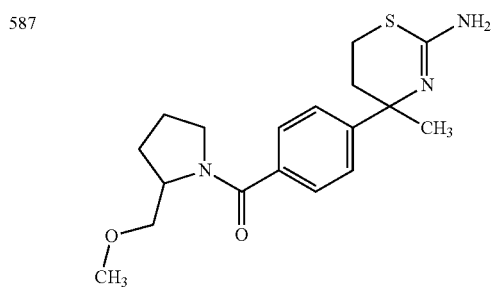 |
| 588 | 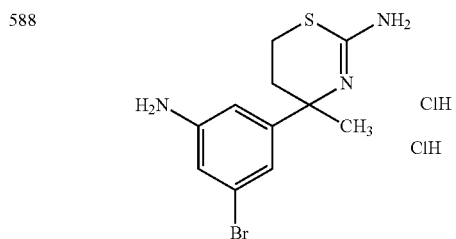 |
| 589 | 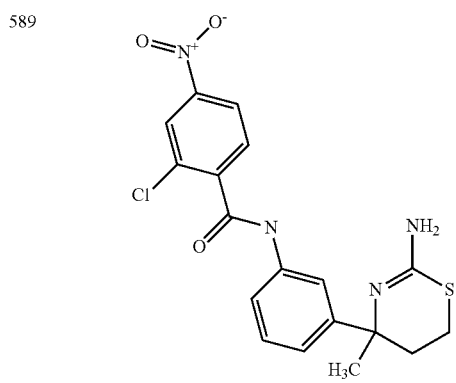 |
| 590 | 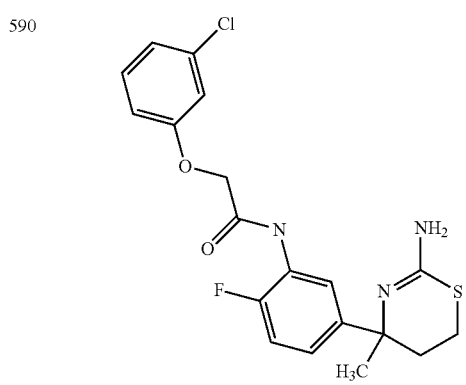 |
TABLE 62-continued
| 591 | 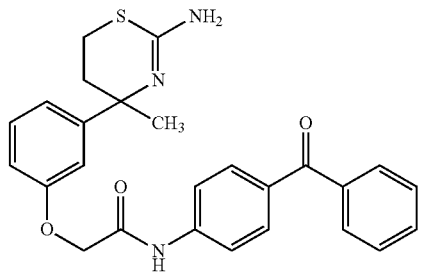 [SMILES: CC1(c2cccc(OCC(=O)Nc3ccc(C(=O)c4ccccc4)cc3)c2)CCSC(N)=N1] |
| --- | --- |
TABLE 63
| 592 | 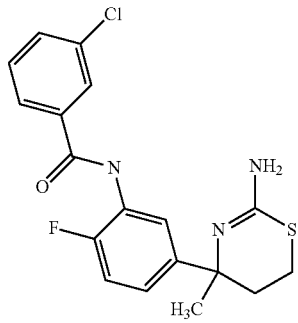 |
| --- | --- |
| 593 | 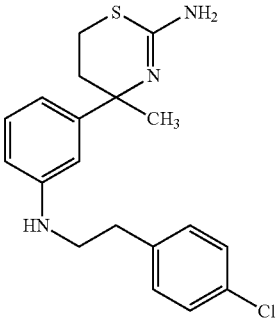 [SMILES: CC1(c2cccc(NCCc3ccc(Cl)cc3)c2)CCSC(N)=N1] |
| 594 | 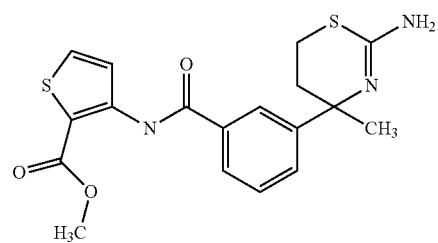 [SMILES: COC(=O)c1sccc1NC(=O)c1cccc(C2(C)CCSC(N)=N2)c1] |
| 595 | 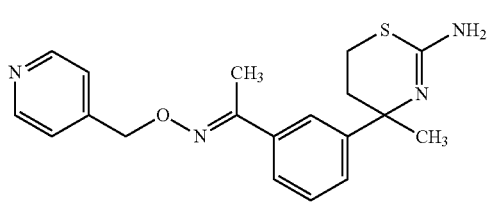 [SMILES: C/C(=N\OCc1ccncc1)c1cccc(C2(C)CCSC(N)=N2)c1] |

TABLE 63-continued
| | |
|---|---|
| 596 | 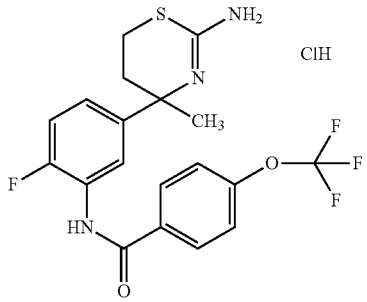 [SMILES: CC1(c2ccc(F)c(NC(=O)c3ccc(OC(F)(F)F)cc3)c2)CCSC(N)=N1 ; Cl] ClH |
| 597 | 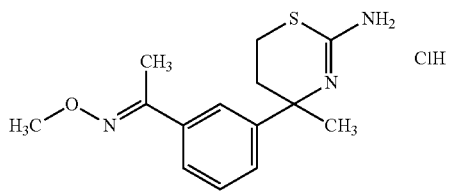 [SMILES: CO/N=C(\C)c1cccc(C2(C)CCSC(N)=N2)c1 ; Cl] ClH |
| 598 | 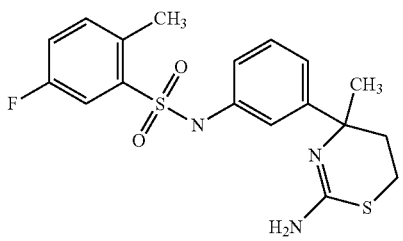 [SMILES: Cc1ccc(F)cc1S(=O)(=O)Nc1cccc(C2(C)CCSC(N)=N2)c1] |
| 599 | 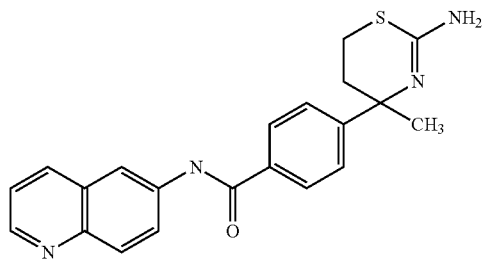 [SMILES: CC1(c2ccc(C(=O)Nc3ccc4ncccc4c3)cc2)CCSC(N)=N1] |
| 600 | 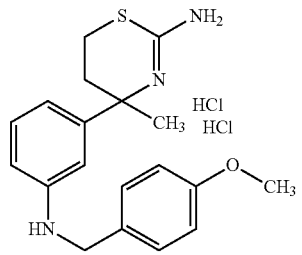 [SMILES: COc1ccc(CNc2cccc(C3(C)CCSC(N)=N3)c2)cc1 ; Cl ; Cl] HCl HCl |
| 601 | 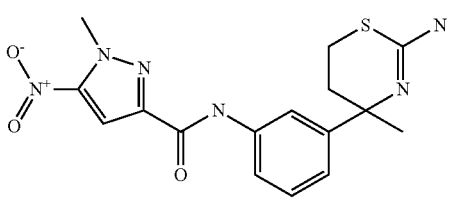 [SMILES: Cn1nc(C(=O)Nc2cccc(C3(C)CCSC(N)=N3)c2)cc1[N+](=O)[O-]] |
TABLE 63-continued
| | |
|---|---|
| 602 | 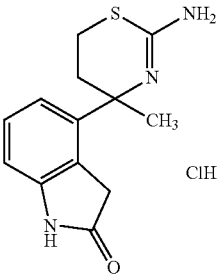 [SMILES: CC1(c2cccc3c2CC(=O)N3)CCSC(N)=N1 ; Cl] ClH |
TABLE 64
| | |
|---|---|
| 603 | 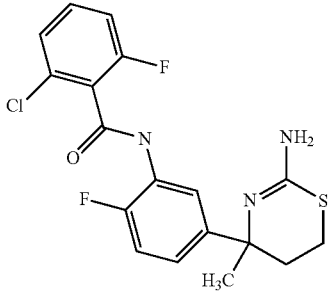 [SMILES: CC1(c2ccc(F)c(NC(=O)c3c(F)cccc3Cl)c2)CCSC(N)=N1] |
| 604 | 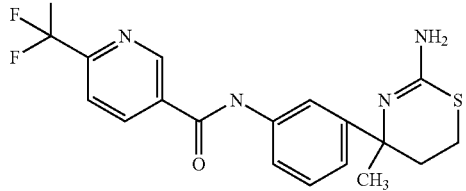 |
| 605 | 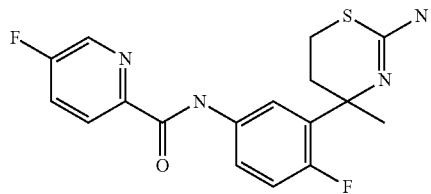 [SMILES: CC1(c2cc(NC(=O)c3ccc(F)cn3)ccc2F)CCSC(N)=N1] |
| 606 | 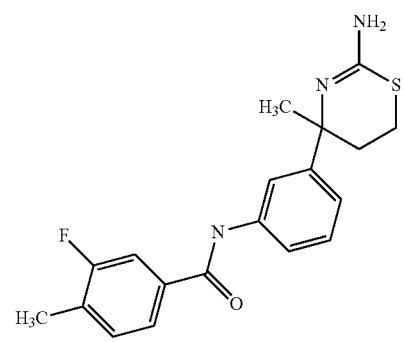 [SMILES: Cc1ccc(C(=O)Nc2cccc(C3(C)CCSC(N)=N3)c2)cc1F] |

TABLE 64-continued
607 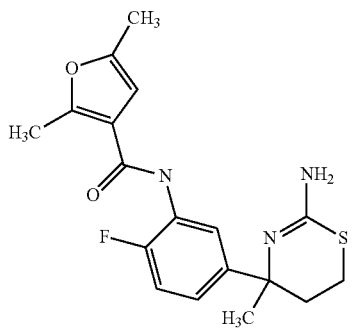 [SMILES: Cc1cc(C(=O)Nc2cc(C3(C)CCSC(N)=N3)ccc2F)c(C)o1]
608 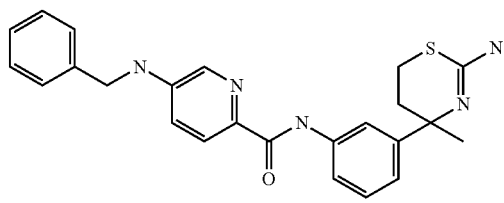 [SMILES: CC1(c2cccc(NC(=O)c3ccc(NCc4ccccc4)cn3)c2)CCSC(N)=N1]
609 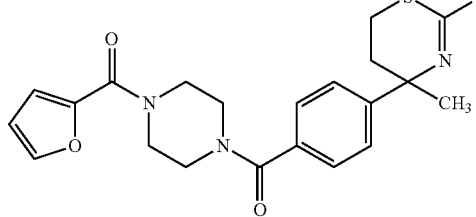
610 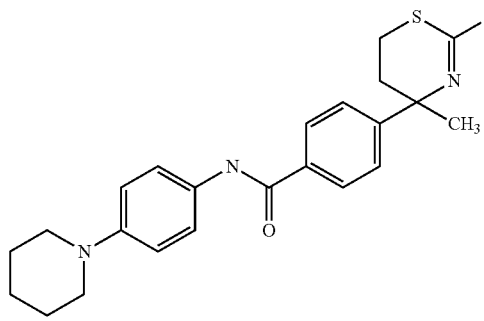
611 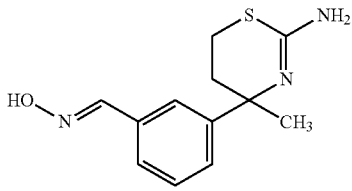 [SMILES: CC1(c2cccc(/C=N/O)c2)CCSC(N)=N1]
612 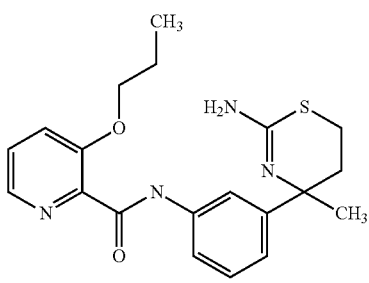 [SMILES: CCCOc1cccnc1C(=O)Nc1cccc(C2(C)CCSC(N)=N2)c1]
TABLE 64-continued
613 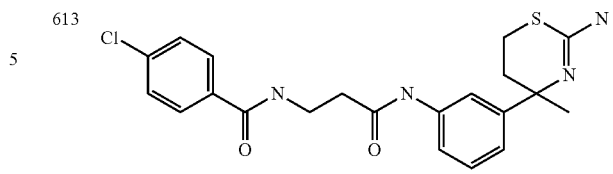
TABLE 65
614 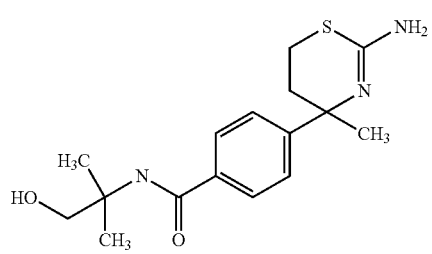 [SMILES: CC(C)(CO)NC(=O)c1ccc(C2(C)CCSC(N)=N2)cc1]
615 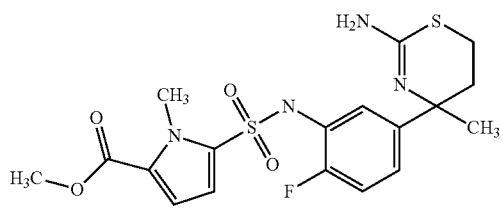
616 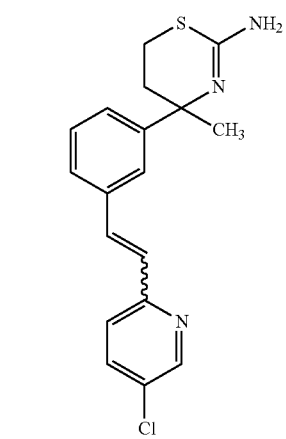 [SMILES: CC1(c2cccc(C=Cc3ccc(Cl)cn3)c2)CCSC(N)=N1]
617 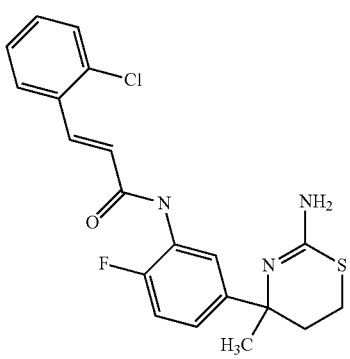 [SMILES: CC1(c2ccc(F)c(NC(=O)/C=C/c3ccccc3Cl)c2)CCSC(N)=N1]

TABLE 65-continued
618 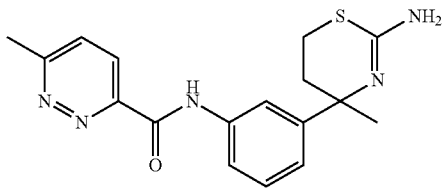 [SMILES: Cc1ccc(C(=O)Nc2cccc(C3(C)CCSC(N)=N3)c2)nn1]
619 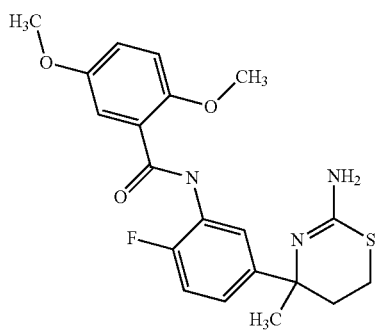 [SMILES: COc1ccc(OC)c(C(=O)Nc2cc(C3(C)CCSC(N)=N3)ccc2F)c1]
620 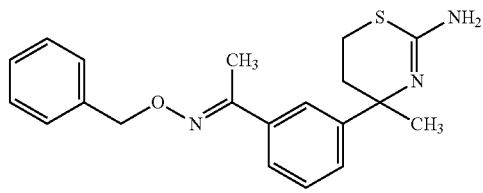 [SMILES: C/C(=N\OCc1ccccc1)c1cccc(C2(C)CCSC(N)=N2)c1]
621 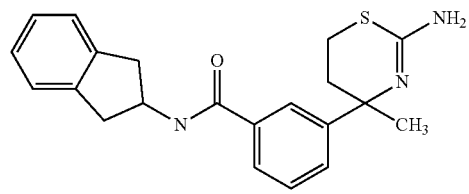 [SMILES: CC1(c2cccc(C(=O)NC3Cc4ccccc4C3)c2)CCSC(N)=N1]
623 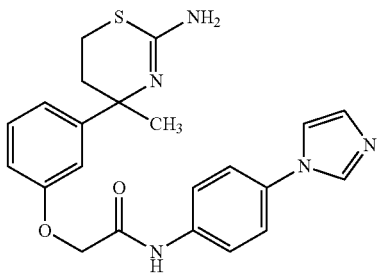 [SMILES: CC1(c2cccc(OCC(=O)Nc3ccc(-n4ccnc4)cc3)c2)CCSC(N)=N1]
624 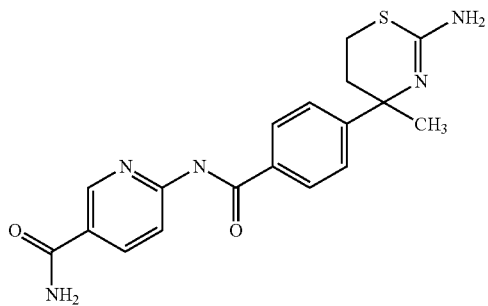 [SMILES: CC1(c2ccc(C(=O)Nc3ccc(C(N)=O)cn3)cc2)CCSC(N)=N1]
TABLE 66
625 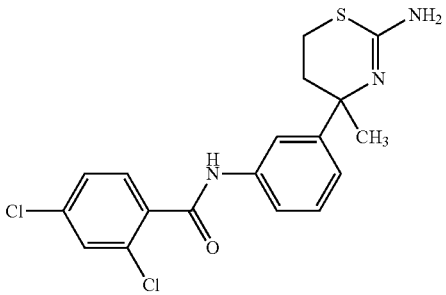 [SMILES: CC1(c2cccc(NC(=O)c3ccc(Cl)cc3Cl)c2)CCSC(N)=N1]
626 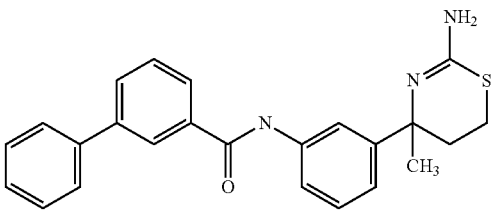 [SMILES: CC1(c2cccc(NC(=O)c3cccc(-c4ccccc4)c3)c2)CCSC(N)=N1]
627 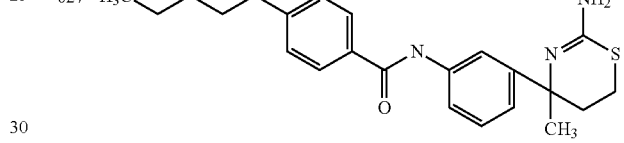
628 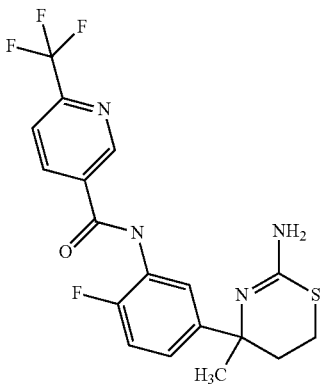 [SMILES: CC1(c2ccc(F)c(NC(=O)c3ccc(C(F)(F)F)nc3)c2)CCSC(N)=N1]
629 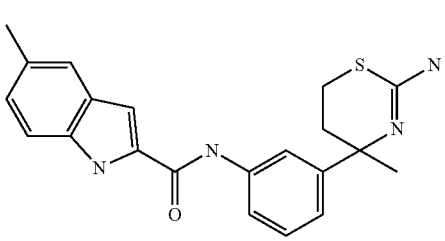 [SMILES: Cc1ccc2[nH]c(C(=O)Nc3cccc(C4(C)CCSC(N)=N4)c3)cc2c1]
630 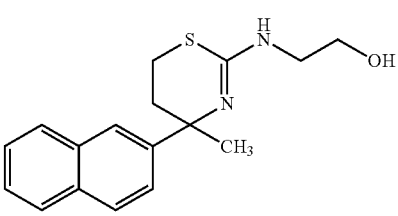 [SMILES: CC1(c2ccc3ccccc3c2)CCSC(NCCO)=N1]

TABLE 66-continued
631 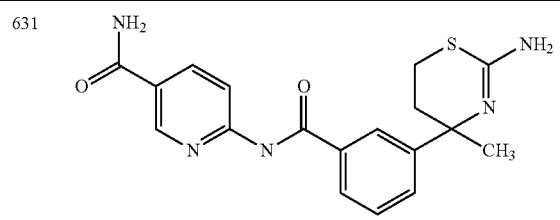
632 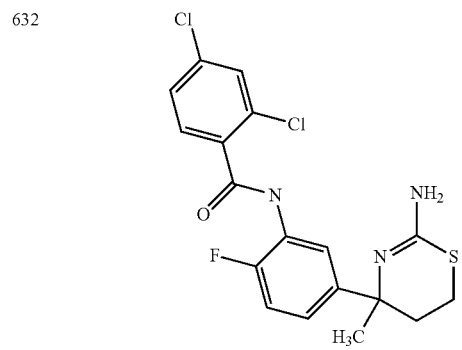
633 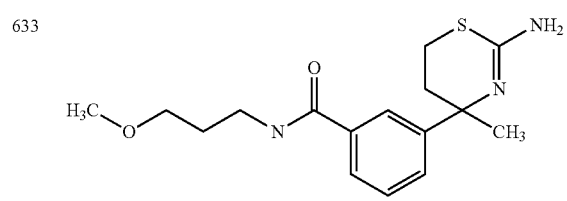
634 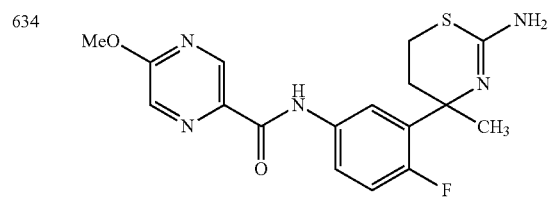
635 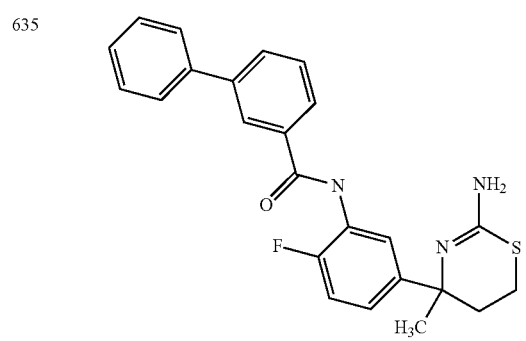
TABLE 67
636 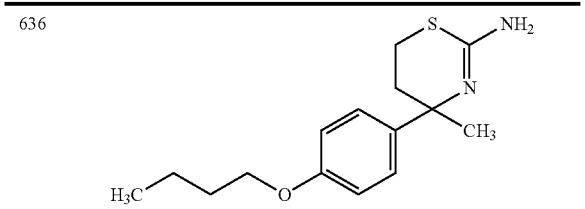
TABLE 67-continued
637 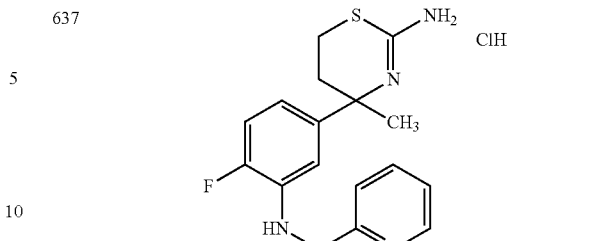
638 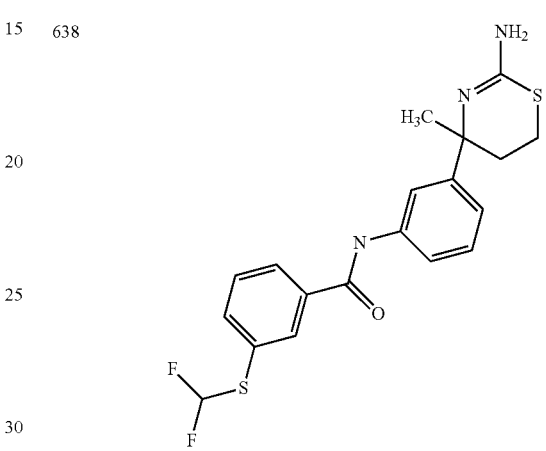
639 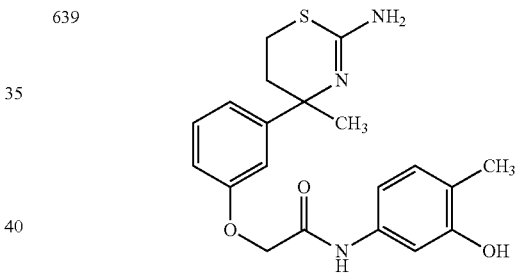
640 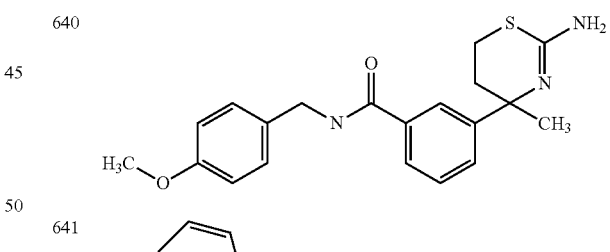
641 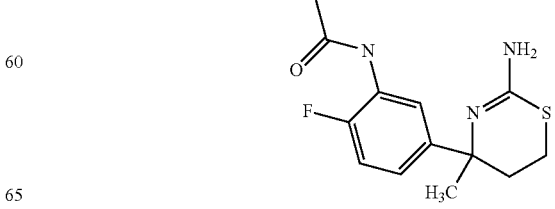

TABLE 67-continued
642 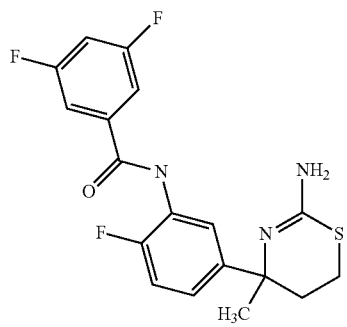 [SMILES: CC1(c2ccc(F)c(NC(=O)c3cc(F)cc(F)c3)c2)CCSC(N)=N1]
643 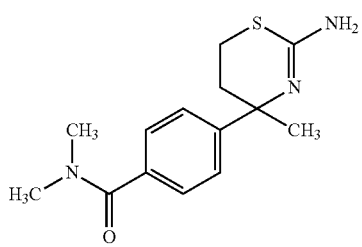
TABLE 68
644 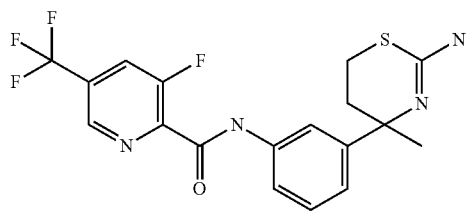 [SMILES: CC1(c2cccc(NC(=O)c3ncc(C(F)(F)F)cc3F)c2)CCSC(N)=N1]
645 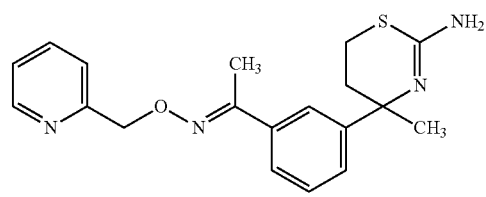 [SMILES: C/C(=N\OCc1ccccn1)c1cccc(C2(C)CCSC(N)=N2)c1]
646 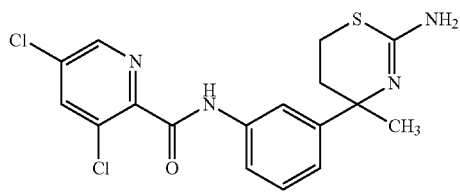 [SMILES: CC1(c2cccc(NC(=O)c3ncc(Cl)cc3Cl)c2)CCSC(N)=N1]
647 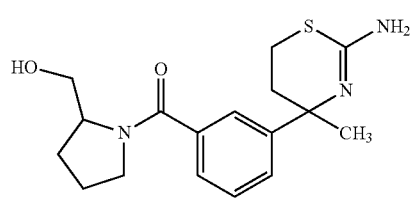 [SMILES: CC1(c2cccc(C(=O)N3CCCC3CO)c2)CCSC(N)=N1]
TABLE 68-continued
648 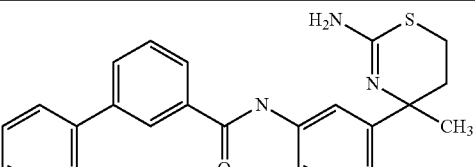
649 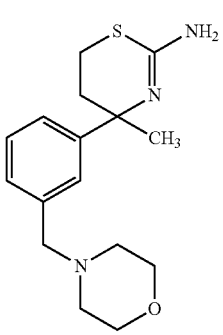 [SMILES: CC1(c2cccc(CN3CCOCC3)c2)CCSC(N)=N1]
650 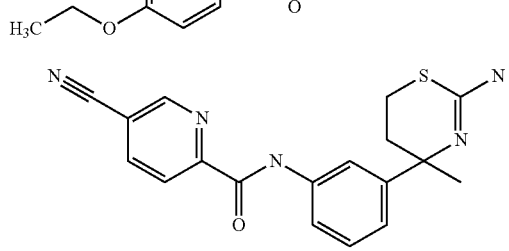
651 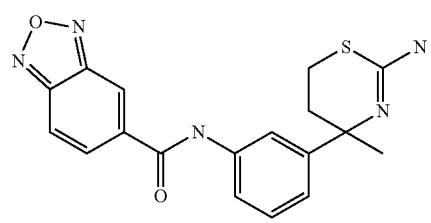 [SMILES: CC1(c2cccc(NC(=O)c3ccc4nonc4c3)c2)CCSC(N)=N1]
652 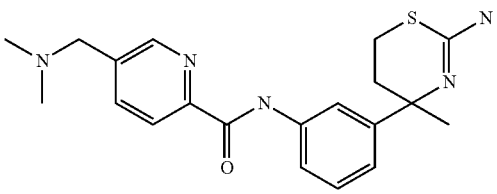 [SMILES: CN(C)Cc1ccc(C(=O)Nc2cccc(C3(C)CCSC(N)=N3)c2)nc1]
653 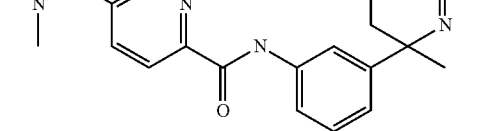
654 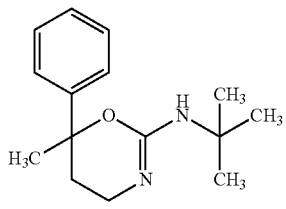

TABLE 68-continued
| 655 | 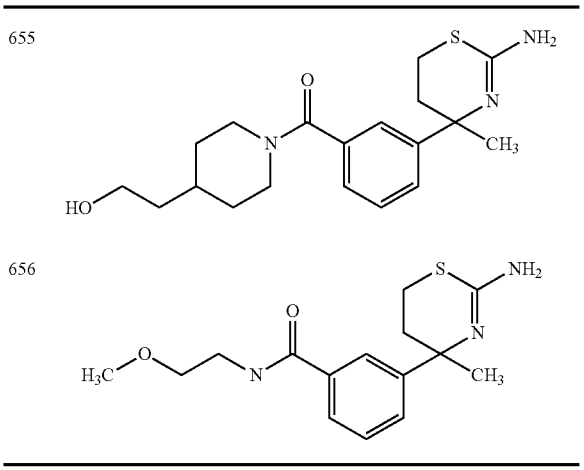 |
| --- | --- |
| 656 | |
TABLE 69
| 657 | 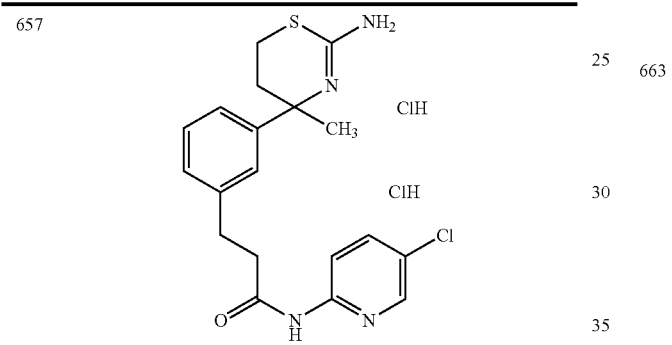 |
| --- | --- |
| 658 | 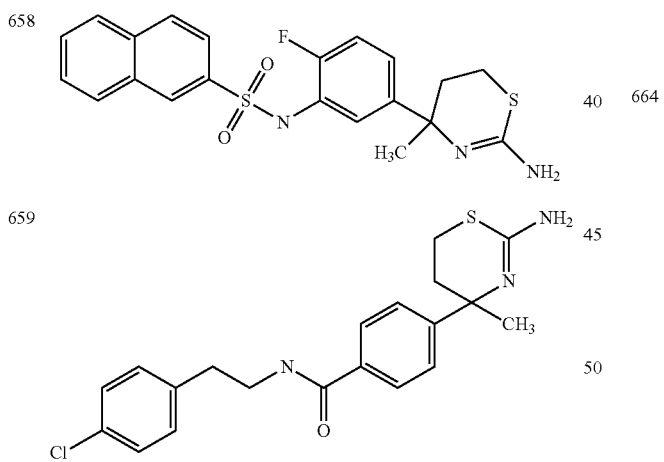 |
| 659 | |
| 660 | 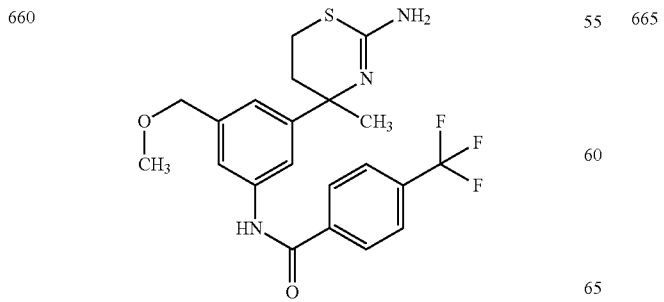 |
TABLE 69-continued
| 661 | 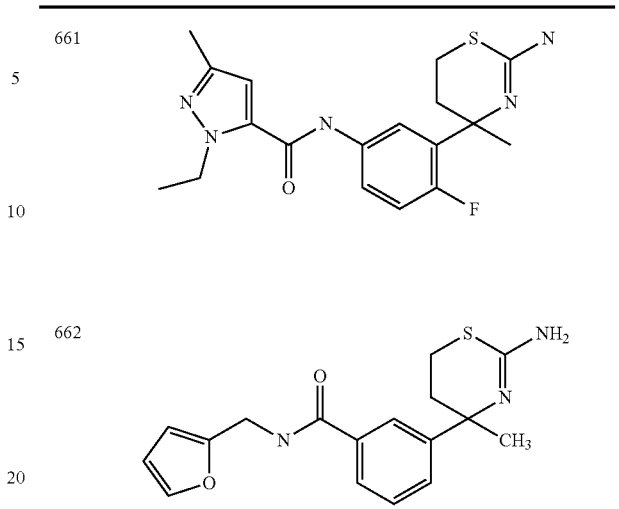 |
| --- | --- |
| 662 | |
| 663 | 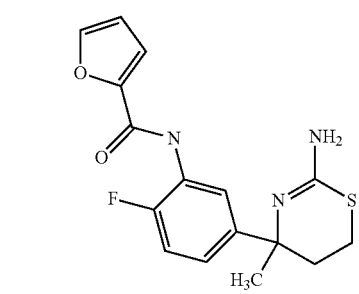 [SMILES: CC1(c2ccc(F)c(NC(=O)c3ccco3)c2)CCSC(N)=N1] |
| 664 | 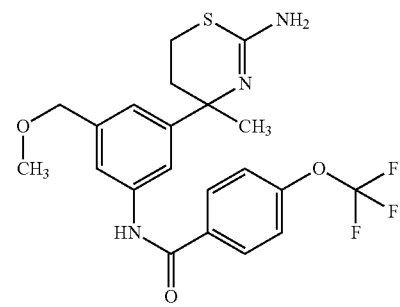 [SMILES: COCc1cc(NC(=O)c2ccc(OC(F)(F)F)cc2)cc(C2(C)CCSC(N)=N2)c1] |
| 665 | 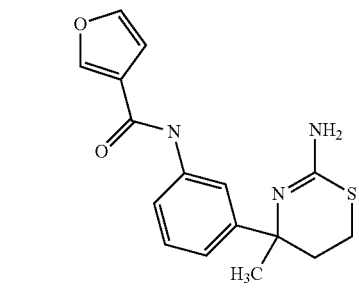 [SMILES: CC1(c2cccc(NC(=O)c3ccoc3)c2)CCSC(N)=N1] |

TABLE 70
666 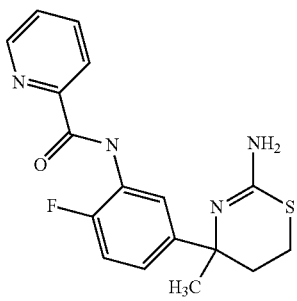 [SMILES: CC1(c2ccc(F)c(NC(=O)c3ccccn3)c2)CCSC(N)=N1]
667 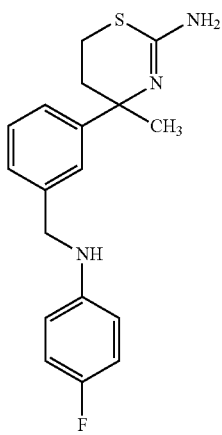
668 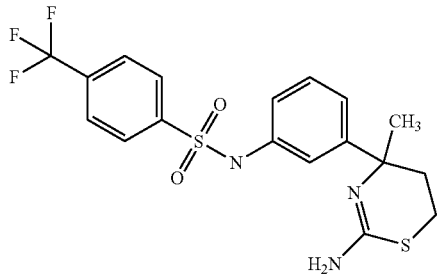 [SMILES: CC1(c2cccc(NS(=O)(=O)c3ccc(C(F)(F)F)cc3)c2)CCSC(N)=N1]
669 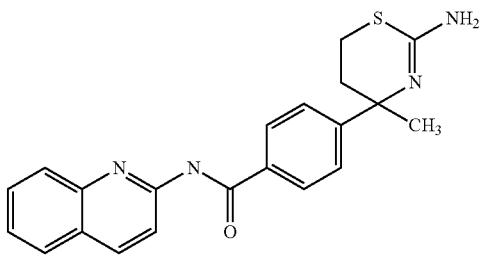 [SMILES: CC1(c2ccc(C(=O)Nc3ccc4ccccc4n3)cc2)CCSC(N)=N1]
670 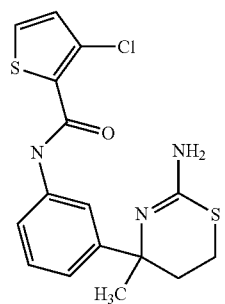 [SMILES: CC1(c2cccc(NC(=O)c3sccc3Cl)c2)CCSC(N)=N1]
TABLE 70-continued
671 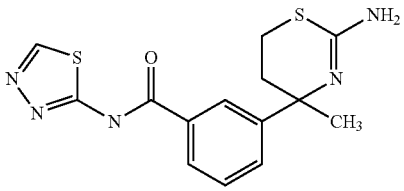 [SMILES: CC1(c2cccc(C(=O)Nc3nncs3)c2)CCSC(N)=N1]
672 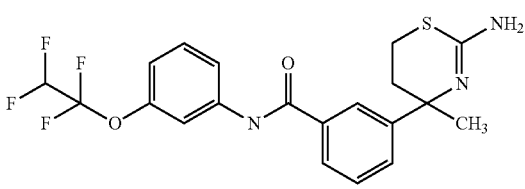 [SMILES: CC1(c2cccc(C(=O)Nc3cccc(OC(F)(F)C(F)F)c3)c2)CCSC(N)=N1]
673 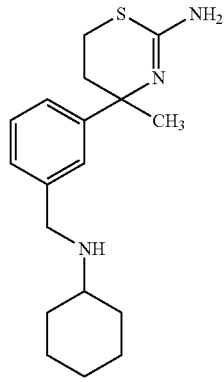 [SMILES: CC1(c2cccc(CNC3CCCCC3)c2)CCSC(N)=N1]
674 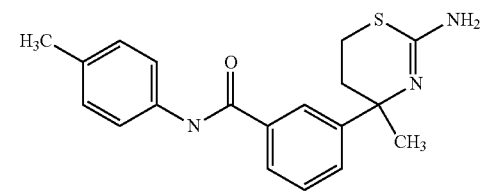 [SMILES: Cc1ccc(NC(=O)c2cccc(C3(C)CCSC(N)=N3)c2)cc1]
TABLE 71
675 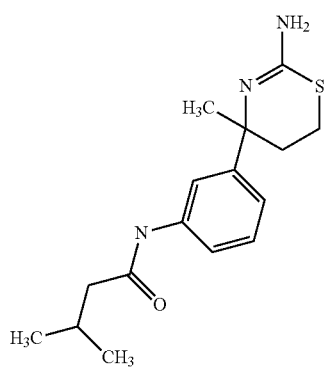 [SMILES: CC(C)CC(=O)Nc1cccc(C2(C)CCSC(N)=N2)c1]

TABLE 71-continued
676 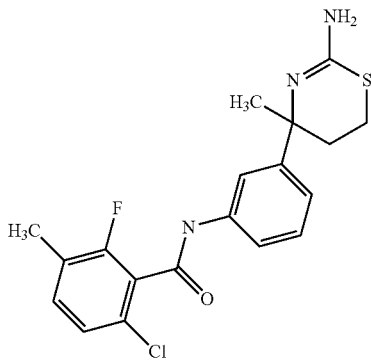 [SMILES: Cc1ccc(Cl)c(C(=O)Nc2cccc(C3(C)CCSC(N)=N3)c2)c1F]
677 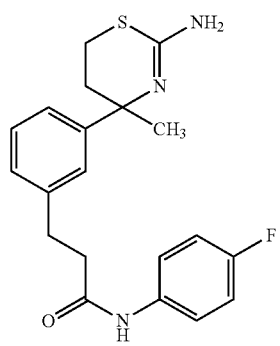 [SMILES: CC1(c2cccc(CCC(=O)Nc3ccc(F)cc3)c2)CCSC(N)=N1]
678 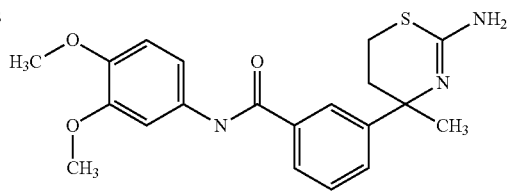
679 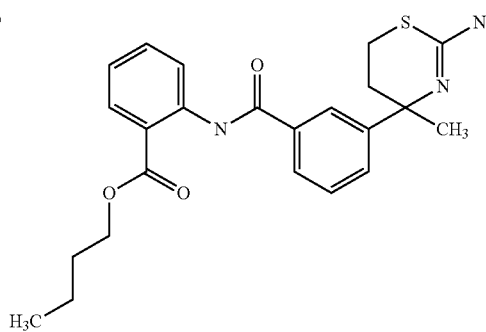
680 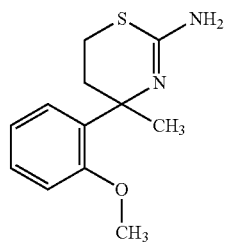 [SMILES: COc1ccccc1C1(C)CCSC(N)=N1]
TABLE 71-continued
681 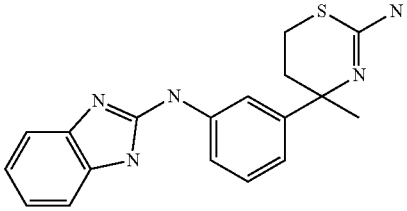 [SMILES: CC1(c2cccc(Nc3nc4ccccc4[nH]3)c2)CCSC(N)=N1]
682 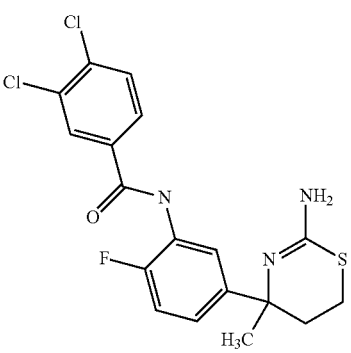 [SMILES: CC1(c2ccc(F)c(NC(=O)c3ccc(Cl)c(Cl)c3)c2)CCSC(N)=N1]
683 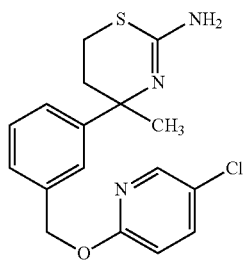 [SMILES: CC1(c2cccc(COc3ccc(Cl)cn3)c2)CCSC(N)=N1]
TABLE 72
684 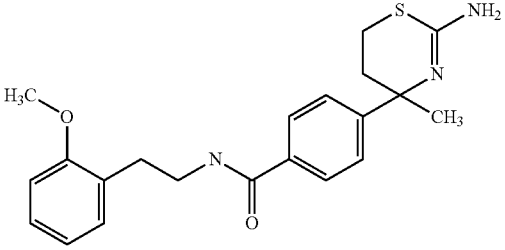 [SMILES: COc1ccccc1CCNC(=O)c1ccc(C2(C)CCSC(N)=N2)cc1]
685 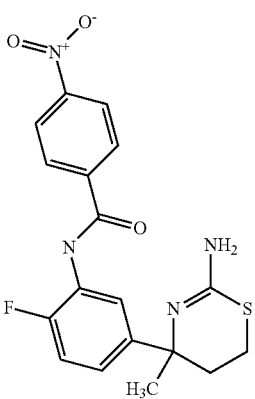 [SMILES: CC1(c2ccc(F)c(NC(=O)c3ccc([N+](=O)[O-])cc3)c2)CCSC(N)=N1]

TABLE 72-continued
686 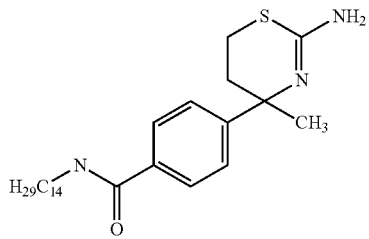
687 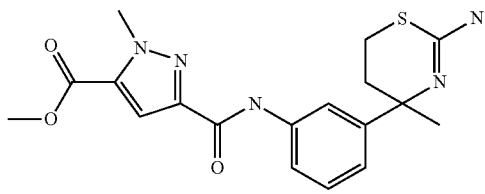 [SMILES: COC(=O)c1cc(C(=O)Nc2cccc(C3(C)CCSC(N)=N3)c2)nn1C]
688 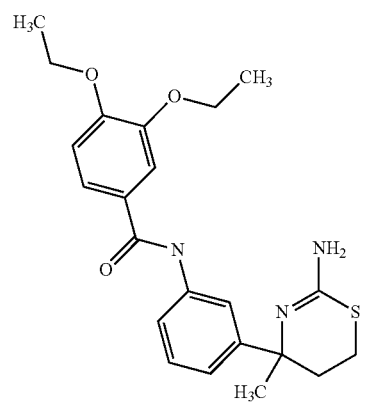 [SMILES: CCOc1ccc(C(=O)Nc2cccc(C3(C)CCSC(N)=N3)c2)cc1OCC]
689 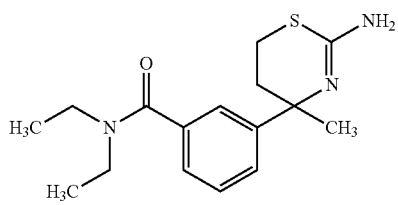 [SMILES: CCN(CC)C(=O)c1cccc(C2(C)CCSC(N)=N2)c1]
690 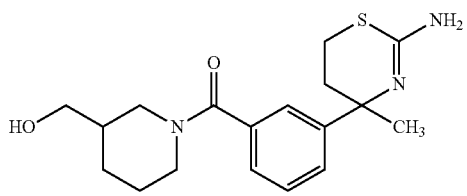 [SMILES: CC1(c2cccc(C(=O)N3CCCC(CO)C3)c2)CCSC(N)=N1]
691 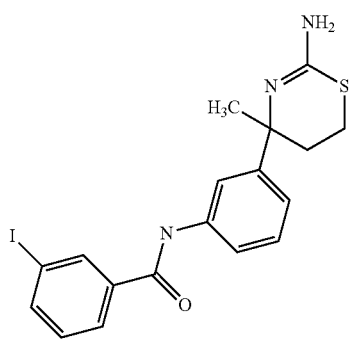 [SMILES: CC1(c2cccc(NC(=O)c3cccc(I)c3)c2)CCSC(N)=N1]
TABLE 72-continued
692 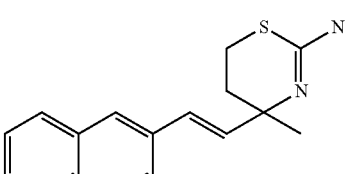
TABLE 73
693 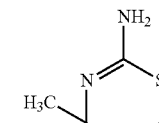
694 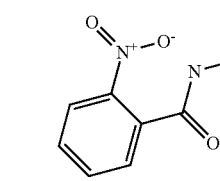
695 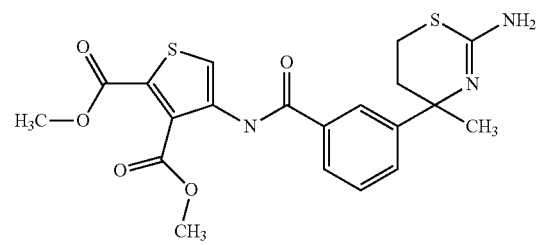 [SMILES: COC(=O)c1scc(NC(=O)c2cccc(C3(C)CCSC(N)=N3)c2)c1C(=O)OC]
696 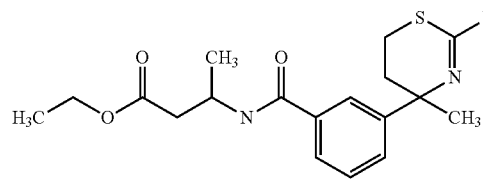
697 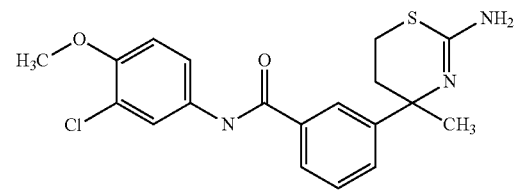 [SMILES: COc1ccc(NC(=O)c2cccc(C3(C)CCSC(N)=N3)c2)cc1Cl]

TABLE 73-continued
698 699 700 701 702
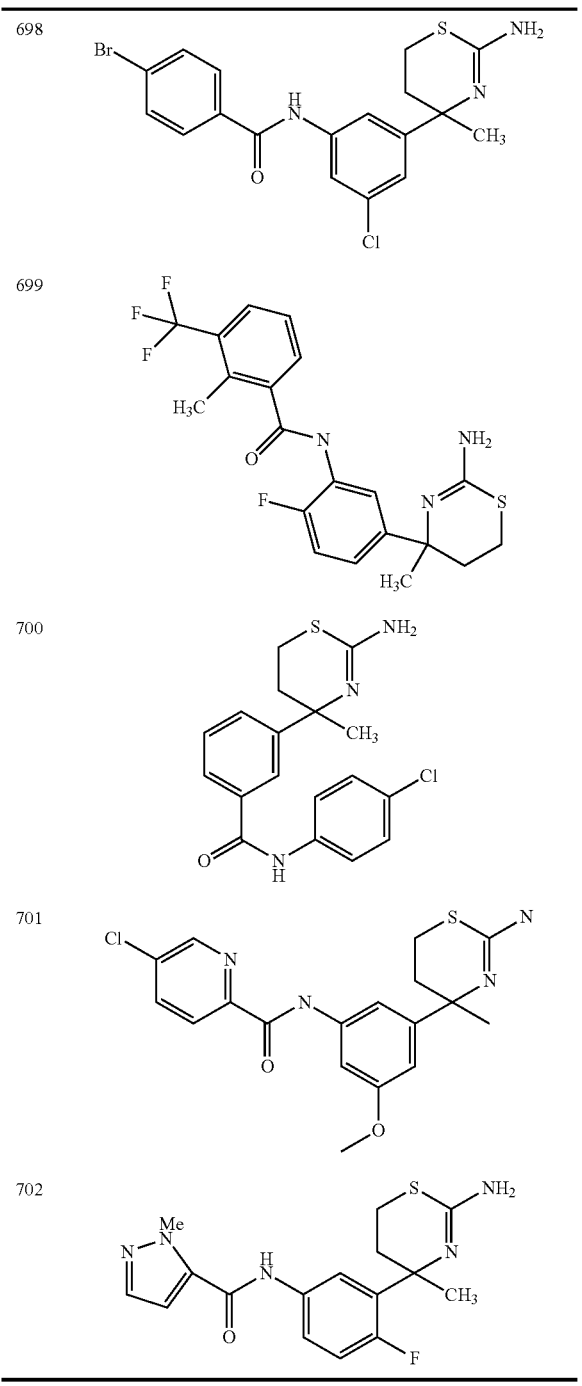
TABLE 74
703
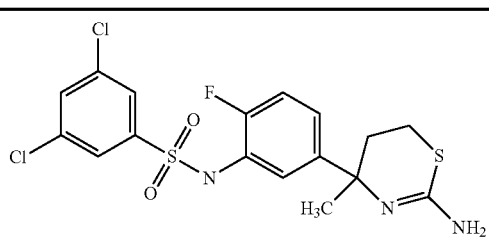
TABLE 74-continued
704 705 706 707 708 709
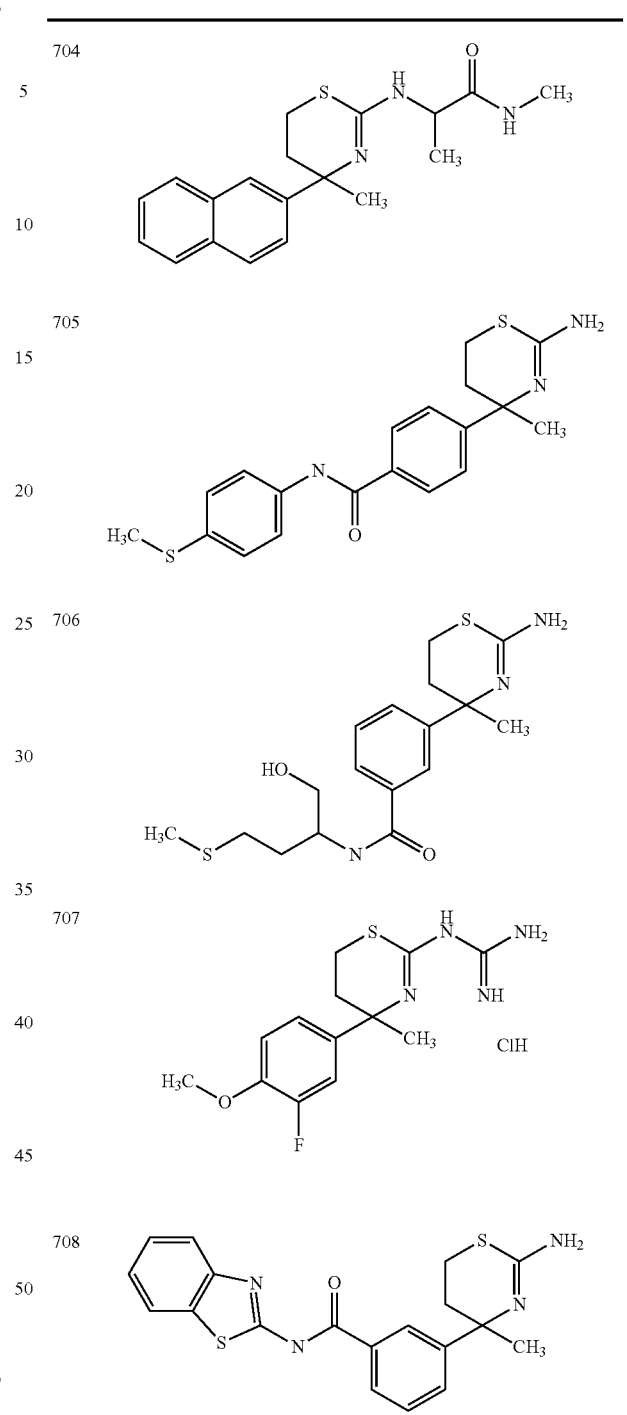

TABLE 74-continued
710 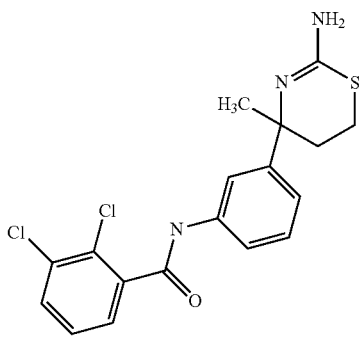 [SMILES: CC1(c2cccc(NC(=O)c3cccc(Cl)c3Cl)c2)CCSC(N)=N1]
711 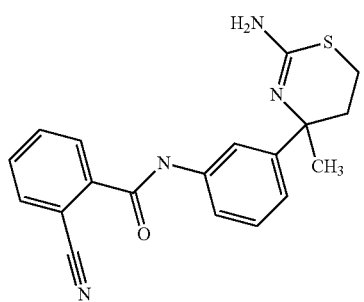 [SMILES: CC1(c2cccc(NC(=O)c3ccccc3C#N)c2)CCSC(N)=N1]
712 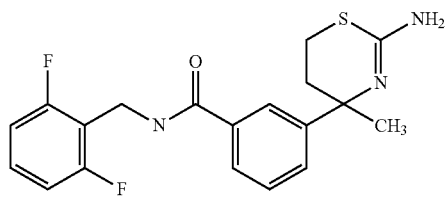 [SMILES: CC1(c2cccc(C(=O)NCc3c(F)cccc3F)c2)CCSC(N)=N1]
TABLE 75
713 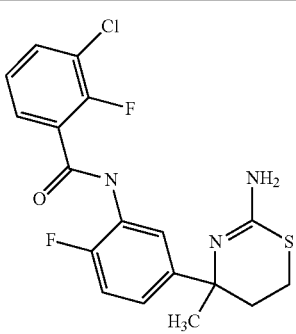 [SMILES: CC1(c2ccc(F)c(NC(=O)c3cccc(Cl)c3F)c2)CCSC(N)=N1]
714 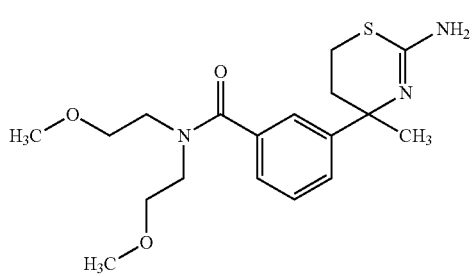 [SMILES: COCCN(CCOC)C(=O)c1cccc(C2(C)CCSC(N)=N2)c1]
TABLE 75-continued
715 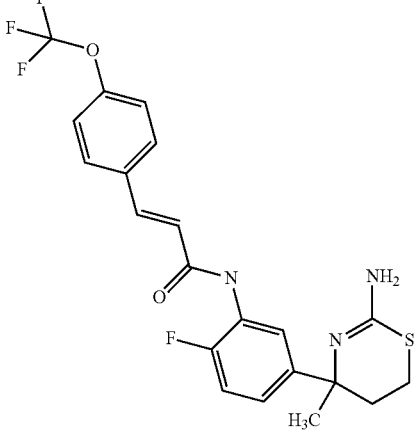
716
717
718 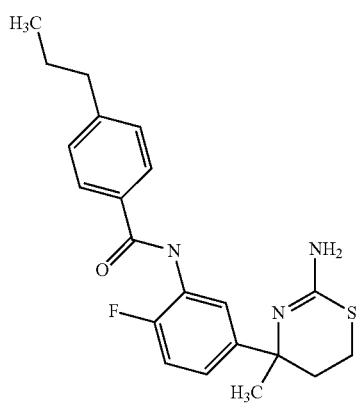 [SMILES: CCCc1ccc(C(=O)Nc2cc(C3(C)CCSC(N)=N3)ccc2F)cc1]
719 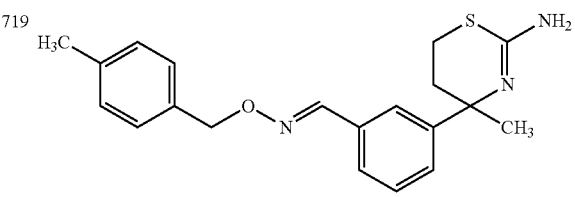

TABLE 76
720 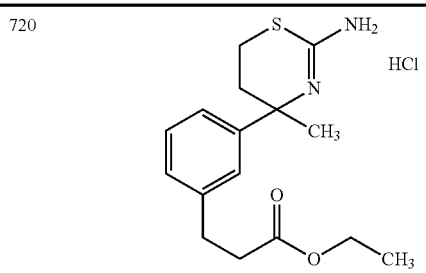
721 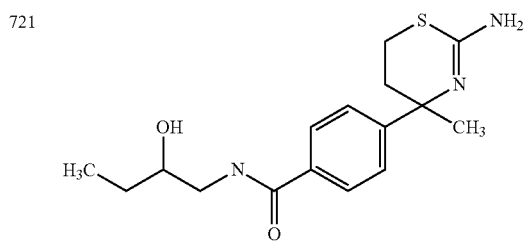
722 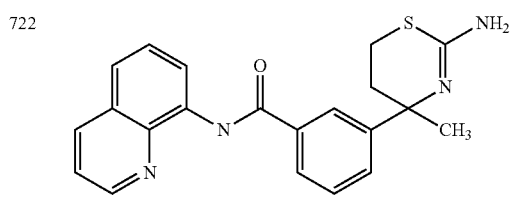
723 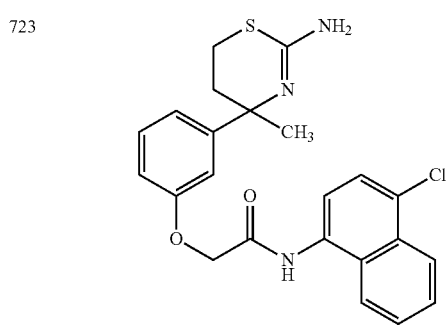
724 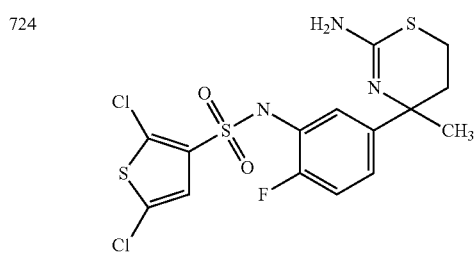
725 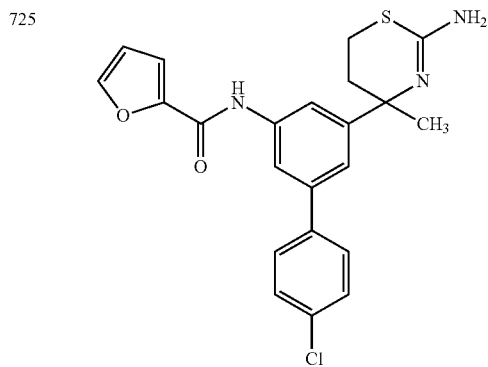
TABLE 76-continued
726 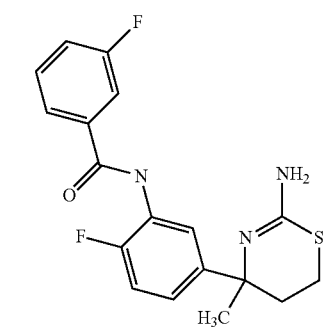
727 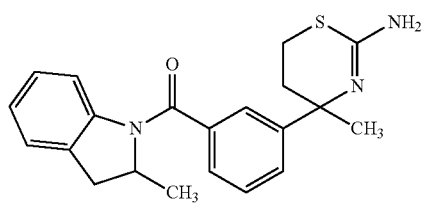
728 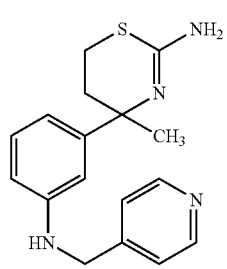 [SMILES: CC1(c2cccc(NCc3ccncc3)c2)CCSC(N)=N1]
729 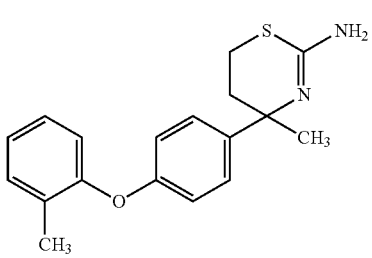 [SMILES: Cc1ccccc1Oc1ccc(C2(C)CCSC(N)=N2)cc1]
TABLE 77
730 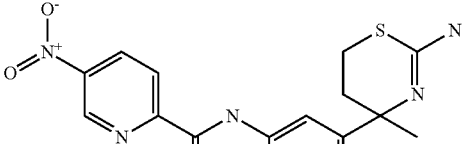
731 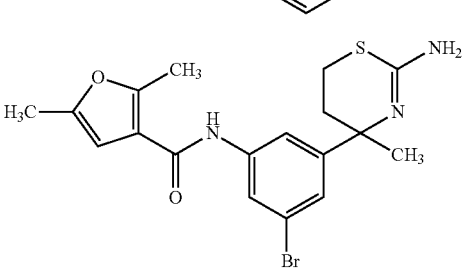

TABLE 77-continued
| | |
|---|---|
| 732 | 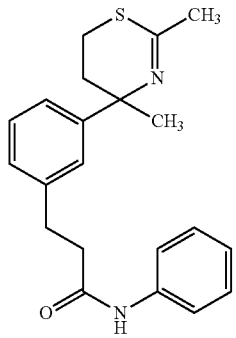 [SMILES: CC1=NC(C)(c2cccc(CCC(=O)Nc3ccccc3)c2)CCS1] |
| 734 | 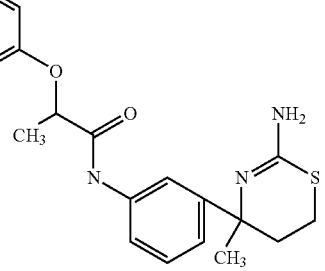 |
| 735 | 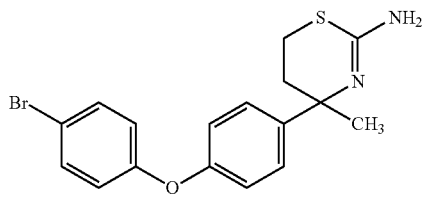 [SMILES: CC1(c2ccc(Oc3ccc(Br)cc3)cc2)CCSC(N)=N1] |
| 736 | 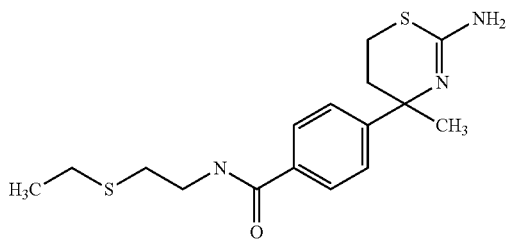 [SMILES: CCSCCNC(=O)c1ccc(C2(C)CCSC(N)=N2)cc1] |
| 737 | 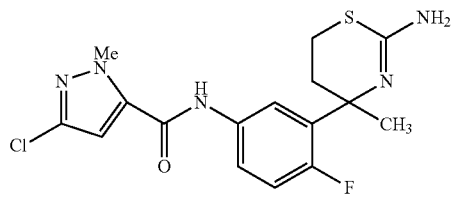 [SMILES: Cn1nc(Cl)cc1C(=O)Nc1ccc(F)c(C2(C)CCSC(N)=N2)c1] |
| 738 | 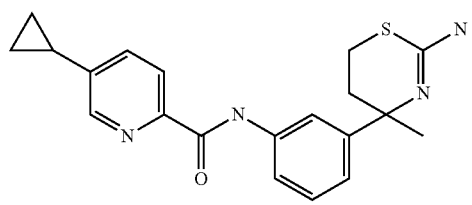 [SMILES: CC1(c2cccc(NC(=O)c3ccc(C4CC4)cn3)c2)CCSC(N)=N1] |
TABLE 77-continued
| | |
|---|---|
| 739 | 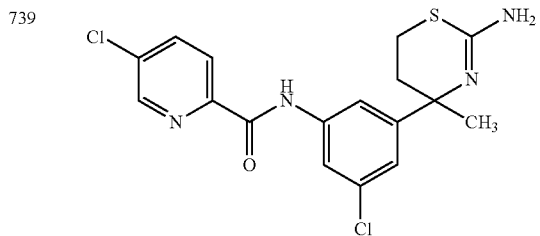 |
| 740 | 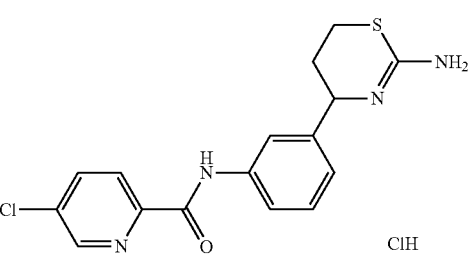 [SMILES: NC1=NC(c2cccc(NC(=O)c3ccc(Cl)cn3)c2)CCS1 ; Cl] ClH |
TABLE 78
| | |
|---|---|
| 741 | 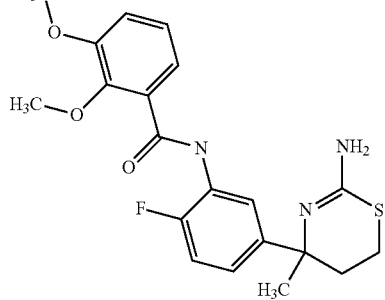 |
| 742 | 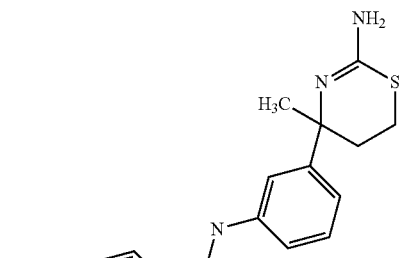 |
| 743 | 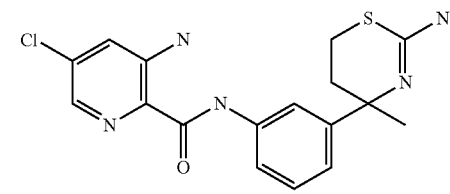 |
| 744 | 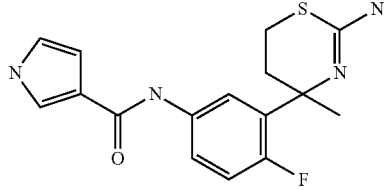 [SMILES: CC1(c2cc(NC(=O)c3cc[nH]c3)ccc2F)CCSC(N)=N1] |

TABLE 78-continued
745 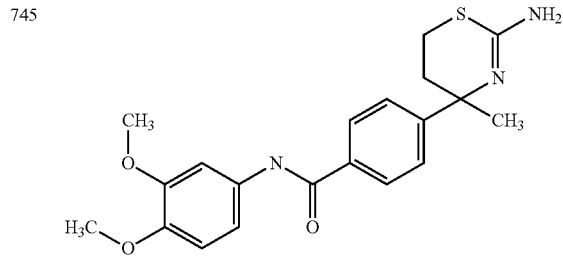
746 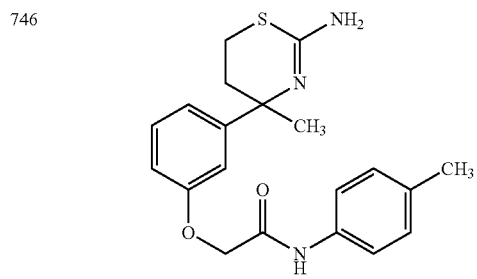
747 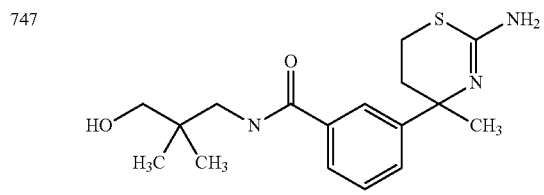
748 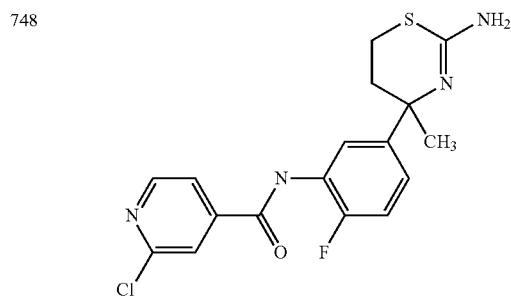
749 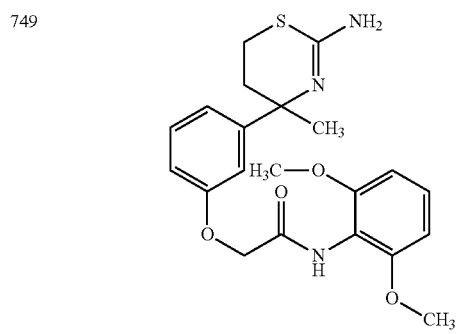
TABLE 79
750 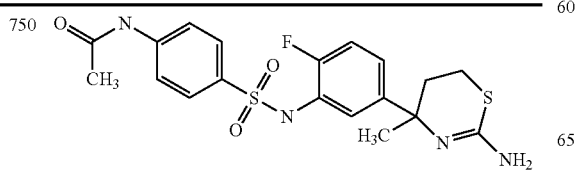
TABLE 79-continued
751 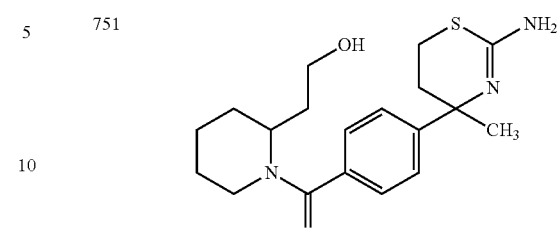
752 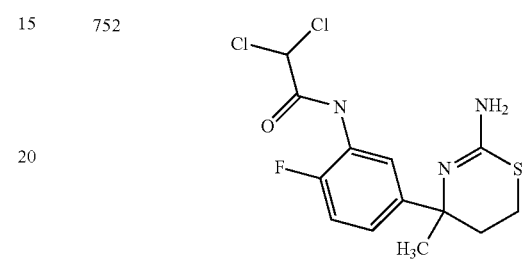
753 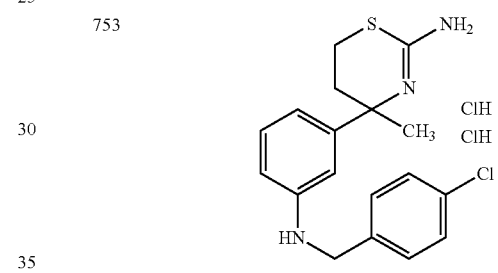
754 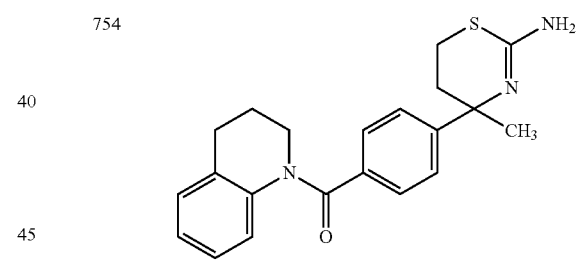
755 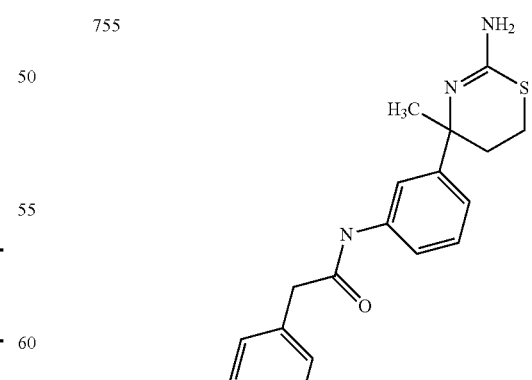

TABLE 79-continued
| | |
|---|---|
| 756 | 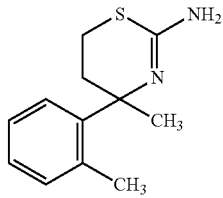 |
| 757 | 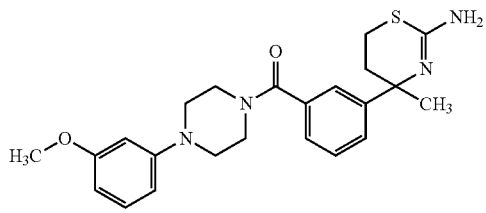 [SMILES: COc1cccc(N2CCN(C(=O)c3cccc(C4(C)CCSC(N)=N4)c3)CC2)c1] |
| 758 | 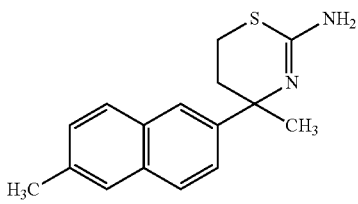 [SMILES: Cc1ccc2cc(C3(C)CCSC(N)=N3)ccc2c1] |
| 759 | 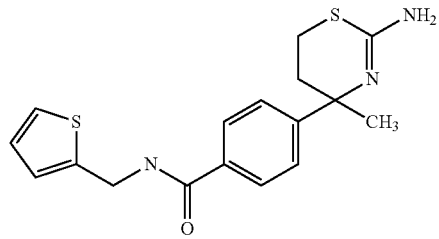 [SMILES: CC1(c2ccc(C(=O)NCc3cccs3)cc2)CCSC(N)=N1] |
TABLE 80
| | |
|---|---|
| 760 | 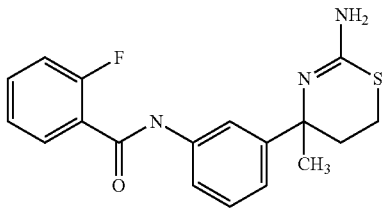 [SMILES: CC1(c2cccc(NC(=O)c3ccccc3F)c2)CCSC(N)=N1] |
| 761 | 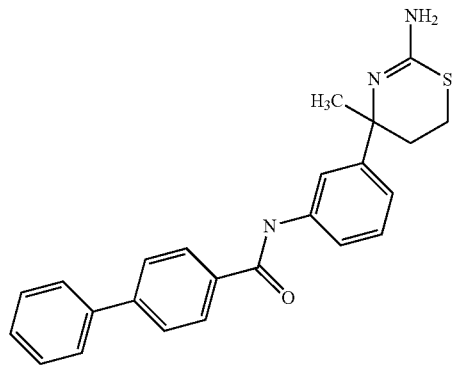 [SMILES: CC1(c2cccc(NC(=O)c3ccc(-c4ccccc4)cc3)c2)CCSC(N)=N1] |
TABLE 80-continued
| | |
|---|---|
| 762 | 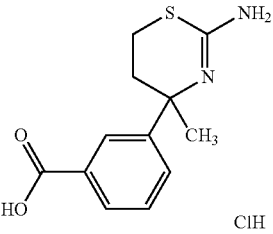 [SMILES: CC1(c2cccc(C(=O)O)c2)CCSC(N)=N1 ; Cl] |
| 763 | 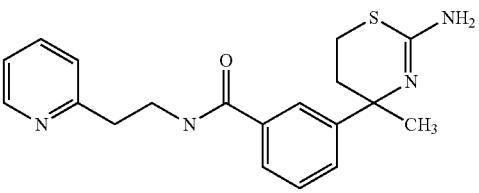 [SMILES: CC1(c2cccc(C(=O)NCCc3ccccn3)c2)CCSC(N)=N1] |
| 764 | 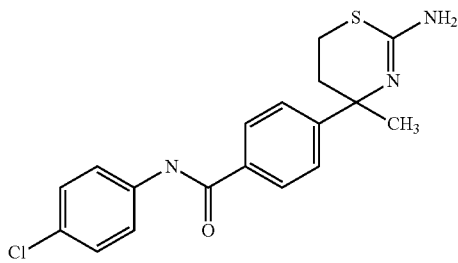 [SMILES: CC1(c2ccc(C(=O)Nc3ccc(Cl)cc3)cc2)CCSC(N)=N1] |
| 765 | 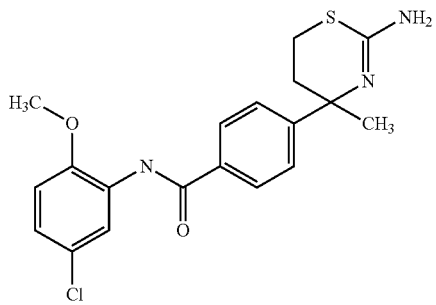 [SMILES: COc1ccc(Cl)cc1NC(=O)c1ccc(C2(C)CCSC(N)=N2)cc1] |
| 766 | 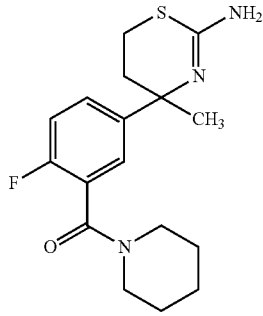 [SMILES: CC1(c2ccc(F)c(C(=O)N3CCCCC3)c2)CCSC(N)=N1] |
| 767 | 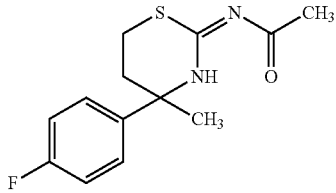 [SMILES: CC(=O)/N=C1\NC(C)(c2ccc(F)cc2)CCS1] |

TABLE 80-continued
768 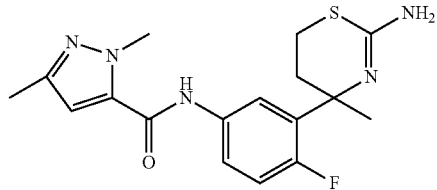 [SMILES: Cc1cc(C(=O)Nc2ccc(F)c(C3(C)CCSC(N)=N3)c2)n(C)n1]
769 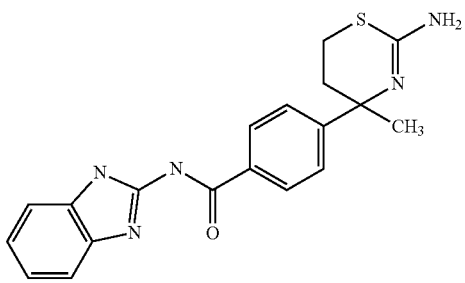
TABLE 81
770 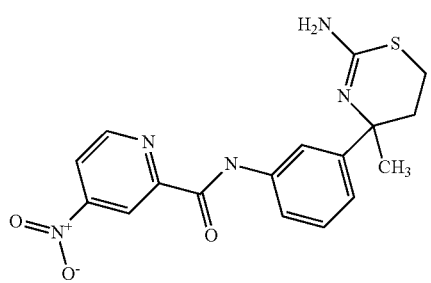 [SMILES: CC1(c2cccc(NC(=O)c3cc([N+](=O)[O-])ccn3)c2)CCSC(N)=N1]
771 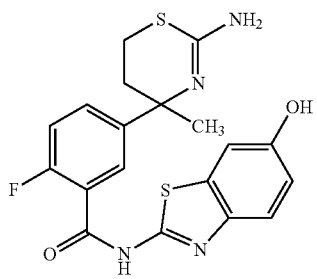 [SMILES: CC1(c2ccc(F)c(C(=O)Nc3nc4ccc(O)cc4s3)c2)CCSC(N)=N1]
772 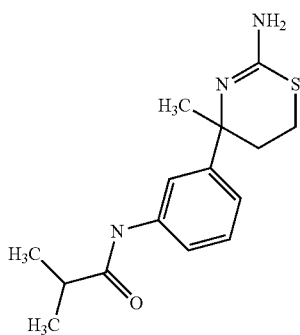 [SMILES: CC(C)C(=O)Nc1cccc(C2(C)CCSC(N)=N2)c1]
TABLE 81-continued
773 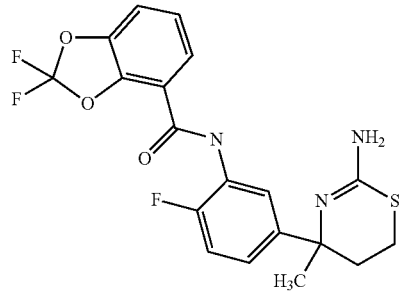
774 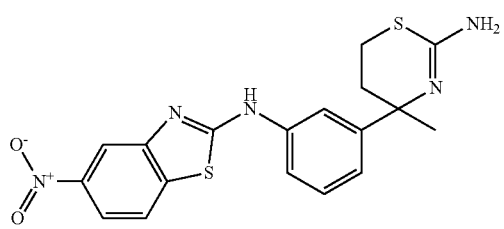 [SMILES: CC1(c2cccc(Nc3nc4cc([N+](=O)[O-])ccc4s3)c2)CCSC(N)=N1]
775 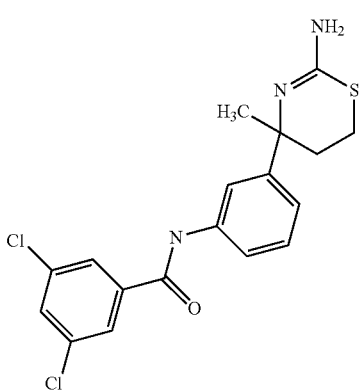 [SMILES: CC1(c2cccc(NC(=O)c3cc(Cl)cc(Cl)c3)c2)CCSC(N)=N1]
776 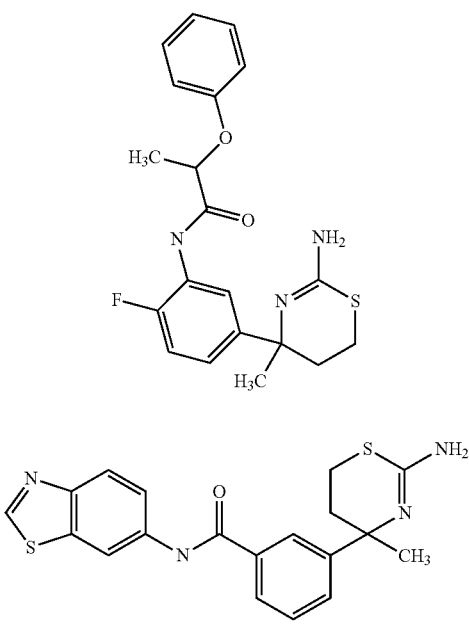
777 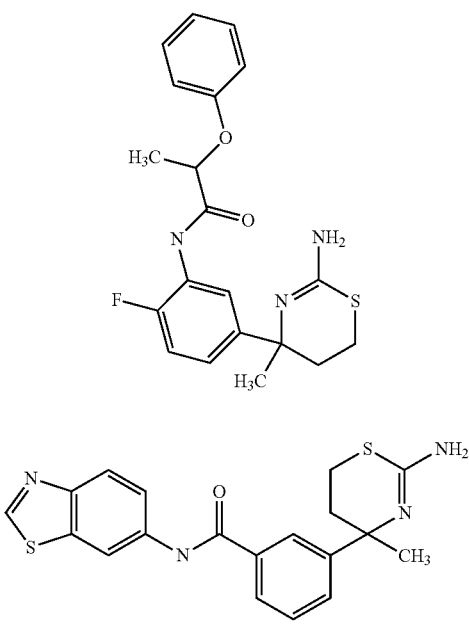

TABLE 82
| | |
|---|---|
| 778 | 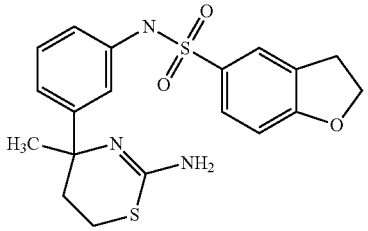 [SMILES: CC1(c2cccc(NS(=O)(=O)c3ccc4c(c3)CCO4)c2)CCSC(N)=N1] |
| 779 | 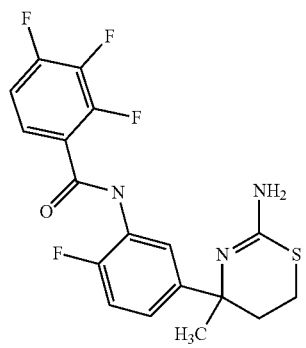 [SMILES: CC1(c2ccc(F)c(NC(=O)c3ccc(F)c(F)c3F)c2)CCSC(N)=N1] |
| 780 | 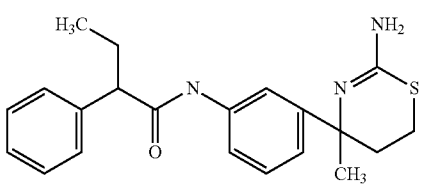 [SMILES: CCC(C(=O)Nc1cccc(C2(C)CCSC(N)=N2)c1)c1ccccc1] |
| 781 | 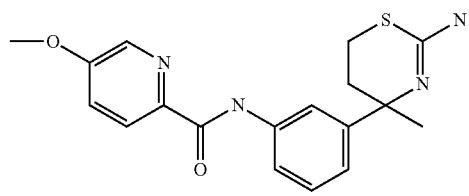 [SMILES: COc1ccc(C(=O)Nc2cccc(C3(C)CCSC(N)=N3)c2)nc1] |
| 782 | 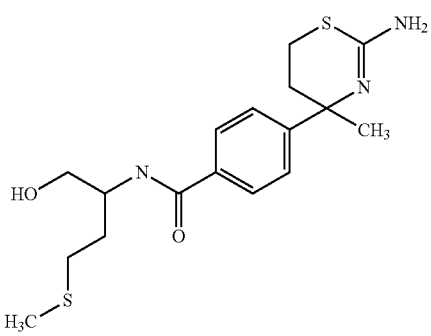 [SMILES: CSCCC(CO)NC(=O)c1ccc(C2(C)CCSC(N)=N2)cc1] |
| 783 | 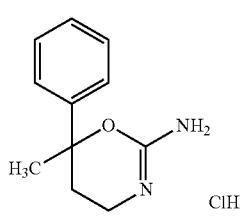 |
TABLE 82-continued
| | |
|---|---|
| 784 | 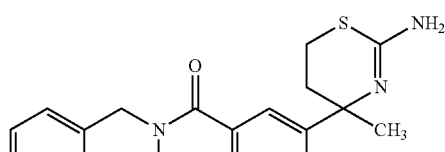 |
| 785 | 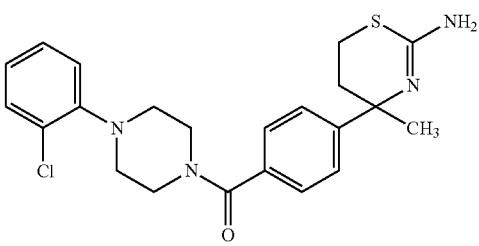 [SMILES: CC1(c2ccc(C(=O)N3CCN(c4ccccc4Cl)CC3)cc2)CCSC(N)=N1] |
| 786 | 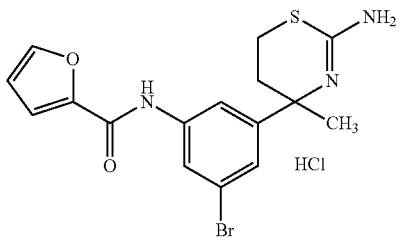 [SMILES: CC1(c2cc(Br)cc(NC(=O)c3ccco3)c2)CCSC(N)=N1 ; Cl] |
| 787 | 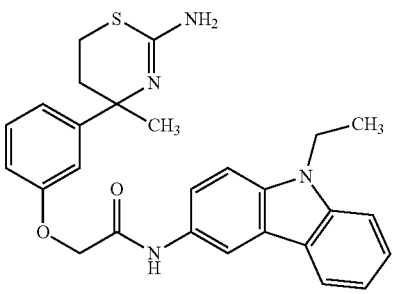 [SMILES: CCn1c2ccccc2c2cc(NC(=O)COc3cccc(C4(C)CCSC(N)=N4)c3)ccc21] |
| 788 | 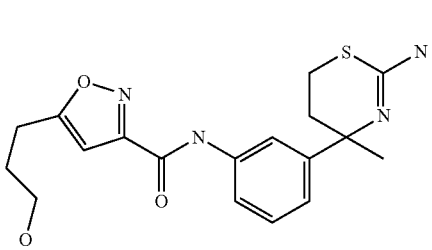 [SMILES: CC1(c2cccc(NC(=O)c3cc(CCCO)on3)c2)CCSC(N)=N1] |
| 789 | 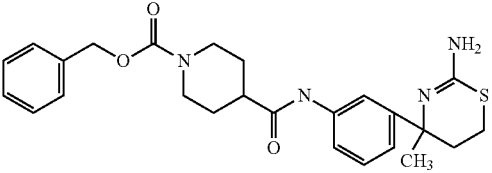 [SMILES: CC1(c2cccc(NC(=O)C3CCN(C(=O)OCc4ccccc4)CC3)c2)CCSC(N)=N1] |

TABLE 83
790 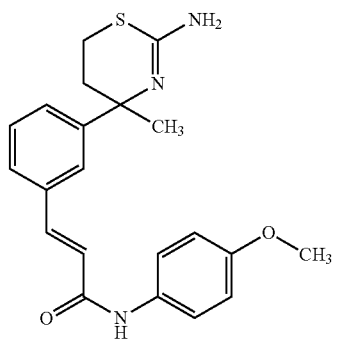 [SMILES: COc1ccc(NC(=O)/C=C/c2cccc(C3(C)CCSC(N)=N3)c2)cc1]
791 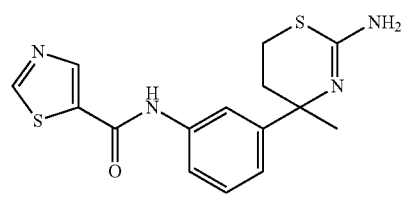 [SMILES: CC1(c2cccc(NC(=O)c3cncs3)c2)CCSC(N)=N1]
792 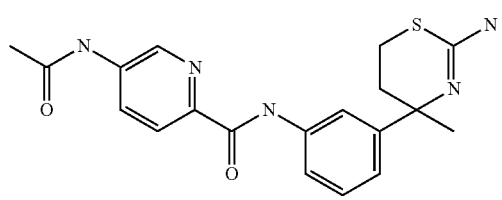 [SMILES: CC(=O)Nc1ccc(C(=O)Nc2cccc(C3(C)CCSC(N)=N3)c2)nc1]
793 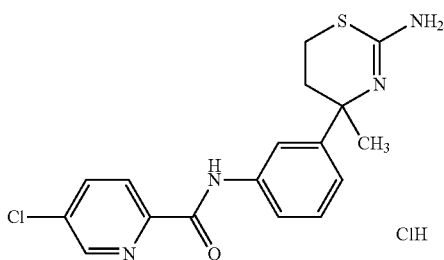 [SMILES: CC1(c2cccc(NC(=O)c3ccc(Cl)cn3)c2)CCSC(N)=N1 ; Cl]
794 
795 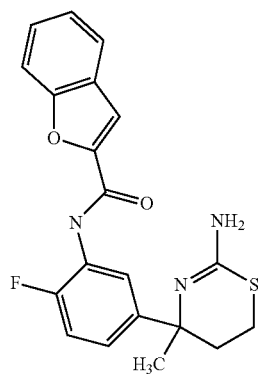
TABLE 83-continued
796 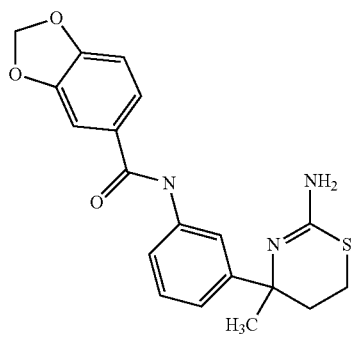 [SMILES: CC1(c2cccc(NC(=O)c3ccc4c(c3)OCO4)c2)CCSC(N)=N1]
797 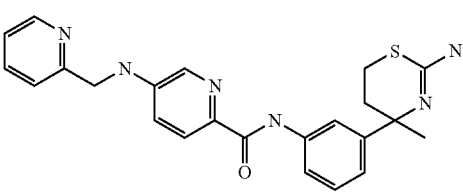 [SMILES: CC1(c2cccc(NC(=O)c3ccc(NCc4ccccn4)cn3)c2)CCSC(N)=N1]
798 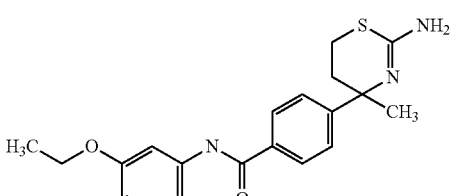
TABLE 84
799 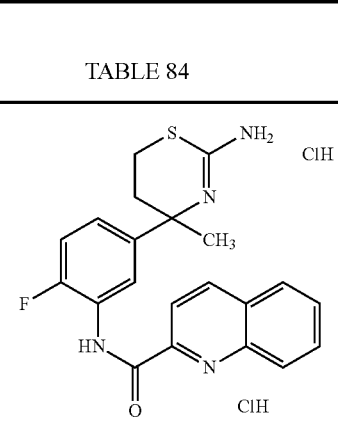
800 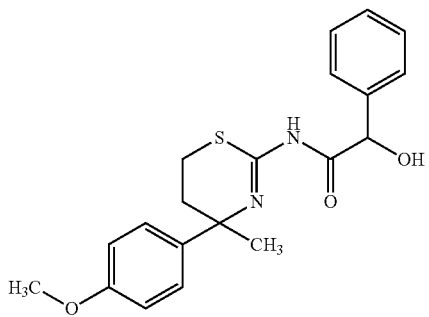 [SMILES: COc1ccc(C2(C)CCSC(NC(=O)C(O)c3ccccc3)=N2)cc1]

TABLE 84-continued
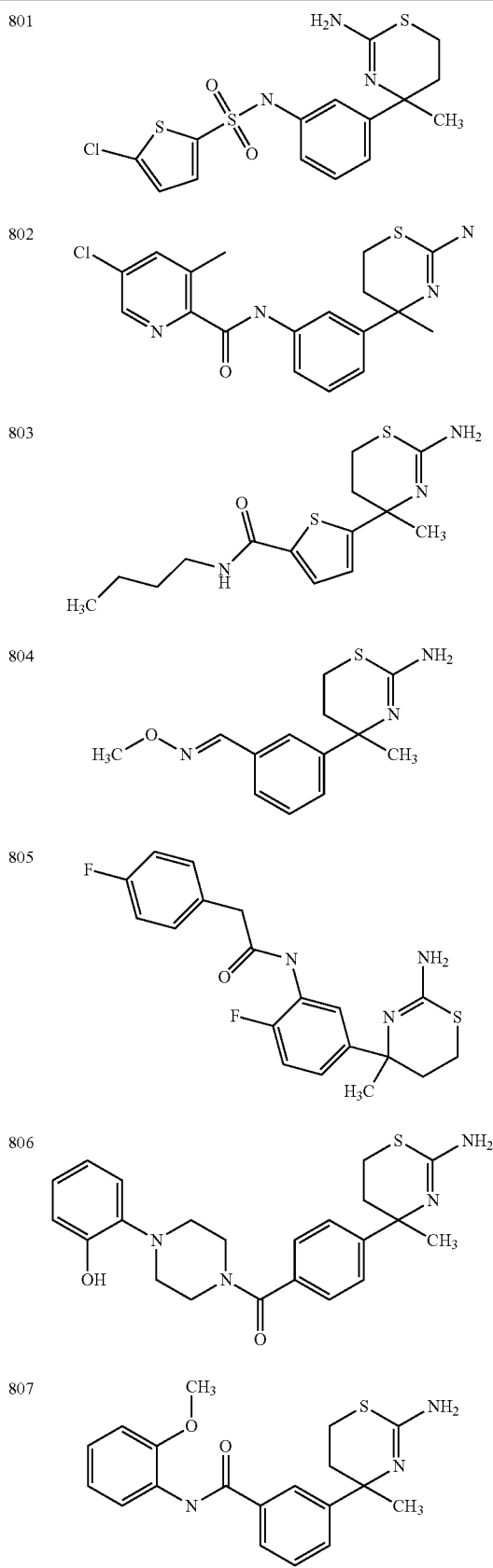
TABLE 84-continued
TABLE 85
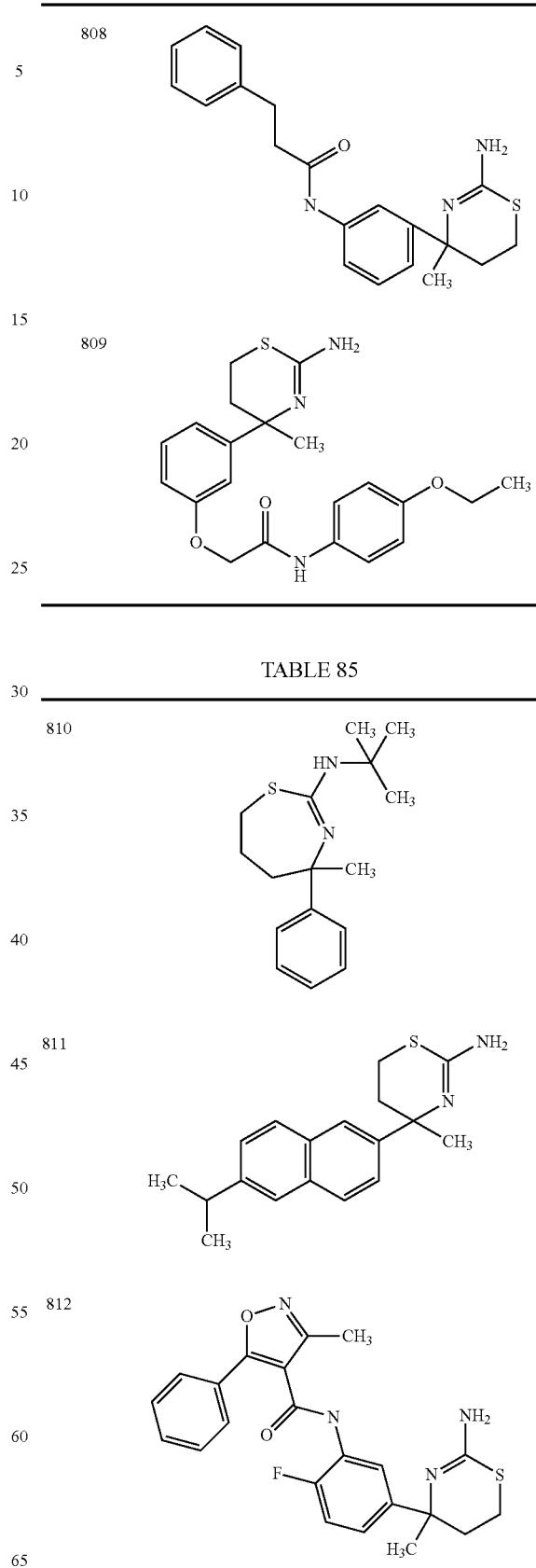

231
TABLE 85-continued
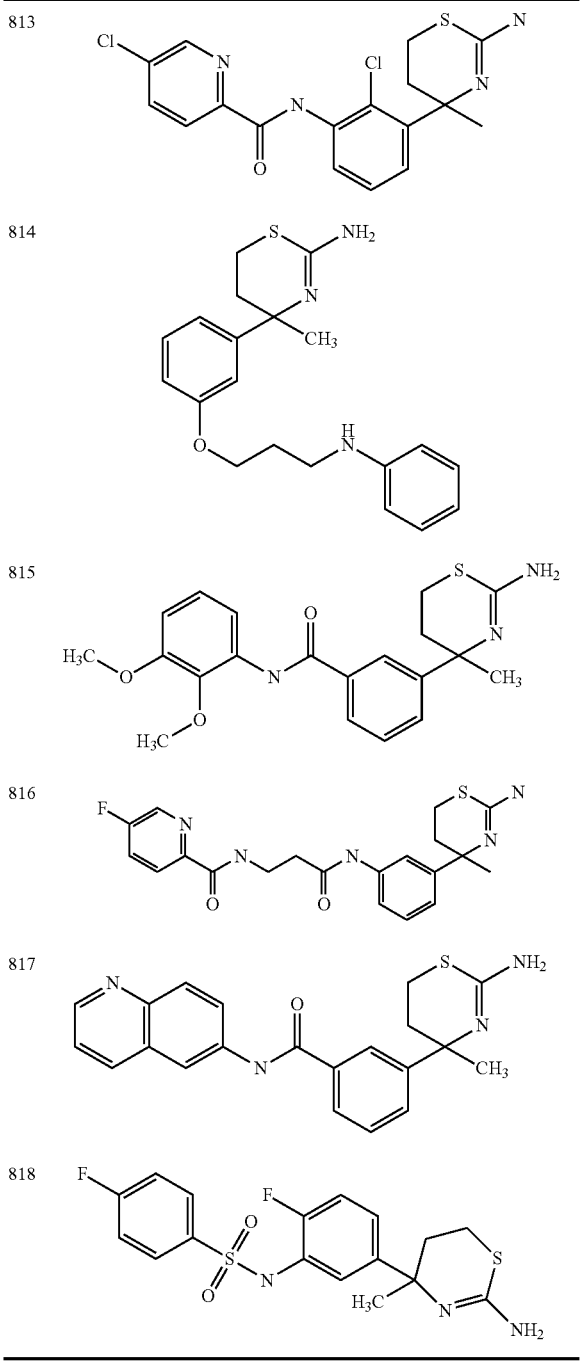
TABLE 86
232
TABLE 86-continued
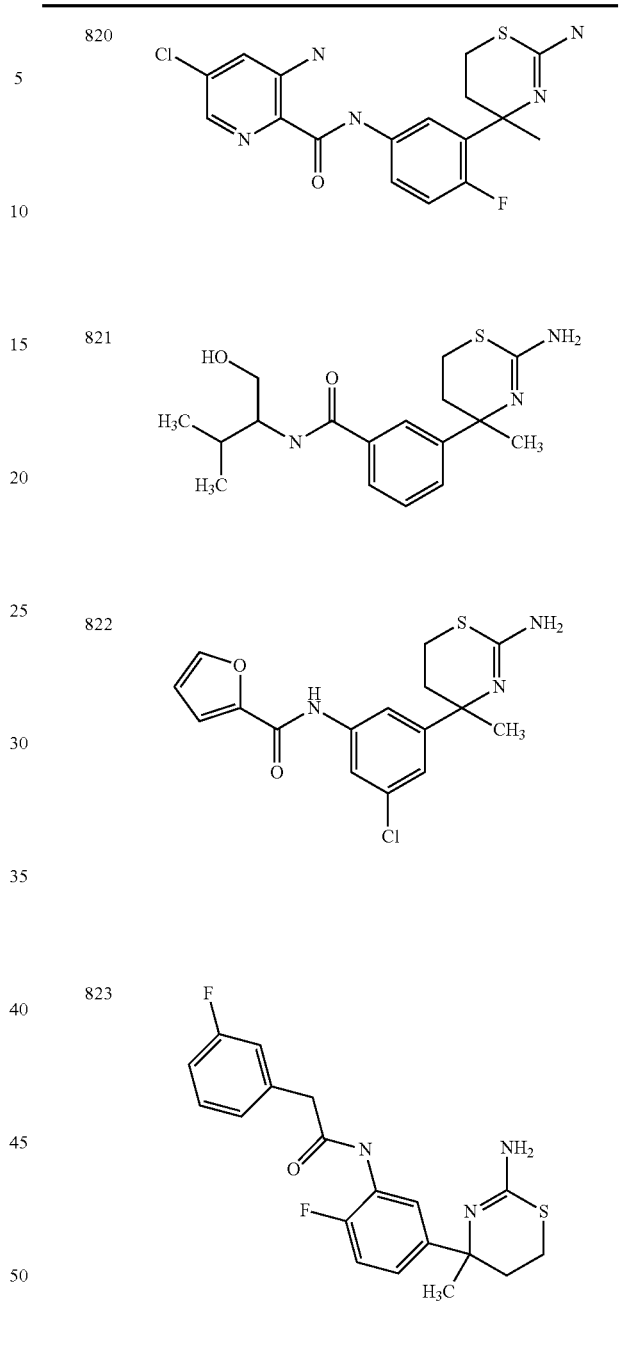

TABLE 86-continued
825 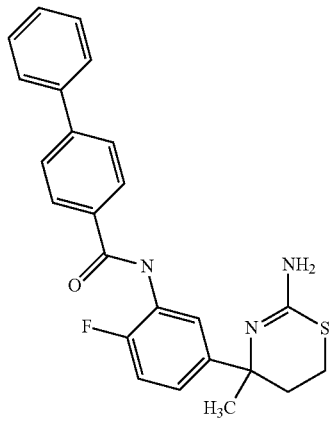 [SMILES: CC1(c2ccc(F)c(NC(=O)c3ccc(-c4ccccc4)cc3)c2)CCSC(N)=N1]
826 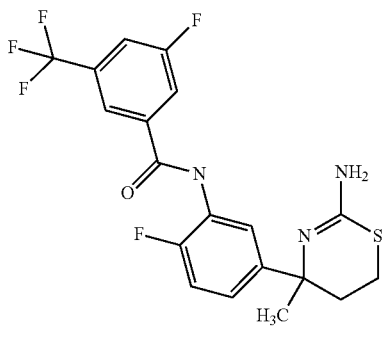 [SMILES: CC1(c2ccc(F)c(NC(=O)c3cc(F)cc(C(F)(F)F)c3)c2)CCSC(N)=N1]
827 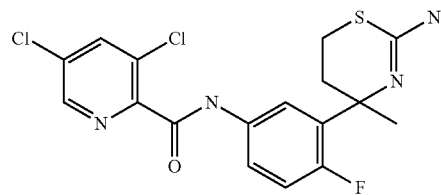 [SMILES: CC1(c2cc(NC(=O)c3ncc(Cl)cc3Cl)ccc2F)CCSC(N)=N1]
TABLE 87
828 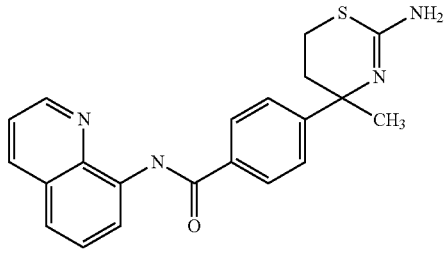 [SMILES: CC1(c2ccc(C(=O)Nc3cccc4cccnc34)cc2)CCSC(N)=N1]
829 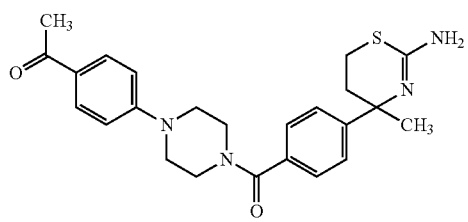 [SMILES: CC(=O)c1ccc(N2CCN(C(=O)c3ccc(C4(C)CCSC(N)=N4)cc3)CC2)cc1]
TABLE 87-continued
830 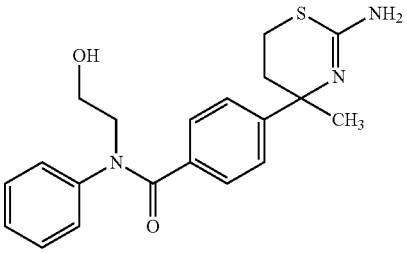 [SMILES: CC1(c2ccc(C(=O)N(CCO)c3ccccc3)cc2)CCSC(N)=N1]
831 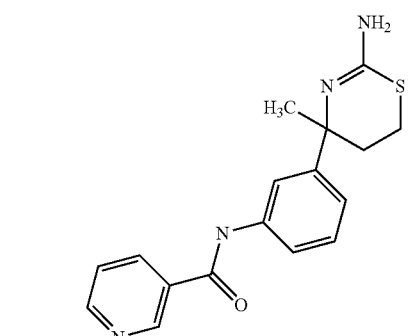
832 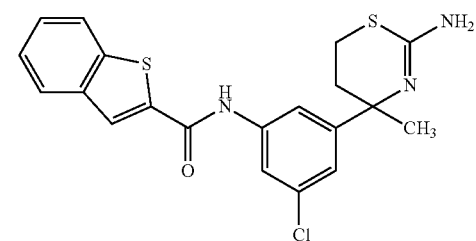 [SMILES: CC1(c2cc(Cl)cc(NC(=O)c3cc4ccccc4s3)c2)CCSC(N)=N1]
833 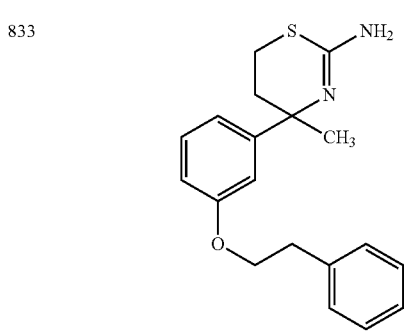
834 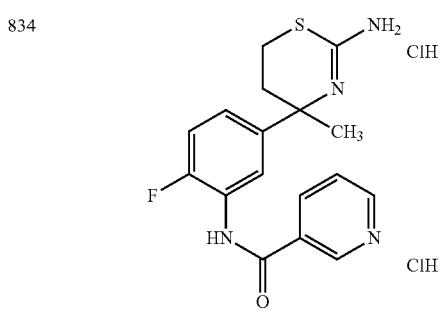

TABLE 87-continued
835 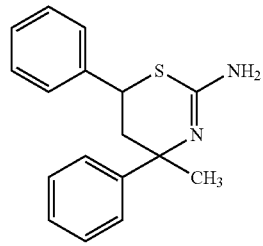 [SMILES: CC1(c2ccccc2)CC(c2ccccc2)SC(N)=N1]
836 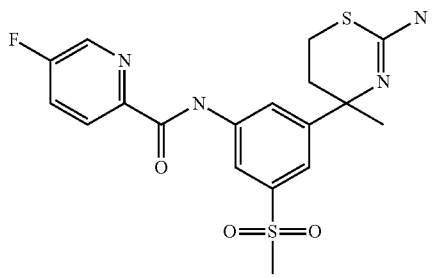 [SMILES: CC1(c2cc(NC(=O)c3ccc(F)cn3)cc(S(C)(=O)=O)c2)CCSC(N)=N1]
TABLE 88
837 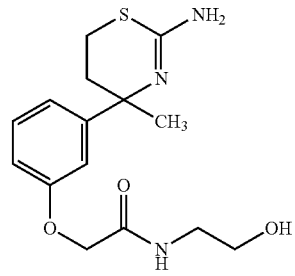 [SMILES: CC1(c2cccc(OCC(=O)NCCO)c2)CCSC(N)=N1]
838 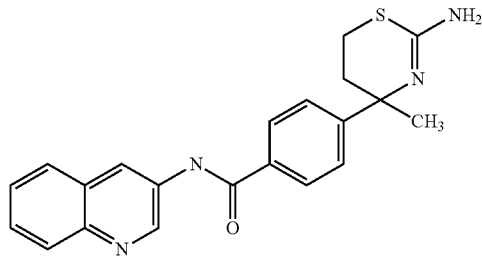 [SMILES: CC1(c2ccc(C(=O)Nc3cnc4ccccc4c3)cc2)CCSC(N)=N1]
839 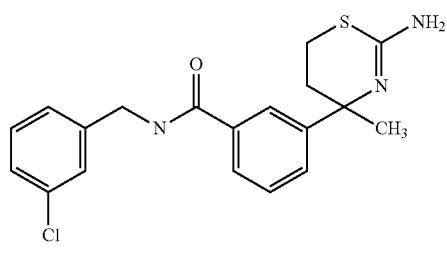
TABLE 88-continued
840 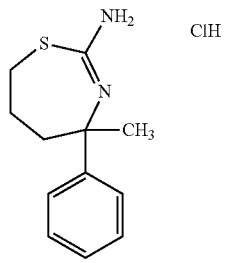
841 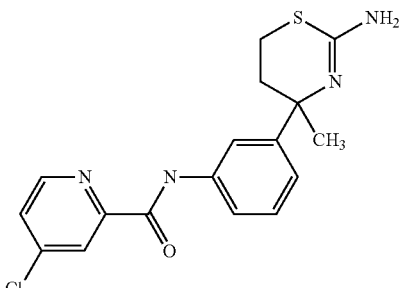
842 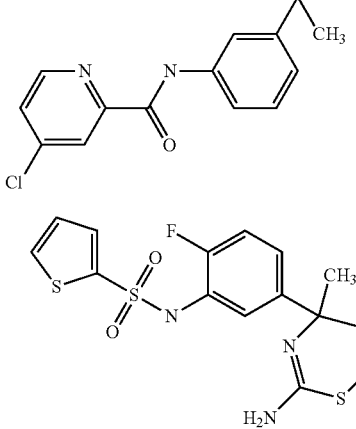
843 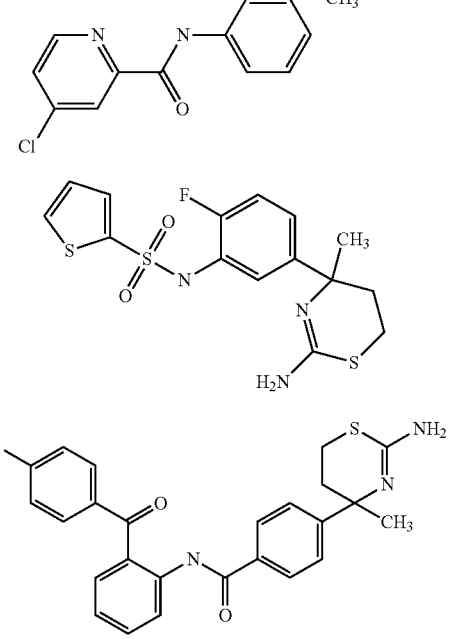
844 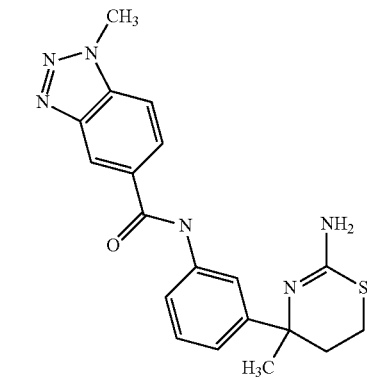 [SMILES: Cn1nnc2cc(C(=O)Nc3cccc(C4(C)CCSC(N)=N4)c3)ccc21]
845 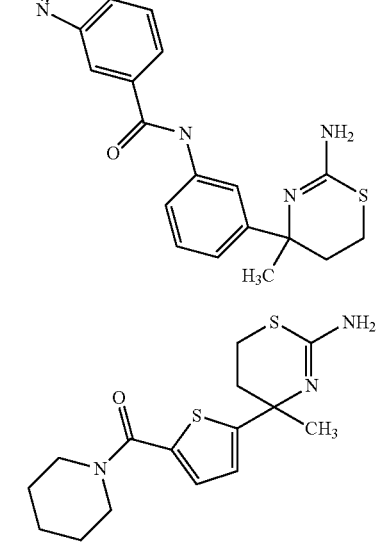

TABLE 88-continued
TABLE 89
846 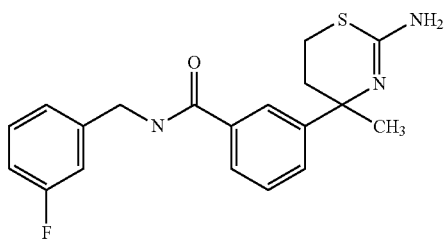 [SMILES: CC1(c2cccc(C(=O)NCc3cccc(F)c3)c2)CCSC(N)=N1]
847 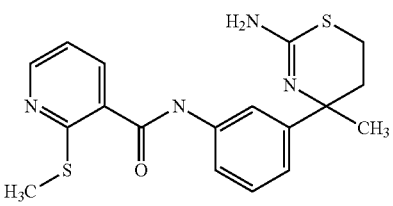
848 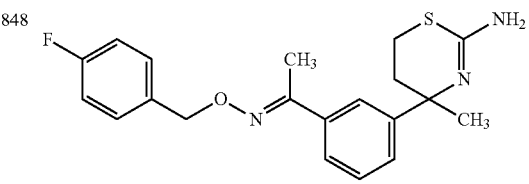
849 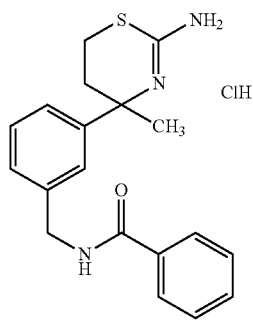
ClH
850 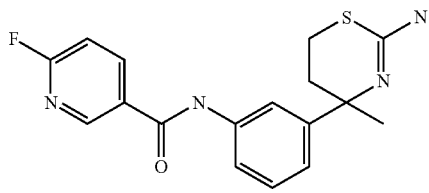 [SMILES: CC1(c2cccc(NC(=O)c3ccc(F)nc3)c2)CCSC(N)=N1]
851 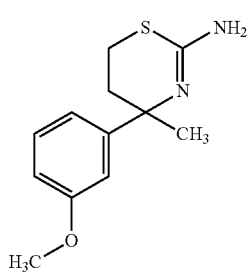 [SMILES: COc1cccc(C2(C)CCSC(N)=N2)c1]
TABLE 89-continued
852 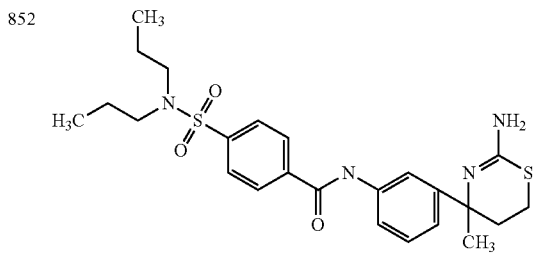
853 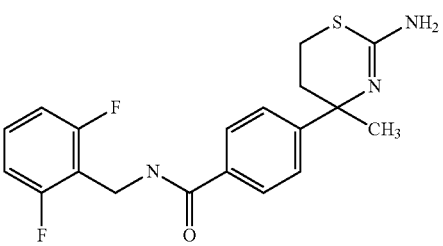 [SMILES: CC1(c2ccc(C(=O)NCc3c(F)cccc3F)cc2)CCSC(N)=N1]
854 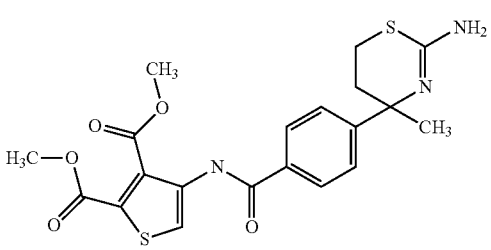 [SMILES: COC(=O)c1scc(NC(=O)c2ccc(C3(C)CCSC(N)=N3)cc2)c1C(=O)OC]
855 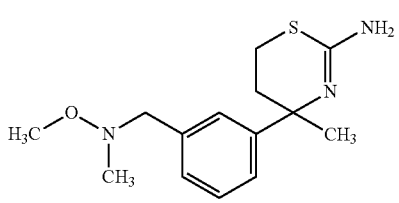 [SMILES: CON(C)Cc1cccc(C2(C)CCSC(N)=N2)c1]
TABLE 90
856 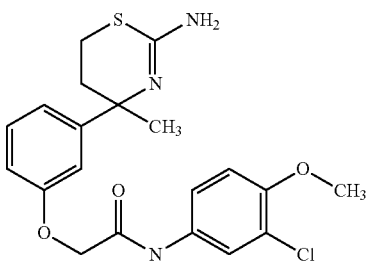
857 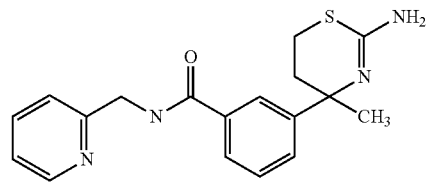 [SMILES: CC1(c2cccc(C(=O)NCc3ccccn3)c2)CCSC(N)=N1]

TABLE 90-continued
858 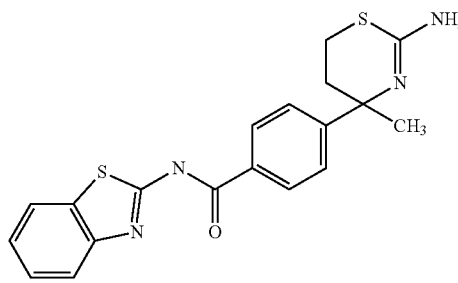
859 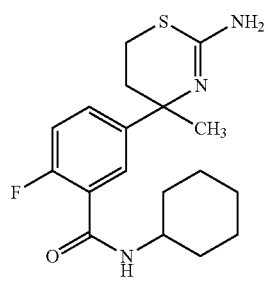 [SMILES: CC1(c2ccc(F)c(C(=O)NC3CCCCC3)c2)CCSC(N)=N1]
860 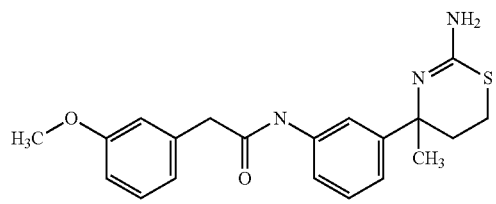 [SMILES: COc1cccc(CC(=O)Nc2cccc(C3(C)CCSC(N)=N3)c2)c1]
861 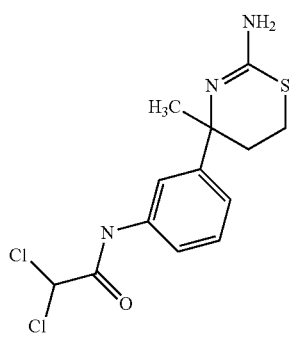 [SMILES: CC1(c2cccc(NC(=O)C(Cl)Cl)c2)CCSC(N)=N1]
862 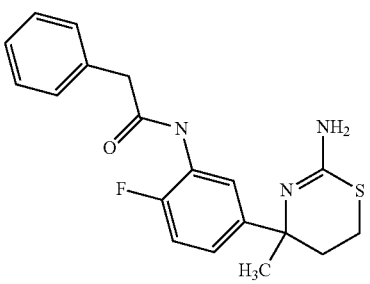 [SMILES: CC1(c2ccc(F)c(NC(=O)Cc3ccccc3)c2)CCSC(N)=N1]
863 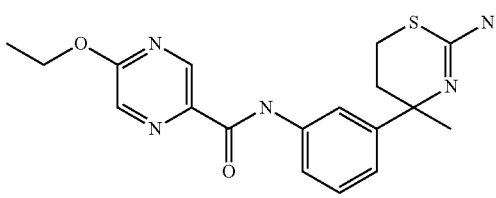 [SMILES: CCOc1cnc(C(=O)Nc2cccc(C3(C)CCSC(N)=N3)c2)cn1]
TABLE 90-continued
864 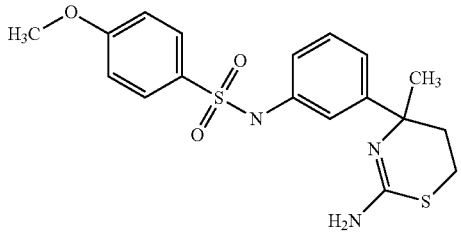 [SMILES: COc1ccc(S(=O)(=O)Nc2cccc(C3(C)CCSC(N)=N3)c2)cc1]
865 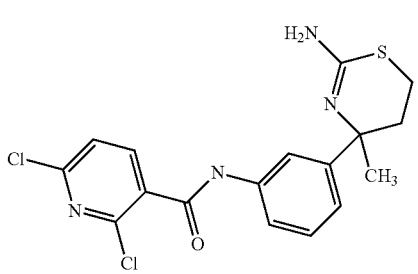 [SMILES: CC1(c2cccc(NC(=O)c3ccc(Cl)nc3Cl)c2)CCSC(N)=N1]
TABLE 91
866 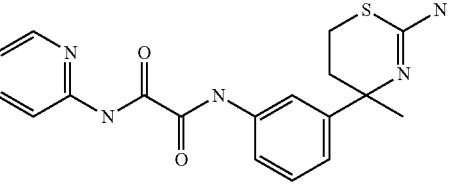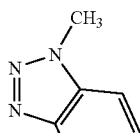
867 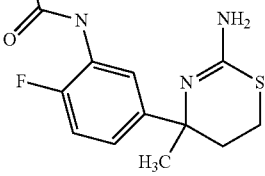
868 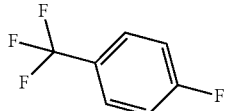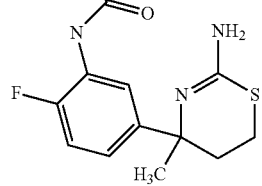

TABLE 91-continued
869 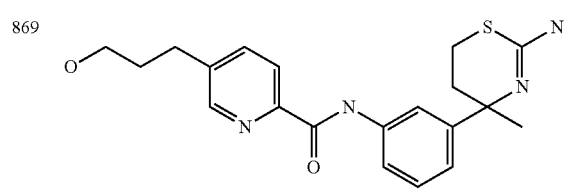
870 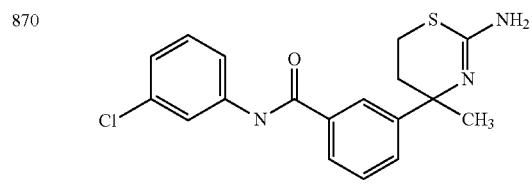
871 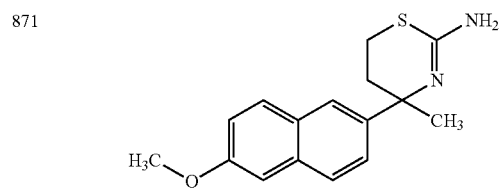
872 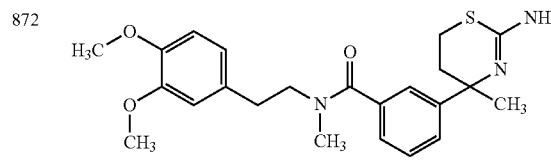
873 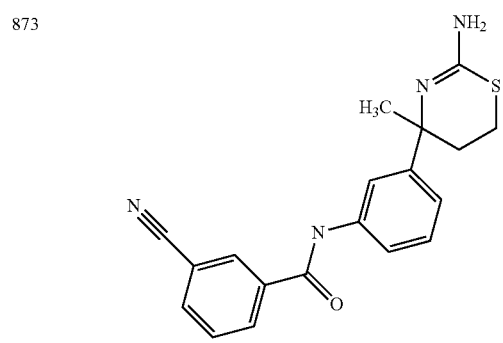
874 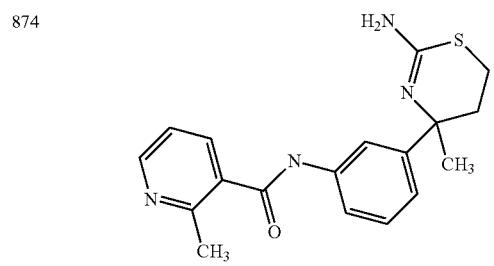
TABLE 91-continued
875 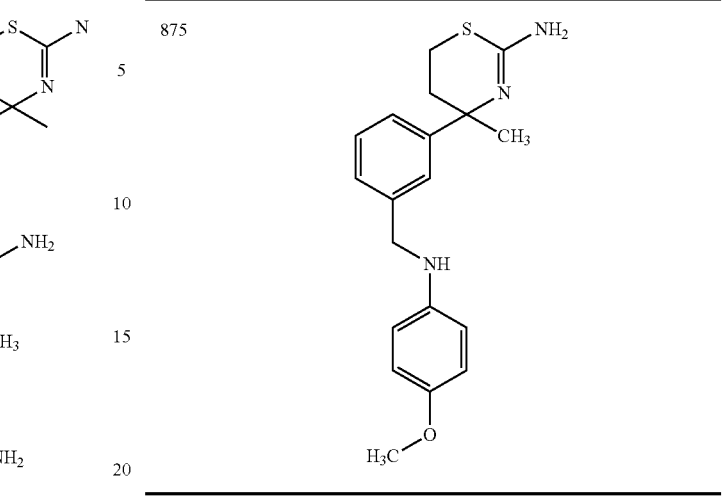
TABLE 92
876 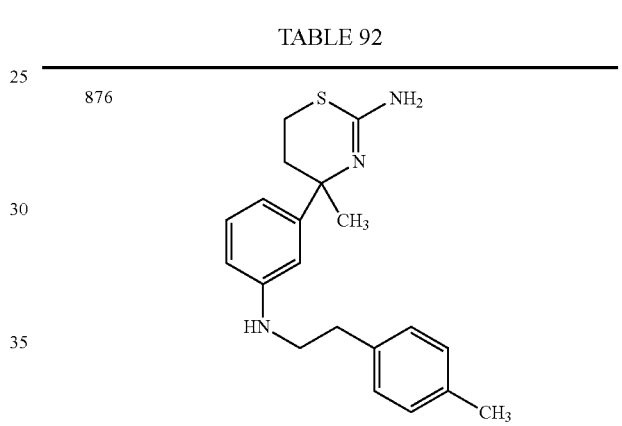
877 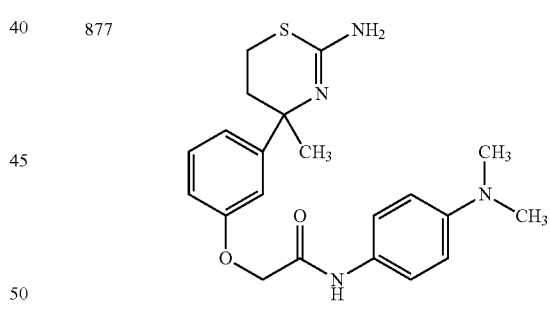
878 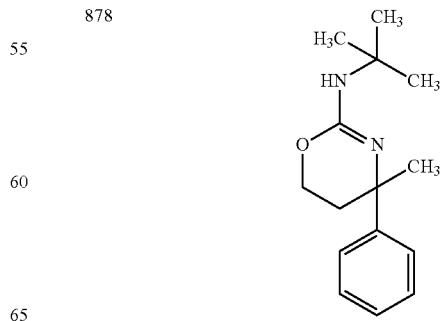

TABLE 92-continued
879 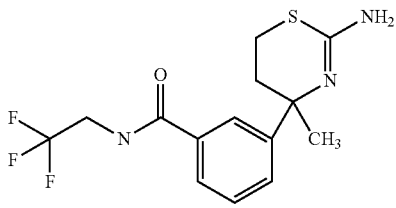 [SMILES: CC1(c2cccc(C(=O)NCC(F)(F)F)c2)CCSC(N)=N1]
880 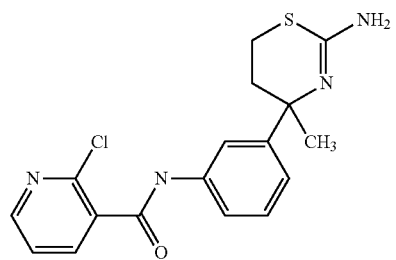 [SMILES: CC1(c2cccc(NC(=O)c3cccnc3Cl)c2)CCSC(N)=N1]
881 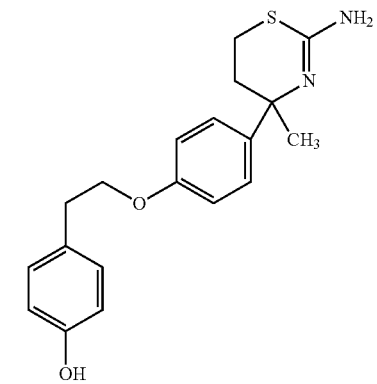 [SMILES: CC1(c2ccc(OCCc3ccc(O)cc3)cc2)CCSC(N)=N1]
882 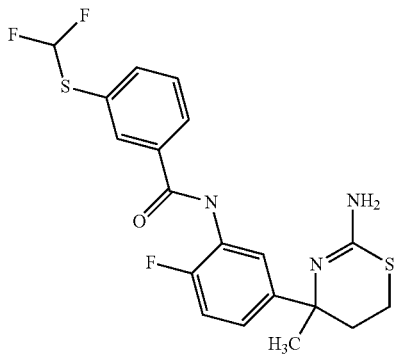 [SMILES: CC1(c2ccc(F)c(NC(=O)c3cccc(SC(F)F)c3)c2)CCSC(N)=N1]
883 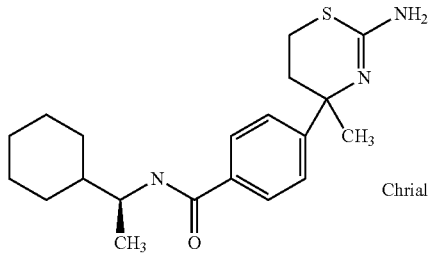 [SMILES: C[C@H](NC(=O)c1ccc(C2(C)CCSC(N)=N2)cc1)C1CCCCC1]
Chrial
TABLE 93
884 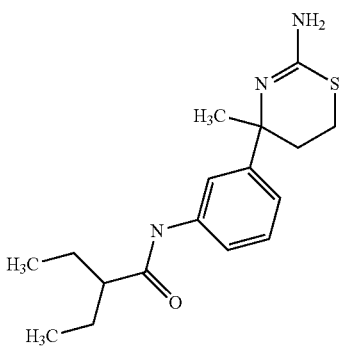 [SMILES: CCC(CC)C(=O)Nc1cccc(C2(C)CCSC(N)=N2)c1]
885 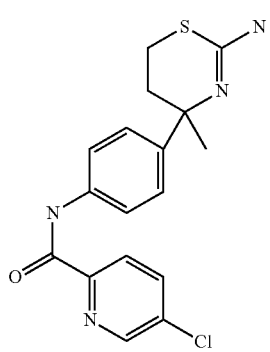 [SMILES: CC1(c2ccc(NC(=O)c3ccc(Cl)cn3)cc2)CCSC(N)=N1]
886 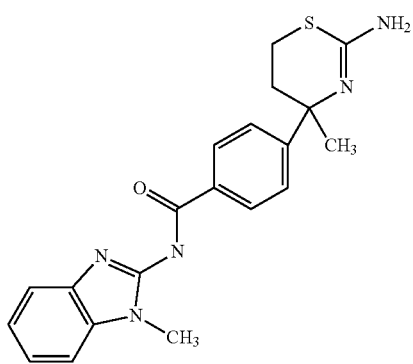 [SMILES: Cn1c(NC(=O)c2ccc(C3(C)CCSC(N)=N3)cc2)nc2ccccc21]
887 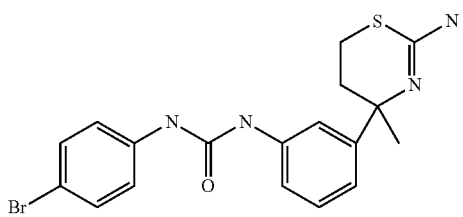 [SMILES: CC1(c2cccc(NC(=O)Nc3ccc(Br)cc3)c2)CCSC(N)=N1]
888 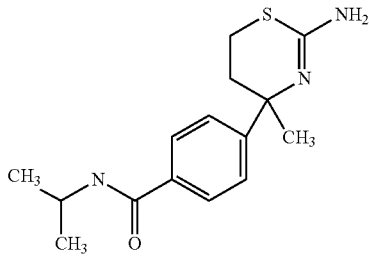 [SMILES: CC(C)NC(=O)c1ccc(C2(C)CCSC(N)=N2)cc1]

TABLE 93-continued
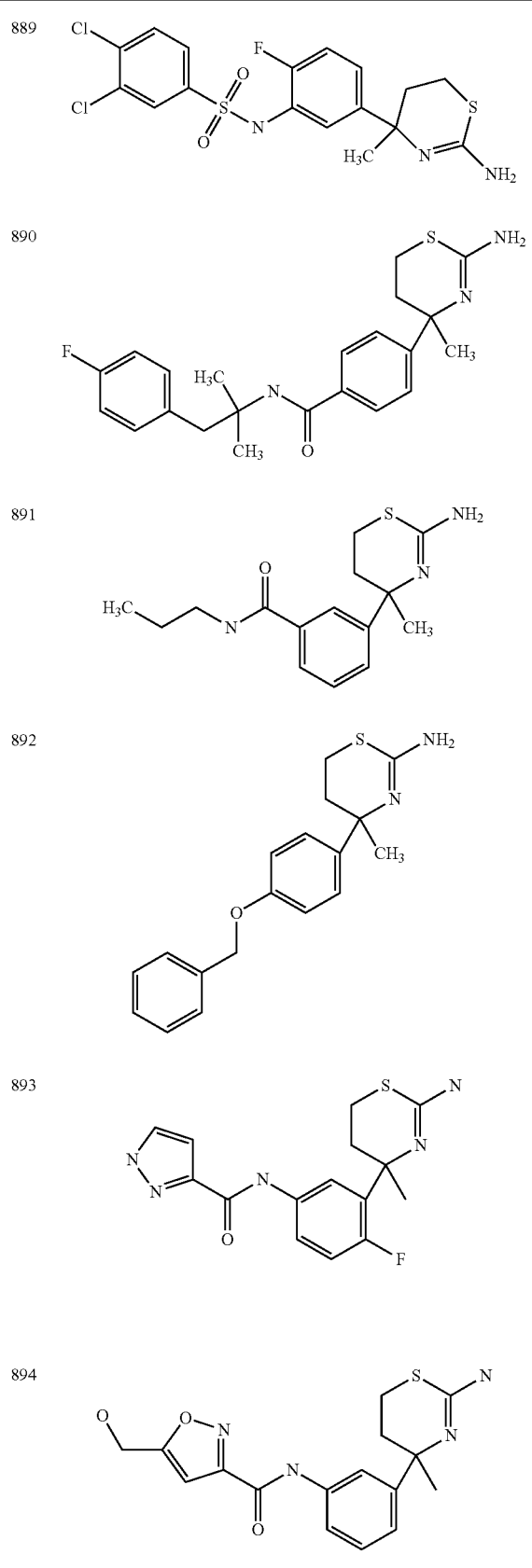
TABLE 94
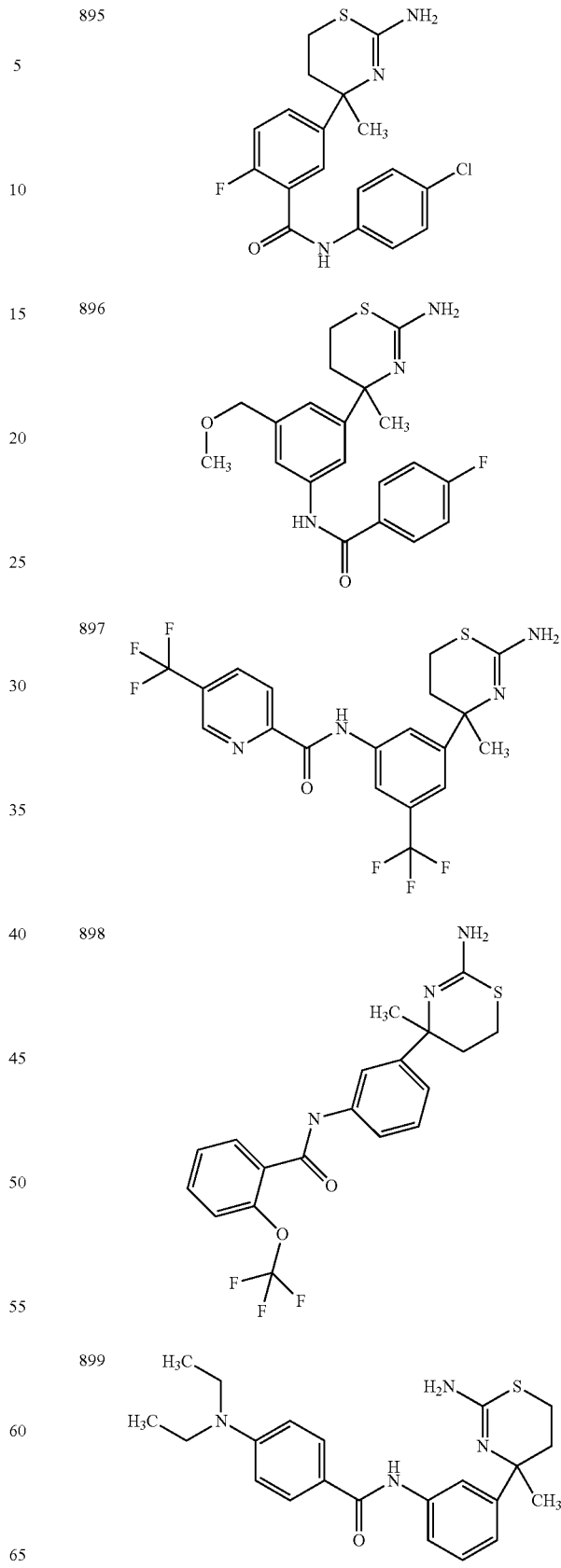

TABLE 94-continued
900 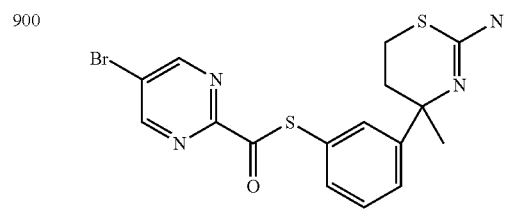
901 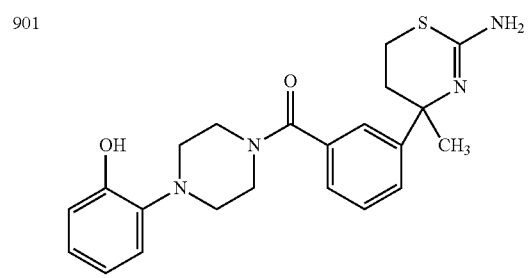
902 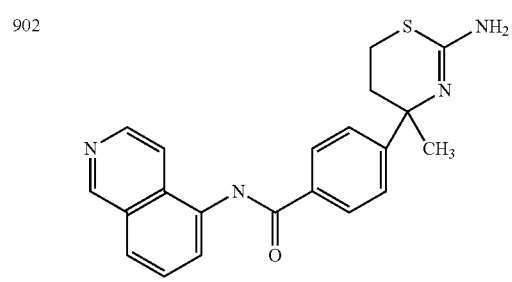
903 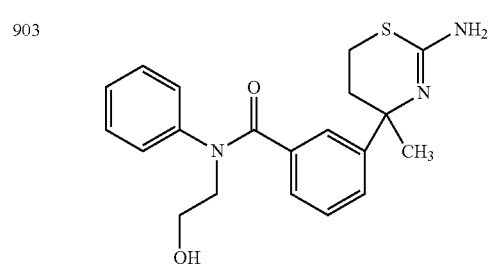
904 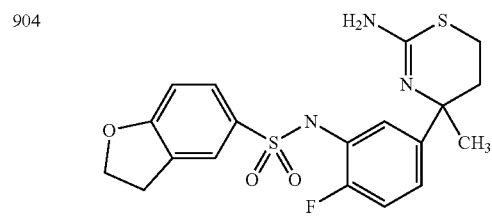
TABLE 95
905 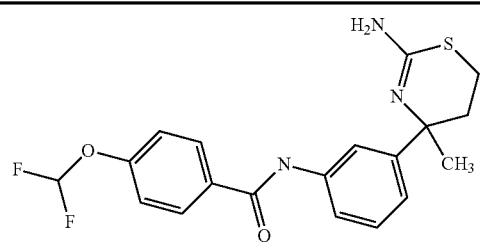
TABLE 95-continued
906 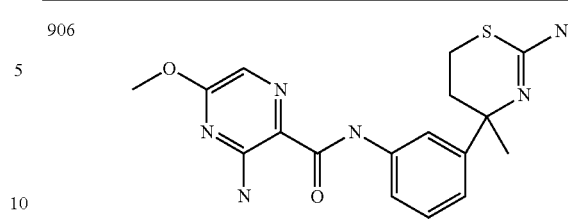
907 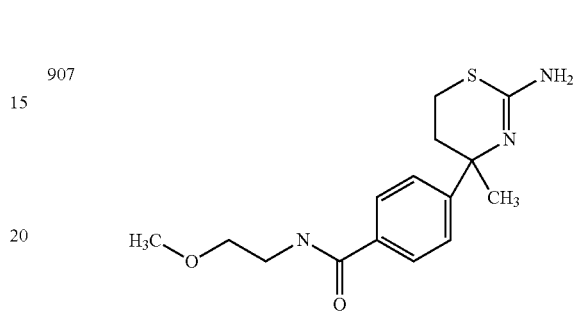
908 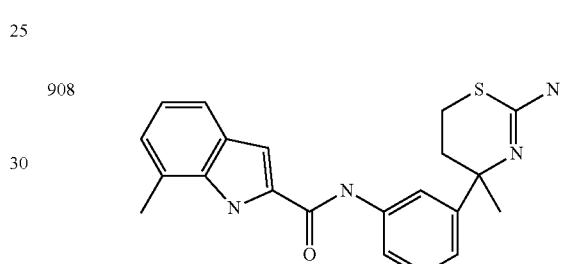
909 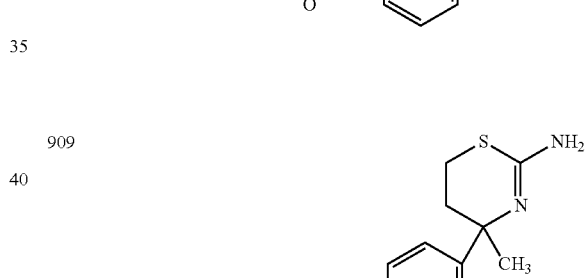
910 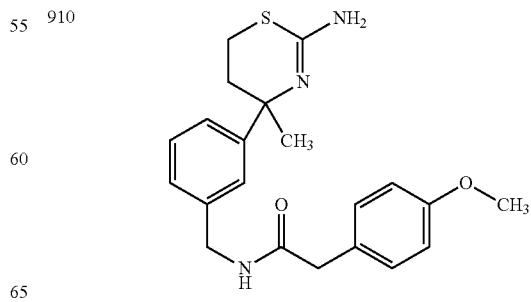

TABLE 95-continued
911 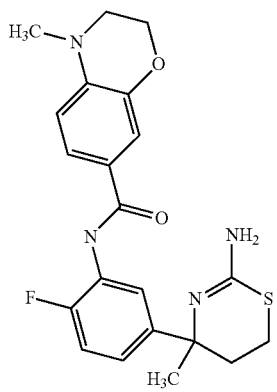 [SMILES: CN1CCOc2cc(C(=O)Nc3cc(C4(C)CCSC(N)=N4)ccc3F)ccc21]
912 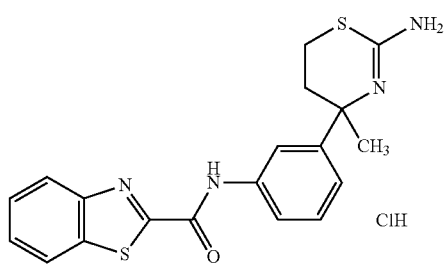 [SMILES: CC1(c2cccc(NC(=O)c3nc4ccccc4s3)c2)CCSC(N)=N1 ; Cl]
913 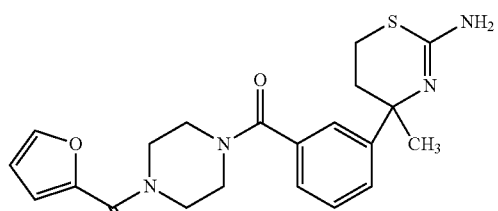
914 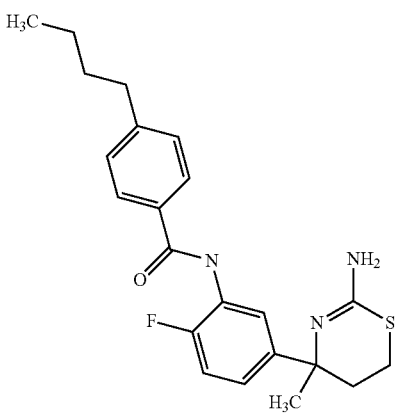 [SMILES: CCCCc1ccc(C(=O)Nc2cc(C3(C)CCSC(N)=N3)ccc2F)cc1]
TABLE 96
915 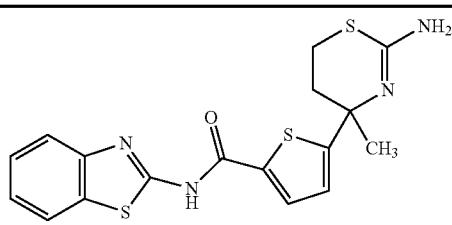
916 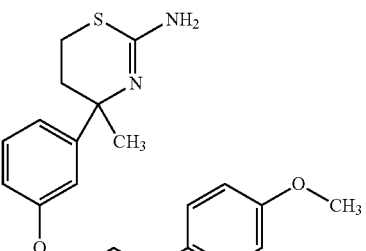
917 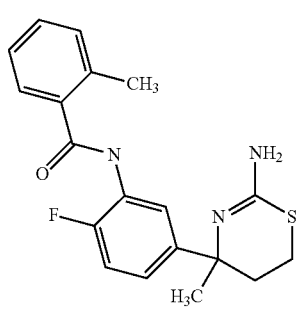 [SMILES: Cc1ccccc1C(=O)Nc1cc(C2(C)CCSC(N)=N2)ccc1F]
918 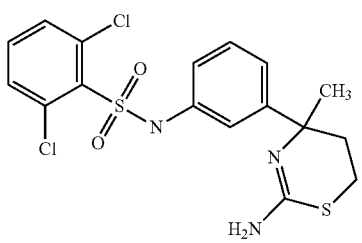 [SMILES: CC1(c2cccc(NS(=O)(=O)c3c(Cl)cccc3Cl)c2)CCSC(N)=N1]
919 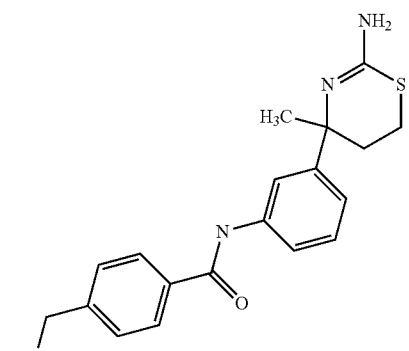
920 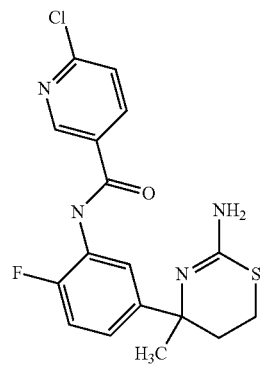 [SMILES: CC1(c2ccc(F)c(NC(=O)c3ccc(Cl)nc3)c2)CCSC(N)=N1]

TABLE 96-continued
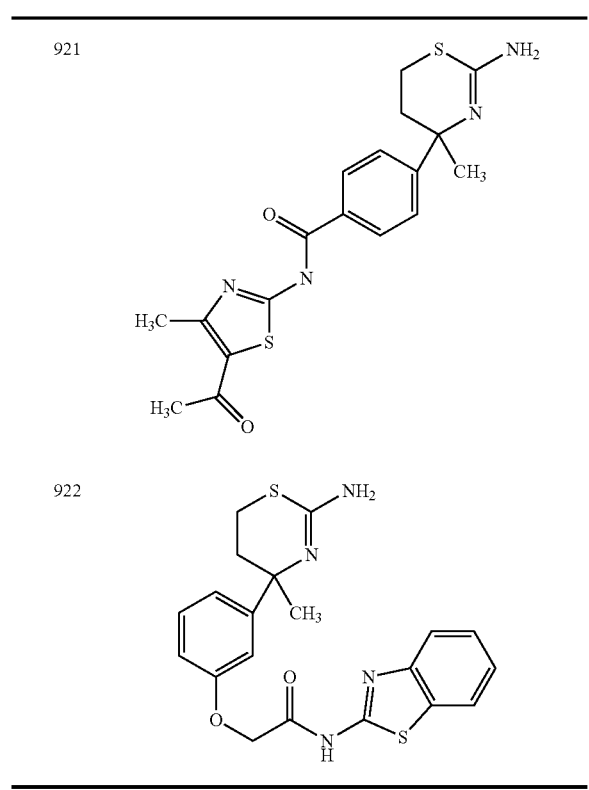
TABLE 97
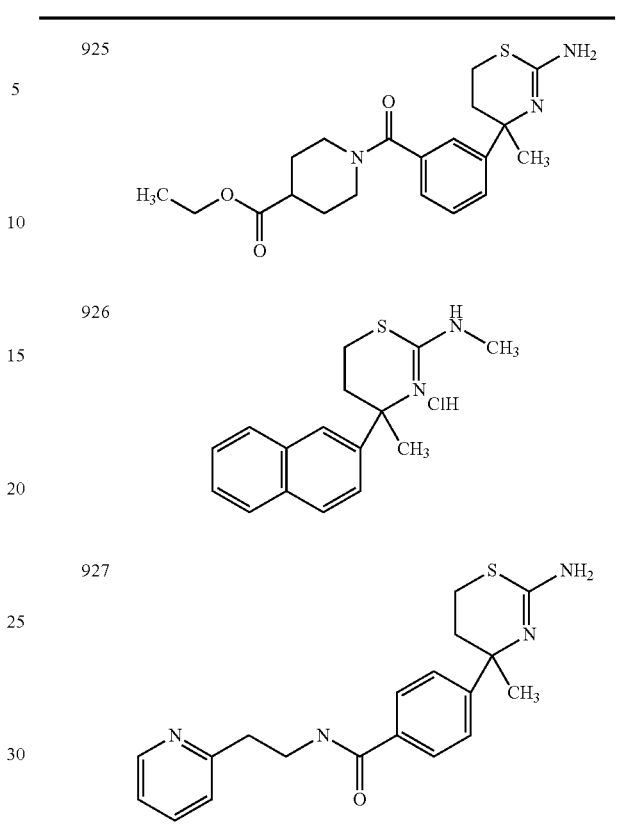
TABLE 97-continued
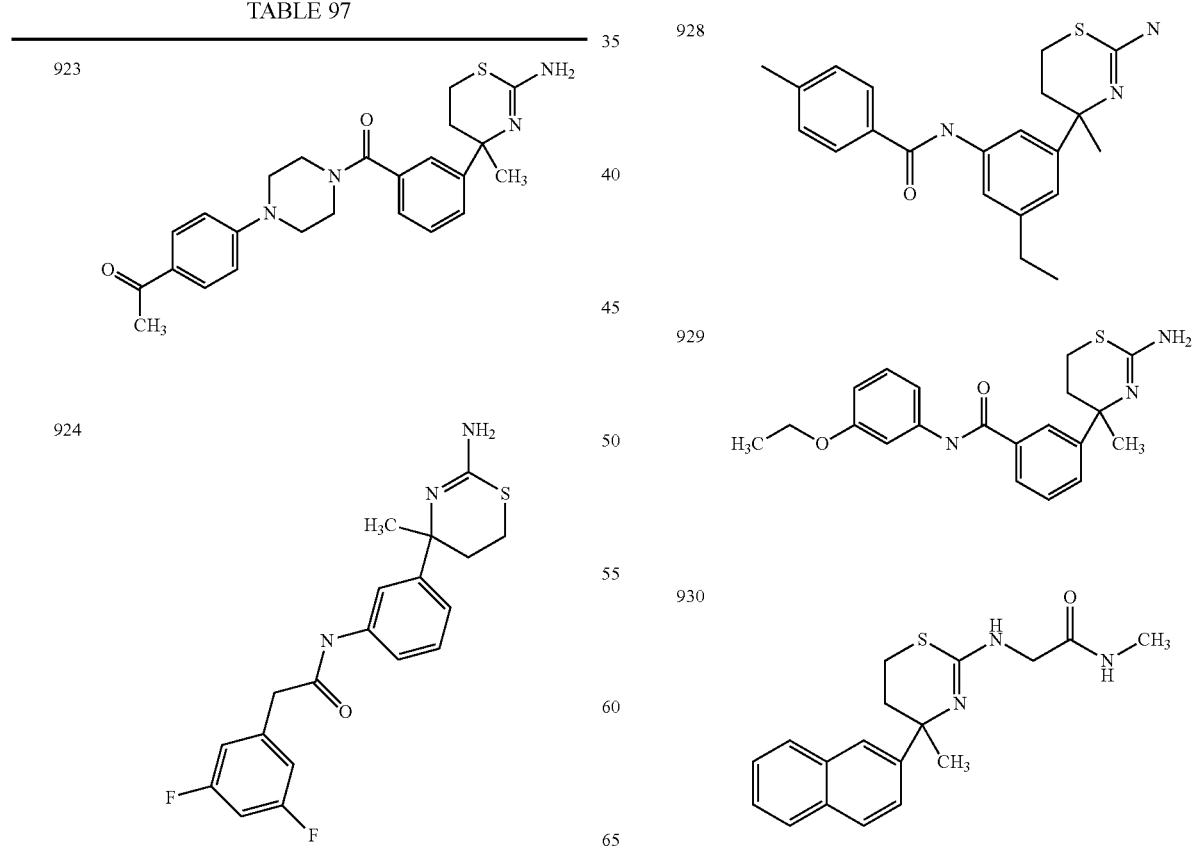

TABLE 97-continued
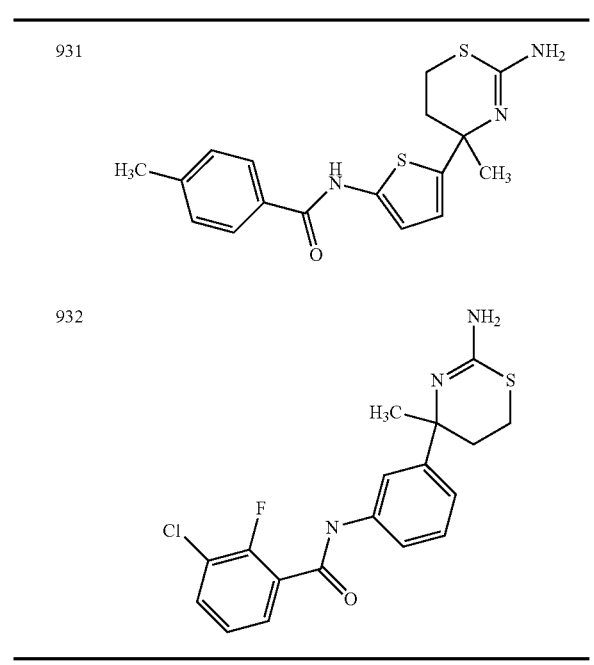
TABLE 98
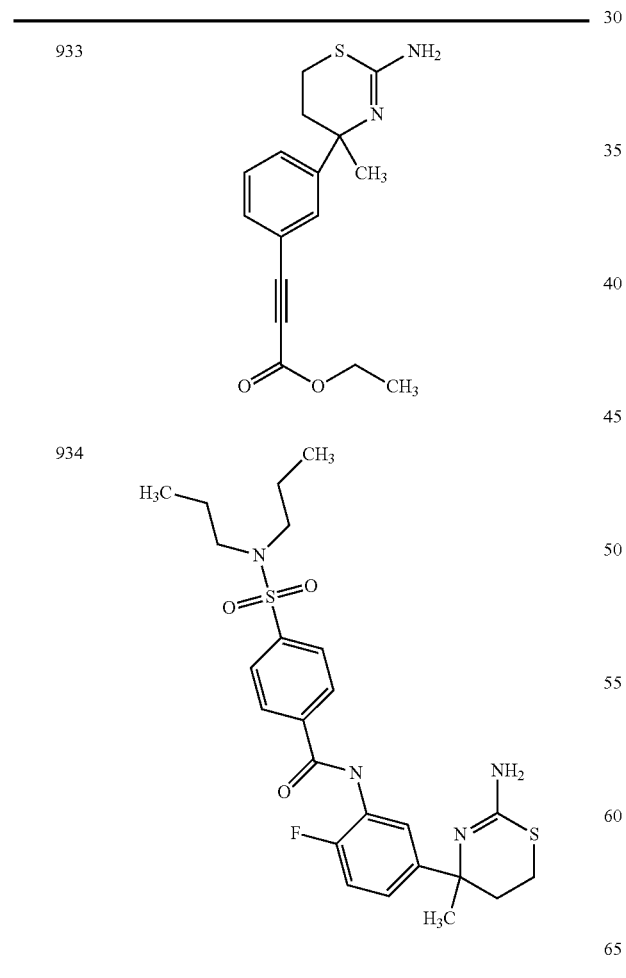
TABLE 98-continued
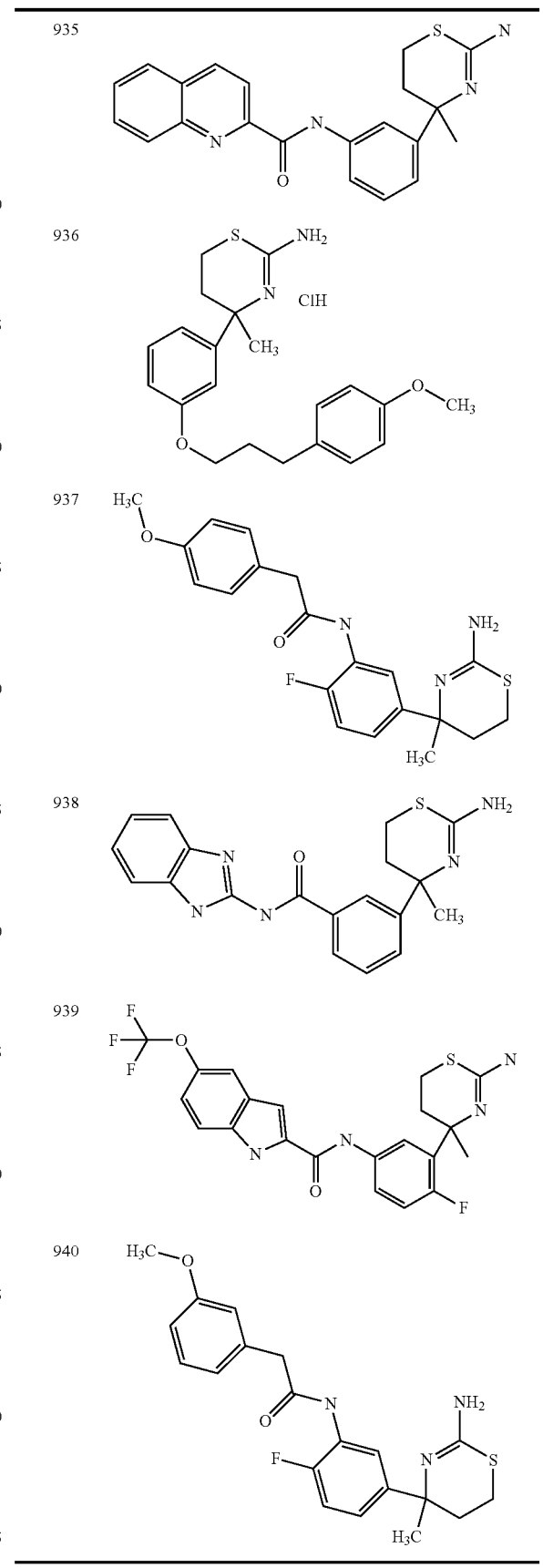

TABLE 99
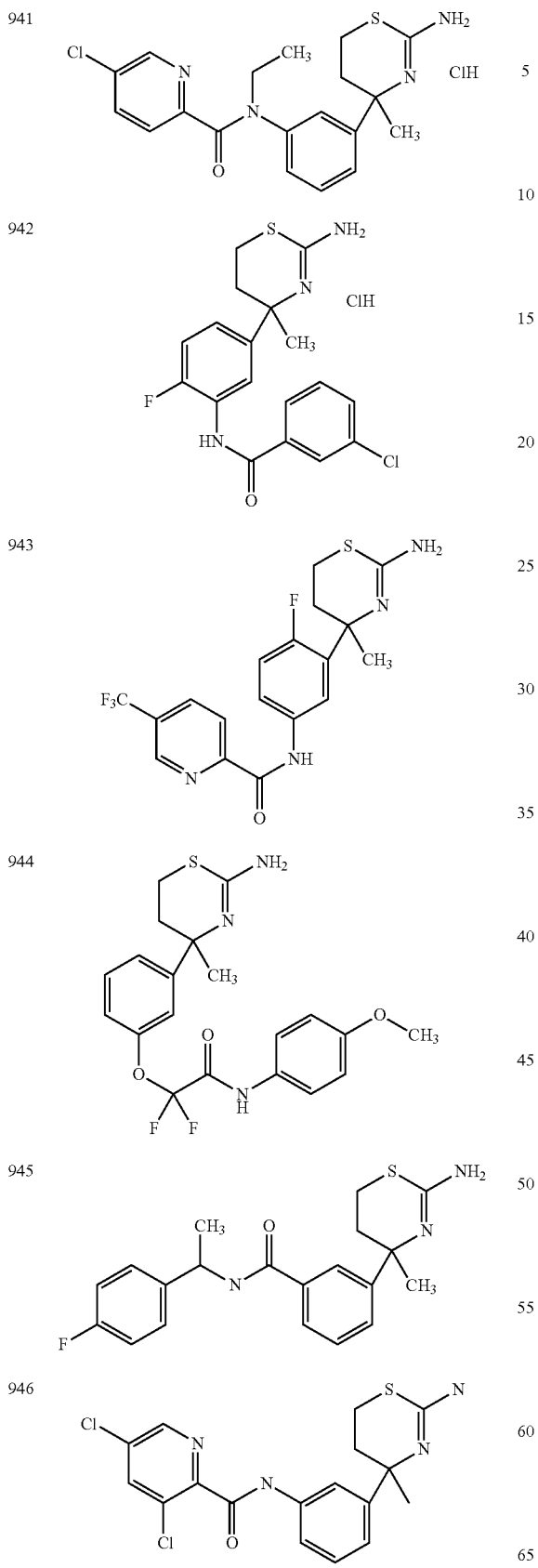
TABLE 99-continued
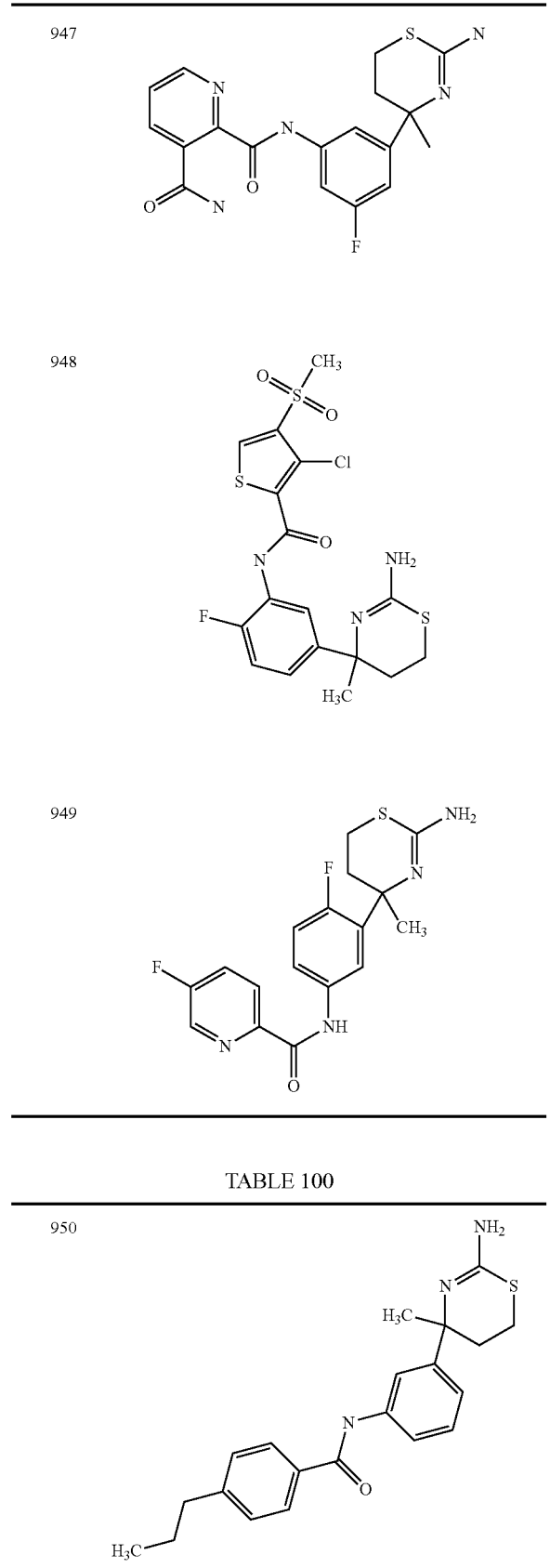
TABLE 100

TABLE 100-continued
951 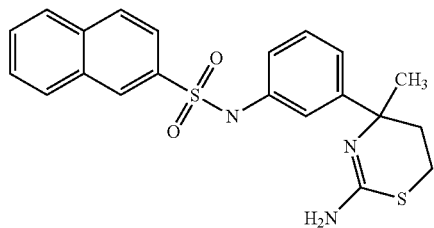 [SMILES: CC1(c2cccc(NS(=O)(=O)c3ccc4ccccc4c3)c2)CCSC(N)=N1]
952 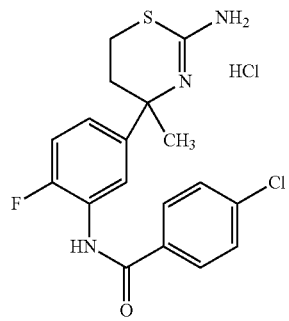 [SMILES: CC1(c2ccc(F)c(NC(=O)c3ccc(Cl)cc3)c2)CCSC(N)=N1 ; Cl]
953 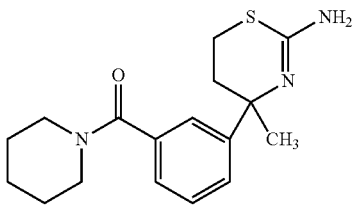 [SMILES: CC1(c2cccc(C(=O)N3CCCCC3)c2)CCSC(N)=N1]
954 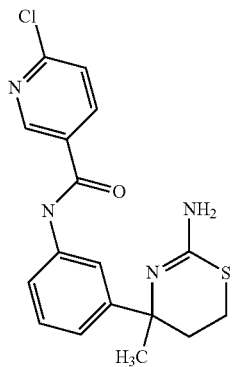 [SMILES: CC1(c2cccc(NC(=O)c3ccc(Cl)nc3)c2)CCSC(N)=N1]
955 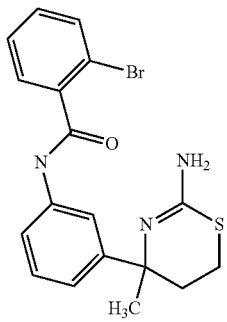 [SMILES: CC1(c2cccc(NC(=O)c3ccccc3Br)c2)CCSC(N)=N1]
TABLE 100-continued
956 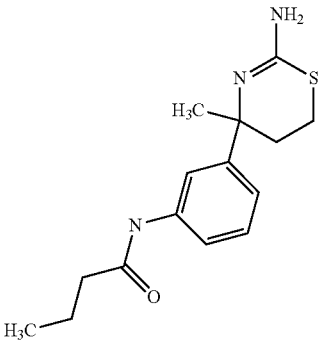 [SMILES: CCCC(=O)Nc1cccc(C2(C)CCSC(N)=N2)c1]
957 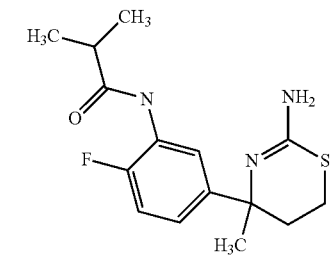 [SMILES: CC(C)C(=O)Nc1cc(C2(C)CCSC(N)=N2)ccc1F]
TABLE 101
958 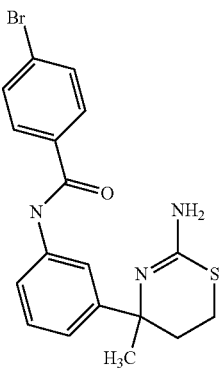 [SMILES: CC1(c2cccc(NC(=O)c3ccc(Br)cc3)c2)CCSC(N)=N1]
959 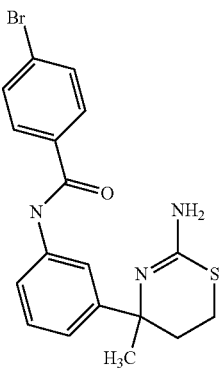 [SMILES: CC1(c2cccc(NC(=O)c3ccc(Br)cc3)c2)CCSC(N)=N1]

TABLE 101-continued
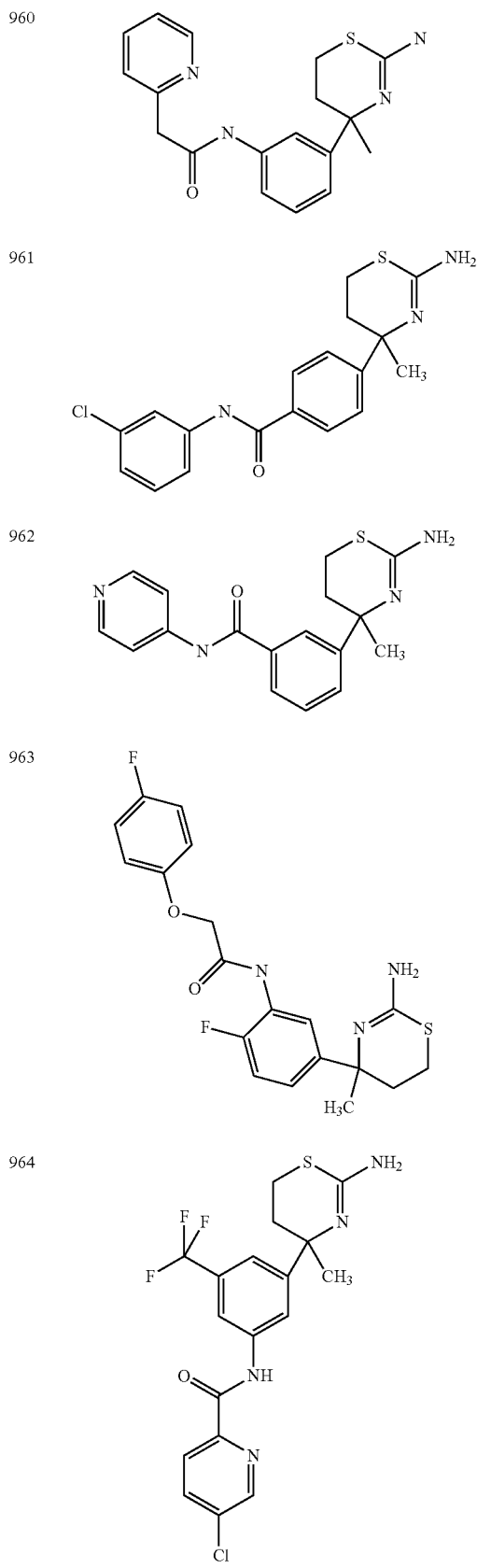
TABLE 102
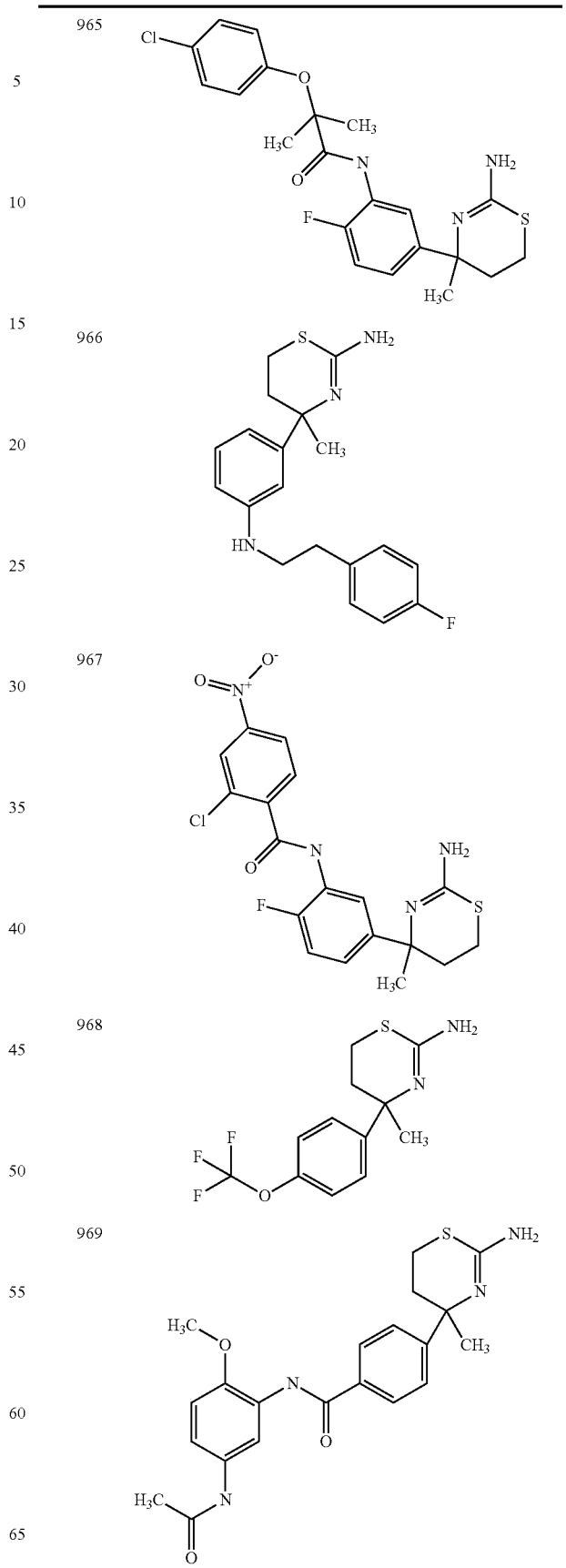

TABLE 102-continued
| | |
|---|---|
| 970 | 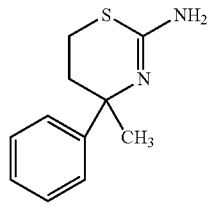 |
| 971 | 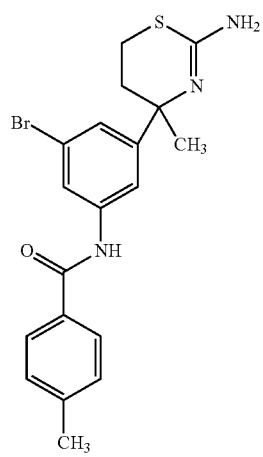 [SMILES: Cc1ccc(C(=O)Nc2cc(Br)cc(C3(C)CCSC(N)=N3)c2)cc1] |
| 972 | 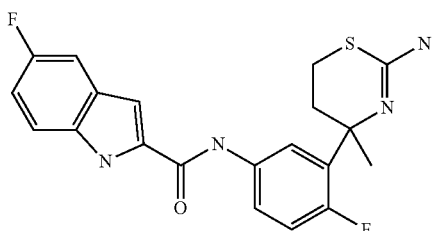 |
TABLE 103
| | |
|---|---|
| 973 | 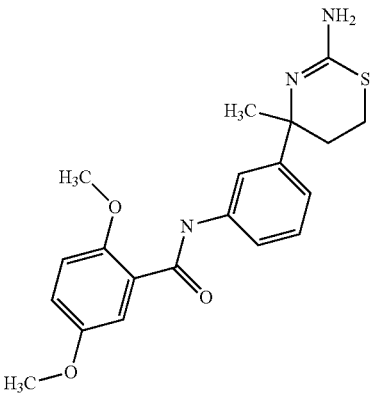 [SMILES: COc1ccc(OC)c(C(=O)Nc2cccc(C3(C)CCSC(N)=N3)c2)c1] |
| 974 | 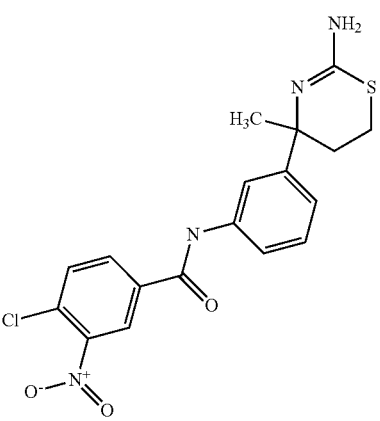 [SMILES: CC1(c2cccc(NC(=O)c3ccc(Cl)c([N+](=O)[O-])c3)c2)CCSC(N)=N1] |
| 975 | 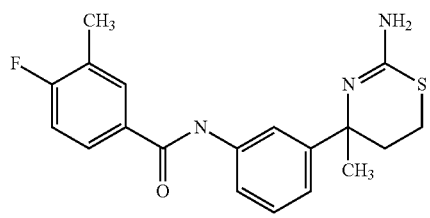 [SMILES: Cc1cc(C(=O)Nc2cccc(C3(C)CCSC(N)=N3)c2)ccc1F] |
| 976 | 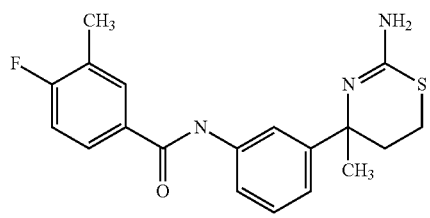 [SMILES: Cc1cc(C(=O)Nc2cccc(C3(C)CCSC(N)=N3)c2)ccc1F] |
| 977 | 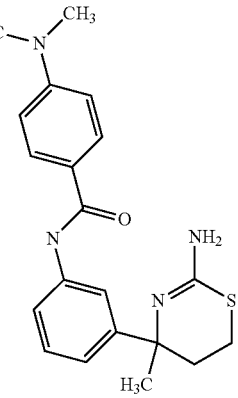 |

TABLE 103-continued
978 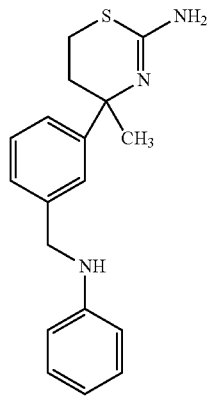 [SMILES: CC1(c2cccc(CNc3ccccc3)c2)CCSC(N)=N1]
979 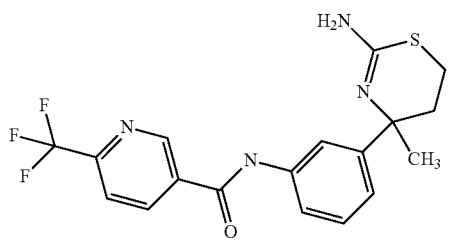 [SMILES: CC1(c2cccc(NC(=O)c3ccc(C(F)(F)F)nc3)c2)CCSC(N)=N1]
980 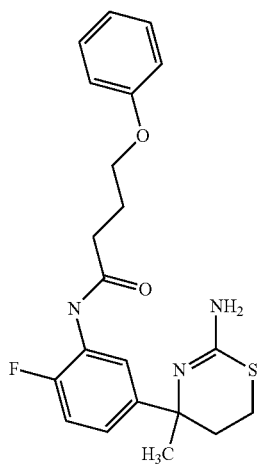 [SMILES: CC1(c2ccc(F)c(NC(=O)CCCOc3ccccc3)c2)CCSC(N)=N1]
TABLE 104
981 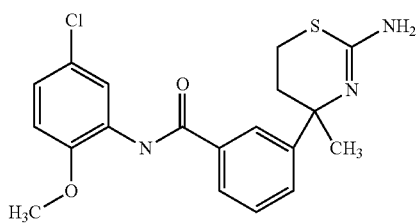 [SMILES: COc1ccc(Cl)cc1NC(=O)c1cccc(C2(C)CCSC(N)=N2)c1]
TABLE 104-continued
982 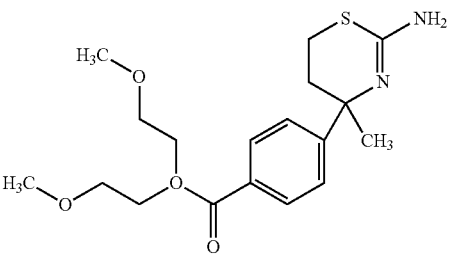
983 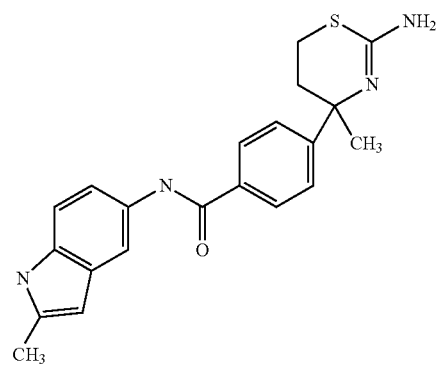 [SMILES: Cc1cc2cc(NC(=O)c3ccc(C4(C)CCSC(N)=N4)cc3)ccc2[nH]1]
984 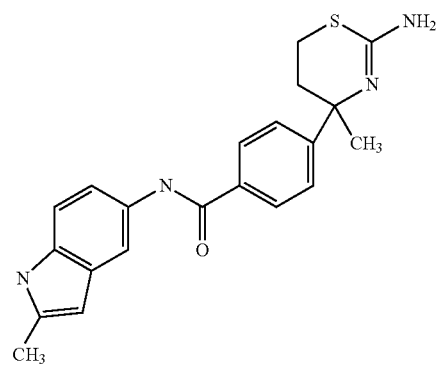 [SMILES: Cc1cc2cc(NC(=O)c3ccc(C4(C)CCSC(N)=N4)cc3)ccc2[nH]1]
985 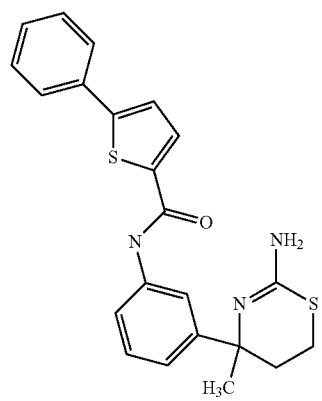 [SMILES: CC1(c2cccc(NC(=O)c3ccc(-c4ccccc4)s3)c2)CCSC(N)=N1]
986 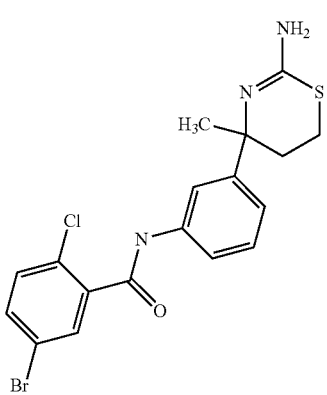 [SMILES: CC1(c2cccc(NC(=O)c3cc(Br)ccc3Cl)c2)CCSC(N)=N1]

TABLE 104-continued
987 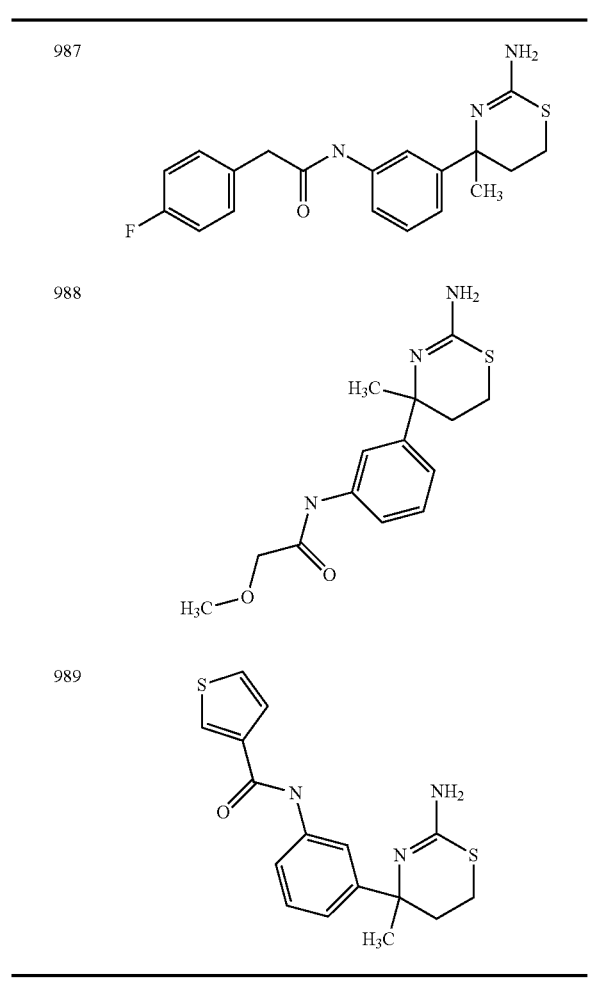
988
989
TABLE 105
990
991
TABLE 105-continued
992 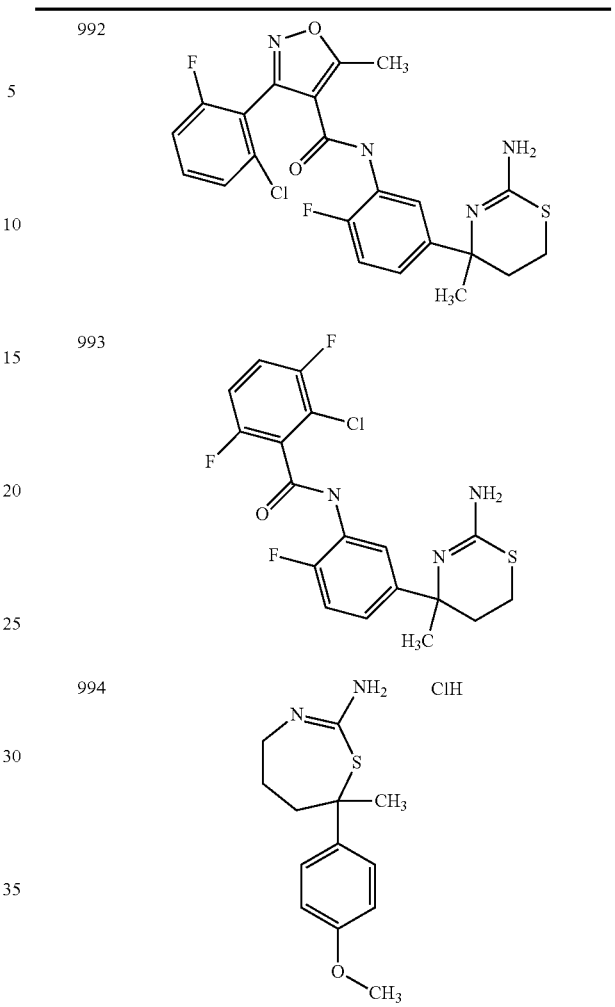
993
994
995 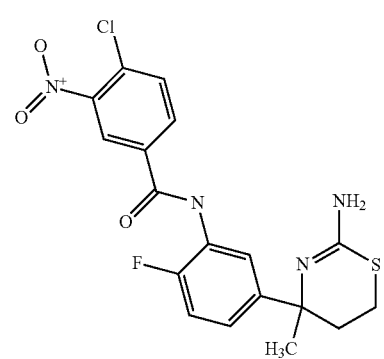
996 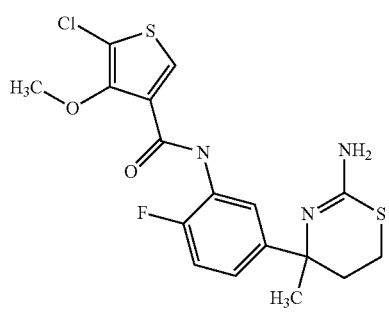 [SMILES: COc1c(C(=O)Nc2cc(C3(C)CCSC(N)=N3)ccc2F)csc1Cl]

TABLE 105-continued
997 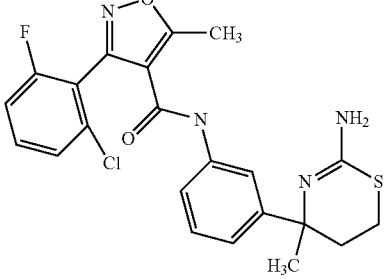
998 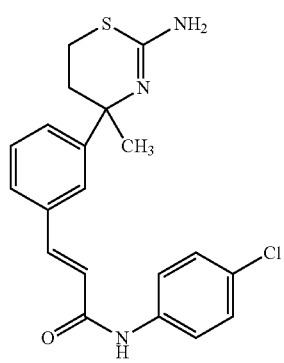 [SMILES: CC1(c2cccc(/C=C/C(=O)Nc3ccc(Cl)cc3)c2)CCSC(N)=N1]
TABLE 106
999 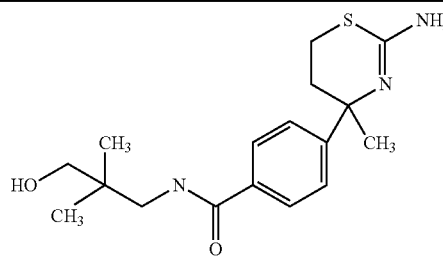
1000 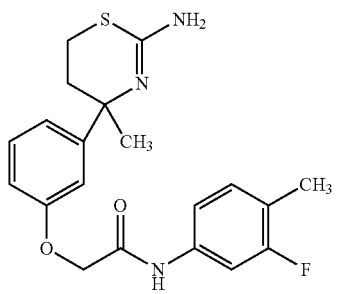 [SMILES: Cc1ccc(NC(=O)COc2cccc(C3(C)CCSC(N)=N3)c2)cc1F]
1001 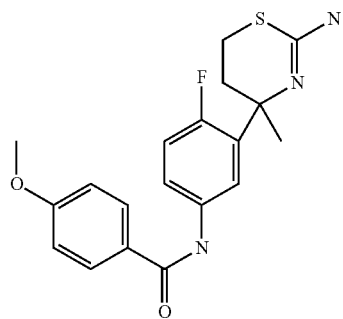 [SMILES: COc1ccc(C(=O)Nc2ccc(F)c(C3(C)CCSC(N)=N3)c2)cc1]
TABLE 106-continued
1002 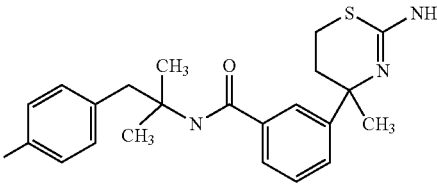
1003 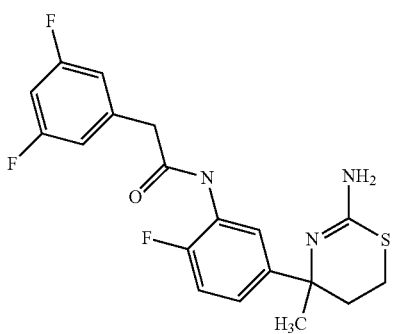 [SMILES: CC1(c2ccc(F)c(NC(=O)Cc3cc(F)cc(F)c3)c2)CCSC(N)=N1]
1004 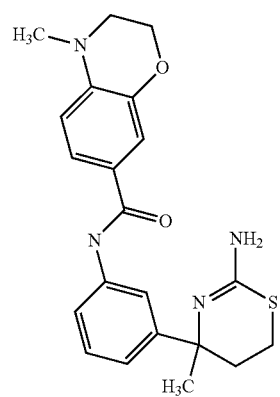 [SMILES: CN1CCOc2cc(C(=O)Nc3cccc(C4(C)CCSC(N)=N4)c3)ccc21]
1005 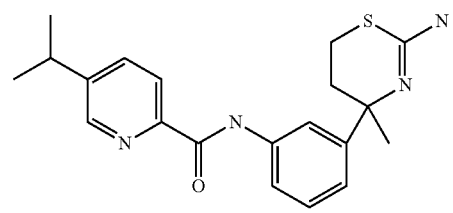 [SMILES: CC(C)c1ccc(C(=O)Nc2cccc(C3(C)CCSC(N)=N3)c2)nc1]
1006 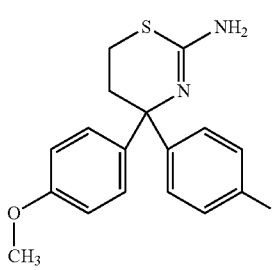

TABLE 106-continued
1007 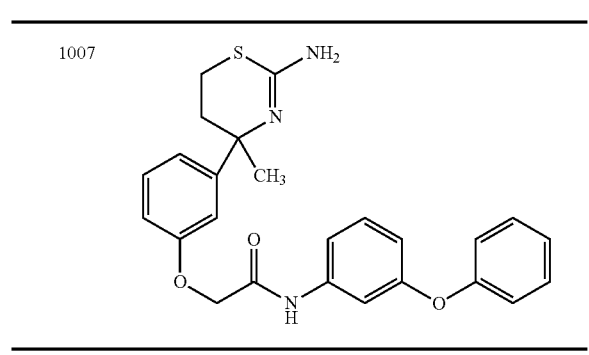
TABLE 107
1008 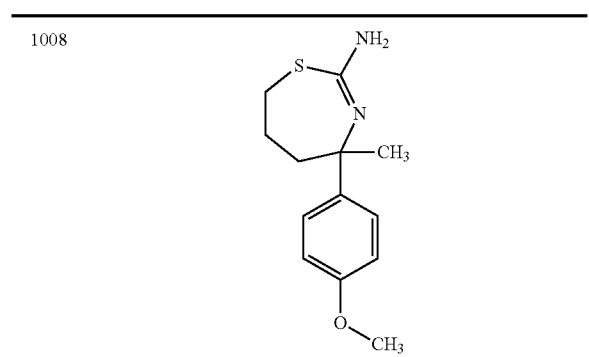
1009 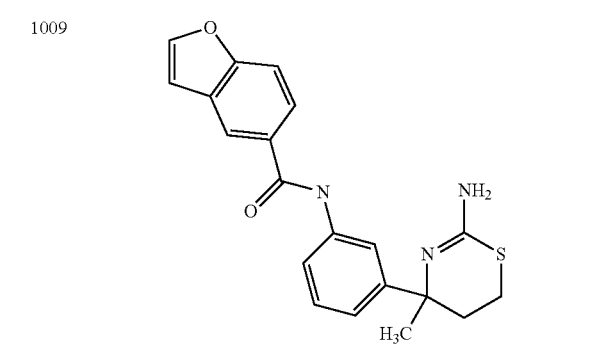
1010 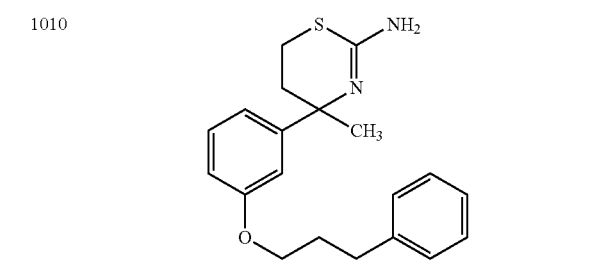
1011 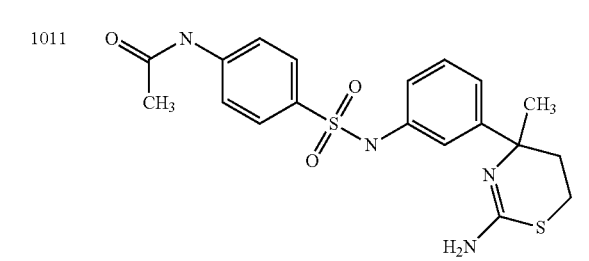
TABLE 107-continued
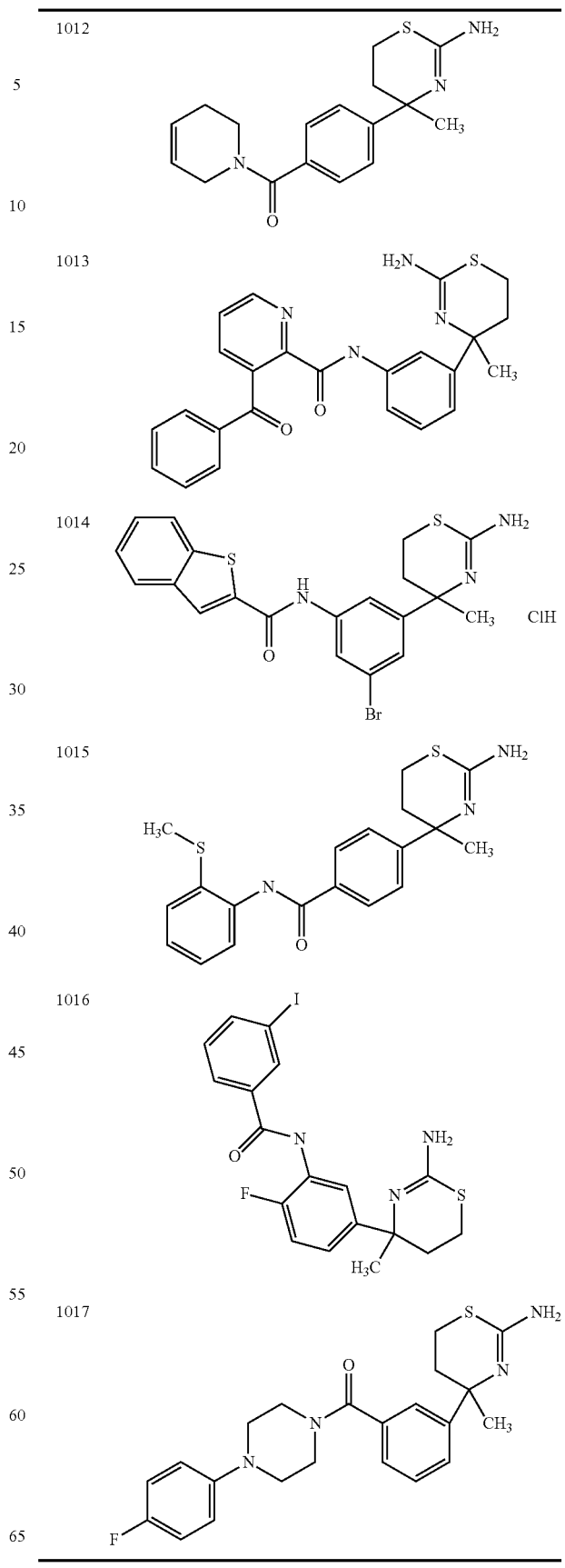

TABLE 108
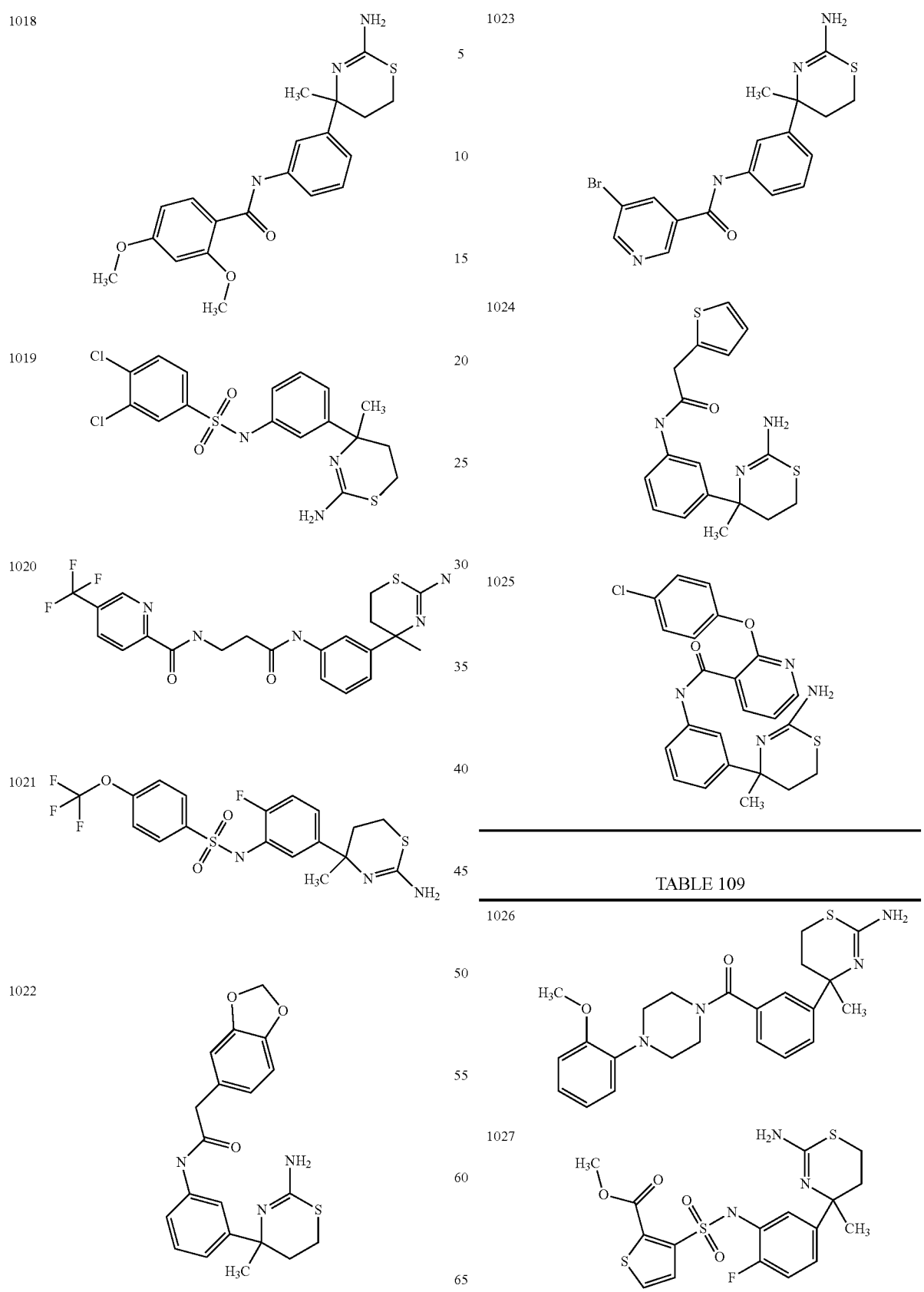
TABLE 108-continued
TABLE 109

TABLE 109-continued
1028 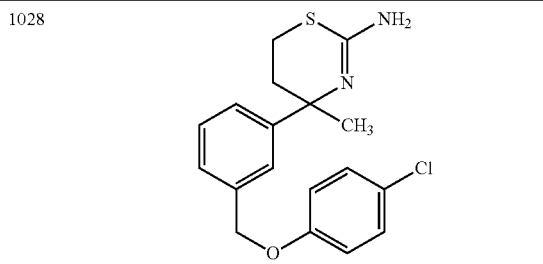
1029 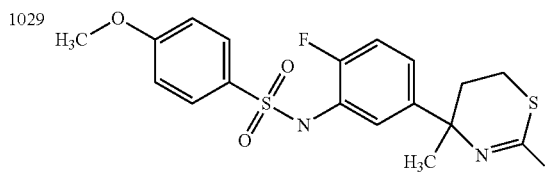
1030 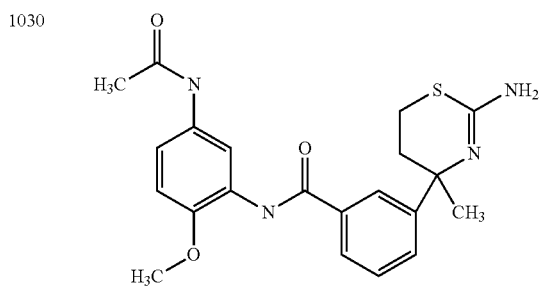
1031 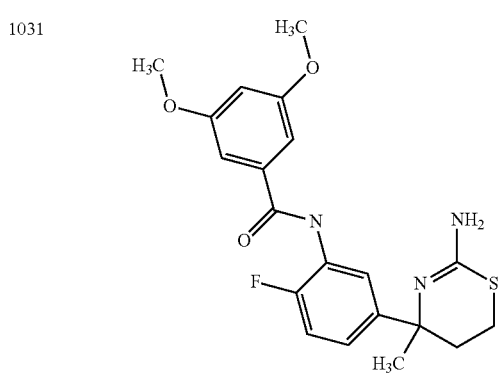
1032 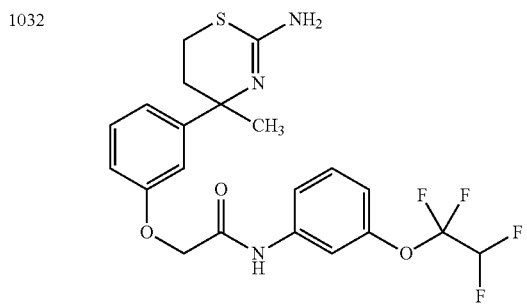
1033 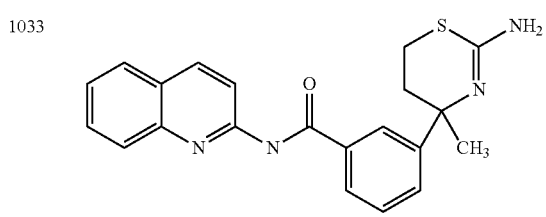
TABLE 109-continued
1034 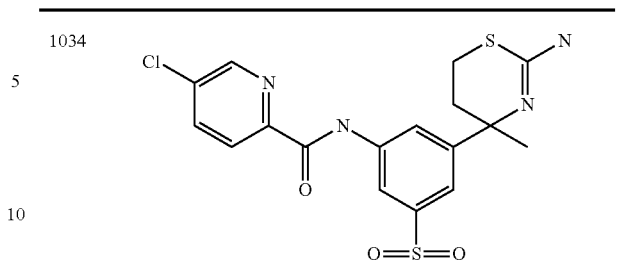
1035 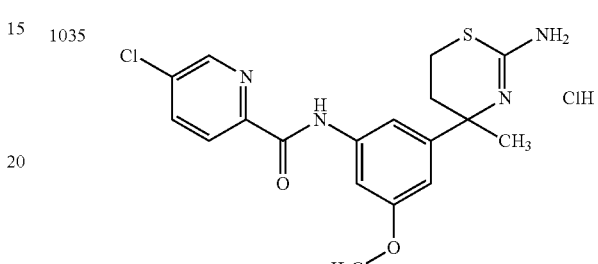
TABLE 110
1036 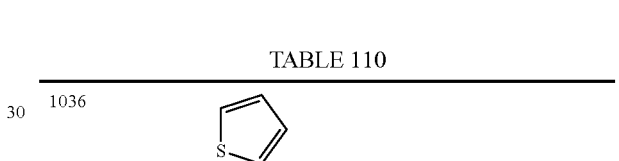
1037 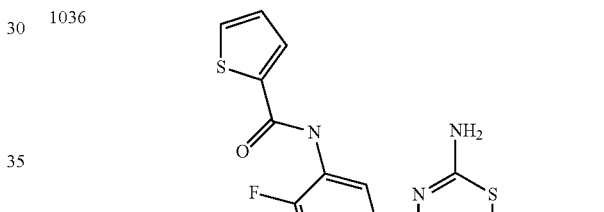
1038 

TABLE 110-continued
1039 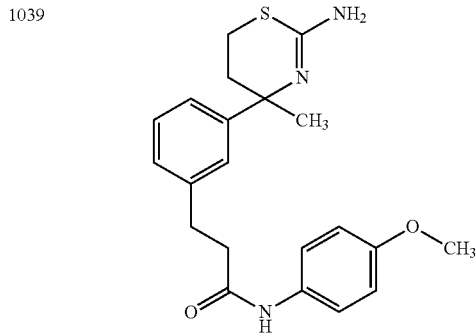
1040 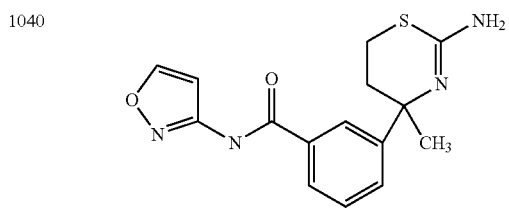
1041 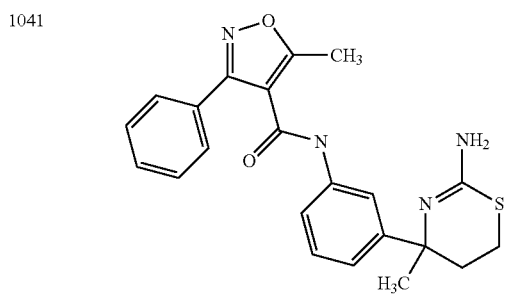
1042 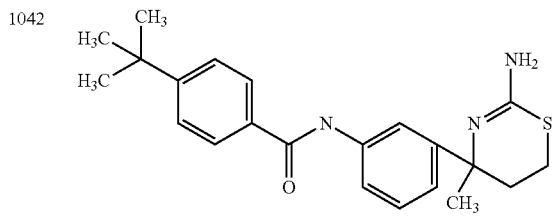
1043 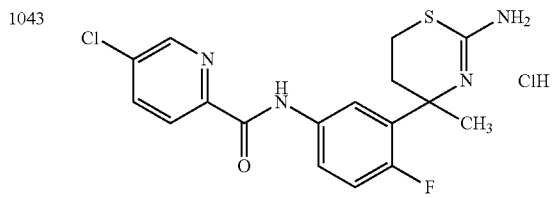
ClH
1044 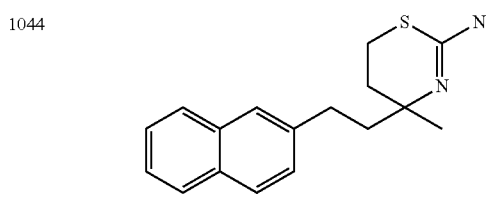
TABLE 111
1045 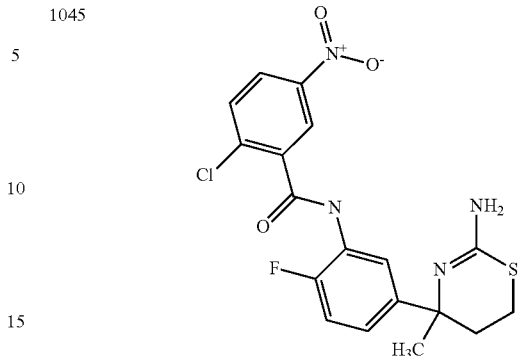
1046 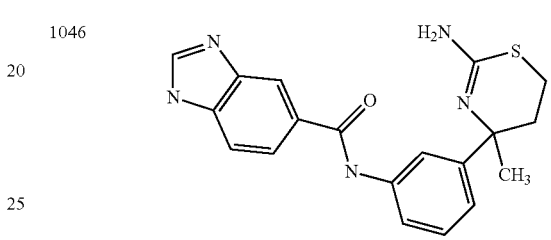
1047 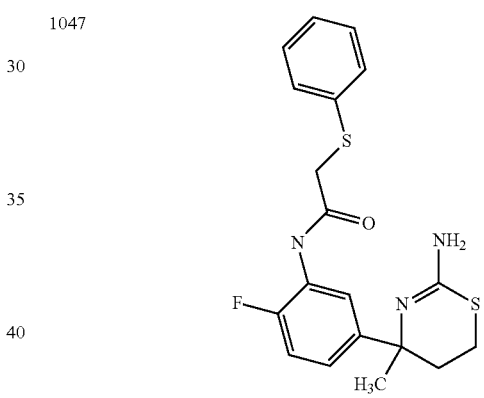
1048 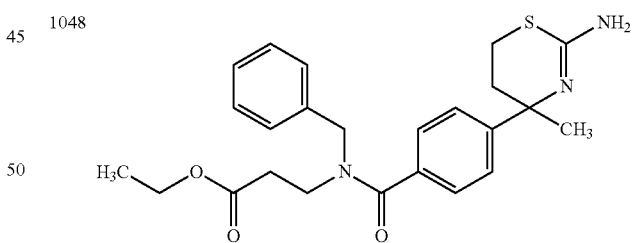
1049 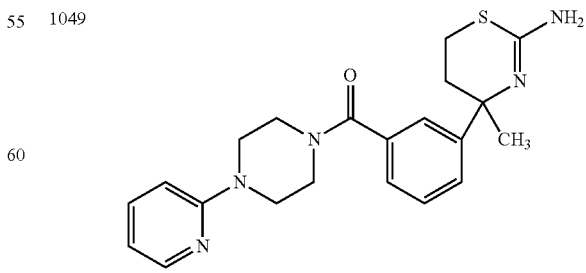

TABLE 111-continued
1050 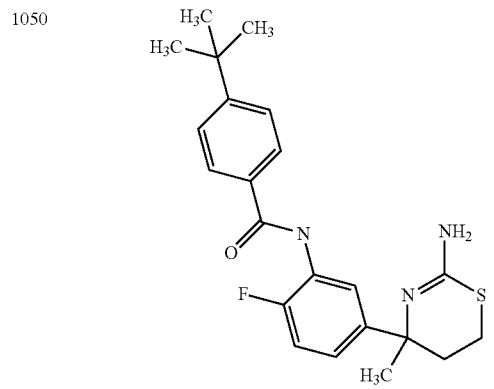
1051 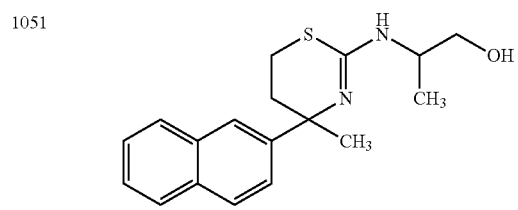
1052 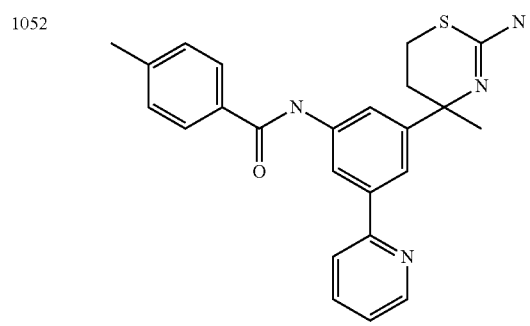
TABLE 112
1053 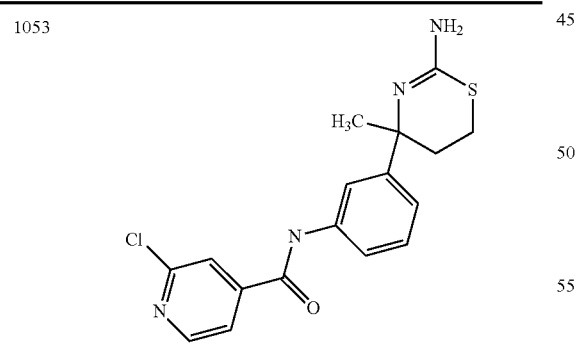
1054 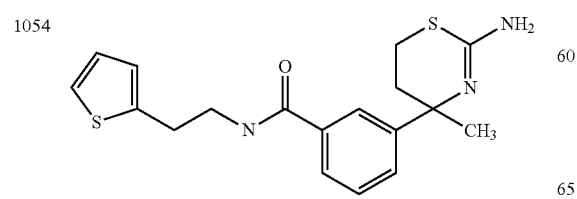
TABLE 112-continued
1055 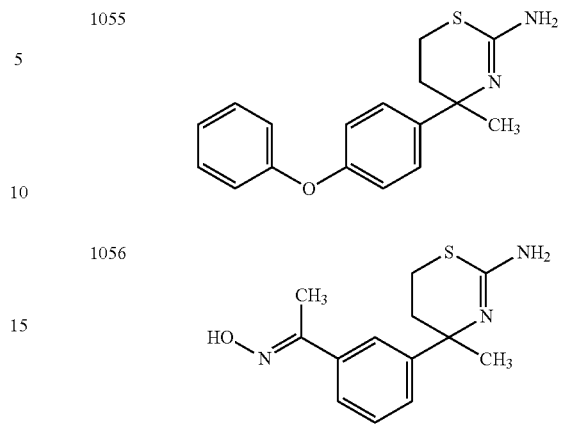
1056 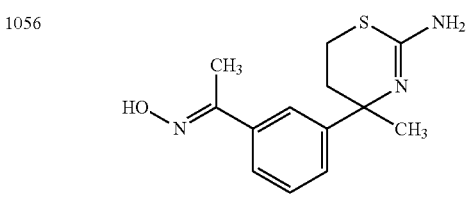
1057 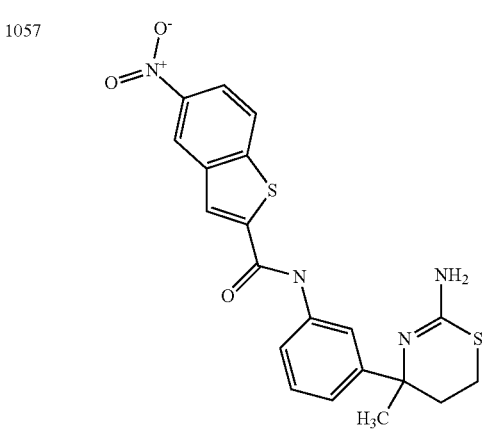
1058 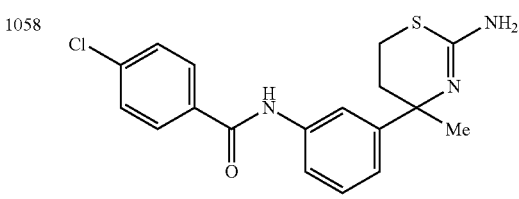
1059 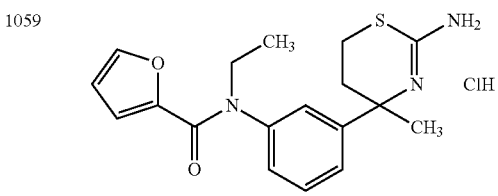
1060 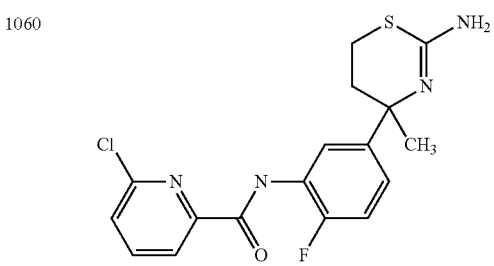

TABLE 112-continued
1061 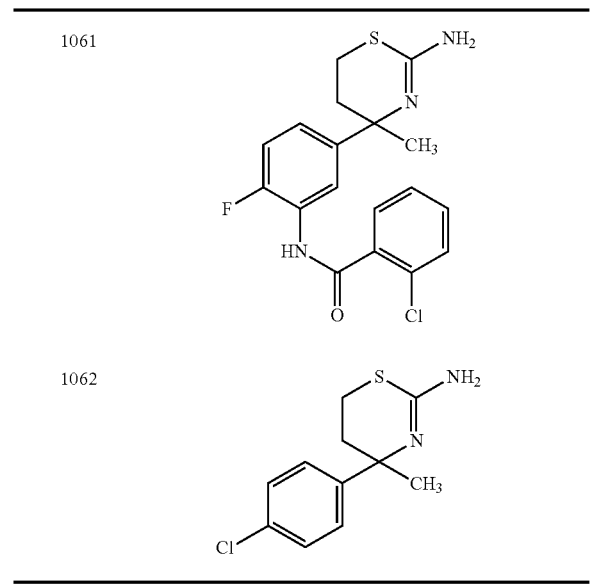
1062 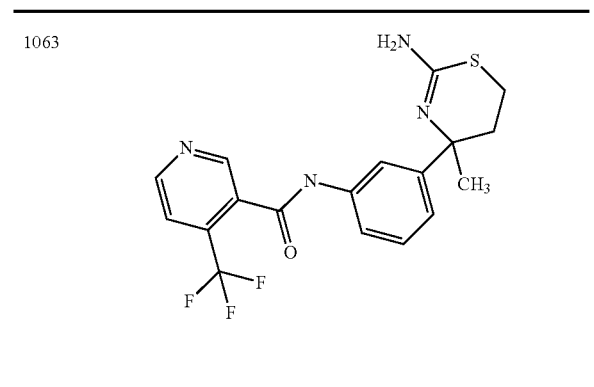
TABLE 113
1063 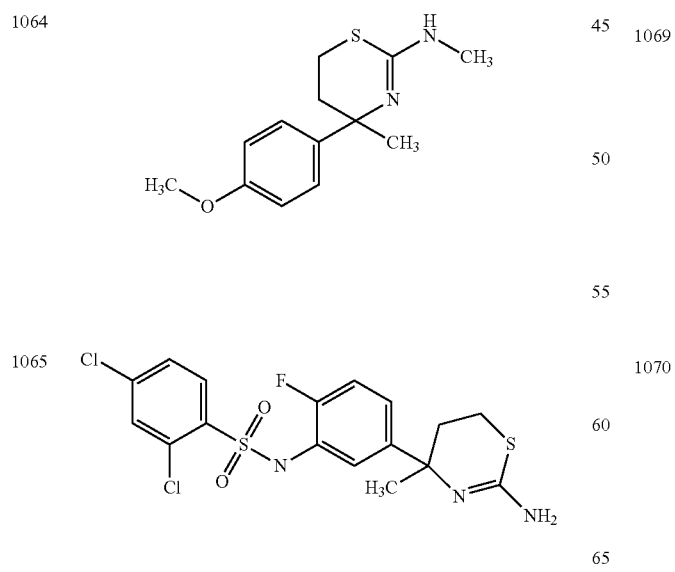
1064
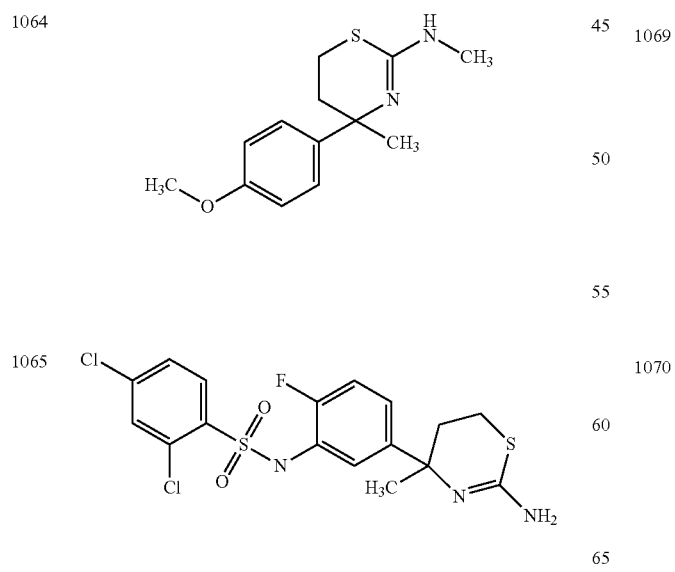
1065
TABLE 113-continued
1066 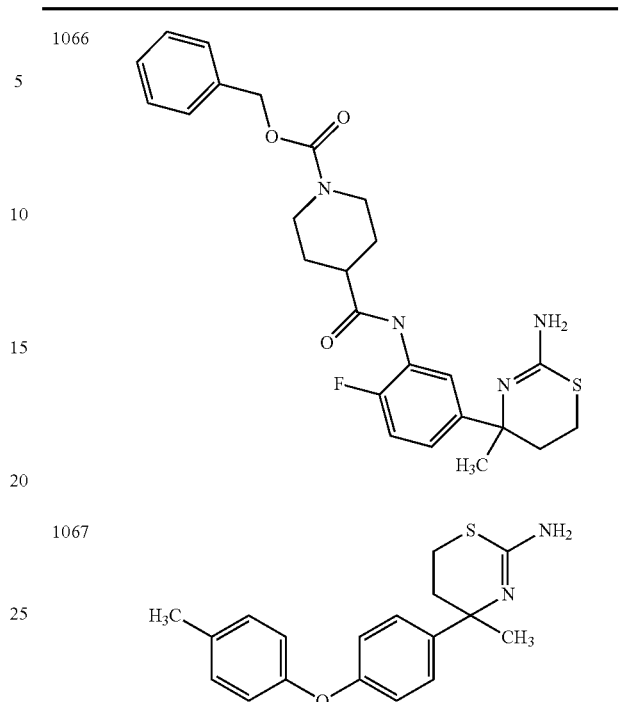
1067
1068 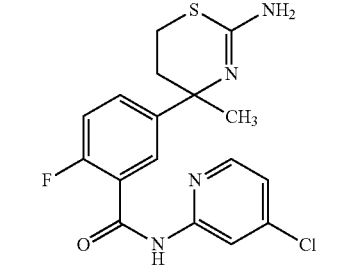 [SMILES: CC1(c2ccc(F)c(C(=O)Nc3cc(Cl)ccn3)c2)CCSC(N)=N1]
1069 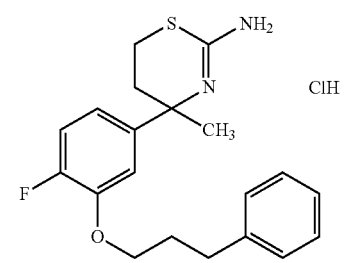 [SMILES: CC1(c2ccc(F)c(OCCCc3ccccc3)c2)CCSC(N)=N1 ; Cl]
1070 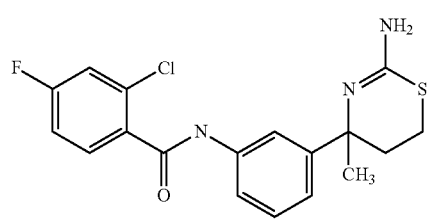 [SMILES: CC1(c2cccc(NC(=O)c3ccc(F)cc3Cl)c2)CCSC(N)=N1]

TABLE 113-continued
1071 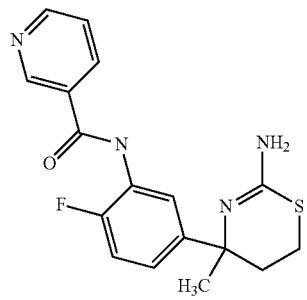 [SMILES: CC1(c2ccc(F)c(NC(=O)c3cccnc3)c2)CCSC(N)=N1]
TABLE 114
1072 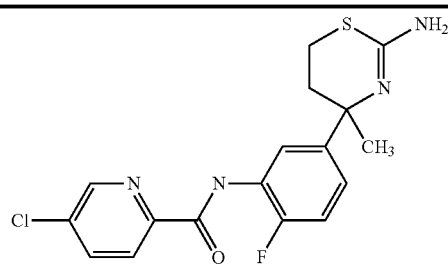
1073 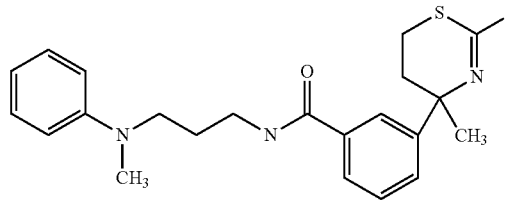
1074 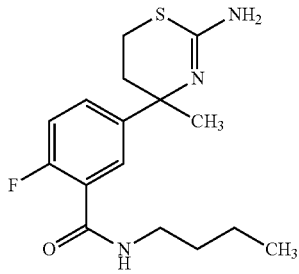 [SMILES: CCCCNC(=O)c1cc(C2(C)CCSC(N)=N2)ccc1F]
1075 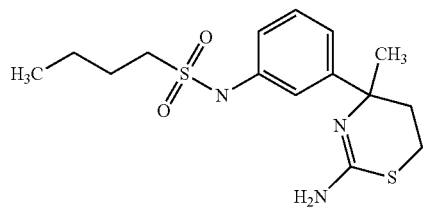 [SMILES: CCCCS(=O)(=O)Nc1cccc(C2(C)CCSC(N)=N2)c1]
1076 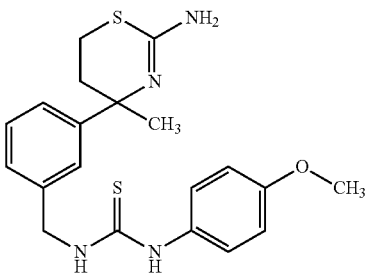 [SMILES: COc1ccc(NC(=S)NCc2cccc(C3(C)CCSC(N)=N3)c2)cc1]
TABLE 114-continued
1077 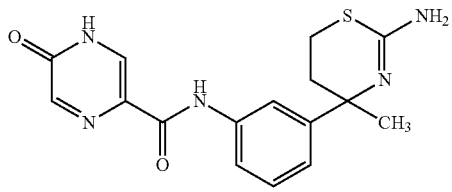 [SMILES: CC1(c2cccc(NC(=O)c3c[nH]c(=O)cn3)c2)CCSC(N)=N1]
1078 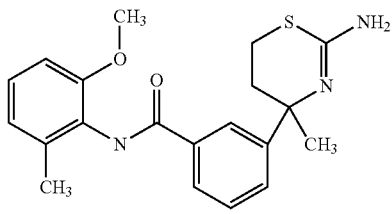 [SMILES: COc1cccc(C)c1NC(=O)c1cccc(C2(C)CCSC(N)=N2)c1]
1079 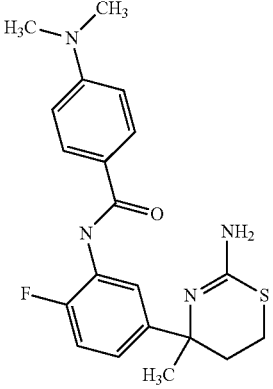 [SMILES: CN(C)c1ccc(C(=O)Nc2cc(C3(C)CCSC(N)=N3)ccc2F)cc1]
1080 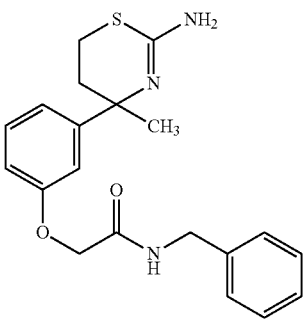 [SMILES: CC1(c2cccc(OCC(=O)NCc3ccccc3)c2)CCSC(N)=N1]
TABLE 115
1081 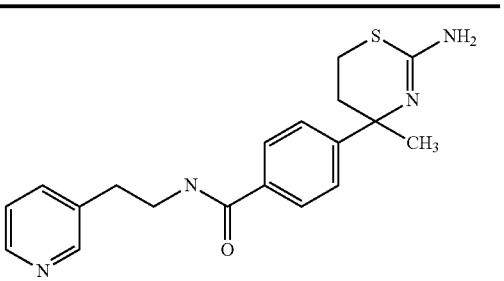

TABLE 115-continued
| | |
|---|---|
| 1082 | 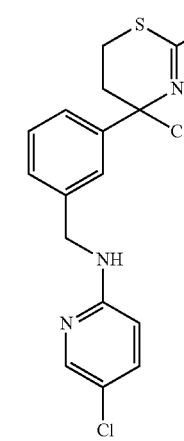 |
| 1083 | |
| 1084 | |
| 1085 | |
| 1086 | |
| 1087 | |
TABLE 115-continued
| | |
|---|---|
| 1088 | 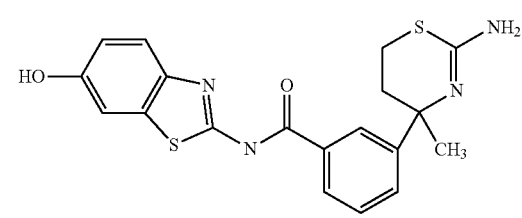 [SMILES: CC1(c2cccc(C(=O)Nc3nc4ccc(O)cc4s3)c2)CCSC(N)=N1] |
| 1089 | |
| 1090 | |
TABLE 116
| | |
|---|---|
| 1091 | |
| 1092 | |

TABLE 116-continued
1093 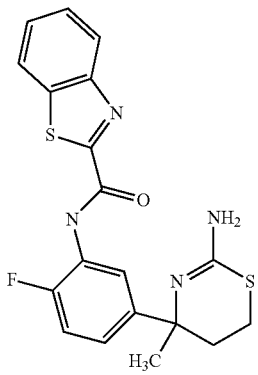 [SMILES: CC1(c2ccc(F)c(NC(=O)c3nc4ccccc4s3)c2)CCSC(N)=N1]
1094 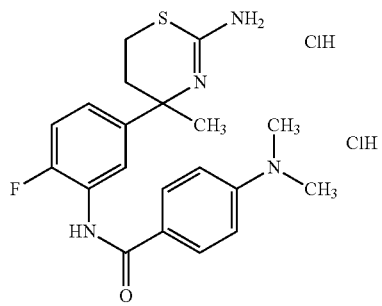 [SMILES: CN(C)c1ccc(C(=O)Nc2cc(C3(C)CCSC(N)=N3)ccc2F)cc1 ; Cl ; Cl]
1095 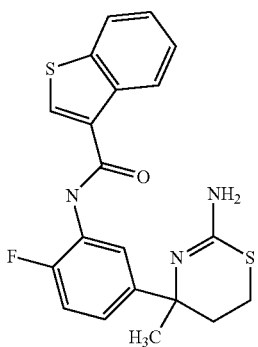 [SMILES: CC1(c2ccc(F)c(NC(=O)c3csc4ccccc34)c2)CCSC(N)=N1]
1096 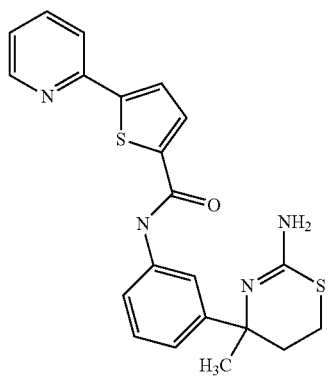 [SMILES: CC1(c2cccc(NC(=O)c3ccc(-c4ccccn4)s3)c2)CCSC(N)=N1]
1097 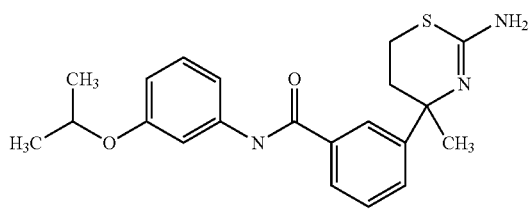 [SMILES: CC(C)Oc1cccc(NC(=O)c2cccc(C3(C)CCSC(N)=N3)c2)c1]
TABLE 116-continued
1098 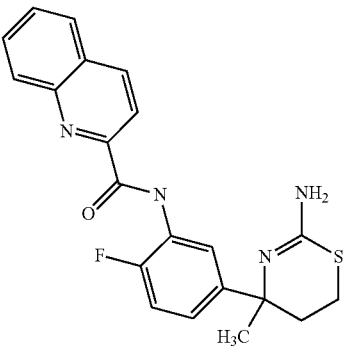 [SMILES: CC1(c2ccc(F)c(NC(=O)c3ccc4ccccc4n3)c2)CCSC(N)=N1]
TABLE 117
1099 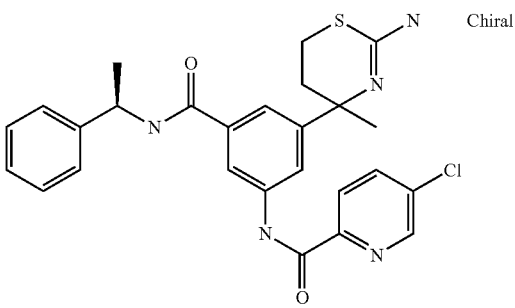 [SMILES: C[C@@H](NC(=O)c1cc(NC(=O)c2ccc(Cl)cn2)cc(C2(C)CCSC(N)=N2)c1)c1ccccc1 ; "Chiral"]
1100 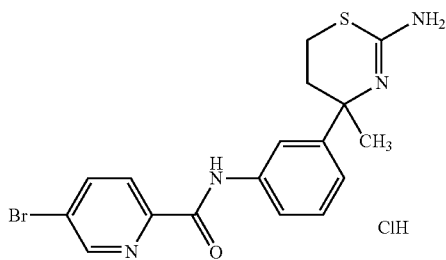
1101 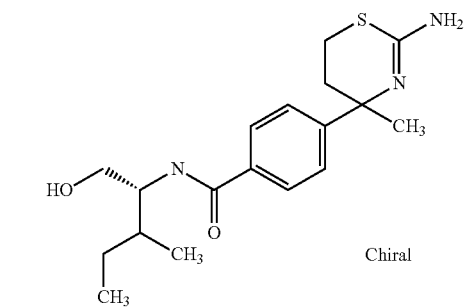 [SMILES: CCC(C)[C@H](CO)NC(=O)c1ccc(C2(C)CCSC(N)=N2)cc1 ; "Chiral"]

TABLE 117-continued
1102 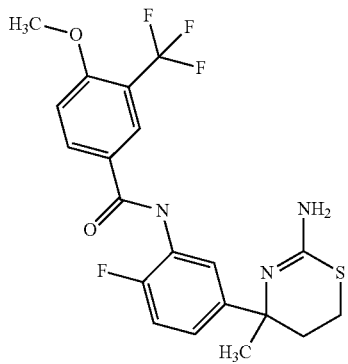 [SMILES: COc1ccc(C(=O)Nc2cc(C3(C)CCSC(N)=N3)ccc2F)cc1C(F)(F)F]
1103 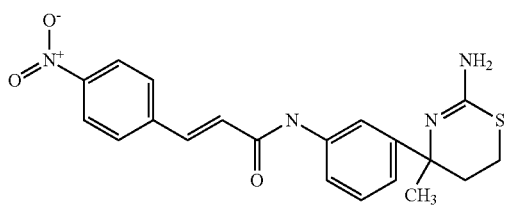 [SMILES: CC1(c2cccc(NC(=O)/C=C/c3ccc([N+](=O)[O-])cc3)c2)CCSC(N)=N1]
1105 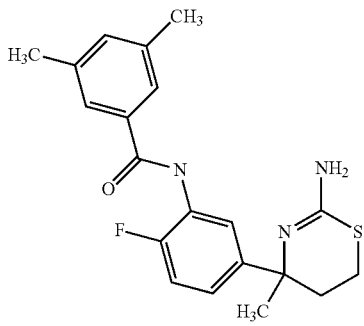 [SMILES: Cc1cc(C)cc(C(=O)Nc2cc(C3(C)CCSC(N)=N3)ccc2F)c1]
1106 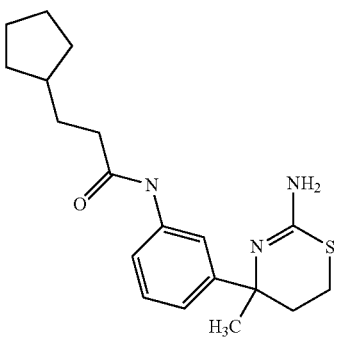 [SMILES: CC1(c2cccc(NC(=O)CCC3CCCC3)c2)CCSC(N)=N1]
1107 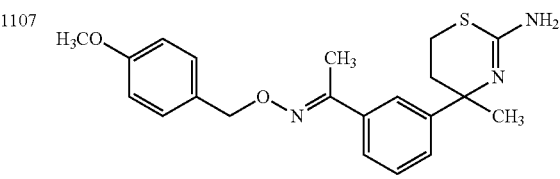
TABLE 118
1108 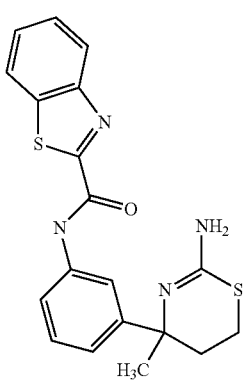
1109 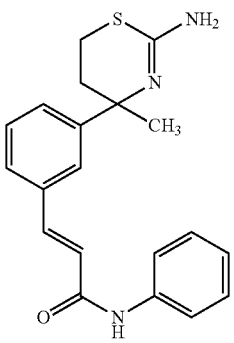 [SMILES: CC1(c2cccc(/C=C/C(=O)Nc3ccccc3)c2)CCSC(N)=N1]
1110 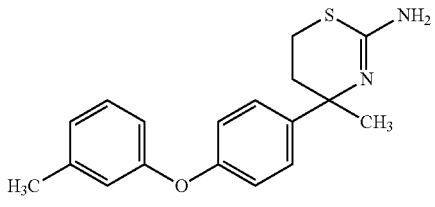 [SMILES: Cc1cccc(Oc2ccc(C3(C)CCSC(N)=N3)cc2)c1]
1111 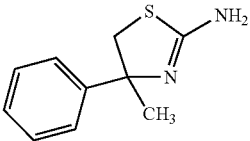
1112 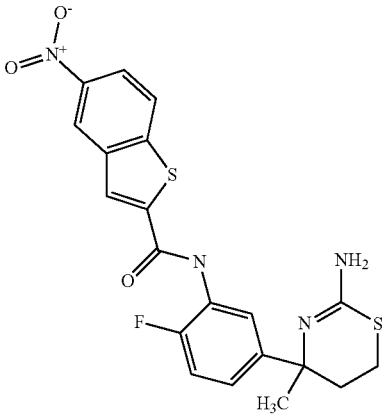 [SMILES: CC1(c2ccc(F)c(NC(=O)c3cc4cc([N+](=O)[O-])ccc4s3)c2)CCSC(N)=N1]

TABLE 118-continued
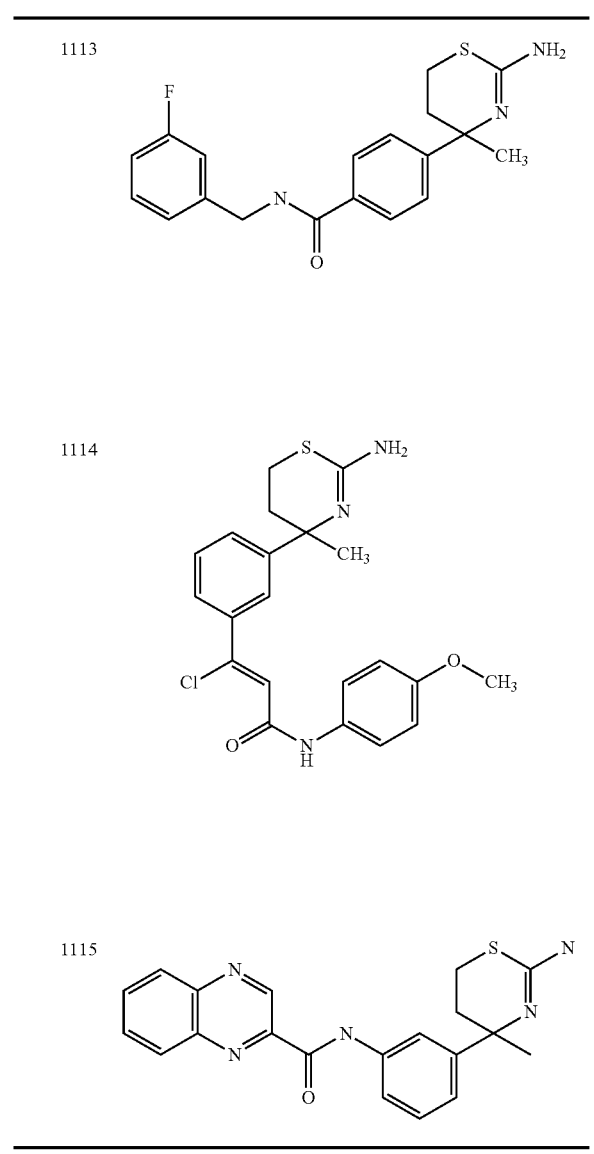
TABLE 119
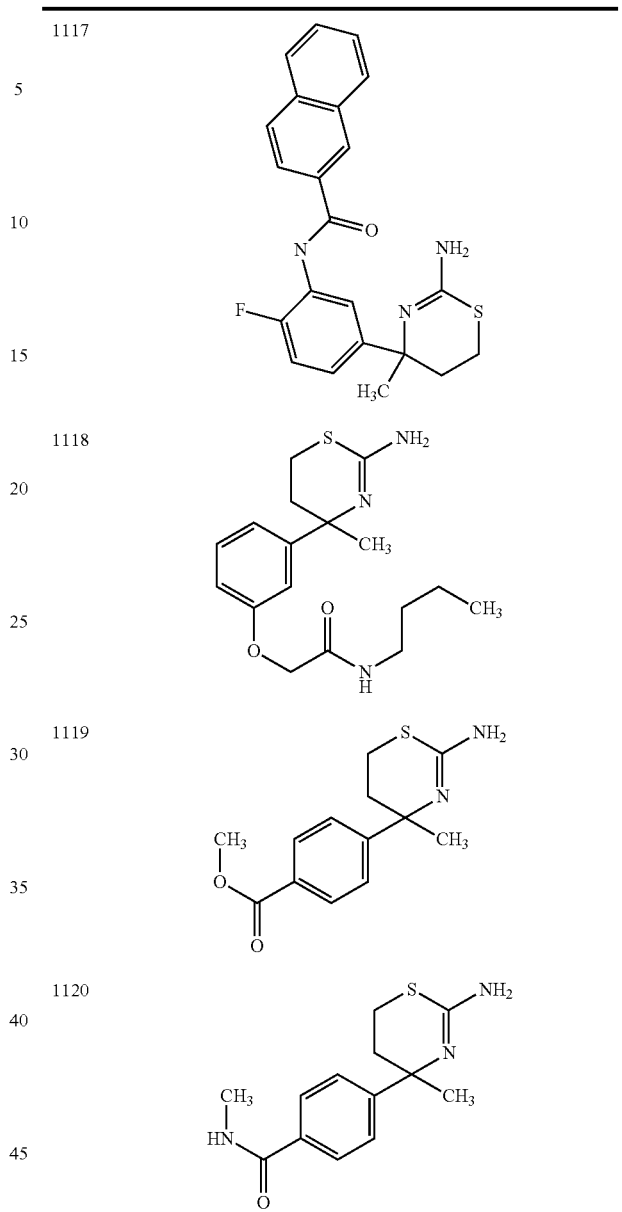
TABLE 119-continued
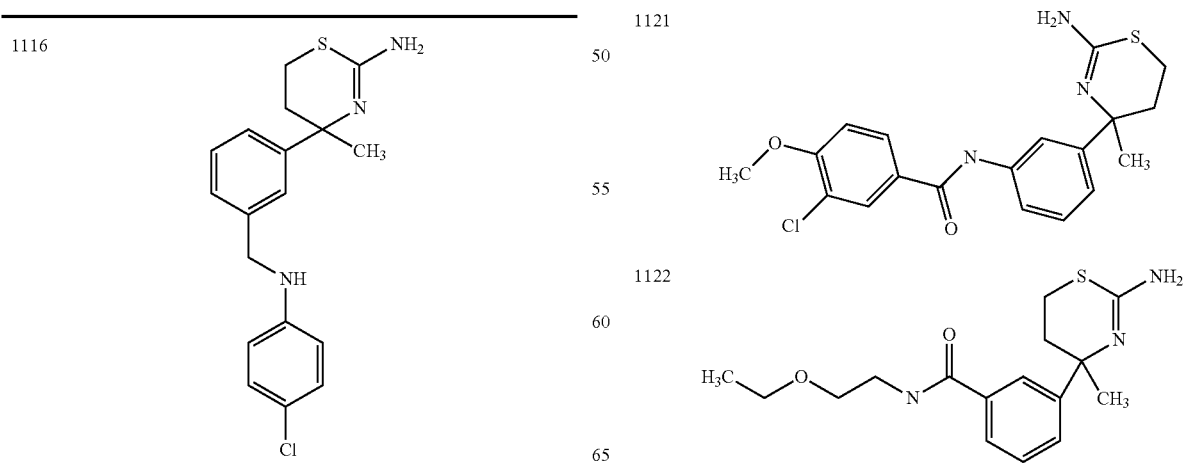

TABLE 119-continued
1123 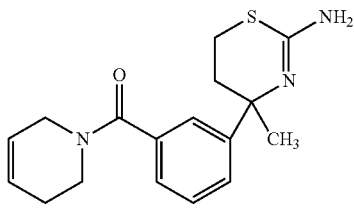 [SMILES: CC1(c2cccc(C(=O)N3CC=CCC3)c2)CCSC(N)=N1]
1124 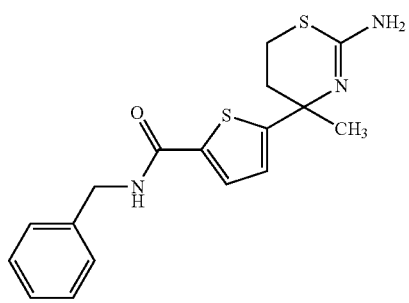 [SMILES: CC1(c2ccc(C(=O)NCc3ccccc3)s2)CCSC(N)=N1]
TABLE 120
1125 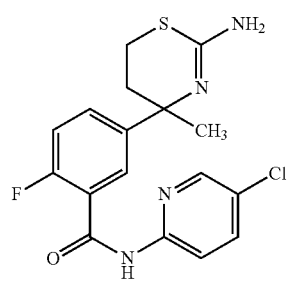 [SMILES: CC1(c2ccc(F)c(C(=O)Nc3ccc(Cl)cn3)c2)CCSC(N)=N1]
1126 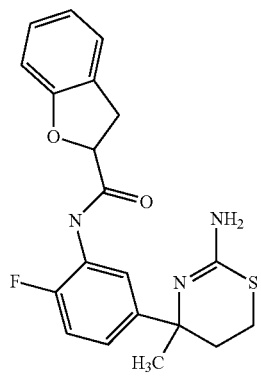 [SMILES: CC1(c2ccc(F)c(NC(=O)C3Cc4ccccc4O3)c2)CCSC(N)=N1]
1127 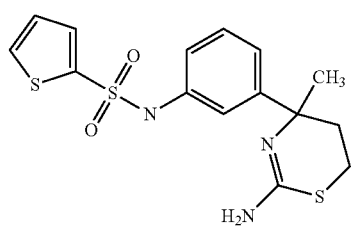 [SMILES: CC1(c2cccc(NS(=O)(=O)c3cccs3)c2)CCSC(N)=N1]
TABLE 120-continued
1128 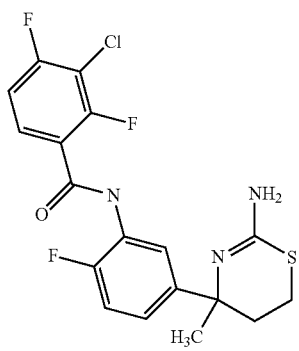 [SMILES: CC1(c2ccc(F)c(NC(=O)c3ccc(F)c(Cl)c3F)c2)CCSC(N)=N1]
1129 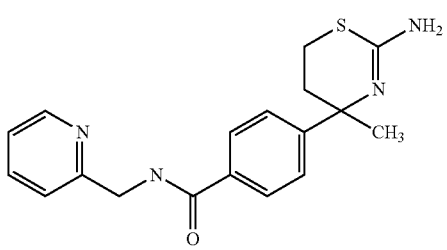 [SMILES: CC1(c2ccc(C(=O)NCc3ccccn3)cc2)CCSC(N)=N1]
1130 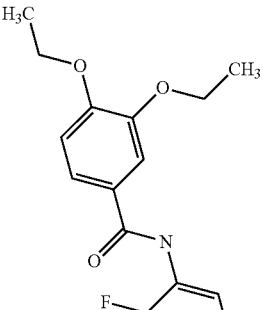
1131 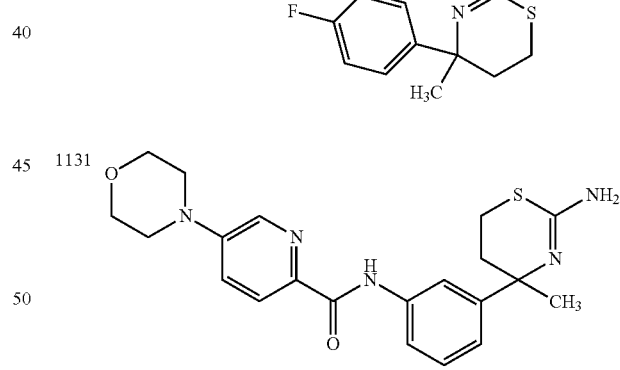
1132 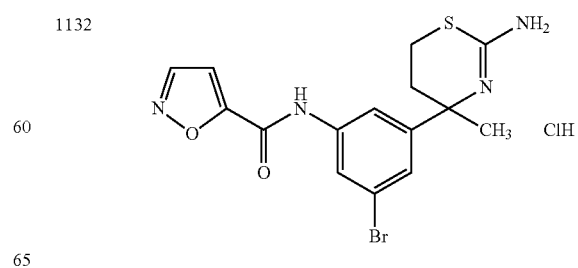

TABLE 121
1133 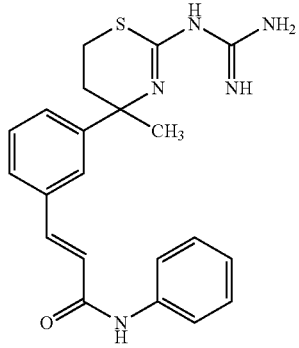 [SMILES: CC1(c2cccc(/C=C/C(=O)Nc3ccccc3)c2)CCSC(NC(=N)N)=N1]
1134 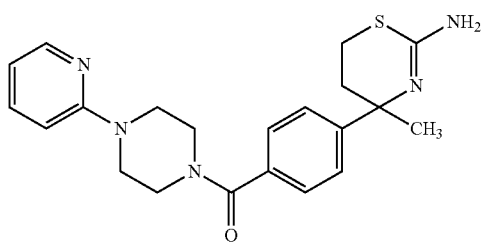 [SMILES: CC1(c2ccc(C(=O)N3CCN(c4ccccn4)CC3)cc2)CCSC(N)=N1]
1135 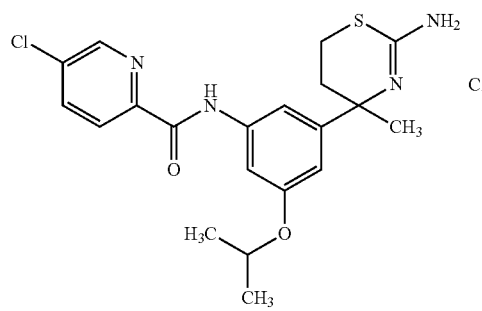 ClH
1136 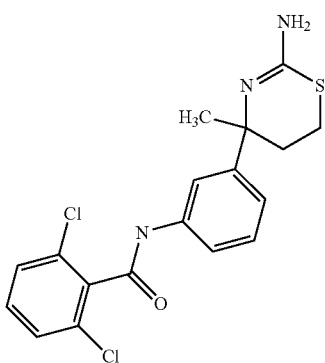
1137 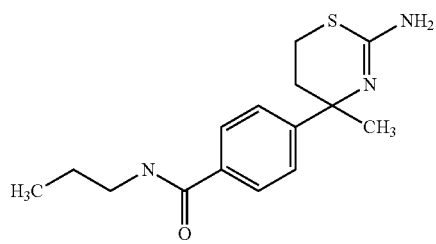 [SMILES: CCCNC(=O)c1ccc(C2(C)CCSC(N)=N2)cc1]
TABLE 121-continued
1138 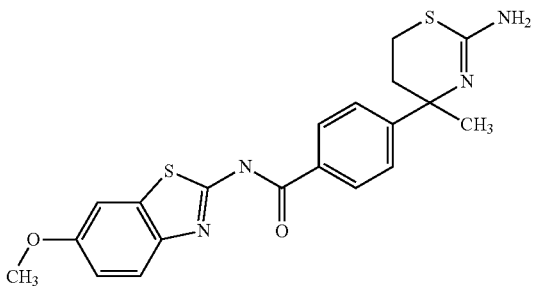 [SMILES: COc1ccc2nc(NC(=O)c3ccc(C4(C)CCSC(N)=N4)cc3)sc2c1]
1139 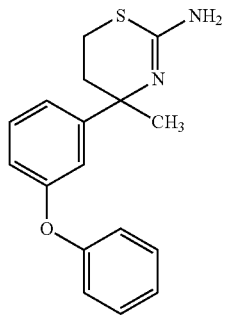 [SMILES: CC1(c2cccc(Oc3ccccc3)c2)CCSC(N)=N1]
1140 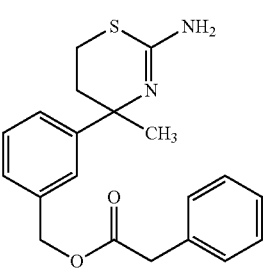 [SMILES: CC1(c2cccc(COC(=O)Cc3ccccc3)c2)CCSC(N)=N1]
TABLE 122
1141 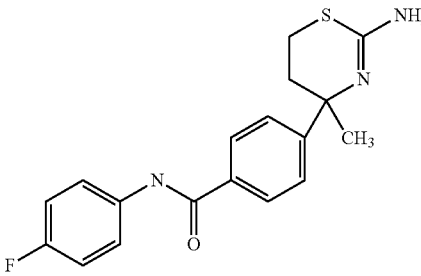
1142 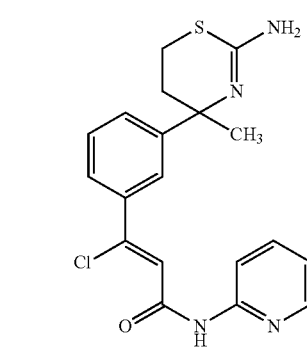

TABLE 122-continued
1143 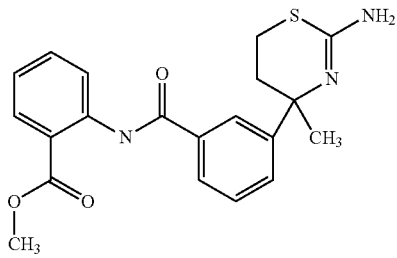 [SMILES: COC(=O)c1ccccc1NC(=O)c1cccc(C2(C)CCSC(N)=N2)c1]
1144 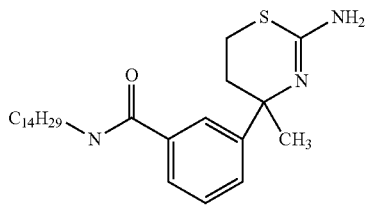
1145 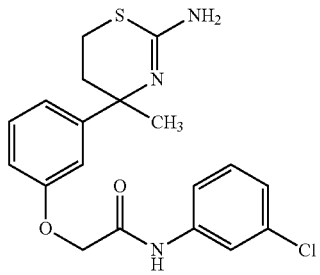 [SMILES: CC1(c2cccc(OCC(=O)Nc3cccc(Cl)c3)c2)CCSC(N)=N1]
1146 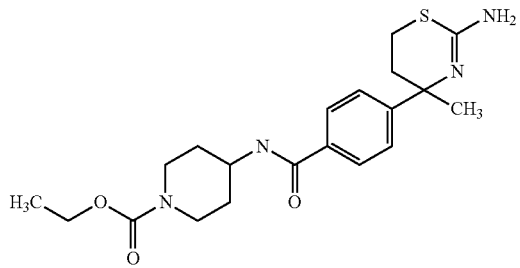 [SMILES: CCOC(=O)N1CCC(NC(=O)c2ccc(C3(C)CCSC(N)=N3)cc2)CC1]
1147 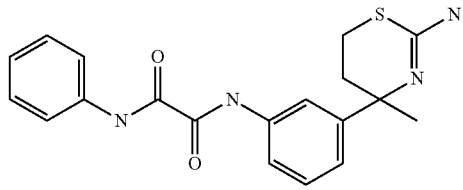 [SMILES: CC1(c2cccc(NC(=O)C(=O)Nc3ccccc3)c2)CCSC(N)=N1]
1148 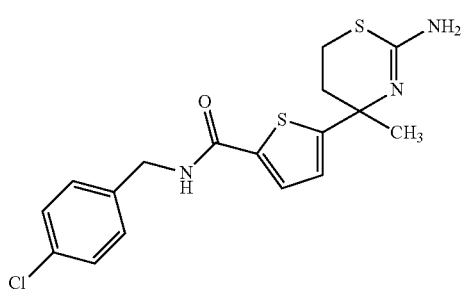 [SMILES: CC1(c2ccc(C(=O)NCc3ccc(Cl)cc3)s2)CCSC(N)=N1]
TABLE 122-continued
1149 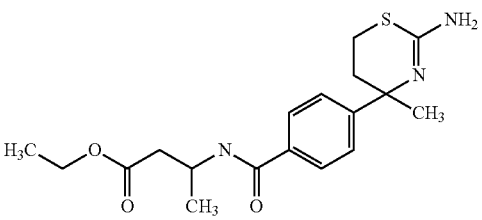 [SMILES: CCOC(=O)CC(C)NC(=O)c1ccc(C2(C)CCSC(N)=N2)cc1]
1150 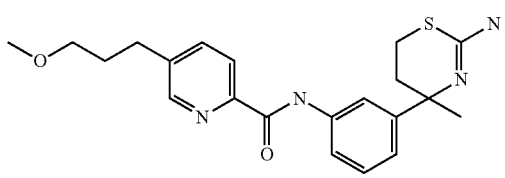 [SMILES: COCCCc1ccc(C(=O)Nc2cccc(C3(C)CCSC(N)=N3)c2)nc1]
1151 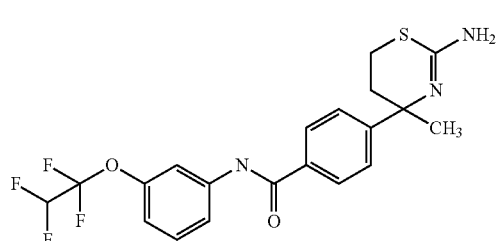
1152 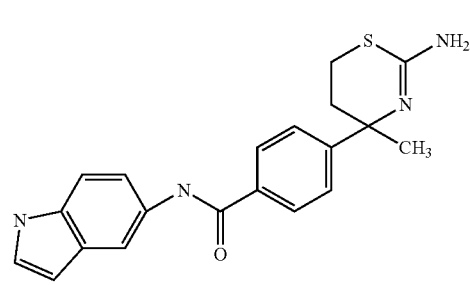 [SMILES: CC1(c2ccc(C(=O)Nc3ccc4[nH]ccc4c3)cc2)CCSC(N)=N1]
TABLE 123
1153 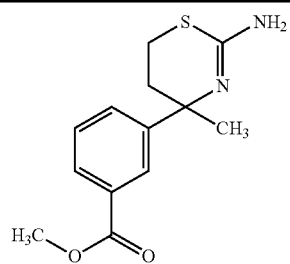
1154 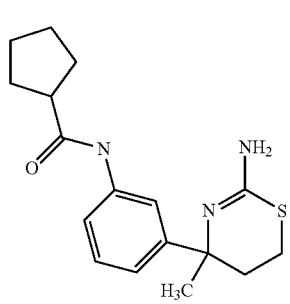 [SMILES: CC1(c2cccc(NC(=O)C3CCCC3)c2)CCSC(N)=N1]

TABLE 123-continued
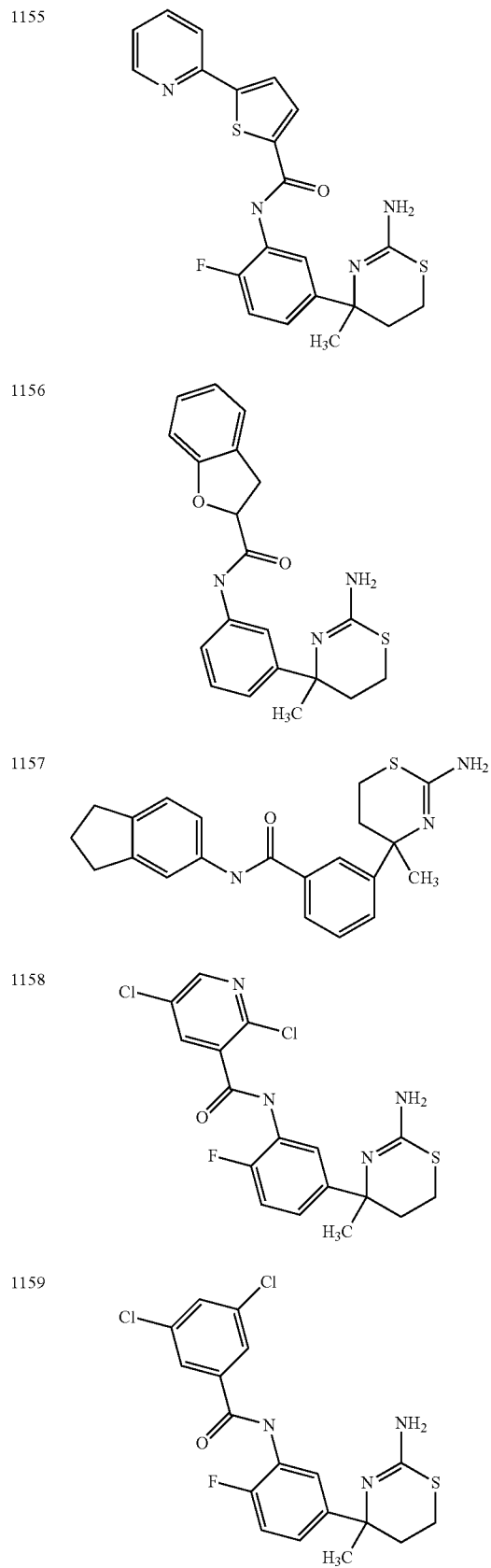
TABLE 123-continued
TABLE 124
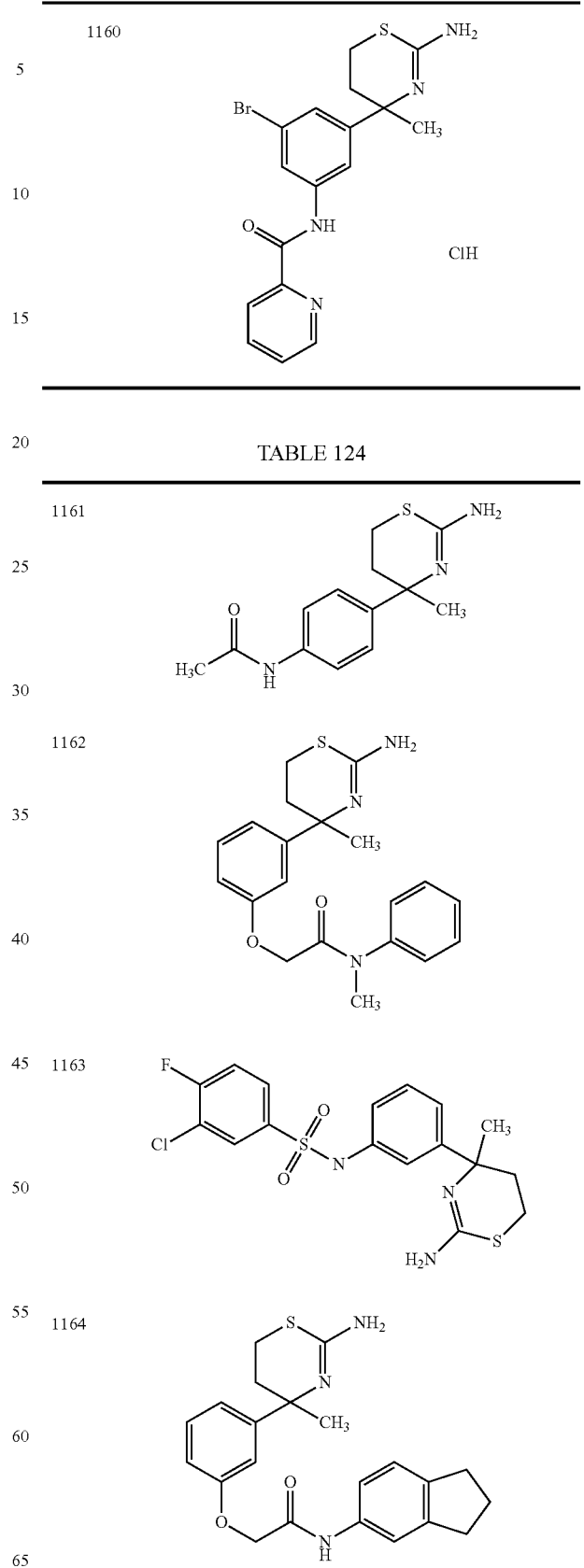

TABLE 124-continued
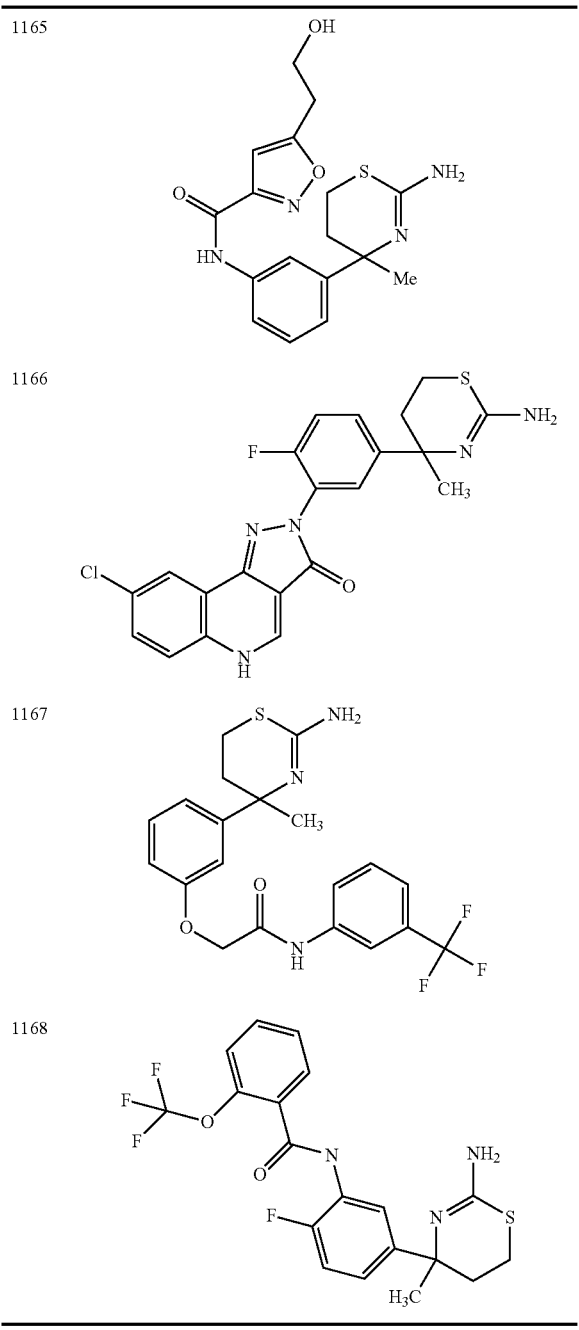
TABLE 125
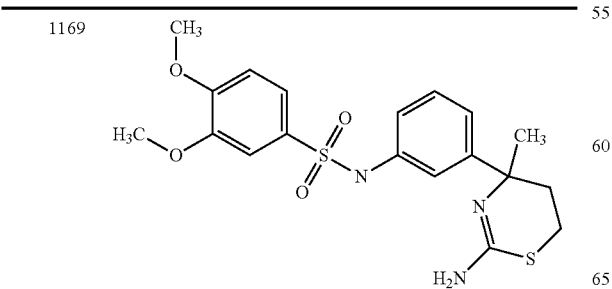
TABLE 125-continued
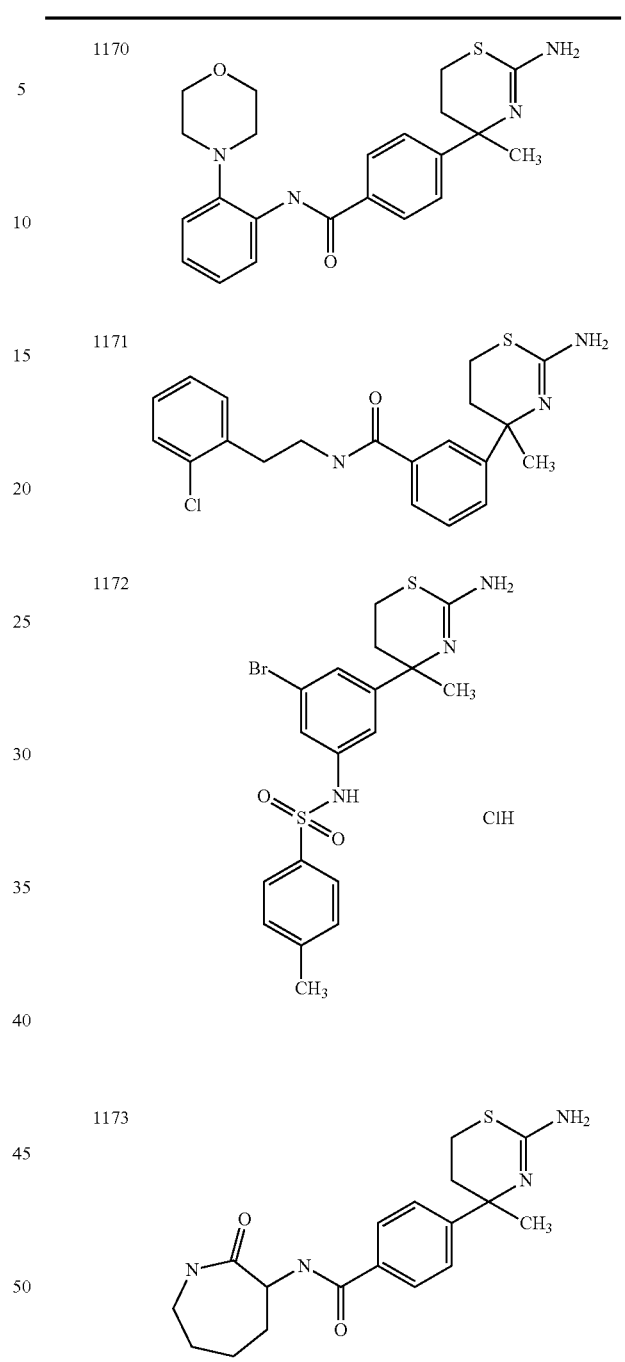
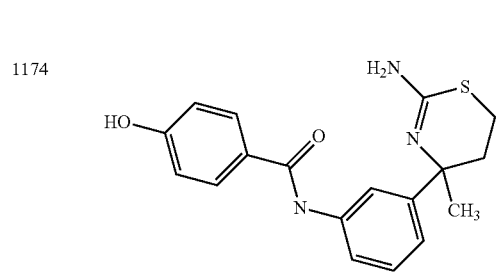

301
TABLE 125-continued
1175
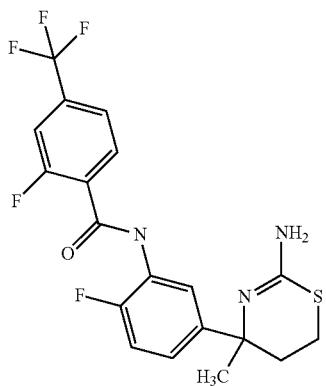 [SMILES: CC1(c2ccc(F)c(NC(=O)c3ccc(C(F)(F)F)cc3F)c2)CCSC(N)=N1]
1176
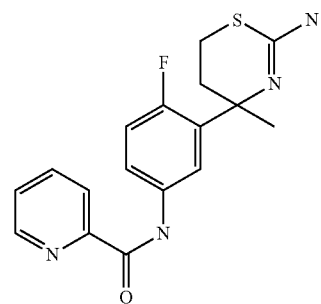 [SMILES: CC1(c2cc(NC(=O)c3ccccn3)ccc2F)CCSC(N)=N1]
1177
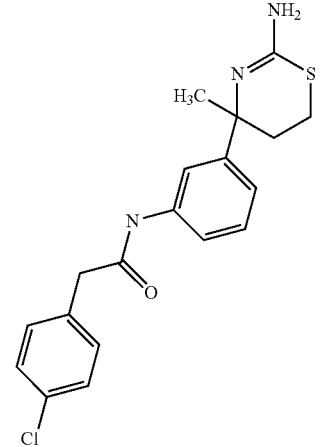 [SMILES: CC1(c2cccc(NC(=O)Cc3ccc(Cl)cc3)c2)CCSC(N)=N1]
TABLE 126
1178
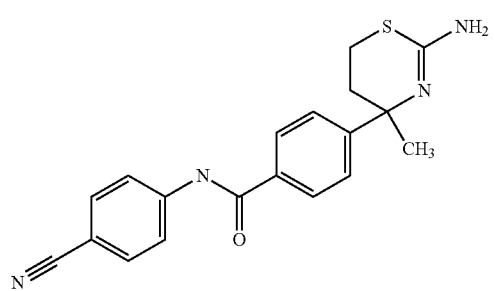 [SMILES: CC1(c2ccc(C(=O)Nc3ccc(C#N)cc3)cc2)CCSC(N)=N1]
302
TABLE 126-continued
1179
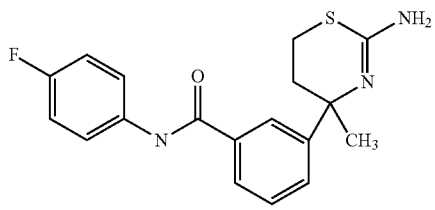 [SMILES: CC1(c2cccc(C(=O)Nc3ccc(F)cc3)c2)CCSC(N)=N1]
1180
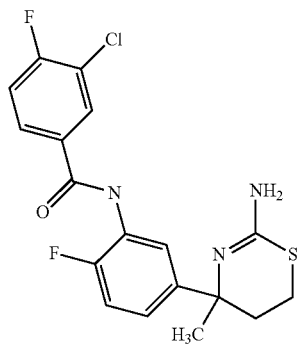 [SMILES: CC1(c2ccc(F)c(NC(=O)c3ccc(F)c(Cl)c3)c2)CCSC(N)=N1]
1181
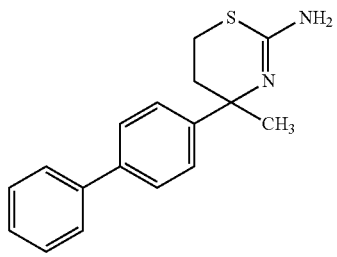 [SMILES: CC1(c2ccc(-c3ccccc3)cc2)CCSC(N)=N1]
1182
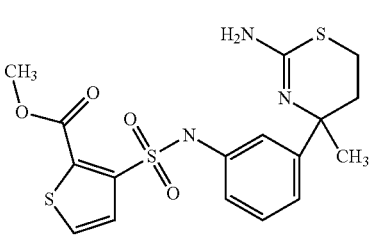 [SMILES: COC(=O)c1sccc1S(=O)(=O)Nc1cccc(C2(C)CCSC(N)=N2)c1]
1183
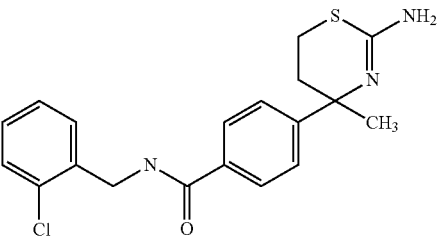 [SMILES: CC1(c2ccc(C(=O)NCc3ccccc3Cl)cc2)CCSC(N)=N1]
1184
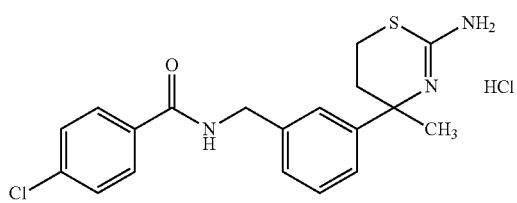 [SMILES: CC1(c2cccc(CNC(=O)c3ccc(Cl)cc3)c2)CCSC(N)=N1 ; Cl]

TABLE 126-continued
1185 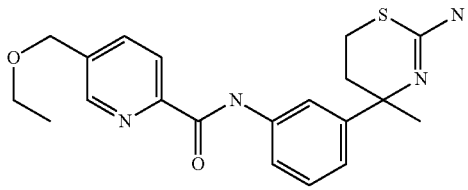 [SMILES: CCOCc1ccc(C(=O)Nc2cccc(C3(C)CCSC(N)=N3)c2)nc1]
1186 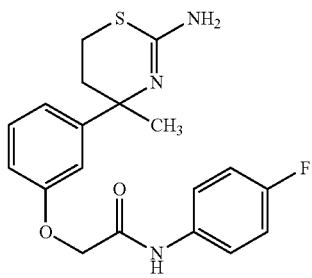 [SMILES: CC1(c2cccc(OCC(=O)Nc3ccc(F)cc3)c2)CCSC(N)=N1]
1187 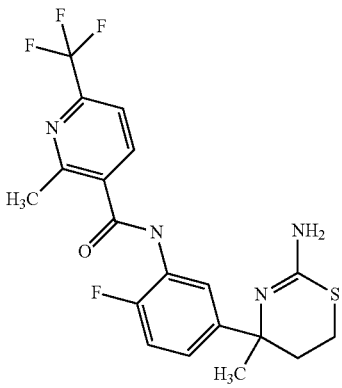 [SMILES: Cc1nc(C(F)(F)F)ccc1C(=O)Nc1cc(C2(C)CCSC(N)=N2)ccc1F]
1188 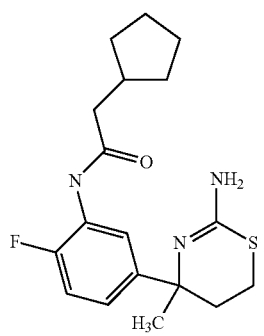 [SMILES: CC1(c2ccc(F)c(NC(=O)CC3CCCC3)c2)CCSC(N)=N1]
TABLE 127
1189 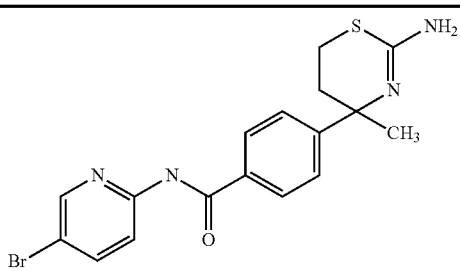
TABLE 127-continued
1190 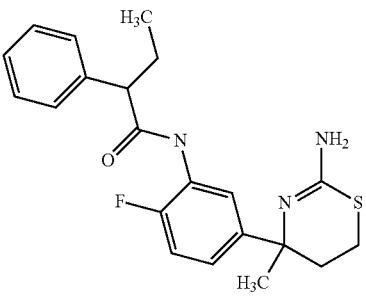 [SMILES: CCC(C(=O)Nc1cc(C2(C)CCSC(N)=N2)ccc1F)c1ccccc1]
1191 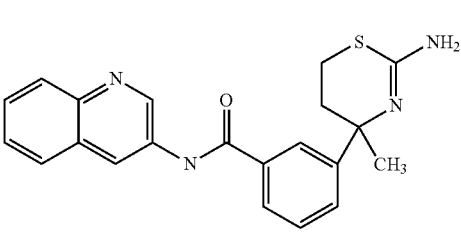 [SMILES: CC1(c2cccc(C(=O)Nc3cnc4ccccc4c3)c2)CCSC(N)=N1]
1192 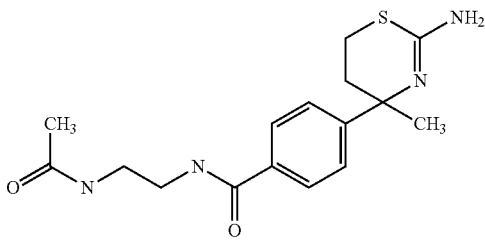 [SMILES: CC(=O)NCCNC(=O)c1ccc(C2(C)CCSC(N)=N2)cc1]
1193 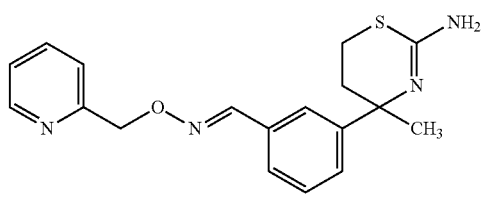 [SMILES: CC1(c2cccc(/C=N/OCc3ccccn3)c2)CCSC(N)=N1]
1194 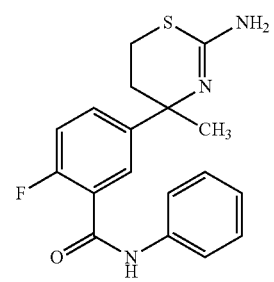 [SMILES: CC1(c2ccc(F)c(C(=O)Nc3ccccc3)c2)CCSC(N)=N1]
1195 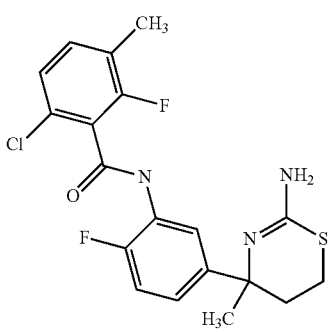 [SMILES: Cc1ccc(Cl)c(C(=O)Nc2cc(C3(C)CCSC(N)=N3)ccc2F)c1F]

TABLE 127-continued
1196 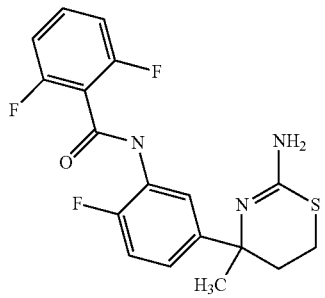 [SMILES: CC1(c2ccc(F)c(NC(=O)c3c(F)cccc3F)c2)CCSC(N)=N1]
1197 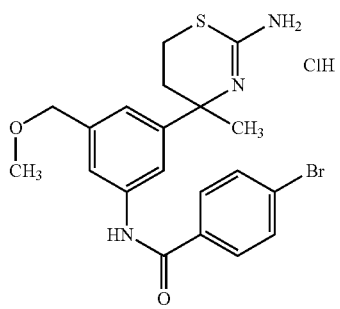 [SMILES: COCc1cc(NC(=O)c2ccc(Br)cc2)cc(C2(C)CCSC(N)=N2)c1 ; Cl]
1198 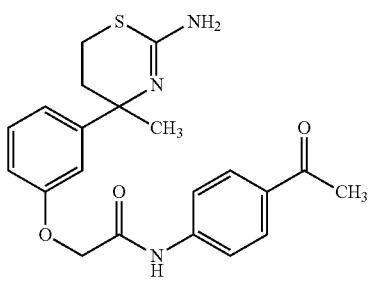 [SMILES: CC(=O)c1ccc(NC(=O)COc2cccc(C3(C)CCSC(N)=N3)c2)cc1]
TABLE 128
1199 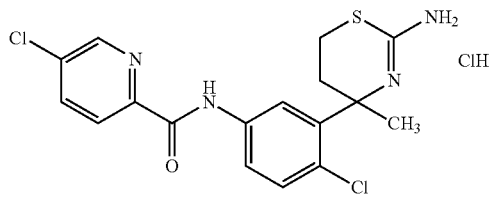 [SMILES: CC1(c2cc(NC(=O)c3ccc(Cl)cn3)ccc2Cl)CCSC(N)=N1 ; Cl]
1200 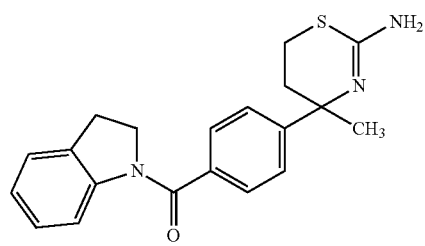 [SMILES: CC1(c2ccc(C(=O)N3CCc4ccccc43)cc2)CCSC(N)=N1]
TABLE 128-continued
1201 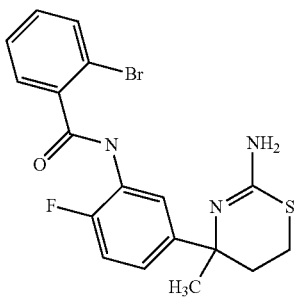 [SMILES: CC1(c2ccc(F)c(NC(=O)c3ccccc3Br)c2)CCSC(N)=N1]
1202 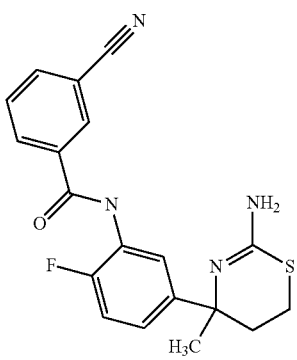 [SMILES: CC1(c2ccc(F)c(NC(=O)c3cccc(C#N)c3)c2)CCSC(N)=N1]
1203 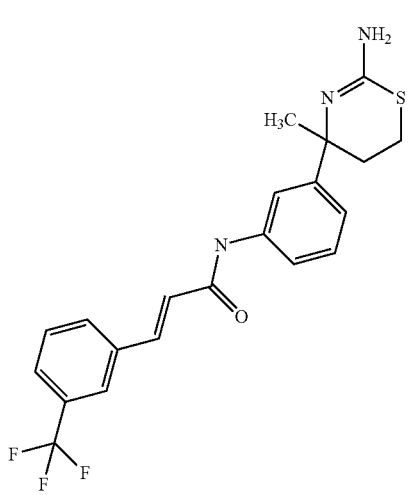 [SMILES: CC1(c2cccc(NC(=O)/C=C/c3cccc(C(F)(F)F)c3)c2)CCSC(N)=N1]
1204 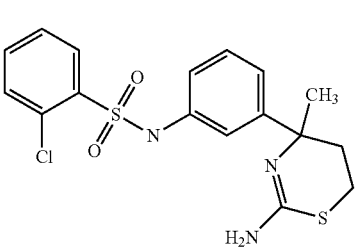 [SMILES: CC1(c2cccc(NS(=O)(=O)c3ccccc3Cl)c2)CCSC(N)=N1]

TABLE 128-continued
1205 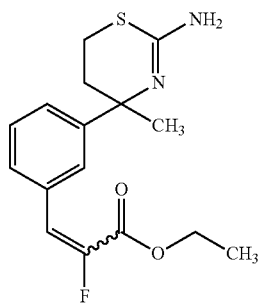 [SMILES: CCOC(=O)C(F)=Cc1cccc(C2(C)CCSC(N)=N2)c1]
1206 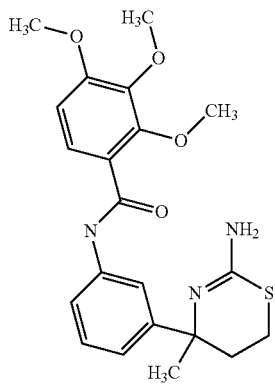 [SMILES: COc1ccc(C(=O)Nc2cccc(C3(C)CCSC(N)=N3)c2)c(OC)c1OC]
1207 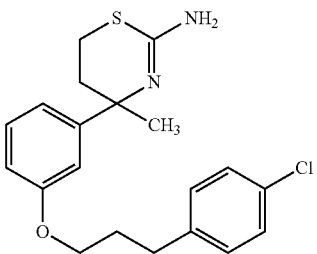 [SMILES: CC1(c2cccc(OCCCc3ccc(Cl)cc3)c2)CCSC(N)=N1]
TABLE 129
1208 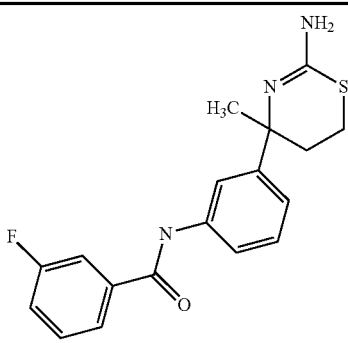
1209 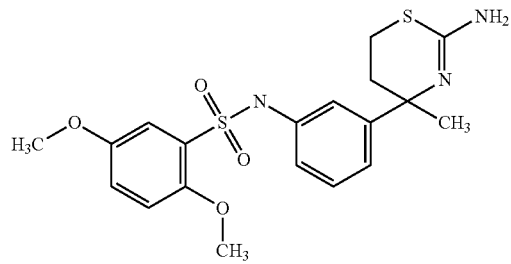 [SMILES: COc1ccc(OC)c(S(=O)(=O)Nc2cccc(C3(C)CCSC(N)=N3)c2)c1]
TABLE 129-continued
1210 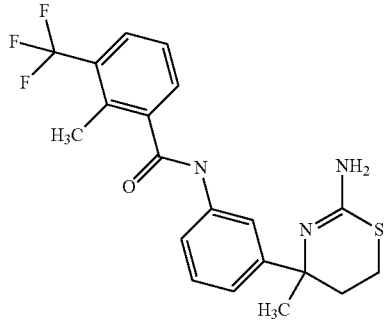 [SMILES: Cc1c(C(=O)Nc2cccc(C3(C)CCSC(N)=N3)c2)cccc1C(F)(F)F]
1211 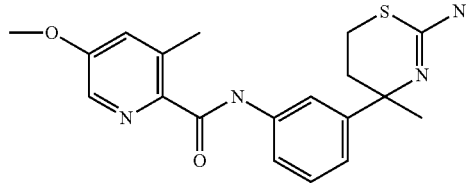 [SMILES: COc1cnc(C(=O)Nc2cccc(C3(C)CCSC(N)=N3)c2)c(C)c1]
1212 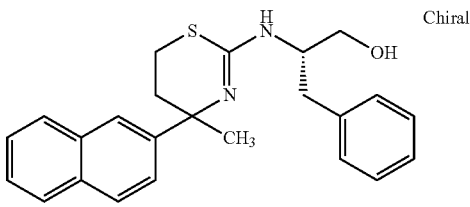 [SMILES: "Chiral" ; CC1(c2ccc3ccccc3c2)CCSC(N[C@H](CO)Cc2ccccc2)=N1]
Chiral
1213 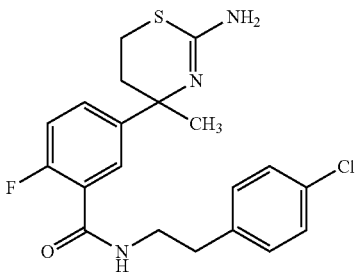 [SMILES: CC1(c2ccc(F)c(C(=O)NCCc3ccc(Cl)cc3)c2)CCSC(N)=N1]
1214 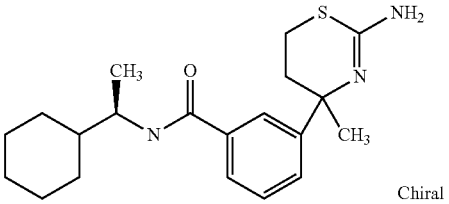 [SMILES: C[C@@H](NC(=O)c1cccc(C2(C)CCSC(N)=N2)c1)C1CCCCC1 ; "Chiral"]
Chiral
1215 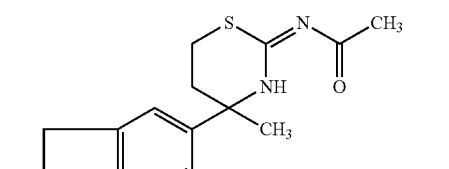
1216 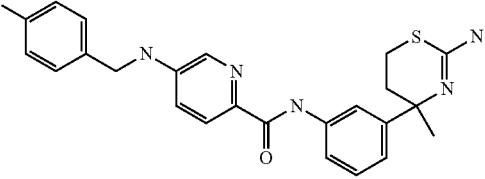

TABLE 129-continued
1217 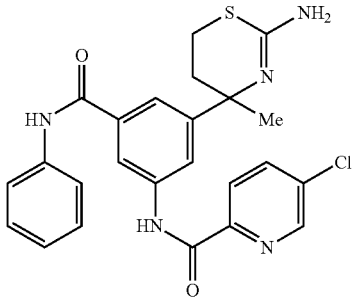 [SMILES: CC1(c2cc(NC(=O)c3ccc(Cl)cn3)cc(C(=O)Nc3ccccc3)c2)CCSC(N)=N1]
TABLE 130
1218 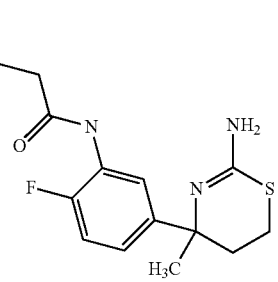
1219 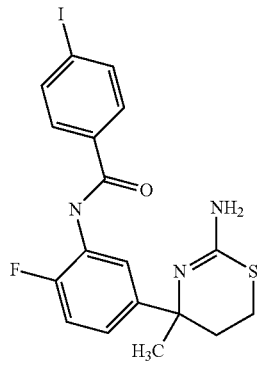 [SMILES: CC1(c2ccc(F)c(NC(=O)c3ccc(I)cc3)c2)CCSC(N)=N1]
1220 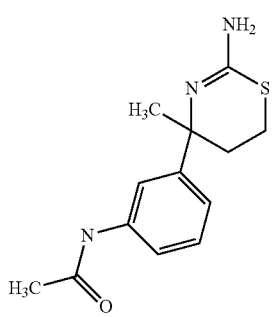 [SMILES: CC(=O)Nc1cccc(C2(C)CCSC(N)=N2)c1]
1221 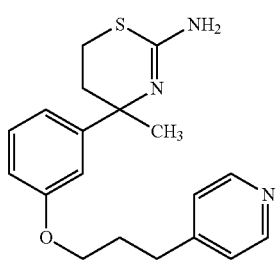 [SMILES: CC1(c2cccc(OCCCc3ccncc3)c2)CCSC(N)=N1]
TABLE 130-continued
1222 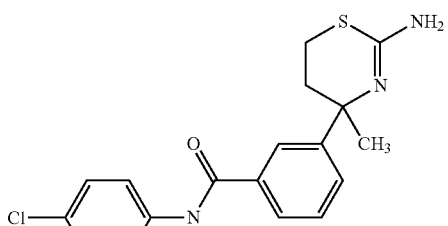
1223 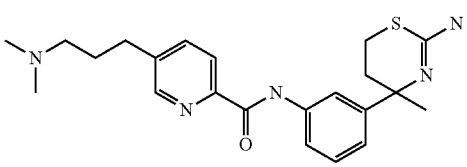 [SMILES: CN(C)CCCc1ccc(C(=O)Nc2cccc(C3(C)CCSC(N)=N3)c2)nc1]
1224 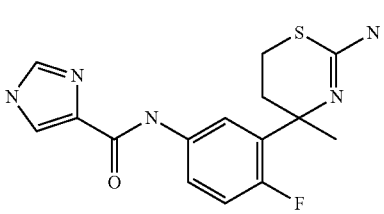 [SMILES: CC1(c2cc(NC(=O)c3c[nH]cn3)ccc2F)CCSC(N)=N1]
1225 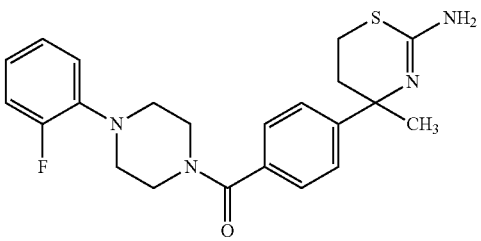 [SMILES: CC1(c2ccc(C(=O)N3CCN(c4ccccc4F)CC3)cc2)CCSC(N)=N1]
1226 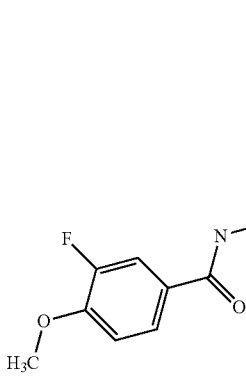 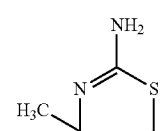
TABLE 131
1227 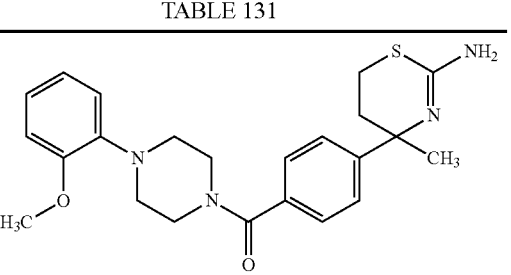

TABLE 131-continued
1228 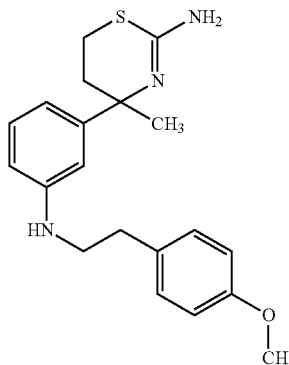
1229 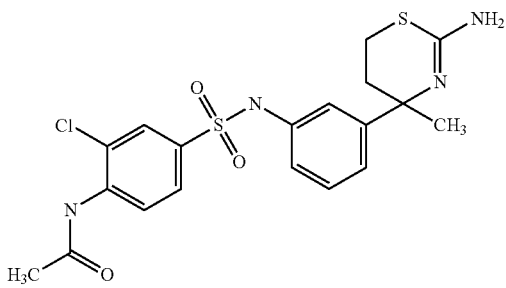 [SMILES: CC(=O)Nc1ccc(S(=O)(=O)Nc2cccc(C3(C)CCSC(N)=N3)c2)cc1Cl]
1230 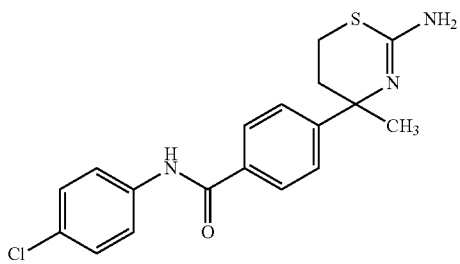 [SMILES: CC1(c2ccc(C(=O)Nc3ccc(Cl)cc3)cc2)CCSC(N)=N1]
1231 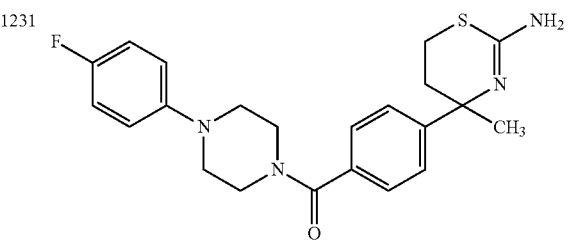
1232 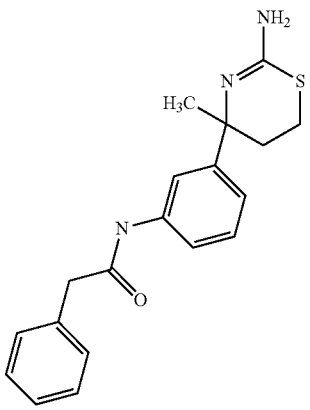 [SMILES: CC1(c2cccc(NC(=O)Cc3ccccc3)c2)CCSC(N)=N1]
TABLE 131-continued
1233 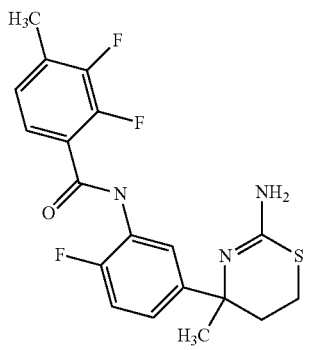 [SMILES: Cc1ccc(C(=O)Nc2cc(C3(C)CCSC(N)=N3)ccc2F)c(F)c1F]
1234 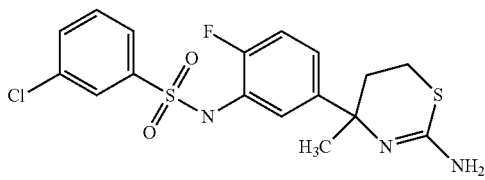 [SMILES: CC1(c2ccc(F)c(NS(=O)(=O)c3cccc(Cl)c3)c2)CCSC(N)=N1]
1235 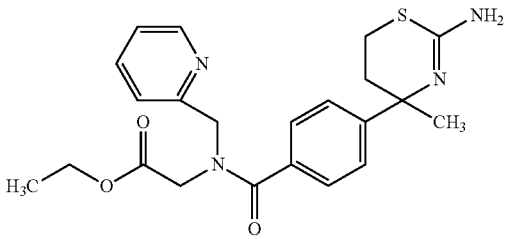 [SMILES: CCOC(=O)CN(Cc1ccccn1)C(=O)c1ccc(C2(C)CCSC(N)=N2)cc1]
1236 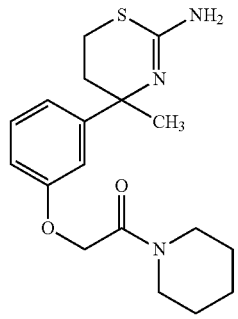 [SMILES: CC1(c2cccc(OCC(=O)N3CCCCC3)c2)CCSC(N)=N1]
TABLE 132
1237 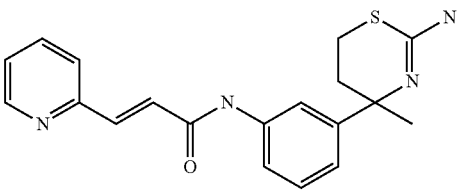 [SMILES: CC1(c2cccc(NC(=O)/C=C/c3ccccn3)c2)CCSC(N)=N1]

TABLE 132-continued
| 1238 | 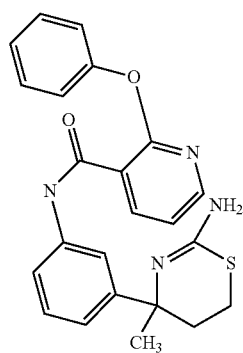 [SMILES: CC1(c2cccc(NC(=O)c3cccnc3Oc3ccccc3)c2)CCSC(N)=N1] |
| --- | --- |
| 1239 | 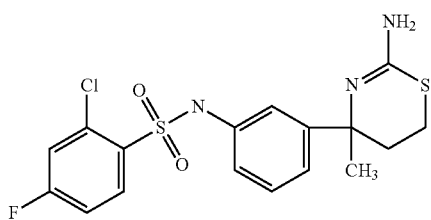 [SMILES: CC1(c2cccc(NS(=O)(=O)c3ccc(F)cc3Cl)c2)CCSC(N)=N1] |
| 1240 | 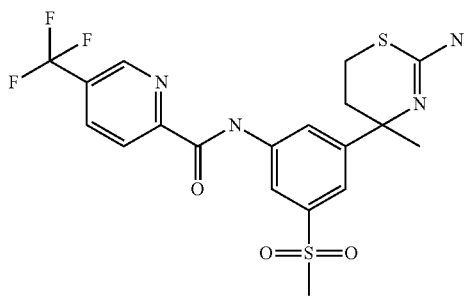 [SMILES: CC1(c2cc(NC(=O)c3ccc(C(F)(F)F)cn3)cc(S(C)(=O)=O)c2)CCSC(N)=N1] |
| 1241 | 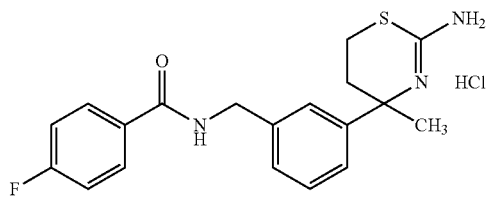 [SMILES: CC1(c2cccc(CNC(=O)c3ccc(F)cc3)c2)CCSC(N)=N1 ; Cl] |
| 1242 | 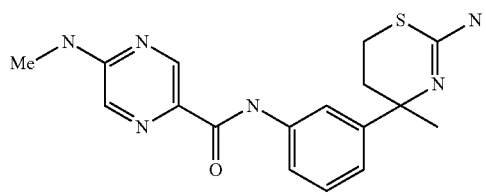 [SMILES: CNc1cnc(C(=O)Nc2cccc(C3(C)CCSC(N)=N3)c2)cn1] |
| 1243 | 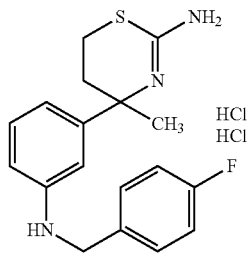 [SMILES: CC1(c2cccc(NCc3ccc(F)cc3)c2)CCSC(N)=N1 ; Cl ; Cl] |
TABLE 132-continued
| 1244 | 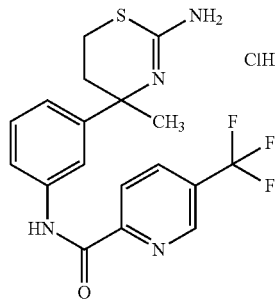 [SMILES: CC1(c2cccc(NC(=O)c3ccc(C(F)(F)F)cn3)c2)CCSC(N)=N1 ; Cl] |
| --- | --- |
| 1245 | 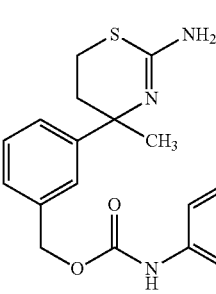 |
| 1246 | 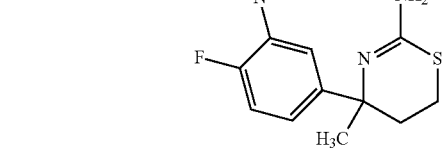 |
TABLE 133
| 1247 | 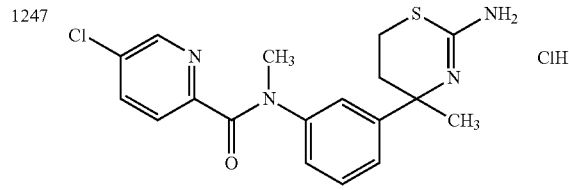 |
| --- | --- |

TABLE 133-continued
1248 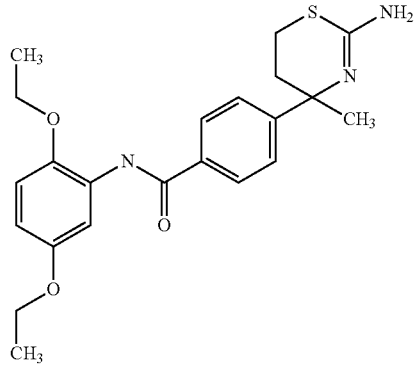 [SMILES: CCOc1ccc(OCC)c(NC(=O)c2ccc(C3(C)CCSC(N)=N3)cc2)c1]
1249 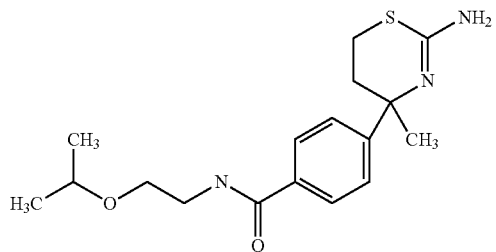 [SMILES: CC(C)OCCNC(=O)c1ccc(C2(C)CCSC(N)=N2)cc1]
1250 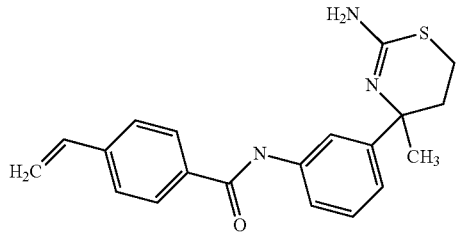 [SMILES: C=Cc1ccc(C(=O)Nc2cccc(C3(C)CCSC(N)=N3)c2)cc1]
1251 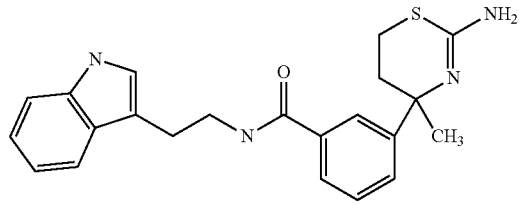 [SMILES: CC1(c2cccc(C(=O)NCCc3c[nH]c4ccccc34)c2)CCSC(N)=N1]
1252 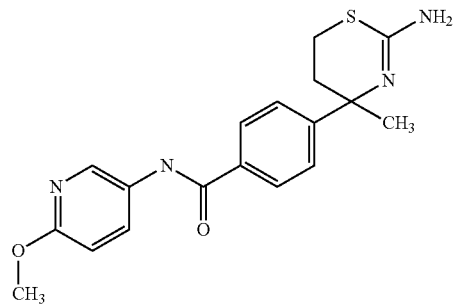 [SMILES: COc1ccc(NC(=O)c2ccc(C3(C)CCSC(N)=N3)cc2)cn1]
TABLE 133-continued
1253 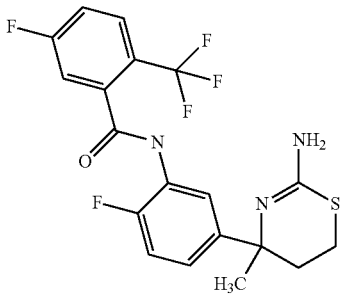 [SMILES: CC1(c2ccc(F)c(NC(=O)c3cc(F)ccc3C(F)(F)F)c2)CCSC(N)=N1]
1254 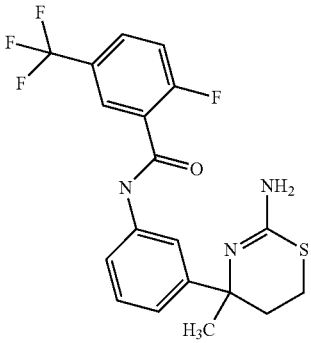 [SMILES: CC1(c2cccc(NC(=O)c3cc(C(F)(F)F)ccc3F)c2)CCSC(N)=N1]
1255 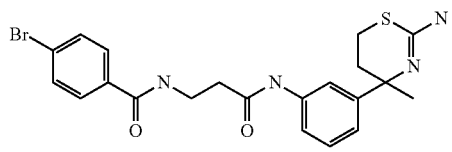 [SMILES: CC1(c2cccc(NC(=O)CCNC(=O)c3ccc(Br)cc3)c2)CCSC(N)=N1]
1256 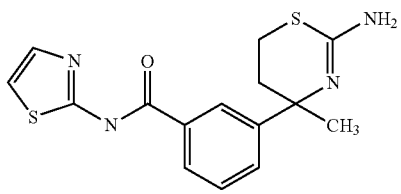 [SMILES: CC1(c2cccc(C(=O)Nc3nccs3)c2)CCSC(N)=N1]
1257 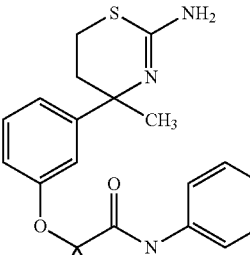
TABLE 134
1258 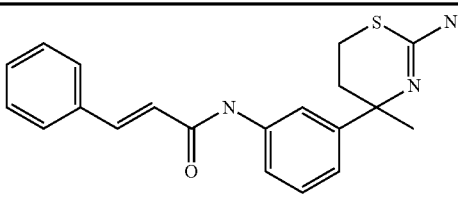

TABLE 134-continued
| | |
|---|---|
| 1259 | 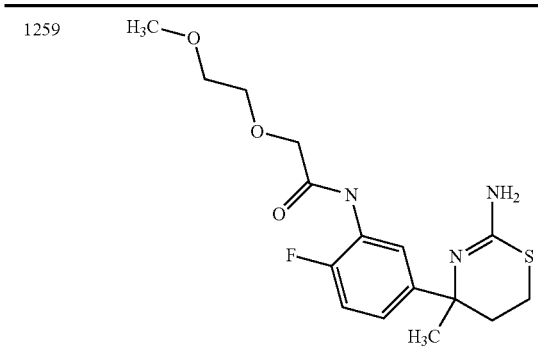 |
| 1260 | 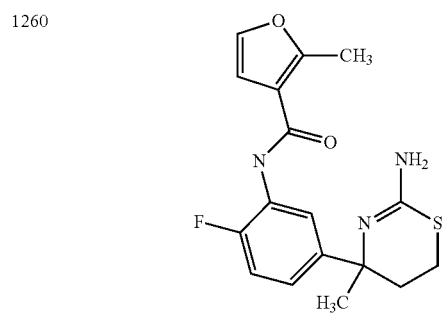 |
| 1261 | 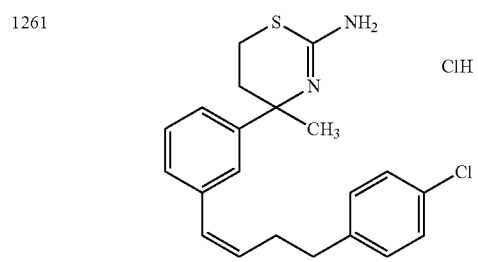 ClH |
| 1262 | 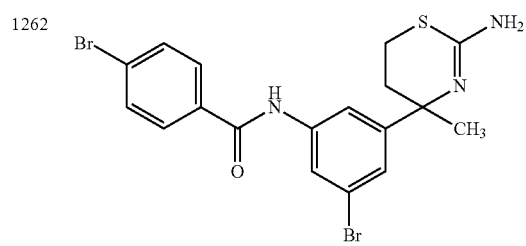 ClH |
| 1263 | 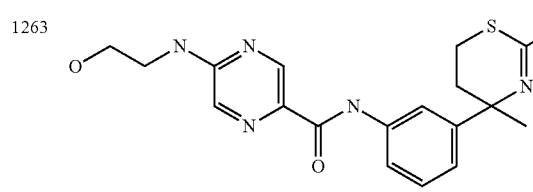 |
| 1264 | 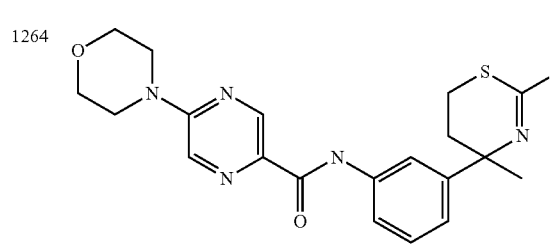 |
| 1265 | 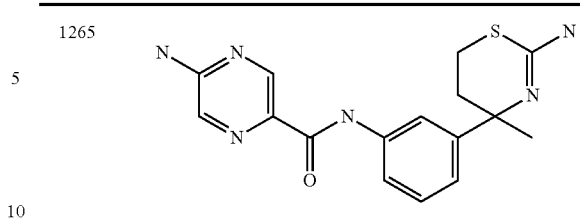 |
| 1266 | 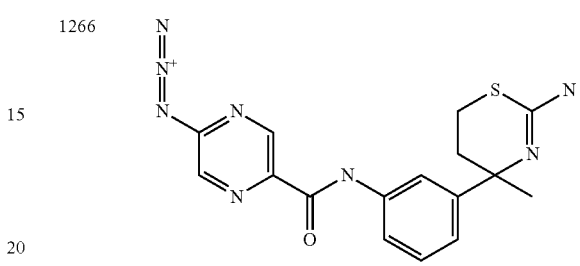 |
| 1267 | 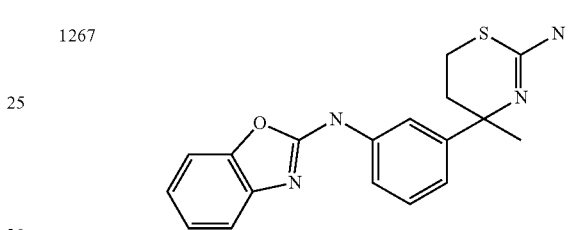 |
| 1268 | 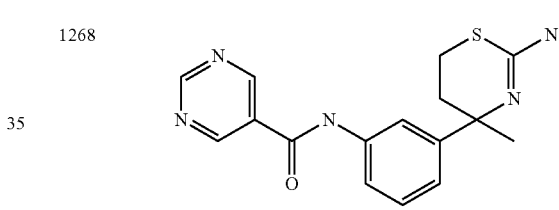 |
| 1269 | 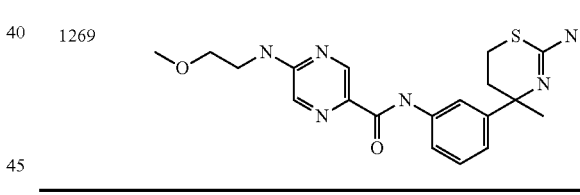 |
TABLE 135
| | |
|---|---|
| 1270 | 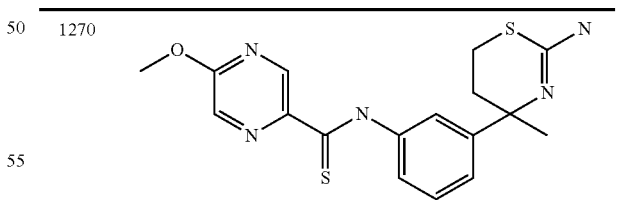 |
| 1271 | 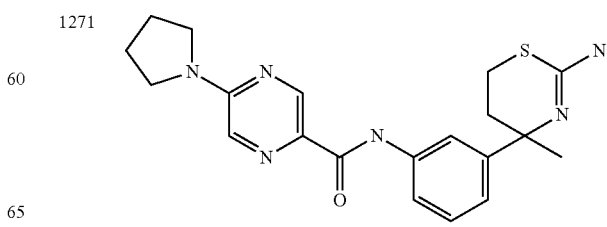 |

TABLE 135-continued
1272 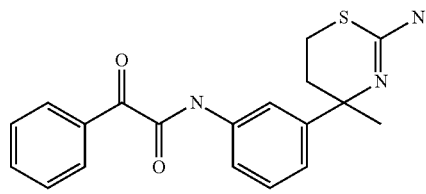 [SMILES: CC1(c2cccc(NC(=O)C(=O)c3ccccc3)c2)CCSC(N)=N1]
1273 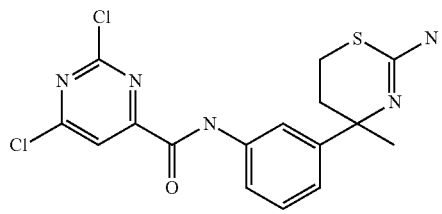 [SMILES: CC1(c2cccc(NC(=O)c3cc(Cl)nc(Cl)n3)c2)CCSC(N)=N1]
1274 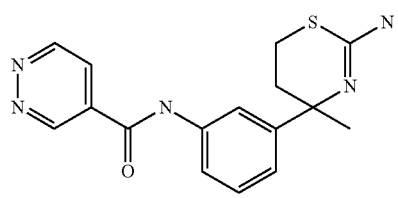 [SMILES: CC1(c2cccc(NC(=O)c3ccnnc3)c2)CCSC(N)=N1]
1275 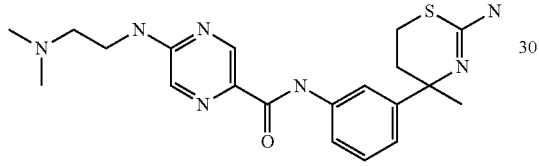
1276 
1277 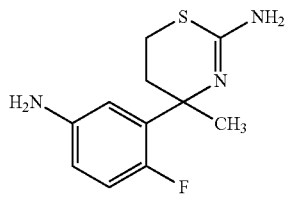 [SMILES: CC1(c2cc(N)ccc2F)CCSC(N)=N1]
TABLE 135-continued
1279 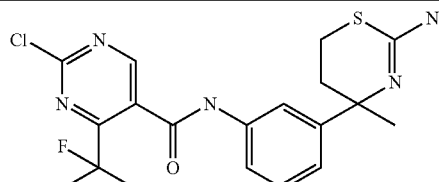
1280 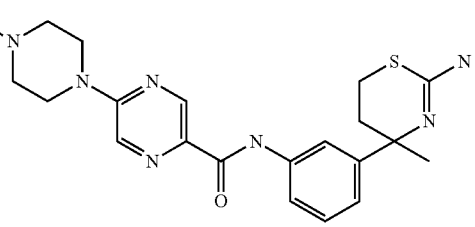
1281 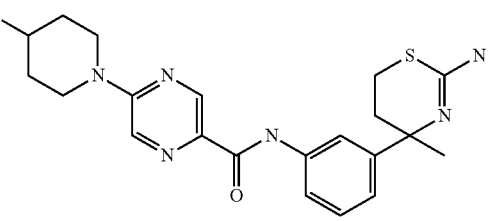
1282 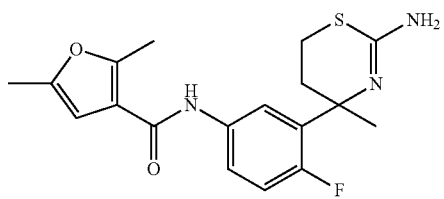 [SMILES: Cc1cc(C(=O)Nc2ccc(F)c(C3(C)CCSC(N)=N3)c2)c(C)o1]
[Chemical formula 65]
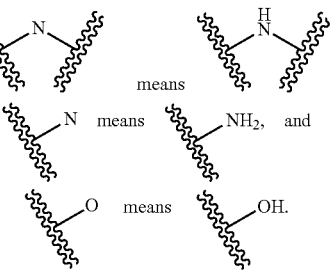
in formula,
TABLE 136
| Compound No. | Melting Point (° C.) | 1H-NMR (d) | MS (m/z) | UV (λmax:nm) |
|---|---|---|---|---|
| 1 | | | | 213.4 305.3 |
| 3 | 285 (dec.) | | | |
| 4 | amorphous | | | 219 |
| 5 | | | | 215, 262 |
| 6 | 147-148 | | | |
| 8 | 214-217 | | | |
| 9 | oil | | | 220 |
| 18 | 181-183 | | | |

TABLE 136-continued

| Compound No. | Melting Point (° C.) | 1H-NMR (d) | MS (m/z) | UV (λmax:nm) |
|---|---|---|---|---|
| 23 | | | | 213.4<br>272.2<br>305.3 |
| 24 | 116-117 | | | |
| 26 | 182-184 | | | |
| 30 | | | | 267.4 |
| 33 | | | | 253.3<br>305.3 |
| 37 | amorphous | | | 219, 275 |
| 38 | 240-244 (dec.) | | | |
| 39 | | | | 285.2 |
| 42 | 187-188 | | | |
| 43 | | | | 218.1<br>275.7 |
| 48 | | | | 230<br>275 |
| 57 | 197-198 | | | |
| 58 | 234-240 | | | |
| 62 | 198-201 | | | |
| 69 | 194-195 | | | |
| 71 | | | | 216.9<br>268.6 |
| 73 | 266-269 | | | |
| 77 | | d in d20-DMSO: 1.67(3H, s), 2.13-2.06(1H, m), 2.63-2.55(2H, m), 3.16-3.13(4H, m) 3.65-3.63(2H, m), 4.76-4.73(2H, m), 7.15-7.08(2H, m), 7.30(1H, t, J = 8.0 Hz), 7.35(1H, s), 7.42(1H, t, J = 8.0 Hz), 7.60(1H, d, J = 8.0 Hz), 7.69(1H, d, J = 8.0 Hz), 7.73(1H, brs), 7.86(1H, d, J = 8.0 Hz), 10.52(1H, s) | | 422.543 |
| 78 | | $^1$H-NMR (CDCl$_3$) d: 1.76 (3H, s), 2.02 (1H, s), 2.58 (1H, d, J = 14.1 Hz), 2.78 (2H, d, J = 6.9 Hz), 3.80 (3H, d, J = 13.1 Hz), 4.54 (2H, s), 6.45 (1H, s), 6.55-6.57 (2H, m), 6.66 (1H, d, J = 8.7 Hz), 7.10 (1H, t, J = 7.0 Hz), 7.22 (2H, td, J = 7.7, 1.4 Hz), 7.34 (1H, d, J = 9.1 Hz), 7.56 (1H, d, J = 7.7 Hz). | 365[M + 1] | |
| 80 | | | | 220.4<br>280.4 |

TABLE 137

| Compound No. | Melting Point (° C.) | 1H-NMR (d) | MS (m/z) | UV (λmax:nm) |
|---|---|---|---|---|
| 85 | 147-148 | 1.54(3H, s), 1.75-1.86(1H, m), 2.08-2.18(1H, m), 2.33(3H, s), 2.63-2.74(1H, m), 2.81-2.90(1H, m), 4.36(2H, br), 7.13(2H, d, J = 8.6 Hz), 7.20(2H, d, J = 8.6 Hz) (solvent: CDCl3) | | |
| 86 | 141-142 | | | |
| 91 | | | 372[M + 1]<br>296 | 201<br>206<br>216 |
| 96 | | | | 309 |
| 97 | | d in d13-DMSO: 1.64(3H, s), 2.03-1.97(1H, m), 2.63-2.57(2H, m), 3.28-3.25(1H, m), 7.22(1H, q, J = 12.4, 9.0 Hz), 7.82-7.77(2H, m), 8.60(1H, s), 8.79(1H, s), 10.37(1H, s). | | |
| 99 | 221-224 | | | |
| 101 | 264-265 | | | |
| 104 | amorphous | | | 229, 280 |
| 113 | | 1.58 (s, 3H), 1.88 (ddd, J = 14.1, 10.9, 3.7 Hz, 1H), 2.24 (ddd, J = 14.1, 5.9, 3.5 Hz, 1H), 2.73 (ddd, J = 12.3, 10.9, 3.5Hz, 1H), 2.88 (ddd, J = 12.3, 5.9, 3.7 Hz, 1H), 3.83 (d, J = 15.4 Hz, 1H), 3.87 (d, J = 15.4 Hz, 1H), 7.02-7.04 (m, 1H), 7.25-7.31 (m, 2H), 7.36 (d, J = 2.0 Hz, 1H), 7.45-7.50 (m, 2H), 8.52 (d, J = 5.2 Hz, 1H), 9.43 (s, 1H) (solvent: CDCl3) | | |
| 114 | | | | 214.5<br>306.5 |

TABLE 137-continued

| Compound No. | Melting Point (° C.) | 1H-NMR (d) | MS (m/z) | UV (λmax:nm) |
|---|---|---|---|---|
| 115 | | d in d6-DMSO: 1.47(3H, s), 1.80-1.74(1H, m, 2.22-2.18(1H, m), 2.60-2.55(1H, m), 2.96-2.93(1H, m), 6.14(1H, s), 6.93(1H, s), 7.09-7.04(2H, m), 7.63-7.61(1H, m), 7.68-7.66(1H, m), 9.85(1H, s), 11.63(1H, brs) | | |
| 120 | amorphous | | | 213 |
| 121 | 166-167 | | | |
| 125 | >300 | | | |
| 126 | amorphous | | | 229, 271 |
| 127 | 280-285 | | | |
| 128 | 159-163 | | | |
| 129 | 219-222 | | | |
| 130 | 128-131 | 1.56 (3H, s), 1.83-1.93 (1H, m), 2.16 (1H, dq, J = 13.85, 3.41 Hz), 2.29 (3H, s), 2.72-2.77 (1H, m), 2.90-2.94 (1H, m), 4.13 (3H, s), 6.42 (1H, s), 7.10-7.14 (1H, m), 7.32 (1H, d, J = 7.91 Hz), 7.37-7.38 (1H, m), 7.60-7.63 (1H, m). (solvent: CDCl3) | 344[M + 1] | |
| 132 | 147-150 | | | |
| 134 | | | | 228.5 |

TABLE 138

| Compound No. | Melting Point (° C.) | 1H-NMR (d) | MS (m/z) | UV (λmax:nm) |
|---|---|---|---|---|
| 139 | 287-290 | 1.77 (s, 3H), 2.10 (ddd, J = 14.0, 10.8, 3.6 Hz, 1H), 2.64-2.70 (4H, m), 2.76 (td, J = 12.8, 3.6 Hz, 1H), 2.90 (dt, J = 12.8, 3.6 Hz, 1H), 7.05 (ddd, J = 8.0, 2.0, 0.8 Hz, 1H), 7.41 (t, J = 8.0 Hz, 1H), 7.69-7.72 (m, 2H), 8.32 (dd, J = 8.0, 0.8 Hz, 1H), 8.40 (dd, J = 8.0, 2.0 Hz, 1H), 9.14 (dd, J = 2.0, 0.8 Hz, 1H) (solvent: CDCl3 + CD3OD) | | |
| 141 | | d in d17-DMSO: 1.41(3H, s), 1.75-1.70(1H, m), 2.03-1.99(1H, m), 2.62-2.56(1H, m), 2.94-2.89(1H, m), 3.89(3H, s), 6.88(1H, d, J = 8.8 Hz), 7.05(1H, d, J = 7.6 Hz), 7.24(1H, t, J = 8.0 Hz), 7.66-7.63(3H, m), 8.45-8.44(1H, m), 9.90(1H, s) | | |
| 148 | | | 362[M + 1] 286 | 200 208 212 218 262 |
| 149 | 143-145 | | | |
| 157 | | d in d6-DMSO: 1.20(6H, d, J = 6.6 Hz), 1.41(3H, s), 1.65-1.77(1H, m), 1.96-2.07(1H, m), 2.55-2.63(1H, m), 2.85-2.95(1H, m), 4.04-4.16(1H, m), 5.79(2H, bs), 7.07(1H, d, J = 8.1 Hz), 7.25(1H, t, J = 8.1 Hz), 7.72-7.78(3H, m), 7.93(1H, s), 8.64(1H, s), 9.96(1H, s). | | |
| 159 | amorphous | | | 285 |
| 161 | 247-251 | | | |
| 163 | amorphous | | | |
| 164 | 91-96 | 1.68(s, 3H), 2.07-2.15(m, 1H), 3.13-3.20(m, 1H), 7.12(d, J = 7.6 Hz, 1H), 7.46(t, J = 7.6 Hz, 1H), 7.90-7.94(m, 2H), 8.83(br s, 1H), 8.96(br s, 1H), 9.31(br s, 1H), 10.36(s, 1H), 10.86(s, 1H) | | |
| 165 | 246-248 | | | |
| 166 | amorphous | | | 220, 275 |
| 176 | amorphous | | | 217, 278 |
| 178 | 224-225 | | | |
| 181 | | | | 261.5 |
| 189 | | | | 259 |
| 193 | 266-268 | | | |
| 196 | | | | 212 |
| 202 | 117-118 | 0.85(3H, t, J = 7.3 Hz), 1.02-1.19(1H, m), 1.34-1.54(1H, m), 1.72-1.89(3H, m), 2.04-2.15(1H, m), 2.61-2.82(2H, m), 3.80(3H, s), 4.32(2H, br), 6.85(2H, d, J = 8.9 Hz), 7.18(2H, d, J = 8.9 Hz) (solvent: CDCl3) | | |

TABLE 139

| Compound No. | Melting Point (° C.) | 1H-NMR (d) | MS (m/z) | UV (λmax:nm) |
|---|---|---|---|---|
| 204 | 205-208 | 1.64 (d, J = 1.2 Hz, 3H), 1.95 (ddd, J = 14.0, 10.8, 3.6 Hz, 1H), 2.45 (ddd, J= 14.0, 6.4, 3.6 Hz, 1H), 2.75 (ddd, J = 12.4, 10.8, 3.6 Hz, 1H), 2.99 (ddd, J = 12.4, 6.4, 3.6 Hz, 1H), 7.09 (dd, J = 11.6, 8.8 Hz, 1H), 7.47 (dd, J = 7.2, 2.8 Hz, 1H), 8.03 (ddd, J = 8.8, 4.4, 2.8 Hz, 1H), 8.89 (s, 2H), 9.75 (s, 1H) (solvent: CDCl3) | | |
| 213 | oil | | | 216, 272 |
| 214 | | | | 212.2 292.3 356.5 |
| 216 | | | | 242.7 |
| 220 | 191-193 | | 363[M + 3] 361[M + 1] 287 285 | |
| 224 | oil | 1.58(3H, s), 1.87(1H, ddd, J = 13.9, 10.5, 3.7), 2.13(1H, ddd, J = 13.9, 6.3, 3.7), 2.25(3H, s), 2.68(1H, ddd, J = 12.1, 10.5, 6.2), 2.89(1H, ddd, J = 12.1, 6.3, 3.7), 5.23(2H, s), 7.28-7.48(4H, m), 7.60(1H, s), 7.75(1H, d, J = 8.0), 8.56(1H, dd, J = 5.0, 1.4), 8.70(1H, d, J = 1.4) (solvent: CDCl3) | | 222 |
| 227 | | | | 213 |
| 232 | | 1H-NMR (CDCl3) d: 1.59 (3H, s), 1.83-1.90 (1H, m), 2.35-2.47 (4H, m), 2.60-2.67 (1H, m), 2.87-2.92 (1H, m), 4.70 (2H, br s), 6.87-6.98 (2H, m), 7.16 (1H, d, J = 6.6 Hz), 7.27 (2H, d, J = 7.8 Hz), 7.61 (2H, d, J = 8.1 Hz). | 378[M + 1] | |
| 233 | oil | | | 224, 272 |
| 235 | 196-200 | | | |
| 238 | | $^1$H-NMR (CDCl$_3$) d: 1.68 (3H, s), 1.97-2.00 (1H, m), 2.53 (1H, dt, J = 14.4, 3.7 Hz), 2.63-2.79 (2H, m), 4.52 (2H, s), 6.56-6.66 (3H, m), 7.17 (1H, t, J = 8.0 Hz), 7.43-7.52 (3H, m), 7.81 (4H, dd, J = 11.6, 5.7 Hz). | 362[M + 1] | |
| 241 | 187-190 | 1H-NMR (DMSO-d6) d: 1.49 (3H, s), 1.78-1.86 (1H, m), 2.13-2.21 (1H, m), 2.59-2.67 (1H, m), 2.96-3.02 (1H, m), 7.11 (1H, t, J = 10.7 Hz), 7.29 (1H, t, J = 7.8 Hz), 7.45 (1H, t, J = 7.5 Hz), 7.66 (1H, d, J = 8.8 Hz), 7.74-7.78 (1H, m), 7.80-7.83 (1H, m), 8.21 (1H, d, J = 8.6 Hz), 10.25 (1H, s). | | |
| 243 | 182-184 | 1.46(s, 3H), 1.75-1.83(m, 1H), 2.08-2.16(m, 1H), 2.55-2.63(m, 1H), 2.92-2.98(m, 1H), 4.02(s, 3H), 7.11(d, J = 8.0 Hz, 1H), 7.31(t, J = 8.0 Hz, 1H), 7.77(d, J = 8.0 Hz, 1H), 7.82(br s, 1H), 8.41(d, J = 1.2 Hz, 1H), 8.90(d, J = 1.2 Hz, 1 H), 10.38(s, 1H) (solvent: CDCl3) | | |

TABLE 140

| Compound No. | Melting Point (° C.) | 1H-NMR (d) | MS (m/z) | UV (λmax:nm) |
|---|---|---|---|---|
| 244 | 222-224 | | | |
| 251 | | | 351[M + 1] 311 275 | 200 204 215 285 |
| 255 | 238-239 | | | |
| 256 | oil | | | 215, 257 |
| 259 | amorphous | 1.58(3H, s), 2.01(1H, ddd, J = 15.2, 12.2, 3.4), 2.46-2.56(2H, m), 3.07(1H, ddd, J = 13.3, 5.7, 3.5), 4.24(2H, s), 6.53(1H, d, J = 7.6), 6.59-6.61(2H, m), 7.09-7.12(1H, m), 7.11(2H, d, J = 7.6), 7.24(2H, d, J = 7.6), 8.82(2H, br) (solvent: DMSO-d6) | | 229 298 |
| 263 | | | 363[M + 1] 287 | 200 284 |
| 267 | 114-115 | | | |
| 268 | | | | 214.5 298.2 |
| 271 | oil | | | 229, 276 |

TABLE 140-continued

| Compound No. | Melting Point (° C.) | 1H-NMR (d) | MS (m/z) | UV (λmax:nm) |
|---|---|---|---|---|
| 275 | | (CDCl3) 1.66(3H, d, J= 1.2 Hz), 1.98(1H, ddd, J= 14.0, 10.4, 3.7 Hz), 2.47(1H, ddd, J= 14.0, 6.7, 3.5 Hz), 2.79(1H, ddd, J= 12.0, 10.4, 3.5 Hz), 3.02(1H, ddd, J = 12, 0, 6.7, 3.7 Hz), 4.45(2H, br), 6.16(2H, br), 7.04-7.11(2H, m), 7.38(1H, dd, J = 7.2, 2.9 Hz), 7.88(1H, d, J = 2.0 Hz), 7.96(1H, ddd, J = 8.9, 4.2, 2.9 Hz), 9.88(1H, s) | | |
| 277 | | | | 216, 228, 281 |
| 279 | | | | 214.5, 292.3 |
| 281 | amorphous | 1.55(3H, s), 1.83(1H, ddd, J = 13.9, 10.6, 3.9), 2.10(1H, ddd, J = 13.9, 6.5, 3.6), 2.67(1H, ddd, J = 12.2, 10.6, 3.6), 2.87(1H, ddd, J = 12.2, 6.5, 3.9), 4.49(2H, d, J = 5.6), 4.85(1H, br), 6.38(1H, dt, J = 8.5, 0.9), 6.59(1H, ddd, J = 7.2, 5.2, 0.9), 7.21-7.24(2H, m), 7.28-7.32(2H, m), 7.40(1H, ddd, J = 8.5, 7.2, 1.8), 8.11(1H, ddd, J = 5.2, 1.8, 0.8) (solvent: CDCl3) | 233 | 301 |
| 282 | 146-147 | | | |
| 284 | 181.5 | | | |
| 293 | | 1.57 (s, 3H), 1.78-1.89 (m, 1H), 2.10-2.19 (m, 1H), 2.69 (ddd, J = 11.9, 10.8, 3.5 Hz, 1H), 2.83-2.91 (m, 1H), 7.15-7.35 (m, 5H) (solvent: CDCl3) | | |
| 299 | | | | 293.5 |

TABLE 141

| Compound No. | Melting Point (° C.) | 1H-NMR (d) | MS (m/z) | UV (λmax:nm) |
|---|---|---|---|---|
| 301 | | (CDCl3) 1.53(3H, s), 1.80(1H, ddd, J = 14.0, 10, 4, 3.6 Hz), 2.12(1H, ddd, J = 14.0, 6.0, 3.6 Hz), 2.75(1H, ddd, J = 12.0, 10.4, 3.6 Hz), 2.85(1H, ddd, J = 12, 0, 6.0, 3.6 Hz), 3.64(2H, s), 4.32 (2H, br), 6.55(1H, ddd, J = 8.0, 2.0, 0.8 Hz), 6.66(1H, t, J = 2.0 Hz), 6.70 (1H, ddd, J = 8.0, 2.0, 0.8 Hz), 7.11(1H, t, J = 8.0 Hz) | | |
| 302 | 122-126 | 1.41(s, 3H), 1.67-1.76(m, 1H), 1.98-2.06(m, 1H), 2.55-2.63(m, 1H), 2.86-2.94(m, 1H), 3.19(s, 6H), 5.75(s, 2H), 7.08(d, J = 8.0 Hz, 1H), 7.26(t, J = 8.0 Hz, 1H), 7.73(d, J = 8.0 Hz, 1H), 7.76(br s, 1H), 8.16(s, 1H), 8.73(s, 1H), 10.00(s, 1H)(solvent: CDCl3) | | |
| 306 | | | 231, 258, 289 | |
| 307 | | 1.83 (ddd, J = 13.9, 10.3, 3.6 Hz, 1H), 2.13 (ddd, J = 13.6, 6.2, 3.5 Hz, 1H), 2.53 (s, 3H), 2.66-2.75 (m, 1H), 2.90 (ddd, J = 12.2, 6.3, 3.8 Hz, 1H), 7.09 (d, J = 7.8 Hz, 1H), 7.32 (t, J = 8.0 Hz, 1H), 7.37 (s, 1H), 7.63 (d, J = 7.8 Hz, 1H), 8.79 (s, 1H) (solvent: CDCl3) | | |
| 308 | 167-168 | | | |
| 309 | 241-244 | | | |
| 319 | | | | 308.9 |
| 329 | 238-239 | | | |
| 330 | | | | 213.4, 263.9 |
| 332 | | | | 212.2 |
| 333 | 154-158 | | | |
| 339 | 217-218 | | | |
| 341 | amorphous | | | 216, 249 |
| 342 | 184-187 | | | |
| 344 | | (DMSO) 1.49(3H, s), 1.73-1.85(1H, m), 2.15-2.28(1H, m), 2.54-2.66(1H, m), 2.92-3.04(1H, m), 5.86(2H, s), 7.03-7.25(3H, m), 7.40-7.48(2H, m), 7.64-7.78(3H, m), 10.31(1H, s), 11.74(1H, s) | | |
| 353 | | | | 279.3, 364.5 |

TABLE 141-continued

| Compound No. | Melting Point (° C.) | 1H-NMR (d) | MS (m/z) | UV (λmax:nm) |
|---|---|---|---|---|
| 354 | 102-103 | | | |
| 356 | amorphous | 1.73 (s, 3H), 2.09-2.17 (m, 1H), 2.40(s, 3H), 2.65-2.73 (m, 2H), 3.15-3.23 (m, 1H), 3.81(s, 3H), 7.07 (d, J = 7.2 Hz, 2H), 7.29 (br s, 1H), 7.36 (d, J = 8.0 Hz, 2H), 7.61 (d, J = 8.0 Hz, 2H), 7.78 (br s, 1H), 7.90 (d, J = 7.2 Hz, 2H), 8.00 (br s, 1H), 10.32 (s, 1H)(solvent: DMSO-d6) | 267 | |
| 357 | amorphous | | | 224, 298 |

TABLE 142

| Compound No. | Melting Point (° C.) | 1H-NMR (d) | MS (m/z) | UV (λmax:nm) |
|---|---|---|---|---|
| 358 | | 1.57(3H, s), 1.80-1.91 (1H, m), 2.15-2.18 (1H, m) 2.70-2.94 (2H, m), 3.94 (3H, s), 4.67 (2H, s), 6.75 (1H, s), 7.05-7.08 (1H, m), 7.31 (1H, t, J = 7.91 Hz), 7.53 (1H, t, J = 1.98 Hz), 7.64-7.67 (1H, m), 8.64 (1H, s).(solvent: CDCl3) | 360[M + 1] | |
| 359 | 212-214 | 1.46(s, 3H), 1.73-1.83(m, 1H), 2.13-2.20(m, 1H), 2.54-2.61(m, 1H), 2.62(s, 3H), 2.93-3.00(m, 1H), 5.84(br s, 2H), 7.12(dd, J = 12.0, 8.8 Hz, 1H), 7.73-7.78(m, 1H), 7.81(dd, J = 7.2, 2.4 Hz, 1H), 8.68(s, 1H), 9.13(s, 1H), 10.59(s, 1H)(solvent: CDCl3) | | |
| 360 | amorphous | | | 222 |
| 361 | | | | 280.4 |
| 364 | oil | | 344[M + 1] | 227, 271 |
| 367 | | (CDCl3) 1.78(3H, s), 2.07(1H, ddd, J = 14.0, 12, 4, 3.6 Hz), 2.61(1H, br d, J = 14.0 Hz), 2.84(1H, td, J = 12.4, 3.2 Hz), 2.94(1H, td, J = 12.4, 3.6 Hz), 4.08(3H, s), 7.07(1H, ddd, J = 8.0, 2.0, 0.8 Hz), 7.40(1H, t, J = 8.0 Hz), 7.63(1H, ddd, J = 8.0, 2.0, 0.8 Hz), 7.74(1H, t, J = 2.0 Hz), 8.18(1H, d, J = 1.2 Hz), 9.02(1H, d, J = 1.2 Hz), 9.56(1H, s) | | |
| 375 | | | | 217 |
| 380 | 181-182 | 0.86 (t, J = 7.2 Hz, 3H), 1.82-1.98 (m, 3H), 2.24 (br, 1H), 2.74 (td, J = 12.0, 3.6 Hz, 1H), 2.84 (dt, J = 12.0, 4.0 Hz, 1H), 7.08 (ddd, J = 8.0, 2.0, 0.8 Hz, 1H), 7.37 (t, J = 8.0 Hz, 1H), 7.58 (t, J = 2.0 Hz, 2H), 7.76 (ddd, J = 8.0, 2.0, 0.8 Hz, 1H), 7.88 (dd, J = 8.4, 2.4 Hz, 1H), 8.25 (dd, J = 8.4, 0.8 Hz, 1H), 8.57 (dd, J = 2.4, 0.8 Hz, 1H), 9.84 (s, 1H) (solvent: CDCl3) | | |
| 383 | oil | | | 225, 269, 288 |
| 389 | amorphous | | | 292 |
| 393 | | | | 213.4 316.0 |
| 395 | amorphous | | | 217, 269 |
| 396 | 211-213 | 1.64 (s, 3H), 1.96 (ddd, J = 14.0, 10.4, 4.0 Hz, 1H), 2.44 (ddd, J = 14.0, 6.8, 3.6 Hz, 1H), 2.75 (ddd, J = 12.4, 10.4, 3.6 Hz, 1H),, 2.99 (ddd, J = 12.4, 6.8, 4.0 Hz, 1H), 4.50 (2H, br), 7.08 (dd, J = 11.6, 8.8 Hz, 1H), 7.45 (dd, J = 6.8, 2.8 Hz, 1H), 8.01 (ddd, J = 8.8, 4.4, 2.8 Hz, 1H), 8.16 (ddd, J = 8.0, 2.0, 0.8 Hz, 1H), 8.43 (d, J = 8.0 Hz, 1H), 8.89 (dd, J = 2.0. 0.8 Hz, 1H), 9.91 (s, 1H) (solvent: CDCl3) | | |
| 401 | 106-107 | | | |

TABLE 143

| Compound No. | Melting Point (° C.) | 1H-NMR (d) | MS (m/z) | UV (λmax:nm) |
|---|---|---|---|---|
| 405 | 192-194 | 1.41(s, 3H), 1.68-1.77(m, 1H), 1.96-2.05(m, 1H), 2.55-2.63(m, 1H), 2.88-2.95(m, 1H), 4.15(s, 3H), 5.74(s, 2H), 7.13(d, J = 8.0 Hz, 1H), 7.29(t, J = 8.0 Hz, 1H), 7.44(d, J = 8.8 Hz, 1H), 7.75(d, J = 8.0 Hz, 1H), 7.86(br s, 1H), 8.20(d, J = 8.8 Hz, 1H), 10.73(s, 1H) (solvent: CDCl3) | | |
| 406 | | | | 276.9 |
| 408 | 221-224 | 1.74(3H, s), 2.28(2H, m), 2.67(2H, m), 2.91(3H, s), 3.82(3H, s), 6.90(2H, d, J = 9.0), 7.19(2H, d, J = 9.0) (solvent: CDCl3) | | |
| 409 | oil | | | 215 |
| 410 | 178-182 | 1.37(d, J = 6.0 Hz, 6H), 1.42(s, 3H), 1.70-1.78(m, 1H), 2.00-2.08(m, 1H), 2.53-2.61(m, 1H), 2.88-2.95(m, 1H), 5.36(quintet, J = 6.0 Hz, 1H), 7.11(d, J = 8.0 Hz, 1H), 7.29(t, J = 8.0 Hz, 1H), 7.75(d, J = 8.0 Hz, 1H), 7.80(br s, 1H), 8.32(d, J = 1.2 Hz, 1H), 8.87(d, J = 1.2 Hz, 1H), 10.32(s, 1H) (solvent: CDCl3) | | |
| 411 | | | | 218, 264 |
| 413 | 251-254 | | | |
| 415 | amorphous | | | 226, 290 |
| 417 | 137-139 | | | |
| 422 | | (CDCl3) 1.45(3H, s), 1.70-1.84(1H, m), 1.96-2.04(1H, m), 2.88-2.96(1H, m), 3.04-3.14(1H, m), 6.86(1H, d, J = 15.9 Hz), 6.42(1H, d, J = 15.9 Hz), 7.22-7.41(5H, m) | | |
| 426 | | | | 211.0 312.4 |
| 427 | | | | 216 |
| 429 | oil | | | 211 259 |
| 430 | | (DMSO) 1.07(3H, s), 1.53-1.66(4H, m), 2.50-2.70(2H, m), 2.92-3.10(2H, m), 5.48(1H, s), 7.11-7.21(3H, m), 7.23-7.29(2H, m) | | |
| 432 | oil | | | 216, 272 |
| 436 | 254-256 | | | |
| 441 | 161-165 | | | |
| 443 | | ¹H-NMR (CDCl₃) d: 1.55 (4H, s), 1.74-1.80 (1H, m), 2.13-2.17 (1H, m), 2.68-2.73 (2H, m), 4.33 (1H, br s), 4.48 (2H, d, J = 4.0 Hz), 4.76 (2H, t, J = 20.1 Hz), 6.52 (1H, dd, J = 7.9, 1.8 Hz), 6.63-6.65 (2H, m), 7.13 (1H, t, J = 7.8 Hz), 7.45-7.51 (2H, m), 7.79-7.82 (4H, m). | 362[M + 1] | |

TABLE 144

| Compound No. | Melting Point (° C.) | 1H-NMR (d) | MS (m/z) | UV (λmax:nm) |
|---|---|---|---|---|
| 444 | 214-215 | 1.41(s, 3H), 1.66-1.76(m, 1H), 1.97-2.05(m, 1H), 2.53-2.62(m, 1H), 2.62(s, 3H), 2.86-2.93(m, 1H), 5.79(br s, 2H), 7.12(d, J = 8.0 Hz, 1H), 7.28(t, J = 8.0 Hz, 1H), 7.74(d, J = 8.0 Hz, 1H), 7.81(br s, 1H), 8.68(s, 1H), 9.14(s, 1H), 10.52(s, 1H) (solvent: CDCl3) | | |
| 445 | 92-93 | | | |
| 446 | oil | 1.57(3H, s), 1.86(1H, ddd, J = 13.9, 10.4, 3.7), 2.13(1H, ddd, J = 13.9, 6.5, 3.6), 2.25(3H, s), 2.35(3H, s), 2.70(1H, ddd, J = 12.2, 10.4, 3.6), 2.89(1H, ddd, J = 12.2, 6.5, 3.7), 4.35(2H, br), 5.19(2H, s), 7.17(2H, d, J = 8.0), 7.31-7.34(4H, m), 7.50(1H, ddd, J = 5.8, 3.0, 1.8), 7.55-7.60(1H, m) (solvent: CDCl3) | | 219 252 |
| 448 | | d in d6-DMSO: 1.41(3H, s), 1.67-1.75(1H, m), 1.98-2.05(1H, m), 2.52-2.61(1H, m), 2.86-2.94(1H, m), 5.79(2H, bs), 7.14(1H, d, J = 7.8 Hz), 7.30(1H, t, J = 7.8 Hz), 7.73(1H, bd, J = 7.8 Hz), 7.81(1H, t, J = 1.8 Hz), 8.94(1H, m), 9.11(1H, m), 10.63(1H, bs). | | |
| 452 | 132-134 | | | |
| 456 | 147-149 | | | |
| 457 | 153-155 | | | |
| 465 | 194.6 | | | |
| 466 | | | | 211 |
| 470 | 281 (dec.) | | | |

TABLE 144-continued

| Compound No. | Melting Point (° C.) | 1H-NMR (d) | MS (m/z) | UV (λmax:nm) |
|---|---|---|---|---|
| 482 | | 1.60 (s, 3H), 1.91 (ddd, J = 14.0, 10.8, 4.0 Hz, 1H), 2.23 (ddd, J = 14.0, 6.4, 3.6 Hz, 1H), 2.77 (ddd, J = 12.0, 10.8, 3.6 Hz, 1H), 2.93 (ddd, J = 12.0, 6.4, 4.0 Hz, 1H), 7.16 (ddd, J = 8.0, 2.0, 0.8 Hz, 1H), 7.37 (t, J = 8.0 Hz, 1H), 7.61 (t, J = 2.0 Hz, 1H), 7.75 (ddd, J = 8.0, 2.0, 0.8 Hz, 1H), 8.14 (d, J = 1.6 Hz, 1H), 8.80 (d, J = 1.6 Hz, 1H), 9.79 (s, 1H) (solvent: CDCl3) | | |
| 483 | 224-227 | | | 211, 289 |
| 490 | | 1.64 (3H, s) 2.03-2.12 (1H, m) 2.49-2.62 (m) 3.12-3.16 (1H m) 7.22 (1H, dd, J = 4.2 Hz) 7.27 (1H, bs) 7.75 (1H bs) 7.87 (1H, dd, J = 4.2 Hz) 8.04 (1H, s) 8.12 (1H, dd, J = 4.2 Hz) 10.64 (1H, s) 10.72 (1H, s)(solvent: DMSO-d6) | | |
| 491 | | 1.58 (s, 3H), 1.85-1.96 (m, 1H), 2.15-2.24 (m, 1H), 2.50 (s, 3H), 2.67 (s, 3H), 2.71-2.81 (m, 1H), 2.90-2.98 (m, 1H), 7.13 (d, J = 6.2 Hz, 1H), 7.35 (t, J = 8.0 Hz, 1H), 7.40 (s, 1H), 7.55 (d, J = 7.6 Hz, 1H) (solvent: CDCl3) | | |
| 493 | | | | 216 |

TABLE 145

| Compound No. | Melting Point (° C.) | 1H-NMR (d) | MS (m/z) | UV (λmax:nm) |
|---|---|---|---|---|
| 494 | | d in d6-DMSO: 1.37(3H, s), 1.62-1.70(1H, m), 2.0-2.12(1H, m), 2.40-2.50(1H, m), 2.79-2.83(1H, m), 3.82(3H, s), 4.52(2H, d, J = 5.4 Hz), 6.19(1H, m), 6.54(1H, d, J = 7.8 Hz), 6.62(1H, d, J = 8.1 Hz), 6.75(1H, s), 7.01(1H, t, J = 8.1 Hz), 7.14-7.25(2H, m), 7.51(1H, d, J = 8.1 Hz), 7.60(1H, d, J = 7.5 Hz). | 366[M + 1] | |
| 496 | 152-154 | | | |
| 497 | | d in d6-DMSO: 1.48(3H, s), 1.83-1.77(1H, m), 2.61-2.56(1H, m), 2.99-2.95(1H, m), 3.86(3H, s), 6.07(1H, s), 6.95(1H, s), 7.03-7.02(1H, m), 7.09-7.06(1H, m), 7.58-7.57(1H, m), 7.64-7.62(1H, m), 9.83(1H, s) | | |
| 498 | 122-125 | | | |
| 500 | 181-184 | | | |
| 501 | 155-156 | | | |
| 502 | 137-138 | | | |
| 504 | 209-219 | | | |
| 511 | 211-214 | 1.58 (s, 3H), 1.90 (ddd, J = 14.0, 10.0, 3.6 Hz, 1H), 2.15 (ddd, J = 14.0, 6.8, 3.6 Hz, 1H), 2.77 (ddd, J = 12.4, 10.0, 3.6 Hz, 1H), 2.94 (ddd, J = 12.4, 6.8, 3.6 Hz, 1H), 4.34 (2H, br), 7.17 (ddd, J = 8.0, 2.0, 0.8 Hz, 1H), 7.38 (t, J = 8.0 Hz, 1H), 7.50 (d, J = 2.0 Hz, 1H), 7.56 (td, J = 2.0 Hz, 1H), 7.70 (ddd, J = 8.0, 2.0, 0.8 Hz, 1H), 8.08 (d, J = 1.6 Hz, 1H), 9.70 (s, 1H) (solvent: CDCl3) | | |
| 515 | 204-206 | 1.61 (s, 3H), 1.90 (ddd, J = 14.0, 10.8, 3.6 Hz, 1H), 2.22 (ddd, J = 14.0, 6.0, 3.6 Hz, 1H), 2.77 (ddd, J = 12.4, 10.8, 3.6 Hz, 1H), 2.93 (ddd, J = 12.4, 6.0, 3.6 Hz, 1H), 7.15 (ddd, J = 8.0, 2.0, 0.8 Hz, 1H), 7.39 (t, J = 8.0 Hz, 1H), 7.65 (t, J = 2.0 Hz, 1H), 7.80 (ddd, J = 8.0, 2.0, 0.8 Hz, 1H), 8.89 (s, 2H), 9.77 (s, 1H) (solvent: CDCl3) | | |
| 516 | | | | 292.3 |
| 525 | 105-106 | | | |
| 528 | 173-174 | 1.60 (s, 3H), 1.89 (ddd, J = 14.0, 10.8, 3.6 Hz, 1H), 2.22 (ddd, J = 14.0, 6.4, 3.2 Hz, 1H), 2.44 (s, 3H), 2.77 (ddd, J = 12.4, 10.8, 3.2 Hz, 1H), 2.91 (ddd, J = 12.4, 6.4, 3.6 Hz, 1H), 4.50 (br, 2H), 7.11 (ddd, J = 8.0, 2.0, 0.8 Hz, 1H), 7.35 (t, J = 8.0 Hz, 1H), 7.67-7.71 (m, 2H), 7.74 (ddd, J = 8.0, 2.0, 0.8 Hz, 1H), 8.18 (d, J = 8.4 Hz, 1H), 8.44(d, J = 1.6 Hz, 1H), 9.98 (s, 1H) (solvent: CDCl3) | | |
| 532 | | | | 305.3 |
| 533 | 180-181 | | | |
| 534 | 201-204 | | | |
| 549 | 100-101 | | | |
| 551 | 139-141 | | | |
| 554 | | | | 216 |

TABLE 146

| Compound No. | Melting Point (° C.) | 1H-NMR (d) | MS (m/z) | UV (λmax:nm) |
|---|---|---|---|---|
| 556 | | (CDCl3) 1.67(3H, d, J = 1.2 Hz), 1.98(1H, ddd, J = 14.0, 10.4, 3.7 Hz), 2.47(1H, ddd, J = 14.0, 6.7, 3.5 Hz), 2.79(1H, ddd, J = 12.0, 10.4, 3.5 Hz), 3.02(1H, ddd, J = 12.0, 6.7, 3.7 Hz), 4.11(3H, s), 4.45(2H, br), 7.10(1H, dd, J = 11.7, 8.8 Hz), 7.41(1H, dd, J = 6.9, 2.8 Hz), 8.04(1H, ddd, J = 8.8, 4.0, 2.8 Hz), 8.20(1H, d, J = 1.4 Hz), 9.06(1H, d, J = 1.4 Hz), 9.51(1H, s) | | |
| 558 | | | 358[M + 1] 282 | 200 |
| 559 | | | | 224 |
| 560 | | d in d10-DMSO: 1.72(3H, s), 2.12-2.05(1H, m), 2.71-2.61(2H, m), 3.22-3.19(1H, m), 6.52(1H, s), 7.26(1H, q, J = 11.6, 9.2 Hz), 7.55(1H, s), 7.66-7.62(2H, m), 7.79-7.77(1H, m), 7.90-7.88(1H, m), 8.07(1H, s), 10.42(1H, s), 11.55(1H, s) | | |
| 561 | 235-240 | | | |
| 567 | oil | | | 212 |
| 570 | 186-187 | | | |
| 573 | 112-114 | | | |
| 577 | | d in d19-DMSO: 2.14-2.07(1H, m), 2.88-2.70(3H, m), 3.07, 3.26(2H, abq, J = 12.0 Hz), 3.73(3H, s), 5.40(2H, s), 6.51(1H, s), 6.85(1H, d, J = 12.0 Hz), 7.34(1H, d, J = 8.0 Hz) | | |
| 584 | 152-153 | | | |
| 586 | | d in d7-DMSO: 1.71(3H, s), 2.10-2.04(1H, m), 2.69-2.59(2H, m), 3.20-3.17(1H, m), 4.00(3H, s), 7.13(1H, d, J = 7.4 Hz), 7.33-7.23(3H, m), 7.55(1H, d, J = 8.4 Hz), 7.72-7.68(1H, m), 7.92-7.90(1H, m), 10.60(1H, s) | | |
| 588 | 155-156 | | | |
| 593 | oil | | | 226 |
| 595 | oil | 1.56(3H, s), 1.86(1H, ddd, J = 13.9, 10.1, 3.7), 2.11(1H, ddd, J = 13.9, 6.6, 3.6), 2.32(3H, s), 2.70(1H, ddd, J = 12.3, 10.1, 3.6), 2.90(1H, ddd, J = 12.3, 6.6, 3.7), 5.25(2H, s), 7.29-7.35(4H, m), 7.47(1H, dt, J = 6.8, 2.0), 7.56-7.58(1H, m), 8.59(2H, d, J = 6.0) (solvent: CDCl3) | | 220 |
| 596 | | | | 215 |
| 597 | 192-194 | | | |
| 600 | 178-180 | | | |
| 601 | 181-192 | 1.59 (3H, s), 1.85-1.95 (1H, m), 2.15-2.22 (1H, m), 2.72-2.78 (1H, m), 2.88-2.96 (1H, m), 4.31 (3H, s), 7.13 (1H, d, J = 7.25 Hz), 7.33 (1H, t, J = 7.91 Hz), 7.59 (1H, s), 7.68 (1H, d, J = 7.91 Hz), 7.75 (1H, s). (solvent: CDCl3) | 375[M + 1] | |
| 602 | 272-285 (dec.) | | | |

TABLE 147

| Compound No. | Melting Point (° C.) | 1H-NMR (d) | MS (m/z) | UV (λmax:nm) |
|---|---|---|---|---|
| 605 | 230-233 | 1.63 (s, 3H), 1.94 (ddd, J = 14.0, 10.4, 3.6 Hz, 1H), 2.44 (ddd, J = 14.0, 6.4, 3.6 Hz, 1H), 2.75 (ddd, J = 12.4, 10.4, 3.6 Hz, 1H),, 2.98 (ddd, J = 12.4, 6.4, 3.6 Hz, 1H), 4.50 (2H, br), 7.06 (dd, J = 11.6, 8.8 Hz, 1H), 7.40 (dd, J = 7.2, 2.8 Hz, 1H), 7.59 (ddd, J = 8.8, 8.0, 2.8 Hz, 1H), 7.99 (ddd, J = 8.8, 4.4, 2.8 Hz, 1H), 8.33 (dd, J = 8.8, 4.4 Hz, 1H), 8.45 (d, J = 2.8 Hz, 1H), 9.78 (s, 1H) (solvent: CDCl3) | | |
| 608 | | | | 213.4 304.1 |
| 611 | 200-202 | | | |
| 613 | | | | 238 |
| 618 | | 1.74(s, 3H), 1.97-2.07(m, 1H), 2.45-2.55(m, 1H), 2.77-2.85(m, 1H), 2.84(s, 3H), 2.90-2.96(m, 1H), 7.11(d, J = 8.0 Hz, 1H), 7.42(t, J = 8.0 Hz, 1H), 7.57(d, J = 8.0 Hz, 1H), 7.70(d, J = 8.0 Hz, 1H), 7.74(br s, 1H), 8.29(d, J = 8.8 Hz, 1H), 10.12(s, 1H) (solvent: CDCl3) | | |
| 620 | | | | 212, 253 |
| 625 | 107-109 | | | |

TABLE 147-continued

| Compound No. | Melting Point (° C.) | 1H-NMR (d) | MS (m/z) | UV (λmax:nm) |
|---|---|---|---|---|
| 629 | | d in d14-DMSO: 1.66(3H, s), 2.11-2.05(1H, m), 2.37(3H, s), 2.63-2.53(2H, m), 3.14-3.11(1H, m), 7.08-7.04(2H, t, J = 7.0 Hz), 7.43-7.35(4H, m), 7.83-7.80(2H, m), 10.39(1H, s), 11.69(1H, s) | | |
| 630 | | 1.28 (3H, t, J = 7.7 Hz), 1.96 (1H, ddd, J = 3.8, 9.9, 13.7 Hz), 2.19 (1H, ddd, J = 3.5, 7.0, 13.7 Hz), 2.74 (1H, ddd, J = 3.6, 9.9, 12.2 Hz), 2.93 (1H, ddd, J = 3.8, 7.0, 12.1 Hz), 4.05-4.49 (4H, m), 7.40-7.50 (3H, m), 7.77-7.86 (1H, m) (solvent: CDCl3) | 301[M + 1] | |
| 634 | | (CDCl3) 1.67(3H, d, J = 1.2 Hz), 1.98(1H, ddd, J = 14.0, 10.4, 3.7 Hz), 2.47(1H, ddd, J = 14.0, 6.7, 3.5 Hz), 2.79(1H, ddd, J = 12.0, 10.4, 3.5 Hz), 3.02(1H, ddd, J = 12.0, 6.7, 3.7 Hz), 4.11(3H, s), 4.45(2H, br), 7.10(1H, dd, J = 11.7, 8.8 Hz), 7.41(1H, dd, J = 6.9, 2.8 Hz), 8.04(1H, ddd, J = 8.8, 4.0, 2.8 Hz), 8.20(1H, d, J = 1.4 Hz), 9.06(1H, d, J = 1.4 Hz), 9.51(1H, s) | | |
| 636 | 118-119 | | | |
| 637 | | | | 229, 275 |
| 643 | 155-157 | 1.60 (s, 3H), 1.90 (ddd, J = 14.0, 10.4, 3.6 Hz, 1H), 2.20 (ddd, J = 14.0, 6.8, 3.6 Hz, 1H), 2.77 (ddd, J = 12.0, 10.4, 3.6 Hz, 1H),, 2.93 (ddd, J = 12.0, 6.8, 3.6 Hz, 1H), 4.59 (brs, 1H), 7.16 (ddd, J = 8.0, 2.0, 0.8 Hz, 1H), 7.37 (t, J = 8.0 Hz, 1H), 7.67 (t, J = 2.0 Hz, 1H), 7.71 (ddd, J = 8.0, 2.0, 0.8 Hz, 1H), 7.87 (dd, J = 10.0, 1.2 Hz, 1H), 8.73 (d, J = 1.2 Hz, 1H), 9.74 (s, 1H) (solvent: CDCl3) | | |
| 644 | 201-203 | | | |

TABLE 148

| Compound No. | Melting Point (° C.) | 1H-NMR (d) | MS (m/z) | UV (λmax:nm) |
|---|---|---|---|---|
| 645 | oil | 1.58(3H, s), 1.87(1H, ddd, J = 14.0, 10.4, 3.6), 2.16(1H, ddd, J = 14.0, 6.3, 3.5), 2.34(3H, s), 2.70(1H, ddd, J = 12.3, 10.4, 3.5), 2.90(1H, ddd, J = 12.3, 6.3, 3.6), 5.38(2H, s), 7.18-7.33(3H, m), 7.43(1H, d, J = 8.0), 7.49-7.60(2H, m), 7.69(1H, dt, J = 7.7, 1.9), 8.59(1H, ddd, J = 4.9, 1.9, 1.1) (solvent: CDCl3) | | 222 |
| 649 | 161-162 | | | |
| 651 | 193-196 | 1.59 (s, 3H), 1.90 (ddd, J = 14.0, 10.4, 3.6 Hz, 1H), 2.18 (ddd, J = 14.0, 6.4, 3.6 Hz, 1H), 2.76 (ddd, J = 12.4, 10.4, 3.6 Hz, 1H),, 2.93 (ddd, J = 12.4, 6.4, 3.6 Hz, 1H), 4.42 (br, 2 H), 7.17 (ddd, J = 8.0, 2.0, 0.8 Hz, 1H), 7.38 (t, J = 8.0 Hz, 1H), 7.64 (t, J = 2.0 Hz, 1H), 7.77 (ddd, J = 8.0, 2.0, 0.8 Hz, 1H), 8.20 (dd, J = 8.0, 2.0 Hz, 1H), 8.44 (dd, J = 8.0, 0.8 Hz, 1H), 8.91 (dd, J = 2.0, 0.8 Hz, 1H), 9.87 (s, 1H) (solvent: CDCl3) | | |
| 652 | | d in d21-DMSO: 1.67(3H, s), 2.14-2.07(1H, m), 2.62-2.57(2H, m), 3.17-3.14(1H, m), 5.74(1H, s), 7.14(1H, d, J = 8.0 Hz), 7.44(1H, t, J = 8.0 Hz), 7.85-7.81(2H, m), 8.01(1H, d, J = 12.0 Hz), 8.16(1H, d, J = 8.0 Hz), 8.77(1H, s), 10.95(1H, s) | | |
| 653 | 193-194 | | | |
| 654 | oil | | | 257 |
| 657 | 199-203 | | | |
| 660 | amorphous | | | 223, 266 |
| 661 | | d in d9-DMSO: 1.30(3H, t, J = 7.0 Hz), 1.69(3H, s), 2.10-2.04(1H, m), 2.20(3H, s), 2.67-2.62(2H, m), 3.20-3.17(1H, m), 4.40(2H, q, J = 14.0, 7.0 Hz), 6.83(1H, s), 7.25(1H, q, J = 12.0, 9.0 Hz), 7.62-7.61(1H, m), 7.85-7.83(1H, m), 10.42(1H, s) | | |
| 664 | amorphous | | | 225, 267 |
| 667 | amorphous | | | 226 |
| 673 | oil | | | 224 |
| 677 | amorphous | | | 216 |
| 680 | 159-160 | 1.63(3H, s), 1.65-1.80(1H, m), 2.53-2.64(1H, m), 2.75-2.88(2H, m), 3.83(3H, s), 4.32(2H, br), 6.87-6.96(2H, m), 7.19-7.33(2H, m) (solvent: CDCl3) | | |

TABLE 148-continued

| Compound No. | Melting Point (° C.) | 1H-NMR (d) | MS (m/z) | UV (λmax:nm) |
|---|---|---|---|---|
| 681 | | d in d6-DMSO: 1.43(3H, s), 1.66-1.74(1H, m), 2.02-2.07(1H, m), 2.56-2.63(1H, m), 2.85-2.90(1H, m), 5.80(2H, bs), 6.91(1H, d, J = 7.8 Hz), 6.96-6.98(2H, m), 7.25(1H, t, J = 7.8 Hz), 7.2-7.36(2H, m), 7.40(1H, m), 7.89-7.92(1H, m), 9.42(1H, bs), 10.78(1H, bs). | 338[M + 1] | |
| 683 | 166-168 | | | |

TABLE 149

| Compound No. | Melting Point (° C.) | 1H-NMR (d) | MS (m/z) | UV (λmax:nm) |
|---|---|---|---|---|
| 687 | 164-167 | 1.60 (3H, s), 1.84-1.95 (1H, m), 2.21-2.26 (1H, m), 2.73-2.94 (2H, m), 3.92 (3H, s), 4.25 (3H, s), 7.10 (1H, d, J = 7.58 Hz), 7.34 (1H, t, J = 7.91 Hz), 7.40 (1H, s), 7.57 (1H, br s), 7.66 (1H, d, J = 7.91 Hz), 8.67 (1H, s). (solvent: CDCl3) | 388[M + 1] | |
| 692 | | (CDCl3) 1.50(3H, s), 1.75-1.88(1H, m), 2.00-2.10(1H, m), 2.91-2.99(1H, m), 3.08-3.18(1H, m), 6.21(1H, d, J = 15.9 Hz), 6.59(1H, d, J = 15.9 Hz), 7.42-7.47(3H, m), 7.59(1H, dd, J = 8.6, 2.0 Hz), 7.74-7.83(4H, m) | | |
| 698 | | | | 269 |
| 700 | 177-178 | | | |
| 701 | | 1.61(s, 3H), 1.90(m, 1H), 2.25(m, 1H), 2.81(m, 1H), 2.92(m, 1H), 3.86(s, 3H), 6.71(t-like, J = 1.8 Hz, 1H), 7.12(t-like, J = 1.8 Hz, 1H), 7.53(t-like, J = 1.8 Hz, 1H), 7.89(dd, J = 8.3 Hz, 2.4 Hz, 1H), 8.24(d, J = 8.3 Hz, 1H), 8.58(d, J = 2.4 Hz, 1H), 9.85(br, 1H) (solvent: CDCl3) | | |
| 702 | | 1H-NMR (CDCl3) d: 1.65 (3H, s), 1.91-1.98 (1H, m), 2.57-2.62 (1H, m), 2.68-2.75 (1H, m), 2.92-2.97 (1H, m), 4.18 (3H, s), 6.82 (1H, br s), 7.02-7.08 (1H, m), 7.28-7.32 (1H, m), 7.44 (1H, s), 7.92-7.96 (1H, m). | | |
| 707 | 167-174 | | | |
| 709 | 99-100 | 0.82(3H, t, J = 7.3 Hz), 1.72-1.90(3H, m), 2.06-2.15(1H, m), 2.61-2.82(2H, m), 3.80(3H, s), 4.36(2H, br), 6.86(2H, d, J = 8.9 Hz), 7.17(2H, d, J = 8.9 Hz) (solvent: CDCl3) | | |
| 717 | 157-162 | 1.58 (s, 3H), 1.90 (ddd, J = 14.0, 10.4, 3.6 Hz, 1H), 2.15 (ddd, J = 14.0, 6.8, 3.6 Hz, 1H), 2.76 (ddd, J = 12.4, 10.4, 3.6 Hz, 1H), 2.94 (ddd, J = 12.4, 6.8, 3.6 Hz, 1H), 3.49 (1H, S), 3.76 (2H, br), 7.17 (ddd, J = 8.0, 2.0, 0.8 Hz, 1H), 7.36 (t, J = 8.0 Hz, 1H), 7.38 (d, J = 1.6 Hz, 1H), 7.50 (t, J = 2.0 Hz, 1H), 7.73 (ddd, J = 8.0, 2.0, 0.8 Hz, 1H), 8.22 (d, J = 2.4 Hz), 9.26 (d, J = 2.4 Hz, 1H), 10.12 (s, 1H) (solvent: CDCl3) | | |
| 719 | oil | | | 226 |
| | | | | 254 |
| 720 | 133-138 | | | |
| 725 | amorphous | 1.62 (s, 3H), 1.96-2.03(m, 1H), 2.38-2.49 (m, 1H), 2.63-2.71 (m, 1H), 3.05-3.12 (m, 1H), 6.73 (dd, J = 3.2, 1.6 Hz, 2H), 7.35(d, J = 3.2 Hz, 1H), 7.37 (br s, 1H), 7.57 (d, J = 8.4 Hz, 2H), 7.67 (d, J = 8.4 Hz, 2H), 7.77 (br s, 1H), 7.96(br s, 1H), 8.01(br s, 1H), 10.35 (s, 1H) (solvent: DMSO-d6) | | 265 |
| 728 | 179-182 | | | |
| 729 | 167-169 | | | |

TABLE 150

| Compound No. | Melting Point (° C.) | 1H-NMR (d) | MS (m/z) | UV (λmax:nm) |
|---|---|---|---|---|
| 730 | | | | 211.0 |
| | | | | 289.9 |
| 731 | 91-94 | | | |
| 732 | amorphous | | | 211 |
| 735 | 166-168 | | | |

TABLE 150-continued

| Compound No. | Melting Point (° C.) | 1H-NMR (d) | MS (m/z) | UV (λmax:nm) |
|---|---|---|---|---|
| 737 | | 1H-NMR (CDCl3) d: 1.59 (3H, s), 1.87-1.94 (1H, m), 2.47-2.53 (1H, m), 2.67-2.73 (1H, m), 2.93-2.99 (1H, m), 4.10 (3H, s), 6.62 (1H, s), 7.04 (1H, t, J = 10.2 Hz), 7.33 (1H, d, J = 4.3 Hz), 7.85 (1H, br s). | | |
| 738 | 181-183 | | | |
| 739 | | | | 285 |
| 740 | 250 (dec.) | | | |
| 743 | 148-150 | 1.60 (s, 3H), 179-2.93 (m, 4H), 4.46 (2H, br), 7.09 (d, J = 2.0 Hz, 1H), 7.12 (ddd, J = 7.6, 2.0, 0.8 Hz, 1H), 7.18 (t, J = 2.0 Hz, 1H), 7.36 (d, J = 7.6, 2.0, 0.8 Hz, 1H), 7.43 (t, J = 7.6 Hz, 1H), 8.21 (d, J = 2.0 Hz) (solvent: CDCl3) | | |
| 744 | | d in d8-DMSO: 1.47(3H, s), 1.82-1.78(1H, m), 2.22-2.18(1H, m), 2.62-2.56(1H, m), 3.00-2.96(1H, m), 6.79(1H, s), 6.63(1H, s), 7.08-7.03(1H, m), 7.51(1H, s), 7.64-7.57(2H, m), 9.57(1H, s), 11.25(1H, s) | | |
| 753 | amorphous | | | 225, 299 |
| 756 | 110-111 | 1.55(3H, s), 1.76-1.87(1H, m), 2.08-2.17(1H, m), 2.35(3H, s), 2.65-2.76(1H, m), 2.82-2.92(1H, m), 4.35(2H, br), 7.01-7.25(4H, m) (solvent: CDCl3) | | |
| 758 | 156-157 | | | |
| 766 | | | 336[M + 1] 260 | 203 212 |
| 767 | 98-100 | | | |
| 768 | | 1.60 (3H, d, J = 1.3 Hz), 1.89-1.99 (1H, m), 2.29 (3H, s), 2.37-2.42 (1H, m), 2.70-2.75 (1H, m), 2.96-3.00 (1H, m), 4.12 (3H, s), 6.39 (1H, s), 7.04 (1H, dd, J = 11.5, 8.9 Hz), 7.18 (1H, dd, J = 6.9, 2.6 Hz), 7.60 (1H, s), 7.82-7.86 (1H, m). (solvent: CDCl3) | 362[M + 1] | 213 263 |
| 771 | | | 417[M + 1] 341 | 201 |
| 774 | | ¹H-NMR (CDCl₃) d: 1.77 (3H, s), 2.11-2.21 (1H, m), 2.71-2.80 (1H, m), 2.87-2.99 (2H, m), 6.91 (1H, d, J = 6.9 Hz), 7.28 (2H, s), 7.47 (1H, t, J = 8.1 Hz), 7.75 (1H, t, J = 8.6 Hz), 8.04 (1H, dd, J = 8.6, 2.3 Hz), 8.29 (1H, d, J = 8.2 Hz), 8.46 (1H, d, J = 2.2 Hz). | 400[M + 1] | |

TABLE 151

| Compound No. | Melting Point (° C.) | 1H-NMR (d) | MS (m/z) | UV (λmax:nm) |
|---|---|---|---|---|
| 781 | | 1.63 (s, 3H), 1.92 (ddd, J = 14.0, 10.8, 4.0 Hz, 1H), 2.29 (m, 1H), 2.78 (ddd, J = 12.4, 10.8, 3.6 Hz, 1H),, 2.91 (ddd, J = 12.4, 6.4, 4.0 Hz, 1H), 3.94 (3H, s), 7.09 (ddd, J = 8.0, 2.0, 0.8 Hz, 1H), 7.34 (dd, J = 8.8, 2.8 Hz, 1H), 7.35 (t, J = 8.0 Hz, 1H), 7.68 (t, J = 2.0 Hz, 1H), 7.71 (ddd, J = 8.0, 2.0, 0.8 Hz, 1H), 8.24 (d, J = 8.8 Hz, 1H), 8.28 (d, J = 2.8 Hz, 1H), 9.86 (s, 1H) (solvent: CDCl3) | | |
| 783 | 205-206 | | | |
| 786 | | 1.66(3H, s), 2.10(1H, m), 2.57-2.64(2H, m), 3.16(1H, m), 6.74(1H, m), 7.30(1H, s), 7.36(1H, s), 7.74(1H, s), 7.98(1H, s), 8.06(1H, s), 10.33(1H, s), 10.47(1H, s) (solvent: DMSO-d6) | | |
| 790 | amorphous | | | 223, 290 |
| 791 | | d in d18-DMSO: 1.41(3H, s), 1.76-1.69(1H, m), 2.02-1.98(1H, m), 2.62-2.55(1H, m), 2.92-2.89(1H, m), 7.13(1H, d, J = 7.6 Hz), 7.29(1H, t, J = 7.6 Hz), 7.62-7.59(2H, m), 8.71(1H, s), 9.28(1H, s), 10.46(1H, brs) | | |
| 792 | | | | 299.4 |
| 793 | 269 (dec.) | | | |
| 797 | | | | 213.4 312.4 |
| 799 | | | | 215, 240 |
| 800 | | | | 225, 275 |
| 802 | | 1.63 (s, 3H), 1.92 (ddd, J = 14.0, 11.2, 3.6 Hz, 1H), 2.28 (br, 1H), 2.78 (ddd, J = 12.4, 11.2, 3.6 Hz, 1H), 2.81 (s, 3H), 2.92 (ddd, J = 12.4, 6.4, 4.0 Hz, 1H), 7.10 (ddd, J = 8.0, 2.0, 0.8 Hz, 1H), 7.35 (t, J = 8.0 Hz, 1H), 7.56 (t, J = 2.0 Hz, 1H), 7.65 (d, J = 2.4 Hz, 1H), 7.74 (ddd, J = 8.0, 2.0, 0.8 Hz, 1H), 8.41 (d, J = 2.4 Hz, 1H), 10.03 (s, 1H) (solvent: CDCl3) | | |

TABLE 151-continued

| Compound No. | Melting Point (° C.) | 1H-NMR (d) | MS (m/z) | UV (λmax:nm) |
|---|---|---|---|---|
| 803 | | | | 271 |
| 804 | 135-136 | | | |
| 810 | 47-48 | | | |
| 811 | 138-139 | | | |
| 813 | 204-205 | 182 (s, 3H), 1.89-1.94 (m, 1H), 2.78 (ddd, J = 12.4, 6.4, 3.6 Hz, 1H), 4.50 (2H, br), 7.06 (dd, J = 11.6, 8.8 Hz, 1H), 7.40 (dd, J = 7.2, 2.8 Hz, 1H), 7.59 (ddd, J = 8.8, 8.0, 2.8 Hz, 1H), 7.99 (ddd, J = 8.8, 4.4, 2.8 Hz, 1H), 8.33 (dd, J = 8.8, 4.4 Hz, 1H), 8.45 (d, J = 2.8 Hz, 1H), 9.78 (s, 1H)(solvent: CDCl3) | | |
| 814 | oil | | | 218, 272 |
| 816 | | | | 214.5 |

TABLE 152

| Compound No. | Melting Point (° C.) | 1H-NMR (d) | MS (m/z) | UV (λmax:nm) |
|---|---|---|---|---|
| 820 | | (CDCl3) 1.66(3H, d, J = 1.2 Hz), 1.98(1H, ddd, J = 14.0, 10.4, 3.7 Hz), 2.47(1H, ddd, J = 14.0, 6.7, 3.5 Hz), 2.79(1H, ddd, J = 12.0, 10.4, 3.5 Hz), 3.02(1H, ddd, J = 12.0, 6.7, 3.7 Hz), 4.45(2H, br), 6.16(2H, br), 7.04-7.11(2H, m), 7.38(1H, dd, J = 7.2, 2.9 Hz), 7.88(1H, d, J = 2.0 Hz), 7.96(1H, ddd, J = 8.9, 4.2, 2.9 Hz), 9.88(1H, s), | | |
| 822 | | | | 279 |
| 827 | 134-137 | | | 214.5 284.0 |
| 832 | | | | 212, 299 |
| 833 | oil | | | 212, 273 |
| 834 | | | | 217, 267 |
| 835 | 139-140 | | | |
| 836 | | | | 221.6 279.3 |
| 840 | 223-225 | | | |
| 848 | oil | | | 223, 254 |
| 849 | 143-145 | | | |
| 850 | | d in d16-DMSO: 1.41(3H, s), 1.75-1.70(1H, m), 2.02-1.99(1H, m), 2.61-2.56(1H, m), 2.93-2.88(1H, m), 7.13(1H, d, J = 8.0), 7.29(1H, t, J = 7.8 Hz), 7.35(1H, q, J = 8.4, 2.4 Hz), 7.66-7.63(2H, m), 8.52-8.47(1H, m), 8.81(1H, s), 10.44(1H, s) | | |
| 851 | 82-83 | 1.55(3H, s), 1.76-1.88(1H, m), 2.10-2.18(1H, m), 2.66-2.77(1H, m), 2.82-2.91(1H, m), 3.81(3H, s), 6.73-6.78(1H, m), 6.88-6.92(2H, m), 7.21-7.29(1H, m) (solvent: CDCl3) | | |
| 855 | oil | | | 219 |
| 859 | | | 350[M + 1] 274 | 200 208 254 |
| 863 | 192-194 | 1.39(t, J = 7.2 Hz, 3H), 1.42(s, 3H), 1.71-1.79(m, 1H), 2.02-2.10(m, 1H), 2.55-2.62(m, 1H), 2.88-2.96(m, 1H), 4.47(q, J = 7.2 Hz, 2H), 5.70-6.20(br s, 2H), 7.11(d, J = 8.0 Hz, 1H), 7.29(t, J = 8.0 Hz, 1H), 7.75(d, J = 8.0 Hz, 1H), 7.80(br s, 1H), 8.38(d, J = 1.2 Hz, 1H), 8.87(d, J = 1.2 Hz, 1H), 10.34(s, 1H) (solvent: CDCl3) | | |
| 866 | | | | 293.5 |
| 869 | | 1.65 (s, 3H), 1.90-2.01 (m, 3H), 2.32 (br, 1H), 2.80 (td, J = 12.0, 3.6 Hz, 1H), 2.85 (t, J = 8.0 Hz, 2H), 2.92 (ddd, J = 12.0, 5.6, 3.6 Hz, 1H), 3.75 (t, J = 8.0 Hz, 2H), 7.11 (ddd, J = 8.0, 2.0, 0.8 Hz, 1H), 7.37 (t, J = 8.0 Hz, 1H), 7.70 (t, J = 2.0 Hz, 1H), 7.73-7.76 (m, 2H), 8.22 (d, J = 7.6 Hz, 1H), 8.48 (d, J = 2.0 Hz, 1H), 10.00 (s, 1H) (solvent: CDCl3) | | |
| 871 | 212-213 | | | |

TABLE 153

| Compound No. | Melting Point (° C.) | 1H-NMR (d) | MS (m/z) | UV (λmax:nm) |
|---|---|---|---|---|
| 875 | oil | | | 222, 271 |
| 876 | oil | | | 222 |
| 878 | oil | | | 211 |
| 881 | 141-144 | | | |
| 887 | | | | 262.7 |
| 892 | 251 (dec.) | | | |
| 893 | | d in d12-DMSO: 1.70(3H, s), 2.10-2.04(1H, m), 2.69-2.59(2H, m), 3.20-3.17(1H, m), 6.80(1H, brs), 7.26-7.20(1H, m), 7.88-7.81(3H, m), 10.35(1H, s)13.53(1H, brs) | | |
| 895 | | | 378[M + 1] 302 | 202 208 216 221 265 |
| 896 | amorphous | | | 219, 264 |
| 897 | 212-214 | | | |
| 900 | 205-207 | 1.61 (s, 3H), 1.91 (ddd, J = 14.0, 10.8, 4.0 Hz, 1H), 2.23 (ddd, J = 14.0, 6.4, 3.6 Hz, 1H), 2.77 (ddd, J = 12.4, 10.8, 3.6 Hz, 1H), 2.92 (ddd, J = 12.4, 6.4, 4.0 Hz, 1H), 7.15 (ddd, J = 8.0, 2.0, 0.8 Hz, 1H), 7.38 (t, J = 8.0 Hz, 1H), 7.65 (t, J = 2.0 Hz, 1H), 7.79 (ddd, J = 8.0, 2.0, 0.8 Hz, 1H), 8.99 (s, 2H), 9.78 (s, 1H) (solvent: CDCl3) | | |
| 906 | | | | 212.2 273.4 350.5 |
| 908 | | d in d15-DMSO: 1.66(3H, s), 2.11-2.05(1H, m), 2.37(3H, s), 2.63-2.54(2H, m), 3.16-3.11(1H, m), 3.16(3H, s), 7.08-6.96(3H, m), 7.49-7.41(3H, m), 7.85-7.81(2H, m), 10.52(1H, s)11.69(1H, s) | | |
| 910 | oil | | | 211, 276 |
| 916 | 131-132 | | | |
| 926 | | 1.89(3H, s), 2.15(1H, m), 2.71-2.82(2H, m), 2.96(1H, m), 3.04(3H, d, J = 4.9), 7.35(1H, dd, J = 8.7, 1.8), 7.50-7.55(2H, m), 7.74(1H, s), 7.82-7.90(3H, s), 10.40(1H, br), 11.36(1H, Br) (solvent: CDCl3) | | |
| 928 | | 1.20(t, J = 7.6 Hz, 3H), 1.53(br s, 3H), 1.82-1.97(m, 1H), 2.39(s, 3H), 2.61(q, J = 7.6 Hz, 2H), 2.99-3.07(m, 1H), 6.93(br s, 1H), 7.33(d, J = 8.4 Hz, 2H), 7.54-7.58(m, 2H), 7.87(d, J = 8.4 Hz, 2H), 10.13(s, 1H) (solvent: CDCl3) | | |
| 930 | 132.1-134.4 | | 328[M + 1] | |
| 931 | | | | 299 |
| 933 | amorphous | | | 212, 259 |

TABLE 154

| Compound No. | Melting Point (° C.) | 1H-NMR (d) | MS (m/z) | UV (λmax:nm) |
|---|---|---|---|---|
| 935 | 161-165 | 1.62 (s, 3H), 1.91 (ddd, J = 14.0, 10.4, 4.0 Hz, 1H), 2.24 (ddd, J = 14.0, 6.4, 3.6 Hz, 1H), 2.80 (ddd, J = 12.0, 10.4, 3.6 Hz, 1H), 2.93 (ddd, J = 12.0, 6.4, 4.0 Hz, 1H), 7.15 (ddd, J = 8.0, 2.0, 1.2 Hz, 1H), 7.39 (t, J = 8.0 Hz, 1H), 7.66 (ddd, J = 8.4, 7.2, 1.2 Hz, 1H), 7.75 (t, J = 2.0 Hz, 1H), 7.80-7.84 (m, 2H), 7.93 (ddd, J = 8.0, 2.0, 1.2 Hz, 1H), 8.21 (d, J = 8.4 Hz, 1H), 8.38 (d, J = 8.0 Hz, 1H), 8.41 (d, J = 8.0 Hz, 1H), 10.25 (s, 1H) (solvent: CDCl3) | | |
| 936 | 169-170 | | | |
| 939 | | d in d6-DMSO: 1.72(3H, s), 2.11-2.05(1H, m), 2.70-2.60(2H, m), 3.21-3.18(1H, m), 7.20(1H, d, J = 9.2 Hz), 7.28(1H, q, J = 11.6, 9.2 Hz), 8.56-7.54(2H, m), 7.69(1H, s), 7.90-7.85(2H, m), 10.69(1H, s), 12.17(1H, brs) | | |
| 941 | | | | 220 |
| 944 | amorphous | | | 219, 256 |

TABLE 154-continued

| Compound No. | Melting Point (° C.) | 1H-NMR (d) | MS (m/z) | UV (λmax:nm) |
|---|---|---|---|---|
| 946 | | 1.61 (s, 3H), 1.91 (ddd, J = 14.0, 10.8, 3.6 Hz, 1H), 2.26 (ddd, J = 14.0, 6.4, 3.6 Hz, 1H), 2.77 (ddd, J = 12.4, 10.8, 3.6 Hz, 1H),, 2.92 (ddd, J = 12.4, 6.4, 3.6 Hz, 1H), 7.13 (ddd, J = 8.0, 2.0, 1.2 Hz, 1H), 7.36 (t, J = 8.0 Hz, 1H), 7.61 (t, J = 2.0 Hz, 1H), 7.72 (ddd, J = 8.0, 2.0, 1.2 Hz, 1H), 7.91 (d, J = 2.4 Hz, 1H), 8.49 (d, J = 2.4 Hz, 1H), 9.75 (s, 1H) (solvent: CDCl3) | | |
| 947 | | | | 215.7 276.9 |
| 960 | | | | 261.5 |
| 964 | 185-187 | | | |
| 966 | oil | | | 216 |
| 968 | 107-109 | | | |
| 970 | | 1.57 (s, 3H), 1.78-1.89 (m, 1H), 2.10-2.19 (m, 1H), 2.69 (ddd, J = 11.9, 10.8, 3.5 Hz, 1H), 2.83-2.91 (m, 1H), 7.15-7.35 (m, 5H) (solvent: CDCl3) | | |
| 971 | | (DMSO) 1.49(3H, s), 1.73-1.86(1H, m), 2.16-2.30(1H, m), 2.54-2.65(1H, m), 2.92-3.03(1H, m), 5.86(2H, s), 7.04-7.18(2H, m), 7.38-7.50(3H, m), 7.66-7.78(2H, m), 10.35(1H, s), 11.84(1H, s) | | |
| 972 | | 1.51 (3H, s) 1.91-1.95 (1H, m) 2.37 (3H, s) 3.00-3.05 (1H, m) 7.24 (1H s) 7.33 (2H, d J = 9.0 Hz) 7.66 (1H, s) 7.85 (2H, d J = 9.0 Hz) 8.03 (1H, s) 10.37 (1H, s) (solvent: DMSO-d6) | | |
| 974 | amorphous | | | 219 |
| 978 | oil | | | 222 |
| 984 | | | | 255.7 318.4 |
| 990 | 126-129 | | | |
| 994 | 130-131 | | | |

TABLE 155

| Compound No. | Melting Point (° C.) | 1H-NMR (d) | MS (m/z) | UV (λmax:nm) |
|---|---|---|---|---|
| 998 | amorphous | | | 229, 290 |
| 1005 | 191-193 | | | |
| 1006 | 88-90 | 2.42-2.47(2H, m), 2.80-2.86(2H, m), 7.78(6H, s), 6.83(4H, d, J = 8.9 Hz), 7.22(4H, d, J = 8.9 Hz) (solvent: CDCl3) | | |
| 1008 | 125-126 | | | |
| 1010 | 90-91 | | | |
| 1014 | 206-210 | | | |
| 1020 | | | | 216.9 245.1 |
| 1028 | 105-106 | | | |
| 1034 | | | | 212.2 286.4 |
| 1035 | 247-251 (dec.) | | | |
| 1037 | amorphous | | | 224, 272 |
| 1039 | amorphous | | | 217 249 |
| 1043 | 277-281 | | | |
| 1044 | | (DMSO) 1.12(3H, s), 1.60(2H, d, J = 6.2 Hz), 1.73(2H, d, J = 8.6 Hz), 2.65-2.90(2H, m), 2.93-3.13(2H, m), 5.55(1H, s), 7.34-7.52(3H, m), 7.68(1H, s), 7.79-7.90(3H, m) | | |
| 1052 | | 1.75(s, 3H), 2.12-2.21(m, 1H), 2.40(s, 3H), 2.65-2.73(m, 2H), 3.17-3.23(m, 2H), 7.37(d, J = 8.4 Hz, 2H), 7.40-7.44(m, 1H), 7.77(br s, 1H), 7.92-7.99(m, 5H), 8.47(br s, 1H), 8.70(d, J = 4.8 Hz, 1H), 10.37(s, 1H), 10.41(s, 1H) (solvent: CDCl3) | | |
| 1055 | 169-170 | 1.56(3H, s), 1.78-1.89(1H, m), 2.04-2.15(1H, m), 2.68-2.79(1H, m), 2.86-2.95(1H, m), 4.32(2H, br), 6.94-7.02(4H, m), 7.05-7.12(1H, m), 7.25-7.37(4H, m) (solvent: CDCl3) | | |
| 1056 | | | | 219 |
| 1059 | 262-267 | | | |
| 1061 | | | | 216 |
| 1062 | 136-137 | 1.53(3H, s), 1.76-1.88(1H, m), 2.03-2.13(1H, m), 2.63-2.73(1H, m), 2.85-2.94(1H, m), 4.35(2H, br), 7.23-7.32(4H, m) (solvent: CDCl3) | | |

TABLE 155-continued

| Compound No. | Melting Point (° C.) | 1H-NMR (d) | MS (m/z) | UV (λmax:nm) |
|---|---|---|---|---|
| 1064 | 84-85 | 1.52(3H, s), 1.73-1.89(1H, m), 1.97-2.07(1H, m), 2.64-2.81(1H, m), 2.82-2.91(1H, m), 2.87(3H, s), 3.77(3H, s), 4.10(1H, brs), 6.84(2H, d, J = 8.9 Hz), 7.28(2H, d, J = 8.6 Hz) (solvent: CDCl3) | | |
| 1067 | 162-165 | | | |
| 1068 | 132-134 | | | 230 |
| 1069 | 194-196 | | | |
| 1074 | | | 324[M + 1] | 200 |
| | | | 248 | 207 |
| 1076 | amorphous | | | 217 |

TABLE 156

| Compound No. | Melting Point (° C.) | 1H-NMR (d) | MS (m/z) | UV (λmax:nm) |
|---|---|---|---|---|
| 1084 | 146-149 | | | |
| 1087 | | | | 311.2 |
| 1088 | amorphous | 1.55(3H, s), 1.83(1H, ddd, J = 13.9, 10.5, 3.7), 2.09(1H, ddd, J = 13.9, 6.6, 3.6), 2.67(1H, ddd, J = 12.3, 10.5, 3.6), 2.88(1H, ddd, J = 12.3, 6.6, 3.7), 4.48(2H, d, J = 6.0), 4.91(1H, br), 6.33(1H, dd, J = 8.8, 0.8), 7.19(1H, d, J = 7.3, 7.23-7.30(2H, m), 7.35(1H, dd, J = 8.8, 2.8), 8.05(1H, dd, J = 2.8, 0.8) (solvent: CDCl3) | | 229 318 |
| 1094 | | | | 216, 322 |
| 1100 | 278 (dec.) | | | |
| 1107 | oil | 1.58(3H, s), 1.90(1H, ddd, J = 13.9, 10.1, 3.7), 2.14(1H, ddd, J = 13.9, 6.8, 3.6), 2.69(1H, ddd, J = 12.2, 10.1, 3.6), 2.94(1H, ddd, J = 12.2, 6.8, 3.7), 3.81(3H, s), 4.62(2H, s), 6.90(2H, d, J = 8.8), 7.30(2H, d, J = 8.8), 7.43(1H, t, J = 7.4), 7.57(1H, ddd, J = 7.4, 1.6, 1.2), 7.81(1H, ddd, J = 7.6, 1.6, 1.2), 7.95(1H, t, J = 1.6) (solvent: CDCl3) | | 226 284 |
| 1109 | 134-140 | | | |
| 1110 | 109-110 | | | |
| 1111 | 118-119 | | | |
| 1114 | 121-124 | | | |
| 1115 | 167-170 | 1.63 (s, 3H), 1.93 (ddd, J = 14.0, 10.4, 4.0 Hz, 1H), 2.24 (ddd, J = 14.0, 6.4, 3.6 Hz, 1H), 2.81 (ddd, J = 12.4, 10.4, 3.6 Hz, 1H), 2.96 (ddd, J = 12.4, 6.4, 4.0 Hz, 1H), 4.49 (br, 2H), 7.19 (ddd, J = 8.0, 2.0, 0.8 Hz, 1H), 7.42 (t, J = 8.0 Hz, 1H), 7.74 (t, J = 2.0 Hz, 1H), 7.84 (ddd, J = 8.0, 2.0, 0.8 Hz, 1H), 7.88-7.95 (m, 2H), 8.22-8.26 (m, 2H), 9.80 (s, 1H), 9.89 (s, 1H) (solvent: CDCl3) | | |
| 1116 | oil | | | 220, 255, 307 |
| 1119 | 153-157 | | | |
| 1120 | 213-214 | | | |
| 1124 | 169-172 | | | 225 |
| 1125 | 195-198 | | | 222 256 289 |
| 1131 | 189-191 | | | |
| 1132 | 175-180 (dec) | | | |
| 1133 | amorphous | | | 219, 292 |
| 1135 | 255-260 (dec.) | | | |
| 1139 | 140-141 | | | |
| 1140 | oil | | | 218 |
| 1142 | 182-186 (dec.) | | | |

TABLE 157

| Compound No. | Melting Point (° C.) | 1H-NMR (d) | MS (m/z) | UV (λmax:nm) |
|---|---|---|---|---|
| 1147 | | | | 214.5 275.7 |
| 1150 | | | | 221.6 279.3 |
| 1153 | 156-159 | | | |
| 1160 | | 1.64 (3H, s) 2.02-2.12 (1H, m) 2.54-2.63 (1H, m) 3.11-3.16 (1H, m) 7.28 (1H, s) 7.70 (1H, dd J = 8.1 Hz) 7.85 (1H, s) 8.04-8.17 (2H, m) 8.28 (1H s) 8.74 (1H d J = 5.1 Hz) 10.81 (1H, s) 10.96 (1H, s) (solvent: DMSO-d6) | | |
| 1161 | 192-193 | | | |
| 1166 | 290-295 | | 444[M + 3] 442[M + 1] 368 366 | |
| 1172 | | 1.55 (3H, s) 1.94-2.03 (1H, m) 2.18-2.27 (1H, m) 2.32 (3H, s) 3.03-3.07 (1H, m) 7.05 (1H, s) 7.09 (1H, s) 7.14 (1H, s) 7.37 (2H, d J = 9.0 Hz) 7.66 (2H, d J = 9.0 Hz) 10.65 (1H, s) 10.70 (1H, s) (solvent: DMSO-d6) | | |
| 1181 | 194-195 | 1.60(3H, s), 1.81-1.93(1H, m), 2.13-2.22(1H, m), 2.70-2.81(1H, m), 2.86-2.96(1H, m), 4.36(2H, br), 7.29-7.46(5H, m), 7.53-7.61(4H, m) (solvent: CDCl3) | | |
| 1184 | 149-150 | | | |
| 1185 | | | | 225.1 280.4 |
| 1193 | 182-183 | | | |
| 1194 | | | 344[M + 1] 268 | 209 214 261 |
| 1197 | 250-255 (dec.) | | | |
| 1199 | 274-283 | | | |
| 1205 | oil | | | E 213, 273 Z 219, 275 |
| 1207 | 106-108 | | | |
| 1211 | | 1.77 (s, 3H), 1.98-2.54 (m, 2H), 2.81 (s, 3H), 2.81-2.94 (m, 2H), 3.93 (s, 3H), 7.03 (ddd, J = 8.0, 2.0, 0.8 Hz, 1H), 7.08 (d, J = 2.4 Hz, 1H), 7.36 (t, J = 8.0 Hz, 1H), 7.63 (t, J = 2.0 Hz, 1H), 7.69 (ddd, J = 8.0, 2.0, 0.8 Hz, 1H), 8.14 (d, J = 2.4 Hz, 1H), 10.13 (s, 1H) (solvent: CDCl3) | | |
| 1213 | | | 406[M + 1] 330 | 20 209 213 |

TABLE 158

| Compound No. | Melting Point (° C.) | 1H-NMR (d) | MS (m/z) | UV (λmax:nm) |
|---|---|---|---|---|
| 1215 | amorphous | 1.64 (s, 3H), 2.07 (ddd, J = 14.1, 11.5, 3.8 Hz, 1H), 2.17 (s, 3H), 2.39 (ddd, J = 14.1, 5.3, 3.5 Hz, 1H), 2.72 (ddd, J = 12.6, 11.5, 3.5 Hz, 1H), 2.80 (ddd, J = 12.6, 5.3, 3.8 Hz, 1H), 3.21 (t, J = 8.9 Hz, 2H), 4.58 (t, J = 8.9 Hz, 2H), 6.76 (d, J = 8.4 Hz, 1H), 6.97-7.02 (m, 1H), 7.08-7.11 (m, 1H) (solvent: CDCl3) | | |
| 1216 | | | | 305.3 |
| 1217 | 263-266 | | | |
| 1221 | amorphous | | | 220, 253 |
| 1223 | | | | 226.3 280.4 |
| 1224 | | d in d11-DMSO: 1.46(3H, s), 1.83-1.77(1H, m), 2.18-2.15(1H, m), 2.61-2.56(1H, m), 2.99-2.95(1H, m), 7.08(1H, q, J = 12.0, 8.4 Hz), 7.72-7.66(2H, m), 7.79(2H, d, J = 9.2)9.67(1H, s) | | |
| 1228 | oil | | | 224 |
| 1230 | 232-234 | | | |
| 1240 | | | | 216.9 285.2 |
| 1241 | 194-195 | | | |

TABLE 158-continued

| Compound No. | Melting Point (° C.) | 1H-NMR (d) | MS (m/z) | UV (λmax:nm) |
|---|---|---|---|---|
| 1242 | | d in d21-DMSO: 1.41(3H, m), 1.75-1.68(1H, m), 2.04-1.99(1H, m), 2.61-2.56(1H, m), 2.89(4H, s), 5.75(2H, brs), 7.07(1H, d, J = 4.0 Hz), 7.25(1H, t, J = 8.0 Hz), 7.72(1H, d, J = 8.0 Hz), 7.75(1H, s), 7.83(1H, brs), 7.96(1H, s), 8.67(1H, s), 9.96(1H, s) | | |
| 1243 | amorphous | 1.58(3H, s), 2.00(1H, ddd, J = 14.3, 11.5, 3.1), 2.53(1H, m), 2.56(1H, m), 3.07(1H, dt, J = 12.5, 3.1), 4.26(2H, s), 6.47-6.56(3H, m), 7.07-7.15(1H, m), 7.12(2H, t, J = 8.8), 7.39(2H, dd, J = 8.8, 5.6), 8.76(2H, br) (solvent: DMSO-d6) | | 223 299 |
| 1244 | 268-288 | 1.68 (s, 3H), 2.11 (ddd, J = 15.2, 12.0, 4.0 Hz, 1H), 2.57-2.64 (m, 2H), 3.16 (dt, J = 12.0, 4.0 Hz, 1H), 7.13 (ddd, J = 8.0, 2.0, 0.8 Hz, 1H), 7.46 (t, J = 8.0 Hz, 1H), 7.89 (t, J = 2.0 Hz, 1H), 7.97 (ddd, J = 8.0, 2.0, 0.8 Hz, 1H), 8.35 (d, J = 8.0 Hz, 1H), 8.52 (dd, J = 8.0, 2.4 Hz, 1H), 9.12 (d, J = 2.4 Hz, 1H), 10.68 (s, 1H), 10.92 (s, 1H) (solvent: DMSO-d6) | | 219 288 |
| 1245 | oil | | | 286 |
| 1247 | | | | 211 |
| 1255 | | | | 242.7 |
| 1257 | amorphous | | | 211 |
| 1258 | | | 352[M + 1] | 228 276 301 |
| 1261 | 179-180 | | | |
| 1262 | 278-281 | | | |

TABLE 159

| Compound No. | Melting Point (° C.) | 1H-NMR (d) | MS (m/z) | UV (λmax:nm) |
|---|---|---|---|---|
| 1263 | | 1H-NMR(d in d6-DMSO): 1.41(3H, s), 1.65-1.77(1H, m), 1.95-2.07(1H, m), 2.54-2.63(1H, m), 2.84-2.94(1H, m), 3.39-3.46(2H, m), 3.53-3.61(2H, m), 4.83(1H, t, J = 5.4 Hz), 5.79(2H, bs), 7.07(1H, d, J = 7.5 Hz), 7.25(1H, t, J = 7.8 Hz), 7.73(1H, d, J = 7.8 Hz), 7.76(1H, m), 7.87-7.93(1H, m), 8.02(1H, d, J = 1.2 Hz), 8.63(1H, d, J = 1.2 Hz), 9.97(1H, s). | 387[M + 1] | |
| 1264 | | 1H-NMR(d in d6-DMSO): 1.41(3H, s), 1.65-1.77(1H, m), 1.95-2.07(1H, m), 2.53-2.63(1H, m), 2.84-2.95(1H, m), 3.73(8H, s), 5.79(2H, bs), 7.09(1H, d, J = 7.8 Hz), 7.26(1H, t, J = 7.8 Hz), 7.72(1H, d, J = 7.8 Hz), 7.75-7.78(1H, m), 8.34(1H, d, J = 1.2 Hz), 8.76(1H, d, J = 1.2 Hz), 10.08(1H, bs). | 413[M + 1] | |
| 1265 | | 1H-NMR (DMSO-d6) d: 1.42 (3H, s), 1.70-1.76 (1H, m), 2.02-2.05 (1H, m), 2.56-2.59 (1H, m), 2.87-2.93 (2H, m), 7.07 (1H, d, J = 7.6 Hz), 7.23-7.26 (3H, m), 7.72-7.74 (2H, m), 7.93 (1H, s), 8.60 (1H, s), 9.99 (1H, s). | | |
| 1266 | | 1H-NMR(d in d6-DMSO): 1.43(3H, s), 1.70-1.81(1H, m), 1.97-2.10(1H, m), 2.55-2.64(1H, m), 2.89-2.95(1H, m), 5.84(2H, bs), 7.17(1H, d, J = 7.8 Hz), 7.33(1H, t, J = 7.8 Hz), 9.98(1H, d, J = 1.2 Hz), 10.01(1H, d, J = 1.2 Hz), 10.74(1H, bs). | 369[M + 1] | |
| 1267 | | 1H-NMR (CDCl3) d: 1.82-1.91 (1H, m), 2.04 (3H, s), 2.22 (1H, ddd, J = 13.8, 5.2, 3.6 Hz), 2.67 (1H, dt, J = 16.7, 5.8 Hz), 2.80 (1H, dt, J = 12.4, 4.7 Hz), 6.95 (2H, d, J = 8.1 Hz), 7.06 (2H, td, J = 7.8, 1.2 Hz), 7.18 (1H, td, J = 7.6, 1.1 Hz), 7.27 (1H, d, J = 1.7 Hz), 7.32 (1H, d, J = 7.9 Hz), 7.42-7.44 (2H, m), 7.80 (1H, dd, J = 8.0, 1.9 Hz). | 338[M + 1] | |
| 1268 | | 1H-NMR (CDCl3) d: 1.62 (3H, s), 1.89 (1H, t, J = 12.3 Hz), 2.27-2.30 (1H, m), 2.69-2.76 (1H, m), 2.85-2.88 (1H, m), 7.11 (1H, dd, J = 11.4, 7.7 Hz), 7.30-7.53 (2H, m), 7.63 (1H, s), 7.71 (1H, d, J = 6.9 Hz). | 327[M + 1] | |
| 1269 | | 1H-NMR (DMSO-d6) d: 1.40 (3H, s), 1.70-1.73 (1H, m), 1.99-2.02 (1H, m), 2.57-2.60 (1H, m), 2.88-2.90 (1H, m), 3.29 (3H, s), 3.52 (4H, s), 5.75 (2H, br s), 7.07 (1H, d, J = 7.6 Hz), 7.25 (1H, t, J = 7.7 Hz), 7.72 (1H, d, J = 8.3 Hz), 7.75 (1H, s), 7.92 (1H, br s), 8.03 (1H, s), 8.64 (1H, s), 9.96 (1H, s). | | |

TABLE 159-continued

| Compound No. | Melting Point (° C.) | 1H-NMR (d) | MS (m/z) | UV (λmax:nm) |
|---|---|---|---|---|
| 1271 | | 1H-NMR(d in d6-DMSO): 1.41(3H, s), 1.65-1.75(1H, m), 1.99-2.06(5H, m), 2.52-2.61(1H, m), 2.85-2.93(1H, m), 3.55(4H, t, J = 6.6 Hz), 5.79(2H, bs), 7.05(1H, d, J = 7.8 Hz), 7.25(1H, t, J = 7.8 Hz), 7.70-7.75(1H, m), 7.73-7.77(1H, m), 7.97(1H, d, J = 1.2 Hz), 8.72(1H, d, J = 1.2 Hz), 10.00(1H, s). | 397[M + 1] | |

TABLE 160

| Compound No. | Melting Point (° C.) | 1H-NMR (d) | MS (m/z) | UV (λmax:nm) |
|---|---|---|---|---|
| 1272 | | (CDCl3) 1.61(3H, s), 1.85-1.96(1H, m), 2.17-2.27(1H, m), 2.69-2.79(1H, m), 2.87-2.97(1H, m), 7.17 (1H, d, J = 8.1 Hz), 7.38 (1H, t, J = 8.1 Hz), 7.48-7.74(5H, m), 8.40(2H, d, J = 7.5 Hz) | | |
| 1273 | | 1H-NMR (CDCl3) d: 1.58 (3H, s), 1.89 (1H, t, J = 11.2 Hz), 2.27 (1H, s), 2.75-2.82 (2H, m), 6.61 (1H, dd, J = 20.3, 8.4 Hz), 7.10 (1H, d, J = 7.2 Hz), 7.37 (1H, dd, J = 15.0, 8.8 Hz), 7.90 (1H, d, J = 7.6 Hz), 8.10 (1H, d, J = 3.2 Hz), 9.37 (1H, d, J = 4.9 Hz), 9.69 (1H, s). | 395[M + 1] | |
| 1274 | | 1H-NMR (CDCl3) d: 1.61 (3H, s), 1.84-1.93 (1H, m), 2.30 (1H, t, J = 13.1 Hz), 2.77-2.86 (2H, m), 6.64 (1H, dd, J = 20.6, 8.6 Hz), 7.13 (1H, d, J = 7.9 Hz), 7.38-7.43 (1H, m), 7.93 (1H, d, J = 8.1 Hz), 8.13 (1H, s), 9.40 (1H, d, J = 4.9 Hz), 9.72 (1H, s). | 327[M + 1] | |
| 1275 | | 1H-NMR (DMSO-d6) d: 1.40 (3H, s), 1.70-1.72 (1H, m), 2.01-2.04 (1H, m), 2.18 (6H, s), 2.44 (2H, t, J = 6.3 Hz), 2.56-2.59 (1H, m), 2.86-2.92 (1H, m), 7.06 (1H, d, J = 7.6 Hz), 7.25 (1H, t, J = 7.7 Hz), 7.71-7.73 (3H, m), 8.02 (1H, s), 8.64 (1H, s), 9.95 (1H, s). | | |
| 1276 | | 1H-NMR (DMSO-d6) d: 1.70-1.73 (1H, m), 1.99-2.02 (1H, m), 2.57-2.60 (1H, m), 2.88-2.91 (1H, m), 3.04 (3H, s), 3.43 (3H, t, J = 6.3 Hz), 3.79-3.81 (2H, m), 5.75 (3H, br s), 7.08 (1H, d, J = 7.3 Hz), 7.26 (1H, t, J = 7.8 Hz), 7.72 (1H, d, J = 7.8 Hz), 7.76 (1H, s), 8.04 (1H, s), 8.09 (1H, br s), 8.70 (1H, s), 10.01 (1H, s). | | |
| 1279 | | 1H-NMR (CDCl3) d: 1.73 (3H, s), 2.04 (1H, dt, J = 18.2, 6.5 Hz), 2.45 (1H, d, J = 13.6 Hz), 2.78 (2H, t, J = 11.8 Hz), 2.89 (2H, t, J = 11.5 Hz), 6.60 (1H, s), 6.99 (1H, d, J = 8.2 Hz), 7.34 (1H, t, J = 8.0 Hz), 7.48 (1H, s), 7.70 (1H, d, J = 8.2 Hz). | 328[M + 1] | |
| 1280 | | 1H-NMR(d in d6-DMSO): 1.42(3H, s), 1.68-1.82(1H, m), 2.02-2.09(1H, m), 2.23(3H, s), 2.43(4H, t, J = 5.1 Hz), 2.53-2.61(1H, m), 2.87-2.95(1H, m), 3.73(4H, t, J = 5.1 Hz), 6.01(2H, bs), 7.07(1H, d, J = 7.8 Hz), 7.26(1H, t, J = 7.8 Hz), 7.73(1H, d, J = 7.8 Hz), 7.73-7.78(1H, m), 8.33(1H, d, J = 1.2 Hz), 8.72(1H, d, J = 1.2 Hz), 10.06(1H, s). | 426[M + 1] | |
| 1281 | | 1H-NMR(d in d6-DMSO): 1.40(3H, s), 1.30-1.50(2H, m), 1.69-1.76(1H, m), 1.82-1.88(2H, m), 2.01-2.07(1H, m), 2.52-2.61(1H, m), 2.86-2.94(1H, m), 3.76-3.83(1H, m), 4.10-4.18(2H, m), 4.82(1H, d, J = 4.2 Hz), 5.91(2H, bs), 7.07(1H, d, J = 7.8 Hz), 7.26(1H, t, J = 7.8 Hz), 7.70-7.77(2H, m), 8.33(1H, d, J = 1.2 Hz), 8.70(1H, d, J = 1.2 Hz), 10.02(1H, s). | 427[M + 1] | |

TABLE 161

| compound No. | MS(m/z) |
|---|---|
| 2 | 336[M + 1] |
| 7 | 394[M + 1] |
| 10 | 431[M + 3] |
| | 429[M + 1] |
| 11 | 356[M + 1] |
| 12 | 354[M + 1] |
| 13 | 363[M + 3] |
| | 361[M + 1] |
| 14 | 394[M + 1] |
| 15 | 409[M + 1] |
| 16 | 425[M + 1] |
| 17 | 374[M + 1] |
| 19 | 362[M + 3] |
| | 360[M + 1] |
| 20 | 438[M + 1] |
| 21 | 380[M + 3] |
| | 378[M + 1] |

TABLE 161-continued

| compound No. | MS(m/z) |
|---|---|
| 22 | 380[M + 3] |
|  | 378[M + 1] |
| 25 | 354[M + 1] |
| 27 | 338[M + 1] |
| 28 | 356[M + 1] |
| 29 | 372[M + 1] |
| 31 | 378[M + 1] |
| 32 | 417[M + 1] |
| 34 | 358[M + 1] |
| 35 | 398[M + 3] |
|  | 396[M + 1] |
| 36 | 370[M + 1] |
| 40 | 416[M + 1] |
|  | 340 |
| 41 | 414[M + 1] |
| 44 | 362[M + 3] |
|  | 360[M + 1] |
| 45 | 365[M + 1] |
| 46 | 362[M + 1] |
| 47 | 416[M + 3] |
|  | 414[M + 1] |
| 49 | 394[M + 3] |
|  | 392[M + 1] |
| 50 | 292[M + 1] |
| 51 | 388[M + 1] |
| 52 | 360[M + 1] |
|  | 284 |
| 53 | 380[M + 1] |
| 54 | 332[M + 1] |
| 55 | 412[M + 3] |
|  | 410[M + 1] |
| 56 | 397[M + 1] |
|  | 395[M + 1] |
| 59 | 412[M + 1] |
| 60 | 422[M + 1] |
|  | 420[M + 1] |
| 61 | 394[M + 1] |
| 63 | 366[M + 1] |
| 64 | 441[M + 1] |
|  | 365 |
| 65 | 384[M + 1] |
| 66 | 398[M + 1] |
| 67 | 386[M + 1] |
|  | 310 |
| 68 | 376[M + 1] |
| 70 | 372[M + 1] |
| 72 | 330[M + 1] |
| 74 | 322[M + 1] |
| 75 | 412[M + 1] |
| 76 | 363[M + 3] |
|  | 361[M + 1] |
| 79 | 310[M + 1] |
| 81 | 386[M + 1] |
| 82 | 306[M + 1] |
| 83 | 336[M + 1] |
| 84 | 380[M + 1] |
| 87 | 415[M + 1] |
| 88 | 426[M + 1] |
| 89 | 370[M + 1] |
| 90 | 354[M + 1] |
| 92 | 417[M + 1] |
| 93 | 407[M + 1] |
| 94 | 350[M + 1] |
| 95 | 406[M + 3] |
|  | 404[M + 1] |
| 98 | 398[M + 3] |
|  | 396[M + 1] |
| 100 | 332[M + 1] |
| 102 | 424[M + 3] |
|  | 422[M + 1] |
| 103 | 444[M + 1] |
| 105 | 424[M + 1] |
|  | 348 |
| 106 | 490[M + 1] |
|  | 414 |
| 107 | 414[M + 3] |
|  | 412[M + 1] |
| 108 | 332[M + 1] |

TABLE 161-continued

| compound No. | MS(m/z) |
|---|---|
| 109 | 412[M + 1] |
| 110 | 404[M + 1] |
| 111 | 469[M + 1] |
|  | 393 |
| 112 | 377[M + 1] |
| 116 | 408[M + 1] |
| 117 | 413[M + 1] |
| 118 | 372[M + 1] |
| 119 | 424[M + 1] |
| 122 | 338[M + 1] |
| 124 | 471[M + 1] |
| 131 | 412[M + 3] |
|  | 410[M + 1] |
| 133 | 404[M + 1] |
| 135 | 416[M + 1] |
| 136 | 380[M + 1] |
| 137 | 327[M + 1] |
| 138 | 394[M + 1] |
| 140 | 456[M + 1] |
| 142 | 446[M + 1] |
| 143 | 399[M + 1] |
| 144 | 432[M + 1] |
| 145 | 394[M + 3] |
|  | 392[M + 1] |
| 146 | 433[M + 3] |
|  | 431[M + 1] |
| 147 | 324[M + 1] |
| 150 | 418[M + 1] |
| 151 | 458[M + 3] |
|  | 456[M + 1] |
| 152 | 371[M + 1] |
| 153 | 398[M + 1] |
| 154 | 401[M + 1] |
| 155 | 322[M + 1] |
| 156 | 332[M + 3] |
|  | 330[M + 1] |
| 158 | 394[M + 1] |

TABLE 162

| compound No. | MS(m/z) |
|---|---|
| 160 | 427[M + 1] |
| 162 | 416[M + 3] |
|  | 414[M + 1] |
| 167 | 392[M + 3] |
|  | 390[M + 1] |
| 168 | 380[M + 3] |
|  | 378[M + 1] |
| 169 | 346[M + 1] |
| 170 | 356[M + 1] |
| 171 | 334[M + 1] |
| 172 | 376[M + 3] |
|  | 374[M + 1] |
| 173 | 424[M + 3] |
|  | 422[M + 1] |
| 174 | 369[M + 1] |
| 175 | 410[M + 1] |
| 177 | 357[M + 1] |
| 179 | 334[M + 1] |
| 180 | 426[M + 1] |
| 182 | 396[M + 3] |
|  | 394[M + 1] |
| 183 | 372[M + 1] |
| 184 | 346[M + 1] |
| 185 | 330[M + 1] |
| 186 | 393[M + 3] |
|  | 391[M + 1] |
| 187 | 374[M + 1] |
| 188 | 423[M + 1] |
| 190 | 278[M + 1] |
| 191 | 448[M + 1] |
| 192 | 436[M + 3] |
|  | 434[M + 1] |
| 194 | 384[M + 1] |
| 195 | 369[M + 1] |
| 197 | 382[M + 1] |

TABLE 162-continued

| | |
|---|---|
| 198 | 355[M + 1] |
| 199 | 361[M + 1] |
| 200 | 356[M + 1] |
| 280 | |
| 201 | 452[M + 1] |
| 203 | 397[M + 1] |
| 205 | 427[M + 1] |
| 206 | 386[M + 1] |
| 310 | |
| 207 | 384[M + 1] |
| 208 | 386[M + 3] |
| | 384[M + 1] |
| 209 | 371[M + 1] |
| 210 | 366[M + 1] |
| 211 | 442[M + 1] |
| 366 | |
| 212 | 345[M + 1] |
| 215 | 425[M + 3] |
| | 423[M + 1] |
| 217 | 362[M + 1] |
| 218 | 322[M + 1] |
| 219 | 347[M + 1] |
| 221 | 444[M + 1] |
| 222 | 329[M + 1] |
| 223 | 413[M + 1] |
| 225 | 402[M + 1] |
| 226 | 390[M + 1] |
| 228 | 383[M + 1] |
| 229 | 366[M + 1] |
| 230 | 368[M + 1] |
| 231 | 336[M + 1] |
| 234 | 376[M + 1] |
| 236 | 392[M + 1] |
| 237 | 348[M + 1] |
| 239 | 384[M + 1] |
| 240 | 341[M + 1] |
| 242 | 446[M + 1] |
| 245 | 374[M + 1] |
| 246 | 390[M + 1] |
| 314 | |
| 247 | 374[M + 1] |
| 248 | 370[M + 1] |
| 249 | 336[M + 1] |
| 250 | 366[M + 1] |
| 252 | 401[M + 1] |
| 253 | 397[M + 1] |
| 254 | 434[M + 1] |
| 257 | 321[M + 1] |
| 258 | 398[M + 1] |
| 260 | 440[M + 1] |
| 261 | 308[M + 1] |
| 262 | 466[M + 3] |
| | 464[M + 1] |
| 264 | 336[M + 1] |
| 265 | 435[M + 1] |
| 266 | 432[M + 3] |
| | 430[M + 1] |
| 269 | 372[M + 1] |
| 296 | |
| 270 | 338[M + 1] |
| 272 | 349[M + 1] |
| 273 | 406[M + 3] |
| | 404[M + 1] |
| 274 | 380[M + 1] |
| 276 | 398[M + 3] |
| | 396[M + 1] |
| 278 | 404[M + 1] |
| 280 | 433[M + 3] |
| | 431[M + 1] |
| 283 | 322[M + 1] |
| 285 | 340[M + 1] |
| 286 | 433[M + 3] |
| | 431[M + 1] |
| 287 | 440[M + 1] |
| 288 | 354[M + 1] |
| 289 | 341[M + 1] |
| 290 | 363[M + 3] |
| | 361[M + 1] |
| 291 | 317[M + 1] |
| 292 | 426[M + 1] |

TABLE 162-continued

| | |
|---|---|
| 294 | 424[M + 3] |
| | 422[M + 1] |
| 295 | 394[M + 3] |
| | 392[M + 1] |
| 296 | 389[M + 1] |
| 297 | 448[M + 3] |
| | 446[M + 1] |
| 298 | 363[M + 3] |
| | 361[M + 1] |
| 300 | 356[M + 1] |
| 303 | 366[M + 1] |
| 304 | 402[M + 1] |
| 305 | 407[M + 3] |
| | 405[M + 1] |
| 310 | 411[M + 1] |

TABLE 163

| | |
|---|---|
| 311 | 388[M + 1] |
| 312 | 428[M + 1] |
| 313 | 453[M + 1] |
| 314 | 368[M + 1] |
| 315 | 322[M + 1] |
| 316 | 386[M + 1] |
| 317 | 328[M + 1] |
| 318 | 362[M + 1] |
| 320 | 327[M + 1] |
| 321 | 392[M + 1] |
| 322 | 404[M + 1] |
| 328 | |
| 323 | 394[M + 1] |
| 324 | 384[M + 1] |
| 325 | 399[M + 1] |
| 326 | 440[M + 1] |
| 364 | |
| 327 | 314[M + 1] |
| 328 | 384[M + 1] |
| 331 | 360[M + 1] |
| 334 | 412[M + 1] |
| 335 | 316[M + 1] |
| 336 | 356[M + 1] |
| 337 | 428[M + 1] |
| 338 | 466[M + 3] |
| | 464[M + 1] |
| 340 | 344[M + 1] |
| 343 | 399[M + 1] |
| 345 | 412[M + 1] |
| 346 | 384[M + 1] |
| 347 | 430[M + 1] |
| 348 | 341[M + 1] |
| 349 | 335[M + 1] |
| 350 | 412[M + 1] |
| 351 | 322[M + 1] |
| 352 | 327[M + 1] |
| 355 | 397[M + 1] |
| 362 | 366[M + 1] |
| 363 | 376[M + 3] |
| | 374[M + 1] |
| 365 | 366[M + 1] |
| 366 | 409[M + 1] |
| 368 | 384[M + 1] |
| 369 | 396[M + 3] |
| | 394[M + 1] |
| 371 | 398[M + 3] |
| | 396[M + 1] |
| 372 | 348[M + 1] |
| 373 | 358[M + 1] |
| 374 | 364[M + 1] |
| 376 | 412[M + 1] |
| 377 | 425[M + 1] |
| 378 | 380[M + 3] |
| | 378[M + 1] |
| 379 | 377[M + 1] |
| 381 | 409[M + 1] |
| 382 | 340[M + 1] |
| 384 | 388[M + 1] |
| 385 | 384[M + 1] |

TABLE 163-continued

| | |
|---|---|
| 386 | 352[M + 1] |
| 387 | 376[M + 1] |
| 388 | 440[M + 1] |
| 390 | 407[M + 1] |
| | 331 |
| 391 | 362[M + 1] |
| 392 | 390[M + 1] |
| 394 | 363[M + 3] |
| | 361[M + 1] |
| 397 | 460[M + 3] |
| | 458[M + 1] |
| 398 | 408[M + 1] |
| 399 | 372[M + 1] |
| 400 | 374[M + 1] |
| 402 | 372[M + 1] |
| | 296 |
| 403 | 436[M + 1] |
| 404 | 376[M + 3] |
| | 374[M + 1] |
| 407 | 449[M + 3] |
| | 447[M + 1] |
| 412 | 410[M + 1] |
| 414 | 331[M + 1] |
| 416 | 282[M + 1] |
| 418 | 322[M + 1] |
| 419 | 420[M + 3] |
| | 418[M + 1] |
| 420 | 332[M + 1] |
| 421 | 388[M + 3] |
| | 386[M + 1] |
| 423 | 412[M + 3] |
| | 410[M + 1] |
| 424 | 370[M + 1] |
| 425 | 380[M + 3] |
| | 378[M + 1] |
| 428 | 350[M + 1] |
| 431 | 391[M + 1] |
| 433 | 454[M + 3] |
| | 452[M + 1] |
| 434 | 448[M + 3] |
| | 446[M + 1] |
| 435 | 431[M + 3] |
| | 429[M + 1] |
| 437 | 382[M + 1] |
| 438 | 400[M + 1] |
| | 324 |
| 439 | 380[M + 1] |
| 440 | 358[M + 1] |
| 442 | 394[M + 1] |
| | 318 |
| 447 | 370[M + 1] |
| 449 | 336[M + 1] |
| 450 | 455[M + 1] |
| 451 | 390[M + 3] |
| | 388[M + 1] |
| 453 | 358[M + 1] |
| 454 | 407[M + 1] |
| | 331 |
| 455 | 296[M + 1] |
| 458 | 382[M + 1] |
| 459 | 392[M + 1] |
| 460 | 431[M + 1] |
| 461 | 369[M + 1] |
| 462 | 381[M + 3] |
| | 379[M + 1] |
| 463 | 440[M + 3] |
| | 438[M + 1] |
| 464 | 338[M + 1] |
| | 262 |
| 467 | 387[M + 1] |
| 468 | 439[M + 1] |
| | 363 |
| 469 | 360[M + 1] |
| 471 | 363[M + 3] |
| | 361[M + 1] |

TABLE 164

| | |
|---|---|
| 472 | 376[M + 1] |
| 473 | 414[M + 1] |
| 474 | 334[M + 1] |
| 475 | 317[M + 1] |
| 476 | 324[M + 1] |
| 477 | 437[M + 1] |
| 478 | 379[M + 1] |
| 479 | 394[M + 1] |
| 480 | 370[M + 1] |
| 481 | 431[M + 1] |
| 484 | 314[M + 3] |
| | 312[M + 1] |
| 485 | 448[M + 1] |
| 486 | 350[M + 1] |
| 487 | 338[M + 1] |
| 488 | 306[M + 1] |
| 489 | 335[M + 1] |
| 492 | 380[M + 1] |
| 495 | 334[M + 1] |
| 499 | 370[M + 1] |
| 503 | 412[M + 1] |
| 505 | 363[M + 3] |
| | 361[M + 1] |
| 506 | 386[M + 1] |
| 507 | 400[M + 1] |
| 508 | 372[M + 1] |
| 509 | 414[M + 1] |
| | 338 |
| 510 | 374[M + 1] |
| 512 | 320[M + 1] |
| 513 | 420[M + 3] |
| | 418[M + 1] |
| 514 | 372[M + 1] |
| 517 | 369[M + 1] |
| 518 | 376[M + 1] |
| 519 | 411[M + 1] |
| 520 | 395[M + 1] |
| 521 | 372[M + 1] |
| 522 | 390[M + 1] |
| 523 | 414[M + 1] |
| 524 | 341[M + 1] |
| 526 | 426[M + 1] |
| 527 | 381[M + 3] |
| | 379[M + 1] |
| 529 | 320[M + 1] |
| 530 | 390[M + 3] |
| | 388[M + 1] |
| 531 | 410[M + 1] |
| 535 | 356[M + 1] |
| 536 | 372[M + 1] |
| 537 | 377[M + 1] |
| 538 | 406[M + 1] |
| 539 | 411[M + 1] |
| 540 | 354[M + 1] |
| 541 | 342[M + 1] |
| 542 | 361[M + 1] |
| 543 | 344[M + 1] |
| 544 | 412[M + 1] |
| 545 | 366[M + 1] |
| 546 | 383[M + 1] |
| 547 | 430[M + 1] |
| | 428[M + 1] |
| 548 | 427[M + 1] |
| 550 | 340[M + 1] |
| 552 | 400[M + 1] |
| 553 | 304[M + 1] |
| 555 | 383[M + 1] |
| 557 | 304[M + 1] |
| 562 | 374[M + 1] |
| 563 | 366[M + 1] |
| 564 | 395[M + 1] |
| 565 | 336[M + 1] |
| 566 | 427[M + 1] |
| | 351 |
| 568 | 362[M + 3] |
| | 360[M + 1] |
| 569 | 356[M + 1] |
| 571 | 356[M + 1] |
| 572 | 473[M + 3] |
| | 471[M + 1] |

TABLE 164-continued

| | |
|---|---|
| 574 | 381[M + 3] |
| | 379[M + 1] |
| 575 | 360[M + 1] |
| 576 | 384[M + 1] |
| 578 | 344[M + 1] |
| 579 | 370[M + 1] |
| 580 | 347[M + 1] |
| 581 | 409[M + 1] |
| 582 | 334[M + 1] |
| 583 | 392[M + 1] |
| 585 | 358[M + 1] |
| 587 | 348[M + 1] |
| 589 | 407[M + 3] |
| | 405[M + 1] |
| 590 | 410[M + 3] |
| | 408[M + 1] |
| 591 | 460[M + 1] |
| | 384 |
| 592 | 380[M + 3] |
| | 378[M + 1] |
| 594 | 390[M + 1] |
| 598 | 394[M + 1] |
| 599 | 377[M + 1] |
| 603 | 398[M + 3] |
| | 396[M + 1] |
| 604 | 395[M + 1] |
| 606 | 358[M + 1] |
| 607 | 362[M + 1] |
| 609 | 413[M + 1] |
| 610 | 409[M + 1] |
| 612 | 385[M + 1] |
| 614 | 322[M + 1] |
| 615 | 441[M + 1] |
| 616 | 346[M + 3] |
| | 344[M + 1] |
| | 270 |
| | 268 |
| 617 | 406[M + 3] |
| | 404[M + 1] |
| 619 | 404[M + 1] |
| 621 | 366[M + 1] |
| 623 | 422[M + 1] |
| | 346 |
| 624 | 370[M + 1] |
| 626 | 402[M + 1] |
| 627 | 398[M + 3] |
| | 396[M + 1] |
| 628 | 413[M + 1] |
| 631 | 370[M + 1] |
| 632 | 414[M + 3] |
| | 412[M + 1] |

TABLE 165

| | |
|---|---|
| 633 | 322[M + 1] |
| 635 | 420[M + 1] |
| 638 | 408[M + 1] |
| 639 | 386[M + 1] |
| | 310 |
| 640 | 370[M + 1] |
| 641 | 437[M + 1] |
| 642 | 380[M + 1] |
| 646 | 395[M + 1] |
| 647 | 334[M + 1] |
| 648 | 403[M + 1] |
| 650 | 370[M + 1] |
| 655 | 362[M + 1] |
| 656 | 308[M + 1] |
| 658 | 430[M + 1] |
| 659 | 340[M + 3] |
| | 388[M + 1] |
| 662 | 330[M + 1] |
| 663 | 334[M + 1] |
| 665 | 316[M + 1] |
| 666 | 345[M + 1] |
| 668 | 430[M + 1] |
| 669 | 377[M + 1] |

TABLE 165-continued

| | |
|---|---|
| 670 | 368[M + 3] |
| | 366[M + 1] |
| 671 | 334[M + 1] |
| 672 | 442[M + 1] |
| 674 | 340[M + 1] |
| 675 | 306[M + 1] |
| 676 | 392[M + 1] |
| 678 | 386[M + 1] |
| 679 | 426[M + 1] |
| 682 | 414[M + 3] |
| | 412[M + 1] |
| 684 | 384[M + 1] |
| 685 | 389[M + 1] |
| 686 | 446[M + 1] |
| 688 | 414[M + 1] |
| 689 | 306[M + 1] |
| 690 | 348[M + 1] |
| 691 | 452[M + 1] |
| 693 | 371[M + 1] |
| 694 | 448[M + 1] |
| 695 | 364[M + 1] |
| 696 | 392[M + 3] |
| | 390[M + 1] |
| 697 | 358[M + 1] |
| 699 | 426[M + 1] |
| 703 | 451[M + 3] |
| | 449[M + 1] |
| 704 | 342[M + 1] |
| 705 | 372[M + 1] |
| 706 | 368[M + 1] |
| 708 | 383[M + 1] |
| 710 | 396[M + 3] |
| | 394[M + 1] |
| 711 | 351[M + 1] |
| 712 | 376[M + 1] |
| 713 | 398[M + 3] |
| | 396[M + 1] |
| 714 | 366[M + 1] |
| 715 | 454[M + 1] |
| 716 | 381[M + 3] |
| | 379[M + 1] |
| 718 | 386[M + 1] |
| 721 | 322[M + 1] |
| 722 | 377[M + 1] |
| 723 | 440[M + 1] |
| | 364 |
| 724 | 457[M + 3] |
| | 455[M + 1] |
| 726 | 362[M + 1] |
| 727 | 366[M + 1] |
| 734 | 370[M + 1] |
| 738 | 338[M + 1] |
| 741 | 404[M + 1] |
| 742 | 351[M + 1] |
| 745 | 386[M + 1] |
| 746 | 370[M + 1] |
| | 294 |
| 747 | 336[M + 1] |
| 748 | 381[M + 3] |
| | 379[M + 1] |
| 749 | 416[M + 1] |
| | 340 |
| 750 | 437[M + 1] |
| 751 | 362[M + 1] |
| 752 | 352[M + 3] |
| | 350[M + 1] |
| 754 | 366[M + 1] |
| 755 | 354[M + 1] |
| 757 | 425[M + 1] |
| 759 | 346[M + 1] |
| 760 | 344[M + 1] |
| 761 | 402[M + 1] |
| 762 | 251[M + 1] |
| 763 | 355[M + 1] |
| 764 | 362[M + 3] |
| | 360[M + 1] |
| 765 | 392[M + 3] |
| | 390[M + 1] |
| 769 | 366[M + 1] |
| 770 | 372[M + 1] |

TABLE 165-continued

| | |
|---|---|
| 772 | 292[M + 1] |
| 773 | 424[M + 1] |
| 775 | 396[M + 3] |
| | 394[M + 1] |
| 776 | 388[M + 1] |
| 777 | 383[M + 1] |
| 778 | 404[M + 1] |
| 779 | 398[M + 1] |
| 780 | 368[M + 1] |
| 782 | 368[M + 1] |
| 784 | 369[M + 1] |
| 785 | 431[M + 3] |
| | 429[M + 1] |
| 787 | 473[M + 1] |
| | 397 |
| 788 | 375[M + 1] |
| 789 | 467[M + 1] |
| 794 | 327[M + 1] |
| 795 | 384[M + 1] |
| 796 | 370[M + 1] |
| 798 | 370[M + 1] |
| 801 | 404[M + 3] |
| | 402[M + 1] |
| 805 | 376[M + 1] |
| 806 | 411[M + 1] |
| 807 | 356[M + 1] |

TABLE 166

| | |
|---|---|
| 808 | 354[M + 1] |
| 809 | 400[M + 1] |
| | 324 |
| 812 | 425[M + 1] |
| 815 | 386[M + 1] |
| 817 | 377[M + 1] |
| 818 | 398[M + 1] |
| 819 | 352[M + 1] |
| 821 | 336[M + 1] |
| 823 | 362[M + 1] |
| 824 | 363[M + 1] |
| | 287 |
| 825 | 420[M + 1] |
| 826 | 430[M + 1] |
| 828 | 377[M + 1] |
| 829 | 437[M + 1] |
| 830 | 370[M + 1] |
| 831 | 327[M + 1] |
| 837 | 324[M + 1] |
| | 248 |
| 838 | 377[M + 1] |
| 839 | 376[M + 3] |
| | 374[M + 1] |
| 841 | 363[M + 3] |
| | 361[M + 1] |
| 842 | 386[M + 1] |
| 843 | 466[M + 3] |
| | 464[M + 1] |
| 844 | 381[M + 1] |
| 845 | 324[M + 1] |
| | 248 |
| 846 | 358[M + 1] |
| 847 | 373[M + 1] |
| 852 | 489[M + 1] |
| 853 | 376[M + 1] |
| 854 | 448[M + 1] |
| 856 | 420[M + 1] |
| | 344 |
| 857 | 341[M + 1] |
| 858 | 383[M + 1] |
| 860 | 370[M + 1] |
| 861 | 334[M + 3] |
| | 332[M + 1] |
| 862 | 358[M + 1] |
| 864 | 392[M + 1] |
| 865 | 398[M + 3] |
| | 396[M + 1] |
| 867 | 399[M + 1] |

TABLE 166-continued

| | |
|---|---|
| 868 | 430[M + 1] |
| 870 | 362[M + 3] |
| | 360[M + 1] |
| 872 | 428[M + 1] |
| 873 | 351[M + 1] |
| 874 | 341[M + 1] |
| 877 | 399[M + 1] |
| | 323 |
| 879 | 332[M + 1] |
| 880 | 363[M + 3] |
| | 361[M + 1] |
| 882 | 426[M + 1] |
| 883 | 360[M + 1] |
| 884 | 320[M + 1] |
| 885 | 361[M + 1] |
| 886 | 380[M + 1] |
| 888 | 292[M + 1] |
| 889 | 451[M + 1] |
| | 449[M + 1] |
| 890 | 400[M + 1] |
| 891 | 292[M + 1] |
| 894 | 347[M + 1] |
| 898 | 412[M + 3] |
| | 410[M + 1] |
| 899 | 397[M + 1] |
| 901 | 411[M + 1] |
| 902 | 377[M + 1] |
| 903 | 370[M + 1] |
| 904 | 422[M + 1] |
| 905 | 392[M + 1] |
| 907 | 308[M + 1] |
| 909 | 393[M + 1] |
| 911 | 415[M + 1] |
| 912 | 383[M + 1] |
| 913 | 413[M + 1] |
| 914 | 400[M + 1] |
| 915 | 389[M + 1] |
| | 313 |
| 917 | 358[M + 1] |
| 918 | 433[M + 3] |
| | 431[M + 1] |
| 919 | 354[M + 1] |
| 920 | 381[M + 3] |
| | 379[M + 1] |
| 921 | 389[M + 1] |
| 922 | 413[M + 1] |
| | 337 |
| 923 | 437[M + 1] |
| 924 | 376[M + 1] |
| 925 | 390[M + 1] |
| 927 | 355[M + 1] |
| 929 | 370[M + 1] |
| 932 | 380[M + 3] |
| | 378[M + 1] |
| 934 | 507[M + 1] |
| 937 | 388[M + 1] |
| 938 | 366[M + 1] |
| 940 | 388[M + 1] |
| 942 | 378[M + 1] |
| 943 | 413[M + 1] |
| 945 | 372[M + 1] |
| 948 | 462[M + 1] |
| 949 | 363[M + 1] |
| 950 | 368[M + 1] |
| 951 | 412[M + 1] |
| 952 | 378[M + 1] |
| 953 | 318[M + 1] |
| 954 | 363[M + 3] |
| | 361[M + 1] |
| 955 | 406[M + 3] |
| | 404[M + 1] |
| 956 | 292[M + 1] |
| 957 | 398[M + 3] |
| | 396[M + 1] |
| 958 | 310[M + 1] |
| 959 | 406[M + 3] |
| | 404[M + 1] |

TABLE 166-continued

| | |
|---|---|
| 961 | 362[M + 3] |
| | 360[M + 1] |
| 962 | 327[M + 1] |
| 963 | 392[M + 1] |

TABLE 167

| | |
|---|---|
| 965 | 438[M + 3] |
| | 436[M + 1] |
| 967 | 425[M + 3] |
| | 423[M + 1] |
| 969 | 413[M + 1] |
| 973 | 386[M + 1] |
| 975 | 407[M + 3] |
| | 405[M + 1] |
| 976 | 358[M + 1] |
| 977 | 369[M + 1] |
| 979 | 395[M + 1] |
| 980 | 402[M + 1] |
| 981 | 392[M + 3] |
| | 390[M + 1] |
| 982 | 366[M + 1] |
| 983 | 379[M + 1] |
| 985 | 408[M + 1] |
| 986 | 440[M + 3] |
| | 438[M + 1] |
| 987 | 358[M + 1] |
| 988 | 294[M + 1] |
| 989 | 332[M + 1] |
| 991 | 356[M + 1] |
| 992 | 477[M + 1] |
| 993 | 416[M + 3] |
| | 414[M + 1] |
| 995 | 425[M + 3] |
| | 423[M + 1] |
| 996 | 416[M + 3] |
| | 414[M + 1] |
| 997 | 363[M + 3] |
| | 361[M + 1] |
| 999 | 336[M + 1] |
| 1000 | 388[M + 1] |
| | 312 |
| 1001 | 374[M + 1] |
| 1002 | 400[M + 1] |
| 1003 | 394[M + 1] |
| 1004 | 397[M + 1] |
| 1007 | 448[M + 1] |
| | 372 |
| 1009 | 366[M + 1] |
| 1011 | 419[M + 1] |
| 1012 | 316[M + 1] |
| 1013 | 431[M + 1] |
| 1015 | 372[M + 1] |
| 1016 | 470[M + 1] |
| 1017 | 413[M + 1] |
| 1018 | 386[M + 1] |
| 1019 | 433[M + 3] |
| | 431[M + 1] |
| 1021 | 464[M + 1] |
| 1022 | 384[M + 1] |
| 1023 | 407[M + 3] |
| | 405[M + 1] |
| 1024 | 346[M + 1] |
| 1025 | 455[M + 3] |
| | 453[M + 1] |
| 1026 | 425[M + 1] |
| 1027 | 444[M + 1] |
| 1029 | 410[M + 1] |
| 1030 | 413[M + 1] |
| 1031 | 404[M + 1] |
| 1032 | 472[M + 1] |
| | 386 |
| 1033 | 377[M + 1] |
| 1036 | 350[M + 1] |
| 1038 | 364[M + 1] |
| 1040 | 317[M + 1] |
| 1041 | 407[M + 1] |

TABLE 167-continued

| | |
|---|---|
| 1042 | 382[M + 1] |
| 1045 | 425[M + 3] |
| | 423[M + 1] |
| 1046 | 366[M + 1] |
| 1047 | 390[M + 1] |
| 1048 | 440[M + 1] |
| 1049 | 396[M + 1] |
| 1050 | 400[M + 1] |
| 1051 | 315[M + 1] |
| 1053 | 363[M + 3] |
| | 361[M + 1] |
| 1054 | 360[M + 1] |
| 1057 | 427[M + 1] |
| 1058 | 360[M + 1] |
| 1060 | 381[M + 3] |
| | 379[M + 1] |
| 1063 | 395[M + 1] |
| 1065 | 451[M + 1] |
| | 449[M + 1] |
| 1066 | 485[M + 1] |
| 1070 | 380[M + 3] |
| | 378[M + 1] |
| 1071 | 345[M + 1] |
| 1072 | 381[M + 3] |
| | 379[M + 1] |
| 1073 | 397[M + 1] |
| 1075 | 342[M + 1] |
| 1077 | 344[M + 1] |
| 1078 | 370[M + 1] |
| 1079 | 387[M + 1] |
| 1080 | 370[M + 1] |
| | 294 |
| 1081 | 355[M + 1] |
| 1082 | 398[M + 3] |
| | 396[M + 1] |
| 1083 | 318[M + 1] |
| 1085 | 439[M + 3] |
| | 437[M + 1] |
| 1086 | 428[M + 1] |
| 1089 | 399[M + 1] |
| 1090 | 398[M + 1] |
| 1091 | 434[M + 3] |
| | 432[M + 1] |
| 1092 | 398[M + 3] |
| | 396[M + 1] |
| 1093 | 401[M + 1] |
| 1095 | 400[M + 1] |
| 1096 | 409[M + 1] |
| 1097 | 384[M + 1] |
| 1098 | 395[M + 1] |
| 1099 | 511[M + 4] |
| | 510[M + 3] |
| | 509[M + 2] |
| | 508[M + 1] |
| 1101 | 350[M + 1] |
| 1102 | 442[M + 1] |
| 1103 | 397[M + 1] |
| 1105 | 372[M + 1] |
| 1106 | 346[M + 1] |
| 1108 | 383[M + 1] |
| 1112 | 445[M + 1] |

TABLE 168

| | |
|---|---|
| 1113 | 358[M + 1] |
| 1117 | 394[M + 1] |
| 1118 | 336[M + 1] |
| | 260 |
| 1121 | 392[M + 3] |
| | 390[M + 1] |
| 1122 | 322[M + 1] |
| 1123 | 316[M + 1] |
| 1126 | 386[M + 1] |
| 1127 | 368[M + 1] |
| 1128 | 416[M + 3] |
| | 414[M + 1] |
| 1129 | 341[M + 1] |

TABLE 168-continued
| | |
|---|---|
| 1130 | 432[M + 1] |
| 1134 | 396[M + 1] |
| 1136 | 396[M + 3] |
| | 394[M + 1] |
| 1137 | 292[M + 1] |
| 1138 | 413[M + 1] |
| 1141 | 344[M + 1] |
| 1143 | 384[M + 1] |
| 1144 | 446[M + 1] |
| 1145 | 390[M + 1] |
| | 314 |
| 1146 | 405[M + 1] |
| 1148 | 380[M + 1] |
| | 304 |
| 1149 | 364[M + 1] |
| 1151 | 442[M + 1] |
| 1152 | 365[M + 1] |
| 1154 | 318[M + 1] |
| 1155 | 427[M + 1] |
| 1156 | 368[M + 1] |
| 1157 | 366[M + 1] |
| 1158 | 415[M + 3] |
| | 413[M + 1] |
| 1159 | 414[M + 3] |
| | 412[M + 1] |
| 1162 | 370[M + 1] |
| | 294 |
| 1163 | 416[M + 3] |
| | 414[M + 1] |
| 1164 | 396[M + 1] |
| | 320 |
| 1165 | 361[M + 1] |
| 1167 | 424[M + 1] |
| | 348 |
| 1168 | 428[M + 1] |
| 1169 | 422[M + 1] |
| 1170 | 411[M + 1] |
| 1171 | 390[M + 3] |
| | 388[M + 1] |
| 1173 | 361[M + 1] |
| 1174 | 342[M + 1] |
| 1175 | 430[M + 1] |
| 1176 | 345[M + 1] |
| 1177 | 376[M + 3] |
| | 374[M + 1] |
| 1178 | 351[M + 1] |
| 1179 | 344[M + 1] |
| 1180 | 398[M + 3] |
| | 396[M + 1] |
| 1182 | 426[M + 1] |
| 1183 | 376[M + 3] |
| | 374[M + 1] |
| 1186 | 374[M + 1] |
| | 298 |
| 1187 | 427[M + 1] |
| 1188 | 350[M + 1] |
| 1189 | 408[M + 3] |
| | 406[M + 1] |
| 1190 | 386[M + 1] |
| 1191 | 377[M + 1] |
| 1192 | 335[M + 1] |
| 1195 | 412[M + 3] |
| | 410[M + 1] |
| 1196 | 380[M + 1] |
| 1198 | 398[M + 1] |
| | 322 |
| 1200 | 352[M + 1] |
| 1201 | 424[M + 3] |
| | 422[M + 1] |
| 1202 | 369[M + 1] |
| 1203 | 420[M + 1] |
| 1204 | 398[M + 3] |
| | 396[M + 1] |
| 1206 | 416[M + 1] |
| 1208 | 344[M + 1] |
| 1209 | 422[M + 1] |
| 1210 | 408[M + 1] |
| 1212 | 391[M + 1] |
| 1214 | 360[M + 1] |
| 1218 | 372[M + 1] |
TABLE 168-continued
| | |
|---|---|
| 1219 | 470[M + 1] |
| 1220 | 264[M + 1] |
| 1222 | 362[M + 3] |
| | 360[M + 1] |
| 1225 | 413[M + 1] |
| 1226 | 374[M + 1] |
| 1227 | 425[M + 1] |
| 1229 | 455[M + 3] |
| | 453[M + 1] |
| 1231 | 413[M + 1] |
| 1232 | 340[M + 1] |
| 1233 | 394[M + 1] |
| 1234 | 416[M + 3] |
| | 414[M + 1] |
| 1235 | 427[M + 1] |
| 1236 | 348[M + 1] |
| | 272 |
| 1237 | 353[M + 1] |
| 1238 | 419[M + 1] |
| 1239 | 416[M + 3] |
| | 414[M + 1] |
| 1246 | 474[M + 1] |
| 1248 | 414[M + 1] |
| 1249 | 336[M + 1] |
| 1250 | 352[M + 1] |
| 1251 | 393[M + 1] |
| 1252 | 357[M + 1] |
| 1253 | 430[M + 1] |
| 1254 | 412[M + 1] |
| 1256 | 333[M + 1] |
| 1259 | 356[M + 1] |
| 1260 | 348[M + 1] |
| 1270 | 374[M + 1] |
| 1282 | 362[M + 1] |
[Chemical formula 66]
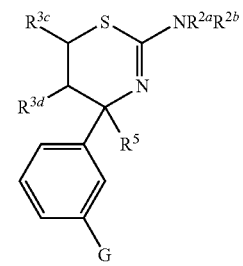
(Ia)
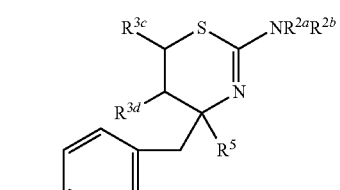
(Ib)
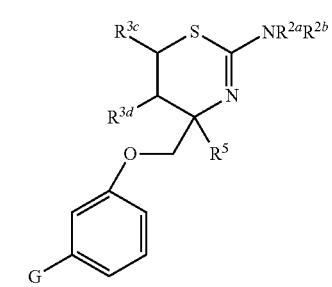
(Ic)

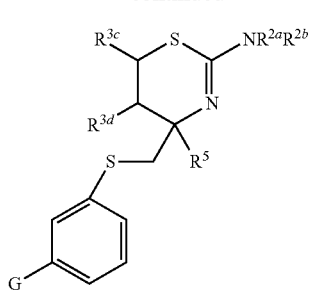
(Id)

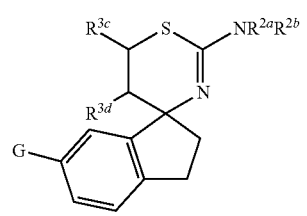
(Ie)

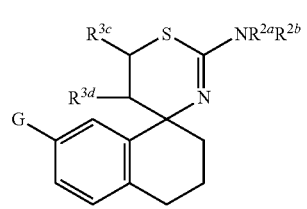
(If)

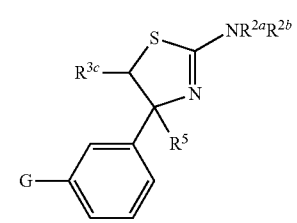
(Ig)

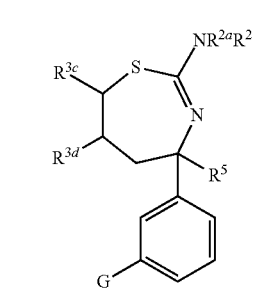
(Ih)

In above structural formula (Ia) to (Ih), the combination of $NR^{2a}R^{2b}$, $R^{3c}$, $R^{3d}$, $R^5$ and G ($NR^{2a}R^{2b}$, $R^{3c}$, $R^{3d}$, $R^5$, G) are the following compounds.

(NHMe,H,H,Me,CONHPh),(NHMe,H,H,Me,CONH-3-pyridyl),(NHMe,H,H,Me,NHCOPh), (NHMe,H,H,Me,NHCO-2-furyl),(NHMe,H,H,Me,NHCONHPh),(NHMe,H,H,Me,NHCOCONHPh), (NHMe,H,H,Et,CONHPh), (NHMe,H,H,Et,CONH-3-pyridyl), (NHMe,H,H,Et,NHCOPh),(NHMe,H,H,Et,NHCO-2-furyl),(NHMe,H,H,Et,NHCONHPh), (NHMe,H,H,Et,NHCOCONHPh),(NHMe,H,H,CH2OH,CONHPh),(NHMe,H,H,CH2OH,CONH-3-pyridyl),(NHMe,H,H,CH2OH,NHCOPh),(NHMe,H,H,CH2OH,NHCO-2-furyl), (NHMe,H,H,CH2OH,NHCONHPh),(NHMe,H,H,CH2OH,NHCOCONAPh), (NHMe,H,Me,Me,CONHPh),(NHMe,H,Me,Me,CONH-3-pyridyl),(NHMe,H,Me,Me,NHCOPh), (NHMe,H,Me,Me,NHCO-2-furyl),(NHMe,H,Me,Me,NHCONHPh),(NHMe,H,Me,Me,NHCOCONHPh),(NHMe,H,Me,Et,CONHPh),(NHMe,H,Me,Et,CONH-3-pyridyl),(NHMe,H,Me,Et,NHCOPh),(NHMe,H,Me,Et,NHCO-2-furyl),(NHMe,H,Me,Et,NHCONHPh),(NHMe,H,Me,Et,NHCOCONHPh),(NHMe,H,Me,CH2OH,CONHPh),(NHMe,H,Me,CH2OH,CONH-3-pyridyl),(NHMe,H,Me,CH2OH,NHCOPh),(NHMe,H,Me,CH2OH,NHCO-2-furyl),(NHMe,H,Me,CH2OH,NHCONHPh),(NHMe,H,Me,CH2OH,NHCOCONHPh), (NHMe,H,Ph,Me,CONHPh),(NHMe,H,Ph,Me,CONH-3-pyridyl),(NHMe,H,Ph,Me,NHCOPh),(NHMe,H,Ph,Me,NHCO-2-furyl),(NHMe,H,Ph,Me,NHCONHPh),(NHMe,H,Ph,Me,NHCOCONHPh),(NHMe,H,Ph,Et,CONHPh), (NHMe,H,Ph,Et,CONH-3-pyridyl),(NHMe,H,Ph,Et,NHCOPh),(NHMe,H,Ph,Et,NHCO-2-furyl),(NHMe,H,Ph,Et,NHCONHPh),(NHMe,H,Ph,Et,NHCOCONHPh),(NHMe,H,Ph,CH2OH,CONHPh),(NHMe,H,Ph,CH2OH,CONH-3-pyridyl),(NHMe,H,Ph,CH2OH,NHCOPh), (NHMe,H,Ph,CH2OH,NHCO-2-furyl),(NHMe,H,Ph,CH2OH,NHCONHPh),(NHMe,H,Ph,CH2OH,NHCOCONHPh),(NHMe,H,OH,Me,CONHPh),(NHMe,H,OH,Me,CONH-3-pyridyl),(NHMe,H,OH,Me,NHCOPh),(NHMe,H,OH,Me,NHCO-2-furyl),(NHMe,H,OH,Me,NHCONHPh),(NHMe,H,OH,Me,NHCOCONHPh),(NHMe,H,OH,Et,CONHPh),(NHMe,H,OH,Et,CONH-3-pyridyl),(NHMe,H,OH,Et,NHCOPh),(NHMe,H,OH,Et,NHCO-2-furyl),(NHMe,H,OH,Et,NHCONHPh),(NHMe,H,OH,Et,NHCOCONHPh),(NHMe,H2OH,CH2OH,CONHPh),(NHMe,H,OH,CH2OH,CONH-3-pyridyl), (NHMe,H,OH,CH2OH,NHCOPh),(NHMe,H,OH,CH2OH,NHCO-2-furyl),(NHMe,H,OH,CH2OH,NHCONHPh), (NHMe,H,OH,CH2OH,NHCOCONHPh),(NHMe,Me,H,Me,CONHPh),(NBMe,Me,H,Me,CONH-3-pyridyl), (NHMe,Me,H,Me,NHCOPh),(NHMe,Me,H,Me,NHCO-2-furyl),(NHMe,Me,H,Me,NHCONHPh),(NHMe,Me,H,Me,NHCOCONHPh),(NHMe,Me,H,Et,CONHPh),(NHMe,Me,H,Et,CONH-3-pyridyl),(NHMe,Me,H,Et,NHCOPh), (NHMe,Me,H,Et,NHCO-2-furyl),(NHMe,Me,H,Et,NHCONHPh),(NHMe,Me,H,Et,NHCOCONHPh),(NHMe,Me,H,CH2OH,CONHPh),(NBMe,Me,H,CH2OH,CONH-3-pyridyl),(NHMe,Me,H,CH2OH,NHCOPh),(NHMe,Me,H,CH2OH,NHCO-2-furyl),(NHMe,Me,H,CH2OH,NHCONHPh),(NHMe,Me,H,CH2OH,NHCOCONHPh), (NHMe,Me,Me,Me,CONHPh),(NHMe,Me,Me,Me,CONH-3-pyridyl),(NHMe,Me,Me,Me,NHCOPh),(NHMe,Me,Me,Me,NHCO-2-furyl),(NHMe,Me,Me,Me,NHCONHPh), (NHMe,Me,Me,Me,NHCOCONHPh),(NHMe,Me,Me,Et,CONHPh),(NHMe,Me,Me,Et,CONH-3-pyridyl),(NHMe,Me,Me,Et,NHCOPh),(NHMe,Me,Me,Et,NHCO-2-furyl), (NHMe,Me,Me,Et,NHCONHPh),(NHMe,Me,Me,Et,NHCOCONHPh),(NHMe,Me,Me,CH2OH,CONHPh), (NHMe,Me,Me,CH2OH,CONH-3-pyridyl),(NHMe,Me,Me,CH2OH,NHCOPh),(NHMe,Me,Me,CH2OH,NHCO-2-furyl),(NHMe,Me,Me,CH2OH,NHCONHPh),(NHMe,Me,Me,CH2OH,NHCOCONHPh),(NHMe,Me,Ph,Me,CONHPh),(NHMe,Me,Ph,Me,CONH-3-pyridyl),(NHMe,Me,Ph,Me,NHCOPh),(NHMe,Me,Ph,Me,NHCO-2-furyl), (NHMe,Me,Ph,Me,NHCONHPh),(NHMe,Me,Ph,Me,NHCOCONHPh),(NHMe,Me,Ph,Et,CONHPh),(NHMe,Me,Ph,Et,CONH-3-pyridyl),(NHMe,Me,Ph,Et,NHCOPh), (NHMe,Me,Ph,Et,NHCO-2-furyl),(NHMe,Me,Ph,Et,NHCONHPh),(NHMe,Me,Ph,Et,NHCOCONHPh),(NHMe,Me,Ph,CH2OH,CONHPh),(NHMe,Me,Ph,CH2OH,CONH- 3-pyridyl),(NHMe,Me,Ph,CH2OH,NHCOPh),(NHMe,Me, Ph,CH2OH,NHCO-2-furyl),(NHMe,Me,Ph,CH2OH, NHCONHPh),(NHMe,Me,Ph,CH2OH,NHCOCONHPh), (NHMe,Me,OH,Me,CONHPh),(NHMe,Me,OH,Me, CONH-3-pyridyl),(NHMe,Me,OH,Me,NHCOPh),(NHMe, Me,OH,Me,NHCO-2-furyl),(NHMe,Me,OH,Me, NHCONHPh),(NHMe,Me,OH,Me,NHCOCONHPh), (NHMe,Me,OH,Et,CONHPh),(NHMe,Me,OH,Et,CONH-3-pyridyl),(NHMe,Me,OH,Et,NHCOPh),(NHMe,Me,OH, Et,NHCO-2-furyl),(NHMe,Me,OH,Et,NHCONHPh), (NHMe,Me,OH,Et,NHCOCONHPh),(NHMe,Me,OH, CH2OH,CONHPh),(NHMe,Me,OH,CH2OH,CONH-3-pyridyl),(NHMe,Me,OH,CH2OH,NHCOPh),(NHMe,Me, OH,CH2OH,NHCO-2-furyl),(NHMe,Me,OH,CH2OH, NHCONHPh),(NHMe,Me,OH,CH2OH,NHCOCONHPh), (NHMe,Ph,H,Me,CONHPh),(NHMe,Ph,H,Me,CONH-3-pyridyl),(NHMe,Ph,H,Me,NHCOPh),(NHMe,Ph,H,Me, NHCO-2-furyl),(NHMe,Ph,H,Me,NHCONHPh),(NHMe, Ph,H,Me,NHCOCONHPh),(NHMe,Ph,H,Et,CONHPh), (NHMe,Ph,H,Et,CONH-3-pyridyl),(NHMe,Ph,H,Et, NHCOPh),(NHMe,Ph,H,Et,NHCO-2-furyl),(NHMe,Ph,H, Et,NHCONHPh),(NHMe,Ph,H,Et,NHCOCONHPh), (NHMe,Ph,H,CH2OH,CONHPh),(NHMe,Ph,H,CH2OH, CONH-3-pyridyl),(NHMe,Ph,H,CH2OH,NHCOPh), (NHMe,Ph,H,CH2OH,NHCO-2-furyl),(NHMe,Ph,H, CH2OH,NHCONHPh),(NHMe,Ph,H,CH2OH, NHCOCONHPh),(NHMe,Ph,Me,Me,CONHPh),(NHMe, Ph,Me,Me,CONH-3-pyridyl),(NHMe,Ph,Me,Me, NHCOPh),(NHMe,Ph,Me,Me,NHCO-2-furyl),(NHMe,Ph, Me,Me,NHCONHPh),(NHMe,Ph,Me,Me, NHCOCONHPh),(NHMe,Ph,Me,Et,CONHPh),(NHMe,Ph, Me,Et,CONH-3-pyridyl),(NHMe,Ph,Me,Et,NHCOPh), (NHMe,Ph,Me,Et,NHCO-2-furyl),(NHMe,Ph,Me,Et, NHCONHPh),(NHMe,Ph,Me,Et,NHCOCONHPh),(NHMe, Ph,Me,CH2OH,CONHPh),(NHMe,Ph,Me,CH2OH,CONH-3-pyridyl),(NHMe,Ph,Me,CH2OH,NHCOPh),(NHMe,Ph, Me,CH2OH,NHCO-2-furyl),(NHMe,Ph,Me,CH2OH, NHCONHPh),(NHMe,Ph,Me,CH2OH,NHCOCONHPh), (NHMe,Ph,Ph,Me,CONHPh),(NHMe,Ph,Ph,Me,CONH-3-pyridyl),(NHMe,Ph,Ph,Me,NHCOPh),(NHMe,Ph,Ph,Me, NHCO-2-furyl),(NHMe,Ph,Ph,Me,NHCONHPh),(NHMe, Ph,Ph,Me,NHCOCONHPh),(NHMe,Ph,Ph,Et,CONHPh), (NHMe,Ph,Ph,Et,CONH-3-pyridyl),(NHMe,Ph,Ph,Et, NHCOPh),(NHMe,Ph,Ph,Et,NHCO-2-furyl),(NHMe,Ph, Ph,Et,NHCONHPh),(NHMe,Ph,Ph,Et,NHCOCONHPh), (NHMe,Ph,Ph,CH2OH,CONHPh),(NHMe,Ph,Ph,CH2OH, CONH-3-pyridyl),(NHMe,Ph,Ph,CH2OH,NHCOPh), (NHMe,Ph,Ph,CH2OH,NHCO-2-furyl),(NHMe,Ph,Ph, CH2OH,NHCONHPh),(NHMe,Ph,Ph,CH2OH, NHCOCONHPh),(NHMe,Ph,OH,Me,CONHPh),(NHMe, Ph,OH,Me,CONH-3-pyridyl),(NHMe,Ph,OH,Me, NHCOPh),(NHMe,Ph,OH,Me,NHCO-2-furyl),(NHMe,Ph, OH,Me,NHCONHPh),(NHMe,Ph,OH,Me, NHCOCONHPh),(NHMe,Ph,OH,Et,CONHPh),(NHMe,Ph, OH,Et,CONH-3-pyridyl),(NHMe,Ph,OH,Et,NHCOPh), (NHMe,Ph,OH,Et,NHCO-2-furyl),(NHMe,Ph,OH,Et, NHCONHPh),(NHMe,Ph,OH,Et,NHCOCONHPh), (NHMe,Ph,OH,CH2OH,CONHPh),(NHMe,Ph,OH, CH2OH,CONH-3-pyridyl),(NHMe,Ph,OH,CH2OH, NHCOPh),(NHMe,Ph,OH,CH2OH,NHCO-2-furyl), (NHMe,Ph,OH,CH2OH,NHCONHPh),(NHMe,Ph,OH, CH2OH,NHCOCONHPh),
(NHCH2CH2OH,H,H,Me,CONHPh),(NHCH2CH2OH,H, H,Me,CONH-3-pyridyl),(NHCH2CH2OH,H,H,Me,NH-COPh),(NHCH2CH2OH,H,H,Me,NHCO-2-furyl), (NHCH2CH2OH,H,H,Me,NHCONHPh),(NHCH2CH2OH, H,H,Me,NHCOCONHPh),(NHCH2CH2OH,H,H,Et,CON-HPh),(NHCH2CH2OH,H,H,Et,CONH-3-pyridyl), (NHCH2CH2OH,H,H,Et,NHCOPh),(NHCH2CH2OH,H,H, Et,NHCO-2-furyl),(NHCH2CH2OH,H,H,Et,NHCONHPh), (NHCH2CH2OH,H,H,Et,NHCOCONHPh), (NHCH2CH2OH,H,H,CH2OH,CONHPh), (NHCH2CH2OH,H,H,CH2OH,CONH-3-pyridyl), (NHCH2CH2OH,H,H,CH2OH,NHCOPh), (NHCH2CH2OH,H,H,CH2OH,NHCO-2-furyl), (NHCH2CH2OH,H,H,CH2OH,NHCONHPh), (NHCH2CH2OH,H,H,CH2OH,NHCOCONHPh), (NHCH2CH2OH,H,Me,Me,CONHPh),(NHCH2CH2OH, H,Me,Me,CONH-3-pyridyl),(NHCH2CH2OH,H,Me,Me, NHCOPh),(NHCH2CH2OH,H,Me,Me,NHCO-2-furyl), (NHCH2CH2OH,H,Me,Me,NHCONHPh), (NHCH2CH2OH,H,Me,Me,NHCOCONHPh), (NHCH2CH2OH,H,Me,Et,CONHPh),(NHCH2CH2OH,H, Me,Et,CONH-3-pyridyl),(NHCH2CH2OH,H,Me,Et, NHCOPh),(NHCH2CH2OH,H,Me,Et,NHCO-2-furyl), (NHCH2CH2OH,H,Me,Et,NHCONHPh), (NHCH2CH2OH,H,Me,Et,NHCOCONHPh), (NHCH2CH2OH,H,Me,CH2OH,CONHPh), (NHCH2CH2OH,H,Me,CH2OH,CONH-3-pyridyl), (NHCH2CH2OH,H,Me,CH2OH,NHCOPh), (NHCH2CH2OH,H,Me,CH2OH,NHCO-2-furyl), (NHCH2CH2OH,H,Me,CH2OH,NHCONHPh), (NHCH2CH2OH,H,Me,CH2OH,NHCOCONHPh), (NHCH2CH2OH,H,Ph,Me,CONHPh),(NHCH2CH2OH,H, Ph,Me,CONH-3-pyridyl),(NHCH2CH2OH,H,Ph,Me, NHCOPh),(NHCH2CH2OH,H,Ph,Me,NHCO-2-furyl), (NHCH2CH2OH,H,Ph,Me,NHCONHPh), (NHCH2CH2OH,H,Ph,Me,NHCOCONHPh), (NHCH2CH2OH,H,Ph,Et,CONHPh),(NHCH2CH2OH,H, Ph,Et,CONH-3-pyridyl),(NHCH2CH2OH,H,Ph,Et, NHCOPh),(NHCH2CH2OH,H,Ph,Et,NHCO-2-furyl), (NHCH2CH2OH,H,Ph,Et,NHCONHPh),(NHCH2CH2OH, H,Ph,Et,NHCOCONHPh),(NHCH2CH2OH,H,Ph,CH2OH, CONHPh),(NHCH2CH2OH,H,Ph,CH2OH,CONH-3-pyridyl),(NHCH2CH2OH,H,Ph,CH2OH,NHCOPh), (NHCH2CH2OH,H,Ph,CH2OH,NHCO-2-furyl), (NHCH2CH2OH,H,Ph,CH2OH,NHCONHPh), (NHCH2CH2OH,H,Ph,CH2OH,NHCOCONHPh), (NHCH2CH2OH,H,OH,Me,CONHPh),(NHCH2CH2OH, H,OH,Me,CONH-3-pyridyl),(NHCH2CH2OH,H,OH,Me, NHCOPh),(NHCH2CH2OH,H,OH,Me,NHCO-2-furyl), (NHCH2CH2OH,H,OH,Me,NHCONHPh), (NHCH2CH2OH,H,OH,Me,NHCOCONHPh), (NHCH2CH2OH,H,OH,Et,CONHPh),(NHCH2CH2OH,H, OH,Et,CONH-3-pyridyl),(NHCH2CH2OH,H,OH,Et, NHCOPh),(NHCH2CH2OH,H,OH,Et,NHCO-2-furyl), (NHCH2CH2OH,H,OH,Et,NHCONHPh), (NHCH2CH2OH,H,OH,Et,NHCOCONHPh), (NHCH2CH2OH,H,OH,CH2OH,CONHPh), (NHCH2CH2OH,H,OH,CH2OH,CONH-3-pyridyl), (NHCH2CH2OH,H,OH,CH2OH,NHCOPh), (NHCH2CH2OH,H,OH,CH2OH,NHCO-2-furyl), (NHCH2CH2OH,H,OH,CH2OH,NHCONHPh), (NHCH2CH2OH,H,OH,CH2OH,NHCOCONHPh), (NHCH2CH2OH,Me,H,Me,CONHPh),(NHCH2CH2OH, Me,H,Me,CONH-3-pyridyl),(NHCH2CH2OH,Me,H,Me, NHCOPh),(NHCH2CH2OH,Me,H,Me,NHCO-2-furyl), (NHCH2CH2OH,Me,H,Me,NHCONHPh), (NHCH2CH2OH,Me,H,Me,NHCOCONHPh), (NHCH2CH2OH,Me,H,Et,CONHPh),(NHCH2CH2OH, Me,H,Et,CONH-3-pyridyl),(NHCH2CH2OH,Me,H,Et, NHCOPh),(NHCH2CH2OH,Me,H,Et,NHCO-2-furyl), (NHCH2CH2OH,Me,H,Et,NHCONHPh), (NHCH2CH2OH,Me,H,Et,NHCOCONHPh), (NHCH2CH2OH,Me,H,CH2OH,CONHPh),
(NHCH2CH2OH,Me,H,CH2OH,CONH-3-pyridyl),
(NHCH2CH2OH,Me,H,CH2OH,NHCOPh),
(NHCH2CH2OH,Me,H,CH2OH,NHCO-2-furyl),
(NHCH2CH2OH,Me,H,CH2OH,NHCONHPh),
(NHCH2CH2OH,Me,H,CH2OH,NHCOCONHPh),
(NHCH2CH2OH,Me,Me,Me,CONHPh),(NHCH2CH2OH,
Me,Me,Me,CONH-3-pyridyl),(NHCH2CH2OH,Me,Me,
Me,NHCOPh),(NHCH2CH2OH,Me,Me,Me,NHCO-2-
furyl),(NHCH2CH2OH,Me,Me,Me,NHCONHPh),
(NHCH2CH2OH,Me,Me,Me,NHCOCONHPh),
(NHCH2CH2OH,Me,Me,Et,CONHPh),(NHCH2CH2OH,
Me,Me,Et,CONH-3-pyridyl),(NHCH2CH2OH,Me,Me,Et,
NHCOPh),(NHCH2CH2OH,Me,Me,Et,NHCO-2-furyl),
(NHCH2CH2OH,Me,Me,Et,NHCONHPh),
(NHCH2CH2OH,Me,Me,Et,NHCOCONHPh),
(NHCH2CH2OH,Me,Me,CH2OH,CONHPh),
(NHCH2CH2OH,Me,Me,CH2OH,CONH-3-pyridyl),
(NHCH2CH2OH,Me,Me,CH2OH,NHCOPh),
(NHCH2CH2OH,Me,Me,CH2OH,NHCO-2-furyl),
(NHCH2CH2OH,Me,Me,CH2OH,NHCONHPh),
(NHCH2CH2OH,Me,Me,CH2OH,NHCOCONHPh),
(NHCH2CH2OH,Me,Ph,Me,CONHPh),(NHCH2CH2OH,
Me,Ph,Me,CONH-3-pyridyl),(NHCH2CH2OH,Me,Ph,Me,
NHCOPh),(NHCH2CH2OH,Me,Ph,Me,NHCO-2-furyl),
(NHCH2CH2OH,Me,Ph,Me,NHCONHPh),
(NHCH2CH2OH,Me,Ph,Me,NHCOCONHPh),
(NHCH2CH2OH,Me,Ph,Et,CONHPh),(NHCH2CH2OH,
Me,Ph,Et,CONH-3-pyridyl),(NHCH2CH2OH,Me,Ph,Et,
NHCOPh),(NHCH2CH2OH,Me,Ph,Et,NHCO-2-furyl),
(NHCH2CH2OH,Me,Ph,Et,NHCONHPh),
(NHCH2CH2OH,Me,Ph,Et,NHCOCONHPh),
(NHCH2CH2OH,Me,Ph,CH2OH,CONHPh),
(NHCH2CH2OH,Me,Ph,CH2OH,CONH-3-pyridyl),
(NHCH2CH2OH,Me,Ph,CH2OH,NHCOPh),
(NHCH2CH2OH,Me,Ph,CH2OH,NHCO-2-furyl),
(NHCH2CH2OH,Me,Ph,CH2OH,NHCONHPh),
(NHCH2CH2OH,Me,Ph,CH2OH,NHCOCONHPh),
(NHCH2CH2OH,Me,OH,Me,CONHPh),(NHCH2CH2OH,
Me,OH,Me,CONH-3-pyridyl),(NHCH2CH2OH,Me,OH,
Me,NHCOPh),(NHCH2CH2OH,Me,OH,Me,NHCO-2-
furyl),(NHCH2CH2OH,Me,OH,Me,NHCONHPh),
(NHCH2CH2OH,Me,OH,Me,           NHCOCONHPh),
(NHCH2CH2OH,Me,OH,Et,CONHPh),(NHCH2CH2OH,
Me,OH,Et,CONH-3-pyridyl),(NHCH2CH2OH,Me,OH,Et,
NHCOPh),(NHCH2CH2OH,Me,OH,Et,NHCO-2-furyl),
(NHCH2CH2OH,Me,OH,Et,NHCONHPh),
(NHCH2CH2OH,Me,OH,Et,NHCOCONHPh),
(NHCH2CH2OH,Me,OH,CH2OH,CONHPh),
(NHCH2CH2OH,Me,OH,CH2OH,CONH-3-pyridyl),
(NHCH2CH2OH,Me,OH,CH2OH,NHCOPh),
(NHCH2CH2OH,Me,OH,CH2OH,NHCO-2-furyl),
(NHCH2CH2OH,Me,OH,CH2OH,NHCONHPh),
(NHCH2CH2OH,Me,OH,CH2OH,NHCOCONHPh),
(NHCH2CH2OH,Ph,H,Me,CONHPh),(NHCH2CH2OH,
Ph,H,Me,CONH-3-pyridyl),(NHCH2CH2OH,Ph,H,Me,
NHCOPh),(NHCH2CH2OH,Ph,H,Me,NHCO-2-furyl),
(NHCH2CH2OH,Ph,H,Me,NHCONHPh),
(NHCH2CH2OH,Ph,H,Me,NHCOCONHPh),
(NHCH2CH2OH,Ph,H,Et,CONHPh),(NHCH2CH2OH,Ph,
H,Et,CONH-3-pyridyl),(NHCH2CH2OH,Ph,H,Et,
NHCOPh),(NHCH2CH2OH,Ph,H,Et,NHCO-2-furyl),
(NHCH2CH2OH,Ph,H,Et,NHCONHPh),(NHCH2CH2OH,
Ph,H,Et,NHCOCONHPh),(NHCH2CH2OH,Ph,H,CH2OH,
CONHPh),(NHCH2CH2OH,Ph,H,CH2OH,CONH-3-
pyridyl),(NHCH2CH2OH,Ph,H,CH2OH,NHCOPh),
(NHCH2CH2OH,Ph,H,CH2OH,NHCO-2-furyl),
(NHCH2CH2OH,Ph,H,CH2OH,NHCONHPh),
(NHCH2CH2OH,Ph,H,CH2OH,NHCOCONHPh),
(NHCH2CH2OH,Ph,Me,Me,CONHPh),(NHCH2CH2OH,
Ph,Me,Me,CONH-3-pyridyl),(NHCH2CH2OH,Ph,Me,Me,
NHCOPh),(NHCH2CH2OH,Ph,Me,Me,NHCO-2-furyl),
(NHCH2CH2OH,Ph,Me,Me,NHCONHPh),
(NHCH2CH2OH,Ph,Me,Me,NHCOCONHPh),
(NHCH2CH2OH,Ph,Me,Et,CONHPh),(NHCH2CH2OH,
Ph,Me,Et,CONH-3-pyridyl),(NHCH2CH2OH,Ph,Me,Et,
NHCOPh),(NHCH2CH2OH,Ph,Me,Et,NHCO-2-furyl),
(NHCH2CH2OH,Ph,Me,Et,NHCONHPh),
(NHCH2CH2OH,Ph,Me,Et,NHCOCONHPh),
(NHCH2CH2OH,Ph,Me,CH2OH,CONHPh),
(NHCH2CH2OH,Ph,Me,CH2OH,CONH-3-pyridyl),
(NHCH2CH2OH,Ph,Me,CH2OH,NHCOPh),
(NHCH2CH2OH,Ph,Me,CH2OH,NHCO-2-furyl),
(NHCH2CH2OH,Ph,Me,CH2OH,NHCONHPh),
(NHCH2CH2OH,Ph,Me,CH2OH,NHCOCONHPh),
(NHCH2CH2OH,Ph,Ph,Me,CONHPh),(NHCH2CH2OH,
Ph,Ph,Me,CONH-3-pyridyl),(NHCH2CH2OH,Ph,Ph,Me,
NHCOPh),(NHCH2CH2OH,Ph,Ph,Me,NHCO-2-furyl),
(NHCH2CH2OH,Ph,Ph,Me,NHCONHPh),
(NHCH2CH2OH,Ph,Ph,Me,NHCOCONHPh),
(NHCH2CH2OH,Ph,Ph,Et,CONHPh),(NHCH2CH2OH,
Ph,Ph,Et,CONH-3-pyridyl),(NHCH2CH2OH,Ph,Ph,Et,
NHCOPh),(NHCH2CH2OH,Ph,Ph,Et,NHCO-2-furyl),
(NHCH2CH2OH,Ph,Ph,Et,NHCONHPh),
(NHCH2CH2OH,Ph,Ph,Et,NHCOCONTIPh),
(NHCH2CH2OH,Ph,Ph,CH2OH,CONHPh),
(NHCH2CH2OH,Ph,Ph,CH2OH,CONH-3-pyridyl),
(NHCH2CH2OH,Ph,Ph,CH2OH,NHCOPh),
(NHCH2CH2OH,Ph,Ph,CH2OH,NHCO2-furyl),
(NHCH2CH2OH,Ph,Ph,CH2OH,NHCONHPh),
(NHCH2CH2OH,Ph,Ph,CH2OH,NHCOCONHPh),
(NHCH2CH2OH,Ph,OH,Me,CONHPh),(NHCH2CH2OH,
Ph,OH,Me,CONH-3-pyridyl),(NHOH2CH2OH,Ph,OH,Me,
NHCOPh),(NHCH2CH2OH,Ph,OH,Me,NHCO-2-furyl),
(NHCH2CH2OH,Ph,OH,Me,NHCONHPh),
(NHCH2CH2OH,Ph,OH,Me,NHCOCONHPh),
(NHCH2CH2OH,Ph,OH,Et,CONHPh),(NHCH2CH2OH,
Ph,OH,Et,CONH-3-pyridyl),(NHCH2CH2OH,Ph,OH,Et,
NHCOPh),(NHCH2CH2OH,Ph,OH,Et,NHCO-2-furyl),
(NHCH2CH2OH,Ph,OH,Et,NHCONHPh),
(NHCH2CH2OH,Ph,OH,Et,NHCOCONHPh),
(NHCH2CH2OH,Ph,OH,CH2OH,CONHPh),
(NHCH2CH2OH,Ph,OH,CH2OH,CONH-3-pyridyl),
(NHCH2CH2OH,Ph,OH,CH2OH,NHCOPh),
(NHCH2CH2OH,Ph,OH,CH2OH,NHCO-2-furyl),
(NHCH2CH2OH,Ph,OH,CH2OH,NHCONHPh),
(NHCH2CH2OH,Ph,OH,CH2OH,NHCOCONHPh),
(NHCH2CONH2,H,H,Me,CONHPh),(NHCH2CONH2,H,
H,Me,CONH-3-pyridyl),(NHCH2CONH2,H,H,Me,NH-
COPh),(NHCH2CONH2,H,H,Me,NHCO-2-furyl),
(NHCH2CONH2,H,H,Me,NHCONHPh),(NHCH2CONH2,
H,H,Me,NHCOCONHPh),(NHCH2CONH2,H,H,Et,
CONHPh),(NHCH2CONH2,H,H,Et,CONH-3-pyridyl),
(NHCH2CONH2,H,H,Et,NHCOPh),(NHCH2CONH2,H,H,
Et,NHCO-2-furyl),(NHCH2CONH2,H,H,Et,NHCONHPh),
(NHCH2CONH2,H,H,Et,NHCOCONHPh),
(NHCH2CONH2,H,H,CH2OH,CONHPh),
(NHCH2CONH2,H,H,CH2OH,CONH-3-pyridyl),
(NHCH2CONH2,H,H,CH2OH,NHCOPh),
(NHCH2CONH2,H,H,CH2OH,NHCO-2-furyl),
(NHCH2CONH2,H,H,CH2OH,NHCONHPh),
(NHCH2CONH2,H,H,CH2OH,NHCOCONHPh),
(NHCH2CONH2,H,Me,Me,CONHPh),(NHCH2CONH2,
H,Me,Me,CONH-3-pyridyl),(NHCH2CONH2,H,Me,Me, NHCOPh),(NHCH2CONH2,H,Me,Me,NHCO-2-furyl),
(NHCH2CONH2,H,Me,Me,NHCONHPh),
(NHCH2CONH2,H,Me,Me,NHCOCONHPh),
(NHCH2CONH2,H,Me,Et,CONHPh),(NHCH2CONH2,H,
Me,Et,CONN-3-pyridyl),(NHCH2CONH2,H,Me,Et,
NHCOPh),(NHCH2CONH2,H,Me,Et,NHCO-2-furyl),
(NHCH2CONH2,H,Me,Et,NHCONHPh),
(NHCH2CONH2,H,Me,Et,NHCOCONHPh),
(NHCH2CONH2,H,Me,CH2OH,CONHPh),
(NHCH2CONH2,H,Me,CH2OH,CONH-3-pyridyl),
(NHCH2CONH2,H,Me,CH2OH,NHCOPh),
(NHCH2CONH2,H,Me,CH2OH,NHCO-2-furyl),
(NHCH2CONH2,H,Me,CH2OH,NHCONHPh),
(NHCH2CONH2,H,Me,CH2OH,NHCOCONHPh),
(NHCH2CONH2,H,Ph,Me,CONHPh),(NHCH2CONH2,H,
Ph,Me,CONH-3-pyridyl),(NHCH2CONH2,H,Ph,Me,
NHCOPh),(NHCH2CONH2,H,Ph,Me,NHCO-2-furyl),
(NHCH2CONH2,H,Ph,Me,NHCONHPh),
(NHHCH2CONH2,H,Ph,Me,NHCOCONHPh),
(NHCH2CONH2,H,Ph,Et,CONHPh),(NHCH2CONH2,H,
Ph,Et,CONH-3-pyridyl),(NHCH2CONH2,H,Ph,Et,
NHCOPh),(NHCH2CONH2,H,Ph,Et,NHCO-2-furyl),
(NHCH2CONH2,H,Ph,Et,NHCONHPh),(NHCH2CONH2,
H,Ph,Et,NHCOCONHPh),(NHCH2CONH2,H,Ph,CH2OH,
CONHPh),(NHCH2CONH2,H,Ph,CH2OH,CONH-3-
pyridyl),(NHCH2CONH2,H,Ph,CH2OH,NHCOPh),
(NHCH2CONH2,H,Ph,CH2OH,NHCO-2-furyl),
(NHCH2CONH2,H,Ph,CH2OH,NHCONHPh),
(NHCH2CONH2,H,Ph,CH2OH,NHCOCONHPh),
(NHCH2CONH2,H,OH,Me,CONHPh),(NHCH2CONH2,
H,OH,Me,CONH-3-pyridyl),(NHCH2CONH2,H,OH,Me,
NHCOPh),(NHCH2CONH2,H,OH,Me,NHCO-2-furyl),
(NHCH2CONH2,H,OH,Me,NHCONHPh),
(NHCH2CONH2,H,OH,Me,NHCOCONHPh),
(NHCH2CONH2,H,OH,Et, CONHPh),(NHCH 2CONH2,
H,OH,Et,CONH-3-pyridyl),(NHCH2CONH2,H,OH,Et,
NHCOPh),(NHCH2CONH2,H,OH,Et,NHCO-2-furyl),
(NHCH2CONH2,H,OH,Et,NHCONHPh),
(NHCH2CONH2,H,OH,Et,NHCOCONHPh),
(NHCH2CONH2,H,OH,CH2OH,CONHPh),
(NHCH2CONH2,H,OH,CH2OH,CONH-3-pyridyl),
(NHCH2CONH2,H,OH,CH2OH,NHCOPh),
(NHCH2CONH2,H,OH,CH2OH,NHCO-2-furyl),
(NHCH2CONH2,H,OH,CH2OH,NHCONHPh),
(NHCH2CONH2,H,OH,CH2OH,NHCOCONHPh),
(NHCH2CONH2,Me,H,Me,CONHPh),(NHCH2CONH2,
Me,H,Me,CONH-3-pyridyl),(NHCH2CONH2,Me,H,Me,
NHCOPh),(NHCH2CONH2,Me,H,Me,NHCO-2-furyl),
(NHCH2CONH2,Me,H,Me,NHCONBPh),
(NHCH2CONH2,Me,H,Me,NHCOCONHPh),
(NHCH2CONH2,Me,H,Et,CONHPh),(NHCH2CONH2,
Me,H,Et,CONH-3-pyridyl),(NHCH2CONH2,Me,H,Et,
NHCOPh),(NHCH2CONH2,Me,H,Et,NHCO-2-furyl),
(NHCH2CONH2,Me,H,Et,NHCONHPh),
(NHCH2CONH2,Me,H,Et,NHCOCONHPh),
(NHCH2CONH2,Me,H,CH2OH,CONHPh),
(NHCH2CONH2,Me,H,CH2OH,CONH-3-pyridyl),
(NHCH2CONH2,Me,H,CH2OH,NHCOPh),
(NHCH2CONH2,Me,H,CH2OH,NHCO-2-furyl),
(NHCH2CONH2,Me,H,CH2OH,NHCONHPh),
(NHCH2CONH2,Me,H,CH2OH,NHCOCONHPh),
(NHCH2CONH2,Me,Me,Me,CONHPh),(NHCH2CONH2,
Me,Me,Me,CONH-3-pyridyl),(NHCH2CONH2,Me,Me,
Me,NHCOPh),(NHCH2CONH2,Me,Me,Me,NHCO-2-
furyl),(NHCH2CONH2,Me,Me,Me,NHCONHPh),
(NHCH2CONH 2,Me,Me,Me,NHCOCONHPh),
(NHCH2CONH2,Me,Me,Et,CONHPh),(NHCH2CONH
2,Me,Me,Et, CONH-3-pyridyl),(NHCH2CONH2,Me,Me,
Et,NHCOPh),(NHCH2CONH2,Me,Me,Et,NHCO-2-furyl),
(NHCH2CONH2,Me,Me,Et,NHCONHPh),
(NHCH2CONH2,Me,Me,Et,NHCOCONHPh),
(NHCH2CONH2,Me,Me,CH2OH,CONHPh),
(NHCH2CONH2,Me,Me,CH2OH,CONH-3-pyridyl),
(NHCH2CONH2,Me,Me,CH2OH,NHCOPh),
(NHCH2CONH2,Me,Me,CH2OH,NHCO-2-furyl),
(NHCH2CONH2,Me,Me,CH2OH,NHCONHPh),
(NHCH2CONH2,Me,Me,CH2OH,NHCOCONHPh),
(NHCH2CONH2,Me,Ph,Me,CONHPh),(NHCH2CONH2,
Me,Ph,Me,CONH-3-pyridyl),(NHCH2CONH2,Me,Ph,Me,
NHCOPh),(NHCH2CONH2,Me,Ph,Me,NHCO-2-furyl),
(NHCH2CONH2,Me,Ph,Me,NHCONHPh),
(NHCH2CONH2,Me,Ph,Me,NHCOCONHPh),
(NHCH2CONH2,Me,Ph,Et,CONHPh),(NHCH2CONH2,
Me,Ph,Et,CONH-3-pyridyl),(NHCH2CONH2,Me,Ph,Et,
NHCOPh),(NHCH2CONH2,Me,Ph,Et,NHCO-2-furyl),
(NHCH2CONH2,Me,Ph,Et,NHCONHPh),
(NHCH2CONH2,Me,Ph,Et,NHCOCONHPh),
(NHCH2CONH2,Me,Ph,CH2OH,CONHPh),
(NHCH2CONH2,Me,Ph,CH2OH,CONH-3-pyridyl),
(NHCH2CONH2,Me,Ph,CH2OH,NHCOPh),
(NHCH2CONH2,Me,Ph,CH2OH,NHCO-2-furyl),
(NHCH2CONH2,Me,Ph,CH2OH,NHCONHPh),
(NHCH2CONH2,Me,Ph,CH2OH,NHCOCONHPh),
(NHCH2CONH2,Me,OH,Me,CONHPh),(NHCH2CONH2,
Me,OH,Me,CONH-3-pyridyl),(NHCH2CONH2,Me,OH,
Me,NHCOPh),(NHCH2CONH2,Me,OH,Me,NHCO-2-
furyl),(NHCH2CONH2,Me,OH,Me,NHCONHPh),
(NHCH2CONH2,Me,OH,Me,NHCOCONHPh),
(NHCH2CONH2,Me,OH,Et,CONHPh),(NHCH2CONH2,
Me,OH,Et,CONH-3-pyridyl),(NHCH2CONH2,Me,OH,Et,
NHCOPh),(NHCH2CONH2,Me,OH,Et,NHCO-2-furyl),
(NHCH2CONH2,Me,OH,Et,NHCONHPh),
(NHCH2CONH2,Me,OH,Et,NHCOCONHPh),
(NHCH2CONH2,Me,OH,CH2OH,CONHPh),
(NHCH2CONH2,Me,OH,CH2OH,CONH-3-pyridyl),
(NHCH2CONH2,Me,OH,CH2OH,NHCOPh),
(NHCH2CONH2,Me,OH,CH2OH,NHCO-2-furyl),
(NHCH2CONH2,Me,OH,CH2OH,NHCONHPh),
(NHCH2CONH2,Me,OH,CH2OH,NHCOCONHPh),
(NHCH2CONH2,Ph,H,Me,CONHPh),(NHCH2CONH2,
Ph,H,Me,CONH-3-pytidyl),(NHCH2CONH2,Ph,H,Me,
NHCOPh),(NHCH2CONH2,Ph,H,Me,NHCO-2-furyl),
(NHCH2CONH2,Ph,H,Me,NHCONHPh),
(NHCH2CONH2,Ph,H,Me,NHCOCONHPh),
(NHCH2CONH2,Ph,H,Et,CONHPh),(NHCH2CONH2,Ph,
H,Et,CONH-3-pyridyl),(NHCH2CONH2,Ph,H,Et,
NHCOPh),(NHCH2CONH2,Ph,H,Et,NHCO-2-furyl),
(NHCH2CONH2,Ph,H,Et,NHCONHPh),(NHCH2CONH2,
Ph,H,Et,NHCOCONHPh),(NHCH2CONH2,Ph,H,CH2OH,
CONHPh),(NHCH2CONH2,Ph,H,CH2OH,CONH-3-
pyridyl),(NHCH2CONH2,Ph,H,CH2OH,NHCOPh),
(NHCH2CONH2,Ph,H,CH2OH,NHCO-2-furyl),
(NHCH2CONH2,Ph,H,CH2OH,NHCONHPh),
(NHCH2CONH2,Ph,H,CH2OH,NHCOCONHPh),
(NHCH2CONH2,Ph,Me,Me,CONHPh),(NHCH2CONH2,
Ph,Me,Me,CONH-3-pyridyl),(NHCH2CONH2,Ph,Me,Me,
NHCOPh),(NHCH2CONH2,Ph,Me,Me,NHCO-2-furyl),
(NHCH2CONH2,Ph,Me,Me,NHCONHPh),
(NHCH2CONH2,Ph,Me,Me,NHCOCONHPh),
(NHCH2CONH2,Ph,Me,Et,CONHPh),(NHCH2CONH2,
Ph,Me,Et,CONH-3-pyridyl),(NHCH2CONH2,Ph,Me,Et,
NHCOPh),(NHCH2CONH2,Ph,Me,Et,NHCO-2-furyl),
(NHCH2CONH2,Ph,Me,Et,NHCONHPh),
(NHCH2CONH2,Ph,Me,Et,NHCOCONHPh), (NHCH2CONH2,Ph,Me,CH2OH,CONHPh),
(NHCH2CONH2,Ph,Me,CH2OH,CONH-3-pyridyl),
(NHCH2CONH2,Ph,Me,CH2OH,NHCOPh),
(NHCH2CONH2,Ph,Me,CH2OH,NHCO-2-furyl),
(NHCH2CONH2,Ph,Me,CH2OH,NHCONHPh),
(NHCH2CONH2,Ph,Me,CH2OH,NHCOCONHPh),
(NHCH2CONH2,Ph,Ph,Me,CONHPh),(NHCH2CONH2,Ph,Ph,Me,CONH-3-pyridyl),(NHCH2CONH2,Ph,Ph,Me,NHCOPh),(NHCH2CONH2,Ph,Ph,Me,NHCO-2-furyl),
(NHCH2CONH2,Ph,Ph,Me,NHCONHPh),
(NHCH2CONH2,Ph,Ph,Me,NHCOCONHPh),
(NHCH2CONH2,Ph,Ph,Et,CONHPh),(NHCH2CONH2,Ph,Ph,Et,CONH-3-pyridyl),(NHCH2CONH2,Ph,Ph,Et,NHCOPh),(NHCH2CONH2,Ph,Ph,Et,NHCO-2-furyl),
(NHCH2CONH2,Ph,Ph,Et,NHCONHPh),
(NHCH2CONH2,Ph,Ph,Et,NHCOCONHPh),
(NHCH2CONH2,Ph,Ph,CH2OH,CONHPh),
(NHCH2CONH2,Ph,Ph,CH2OH,CONH-3-pyridyl),
(NHCH2CONH2,Ph,Ph,CH2OH,NHCOPh),
(NHCH2CONH2,Ph,Ph,CH2OH,NHCO-2-furyl),
(NHCH2CONH2,Ph,Ph,CH2OH,NHCONHPh),
(NHCH2CONH2,Ph,Ph,CH2OH,NHCOCONHPh),
(NHCH2CONH2,Ph,OH,Me,CONHPh),(NHCH2CONH2,Ph,OH,Me,CONH-3-pyridyl),(NHCH2CONH2,Ph,OH,Me,NHCOPh),(NHCH2CONH2,Ph,OH,Me,NHCO-2-furyl),
(NHCH2CONH2,Ph,OH,Me,NHCONHPh),
(NHCH2CONH2,Ph,OH,Me,NHCOCONHPh),
(NHCH2CONH2,Ph,OH,Et,CONHPh),(NHCH2CONH2,Ph,OH,Et,CONH-3-pyridyl),(NHCH2CONH2,Ph,OH,Et,NHCOPh),(NHCH2CONH2,Ph,OH,Et,NHCO-2-furyl),
(NHCH2CONH2,Ph,OH,Et,NHCONHPh),
(NHCH2CONH2,Ph,OH,Et,NHCOCONHPh),
(NHCH2CONH2,Ph,OH,CH2OH,CONHPh),
(NHCH2CONH2,Ph,OH,CH2OH,CONH-3-pyridyl),
(NHCH2CONH2,Ph,OH,CH2OH,NHCOPh),
(NHCH2CONH2,Ph,OH,CH2OH,NHCO-2-furyl),
(NHCH2CONH2,Ph,OH,CH2OH,NHCONHPh),
(NHCH2CONH2,Ph,OH,CH2OH,NHCOCONHPh),
(NHCH(Bn)CONH2,H,H,Me,CONHPh),(NHCH(Bn)CONH2,H,H,Me,CONH-3-pyridyl),(NHCH(Bn)CONH2,H,H,Me,NHCOPh),(NHCH(Bn)CONH2,H,H,Me,NHCO-2-furyl),(NHCH(Bn)CONH2,H,H,Me,NHCONHPh),(NHCH(Bn)CONH2,H,H,Me,NHCOCONHPh),(NHCH(Bn)CONH2,H,H,Et,CONHPh),(NHCH(Bn)CONH2,H,H,Et,CONH-3-pyridyl),(NHCH(Bn)CONH2,H,H,Et,NHCOPh),(NHCH(Bn)CONH2,H,H,Et,NHCO-2-furyl),
(NHCH(Bn)CONH2,H,H,Et,NHCONHPh),(NHCH(Bn)CONH2,H,H,Et,NHCOCONHPh),(NHCH(Bn)CONH2,H,H,CH2OH,CONHPh),(NHCH(Bn)CONH2,H,H,CH2OH,CONH-3-pyridyl),(NHCH(Bn)CONH2,H,H,CH2OH,NHCOPh),(NHCH(Bn)CONH2,H,H,CH2OH,NHCO-2-furyl),(NHCH(Bn)CONH2,H,H,CH2OH,NHCONHPh),
(NHCH(Bn)CONH2,H,H,CH2OH,NHCOCONHPh),
(NHCHNCONH2,H,Me,Me,CONHPh),(NHCH(Bn)CONH2,H,Me,Me,CONH-3-pyridyl),(NHCH(Bn)CONH2,H,Me,Me,NHCOPh),(NHCH(Bn)CONH2,H,Me,Me,NHCO-2-furyl),(NHCH(Bn)CONH2,H,Me,Me,NHCONHPh),(NHCH(Bn)CONH2,H,Me,Me,NHCOCONHPh),(NHCH(Bn)CONH2,H,Me,Et,CONHPh),(NHCH(Bn)CONH2,H,Me,Et,CONH-3-pyridyl),(NHCH(Bn)CONH2,H,Me,Et,NHCOPh),(NHCH(Bn)CONH2,H,Me,Et,NHCO-2-furyl),(NHCH(Bn)CONH2,H,Me,Et,NHCONHPh),(NHCH(Bn)CONH2,H,Me,Et,NHCOCONHPh),(NHCH(Bn)CONH2,H,Me,CH2OH,CONHPh),(NHCH(Bn)CONH2,H,Me,CH2OH,CONH-3-pyridyl),(NHCH(Bn)CONH2,H,Me,CH2OH,NHCOPh),(NHCH(Bn)CONH2,H,Me,CH2OH,NHCO-2-furyl),(NHCH(Bn)CONH2,H,Me,CH2OH,NHCONHPh),
(NHCH(Bn)CONH2,H,Me,CH2OH,NHCOCONHPh),
(NHCH(Bn)CONH2,H,Ph,Me,CONHPh),(NHCH(Bn)CONH2,H,Ph,Me,CONH-3-pyridyl),(NHCH(Bn)CONH2,H,Ph,Me,NHCOPh),(NHCH(Bn)CONH2,H,Ph,Me,NHCO-2-furyl),(NHCH(Bn)CONH2,H,Ph,Me,NHCONHPh),
(NHCH(Bn)CONH2,H,Ph,Me,NHCOCONHPh),(NHCH(Bn)CONH2,H,Ph,Et,CONHPh),(NHCH(Bn)CONH2,H,Ph,Et,CONH-3-pyridyl),(NHCH(Bn)CONH2,H,Ph,Et,NHCOPh),(NHCH(Bn)CONH2,H,Ph,Et,NHCO-2-furyl),
(NHCH(Bn)CONH2,H,Ph,Et,NHCONHPh),(NHCH(Bn)CONH2,H,Ph,Et,NHCOCONHPh),(NHCH(Bn)CONH2,H,Ph,CH2OH,CONHPh),(NHCH(Bn)CONH2,H,Ph,CH2OH,CONH-3-pyridyl),(NHCH(Bn)CONH2,H,Ph,CH2OH,NHCOPh),(NHCH(Bn)CONH2,H,Ph,CH2OH,NHCO-2-furyl),(NHCH(Bn)CONH2,H,Ph,CH2OH,NHCONHPh),
(NHCH(Bn)CONH2,H,Ph,CH2OH,NHCOCONHPh),
(NHCH(Bn)CONH2,H,OH,Me,CONHPh),(NHCH(Bn)CONH2,H,OH,Me,CONH-3-pyridyl),(NHCH(Bn)CONH2,H,OH,Me,NHCOPh),(NHCH(Bn)CONH2,H,OH,Me,NHCO-2-furyl),(NHCH(Bn)CONH2,H,OH,Me,NHCONHPh),(NHCH(Bn)CONH2,H,OH,Me,NHCOCONHPh),(NHCH(Bn)CONH2,H,OH,Et,CONHPh),(NHCH(Bn)CONH2,H,OH,Et,CONH-3-pyridyl),(NHCH(Bn)CONH2,H,OH,Et,NHCOPh),(NHCH(Bn)CONH2,H,OH,Et,NHCO-2-furyl),(NHCH(Bn)CONH2,H,OH,Et,NHCONHPh),(NHCH(Bn)CONH2,H,OH,Et,NHCOCONHPh),(NHCH(Bn)CONH2,H,OH,CH2OH,CONHPh),(NHCH(Bn)CONH2,H,OH,CH2OH,CONH-3-pyridyl),(NHCH(Bn)CONH2,H,OH,CH2OH,NHCOPh),(NHCH(Bn)CONH2,H,OH,CH2OH,NHCO-2-furyl),(NHCH(Bn)CONH2,H,OH,CH2OH,NHCONHPh),
(NHCH(Bn)CONH2,H,OH,CH2OH,NHCOCONHPh),
(NHCH(Bn)CONH2,Me,H,Me,CONHPh),(NHCH(Bn)CONH2,Me,H,Me,CONH-3-pyridyl),(NHCH(Bn)CONH2,Me,H,Me,NHCOPh),(NHCH(Bn)CONH2,Me,H,Me,NHCO-2-furyl),(NHCH(Bn)CONH2,Me,H,Me,NHCONHPh),(NHCH(Bn)CONH2,Me,H,Me,NHCOCONHPh),(NHCH(Bn)CONH2,Me,H,Et,CONHPh),(NHCH(Bn)CONH2,Me,H,Et,CONH-3-pyridyl),(NHCH(Bn)CONH2,Me,H,Et,NHCOPh),(NHCH(Bn)CONH2,Me,H,Et,NHCO-2-furyl),(NHCH(Bn)CONH2,Me,H,Et,NHCONHPh),(NHCH(Bn)CONH2,Me,H,Et,NHCOCONHPh),(NHCH(Bn)CONH2,Me,H,CH2OH,CONHPh),(NHCH(Bn)CONH2,Me,H,CH2OH,CONH-3-pyridyl),(NHCH(Bn)CONH2,Me,H,CH2OH,NHCOPh),(NHCH(Bn)CONH2,Me,H,CH2OH,NHCO-2-furyl),(NHCH(Bn)CONH2,Me,H,CH2OH,NHCONHPh),
(NHCH(Bn)CONH2,Me,H,CH2OH,NHCOCONHPh),
(NHCH(Bn)CONH2,Me,Me,Me,CONHPh),(NHCH(Bn)CONH2,Me,Me,Me,CONH-3-pyridyl),(NHCH(Bn)CONH2,Me,Me,Me,NHCOPh),(NHCH(Bn)CONH2,Me,Me,Me,NHCO-2-furyl),(NHCH(Bn)CONH2,Me,Me,Me,NHCONHPh),(NHCH(Bn)CONH2,Me,Me,Me,NHCOCONHPh),(NHCH(Bn)CONH2,Me,Me,Et,CONHPh),(NHCH(Bn)CONH2,Me,Me,Et,CONH-3-pyridyl),(NHCH(Bn)CONH2,Me,Me,Et,NHCOPh),(NHCH(Bn)CONH2,Me,Me,Et,NHCO-2-furyl),(NFICH(Bn)CONH2,Me,Me,Et,NHCONHPh),(NHCH(Bn)CONH2,Me,Me,Et,NHCOCONHPh),(NHCH(Bn)CONH2,Me,Me,CH2OH,CONHPh),(NHCH(Bn)CONH2,Me,Me,CH2OH,CONH-3-pyridyl),(NHCH(Bn)CONH2,Me,Me,CH2OH,NHCOPh),(NHCH(Bn)CONH2,Me,Me,CH2OH,NHCO-2-furyl),(NHCH(Bn)CONH2,Me,Me,CH2OH,NHCONHPh),
(NHCH(Bn)CONH2,Me,Me,CH2OH,NHCOCONHPh),
(NHCH(Bn)CONH2,Me,Ph,Me,CONHPh),(NHCH(Bn)CONH2,Me,Ph,Me,CONH-3-pyridyl),(NHCH(Bn)

CONH2,Me,Ph,Me,NHCOPh),(NHCH(Bn)CONH2,Me,Ph,Me,NHCO-2-furyl),(NHCH(Bn)CONH2,Me,Ph,Me,NHCONHPh),(NHCH(Bn)CONH2,Me,Ph,Me,NHCOCONHPh),(NHCH(Bn)CONH2,Me,Ph,Et,CONH-3-pyridyl),(NHCH(Bn)CONH2,Me,Ph,Et,NHCOPh),(NHCH(Bn)CONH2,Me,Ph,Et,NHCO-2-furyl),(NHCH(Bn)CONH2,Me,Ph,Et,NHCONHPh),(NHCH(Bn)CONH2,Me,Ph,Et,NHCOCONHPh),(NHCH(Bn)CONH2,Me,Ph,CH2OH,CONHPh),(NHCH(Bn)CONH2,Me,Ph,CH2OH,CONH-3-pyridyl),(NHCH(Bn)CONH2,Me,Ph,CH2OH,NHCOPh),(NHCH(Bn)CONH2,Me,Ph,CH2OH,NHCO-2-furyl),(NHCH(Bn)CONH2,Me,Ph,CH2OH,NHCONHPh),(NHCH(Bn)CONH2,Me,Ph,CH2OH,NHCOCONHPh),(NHCH(Bn)CONH2,Me,OH,Me,CONHPh),(NHCH(Bn)CONH2,Me,OH,Me,CONH-3-pyridyl),(NHCH(Bn)CONH2,Me,OH,Me,NHCOPh),(NHCH(Bn)CONH2,Me,OH,Me,NHCO-2-furyl),(NHCH(Bn)CONH2,Me,OH,Me,NHCONHPh),(NHCH(Bn)CONH2,Me,OH,Me,NHCOCONHPh),(NHCH(Bn)CONH2,Me,OH,Et,CONHPh),(NHCH(Bn)CONH2,Me,OH,Et,CONH-3-pyridyl),(NHCH(Bn)CONH2,Me,OH,Et,NHCOPh),(NHCH(Bn)CONH2,Me,OH,Et,NHCO-2-furyl),(NHCH(Bn)CONH2,Me,OH,Et,NHCONHPh),(NHCH(Bn)CONH2,Me,OH,Et,NHCOCONHPh),(NHCH(Bn)CONH2,Me,OH,CH2OH,CONHPh),(NHCH(Bn)CONH2,Me,OH,CH2OH,CONH-3-pyridyl),(NHCH(Bn)CONH2,Me,OH,CH2OH,NHCOPh),(NHCH(Bn)CONH2,Me,OH,CH2OH,NHCO-2-furyl),(NHCH(Bn)CONH2,Me,OH,CH2OH,NHCONHPh),(NHCH(Bn)CONH2,Me,OH,CH2OH,NHCOCONHPh),(NHCH(Bn)CONH2,Ph,H,Me,CONHPh),(NHCH(Bn)CONH2,Ph,H,Me,CONH-3-pyridyl),(NHCH(Bn)CONH2,Ph,H,Me,NHCOPh),(NHCH(Bn)CONH2,Ph,H,Me,NHCO-2-furyl),(NHCH(Bn)CONH2,Ph,H,Me,NHCONHPh),(NHCH(Bn)CONH2,Ph,H,Me,NHCOCONHPh),(NHCH(Bn)CONH2,Ph,H,Et,CONHPh),(NHCH(Bn)CONH2,Ph,H,Et,CONH-3-pyridyl),(NHCH(Bn)CONH2,Ph,H,Et,NHCOPh),(NHCH(Bn)CONH2,Ph,H,Et,NHCO-2-furyl),(NHCH(Bn)CONH2,Ph,H,Et,NHCONHPh),(NHCH(Bn)CONH2,Ph,H,Et,NHCOCONHPh),(NHCH(Bn)CONH2,Ph,H,CH2OH,CONHPh),(NHCH(Bn)CONH2,Ph,H,CH2OH,CONH-3-pyridyl),(NHCH(Bn)CONH2,Ph,H,CH2OH,NHCOPh),(NHCH(Bn)CONH2,Ph,H,CH2OH,NHCO-2-furyl),(NHCH(Bn)CONH2,Ph,H,CH2OH,NHCONHPh),(NHCH(Bn)CONH2,Ph,H,CH2OH,NHCOCONHPh),(NHCH(Bn)CONH2,Ph,Me,Me,CONHPh),(NHCH(Bn)CONH2,Ph,Me,Me,CONH-3-pyridyl),(NHCH(Bn)CONH2,Ph,Me,Me,NHCOPh),(NHCH(Bn)CONH2,Ph,Me,Me,NHCO-2-furyl),(NHCH(Bn)CONH2,Ph,Me,Me,NHCONHPh),(NHCH(Bn)CONH2,Ph,Me,Me,NHCOCONHPh),(NHCH(Bn)CONH2,Ph,Me,Et,CONHPh),(NHCH(Bn)CONH2,Ph,Me,Et,CONH-3-pyridyl),(NHCH(Bn)CONH2,Ph,Me,Et,NHCOPh),(NHCH(Bn)CONH2,Ph,Me,Et,NHCO-2-furyl),(NHCH(Bn)CONH2,Ph,Me,Et,NHCONHPh),(NHCH(Bn)CONH2,Ph,Me,Et,NHCOCONHPh),(NHCH(Bn)CONH2,Ph,Me,CH2OH,CONHPh),(NHCH(Bn)CONH2,Ph,Me,CH2OH,CONH-3-pyridyl),(NHCH(Bn)CONH2,Ph,Me,CH2OH,NHCOPh),(NHCH(Bn)CONH2,Ph,Me,CH2OH,NHCO-2-furyl),(NHCH(Bn)CONH2,Ph,Me,CH2OH,NHCONHPh),(NHCH(Bn)CONH2,Ph,Me,CH2OH,NHCOCONHPh),(NHCH(Bn)CONH2,Ph,Ph,Me,CONHPh),(NHCH(Bn)CONH2,Ph,Ph,Me,CONH-3-pyridyl),(NHCH(Bn)CONH2,Ph,Ph,Me,NHCOPh),(NHCH(Bn)CONH2,Ph,Ph,Me,NHCO-2-furyl),(NHCH(Bn)CONH2,Ph,Ph,Me,NHCONHPh),(NHCH(Bn)CONH2,Ph,Ph,Me,NHCOCONHPh),(NHCH(Bn)CONH2,Ph,Ph,Et,CONHPh),(NHCH(Bn)CONH2,Ph,Ph,Et,CONH-3-pyridyl),(NHCH(Bn)CONH2,Ph,Ph,Et,NHCOPh),(NHCH(Bn)CONH2,Ph,Ph,Et,NHCO-2-furyl),(NHCH(Bn)CONH2,Ph,Ph,Et,NHCONHPh),(NHCH(Bn)CONH2,Ph,Ph,Et,NHCOCONHPh),(NHCH(Bn)CONH2,Ph,Ph,CH2OH,CONHPh),(NHCH(Bn)CONH2,Ph,Ph,CH2OH,CONH-3-pyridyl),(NHCH(Bn)CONH2,Ph,Ph,CH2OH,NHCOPh),(NHCH(Bn)CONH2,Ph,Ph,CH2OH,NHCO-2-furyl),(NHCH(Bn)CONH2,Ph,Ph,CH2OH,NHCONHPh),(NHCH(Bn)CONH2,Ph,Ph,CH2OH,NHCOCONHPh),(NHCH(Bn)CONH2,Ph,OH,Me,CONHPh),(NHCH(Bn)CONH2,Ph,OH,Me,CONH-3-pyridyl),(NHCH(Bn)CONH2,Ph,OH,Me,NHCOPh),(NHCH(Bn)CONH2,Ph,OH,Me,NHCO-2-furyl),(NHCH(Bn)CONH2,Ph,OH,Me,NHCONHPh),(NHCH(Bn)CONH2,Ph,OH,Me,NHCOCONHPh),(NHCH(Bn)CONH2,Ph,OH,Et,CONHPh),(NHCH(Bn)CONH2,Ph,OH,Et,CONH-3-pyridyl),(NHCH(Bn)CONH2,Ph,OH,Et,NHCOPh),(NHCH(Bn)CONH2,Ph,OH,Et,NHCO-2-furyl),(NHCH(Bn)CONH2,Ph,OH,Et,NHCONHPh),(NHCH(Bn)CONH2,Ph,OH,Et,NHCOCONHPh),(NHCH(Bn)CONH2,Ph,OH,CH2OH,CONHPh),(NHCH(Bn)CONH2,Ph,OH,CH2OH,CONH-3-pyridyl),(NHCH(Bn)CONH2,Ph,OH,CH2OH,NHCOPh),(NHCH(Bn)CONH2,Ph,OH,CH2OH,NHCO-2-furyl),(NHCH(Bn)CONH2,Ph,OH,CH2OH,NHCONHPh),(NHCH(Bn)CONH2,Ph,OH,CH2OH,NHCOCONHPh),(NHCH(Me)CH2OH,H,H,Me,CONHPh),(NHCH(Me)CH2OH,H,H,Me,CONH-3-pyriclyl),(NHCH(Me)CH2OH,H,H,Me,NHCOPh),(NHCH(Me)CH2OH,H,H,Me,NHCO-2-furyl),(NHCH(Me)CH2OH,H,H,Me,NHCONHPh),(NHCH(Me)CH2OH,H,H,Me,NHCOCONHPh),(NHCH(Me)CH2OH,H,H,Et,CONHPh),(NHCH(Me)CH2OH,H,H,Et,CONH-3-pyridyl),(NHCH(Me)CH2OH,H,H,Et,NHCOPh),(NHCH(Me)CH2OH,H,H,Et,NHCO-2-furyl),(NHCH(Me)CH2OH,H,H,Et,NHCONHPh),(NHCH(Me)CH2OH,H,H,Et,NHCOCONHPh),(NHCH(Me)CH2OH,H,H,CH2OH,CONHPh),(NHCH(Me)CH2OH,H,H,CH2OH,CONH-3-pyridyl),(NHCH(Me)CH2OH,H,H,CH2OH,NHCOPh),(NHCH(Me)CH2OH,H,H,CH2OH,NHCO-2-furyl),(NHCH(Me)CH2OH,H,H,CH2OH,NHCONHPh),(NHCH(Me)CH2OH,H,H,CH2OH,NHCOCONHPh),(NHCH(Me)CH2OH,H,Me,Me,CONHPh),(NHCH(Me)CH2OH,H,Me,Me,CONH-3-pyridyl),(NHCH(Me)CH2OH,H,Me,Me,NHCOPh),(NHCH(Me)CH2OH,H,Me,Me,NHCO-2-furyl),(NHCH(Me)CH2OH,H,Me,Me,NHCONHPh),(NHCH(Me)CH2OH,H,Me,Me,NHCOCONHPh),(NHCH(Me)CH2OH,H,Me,Et,CONHPh),(NHCH(Me)CH2OH,H,Me,Et,CONH-3-pyridyl),(NHCH(Me)CH2OH,H,Me,Et,NHCOPh),(NHCH(Me)CH2OH,H,Me,Et,NHCO-2-furyl),(NHCH(Me)CH2OH,H,Me,Et,NHCONEPh),(NHCH(Me)CH2OH,H,Me,Et,NHCOCONHPh),(NHCH(Me)CH2OH,H,Me,CH2OH,CONHPh),(NHCH(Me)CH2OH,H,Me,CH2OH,CONH-3-pyridyl),(NHCH(Me)CH2OH,H,Me,CH2OH,NHCOPh),(NHCH(Me)CH2OH,H,Me,CH2OH,NHCO-2-furyl),(NHCH(Me)CH2OH,H,Me,CH2OH,NHCONHPh),(NHCH(Me)CH2OH,H,Me,CH2OH,NHCOCONHPh),(NHCH(Me)CH2OH,H,Ph,Me,CONHPh),(NHCH(Me)CH2OH,H,Ph,Me,CONH-3-pyridyl),(NHCH(Me)CH2OH,H,Ph,Me,NHCOPh),(NHCH(Me)CH2OH,H,Ph,Me,NHCO-2-furyl),(NHCH(Me)CH2OH,H,Ph,Me,NHCONHPh),(NHCH(Me)CH2OH,H,Ph,Me,NHCOCONHPh),(NHCH(Me)CH2OH,H,Ph,Et,CONHPh),(NHCH(Me)CH2OH,H,Ph,Et,CONH-3-pyridyl),(NHCH(Me)CH2OH,H,Ph,Et,NHCOPh),(NHCH(Me)CH2OH,H,Ph,Et,NHCO-2-furyl),(NHCH(Me)CH2OH,H,Ph,Et,NHCONHPh),(NHCH(Me)CH2OH,H,Ph,Et, NHCOCONHPh),(NHCH(Me)CH2OH,H,Ph,CH2OH,
CONHPh),(NHCH(Me)CH2OH,H,Ph,CH2OH,CONH-3-
pyridyl),(NHCH(Me)CH2OH,H,Ph,CH2OH,NHCOPh),
(NHCH(Me)CH2OH,H,Ph,CH2OH,NHCO-2-furyl),
(NHCH(Me)CH2OH,H,Ph,CH2OH,NHCONHPh),(NHCH
(Me)CH2OH,H,Ph,CH2OH,NHCOCONHPh),(NHCH(Me)
CH2OH,H,OH,Me,CONHPh),(NHCH(Me)CH2OH,H,OH,
Me,CONH-3-pyridyl),(NHCH(Me)CH2OH,H,OH,Me,
NHCOPh),(NHCH(Me)CH2OH,H,OH,Me,NHCO-2-furyl),
(NHCH(Me)CH2OH,H,OH,Me,NHCONHPh),(NHCH
(Me)CH2OH,H,OH,Me,NHCOCONHPh),(NHCH(Me)
CH2OH,H,OH,Et,CONHPh),(NHCH(Me)CH2OH,H,OH,
Et,CONH-3-pyridyl),(NHCH(Me)CH2OH,H,OH,Et,
NHCOPh),(NHCH(Me)CH2OH,H,OH,Et,NHCO-2-furyl),
(NHCH(Me)CH2OH,H,OH,Et,NHCONHPh),(NHCH(Me)
CH2OH,H,OH,Et,NHCOCONHPh),(NHCH(Me)CH2OH,
H,OH,CH2OH,CONHPh),(NHCH(Me)CH2OH,H,OH,
CH2OH,CONH-3-pyridyl),(NHCH(Me)CH2OH,H,OH,
CH2OH,NHCOPh),(NHCH(Me)CH2OH,H,OH,CH2OH,
NHCO-2-furyl),(NHCH(Me)CH2OH,H,OH,CH2OH,
NHCONHPh),(NHCH(Me)CH2OH,H,OH,CH2OH,
NHCOCONHPh),(NHCH(Me)CH2OH,Me,H,Me,
CONHPh),(NHCH(Me)CH2OH,Me,H,Me,CONH-3-
pyridyl),(NHCH(Me)CH2OH,Me,H,Me,NHCOPh),(NHCH
(Me)CH2OH,Me,H,Me,NHCO-2-furyl),(NHCH(Me)
CH2OH,Me,H,Me,NHCONHPh),(NHCH(Me)CH2OH,Me,
H,Me,NHCOCONHPh),(NHCH(Me)CH2OH,Me,H,Et,
CONHPh),(NHCH(Me)CH2OH,Me,H,Et,CONH-3-
pyridyl),(NHCH(Me)CH2OH,Me,H,Et,NHCOPh),(NHCH
(Me)CH2OH,Me,H,Et,NHCO-2-furyl),(NHCH(Me)
CH2OH,Me,H,Et,NHCONHPh),(NHCH(Me)CH2OH,Me,
H,Et,NHCOCONHPh),(NHCH(Me)CH2OH,Me,H,
CH2OH,CONHPh),(NHCH(Me)CH2OH,Me,H,CH2OH,
CONH-3-pyridyl),(NHCH(Me)CH2OH,Me,H,CH2OH,
NHCOPh),(NHCH(Me)CH2OH,Me,H,CH2OH,NHCO-2-
furyl),(NHCH(Me)CH2OH,Me,H,CH2OH,NHCONHPh),
(NHCH(Me)CH2OH,Me,H,CH2OH,NHCOCONHPh),
(NHCH(Me)CH2OH,Me,Me,Me,CONHPh),(NHCH(Me)
CH2OH,Me,Me,Me,CONH-3-pyridyl),(NHCH(Me)
CH2OH,Me,Me,Me,NHCOPh),(NHCH(Me)CH2OH,Me,
Me,Me,NHCO-2-furyl),(NHCH(Me)CH2OH,Me,Me,Me,
NHCONHPh),(NHCH(Me)CH2OH,Me,Me,Me,
NHCOCONHPh),(NHCH(Me)CH2OH,Me,Me,Et,
CONHPh),(NHCH(Me)CH2OH,Me,Me,Et,CONH-3-
pyridyl),(NHCH(Me)CH2OH,Me,Me,Et,NHCOPh),
(NHCH(Me)CH2OH,Me,Me,Et,NHCO-2-furyl),(NHCH
(Me)CH2OH,Me,Me,Et,NHCONHPh),(NHCH(Me)
CH2OH,Me,Me,Et,NHCOCONHPh),(NHCH(Me)CH2OH,
Me,Me,CH2OH,CONHPh),(NHCH(Me)CH2OH,Me,Me,
CH2OH,CONH-3-pyridyl),(NHCH(Me)CH2OH,Me,Me,
CH2OH,NHCOPh),(NHCH(Me)CH2OH,Me,Me,CH2OH,
NHCO-2-furyl),(NHCH(Me)CH2OH,Me,Me,CH2OH,
NHCONHPh),(NHCH(Me)CH2OH,Me,Me,CH2OH,
NHCOCONHPh),(NHCH(Me)CH2OH,Me,Ph,Me,
CONHPh),(NHCH(Me)CH2OH,Me,Ph,Me,CONH-3-
pyridyl),(NHCH(Me)CH2OH,Me,Ph,Me,NHCOPh),
(NHCH(Me)CH2OH,Me,Ph,Me,NHCO-2-furyl),(NHCH
(Me)CH2OH,Me,Ph,Me,NHCONHPh),(NHCH(Me)
CH2OH,Me,Ph,Me,NHCOCONHPh),(NHCH(Me)
CH2OH,Me,Ph,Et,CONHPh),(NHCH(Me)CH2OH,Me,Ph,
Et,CONH-3-pyridyl),(NHCH(Me)CH2OH,Me,Ph,Et,
NHCOPh),(NHCH(Me)CH2OH,Me,Ph,Et,NHCO-2-furyl),
(NHCH(Me)CH2OH,Me,Ph,Et,NHCONHPh),(NHCH(Me)
CH2OH,Me,Ph,Et,NHCOCONHPh),(NHCH(Me)CH2OH,
Me,Ph,CH2OH,CONHPh),(NHCH(Me)CH2OH,Me,Ph,
CH2OH,CONH-3-pyridyl),(NHCH(Me)CH2OH,Me,Ph,
CH2OH,NHCOPh),(NHCH(Me)CH2OH,Me,Ph,CH2OH,
NHCO-2-furyl),(NHCH(Me)CH2OH,Me,Ph,CH2OH,
NHCONHPh),(NHCH(Me)CH2OH,Me,Ph,CH2OH,
NHCOCONHPh),(NHCH(Me)CH2OH,Me,OH,Me,
CONHPh),(NHCH(Me)CH2OH,Me,OH,Me,CONH-3-
pyridyl),(NHCH(Me)CH2OH,Me,OH,Me,NHCOPh),
(NHCH(Me)CH2OH,Me,OH,Me,NHCO-2-furyl),(NHCH
(Me)CH2OH,Me,OH,Me,NHCONHPh),(NHCH(Me)
CH2OH,Me,OH,Me,NHCOCONHPh),(NHCH(Me)
CH2OH,Me,OH,Et,CONHPh),(NHCH(Me)CH2OH,Me,
OH,Et, CONH-3-pyridyl),(NHCH(Me)CH2OH,Me,OH,Et,
NHCOPh),(NHCH(Me)CH2OH,Me,OH,Et,NHCO-2-
furyl),(NHCH(Me)CH2OH,Me,OH,Et,NHCONHPh),
(NHCH(Me)CH2OH,Me,OH,Et,NHCOCONHPh),(NHCH
(Me)CH2OH,Me,OH,CH2OH,CONHPh),(NHCH(Me)
CH2OH,Me,OH,CH2OH,CONH-3-pyridyl),(NHCH(Me)
CH2OH,Me,OH,CH2OH,NHCOPh),(NHCH(Me)CH2OH,
Me,OH,CH2OH,NHCO-2-furyl),(NHCH(Me)CH2OH,Me,
OH,CH2OH,NHCONHPh),(NHCH(Me)CH2OH,Me,OH,
CH2OH,NHCOCONHPh),(NHCH(Me)CH2OH,Ph,H,Me,
CONHPh),(NHCH(Me)CH2OH,Ph,H,Me,CONH-3-
pyridyl),(NHCH(Me)CH2OH,Ph,H,Me,NHCOPh),(NHCH
(Me)CH2OH,Ph,H,Me,NHCO-2-furyl),(NHCH(Me)
CH2OH,Ph,H,Me,NHCONHPh),(NHCH(Me)CH2OH,Ph,
H,Me,NHCOCONHPh),(NHCH(Me)CH2OH,Ph,H,Et,
CONHPh),(NHCH(Me)CH2OH,Ph,H,Et,CONH-3-
pyridyl),(NHCH(Me)CH2OH,Ph,H,Et,NHCOPh),(NHCH
(Me)CH2OH,Ph,H,Et,NHCO-2-furyl),(NHCH(Me)
CH2OH,Ph,H,Et,NHCONHPh),(NHCH(Me)CH2OH,H,Et,
NHCOCONHPh),(NHCH(Me)CH2OH,Ph,H,CH2OH,
CONHPh),(NHCH(Me)CH2OH,Ph,H,CH2OH,CONH-3-
pyridyl),(NHCH(Me)CH2OH,Ph,H,CH2OH,NHCOPh),
(NHCH(Me)CH2OH,Ph,H,CH2OH,NHCO-2-furyl),
(NHCH(Me)CH2OH,Ph,H,CH2OH,NHCONHPh),(NHCH
(Me)CH2OH,Ph,H,CH2OH,NHCOCONHPh),(NHCH(Me)
CH2OH,Ph,Me,Me,CONHPh),(NHCH(Me)CH2OH,Ph,
Me,Me,CONH-3-pyridyl),(NHCH(Me)CH2OH,Ph,Me,Me,
NHCOPh),(NHCH(Me)CH2OH,Ph,Me,Me,NHCO-2-
furyl),(NHCH(Me)CH2OH,Ph,Me,Me,NHCONHPh),
(NHCH(Me)CH2OH,Ph,Me,Me,NHCOCONHPh),(NHCH
(Me)CH2OH,Ph,Me,Et,CONHPh),(NHCH(Me)CH2OH,
Ph,Me,Et,CONH-3-pyridyl),(NHCH(Me)CH2OH,Ph,Me,
Et,NHCOPh),(NHCH(Me)CH2OH,Ph,Me,Et,NHCO-2-
furyl),(NHCH(Me)CH2OH,Ph,Me,Et,NHCONHPh),
(NHCH(Me)CH2OH,Ph,Me,Et,NHCOCONHPh),(NHCH
(Me)CH2OH,Ph,Me,CH2OH,CONHPh),(NHCH(Me)
CH2O H,Ph,Me,CH2OH,CONH-3-pyridyl),(NHCH(Me)
CH2OH,Ph,Me,CH2OH,NHCOPh),(NHCH(Me)CH2OH,
Ph,Me,CH2OH,NHCO-2-furyl),(NHCH(Me)CH2OH,Ph,
Me,CH2OH,NHCONHPh),(NHCH(Me)CH2OH,Ph,Me,
CH2OH,NHCOCONHPh),(NHCH(Me)CH2OH,Ph,Ph,Me,
CONHPh),(NHCH(Me)CH2OH,Ph,Ph,Me,CONH-3-
pyridyl),(NHCH(Me)CH2OH,Ph,Ph,Me,NHCOPh),
(NHCH(Me)CH2OH,Ph,Ph,Me,NHCO-2-furyl),(NHCH
(Me)CH2OH,Ph,Ph,Me,NHCONHPh),(NHCH(Me)
CH2OH,Ph,Ph,Me,NHCOCONHPh),(NHCH(Me)CH2OH,
Ph,Ph,Et,CONHPh),(NHCH(Me)CH2OH,Ph,Ph,Et,CONH-
3-pyridyl),(NHCH(Me)CH2OH,Ph,Ph,Et,NHCOPh),
(NHCH(Me)CH2OH,Ph,Ph,Et,NHCO-2-furyl),(NHCH
(Me)CH2OH,Ph,Ph,Et,NHCONHPh),(NHCH(Me)CH2OH,
Ph,Et,NHCOCONHPh),(NHCH(Me)CH2OH,Ph,Ph,
CH2OH, CONHPh),(NHCH(Me)CH2OH,Ph,Ph,CH2OH,
CONH-3-pyridyl),(NHCH(Me)CH2OH,Ph,Ph,CH2OH,
NHCOPh),(NHCH(Me)CH2OH,Ph,Ph,CH2OH,NHCO-2-
furyl),(NHCH(Me)CH2OH,Ph,Ph,CH2OH,NHCONHPh),
(NHCH(Me)CH2OH,Ph,Ph,CH2OH,NHCOCONHPh),
(NHCH(Me)CH2OH,Ph,OH,Me,CONHPh),(NHCH(Me)
CH2OH,Ph,OH,Me,CONH-3-pyridyl),(NHCH(Me)

CH2OH,Ph,OH,Me,NHCOPh),(NHCH(Me)CH2OH,Ph, OH,Me,NHCO-2-furyl),(NHCH(Me)CH2OH,Ph,OH,Me, NHCONHPh),(NHCH(Me)CH2OH,Ph,OH,Me, NHCOCONHPh),(NHCH(Me)CH2OH,Ph,OH,Et, CONHPh),(NHCH(Me)CH2OH,Ph,OH,Et,CONH-3-pyridyl),(NHCH(Me)CH2OH,Ph,OH,Et,NHCOPh),(NHCH(Me)CH2OH,Ph,OH,Et,NHCO-2-furyl),(NHCH(Me)CH2OH,Ph,OH,Et,NHCONHPh),(NHCH(Me)CH2OH,Ph,OH,Et,NHCOCONHPh),(NHCH(Me)CH2OH,Ph,OH,CH2OH,CONHPh),(NHCH(Me)CH2OH,Ph,OH,CH2OH,CONH-3-pyridyl),(NHCH(Me)CH2OH,Ph,OH,CH2OH,NHCOPh),(NHCH(Me)CH2OH,Ph,OH,CH2OH,NHCO-2-furyl),(NHCH(Me)CH2OH,Ph,OH,CH2OH,NHCONHPh),(NHCH(Me)CH2OH,Ph,OH,CH2OH,NHCOCONHPh),(NHCH(Me)CONHMe,H,H,Me,CONHPh),(NHCH(Me)CONHMe,H,H,Me,CONH-3-pyridyl),(NHCH(Me)CONHMe,H,H,Me,NHCOPh),(NHCH(Me)CONHMe,H,H,Me,NHCO-2-furyl),(NHCH(Me)CONHMe,H,H,Me,NHCONHPh),(NHCH(Me)CONHMe,H,H,Me,NHCOCONHPh),(NHCH(Me)CONHMe,H,H,Et,CONHPh),(NHCH(Me)CONHMe,H,H,Et,CONH-3-pyridl),(NHCH(Me)CONHMe,H,H,Et,NHCOPh),(NHCH(Me)CONHMe,H,H,Et,NHCO-2-furyl),(NHCH(Me)CONHMe,H,H,Et,NHCONHPh),(NHCH(Me)CONHMe,H,H,Et,NHCOCONHPh),(NHCH(Me)CONHMe,H,H,CH2OH,CONHPh),(NHCH(Me)CONHMe,H,H,CH2OH,CONH-3-pyridyl),(NHCH(Me)CONHMe,H,H,CH2OH,NHCOPh),(NHCH(Me)CONHMe,H,H,CH2OH,NHCO-2-furyl),(NHCH(Me)CONHMe,H,H,CH2OH,NHCONHPh),(NHCH(Me)CONHMe,H,H,CH2OH,NHCOCONHPh),(NHCH(Me)CONHMe,H,Me,Me,CONHPh),(NHCH(Me)CONHMe,H,Me,Me,CONH-3-pyridyl),(NHCH(Me)CONHMe,H,Me,Me,NHCOPh),(NHCH(Me)CONHMe,H,Me,Me,NHCO-2-furyl),(NHCH(Me)CONHMe,H,Me,Me,NHCONHPh),(NHCH(Me)CONHMe,H,Me,Me,NHCOCONHPh),(NHCH(Me)CONHMe,H,Me,Et,CONHPh),(NHCH(Me)CONHMe,H,Me,Et,CONH-3-pyridyl),(NHCH(Me)CONHMe,H,Me,Et,NHCOPh),(NHCH(Me)CONHMe,H,Me,Et,NHCO-2-furyl),(NHCH(Me)CONHMe,H,Me,Et,NHCONHPh),(NHCH(Me)CONHMe,H,Me,Et,NHCOCONHPh),(NHCH(Me)CONHMe,H,Me,CH2OH,CONHPh),(NHCH(Me)CONHMe,H,Me,CH2OH,CONH-3-pyridyl),(NHCH(Me)CONHMe,H,Me,CH2OH,NHCOPh),(NHCH(Me)CONHMe,H,Me,CH2OH,NHCO-2-furyl),(NHCH(Me)CONHMe,H,Me,CH2OH,NHCONHPh),(NHCH(Me)CONHMe,H,Me,CH2OH,NHCOCONHPh),(NHCH(Me)CONHMe,H,Ph,Me,CONHPh),(NHCH(Me)CONHMe,H,Ph,Me,CONH-3-pyridyl),(NHCH(Me)CONHMe,H,Ph,Me,NHCOPh),(NHCH(Me)CONHMe,H,Ph,Me,NHCO-2-furyl),(NHCH(Me)CONHMe,H,Ph,Me,NHCONHPh),(NHCH(Me)CONHMe,H,Ph,Me,NHCOCONHPh),(NHCH(Me)CONHMe,H,Ph,Et,CONHPh),(NHCH(Me)CONHMe,H,Ph,Et,CONH-3-pyridyl),(NHCH(Me)CONHMe,H,Ph,Et,NHCOPh),(NHCH(Me)CONHMe,H,Ph,Et,NHCO-2-furyl),(NHCH(Me)CONHMe,H,Ph,Et,NHCONHPh),(NHCH(Me)CONHMe,H,Ph,Et,NHCOCONHPh),(NHCH(Me)CONHMe,H,Ph,CH2OH,CONHPh),(NHCH(Me)CONHMe,H,Ph,CH2OH,CONH-3-pyridyl),(NHCH(Me)CONHMe,H,Ph,CH2OH,NHCOPh),(NHCH(Me)CONHMe,H,Ph,CH2OH,NHCO-2-furyl),(NHCH(Me)CONHMe,H,Ph,CH2OH,NHCONHPh),(NHCH(Me)CONHMe,H,Ph,CH2OH,NHCOCONHPh),(NHCH(Me)CONHMe,H,OH,Me,CONHPh),(NHCH(Me)CONHMe,H,OH,Me,CONH-3-pyridyl),(NHCH(Me)CONHMe,H,OH,Me,NHCOPh),(NHCH(Me)CONHMe,H,OH,Me,NHCO-2-furyl),(NHCH(Me)CONHMe,H,OH,Me,NHCONHPh),(NHCH(Me)CONHMe,H,OH,Me,NHCOCONHPh),(NHCH(Me)CONHMe,H,OH,Et,CONHPh),(NHCH(Me)CONHMe,H,OH,Et,CONH-3-pyridyl),(NHCH(Me)CONHMe,H,OH,Et,NHCOPh),(NHCH(Me)CONHMe,H,OH,Et,NHCO-2-furyl),(NHCH(Me)CONHMe,H,OH,Et,NHCONHPh),(NHCH(Me)CONHMe,H,OH,Et,NHCOCONHPh),(NHCH(Me)CONHMe,H,OH,CH2OH,CONHPh),(NHCH(Me)CONHMe,H,OH,CH2OH,CONH-3-pyridyl),(NHCH(Me)CONHMe,H,OH,CH2OH,NHCOPh),(NHCH(Me)CONHMe,H,OH,CH2OH,NHCO-2-furyl),(NHCH(Me)CONHMe,H,OH,CH2OH,NHCONHPh),(NHCH(Me)CH,OH,CH2OH,NHCOCONHPh),(NHCH(Me)CONHMe,Me,H,Me,CONHPh),(NHCH(Me)CONHMe,Me,H,Me,CONH-3-pyridyl),(NHCH(Me)CONHMe,Me,H,Me,NHCOPh),(NHCH(Me)CONHMe,Me,H,Me,NHCO-2-furyl),(NHCH(Me)CONHMe,Me,H,Me,NHCONHPh),(NHCH(Me)CONHMe,Me,H,Me,NHCOCONHPh),(NHCH(Me)CONHMe,Me,H,Et,CONHPh),(NHCH(Me)CONHMe,Me,H,Et,CONH-3-pyridyl),(NHCH(Me)CONHMe,Me,H,Et,NHCOPh),(NHCH(Me)CONHMe,Me,H,Et,NHCO-2-furyl),(NHCH(Me)CONHMe,Me,H,Et,NHCONHPh),(NHCH(Me)CONHMe,Me,H,Et,NHCOCONHPh),(NHCH(Me)CONHMe,Me,H,CH2OH,CONHPh),(NHCH(Me)CONHMe,Me,H,CH2OH,CONH-3-pyridyl),(NHCH(Me)CONHMe,Me,H,CH2OH,NHCOPh),(NHCH(Me)CONHEMe,Me,H,CH2OH,NHCO-2-furyl),(NHCH(Me)CONHMe,Me,H,CH2OH,NHCONHPh),(NHCH(Me)CONHMe,Me,H,CH2OH,NHCOCONHPh),(NHCH(Me)CONHMe,Me,Me,Me,CONHPh),(NHCH(Me)CONHMe,Me,Me,Me,CONH-3-pyridyl),(NHCH(Me)CONHMe,Me,Me,Me,NHCOPh),(NHCH(Me)CONHMe,Me,Me,Me,NHCO-2-furyl),(NHCH(Me)CONHMe,Me,Me,Me,NHCONHPh),(NHCH(Me)CONHMe,Me,Me,Me,NHCOCONHPh),(NH CH(Me)CONHMe,Me,Me,Et,CONHPh),(NHCH(Me)CONHMe,Me,Me,Et,CONH-3-pyridyl),(NHCH(Me)CONHMe,Me,Me,Et,NHCOPh),(NHCH(Me)CONHMe,Me,Me,Et,NHCO-2-furyl),(NHCH(Me)CONHMe,Me,Me,Et,NHCONHPh),(NHCH(Me)CONHMe,Me,Me,Et,NHCOCONHPh),(NHCH(Me)CONHMe,Me,Me,CH2OH,CONHPh),(NHCH(Me)CONHMe,Me,Me,CH2OH,CONH-3-pyridyl),(NHCH(Me)CONHMe,Me,Me,CH2OH,NHCOPh),(NHCH(Me)CONHMe,Me,Me,CH2OH,NHCO-2-furyl),(NHCH(Me)CONHMe,Me,Me,CH2 OH,NHCONHPh),(NHCH(Me)CONHMe,Me,Me,CH2OH,NHCOCONHPh),(NHCH(Me)CONHMe,Me,Ph,Me,CONHPh),(NHCH(Me)CONHMe,Me,Ph,Me,CONH-3-pyridyl),(NHCH(Me)CONHMe,Me,Ph,Me,NHCOPh),(NHCH(Me)CONHMe,Me,Ph,Me,NHCO-2-furyl),(NHCH(Me)CONHMe,Me,Ph,Me,NHCONHPh),(NHCH(Me)CONHMe,Me,Ph,Me,NHCOCONHPh),(NHCH(Me)CONHMe,Me,Ph,Et,CONHPh),(NHCH(Me)CONHMe,Me,Ph,Et,CONH-3-pyridyl),(NHCH(MeCH(Me)CONHMe,Me,Ph,Et,NHCOPh),(NHCH(Me)CONHMe,Me,Ph,Et,NHCO-2-furyl),(NHCH(Me)CONHMe,Me,Ph,Et,NHCONHPh),(NHCH(Me)CONMe,Me,Ph,Et,NHCOCONHPh),(NHCH(Me)CONHMe,Me,Ph,CH2OH,CONHPh),(NHCH(Me)CONHMe,Me,Ph,CH2OH,CONH-3-pyridyl),(NHCH(Me)CONHMe,Me,Ph,CH2OH,NHCOPh),(NHCH(Me)CONHMe,Me,Ph,CH2OH,NHCO-2-furyl),(NHCH(Me)CONHMe,Me,Ph,CH2OH,NHCONHPh),(NHCH(Me)CONHMe,Me,Ph,CH2OH,NHCOCONHPh),(NHCH(Me)CONEMe,Me,OH,Me,CONHPh),(NHCH(Me)CONHMe,Me,OH,Me,CONH-3-pyridyl),(NHCH(Me)CONHMe,Me,OH,Me,NHCOPh),(NHCH(Me)CONHMe,Me,OH,Me,NHCO-2-furyl),(NHCH(Me)CONHMe,Me,OH,Me, NHCONHPh),(NHCH(Me)CONHMe,Me,OH,Me,NHCO-CONHPh),(NHCH(Me)CONHMe,Me,OH,Et,CONHPh),(NHCH(Me)CONHMe,Me,OH,Et,CONH-3-pyridyl),(NHCH(Me)CONHMe,Me,OH,Et,NHCOPh),(NHCH(Me)CONBMe,Me,OH,Et,NHCO-2-furyl),(NHCH(Me)CONHMe,Me,OH,Et,NHCONHPh),(NHCH(Me)CONHMe,Me,OH,Et,NHCOCONHPh),(NHCH(Me)CONHMe,Me,OH,CH2OH,CONHPh),(NHCH(Me)CONHMe,Me,OH,CH2OH,CONH-3-pyridyl),(NHCH(Me)CONHMe,Me,OH,CH2OH,NHCOPh),(NHCH(CH(Me)CONHMe,Me,OH,CH2OH,NHCO-2-furyl),(NHCH(Me)CONHMe,Me,OH,CH2OH,NHCONHPh),(NHCH(Me)CONHMe,Me,OH,CH2OH,NHCOCONHPh),(NHCH(CH(Me)CONHMe,Ph,H,Me,CONHPh),(NHCH(Me)CONHMe,Ph,H,Me,CONH-3-pyridyl),(NHCH(Me)CONHMe,Ph,H,Me,NHCOPh),(NHCH(Me)CONHMe,Ph,H,Me,NHCO-2-furyl),(NHCH(Me)CONHMe,Ph,H,Me,NHCONHPh),(NHCH(Me)CONHMe,Ph,H,Me,NHCOCONHPh),(NHCH(Me)CONHMe,Ph,H,Et,CONHPh),(NHCH(Me)CONHMe,Ph,H,Et,CONH-3-pyridyl),(NHCH(Me)CONHMe,Ph,H,Et,NHCOPh),(NHCH(Me)CONHMe,Ph,H,Et,NHCO-2-furyl),(NHCH(Me) CONHMe,Ph,H,Et,NHCONHPh),(NHCH(Me)CONHMe,Ph,H,Et,NHCOCONHPh),(NHCH(Me)CONHMe,Ph,H,CH2OH, CONHPh),(NHCH(Me)CONHMe,Ph,H,CH2OH,CONH-3-pyridyl),(NHCH(Me)CONHMe,Ph,H,CH2OH,NHCOPh),(NHCH(Me)CONHMe,Ph,H,CH2OH,NHCO-2-furyl),(NHCH(Me)CONHMe,Ph,H,CH2OH,NHCONHPh),(NHCH(Me)CONHMe,Ph,H,CH2OH,NHCOCONHPh),(NHCH(Me)CONHMe,Ph,Me,Me,CONHPh),(NHCH(Me)CONHMe,Ph,Me,Me,CONH-3-pyridyl),(NHCH(Me)CONHMe,Ph,Me,Me,NHCOPh),(NHCH(Me)CONHMe,Ph,Me,Me,NHCO-2-furyl),(NHCH(Me)CONHMe,Ph,Me,Me,NHCONHPh),(NHCH(Me)CONHMe,Ph,Me,Me,NHCOCONHPh),(NHCH(Me)CONHMe,Ph,Me,Et,CONHPh),(NHCH(Me)CONHMe,Ph,Me,Et,CONH-3-pyridyl),(NHCH(Me)CONHMe,Ph,Me,Et,NHCOPh),(NHCH(Me)CONHMe,Ph,Me,Et,NHCO-2-furyl),(NHCH(Me)CONHMe,Ph,Me,Et,NHCONHPh),(NHCH(Me)CONHMe,Ph,Me,Et,NHCOCONHPh),(NHCH(Me)CONHMe,Ph,Me,CH2OH,CONHPh),(NHCH(Me)CONHMe,Ph,Me,CH2OH,CONH-3-pyridyl),(NHCH(Me)CONHMe,Ph,Me,CH2OH,NHCOPh),(NHCH(Me)CONHMe,Ph,Me,CH2OH,NHCO-2-furyl),(NHCH(Me)CONHMe,Ph,Me,CH2OH,NHCONHPh),(NHCH(Me)CONHMe,Ph,Me,CH2OH,NHCOCONHPh),(NHCH(Me)CONHMe,Ph,Ph,Me,CONHPh),(NHCH(Me)CONHMe,Ph,Ph,Me,CONH-3-pyridyl),(NHCH(Me)CONHMe,Ph,Ph,Me,NHCOPh),(NHCH(Me)CONHMe,Ph,Ph,Me,NHCO-2-furyl),(NHCH(Me)CONHMe,Ph,Ph,Me,NHCONHPh),(NHCH(Me)CONHMe,Ph,Ph,Me,NHCOCONHPh),(NHCH(Me)CONHMe,Ph,Ph,Et,CONHPh),(NHCH(Me)CONHMe,Ph,Ph,Et,CONH-3-pyridyl),(NHCH(Me)CONHMe,Ph,Ph,Et,NHCOPh),(NHCH(Me)CONHMe,Ph,Ph,Et,NHCO-2-furyl),(NHCH(Me)CONHMe,Ph,Ph,Et,NHCONHPh),(NHCH(Me)CONHMe,Ph,Ph,Et,NHCOCONHPh),(NHCH(Me)CONHMe,Ph,Ph,CH2OH,CONHPh),(NHCH(Me)CONHMe,Ph,Ph,CH2OH,CONH-3-pyridyl),(NHCH(Me)CONHMe,Ph,Ph,CH2OH,NHCOPh),(NHCH(Me)CONHMe,Ph,Ph,CH2OH,NHCO-2-furyl),(NHCH(Me)CONHMe,Ph,Ph,CH2OH,NHCONHPh),(NHCH(Me)CONHMe,Ph,Ph,CH2OH,NHCOCONHPh),(NHCH(Me)CONHMe,Ph,OH,Me,CONHPh),(NHCH(Me)CONHMe,Ph,OH,Me,CONH-3-pyridyl),(NHCH(Me)CONMe,Ph,OH,Me,NHCOPh),(NHCH(Me)CONHMe,Ph,OH,Me,NHCO-2-furyl),(NHCH(Me)CONHMe,Ph,OH,Me,NHCONHPh),(NHCH(Me)CONHMe,Ph,OH,Me,NHCOCONHPh),(NHCH(Me)CONHMe,Ph,OH,Et,CONHPh),(NHCH(Me)CONHMe,Ph,OH,Et,CONH-3-pyridyl),(NHCH(Me)CONHMe,Ph,OH,Et,NHCOPh),(NHCH(Me)CONHMe,Ph,OH,Et,NHCO-2-furyl),(NHCH(Me)CONHMe,Ph,OH,Et,NHCONHPh),(NHCH(Me)CONHMe,Ph,OH,Et,NHCOCONHPh),(NHCH(Me)CONHMe,Ph,OH,CH2OH,CONHPh),(NHCH(Me)CONMe,Ph,OH,CH2OH,CONH-3-pyridyl),(NHCH(Me)CONHMe,Ph,OH,CH2OH,NHCOPh),(NHCH(Me)CONHMe,Ph,OH,CH2OH,NHCO-2-furyl),(NHCH(Me)CONHMe,Ph,OH,CH2OH,NHCONHPh),(NHCH(Me)CONHMe,Ph,OH,CH2OH,NHCOCONHPh),(NHCOCH(iPr)OH,H,H,Me,CONHPh),(NHCOCH(iPr)OH,H,H,Me,CONH-3-pyridyl),(NHCOCH(iPr)OH,H,H,Me,NHCOPh),(NHCOCH(iPr)OH,H,H,Me,NHCO-2-furyl),(NHCOCH(iPr)OH,H,H,Me,NHCONHPh),(NHCOCH(iPr)OH,H,H,Me,NHCOCONHPh),(NHCOCH(iPr)OH,H,H,Et,CONHPh),(NHCOCH(iPr)OH,H,H,Et,CONH-3-pyridyl),(NHCOCH(iPr)OH,H,H,Et,NHCOPh),(NHCOCH(iPr)OH,H,H,Et,NHCO-2-furyl),(NHCOCH(iPr)OH,H,H,Et,NHCONHPh),(NHCOCH(iPr)OH,H,H,Et,NHCOCONHPh),(NHCOCH(iPr)OH,H,H,CH2OH,CONHPh),(NHCOCH(iPr)OH,H,H,CH2OH,CONH-3-pyridyl),(NHCOCH(iPr)OH,H,H,CH2OH,NHCOPh),(NHCOCH(iPr)OH,H,H,CH2OH,NHCO-2-furyl),(NHCOCH(iPr)OH,H,H,CH2OH,NHCONHPh),(NHCOCH(iPr)OH,H,H,CH2OH,NHCOCONHPh),(NHCOCH(iPr)OH,H,Me,Me,CONHPh),(NHCOCH(iPr)OH,H,Me,Me,CONH-3-pyridyl),(NHCOCH(iPr)OH,H,Me,Me,NHCOPh),(NHCOCH(iPr)OH,H,Me,Me,NHCO-2-furyl),(NHCOCH(iPr)OH,H,Me,Me,NHCONHPh),(NHCOCH(iPr)OH,H,Me,Me,NHCOCONHPh),(NHCOCH(iPr)OH,H,Me,Et, CONHPh),(NHCOCH(iPr)OH,H,Me,Et,CONH-3-pyridyl),(NHCOCH(iPr)OH,H,Me,Et,NHCOPh),(NHCOCH(iPr)OH,H,Me,Et,NHCO-2-furyl),(NHCOCH(iPr)OH,H,Me,Et,NHCONHPh),(NHCOCH(iPr)OH,H,Me,Et,NHCOCONHPh),(NHCOCH(iPr)OH,H,Me,CH2OH,CONHPh),(NHCOCH(iPr)OH,H,Me,CH2OH,CONH-3-pyridyl),(NHCOCH(iPr)OH,H,Me,CH2OH,NHCOPh),(NHCOCH(iPr)OH,H,Me,CH2OH,NHCO-2-furyl),(NHCOCH(iPr)OH,H,Me,CH2OH,NHCONHPh),(NHCOCH(iPr)OH,H,Me,CH2OH,NHCOCONHPh),(NHCOCH(iPr)OH,H,Ph,Me,CONHPh),(NHCOCH(iPr)OH,H,Ph,Me,CONH-3-pyridyl),(NHCOCH(iPr)OH,H,Ph,Me,NHCOPh),(NHCOCH(iPr)OH,H,Ph,Me,NHCO-2-furyl),(NHCOCH(iPr)OH,H,Ph,Me,NHCONHPh),(NHCOCH(iPr)OH,H,Ph,Me,NHCOCONHPh),(NHCOCH(iPr)OH,H,Ph,Et,CONHPh),(NHCOCH(iPr)OH,H,Ph,Et,CONH-3-pyridyl),(NHCOCH(iPr)OH,H,Ph,Et,NHCOPh),(NHCOCH(iPr)OH,H,Ph,Et,NHCO-2-furyl),(NHCOCH(iPr)OH,H,Ph,Et,NHCONHPh),(NHCOCH(iPr)OH,H,Ph,Et,NHCOCONHPh),(NHCOCH(iPr)OH,H,Ph,CH2OH,CONHPh),(NHCOCH(iPr)OH,H,Ph,CH2OH,CONH-3-pyridyl),(NHCOCH(iPr)OH,H,Ph,CH2OH,NHCOPh),(NHCOCH(iPr)OH,H,Ph,CH2OH,NHCO-2-furyl),(NHCOCH(iPr)OH,H,Ph,CH2OH,NHCONHPh),(NHCOCH(iPr)OH,H,Ph,CH2OH,NHCOCONHPh),(NHCOCH(iPr)OH,H,OH,Me,CONHPh),(NHCOCH(iPr)OH,H,OH,Me, CONH-3-pyridyl),(NHCOCH(iPr)OH,H,OH,Me,NHCOPh),(NHCOCH(iPr)OH,H,OH,Me,NHCO-2-furyl),(NHCOCH(iPr)OH,H,OH,Me,NHCONHPh),(NHCOCH(iPr)OH,H,OH,Me,NHCOCONHPh),(NHCOCH(iPr)OH,H,OH,Et,CONHPh),(NHCOCH(iPr)OH,H,OH,Et,CONH-3-pyridyl),(NHCOCH(iPr)OH,H,OH,Et,NHCOPh),(NHCOCH(iPr)OH,H,OH,Et,NHCO-2-furyl),(NHCOCH(iPr)OH,H,OH,Et,NHCONHPh), (NHCOCH(iPr)OH,H,OH,Et,NHCOCONHPh),(NHCOCH(iPr)OH,H,OH,CH2OH,CONHPh),(NHCOCH(iPr)OH,H,OH,CH2OH,CONH-3-pyridyl),(NHCOCH(iPr)OH,H,OH,CH2OH,NHCOPh),(NHCOCH(iPr)OH,H,OH,CH2OH,NHCO-2-furyl),(NHCOCH(iPr)OH,H,OH,CH2OH,NHCONHPh),(NHCOCH(iPr)OH,H,OH,CH2OH,NHCOCONHPh),(NHCOCH(iPr)OH,Me,H,Me,CONHPh),(NHCOCH(iPr)OH,Me,H,Me,CONH-3-pyridyl),(NHCOCH(iPr)OH,Me,H,Me,NHCOPh),(NHCOCH(iPr)OH,Me,H,Me,NHCO-2-furyl),(NHCOCH(iPr)OH,Me,H,Me,NHCONHPh),(NHCOCH(iPr)OH,Me,H,Me,NHCOCONHPh),(NHCOCH(iPr)OH,Me,H,Et,CONHPh),(NHCOCH(iPr)OH,Me,H,Et,CONH-3-pyridyl),(NHCOCH(iPr)OH,Me,H,Et,NHCOPh),(NHCOCH(iPr)OH,Me,H,Et,NHCO-2-furyl),(NHCOCH(iPr)OH,Me,H,Et,NHCONHPh),(NHCOCH(iPr)OH,Me,H,Et,NHCOCONHPh),(NHCOCH(iPr)OH,Me,H,CH2OH,CONHPh),(NHCOCH(iPr)OH,Me,H,CH2OH,CONH-3-pyridyl),(NHCOCH(iPr)OH,Me,H,CH2OH,NH COPh),(NHCOCH(iPr)OH,Me,H,CH2OH,NHCO-2-furyl),(NHCOCH(iPr)OH,Me,H,CH2OH,NHCONHPh),(NHCOCH(iPr)OH,Me,H,CH2OH,NHCOCONHPh),(NHCOCH(iPr)OH,Me,Me,Me,CONHPh),(NHCOCH(iPr)OH,Me,Me,Me,CONH-3-pyridyl),(NHCOCH(iPr)OH,Me,Me,Me,NHCOPh),(NHCOCH(iPr)OH,Me,Me,Me,NHCO-2-furyl),(NHCOCH(iPr)OH,Me,Me,Me,NHCONHPh),(NHCOCH(iPr)OH,Me,Me,Me,NHCOCONHPh),(NHCOCH(iPr)OH,Me,Me,Et,CONHPh),(NHCOCH(iPr)OH,Me,Me,Et,CONH-3-pyridyl),(NHCOCH(iPr)OH,Me,Me,Et,NHCOPh),(NHCOCH(iPr)OH,Me,Me,Et,NHCO-2-furyl),(NHCOCH(iPr)OH,Me,Me,Et,NHCONHPh),(NHCOCH(iPr)OH,Me,Me,Et,NHCOCONHPh),(NHCOCH(iPr)OH,Me,Me,CH2OH,CONHPh),(NHCOCH(iPr)OH,Me,Me,CH2OH,CONH-3-pyridyl),(NHCOCH(iPr)OH,Me,Me,CH2OH,NHCOPh),(NHCOCH(iPr)OH,Me,Me,CH2OH,NHCO-2-furyl),(NHCOCH(iPr)OH,Me,Me,CH2OH,NHCONHPh),(NHCOCH(iPr)OH,Me,Me,CH2OH,NHCOCONHPh),(NHCOCH(iPr)OH,Me,Ph,Me,CONHPh),(NHCOCH(iPr)OH,Me,Ph,Me,CONH-3-pyridyl),(NHCOCH(iPr)OH,Me,Ph,Me,NHCOPh),(NHCOCH(iPr)OH,Me,Ph,Me,NHCO-2-furyl),(NHCOCH(iPr)OH,Me,Ph,Me,NHCONHPh),(NHCOCH(iPr)OH,Me,Ph,Me,NHCOCONHPh),(NHCOCH(iPr)OH,Me,Ph,Et,CONHPh),(NHCOCH(iPr)OH,Me,Ph,Et,CONH-3-pyridyl),(NHCOCH(iPr)OH,Me,Ph,Et,NHCOPh),(NHCOCH(iPr)OH,Me,Ph,Et,NHCO-2-furyl),(NHCOCH(iPr)OH,Me,Ph,Et,NHCONHPh),(NHCOCH(iPr)OH,Me,Ph,Et,NHCOCONHPh),(NHCOCH(iPr)OH,Me,Ph,CH2OH,CONHPh),(NHCOCH(iPr)OH,Me,Ph,CH2OH,CONH-3-pyridyl),(NHCOCH(iPr)OH,Me,Ph,CH2OH,NHCOPh),(NHCOCH(iPr)OH,Me,Ph,CH2OH,NHCO-2-furyl),(NHCOCH(iPr)OH,Me,Ph,CH2OH,NHCONHPh),(NHCOCH(iPr)OH,Me,Ph,CH2OH,NHCOCONHPh),(NHCOCH(iPr)OH,Me,OH,Me,CONHPh),(NHCOCH(iPr)OH,Me,OH,Me,CONH-3-pyridyl),(NHCOCH(iPr)OH,Me,OH,Me,NHCOPh),(NHCOCH(iPr)OH,Me,OH,Me,NHCO-2-furyl),(NHCOCH(iPr)OH,Me,OH,Me,NHCONHPh),(NHCOCH(iPr)OH,Me,OH,Me,NHCOCONHPh),(NHCOCH(iPr)OH,Me,OH,Et,CONHPh),(NHCOCH(iPr)OH,Me,OH,Et,CONH-3-pyridyl),(NHCOCH(iPr)OH,Me,OH,Et,NHCOPh),(NHCOCH(iPr)OH,Me,OH,Et,NHCO-2-furyl),(NHCOCH(iPr)OH,Me,OH,Et,NHCONHPh),(NHCOCH(iPr)OH,Me,OH,Et,NHCOCONHPh),(NHCOCH(iPr)OH,Me,OH,CH2OH,CONHPh),(NHCOCH(iPr)OH,Me,OH,CH2OH,CONH-3-pyridyl),(NHCOCH(iPr)OH,Me,OH,CH2OH,NHCOPh),(NHCOCH(iPr)OH,Me,OH,CH2OH,NHCO-2-furyl),(NHCOCH(iPr)OH,Me,OH,CH2OH,NHCONHPh),(NHCOCH(iPr)OH,Me,OH,CH2OH,NHCOCONHPh),(NHCOCH(iPr)OH,Me,OH,CH2OH,NHCONHPh),(NHCOCH(iPr)OH,Me,OH,CH2OH,NHCOCONHPh),(NHCOCH(iPr)OH,Ph,H,Me,CONHPh),(NHCOCH(iPr)OH,Ph,H,Me,CONH-3-pyridyl),(NHCOCH(iPr)OH,Ph,H,Me,NHCOPh),(NHCOCH(iPr)OH,Ph,H,Me,NHCO-2-furyl),(NHCOCH(iPr)OH,Ph,H,Me,NHCONHPh),(NHCOCH(iPr)OH,Ph,H,Me,NHCOCONHPh),(NHCOCH(iPr)OH,Ph,H,Et,CONHPh),(NHCOCH(iPr)OH,Ph,H,Et,CONH-3-pyridyl),(NHCOCH(iPr)OH,Ph,H,Et,NHCOPh),(NHCOCH(iPr)OH,Ph,H,Et,NHCO-2-furyl),(NHCOCH(iPr)OH,Ph,H,Et,NHCONHPh),(NHCOCH(iPr)OH,Ph,H,Et,NHCOCONHPh),(NHCOCH(iPr)OH,Ph,H,CH2OH,CONHPh),(NHCOCH(iPr)OH,Ph,H,CH2OH,CONH-3-pyridyl),(NHCOCH(iPr)OH,Ph,H,CH2OH,NHCOPh),(NHCOCH(iPr)OH,Ph,H,CH2OH,NHCO-2-furyl),(NHCOCH(iPr)OH,Ph,H,CH2OH,NHCONHPh),(NHCOCH(iPr)OH,Ph,H,CH2OH,NHCOCONHPh),(NHCOCH(iPr)OH,Ph,Me,Me,CONHPh),(NHCOCH(iPr)OH,Ph,Me,Me,CONH-3-pyridyl),(NHCOCH(iPr)OH,Ph,Me,Me,NHCOPh),(NHCOCH(iPr)OH,Ph,Me,Me,NHCO-2-furyl),(NHCOCH(iPr)OH,Ph,Me,Me,NHCONHPh),(NHCOCH(iPr)OH,Ph,Me,Me,NHCOCONHPh),(NHCOCH(iPr)OH,Ph,Me,Et,CONHPh),(NHCOCH(iPr)OH,Ph,Me,Et,CONH-3-pyridyl),(NHCOCH(iPr)OH,Ph,Me,Et,NHCOPh),(NHCOCH(iPr)OH,Ph,Me,Et,NHCO-2-furyl),(NHCOCH(iPr)OH,Ph,Me,Et,NHCONHPh),(NHCOCH(iPr)OH,Ph,Me,Et,NHCOCONHPh),(NHCOCH(iPr)OH,Ph,Me,CH2OH,CONHPh),(NHCOCH(iPr)OH,Ph,Me,CH2OH,CONH-3-pyridyl),(NHCOCH(iPr)OH,Ph,Me,CH2OH,NH COPh),(NHCOCH(iPr)OH,Ph,Me,CH2OH,NHCO-2-furyl),(NHCOCH(iPr)OH,Ph,Me,CH2OH,NHCONHPh),(NHCOCH(iPr)OH,Ph,Me,CH2OH,NHCOCONHPh),(NHCOCH(iPr)OH,Ph,Ph,Me,CONHPh),(NHCOCH(iPr)OH,Ph,Ph,Me,CONH-3-pyridyl),(NHCOCH(iPr)OH,Ph,Ph,Me,NHCOPh),(NHCOCH(iPr)OH,Ph,Ph,Me,NHCO-2-furyl),(NHCOCH(iPr)OH,Ph,Ph,Me,NHCONHPh),(NHCOCH(iPr)OH,Ph,Ph,Me,NHCOCONHPh),(NHCOCH(iPr)OH,Ph,Ph,Et,CONHPh),(NHCOCH(iPr)OH,Ph,Ph,Et,CONH-3-pyridyl),(NHCOCH(iPr)OH,Ph,Ph,Et,NHCOPh),(NHCOCH(iPr)OH,Ph,Ph,Et,NHCO-2-furyl),(NHCOCH(iPr)OH,Ph,Ph,Et,NHCONHPh),(NHCOCH(iPr)OH,Ph,Ph,Et,NHCOCONHPh),(NHCOCH(iPr)OH,Ph,Ph,CH2OH,CONHPh),(NHCOCH(iPr)OH,Ph,Ph,CH2OH,CONH-3-pyridyl),(NHCOCH(iPr)OH,Ph,Ph,CH2OH,NHCOPh),(NHCOCH(iPr)OH,Ph,Ph,CH2OH,NHCO-2-furyl),(NHCOCH(iPr)OH,Ph,Ph,CH2OH,NHCONHPh),(NHCOCH(iPr)OH,Ph,Ph,CH2OH,NHCOCONHPh),(NHCOCH(iPr)OH,Ph,OH,Me,CONHPh),(NHCOCH(iPr)OH,Ph,OH,Me,CONH-3-pyridyl),(NHCOCH(iPr)OH,Ph,OH,Me,NHCOPh),(NHCOCH(iPr)OH,Ph,OH,Me,NHCO-2-furyl),(NHCOCH(iPr)OH,Ph,OH,Me,NHCONHPh),(NHCOCH(iPr)OH,Ph,OH,Me,NHCOCONHPh),(NHCOCH(iPr)OH,Ph,OH,Et,CONHPh),(NHCOCH(iPr)OH,Ph,OH,Et,CONH-3-pyridyl),(NHCOCH(iPr)OH,Ph,OH,Et,NHCOPh),(NHCOCH(iPr)OH,Ph,OH,Et,NHCO-2-furyl),(NHCOCH(iPr)OH,Ph,OH,Et,NHCONHPh),(NHCOCH(iPr)OH,Ph,OH,Et,NHCOCONHPh),(NHCOCH(iPr)OH,Ph,OH,CH2OH,CONHPh),(NHCOCH(iPr)OH,Ph,OH,CH2OH,CONH-3-pyridyl),(NHCOCH(iPr)OH,Ph,OH,CH2OH,NHCOPh),(NHCOCH(iPOOH,Ph,OH,CH2OH,NHCO-2-furyl),(NHCOCH(iPr)OH,Ph,OH,CH2OH,NHCONHPh),(NHCOCH(iPr)OH,Ph,OH,CH2OH,NHCOCONHPh),(NHSO2Me,H,H,Me,CONHPh),(NHSO2Me,H,H,Me,CONH-3-pyridyl),(NHSO2Me,H,H,Me,NHCOPh),(NHSO2Me,H,H,Me,NHCO-2-furyl),(NHSO2Me,H,H,Me,NHCONHPh),(NHSO2Me,H,H,Me,NHCOCONHPh), (NHSO2Me,H,H,Et,CONHPh),(NHSO2Me,H,H,Et,CONH-3-pyridyl),(NHSO2Me,H,H,Et,NHCOPh),(NHSO2Me,H,H,Et,NHCO-2-furyl),(NHSO2Me,H,H,Et,NHCONHPh),(NHSO2Me,H,H,Et,NHCOCONHPh),(NHSO2Me,H,H,CH2OH,CONHPh),(NHSO2Me,H,H,CH2OH,CONH-3-pyridyl),(NHSO2Me,H,H,CH2OH,NHCOPh),(NHSO2Me,H,H,CH2OH,NHCO-2-furyl),(NHSO2Me,H,H,CH2OH,NHCONHPh),(NHSO2Me,H,H,CH2OH,NHCOCONHPh),(NHSO2Me,H,Me,Me,CONHPh),(NHSO2Me,H,Me,Me,CONH-3-pyridyl),(NHSO2Me,H,Me,Me,NHCOPh),(NHSO2Me,H,Me,Me,NHCO-2-furyl),(NHSO2Me,H,Me,Me,NHCONHPh),(NHSO2Me,H,Me,Me,NHCOCONHPh),(NHSO2Me,H,Me,Et,CONHPh),(NHSO2Me,H,Me,Et,CONH-3-pyridyl),(NHSO2Me,H,Me,Et,NHCOPh),(NHSO2Me,H,Me,Et,NHCO-2-furyl),(NHSO2Me,H,Me,Et,NHCONHPh),(NHSO2Me,H,Me,Et,NHCOCONHPh),(NHSO2Me,H,Me,CH2OH,CONHPh),(NHSO2Me,H,Me,CH2OH,CONH-3-pyridyl),(NHSO2Me,H,Me,CH2OH,NHCOPh),(NHSO2Me,H,Me,CH2OH,NHCO-2-furyl),(NHSO2Me,H,Me,CH2OH,NHCONHPh),(NHSO2Me,H,Me,CH2OH,NHCOCONHPh),(NHSO2Me,H,Ph,Me,CONHPh),(NHSO2Me,H,Ph,Me,CONH-3-pyridyl),(NHSO2Me,H,Ph,Me,NHCOPh),(NHSO2Me,H,Ph,Me,NHCO-2-furyl),(NHSO2Me,H,Ph,Me,NHCONHPh),(NHSO2Me,H,Ph,Me,NHCOCONHPh),(NHSO2Me,H,Ph,Et,CONHPh),(NHSO2Me,H,Ph,Et,CONH-3-pyridyl),(NHSO2Me,H,Ph,Et,NHCOPh),(NHSO2Me,H,Ph,Et,NHCO-2-furyl),(NHSO2Me,H,Ph,Et,NHCONHPh),(NHSO2Me,H,Ph,Et,NHCOCONHPh),(NHSO2Me,H,Ph,CH2OH,CONHPh),(NHSO2Me,H,Ph,CH2OH,CONH-3-pyridyl),(NHSO2Me,H,Ph,CH2OH,NHCOPh),(NHSO2Me,H,Ph,CH2OH,NHCO-2-furyl),(NHSO2Me,H,Ph,CH2OH,NHCONHPh),(NHSO2Me,H,Ph,CH2OH,NHCOCONHPh),(NHSO2Me,H,OH,Me,CONHPh),(NHSO2Me,H,OH,Me,CONH-3-pyridyl),(NHSO2Me,H,OH,Me,NHCOPh),(NHSO2Me,H,OH,Me,NHCO-2-furyl),(NHSO2Me,H,OH,Me,NHCONHPh),(NHSO2Me,H,OH,Me,NHCOCONHPh),(NHSO2Me,H,OH,Et,CONHPh),(NHSO2Me,H,OH,Et,CONH-3-pyridyl),(NHSO2Me,H,OH,Et,NHCOPh),(NHSO2Me,H,OH,Et,NHCO-2-furyl),(NHSO2Me,H,OH,Et,NHCONHPh),(NHSO2Me,H,OH,Et,NHCOCONHPh),(NHSO2Me,H,OH,CH2OH,CONHPh),(NHSO2Me,H,OH,CH2OH,CONH-3-pyridyl),(NHSO2Me,H,OH,CH2OH,NHCOPh),(NHSO2Me,H,OH,CH2OH,NHCO-2-furyl),(NHSO2Me,H,OH,CH2OH,NHCONHPh),(NHSO2Me,H,OH,CH2OH,NHCOCONHPh),(NHSO2Me,Me,H,Me,CONHPh),(NHSO2Me,Me,H,Me,CONH-3-pyridyl),(NHSO2Me,Me,H,Me,NHCO Ph),(NHSO2Me,Me,H,Me,NHCO-2-furyl),(NHSO2Me,Me,H,Me,NHCONHPh),(NHSO2Me,Me,H,Me,NHCOCONHPh),(NHSO2Me,Me,H,Et,CONHPh),(NHSO2Me,Me,H,Et,CONH-3-pyridyl),(NHSO2Me,Me,H,Et,NHCOPh),(NHSO2Me,Me,H,Et,NHCO-2-furyl),(NHSO2Me,Me,H,Et,NHCONHPh),(NHSO2Me,Me,H,Et,NHCOCONHPh)(NHSO2Me,Me,H,CH2OH,CONHPh),(NHSO2Me,Me,H,CH2OH,CONH-3-pyridyl),(NHSO2Me,Me,H,CH2OH,NHCOPh),(NHSO2Me,Me,H,CH2OH,NHCO-2-furyl),(NHSO2Me,Me,H,CH2OH,NHCONHPh),(NHSO2Me,Me,H,CH2OH,NHCOCONHPh),(NHSO2Me,Me,Me,Me,CONHPh),(NHSO2Me,Me,Me,Me,CONH-3-pyridyl),(NHSO2Me,Me,Me,Me,NHCOPh),(NHSO2Me,Me,Me,Me,NHCO-2-furyl),(NHSO2Me,Me,Me,Me,NHCONHPh),(NHSO2Me,Me,Me,Me,NHCOCONHPh),(NHSO2Me,Me,Me,Et,CONHPh),(NHSO2Me,Me,Me,Et,CONH-3-pyridyl),(NHSO2Me,Me,Me,Et,NHCOPh),(NHSO2Me,Me,Me,Et,NHCO-2-furyl),(NHSO2Me,Me,Me,Et,NHCONHPh),(NHSO2Me,Me,Me,Et,NHCOCONHPh),(NHSO2Me,Me,Me,CH2OH,CONHPh),(NHSO2Me,Me,Me,CH2OH,CONH-3-pyridyl),(NHSO2Me,Me,Me,CH2OH,NHCOPh),(NHSO2Me,Me,Me,CH2OH,NHCO-2-furyl),(NHSO2Me,Me,Me,CH2OH,NHCONHPh),(NHSO2Me,Me,Me,CH2OH,NHCOCONHPh),(NHSO2Me,Me,Ph,Me,CONHPh),(NHSO2Me,Me,Ph,Me,CONH-3-pyridyl),(NHSO2Me,Me,Ph,Me,NHCOPh),(NHSO2Me,Me,Ph,Me,NHCO-2-furyl),(NHSO2Me,Me,Ph,Me,NHCONHPh),(NHSO2Me,Me,Ph,Me,NHCOCONHPh),(NHSO2Me,Me,Ph,Et,CONHPh),(NHSO2Me,Me,Ph,Et,CONH-3-pyridyl),(NHSO2Me,Me,Ph,Et,NHCOPh),(NHSO2Me,Me,Ph,Et,NHCO-2-furyl),(NHSO2Me,Me,Ph,Et,NHCONHPh),(NHSO2Me,Me,Ph,Et,NHCOCONHPh),(NHSO2Me,Me,Ph,CH2OH,CONHPh),(NHSO2Me,Me,Ph,CH2OH,CONH-3-pyridyl),(NHSO2Me,Me,Ph,CH2OH,NHCOPh),(NHSO2Me,Me,Ph,CH2OH,NHCO-2-furyl),(NHSO2Me,Me,Ph,CH2OH,NHCONHPh),(NHSO2Me,Me,Ph,CH2OH,NHCOCONHPh),(NHSO2Me,Me,OH,Me,CONHPh),(NHSO2Me,Me,OH,Me,CONH-3-pyridyl),(NHSO2Me,Me,OH,Me,NHCOPh),(NHSO2Me,Me,OH,Me,NHCO-2-furyl),(NHSO2Me,Me,OH,Me,NHCONHPh),(NHSO2Me,Me,OH,Me,NHCOCONHPh),(NHSO2Me,Me,OH,Et,CONHPh),(NHSO2Me,Me,OH,Et,CONH-3-pyridyl),(NHSO2Me,Me,OH,Et,NHCOPh),(NHSO2Me,Me,OH,Et,NHCO-2-furyl),(NHSO2Me,Me,OH,Et,NHCONHPh),(NHSO2Me,Me,OH,Et,NHCOCONHPh),(NHSO2Me,Me,OH,CH2OH,CONHPh),(NHSO2Me,Me,OH,CH2OH,CONH-3-pyridyl),(NHSO2Me,Me,OH,CH2OH,NHCOPh),(NHSO2Me,Me,OH,CH2OH,NHCO-2-furyl),(NHSO2Me,Me,OH,CH2OH,NHCONHPh),(NHSO2Me,Me,OH,CH2OH,NHCOCONHPh),(NHSO2Me,Ph,H,Me,CONHPh),(NHSO2Me,Ph,H,Me,CONH-3-pyridyl),(NHSO2Me,Ph,H,Me,NHCOPh),(NHSO2Me,Ph,H,Me,NHCO-2-furyl),(NHSO2Me,Ph,H,Me,NHCONHPh),(NHSO2Me,Ph,H,Me,NHCOCONHPh),(NHSO2Me,Ph,H,Et,CONHPh),(NHSO2Me,Ph,H,Et,CONH-3-pyridyl),(NHSO2Me,Ph,H,Et,NHCOPh),(NHSO2Me,Ph,H,Et,NHCO-2-furyl),(NHSO2Me,Ph,H,Et,NHCONHPh),(NHSO2Me,Ph,H,Et,NHCOCONHPh),(NHSO2Me,Ph,H,CH2OH,CONHPh),(NHSO2Me,Ph,H,CH2OH,CONH-3-pyridyl),(NHSO2Me,Ph,H,CH2OH,NHCOPh),(NHSO2Me,Ph,H,CH2OH,NHCO-2-furyl),(NHSO2Me,Ph,H,CH2OH,NHCONHPh),(NHSO2Me,Ph,H,CH2OH,NHCOCONHPh),(NHSO2Me,Ph,Me,Me,CONHPh),(NHSO2Me,Ph,Me,Me,CONH-3-pyridyl),(NHSO2Me,Ph,Me,Me,NHCOPh),(NHSO2Me,Ph,Me,Me,NHCO-2-furyl),(NHSO2Me,Ph,Me,Me,NHCONHPh),(NHSO2Me,Ph,Me,Me,NHCOCONHPh),(NHSO2Me,Ph,Me,Et,CONHPh),(NHSO2Me,Ph,Me,Et,CONH-3-pyridyl),(NHSO2Me,Ph,Me,Et,NHCOPh),(NHSO2Me,Ph,Me,Et,NHCO-2-furyl),(NHSO2Me,Ph,Me,Et,NHCONHPh),(NHSO2Me,Ph,Me,Et,NHCOCONHPh),(NHSO2Me,Ph,Me,CH2OH,CONHPh),(NHSO2Me,Ph,Me,CH2OH,CONH-3-pyridyl),(NHSO2Me,Ph,Me,CH2OH,NHCOPh),(NHSO2Me,Ph,Me,CH2OH,NHCO-2-furyl),(NHSO2Me,Ph,Me,CH2OH,NHCONHPh),(NHSO2Me,Ph,Me,CH2OH,NHCOCONHPh),(NHSO2Me,Ph,Ph,Me,CONHPh),(NHSO2Me,Ph,Ph,Me,CONH-3-pyridyl),(NHSO2Me,Ph,Ph,Me,NHCOPh),(NHSO2Me,Ph,Ph,Me,NHCO-2-furyl),(NHSO2Me,Ph,Ph,Me,NHCONHPh),(NHSO2Me,Ph,Ph,Me,NHCOCONHPh),(NHSO2Me,Ph,Ph,Et,CONHPh),(NHSO2Me,Ph,Ph,Et,CONH-3-pyridyl),(NHSO2Me,Ph,Ph,Et,NHCOPh),(NHSO2Me,Ph,Ph,Et,NHCO-2-furyl),(NHSO2Me,Ph,Ph,Et,NHCONHPh),(NHSO2Me,Ph,Ph,Et,NHCOCONHPh),(NHSO2Me,Ph,Ph, CH2OH,CONHPh),(NHSO2Me,Ph,Ph,CH2OH,CONH-3-pyridyl),(NHSO2Me, Ph,Ph,CH2OH,NHCOPh),(NHSO2Me,Ph,Ph,CH2OH,
NHCO-2-furyl),(NHSO2Me,Ph,Ph, CH2OH,NHCONHPh),
(NHSO2Me,Ph,Ph,CH2OH,NHCOCONHPh),(NHSO2Me,
Ph,OH,Me,CONHPh),(NHSO2Me,Ph,OH,Me,CONH-3-
pyridyl),(NHSO2Me,Ph,OH,Me,NHCOPh),(NHSO2Me,
Ph,OH,Me,NHCO-2-furyl),(NHSO2Me,Ph,OH,Me,
NHCONHPh),(NHSO2Me,Ph,OH,Me,NHCOCONHPh),
(NHSO2Me,Ph,OH,Et,CONHPh),(NHSO2Me,Ph,OH,Et,
CONH-3-pyridyl),(NHSO2Me,Ph,OH,Et,NHCOPh),
(NHSO2Me,Ph,OH,Et,NHCO-2-furyl),(NHSO2Me,Ph,OH,
Et,NHCONHPh),(NHSO2Me,Ph,OH,Et,NHCOCONHPh),
(NHSO2Me,Ph,OH,CH2OH,CONHPh),(NHSO2Me,Ph,
OH,CH2OH,CONH-3-pyridyl),(NHSO2Me,Ph,OH,
CH2OH,NHCOPh),(NHSO2Me,Ph,OH,CH2OH,NHCO-2-
furyl),(NHSO2Me,Ph,OH,CH2OH,NHCONHPh),
(NHSO2Me,Ph,OH,CH2OH,NHCOCONHPh),
(NH2,H,H,Me,CONHPh),(NH2,H,H,Me,CONH-3-py-
ridyl),(NH2,H,H,Me,NHCOPh),(NH2,H,H,Me,NHCO-2-
furyl),(NH2,H,H,Me,NHCONHPh),(NH2,H,H,Me,NHCO-
CONHPh),(NH2,H,H,Et,CONHPh),(NH2,H,H,Et,CONH-
3-pyridyl),(NH2,H,H,Et,NHCOPh),(NH2,H,H,Et,NHCO-2-
furyl),(NH2,H,H,Et,NHCONHPh),(NH2,H,H,Et,
NHCOCONHPh),(NH2,H,H,CH2OH,CONHPh),(NH2,H,
H,CH2OH,CONH-3-pyridyl),(NH2,H,H,CH2OH,
NHCONHPh),(NH2,H,H,CH2OH,NHCOCONHPh),(NH2,
H,Me,Me,CONHPh),(NH2,H,Me,Me,CONH-3-pyridyl),
(NH2,H,Me,Me,NHCONHPh),(NH2,H,Me,Me,
NHCOCONHPh),(NH2,H,Me,Et,CONHPh),(NH2,H,Me,
Et,CONH-3-pyridyl),(NH2,H,Me,Et,NHCOPh),(NH2,H,
Me,Et,NHCO-2-furyl),(NH2,H,Me,Et,NHCONHPh),(NH2,
H,Me,Et,NHCOCONHPh),(NH2,H,Me,CH2OH,
CONHPh),(NH2,H,Me,CH2OH,CONH-3-pyridyl),(NH2,
H,Me,CH2OH,NHCONHPh),(NH2,H,Me,CH2OH,
NHCOCONHPh),(NH2,H,Ph,Me,CONHPh),(NH2,H,Ph,
Me,CONH-3-pyridyl),(NH2,H,Ph,Me,NHCONHPh),(NH2,
H,Ph,Me,NHCOCONHPh),(NH2,H,Ph,Et,CONHPh),
(NH2,H,Ph,Et,CONH-3-pyridyl),(NH2,H,Ph,Et,NHCOPh),
(NH2,H,Ph,Et,NHCO-2-furyl),(NH2,H,Ph,Et,
NHCONHPh),(NH2,H,Ph,Et,NHCOCONHPh),(NH2,H,Ph,
CH2OH,CONHPh),(NH2,H,Ph,CH2OH,CONH-3-pyridyl),
(NH2,H,Ph,CH2OH,NHCONHPh),(NH2,H,Ph,CH2OH,
NHCOCONHPh),(NH2,H,OH,Me,CONHPh),(NH2,H,OH,
Me,CONH-3-pyridyl),(NH2,H,OH,Me,NHCONHPh),
(NH2,H,OH,Me,NHCOCONHPh),(NH2,H,OH,Et,
CONHPh),(NH2,H,OH,Et,CONH-3-pyridyl),(NH2,H,OH,
Et,NHCOPh),(NH2,H,OH,Et,NHCO-2-furyl),(NH2,H,OH,
Et,NHCONHPh),(NH2,H,OH,Et,NHCOCONHPh),(NH2,
H,OH,CH2OH,CONHPh),(NH2,H,OH,CH2OH,CONH-3-
pyridyl),(NH2,H,OH,CH2OH,NHCONHPh),(NH2,H,OH,
CH2OH,NHCOCONHPh),(NH2,Me,H,Me,CONHPh),
(NH2,Me,H,Me,CONH-3-pyridyl),(NH2,Me,H,Me,
NHCONHPh),(NH2,Me,H,Me,NHCOCONHPh),(NH2,Me,
H,Et,CONHPh),(NH2,Me,H,Et,CONH-3-pyridyl),(NH2,
Me,H,Et,NHCOPh),(NH2,Me,H,Et,NHCO-2-furyl),(NH2,
Me,H,Et,NHCONHPh),(NH2,Me,H,Et,NHCOCONHPh),
(NH2,Me,H,CH2OH,CONHPh),(NH2,Me,H,CH2OH,
CONH-3-pyridyl),(NH2,Me,H,CH2OH,NHCONHPh),
(NH2,Me,H,CH2OH,NHCOCONHPh),(NH2,Me,Me,Me,
CONHPh),(NH2,Me,Me,Me,CONH-3-pyridyl),(NH2,Me,
Me,Me,NHCONHPh),(NH2,Me,Me,Me,NHCOCONHPh)
(NH2,Me,Me,Et,CONHPh),(NH2,Me,Me,Et,CONH-3-py-
ridyl),(NH2,Me,Me,Et,NHCOPh),(NH2,Me,Me,Et,NHCO-
2-furyl),(NH2,Me,Me,Et,NHCONHPh),(NH2,Me,Me,Et,
NHCOCONHPh),(NH2,Me,Me,CH2OH,CONHPh),(NH2,
Me,Me,CH2OH,CONH-3-pyridyl),(NH2,Me,Me,CH2OH,
NHCONHPh),(NH2,Me,Me,CH2OH,NHCOCONHPh),
(NH2,Me,Ph,Me,CONHPh),(NH2,Me,Ph,Me,CONH-3-
pyridyl),(NH2,Me,Ph,Me,NHCOPh),(NH2,Me,Ph,Me,
NHCO-2-furyl),(NH2,Me,Ph,Me,NHCONHPh),(NH2,Me,
Ph,Me,NHCOCONHPh),(NH2,Me,Ph,Et,CONHPh),(NH2,
Me,Ph,Et,CONH-3-pyridyl),(NH2,Me,Ph,Et,NHCOPh),
(NH2,Me,Ph,Et,NHCO-2-furyl),(NH2,Me,Ph,Et,
NHCONHPh),(NH2,Me,Ph,Et,NHCOCONHPh),(NH2,Me,
Ph,CH2OH,CONHPh),(NH2,Me,Ph,CH2OH,CONH-3-
pyridyl),(NH2,Me,Ph,CH2OH,NHCONHPh),(NH2,Me,Ph,
CH2OH,NHCOCONTHPh),(NH2,Me,OH,Me,CONHPh),
(NH2,Me,OH,Me,CONH-3-pyridyl),(NH2,Me,OH,Me,
NHCONHPh),(NH2,Me,OH,Me,NHCOCONHPh),(NH2,
Me,OH,Et,CONHPh),(NH2,Me,OH,Et,CONH-3-pyridyl),
(NH2,Me,OH,Et,NHCOPh),(NH2,Me,OH,Et,NHCO-2-
furyl),(NH2,Me,OH,Et,NHCONHPh),(NH2,Me,OH,Et,
NHCOCONHPh),(NH2,Me,OH,CH2OH,CONHPh),(NH2,
Me,OH,CH2OH,CONH-3-pyridyl),(NH2,Me,OH,CH2OH,
NHCONHPh),(NH2,Me,OH,CH2OH,NHCOCONHPh),
(NH2,Ph,H,Me,CONHPh),(NH2,Ph,H,Me,CONH-3-
pyridyl),(NH2,Ph,H,Me,NHCONHPh),(NH2,Ph,H,Me,
NHCOCONHPh),(NH2,Ph,H,Et,CONHPh),(NH2,Ph,H,Et,
CONH-3-pyridyl),(NH2,Ph,H,Et,NHCOPh),(NH2,Ph,H,Et,
NHCO-2-furyl),(NH2,Ph,H,Et,NHCONHPh),(NH2,Ph,H,
Et,NHCOCONHPh),(NH2,Ph,H,CH2OH,CONHPh),(NH2,
Ph,H,CH2OH,CONH-3-pyridyl),(NH2,Ph,H,CH2OH,
NHCONHPh),(NH2,Ph,H,CH2OH,NHCOCONHPh),
(NH2,Ph,Me,Me,CONHPh),(NH2,Ph,Me,Me,CONH-3-
pyridyl),(NH2,Ph,Me,Me,NHCONHPh),(NH2,Ph,Me,Me,
NHCOCONHPh),(NH2,Ph,Me,Et,CONHPh),(NH2,Ph,Me,
Et,CONH-3-pyridyl),(NH2,Ph,Me,Et,NHCOPh),(NH2,Ph,
Me,Et,NHCO-2-furyl),(NH2,Ph,Me,Et,NHCONHPh),
(NH2,Ph,Me,Et,NHCOCONHPh),(NH2,Ph,Me,CH2OH,
CONHPh),(NH2,Ph,Me,CH2OH,CONH-3-pyridyl),(NH2,
Ph,Me,CH2OH,NHCONHPh),(NH2,Ph,Me,CH2OH,
NHCOCONHPh),(NH2,Ph,Ph,Me,CONHPh),(NH2,Ph,Ph,
Me,CONH-3-pyridyl),(NH2,Ph,Ph,Me,NHCOPh),(NH2,
Ph,Ph,Me,NHCO-2-furyl),(NH2,Ph,Ph,Me,NHCONHPh),
(NH2,Ph,Ph,Me,NHCOCONHPh),(NH2,Ph,Ph,Et,
CONHPh),(NH2,Ph,Ph,Et,CONH-3-pyridyl),(NH2,Ph,Ph,
Et,NHCOPh),(NH2,Ph,Ph,Et,NHCO-2-furyl),(NH2,Ph,Ph,
Et,NHCONHPh),(NH2,Ph,Ph,Et,NHCOCONHPh),(NH2,
Ph,Ph,CH2OH,CONHPh),(NH2,Ph,Ph,CH2OH,CONH-3-
pyridyl),(NH2,Ph,Ph,CH2OH,NH COPh),(NH2,Ph,Ph,
CH2OH,NHCO-2-furyl),(NH2,Ph,Ph,CH2OH,
NHCONHPh),(NH2,Ph,Ph,CH2OH,NHCOCONHPh),
(NH2,Ph,OH,Me,CONHPh),(NH2,Ph,OH,Me,CONH-3-
pyridyl),(NH2,Ph,OH,Me,NHCONHPh),(NH2,Ph,OH,Me,
NHCOCONHPh),(NH2,Ph,OH,Et,CONHPh),(NH2,Ph,OH,
Et,CONH-3-pyridyl),(NH2,Ph,OH,Et,NHCOPh),(NH2,Ph,
OH,Et,NHCO-2-furyl),(NH2,Ph,OH,Et,NHCONHPh),
(NH2,Ph,OH,Et,NHCOCONHPh),(NH2,Ph,OH, CH2OH,
CONHPh),(NH2,Ph,OH,CH2OH,CONH-3-pyridyl),(NH2,
Ph,OH,CH2OH,NHCOPh),(NH2,Ph,OH,CH2OH,NHCO-
2-furyl),(NH2,Ph,OH,CH2OH,NHCONHPh), (NH2,Ph,
OH,CH2OH,NHCOCONHPh),
(NHCH2CH(OH)CH2OH,H,H,Me,CONHPh),(NHCH2CH
(OH)CH2OH,H,H,Me,CONH-3-pyridyl),(NHCH2CH(OH)
CH2OH,H,H,Me,NHCOPh),(NHCH2CH(OH)CH2OH,H,
H,Me,NHCO-2-furyl),(NHCH2CH(OH)CH2OH,H,H,Me,
NHCONHPh),(NHCH2CH(OH)CH2OH,H,H,Me,
NHCOCONHPh),(NHCH2CH(OH)CH2OMe,H,H,Me,
CONHPh),(NHCH2CH(OH)CH2OMe,H,H,Me,CONH-3-
pyridyl),(NHCH2CH(OH)CH2OMe,H,H,Me,NHCOPh),
(NHCH2CH(OH)CH2OMe,H,H,Me,NHCO-2-furyl),
(NHCH2CH(OH)CH2OMe,H,H,Me,NHCONHPh),
(NHCH2CH(OH)CH2OMe,H,H,Me,NHCOCONHPh),
(NHCH2CH(OH)CH2NH2,H,H,Me,CONHPh),
(NHCH2CH(OH)CH2NH2,H,H,Me,CONH-3-pyridyl), (NHCH2CH(OH)CH2NH2,H,H,Me,NHCOPh),
(NHCH2CH(OH)CH2NH2,H,H,Me,NHCO-2-furyl),
(NHCH2CH(OH)CH2NH2,H,H,Me,NHCONHPh),
(NHCH2CH(OH)CH2NH2,H,H,Me,NHCOCONHPh),
(NHCH2CH(OCH2NHMe,H,H,Me,CONHPh),
(NHCH2CH(OH)CH2NHMe,H,H,Me,CONH-3-pyridyl),
(NHCH2CH(OH)CH2NHMe,H,H,Me,NHCOPh),
(NHCH2CH(OH)CH2NHMe,H,H,Me,NHCO-2-furyl),
(NHCH2CH(OH)CH2NHMe,H,H,Me,NHCONHPh),
(NHCH2CH(OH)CH2NHMe,H,H,Me,NHCOCONHPh),
(NHCH2CH(OH)CH2NHCOMe,H,H,Me,CONHPh),
(NHCH2CH(OH)CH2NHCOMe,H,H,Me,CONH-3-pyridyl),(NHCH2CH(OH)CH2NHCOMe,H,H,Me,
NHCOPh),(NHCH2CH(OH)CH2NHCOMe,H,H,Me,
NHCO-2-furyl),(NHCH2CH(OH)CH2NHCOMe,H,H,Me,
NHCONHPh),(NHCH2CH(OH)CH2NHCOMe,H,H,Me,
NHCOCONHPh),(NHCH2CH(OH)CH2N(Me)Me,H,H,
Me,CONHPh),(NHCH2CH(OH)CH2N(Me)Me,H,H,Me,
CONH-3-pyridyl),(NHCH2CH(OH)CH2N(Me)Me,H,H,
Me,NHCOPh),(NHCH2CH(OH)CH2N(Me)Me,H,H,Me,
NHCO-2-furyl),(NHCH2CH(OH)CH2N(Me)Me,H,H,Me,
NHCONHPh),(NHCH2CH(OH)CH2N(Me)Me,H,H,Me,
NHCOCONHPh),(NH C(O)C(O)NH2,H,H,Me,CONHPh),
(NHC(O)C(O)NH2,H,H,Me,CONH-3-pyridyl),(NHC(O)C
(O)NH2,H,H,Me,NHCOPh),(NHC(O)C(O)NH2,H,H,Me,
NHCO-2-furyl),(NHC(O)C(O)NH2,H,H,Me,
NHCONHPh),(NHC(O)C(O)NH2,H,H,Me,
NHCOCONHPh),(NHC(O)C(O)NHMe,H,H,Me,
CONHPh),(NHC(O)C(O)NHMe,H,H,Me,CONH-3-pyridyl),(NHC(O)C(O)NHMe,H,H,Me,NHCOPh),(NHC
(O)C(O)NHMe,H,H,Me,NHCO-2-furyl),(NHC(O)C(O)
NHMe,H,H,Me,NHCONHPh),(NHC(O)C(O)NHMe,H,H,
Me,NHCOCONHPh),(NHC(O)C(O)N(Me)Me,H,H,Me,
CONHPh),(NHC(O)C(O)N(Me)Me,H,H,Me,CONH-3-pyridyl),(NHC(O)C(O)N(Me)Me,H,H,Me,NHCOPh),
(NHC(O)C(O)N(Me)Me,H,H,Me,NHCO-2-furyl),(NHC
(O)C(O)N(Me)Me,H,H,Me,NHCONHPh),(NHC(O)C(O)N
(Me)Me,H,H,Me,NHCOCONHPh).

[Chemical formula 67]

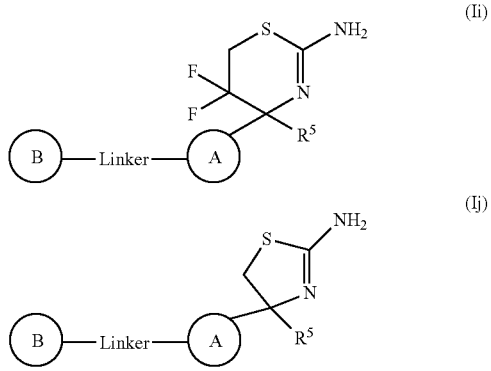

In above structural formula (II) or (Ij), the combination of B, Linker, A, $R^5$ (B, Linker, A, $R^5$) are the following compounds.

TABLE 169

| | B | | Linker | | A | | R5 |
|---|---|---|---|---|---|---|---|
| B1 | Ph— | L1 | (thioamide) | A1 | (pyrimidine) | R51 | —CN |
| B2 | 2-pyridyl- | L2 | (thioamide) | A2 | (pyrimidine) | R52 | —C≡CH |
| B3 | 4-Me—Ph— | L3 | (ketone) | A3 | (cyclohexane) | R53 | —C≡CMe |
| B4 | cHex— | L4 | (ketone) | A4 | (piperidine) | R54 | —CF3 |
| B5 | cHex—CH2— | L5 | (diketone) | A5 | (phenyl) | R55 | —CH2Cl |
| | | | | | | R56 | CHCl2 |

(B, Linker, A, R$^5$)=
(B1,L1,A1,R51),(B1,L1,A1,R52),(B1,L1,A1,R53),(B1,L1, A1,R54),(B1,L1,A1,R55),(B1,L1,A1,R56),(B1,L1,A2, R51),(B1,L1,A2,R52),(B1,L1,A2,R53),(B1,L1,A2,R54), (B1,L1,A2,R55),(B1,L1,A2,R56),(B1,L1,A3,R51),(B1,L1, A3,R52),(B1,L1,A3,R53),(B1,L1,A3,R54),(B1,L1,A3, R55),(B1,L1,A3,R56),(B1,L1,A4,R51),(B1,L1,A4,R52), (B1,L1,A4,R53),(B1,L1,A4,R54),(B1,L1,A4,R55),(B1,L1, A4,R56),(B1,L1,A5,R51),(B1,L1,A5,R52),(B1,L1,A5, R53),(B1,L1,A5,R54),(B1,L1,A5,R55),(B1,L1,A5,R56), (B1,L2,A1,R51),(B1,L2,A1,R52),(B1,L2,A1,R53),(B1,L2, A1,R54),(B1,L2,A1,R55),(B1,L2,A1,R56),(B1,L2,A2, R51),(B1,L2,A2,R52),(B1,L2,A2,R53),(B1,L2,A2,R54), (B1,L2,A2,R55),(B1,L2,A2,R56),(B1,L2,A3,R51),(B1,L2, A3,R52),(B1,L2,A3,R53),(B1,L2,A3,R54),(B1,L2,A3, R55),(B1,L2,A3,R56),(B1,L2,A4,R51),(B1,L2,A4,R52), (B1,L2,A4,R53),(B1,L2,A4,R54),(B1,L2,A4,R55),(B1,L2, A4,R56),(B1,L2,A5,R51),(B1,L2,A5,R52),(B1,L2,A5, R53),(B1,L2,A5,R54),(B1,L2,A5,R55),(B1,L2,A5,R56), (B1,L3,A1,R51),(B1,L3,A1,R52),(B1,L3,A1,R53),(B1,L3, A1,R54),(B1,L3,A1,R55),(B1,L3,A1,R56),(B1,L3,A2, R51),(B1,L3,A2,R52),(B1,L3,A2,R53),(B1,L3,A2,R54), (B1,L3,A2,R55),(B1,L3,A2,R56),(B1,L3,A3,R51),(B1,L3, A3,R52),(B1,L3,A3,R53),(B1,L3,A3,R54),(B1,L3,A3, R55),(B1,L3,A3,R56),(B1,L3,A4,R51),(B1,L3,A4,R52), (B1,L3,A4,R53),(B1,L3,A4,R54),(B1,L3,A4,R55),(B1,L3, A4,R56),(B1,L3,A5,R51),(B1,L3,A5,R52),(B1,L3,A5, R53),(B1,L3,A5,R54),(B1,L3,A5,R55),(B1,L3,A5,R56), (B1,L4,A1,R51),(B1,L4,A1,R52),(B1,L4, A1,R53),(B1,L4, A1,R54),(B1,L4,A1,R55),(B1,L4,A1,R56),(B1,L4,A2, R51),(B1,L4,A2,R52),(B1,L4,A2,R53),(B1,L4,A2,R54), (B1,L4,A2,R55),(B1,L4,A2,R56),(B1,L4,A3,R51),(B1,L4, A3,R52),(B1,L4,A3,R53),(B1,L4,A3,R54),(B1,L4,A3, R55),(B1,L4,A3,R56),(B1,L4,A4,R51),(B1,L4,A4,R52), (B1,L4,A4,R53),(B1,L4,A4,R54),(B1,L4,A4,R55),(B1,L4, A4,R56),(B1,L4,A5,R51),(B1,L4,A5,R52),(B1,L4,A5, R53),(B1,L4,A5,R54),(B1,L4,A5,R55),(B1,L4,A5,R56), (B1,L5,A1,R51),(B1,L5,A1,R52),(B1,L5,A1,R53),(B1,L5, A1,R54),(B1,L5,A1,R55),(B1,L5,A1,R56),(B1,L5,A2, R51),(B1,L5,A2,R52),(B1,L5,A2,R53),(B1,L5,A2,R54), (B1,L5,A2,R55),(B1,L5,A2,R56),(B1,L5,A3,R51),(B1,L5, A3,R52),(B1,L5,A3,R53),(B1,L5,A3,R54),(B1,L5,A3, R55),(B1,L5,A3,R56),(B1,L5,A4,R51),(B1,L5,A4,R52), (B1,L5,A4,R53),(B1,L5,A4,R54),(B1,L5,A4,R55),(B1,L5, A4,R56),(B1,L5,A5,R51),(B1,L5,A5,R52),(B1,L5,A5, R53),(B1,L5,A5,R54),(B1,L5,A5,R55),(B1,L5,A5,R56), (B2,L1,A1,R51),(B2,L1,A1,R52),(B2,L1,A1,R53),(B2,L1, A1,R54),(B2,L1,A1,R55),(B2,L1,A1,R56),(B2,L1,A2, R51),(B2,L1,A2,R52),(B2,L1,A2,R53),(B2,L1,A2,R54), (B2,L1,A2,R55),(B2,L1,A2,R56),(B2,L1,A3,R51),(B2,L1, A3,R52),(B2,L1,A3,R53),(B2,L1,A3,R54),(B2,L1,A3, R55),(B2,L1,A3,R56),(B2,L1,A4,R51),(B2,L1,A4,R52), (B2,L1,A4,R53),(B2,L1,A4,R54),(B2,L1,A4,R55),(B2,L1, A4,R56),(B2,L1,A5,R51),(B2,L1,A5,R52),(B2,L1,A5, R53),(B2,L1,A5,R54),(B2,L1,A5,R55),(B2,L1,A5,R56), (B2,L2,A1,R51),(B2,L2,A1,R52),(B2,L2,A1,R53),(B2,L2, A1,R54),(B2,L2,A1,R55),(B2,L2,A1,R56),(B2,L2,A2, R51),(B2,L2,A2,R52),(B2,L2,A2,R53),(B2,L2,A2,R54), (B2,L2,A2,R55),(B2,L2,A2,R56),(B2,L2,A3,R51),(B2,L2, A3,R52),(B2,L2,A3,R53),(B2,L2,A3,R54),(B2,L2,A3, R55),(B2,L2,A3,R56),(B2,L2,A4,R51),(B2,L2,A4,R52), (B2,L2,A4,R53),(B2,L2,A4,R54),(B2,L2,A4,R55),(B2,L2, A4,R56),(B2,L2,A5,R51),(B2,L2,A5,R52),(B2,L2,A5, R53),(B2,L2,A5,R54),(B2,L2,A5,R55),(B2,L2,A5,R56), (B2,L3,A1,R51),(B2,L3,A1,R52),(B2,L3,A1,R53),(B2,L3, A1,R54),(B2,L3,A1,R55),(B2,L3,A1,R56),(B2,L3,A2, R51),(B2,L3,A2,R52),(B2,L3,A2,R53),(B2,L3,A2,R54), (B2,L3,A2,R55),(B2,L3,A2,R56),(B2,L3,A3,R51),(B2,L3, A3,R52),(B2,L3,A3,R53),(B2,L3,A3,R54),(B2,L3,A3, R55),(B2,L3,A3,R56),(B2,L3,A4,R51),(B2,L3,A4,R52), (B2,L3,A4,R53),(B2,L3,A4,R54),(B2,L3,A4,R55),(B2,L3, A4,R56),(B2,L3,A5,R51),(B2,L3,A5,R52),(B2,L3,A5, R53),(B2,L3,A5,R54),(B2,L3,A5,R55),(B2,L3,A5,R56), (B2,L4,A1,R51),(B2,L4,A1,R52),(B2,L4,A1,R53),(B2,L4, A1,R54),(B2,L4,A1,R55),(B2,L4,A1,R56),(B2,L4,A2, R51),(B2,L4,A2,R52),(B2,L4,A2,R53),(B2,L4,A2,R54), (B2,L4,A2,R55),(B2,L4,A2,R56),(B2,L4,A3,R51),(B2,L4, A3,R52),(B2,L4,A3,R53),(B2,L4,A3,R54),(B2,L4,A3, R55),(B2,L4,A3,R56),(B2,L4,A4,R51),(B2,L4,A4,R52), (B2,L4,A4,R53),(B2,L4,A4,R54),(B2,L4,A4,R55),(B2,L4, A4,R56),(B2,L4,A5,R51),(B2,L4,A5,R52),(B2,L4,A5, R53),(B2,L4,A5,R54),(B2,L4,A5,R55),(B2,L4,A5,R56), (B2,L5,A1,R51),(B2,L5,A1,R52),(B2,L5,A1,R53),(B2,L5, A1,R54),(B2,L5,A1,R55),(B2,L5,A1,R56),(B2,L5,A2, R51),(B2,L5,A2,R52),(B2,L5,A2,R53),(B2,L5,A2,R54), (B2,L5,A2,R55),(B2,L5,A2,R56),(B2,L5,A3,R51),(B2,L5, A3,R52),(B2,L5,A3,R53),(B2,L5,A3,R54),(B2,L5,A3, R55),(B2,L5,A3,R56),(B2,L5,A4,R51),(B2,L5,A4,R52), (B2,L5,A4,R53),(B2,L5,A4,R54),(B2,L5,A4,R55),(B2,L5, A4,R56),(B2,L5,A5,R51),(B2,L5,A5,R52),(B2,L5,A5, R53),(B2,L5,A5,R54),(B2,L5,A5,R55),(B2,L5,A5,R56), (B3,L1,A1,R51),(B3,L1,A1,R52),(B3,L1,A1,R53),(B3,L1, A1,R54),(B3,L1,A1,R55),(B3,L1,A1,R56),(B3,L1,A2, R51),(B3,L1,A2,R52),(B3,L1,A2,R53),(B3,L1,A2,R54), (B3,L1,A2,R55),(B3,L1,A2,R56),(B3,L1,A3,R51),(B3,L1, A3,R52),(B3,L1,A3,R53),(B3,L1,A3,R54),(B3,L1,A3, R55),(B3,L1,A3,R56),(B3,L1,A4,R51),(B3,L1,A4,R52), (B3,L1,A4,R53),(B3,L1,A4,R54),(B3,L1,A4,R55),(B3,L1, A4,R56),(B3,L1,A5,R51),(B3,L1,A5,R52),(B3,L1,A5, R53),(B3,L1,A5,R54),(B3,L1,A5,R55),(B3,L1,A5,R56), (B3,L2,A1,R51),(B3,L2,A1,R52),(B3,L2,A1,R53),(B3,L2, A1,R54),(B3,L2,A1,R55),(B3,L2,A1,R56),(B3,L2,A2, R51),(B3,L2,A2,R52),(B3,L2,A2,R53),(B3,L2,A2,R54), (B3,L2,A2,R55),(B3,L2,A2,R56),(B3,L2,A3,R51),(B3,L2, A3,R52),(B3,L2,A3,R53),(B3,L2,A3,R54),(B3,L2,A3, R55),(B3,L2,A3,R56),(B3,L2,A4,R51),(B3,L2,A4,R52), (B3,L2,A4,R53),(B3,L2,A4,R54),(B3,L2,A4,R55),(B3,L2, A4,R56),(B3,L2,A5,R51),(B3,L2,A5,R52),(B3,L2,A5, R53),(B3,L2,A5,R54),(B3,L2,A5,R55),(B3,L2,A5,R56), (B3,L3,A1,R51),(B3,L3,A1,R52),(B3,L3,A1,R53),(B3,L3, A1,R54),(B3,L3,A1,R55),(B3,L3,A1,R56),(B3,L3,A2, R51),(B3,L3,A2,R52),(B3,L3,A2,R53),(B3,L3,A2,R54), (B3,L3,A2,R55),(B3,L3,A2,R56),(B3,L3,A3,R51),(B3,L3, A3,R52),(B3,L3,A3,R53),(B3,L3,A3,R54),(B3,L3,A3, R55),(B3,L3,A3,R56),(B3,L3,A4,R51),(B3,L3,A4,R52), (B3,L3,A4,R53),(B3,L3,A4,R54),(B3,L3,A4,R55),(B3,L3, A4,R56),(B3,L3,A5,R51),(B3,L3,A5,R52),(B3,L3,A5, R53),(B3,L3,A5,R54),(B3,L3,A5,R55),(B3,L3,A5,R56), (B3,L4,A1,R51),(B3,L4,A1,R52),(B3,L4,A1,R53),(B3,L4, A1,R54),(B3,L4,A1,R55),(B3,L4,A1,R56),(B3,L4,A2, R51),(B3,L4,A2,R52),(B3,L4,A2,R53),(B3,L4,A2,R54), (B3,L4,A2,R55),(B3,L4,A2,R56),(B3,L4,A3,R51),(B3,L4, A3,R52),(B3,L4,A3,R53),(B3,L4,A3,R54),(B3,L4,A3, R55),(B3,L4,A3,R56),(B3,L4,A4,R51),(B3,L4,A4,R52), (B3,L4,A4,R53),(B3,L4,A4,R54),(B3,L4,A4,R55),(B3,L4, A4,R56),(B3,L4,A5,R51),(B3,L4,A5,R52),(B3,L4,A5, R53),(B3,L4,A5,R54),(B3,L4,A5,R55),(B3,L4,A5,R56), (B3,L5,A1,R51),(B3,L5,A1,R52),(B3,L5,A1,R53),(B3,L5, A1,R54),(B3,L5,A1,R55),(B3,L5,A1,R56),(B3,L5,A2, R51),(B3,L5,A2,R52),(B3,L5,A2,R53),(B3,L5,A2,R54), (B3,L5,A2,R55),(B3,L5,A2,R56),(B3,L5,A3,R51),(B3,L5, A3,R52),(B3,L5,A3,R53),(B3,L5,A3,R54),(B3,L5,A3, R55),(B3,L5,A3,R56),(B3,L5,A4,R51),(B3,L5,A4,R52), (B3,L5,A4,R53),(B3,L5,A4,R54),(B3,L5,A4,R55),(B3,L5, A4,R56),(B3,L5,A5,R51),(B3,L5,A5,R52),(B3,L5,A5, R53),(B3,L5,A5,R54),(B3,L5,A5,R55),(B3,L5,A5,R56), (B4,L1,A1,R51),(B4,L1,A1,R52),(B4,L1,A1,R53),(B4,L1, A1,R54),(B4,L1,A1,R55),(B4,L1,A1,R56),(B4,L1,A2, R51),(B4,L1,A2,R52),(B4,L1,A2,R53),(B4,L1,A2,R54), (B4,L1,A2,R55),(B4,L1,A2,R56),(B4,L1,A3,R51), (B4,L1, A3,R52),(B4,L1,A3,R53),(B4,L1,A3,R54),(B4,L1,A3, R55),(B4,L1,A3,R56),(B4,L1,A4,R51),(B4,L1,A4,R52), (B4,L1,A4,R53),(B4,L1,A4,R54),(B4,L1,A4,R55),(B4,L1, A4,R56),(B4,L1,A5,R51),(B4,L1,A5,R52),(B4,L1,A5, R53),(B4,L1,A5,R54),(B4,L1,A5,R55),(B4,L1,A5,R56), (B4,L2,A1,R51),(B4,L2,A1,R52),(B4,L2,A1,R53),(B4,L2, A1,R54),(B4,L2,A1,R55),(B4,L2,A1,R56),(B4,L2,A2, R51),(B4,L2,A2,R52),(B4,L2,A2,R53),(B4,L2,A2,R54), (B4,L2,A2,R55),(B4,L2,A2,R56),(B4,L2,A3,R51),(B4,L2, A3,R52),(B4,L2,A3,R53),(B4,L2,A3,R54),(B4,L2,A3, R55),(B4,L2,A3,R56),(B4,L2,A4,R51),(B4,L2, A4,R52), (B4,L2, A4,R53),(B4,L2,A4,R54),(B4,L2,A4,R55),(B4,L2, A4,R56),(B4,L2,A5,R51),(B4,L2,A5,R52),(B4,L2,A5, R53),(B4,L2,A5,R54),(B4,L2,A5,R55),(B4,L2,A5,R56), (B4,L3,A1,R51),(B4,L3,A1,R52),(B4,L3,A1,R53),(B4,L3, A1,R54),(B4,L3,A1,R55),(B4,L3,A1,R56),(B4,L3,A2, R51),(B4,L3,A2,R52),(B4,L3,A2,R53),(B4,L3,A2,R54), (B4,L3,A2,R55),(B4,L3,A2,R56),(B4,L3,A3,R51),(B4,L3, A3,R52),(B4,L3,A3,R53),(B4,L3,A3,R54),(B4,L3,A3, R55),(B4,L3,A3,R56),(B4,L3,A4,R51),(B4,L3,A4,R52), (B4,L3,A4,R53),(B4,L3,A4,R54),(B4,L3,A4,R55),(B4,L3, A4,R56),(B4,L3,A5,R51),(B4,L3,A5,R52),(B4,L3,A5, R53),(B4,L3,A5,R54),(B4,L3,A5,R55),(B4,L3,A5,R56), (B4,L4,A1,R51),(B4,L4,A1,R52),(B4,L4,A1,R53),(B4,L4, A1,R54),(B4,L4,A1,R55),(B4,L4,A1,R56),(B4,L4,A2, R51),(B4,L4,A2,R52),(B4,L4,A2,R53),(B4,L4,A2,R54), (B4,L4,A2,R55),(B4,L4,A2,R56),(B4,L4,A3,R51),(B4,L4, A3,R52),(B4,L4,A3,R53),(B4,L4,A3,R54),(B4,L4,A3, R55),(B4,L4,A3,R56),(B4,L4,A4,R51),(B4,L4,A4,R52), (B4,L4,A4,R53),(B4,L4,A4,R54),(B4,L4,A4,R55),(B4,L4, A4,R56),(B4,L4,A5,R51),(B4,L4,A5,R52),(B4,L4,A5, R53),(B4,L4,A5,R54),(B4,L4,A5,R55),(B4,L4,A5,R56), (B4,L5,A1,R51),(B4,L5,A1,R52),(B4,L5,A1,R53),(B4,L5, A1,R54),(B4,L5,A1,R55),(B4,L5,A1,R56),(B4,L5,A2, R51),(B4,L5,A2,R52),(B4,L5,A2,R53),(B4,L5,A2,R54), (B4,L5,A2,R55),(B4,L5,A2,R56),(B4,L5,A3,R51),(B4,L5, A3,R52),(B4,L5,A3,R53),(B4,L5,A3,R54),(B4,L5,A3, R55),(B4,L5,A3,R56),(B4,L5,A4,R51),(B4,L5,A4,R52), (B4,L5,A4,R53),(B4,L5,A4,R54),(B4,L5,A4,R55),(B4,L5, A4,R56),(B4,L5,A5,R51),(B4,L5,A5,R52),(B4,L5,A5, R53),(B4,L5,A5,R54),(B4,L5,A5,R55),(B4,L5,A5,R56), (B5,L1,A1,R51),(B5,L1,A1,R52),(B5,L1,A1,R53),(B5,L1, A1,R54),(B5,L1,A1,R55),(B5,L1,A1,R56),(B5,L1,A2, R51),(B5,L1,A2,R52),(B5,L1,A2,R53),(B5,L1,A2,R54), (B5,L1,A2,R55),(B5,L1,A2,R56),(B5,L1,A3,R51),(B5,L1, A3,R52),(B5,L1,A3,R53),(B5,L1,A3,R54),(B5,L1,A3, R55),(B5,L1,A3,R56),(B5,L1,A4,R51),(B5,L1,A4,R52), (B5,L1,A4,R53),(B5,L1,A4,R54),(B5,L1,A4,R55),(B5,L1, A4,R56),(B5,L1,A5,R51),(B5,L1,A5,R52),(B5,L1,A5, R53),(B5,L1,A5,R54),(B5,L1,A5,R55),(B5,L1,A5,R56), (B5,L2,A1,R51),(B5,L2,A1,R52),(B5,L2,A1,R53),(B5,L2, A1,R54),(B5,L2,A1,R55),(B5,L2,A1,R56),(B5,L2,A2, R51),(B5,L2,A2,R52),(B5,L2,A2,R53),(B5,L2,A2,R54), (B5,L2,A2,R55),(B5,L2,A2,R56),(B5,L2,A3,R51),(B5,L2, A3,R52),(B5,L2,A3,R53),(B5,L2,A3,R54),(B5,L2,A3, R55),(B5,L2,A3,R56),(B5,L2,A4,R51),(B5,L2,A4,R52), (B5,L2,A4,R53),(B5,L2,A4,R54),(B5,L2,A4,R55),(B5,L2, A4,R56),(B5,L2,A5,R51),(B5, L2,A5,R52),(B5,L2,A5, R53),(B5,L2,A5,R54),(B5,L2,A5,R55),(B5,L2,A5,R56), (B5,L3,A1,R51),(B5,L3,A1,R52),(B5,L3,A1,R53),(B5,L3, A1,R54),(B5,L3,A1,R55),(B5,L3,A1,R56),(B5,L3,A2, R51),(B5,L3,A2,R52),(B5,L3,A2,R53),(B5,L3,A2,R54), (B5,L3,A2,R55),(B5,L3,A2,R56),(B5,L3,A3,R51),(B5,L3, A3,R52),(B5,L3,A3,R53),(B5,L3,A3,R54),(B5,L3,A3, R55),(B5,L3,A3,R56),(B5,L3,A4,R51),(B5,L3,A4,R52), (B5,L3,A4,R53),(B5,L3,A4,R54),(B5,L3,A4,R55),(B5,L3, A4,R56),(B5,L3,A5,R51),(B5,L3,A5,R52),(B5,L3,A5, R53),(B5,L3, A5,R54),(B5,L3,A5,R55),(B5,L3,A5,R56), (B5,L4,A1,R51),(B5,L4,A1,R52),(B5,L4,A1,R53),(B5,L4, A1,R54),(B5,L4,A1,R55),(B5,L4,A1,R56),(B5,L4,A2, R51),(B5,L4,A2,R52),(B5,L4,A2,R53),(B5,L4,A2,R54), (B5,L4,A2,R55),(B5,L4,A2,R56),(B5,L4,A3,R51),(B5,L4, A3,R52),(B5,L4,A3,R53),(B5,L4,A3,R54),(B5,L4,A3, R55),(B5,L4,A3,R56),(B5,L4,A4,R51),(B5,L4,A4,R52), (B5,L4,A4,R53),(B5,L4,A4,R54),(B5,L4,A4,R55),(B5,L4, A4,R56),(B5,L4,A5,R51),(B5,L4,A5,R52),(B5,L4,A5, R53),(B5,L4,A5,R54),(B5,L4,A5,R55),(B5,L4,A5,R56), (B5,L5,A1,R51),(B5,L5,A1,R52),(B5,L5,A1,R53),(B5,L5, A1,R54),(B5,L5,A1,R55),(B5,L5,A1,R56),(B5,L5,A2, R51),(B5,L5,A2,R52),(B5,L5,A2,R53),(B5,L5,A2,R54), (B5,L5,A2,R55),(B5,L5,A2,R56),(B5,L5,A3,R51),(B5,L5, A3,R52),(B5,L5,A3,R53),(B5,L5,A3,R54),(B5,L5,A3, R55),(B5,L5,A3,R56),(B5,L5,A4,R51),(B5,L5,A4,R52), (B5,L5,A4,R53),(B5,L5,A4,R54),(B5,L5,A4,R55),(B5,L5, A4,R56),(B5,L5,A5,R51),(B5,L5,A5,R52),(B5,L5,A5, R53),(B5,L5,A5,R54),(B5,L5,A5,R55),(B5,L5,A5,R56).

Test: Measurement of Inhibition of β-Secretase Activity

Zero point five μL of the test compounds (dissolved in N,N'-dimethylsulfoxide) were incubated with 48.5 μL of the fluorescence-quenched peptide substrate solution (Biotin-XSEVNLDAEFRHDSGC-Eu:X=ε-amino-n-caproic acid, Eu=Europium cryptate) and 1 μL of recombinant human BACE-1 protein (R&D systems) for 3 h at 30° C. in the 96 well half-area plate (black color plate, Costar). The substrate peptide was synthesized by reacting with Biotin-XSEVNLDAEFRHDSGC (Peptide Institute) and Cryptate TBPCOOH mono SMP (CIS bio international). The final concentration of the substrate peptide and recombinant human BACE-1 protein were 18 nM and 7.4 nM, respectively. The enzymatic reaction was performed in sodium acetate buffer (50 mM sodium acetate (pH5.0), 0.008% Triton X-100). After the reaction, a 50 μL of 8.0 μg/mL Streptavidin-XL665 (CIS bio international) dissolved in phosphate buffer (150 mM $K_2HPO_4$—$KH_2PO_4$ (pH 7.0), 0.008% Triton X-100, 0.8 M KF) was add to each well and incubated for 1 h at 30° C. Then, the fluorescence intensity (excitation wavelength 320 nm, emission wavelength 620 nM and 665 nM) in each well was measured using Wallac 1420 multilabel counter (Perkin Elmer life sciences). The enzymatic activity was calculated by the each fluorescence intensity ratio ([ratio of fluorescence at 665 nm to that at 620 nm]×10,000). $IC_{50}$ values of test compounds were indicated in table 170.

TABLE 170

| Compound No. | $IC_{50}$ value (μM) |
|---|---|
| 1186 | 5.7 |
| 639 | 7.9 |
| 1000 | 8.0 |
| 246 | 2.9 |
| 269 | 7.0 |
| 1010 | 2.8 |
| 417 | 5.0 |
| 161 | 7.7 |
| 220 | 1.5 |
| 1207 | 4.0 |
| 998 | 4.5 |
| 1205 | 8.1 |

TABLE 170-continued

| Compound No. | IC$_{50}$ value (μM) |
|---|---|
| 616 | 5.9 |
| 504 | 2.5 |
| 799 | 6.7 |
| 490 | 5.1 |
| 972 | 0.45 |
| 1160 | 0.72 |
| 753 | 5.6 |
| 786 | 0.156 |
| 165 | 0.0394 |
| 1132 | 2.563 |
| 570 | 0.149 |
| 1014 | 0.165 |
| 731 | 0.278 |
| 1262 | 0.140 |
| 964 | 0.264 |
| 793 | 0.061 |
| 625 | 1.288 |
| 498 | 0.930 |
| 26 | 1.977 |
| 465 | 3.239 |
| 1197 | 0.912 |
| 395 | 1.500 |
| 896 | 8.497 |
| 660 | 4.586 |
| 664 | 3.642 |
| 176 | 1.479 |
| 284 | 0.229 |
| 912 | 0.175 |
| 212 | 0.220 |
| 163 | 2.278 |
| 1244 | 0.130 |
| 52 | 10.0 |
| 698 | 0.165 |
| 96 | 0.163 |
| 822 | 0.243 |
| 739 | 0.049 |
| 832 | 0.222 |
| 897 | 0.816 |
| 1100 | 0.037 |
| 740 | 0.505 |
| 436 | 0.160 |
| 1043 | 0.027 |
| 1199 | 0.032 |
| 73 | 0.435 |
| 127 | 0.054 |
| 309 | 0.833 |
| 1135 | 2.296 |
| 1035 | 0.174 |

The IC$_{50}$ value of the following compounds were less than 100 μM by the same test.

3, 4, 6, 8, 12, 17, 18, 30, 31, 35, 36, 38, 39, 42, 43, 57, 61, 67, 67, 71, 77, 78, 80, 85, 97, 99, 105, 106, 113, 114, 115, 117, 120, 121, 125, 128, 129, 130, 134, 139, 144, 154, 157, 159, 164, 172, 175, 178, 181, 182, 186, 189, 200, 200, 201, 204, 207, 209, 211, 214, 215, 216, 228, 232, 240, 241, 243, 243, 243, 251, 255, 259, 267, 273, 275, 278, 279, 281, 282, 293, 298, 299, 300, 302, 303, 307, 314, 319, 321, 322, 326, 328, 330, 333, 335, 339, 341, 344, 345, 346, 348, 352, 353, 357, 358, 359, 359, 359, 360, 361, 363, 369, 370, 373, 378, 380, 383, 389, 390, 393, 396, 397, 402, 405, 406, 409, 410, 413, 415, 426, 442, 443, 444, 451, 452, 454, 456, 463, 467, 469, 472, 472, 479, 480, 482, 483, 491, 493, 497, 500, 501, 502, 509, 511, 515, 516, 517, 527, 528, 532, 542, 544, 549, 550, 551, 558, 560, 568, 569, 575, 578, 584, 586, 588, 591, 600, 607, 608, 611, 613, 618, 620, 629, 634, 634, 637, 643, 646, 652, 657, 661, 671, 677, 681, 687, 691, 708, 711, 719, 720, 723, 725, 728, 729, 730, 732, 735, 743, 746, 756, 758, 761, 770, 775, 781, 787, 788, 790, 791, 792, 796, 797, 802, 803, 804, 808, 809, 813, 816, 819, 820, 824, 833, 835, 836, 847, 850, 861, 865, 866, 871, 876, 887, 893, 894, 900, 905, 906, 908, 910, 919, 922, 928, 932, 933, 935, 936, 939, 941, 943, 944, 946, 947, 949, 959, 966, 971, 984, 986, 988, 990, 1004, 1005, 1007, 1009, 1013, 1020, 1028, 1034, 1039, 1046, 1055, 1062, 1063, 1069, 1074, 1077, 1084, 1089, 1096, 1099, 1108, 1109, 1114, 1124, 1125, 1131, 1140, 1142, 1145, 1147, 1148, 1150, 1164, 1165, 1172, 1174, 1184, 1185, 1193, 1211, 1217, 1221, 1237, 1241, 1243, 1255, 1256, 1257, 1258, 1261, 1263, 1264, 1265, 1266, 1268, 1269, 1270, 1271, 1272, 1274, and so on.

Formulation Example 1

A granule containing the following ingredients is prepared.

| Ingredient | Compound represented by formula (I) | 10 mg |
|---|---|---|
| | Lactose | 700 mg |
| | Corn starch | 274 mg |
| | HPC-L | 16 mg |
| | | 1000 mg |

The compound represented by the formula (I) and lactose are passed through a 60 mesh sieve. Corn starch is passed through a 120 mesh sieve. These are mixed with a V-type mixer. To a mixed powder is added a HPC-L (lower viscosity hydroxypropylcellulose) aqueous solution, the materials are kneaded, granulated (extrusion granulation, pore diameter 0.5 to 1 mm), and dried. The resulting dry granule is passed through a sieve using a vibration sieve (12/60 mesh) to obtain a granule.

Formulation Example 2

A granule for filling into a capsule containing the following ingredients is prepared.

| Ingredient | Compound represented by formula (I) | 15 mg |
|---|---|---|
| | Lactose | 90 mg |
| | Corn starch | 42 mg |
| | HPC-L | 3 mg |
| | | 150 mg |

The compound represented by the formula (I) and lactose are passed through a 60 mesh sieve. Corn starch is passed through a 120 mesh sieve. These are mixed, to a mixed powder is added a HPC-L solution, the materials are kneaded, granulated, and dried. The resulting dry granule is size-adjusted, 150 mg of which is filled into a No. 4 hard gelatin capsule.

Formulation Example 3

A tablet containing the following ingredients is prepared.

| Ingredient | Compound represented by the formula (I) | 10 mg |
|---|---|---|
| | Lactose | 90 mg |
| | Microcrystalline cellulose | 30 mg |
| | CMC-Na | 15 mg |
| | Magnesium stearate | 5 mg |
| | | 150 mg |

The compound represented by the formula (I), lactose, microcrystalline cellulose, CMC—Na (carboxymethylcellulose sodium salt) are passed through a 60 mesh sieve, and mixed. Into a mixed powder is mixed magnesium stearate to obtain a mixed powder for tabletting. The present mixed powder is compressed to obtain 150 mg of a tablet.

Formulation Example 4

The following ingredients are warmed, mixed, and sterilized to obtain an injectable.

| Ingredient | Compound represented by the formula (I) | 3 mg |
| | Nonionic surfactant | 15 mg |
| | Purified water for injection | 1 ml |

INDUSTRIAL APPLICABILITY

The present invention is useful as an agent for treating disease induced by production, secretion and/or deposition of amyloid β.

The invention claimed is:
1. A compound represented by the general formula (I):

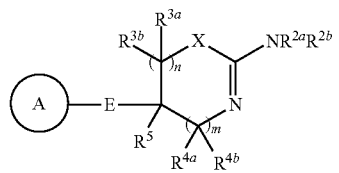

wherein ring A is an optionally substituted heterocyclic group,
the heterocyclic group being substituted optionally with at least one selected from the group consisting of
(A) the substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;
(B) lower alkyl optionally substituted with one or more substituents selected from the group of substituent α;
(C) amino lower alkyl substituted with one or more substituents selected from the group of substituent α;
(D) hydroxyimino lower alkyl;
(E) lower alkoxyimino lower alkyl;
(F) lower alkenyl optionally substituted with one or more substituents selected from the group of substituent α;
(G) lower alkynyl optionally substituted with one or more substituents selected from the group of substituent α;
(H) lower alkoxy optionally substituted with one or more substituents selected from the group of substituent α;
(I) lower alkylthio optionally substituted with one or more substituents selected from the group of substituent α;
(J) lower alkylamino substituted with one or more substituents selected from the group of substituent α;
(K) lower alkylsulfonyl optionally substituted with one or more substituents selected from the group of substituent α;
(L) aryl lower alkoxycarbonyl optionally substituted with one or more substituents selected from the group of substituent α, azido, and lower alkyl;
(M) acyl substituted with one or more substituents selected from the group of substituent α; and the ring part of the carbocyclic carbonyl and the heterocyclic carbonyl is substituted optionally with at least one selected from the group of lower alkyl; the substituent group α; and lower alkyl substituted with at least one selected from the group of the substituent α;
(N) cycloalkyl optionally substituted with one or more substituents selected from the group of substituent α, azido, and lower alkyl;
(O) lower alkylsulfinyl optionally substituted with one or more substituents selected from the group of substituent α;
(P) sulfamoyl;
(Q) aryl optionally substituted with one or more substituents selected from the group of substituent α, azido, and lower alkyl;
(R) heterocyclic group optionally substituted with one or more substituents selected from the group of substituent α, azido, and lower alkyl;
(S) aryloxy optionally substituted with one or more substituents selected from the group of substituent α, azido, and lower alkyl;
(T) heterocyclicoxy optionally substituted with one or more substituents selected from the group of substituent α, azido, and lower alkyl;
(U) arylthio optionally substituted with one or more substituents selected from the group of substituent α, azido, and lower alkyl;
(V) heterocyclic thio optionally substituted with one or more substituents selected from the group of substituent α, azido, and lower alkyl;
(W) arylamino optionally substituted with one or more substituents selected from the group of substituent α, azido, and lower alkyl;
(X) heterocyclicamino optionally substituted with one or more substituents selected from the group of substituent α, azido, and lower alkyl;
(Y) aryl lower alkylamino optionally substituted with one or more substituents selected from the group of substituent α, azido, and lower alkyl;
(Z) heterocyclic lower alkylamino optionally substituted with one or more substituents selected from the group of substituent α, azido, and lower alkyl;
(AA) lower alkyl sulfamoyl optionally substituted with one or more substituents selected from the group of substituent α;
(AB) aryl sulfamoyl optionally substituted with one or more substituents selected from the group of substituent α, azido, and lower alkyl;
(AC) heterocyclic sulfamoyl optionally substituted with one or more substituents selected from the group of substituent α, azido, and lower alkyl;
(AD) arylsulfonyl substituted optionally with one or more substituents selected from the group of substituent α, azido, and lower alkyl;
(AE) heterocyclic sulfonyl optionally substituted with one or more substituents selected from the group of substituent α, azido, and lower alkyl;
(AF) aryl carbamoyl optionally substituted with one or more substituents selected from the group of substituent α, azido, and lower alkyl;

(AG) heterocyclic carbamoyl optionally substituted with one or more substituents selected from the group of substituent α, azido, and lower alkyl;
(AH) aryl lower alkylcarbamoyl optionally substituted with one or more substituents selected from the group of substituent α, azido, and lower alkyl;
(AI) heterocyclic lower alkylcarbamoyl optionally substituted with one or more substituents selected from the group of substituent α, azido, and lower alkyl;
(AJ) aryloxycarbonyl optionally substituted with one or more substituents selected from the group of substituent α, azido, and lower alkyl;
(AK) heterocyclicoxycarbonyl optionally substituted with one or more substituents selected from the group of substituent α, azido, and lower alkyl;
(AL) lower alkylenedioxy substituted optionally with halogen;
(AM) oxo;
(AN) azido; and
(AO) one of the following formulae:

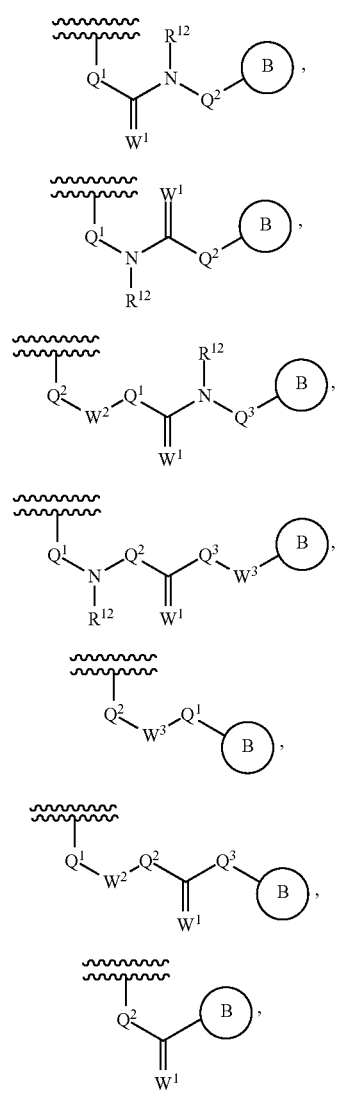
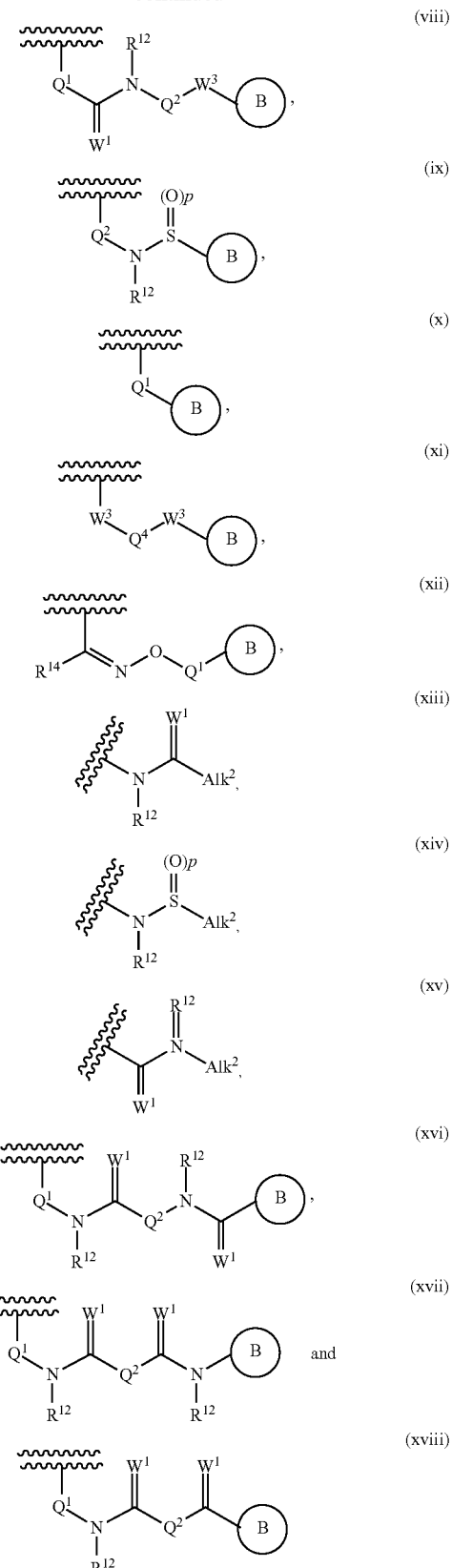

wherein $Q^1$, $Q^2$ and $Q^3$ are each independently a bond, lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$Q^4$ is lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$W^1$ and $W^2$ are each independently O or S;

$W^3$ is O, S or $NR^{12}$;

$R^{12}$ is a hydrogen atom, lower alkyl, hydroxy lower alkyl, lower alkoxy lower alkyl, lower alkoxycarbonyl lower alkyl, carbocyclic group lower alkyl or acyl;

$R^{14}$ is a hydrogen atom or lower alkyl;

ring B is a carbocyclic group or a heterocyclic group, the carbocyclic group and the heterocyclic group being substituted optionally with at least one selected from the group consisting of the above (A) to (AM);

(a) a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

(b) lower alkyl optionally substituted with the substituent α;

(c) amino lower alkyl substituted with the substituent α;

(d) hydroxyimino lower alkyl;

(e) lower alkoxyimino lower alkyl;

(f) lower alkenyl optionally substituted with the substituent α;

(g) lower alkynyl optionally substituted with the substituent α;

(h) lower alkoxy optionally substituted with the substituent α;

(i) lower alkylthio optionally substituted with the substituent α;

(j) lower alkylamino substituted with the substituent α;

(k) lower alkylsulfonyl optionally substituted with the substituent α;

(l) aryl lower alkoxycarbonyl optionally substituted with one or more substituents selected from the group of substituent α and lower alkyl;

(m) acyl substituted with the substituent α; and the ring part of the carbocyclic carbonyl and the heterocyclic carbonyl is substituted optionally with at least one selected from the group of lower alkyl; the substituent group α; and lower alkyl substituted with at least one selected from the group of the substituent α, (n) lower alkylsulfonyl optionally substituted with the substituent α;

(o) sulfamoyl;

(p) lower alkyl sulfamoyl optionally substituted with one or more substituents selected from the group of substituent α;

(q) cycloalkyl optionally substituted with one or more substituents selected from the group of substituent α, azido and lower alkyl;

(r) aryl optionally substituted with one or more substituents selected from the group of substituent α, azido and lower alkyl;

(s) heterocyclic group optionally substituted with one or more substituents selected from the group of substituent α, azido and lower alkyl;

(t) aryloxy optionally substituted with one or more substituents selected from the group of substituent α, azido and lower alkyl;

(u) heterocyclicoxy optionally substituted with one or more substituents selected from the group of substituent α, azido and lower alkyl;

(v) arylthio optionally substituted with one or more substituents selected from the group of substituent α, azido and lower alkyl;

(w) heterocyclic thio optionally substituted with one or more substituents selected from the group of substituent α, azido and lower alkyl;

(x) arylamino optionally substituted with one or more substituents selected from the group of substituent α, azido and lower alkyl;

(y) heterocyclic amino optionally substituted with one or more substituents selected from the group of substituent α, azido and lower alkyl;

(z) aryl lower alkylamino optionally substituted with one or more substituents selected from the group of substituent α, azido and lower alkyl;

(aa) heterocyclic lower alkylamino optionally substituted with one or more substituents selected from the group of substituent α, azido and lower alkyl;

(ab) arylsulfamoyl optionally substituted with one or more substituents selected from the group of substituent α, azido and lower alkyl;

(ac) heterocyclic sulfamoyl optionally substituted with one or more substituents selected from the group of substituent α, azido and lower alkyl;

(ad) arylsulfonyl optionally substituted with one or more substituents selected from the group of substituent α, azido and lower alkyl;

(ae) heterocyclic sulfonyl optionally substituted with one or more substituents selected from the group of substituent α, azido and lower alkyl;

(af) arylcarbamoyl optionally substituted with one or more substituents selected from the group of substituent α, azido and lower alkyl;

(ag) heterocyclic carbamoyl optionally substituted with one or more substituents selected from the group of substituent α, azido and lower alkyl;

(ah) aryl lower alkylcarbamoyl optionally substituted with one or more substituents selected from the group of substituent α, azido and lower alkyl;

(ai) heterocyclic lower alkylcarbamoyl optionally substituted with one or more substituents selected from the group of substituent α, azido and lower alkyl;

(aj) aryloxy carbonyl optionally substituted with one or more substituents selected from the group of substituent α, azido and lower alkyl;

(ak) heterocyclicoxycarbonyl optionally substituted with one or more substituents selected from the group of substituent α, azido and lower alkyl;

(al) lower alkylenedioxy substituted optionally with halogen; and
(am) oxo;

Alk² is lower alkyl, lower alkyl being substituted optionally with at least one selected from the group consisting of a substituent α;

p is an integer of 1 or 2;

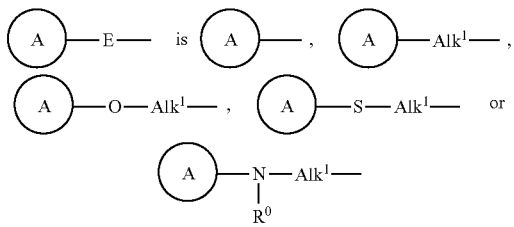

Alk¹ is lower alkylene or lower alkenylene;
R⁰ is a hydrogen atom, lower alkyl, or acyl;
X is S
$R^{2a}$ and $R^{2b}$ are each independently a hydrogen atom, hydroxy, optionally substituted lower alkyl, optionally substituted lower alkenyl, optionally substituted amino, optionally substituted amidino, optionally substituted acyl, optionally substituted carbamoyl, optionally substituted carbamoylcarbonyl, optionally substituted lower alkylsulfonyl, optionally substituted arylsulfonyl, an optionally substituted carbocyclic group, or an optionally substituted heterocyclic group;

lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenyl being substituted optionally with the substituent α, amino being substituted optionally with at least one selected from the group consisting of lower alkyl, acyl, hydroxy, lower alkoxy, lower alkoxycarbonyl, a carbocyclic group and a heterocyclic group, amidino being substituted optionally with at least one selected from the group consisting of lower alkyl, acyl, hydroxy, lower alkoxy, lower alkoxycarbonyl, a carbocyclic group and a heterocyclic group, acyl being substituted optionally with the substituent α; and the ring part of the carbocyclic carbonyl and the heterocyclic carbonyl is substituted optionally with at least one selected from the group of lower alkyl; the substituent group α; and lower alkyl substituted with at least one selected from the group of the substituent α, carbamoyl being substituted optionally with at least one selected from the group consisting of lower alkyl, acyl, hydroxy, lower alkoxy, lower alkoxycarbonyl, a carbocyclic group and a heterocyclic group, carbamoylcarbonyl being substituted optionally with at least one selected from the group consisting of lower alkyl, acyl, hydroxy, lower alkoxy, lower alkoxycarbonyl, a carbocyclic group and a heterocyclic group, lower alkylsulfonyl being substituted optionally with the substituent α, arylsulfonyl being substituted optionally with at least one selected from the group consisting of the substituent α and a lower alkyl, and the carbocyclic group and the heterocyclic group being substituted optionally with at least one selected from the group consisting of the substituent α and lower alkyl;

$R^{3a}$, $R^{3b}$, $R^{4a}$, and $R^{4b}$ are each independently a hydrogen atom, halogen, hydroxy, optionally substituted lower alkyl, optionally substituted lower alkenyl, optionally substituted acyl, carboxy, optionally substituted lower alkoxycarbonyl, optionally substituted amino, optionally substituted carbamoyl, an optionally substituted carbocyclic group, or an optionally substituted heterocyclic group;

lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenyl being substituted optionally with the substituent α, acyl being substituted optionally with the substituent α; and the ring part of the carbocyclic carbonyl and the heterocyclic carbonyl is substituted optionally with at least one selected from the group of lower alkyl; the substituent group α; and lower alkyl substituted with at least one selected from the group of the substituent α, lower alkoxycarbonyl being substituted optionally with the substituent α, amino being substituted optionally with at least one selected from the group consisting of lower alkyl, acyl, hydroxy, lower alkoxy, lower alkoxycarbonyl, a carbocyclic group and a heterocyclic group, carbamoyl being substituted optionally with at least one selected from the group consisting of lower alkyl, acyl, hydroxy, lower alkoxy, lower alkoxycarbonyl, a carbocyclic group and a heterocyclic group, and the carbocyclic group and the heterocyclic group being substituted optionally with at least one selected from the group consisting of the substituent α and a lower alkyl;

n=2 and m=0;

each $R^{3a}$, each $R^{3b}$, each $R^{4a}$, and each $R^{4b}$ may be independently different;

$R^5$ is a hydrogen atom, optionally substituted lower alkyl, optionally substituted lower alkenyl, optionally substituted lower alkynyl, an optionally substituted carbocyclic group, an optionally substituted heterocyclic group;

lower alkyl being substituted optionally with at least one selected from the group consisting of a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenyl being substituted optionally with the substituent α, lower alkynyl being substituted optionally with the substituent α, and the carbocyclic group and the heterocyclic group being substituted optionally with at least one selected from the group consisting of the substituent α and a lower alkyl;
wherein acyl includes aliphatic acyl of a carbon number of 1 to 10, carbocyclic carbonyl and heterocyclic carbonyl; when

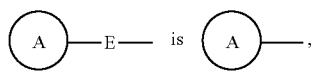

$R^5$ and ring A can be taken together to form

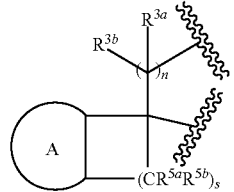

wherein $R^{5a}$ and $R^{5b}$ are each independently a hydrogen atom or lower alkyl;
s is an integer of 1 to 4;
each $R^{5a}$ and each $R^{5b}$ may be different;
or its pharmaceutically acceptable salt thereof.

2. The compound according to claim 1, wherein E is a bond, or its pharmaceutically acceptable salt thereof.

3. The compound according to claim 1, wherein $R^5$ is optionally substituted lower alkyl, optionally substituted lower alkenyl, optionally substituted lower alkynyl, an optionally substituted carbocyclic group, or an optionally substituted heterocyclic group,
lower alkyl being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group,
lower alkenyl being substituted optionally with the substituent α,
lower alkynyl being substituted optionally with the substituent α, and
the carbocyclic group and the heterocyclic group being substituted optionally with at least one selected from the group consisting of the substituent α and lower alkyl,
or its pharmaceutically acceptable salt thereof.

4. The compound according to claim 1, wherein $R^{2a}$ is a hydrogen atom; $R^{2b}$ is a hydrogen atom, optionally substituted lower alkyl, optionally substituted acyl, optionally substituted lower alkylsulfonyl, or optionally substituted amidino,
lower alkyl being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group,
acyl being substituted optionally with the substituent α, and the ring part of the carbocyclic carbonyl and the heterocyclic carbonyl is substituted optionally with at least one selected from the group of lower alkyl; the substituent group α; and lower alkyl substituted with at least one selected from the group of the substituent α,
lower alkylsulfonyl being substituted optionally with the substituent α, and
amidino being substituted optionally with at least one selected from the group consisting of lower alkyl, acyl, hydroxy, lower alkoxy, lower alkoxycarbonyl, a carbocyclic group and a heterocyclic group,
or its pharmaceutically acceptable salt thereof.

5. The compound according to claim 1, wherein $NR^{2a}R^{2b}$ is represented by the formula:

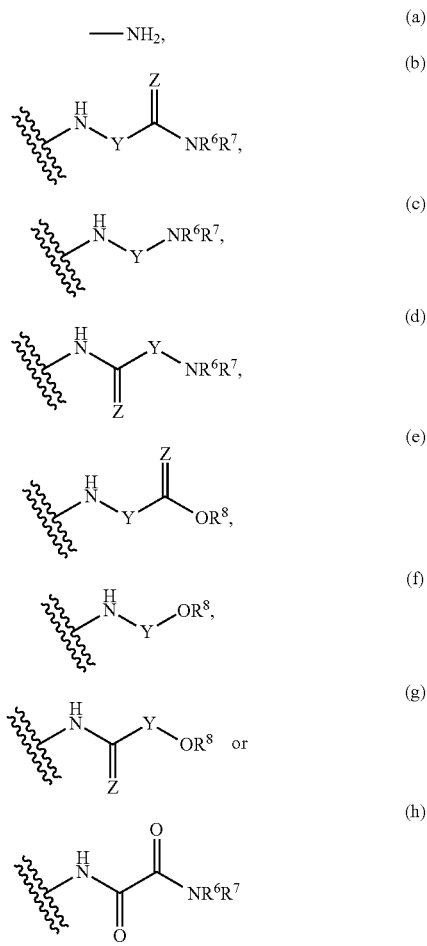

$R^6$, $R^7$, and $R^8$ are each independently a hydrogen atom, lower alkyl, or acyl;
Y is optionally substituted lower alkylene, optionally substituted lower alkenylene, or optionally substituted lower alkynylene;
lower alkylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkenylene being substituted optionally with the substituent α, and lower alkynylene being substituted optionally with the substituent α;

Z is O or S;

or its pharmaceutically acceptable salt thereof.

6. The compound according to 1, wherein $R^5$ is C1 to C3 alkyl, or its pharmaceutically acceptable salt thereof.

7. The compound according to claim 1, wherein $R^5$ is methyl, or its pharmaceutically acceptable salt thereof.

8. The compound according to claim 1, wherein $R^{3a}$ and $R^{3b}$ are each independently a hydrogen atom, halogen, hydroxy, optionally substituted lower alkyl, optionally substituted lower alkoxy, or optionally substituted aryl, lower alkyl being substituted optionally with at least one selected from the group consisting of a substituent α, a hydroxyimino group, and a lower alkoxyimino group, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkoxy being substituted optionally with the substituent α, and aryl being substituted optionally with the substituent α;

or its pharmaceutically acceptable salt thereof.

9. The compound according to claim 1, wherein all of $R^{3a}$ and all of $R^{3b}$ are hydrogen atoms, or its pharmaceutically acceptable salt thereof.

10. The compound according to claim 1, wherein the heterocyclic group in ring A is pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, thiazolyl, thiadiazolyl, isothiazolyl, furyl, thienyl, indolyl, isoindolyl, indazolyl, indolidinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzioxazolyl, benzoxazolyl, benzoxadiazolyl, benzoisothiazolyl, benzothiazolyl, benzothiadiazolyl, benzofuryl, isobenzofuryl, benzothienyl, benzotriazolyl, imidazopyridyl, pyrazolopyridyl, triazolopyridyl, imidazothiazolyl, pyrazinopyridazinyl, quinazolinyl, dihydrobenzofuryl, tetrahydroquinolyl, tetrahydroisoquinolyl, dihydrobenzoxazine, tetrahydrobenzothienyl, carbazolyl, acridinyl, xanthenyl, phenothiazinyl, phenoxathiinyl, phenoxazinyl, dibenzofuryl, imidazoquinolyl, dioxanyl, thiiranyl, oxyranyl, oxathioranyl, azethidinyl, thianyl, pyrrolidinyl, pyrrolinyl, imidazolidinyl, imidazolinyl, pyrazolidinyl, pyrazolinyl, piperidyl, piperazinyl, morpholinyl, morpholino, thiomorpholinyl, thiomorpholino, dihydropyridyl, dihydrobenzoimidazolyl, tetrahydropyridyl, tetrahydrofuryl, tetrahydropyranyl, tetrahydrothiazolyl, tetrahydroisothiazolyl, dihydroxadinyl, hexahydroazepinyl or tetrahydroazepinyl, the heterocyclic group being substituted optionally with at least one selected from the group consisting of the above (A) to (AO), or its pharmaceutically acceptable salt thereof.

11. The compound according to claim 1, wherein the heterocyclic group in ring A is

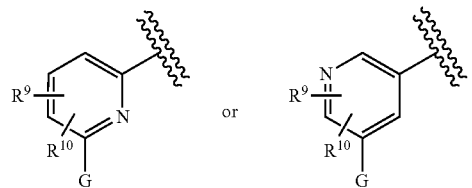

wherein $R^9$ and $R^{10}$ are each independently a hydrogen atom, halogen, hydroxy, optionally substituted lower alkyl, cyano, nitro, optionally substituted lower alkoxy, optionally substituted acyl, optionally substituted amino, optionally substituted carbamoyl, optionally substituted carbamoyloxy, optionally substituted lower alkylsulfonyl, optionally substituted arylsulfonyl, optionally substituted lower alkylsulfonyloxy, optionally substituted arylsulfonyloxy, an optionally substituted carbocyclic group, optionally substituted carbocyclicoxy, an optionally substituted heterocyclic group or optionally substituted heterocyclicoxy, lower alkyl being substituted optionally with at least one selected from the group consisting of a substituent α, a hydroxyimino group, and a lower alkoxyimino group, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group, lower alkoxy being substituted optionally with the substituent α, acyl includes aliphatic acyl of a carbon number of 1 to 10, carbocyclic carbonyl and heterocyclic carbonyl; and acyl being substituted optionally with the substituent α; and the ring part of the carbocyclic carbonyl and the heterocyclic carbonyl is substituted optionally with at least one selected from the group of lower alkyl; the substituent group α; and lower alkyl substituted with at least one selected from the group of the substituent α, amino being substituted optionally with at least one selected from the group consisting of lower alkyl, acyl, hydroxy, lower alkoxy, lower alkoxycarbonyl, a carbocyclic group and a heterocyclic group, carbamoyl being substituted optionally with at least one selected from the group consisting of lower alkyl, acyl, hydroxy, lower alkoxy, lower alkoxycarbonyl, a carbocyclic group and a heterocyclic group, carbamoyloxy being substituted optionally with at least one selected from the group consisting of lower alkyl, acyl, hydroxy, lower alkoxy, lower alkoxycarbonyl, a carbocyclic group and a heterocyclic group, lower alkylsulfonyl being substituted optionally with the substituent α, arylsulfonyl being substituted optionally with at least one selected from the group consisting of the substituent α and lower alkyl, lower alkylsulfonyloxy being substituted optionally with the substituent α, arylsulfonyloxy being substituted optionally with the substituent α, the carbocyclic group, carbocyclicoxy, the heterocyclic group, and heterocyclicoxy being substituted optionally with at least one selected from the group consisting of lower alkyl and the substituent α;

G is represented by the following formula:

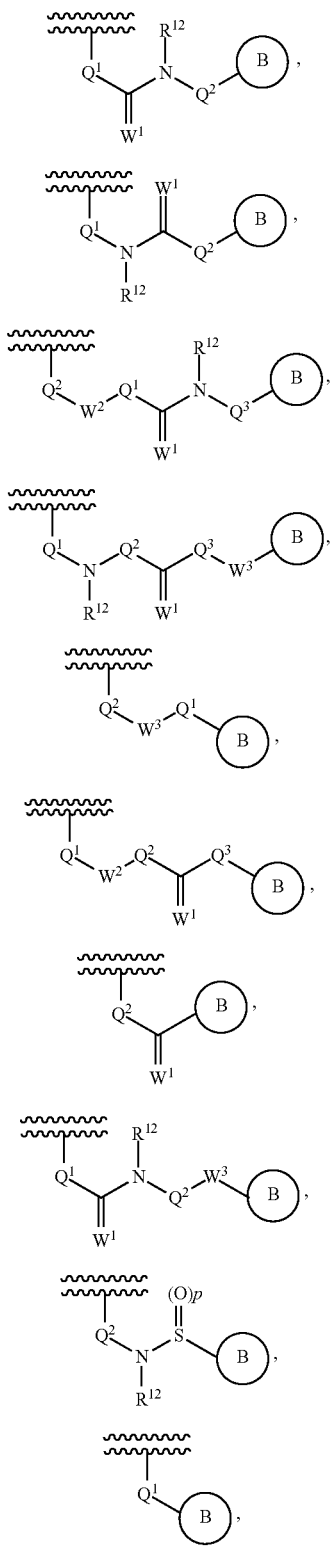

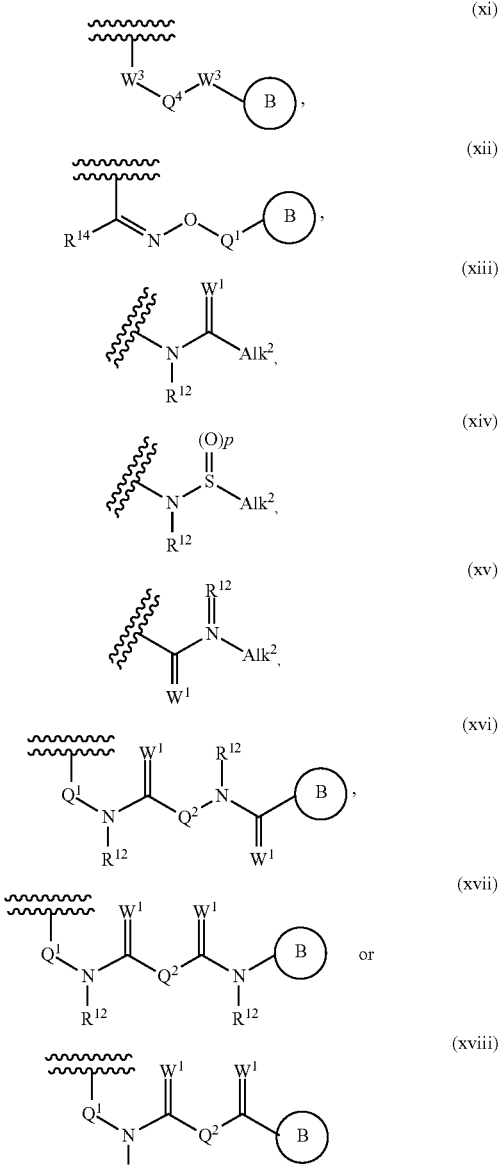

wherein $Q^1$, $Q^2$ and $Q^3$ are each independently a bond, lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$Q^4$ is lower alkylene or lower alkenylene, lower alkylene and lower alkenylene being substituted optionally with a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

$W^1$ and $W^2$ are each independently O or S;

$W^3$ is O, S or $NR^{12}$;

$R^{12}$ is a hydrogen atom, lower alkyl, hydroxy lower alkyl, lower alkoxy lower alkyl, lower alkoxycarbonyl lower alkyl, carbocyclic lower alkyl or acyl;

$R^{14}$ is hydrogen atom or lower alkyl;

ring B is an optionally substituted carbocyclic group or an optionally substituted heterocyclic group;

the carbocyclic group and the heterocyclic group being substituted optionally with at least one selected from the group consisting of:

(a) a substituent α, the substituent α being at least one selected from the group consisting of halogen, hydroxy, lower alkoxy, hydroxy lower alkoxy, lower alkoxy lower alkoxy, acyl, acyloxy, carboxy, lower alkoxycarbonyl, amino, acylamino, lower alkylamino, lower alkylthio, carbamoyl, lower alkylcarbamoyl, hydroxy lower alkylcarbamoyl, sulfamoyl, lower alkylsulfamoyl, lower alkylsulfinyl, cyano, nitro, aryl, and heterocyclic group;

(b) lower alkyl optionally substituted with the substituent α;

(c) amino lower alkyl substituted with the substituent α;

(d) hydroxyimino lower alkyl;

(e) lower alkoxyimino lower alkyl;

(f) lower alkenyl optionally substituted with the substituent α;

(g) lower alkynyl optionally substituted with the substituent α;

(h) lower alkoxy optionally substituted with the substituent α;

(i) lower alkylthio optionally substituted with the substituent α;

(j) lower alkylamino substituted with the substituent α;

(k) lower alkylsulfonyl optionally substituted with the substituent α;

(l) aryl lower alkoxycarbonyl optionally substituted with one or more substituents selected from the group of substituent a and lower alkyl;

(m) acyl substituted with the substituent α;

(n) lower alkylsulfonyl optionally substituted with the substituent α;

(o) sulfamoyl;

(p) lower alkyl sulfamoyl optionally substituted with one or more substituents selected from the group of substituent α;

(q) cycloalkyl optionally substituted with one or more substituents selected from the group of substituent α, azido and lower alkyl;

(r) aryl optionally substituted with one or more substituents selected from the group of substituent α, azido and lower alkyl;

(s) heterocyclic group optionally substituted with one or more substituents selected from the group of substituent α, azido and lower alkyl;

(t) aryloxy optionally substituted with one or more substituents selected from the group of substituent α, azido and lower alkyl;

(u) heterocyclicoxy optionally substituted with one or more substituents selected from the group of substituent α, azido and lower alkyl;

(v) arylthio optionally substituted with one or more substituents selected from the group of substituent α, azido and lower alkyl;

(w) heterocyclic thio optionally substituted with one or more substituents selected from the group of substituent α, azido and lower alkyl;

(x) arylamino optionally substituted with one or more substituents selected from the group of substituent α, azido and lower alkyl;

(y) heterocyclic amino optionally substituted with one or more substituents selected from the group of substituent α, azido and lower alkyl;

(z) aryl lower alkylamino optionally substituted with one or more substituents selected from the group of substituent α, azido and lower alkyl;

(aa) heterocyclic lower alkylamino optionally substituted with one or more substituents selected from the group of substituent α, azido and lower alkyl;

(ab) arylsulfamoyl optionally substituted with one or more substituents selected from the group of substituent α, azido and lower alkyl;

(ac) heterocyclic sulfamoyl optionally substituted with one or more substituents selected from the group of substituent α, azido and lower alkyl;

(ad) arylsulfonyl optionally substituted with one or more substituents selected from the group of substituent α, azido and lower alkyl;

(ae) heterocyclic sulfonyl optionally substituted with one or more substituents selected from the group of substituent α, azido and lower alkyl;

(af) arylcarbamoyl optionally substituted with one or more substituents selected from the group of substituent α, azido and lower alkyl;

(ag) heterocyclic carbamoyl optionally substituted with one or more substituents selected from the group of substituent α, azido and lower alkyl;

(ah) aryl lower alkylcarbamoyl optionally substituted with one or more substituents selected from the group of substituent α, azido and lower alkyl;

(ai) heterocyclic lower alkylcarbamoyl optionally substituted with one or more substituents selected from the group of substituent α, azido and lower alkyl;

(aj) aryloxy carbonyl optionally substituted with one or more substituents selected from the group of substituent α, azido and lower alkyl;

(ak) heterocyclicoxycarbonyl optionally substituted with one or more substituents selected from the group of substituent α, azido and lower alkyl;

(al) lower alkylenedioxy substituted optionally with halogen; and (am) oxo;

$Alk^2$ is lower alkyl, lower alkyl being substituted optionally with at least one selected from the group consisting of a substituent α, and p is 1 or 2, or its pharmaceutically acceptable salt thereof.

* * * * *